US012180517B2

(12) United States Patent
Shah et al.

(10) Patent No.: US 12,180,517 B2
(45) Date of Patent: Dec. 31, 2024

(54) EXPRESSION OF NOVEL CELL TAGS

(71) Applicant: PRECIGEN, INC., Germantown, MD (US)

(72) Inventors: Rutul Shah, Boyds, MD (US); Peter Emtage, Lafayette, CA (US); Ramya Yarlagadda, Gaithersburg, MD (US)

(73) Assignee: PRECIGEN, INC., Germantown, MD (US)

( * ) Notice: Subject to any disclaimer, the term of this patent is extended or adjusted under 35 U.S.C. 154(b) by 342 days.

(21) Appl. No.: 17/303,970

(22) Filed: Jun. 11, 2021

(65) Prior Publication Data

US 2022/0064609 A1 Mar. 3, 2022

Related U.S. Application Data

(62) Division of application No. 16/001,759, filed on Jun. 6, 2018, now Pat. No. 11,118,168.

(60) Provisional application No. 62/516,639, filed on Jun. 7, 2017.

(51) Int. Cl.

| | |
|---|---|
| ***C12N 9/12*** | (2006.01) |
| ***A61K 35/17*** | (2015.01) |
| ***A61K 39/00*** | (2006.01) |
| ***A61K 39/395*** | (2006.01) |
| ***A61P 35/00*** | (2006.01) |
| ***C07K 14/54*** | (2006.01) |
| ***C07K 14/705*** | (2006.01) |
| ***C07K 14/71*** | (2006.01) |
| ***C07K 14/725*** | (2006.01) |
| ***C07K 16/28*** | (2006.01) |
| ***C07K 16/32*** | (2006.01) |

(52) U.S. Cl.

CPC ................ *C12N 9/12* (2013.01); *A61K 35/17* (2013.01); *A61K 39/3955* (2013.01); *A61P 35/00* (2018.01); *C07K 14/5443* (2013.01); *C07K 14/70503* (2013.01); *C07K 14/7051* (2013.01); *C07K 14/70521* (2013.01); *C07K 14/70578* (2013.01); *C07K 14/70592* (2013.01); *C07K 14/70596* (2013.01); *C07K 14/71* (2013.01); *C07K 16/2887* (2013.01); *C07K 16/32* (2013.01); *C12Y 207/10001* (2013.01); *A61K 2039/505* (2013.01); *C07K 2317/622* (2013.01); *C07K 2317/732* (2013.01); *C07K 2317/734* (2013.01); *C07K 2319/00* (2013.01); *C07K 2319/02* (2013.01); *C07K 2319/03* (2013.01); *C07K 2319/33* (2013.01)

(58) Field of Classification Search

None

See application file for complete search history.

(56) References Cited

U.S. PATENT DOCUMENTS

| | | | |
|---|---|---|---|
| 5,122,464 | A | 6/1992 | Wilson et al. |
| 5,283,173 | A | 2/1994 | Fields et al. |
| 5,350,674 | A | 9/1994 | Boenisch et al. |
| 5,585,362 | A | 12/1996 | Wilson et al. |
| 5,770,359 | A | 6/1998 | Wilson et al. |
| 5,858,358 | A | 1/1999 | June et al. |
| 5,880,333 | A | 3/1999 | Goff et al. |
| 5,883,223 | A | 3/1999 | Gray |
| 5,885,827 | A | 3/1999 | Wabl et al. |
| 6,225,042 | B1 | 5/2001 | Cai et al. |
| 6,265,173 | B1 | 7/2001 | Evans et al. |
| 6,352,694 | B1 | 3/2002 | June et al. |
| 6,355,479 | B1 | 3/2002 | Webb et al. |
| 6,362,001 | B1 | 3/2002 | Cai et al. |
| 6,489,458 | B2 | 12/2002 | Hackett et al. |
| 6,534,055 | B1 | 3/2003 | June et al. |
| 6,613,752 | B2 | 9/2003 | Kay et al. |
| 6,692,964 | B1 | 2/2004 | June et al. |
| 6,790,662 | B1 | 9/2004 | Leturco |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,091,038 | B2 | 8/2006 | Palli et al. |
| 7,144,575 | B2 | 12/2006 | June et al. |
| 7,148,203 | B2 | 12/2006 | Hackett et al. |
| 7,172,869 | B2 | 2/2007 | June et al. |
| 7,175,843 | B2 | 2/2007 | June et al. |
| 7,232,566 | B2 | 6/2007 | June et al. |
| 7,531,326 | B2 | 5/2009 | Kapitskaya et al. |
| 7,563,879 | B2 | 7/2009 | Palli et al. |

(Continued)

FOREIGN PATENT DOCUMENTS

| | | | |
|---|---|---|---|
| CN | 108330133 | A | 7/2018 |
| WO | WO-9208796 | | 5/1992 |

(Continued)

OTHER PUBLICATIONS

"Chimeric Antigen Receptor-Modified T cells for the Treatment of Acute Myeloid Leukemia Expressing CD33"—Dec.-May 2016.

(Continued)

*Primary Examiner* — Ruixiang Li

(74) *Attorney, Agent, or Firm* — Barnes & Thornburg LLP; Gene J. Yao

(57) ABSTRACT

Disclosed herein are polynucleotides encoding cell tags for use in immunotherapeutic applications, and systems comprising polynucleotide cell tags for regulating the activity of a cell. The compositions, methods and systems described herein provide tools for regulating activity of genetically engineered cells in a subject.

32 Claims, 22 Drawing Sheets

Specification includes a Sequence Listing.

(56) References Cited

U.S. PATENT DOCUMENTS

| | | | |
|---|---|---|---|
| 7,601,508 | B2 | 10/2009 | Palli et al. |
| 7,776,587 | B2 | 8/2010 | Palli et al. |
| 7,807,417 | B2 | 10/2010 | Palli et al. |
| 7,829,676 | B2 | 11/2010 | Zhang et al. |
| 7,919,269 | B2 | 4/2011 | Zhang et al. |
| 7,935,510 | B2 | 5/2011 | Palli et al. |
| 7,985,559 | B2 | 7/2011 | Freeman et al. |
| 7,985,739 | B2 | 7/2011 | Kay et al. |
| 8,021,878 | B2 | 9/2011 | Palli et al. |
| 8,030,067 | B2 | 10/2011 | Zhang et al. |
| 8,076,454 | B2 | 12/2011 | Palli et al. |
| 8,105,825 | B2 | 1/2012 | Dhadialla et al. |
| 8,168,426 | B2 | 5/2012 | Dhadialla et al. |
| 8,202,718 | B2 | 6/2012 | Palli et al. |
| 8,227,432 | B2 | 7/2012 | Hackett et al. |
| 8,236,556 | B2 | 8/2012 | Kapitskaya et al. |
| 8,497,093 | B2 | 7/2013 | Palli |
| 8,598,409 | B2 | 12/2013 | Kapitskaya et al. |
| 8,603,950 | B2 | 12/2013 | Bowers et al. |
| 8,715,959 | B2 | 5/2014 | Palli et al. |
| 8,790,649 | B2 | 7/2014 | Setlady et al. |
| 8,802,374 | B2 | 8/2014 | Jensen |
| 9,034,652 | B2 | 5/2015 | Belisle et al. |
| 9,228,180 | B2 | 1/2016 | Izsvak et al. |
| 9,402,919 | B2 | 8/2016 | Roeth et al. |
| 9,447,194 | B2 | 9/2016 | Jensen et al. |
| 9,580,685 | B2 | 2/2017 | Jensen et al. |
| 2004/0101519 | A1 | 5/2004 | June et al. |
| 2006/0034810 | A1 | 2/2006 | Riley et al. |
| 2006/0100416 | A1 | 5/2006 | Palli et al. |
| 2006/0121005 | A1 | 6/2006 | Berenson et al. |
| 2009/0004142 | A1 | 1/2009 | Leturcq et al. |
| 2009/0017000 | A1 | 1/2009 | Cai et al. |
| 2009/0123441 | A1 | 5/2009 | Braughler et al. |
| 2009/0123944 | A1 | 5/2009 | Finney et al. |
| 2009/0136465 | A1 | 5/2009 | Merenick et al. |
| 2010/0055093 | A1 | 3/2010 | Shepard et al. |
| 2011/0117072 | A1 | 5/2011 | Izsvak et al. |
| 2011/0212528 | A1 | 9/2011 | Palli et al. |
| 2011/0268766 | A1 | 11/2011 | Beech et al. |
| 2012/0167239 | A1 | 6/2012 | Palli et al. |
| 2013/0195800 | A1 | 8/2013 | Roeth et al. |
| 2015/0118228 | A1 | 4/2015 | Hill |
| 2016/0060345 | A1 | 3/2016 | Setiady et al. |
| 2016/0152723 | A1 | 6/2016 | Chen et al. |
| 2016/0158359 | A1 | 6/2016 | Gilbert |
| 2017/0107285 | A1 | 4/2017 | Jensen |
| 2018/0002397 | A1 | 1/2018 | Shah et al. |

FOREIGN PATENT DOCUMENTS

| | | | |
|---|---|---|---|
| WO | WO-9428143 | | 12/1994 |
| WO | WO-9738117 | A1 | 10/1997 |
| WO | WO-9902683 | A1 | 1/1999 |
| WO | WO-9958155 | A1 | 11/1999 |
| WO | 2002081649 | A2 | 10/2002 |
| WO | WO-2004033685 | A1 | 4/2004 |
| WO | WO-2005108617 | A3 | 2/2006 |
| WO | WO-2006000830 | A3 | 7/2006 |
| WO | WO-2007146959 | A2 | 12/2007 |
| WO | WO-2007103009 | A3 | 10/2008 |
| WO | WO-2009048560 | A1 | 4/2009 |
| WO | WO-2009045370 | A3 | 4/2010 |
| WO | WO-2011119773 | A1 | 9/2011 |
| WO | WO-2012122025 | A3 | 4/2013 |
| WO | 2013123061 | A1 | 8/2013 |
| WO | WO-2014190273 | A1 | 11/2014 |
| WO | WO-2015018306 | A1 | 2/2015 |
| WO | WO-2015095249 | A1 | 6/2015 |
| WO | 2015/123642 | A1 | 8/2015 |
| WO | WO-2015187528 | A1 | 12/2015 |
| WO | 2016/014565 | A2 | 1/2016 |
| WO | WO-2010042189 | A3 | 3/2016 |
| WO | WO-2016048903 | A1 | 3/2016 |
| WO | WO-2016073755 | A3 | 6/2016 |
| WO | WO-2016120216 | A1 | 8/2016 |
| WO | WO-2017062953 | A1 | 4/2017 |
| WO | WO-2017096331 | A1 | 6/2017 |
| WO | WO-2018197675 | A1 | 11/2018 |

OTHER PUBLICATIONS

"Autologous T Cells Modified to Co-express CD33-Specific Chimeric Antigen Receptor and a Kill Switch for Treatment of CD33+ Acute Myeloid Leukemia"—Dec.-Sep. 2017.

"CD19-specific chimeric antigen receptor-modified T cells with safety switch produced under 'Point-of-Care' using the Sleeping Beauty system for the very rapid manufacture and treatment of B-cell malignancies"—Dec.-Sep. 2017.

Database NCBI[online], Accession: 3P0Y_A, uploaded Oct. 10, 2012.

Database NCBI[online], Accession: NP_068769, updated Dec. 29, 2017.

Database NCBI[online], Accession: AAH00644, uploaded Jul. 15, 2006.

Database NCBI[online], Accession: NP_002498, uploaded Nov. 12, 2017.

Pharmaceutical Safety and Environmental Health Bureau, MHLW [online], Report on the Deliberation Results [Brand Name] GAZYVA for Intravenous Infusion 1000mg, Jun. 1, 2018.

PMDA [online], Review Report [Brand Name] ERBITUX Injection 100mg, 2012.

Jonnalagadda, et al., "Efficient selection of genetically modified human T cells using methotrexate-resistant human dihydrofolate reductase", Gene Therapy (2013) 20, 853-860.

Jonnalagadda, et al., "Engineering Human T Cells for Resistance to Methotrexate and Mycophenolate Mofetil as an In Vivo Cell Selection Strategy", PLOS One, Jun. 2013, vol. 8, Issue 6 pp. 1-10.

Paskiewicz, et al., "Targeted antibody-mediated depletion of murine CD19 CAR T cells permanently reverses B cell aplasia", J Clin Invest (2016); 126(11):4262-4272.

Wang, et al., "A transgene-encoded cell surface polypeptide for selection, in vivo tracking, and ablation of engineered cells", Gene Therapy, Blood, Aug. 4, 2011, vol. 118, No. 5.

Sickmier, E. Allen et al., The Panitumumab EGFR Complex Reveals a Binding Mechanism That Overcomes Cetuximab Induced Resistance, PLOS One, doi:10.1371/JOURNAL.PONE0163366, Sep. 22, 2016, pp. 1-11.

Bird, et al. Single-chain antigen-binding proteins. Science. Oct. 21, 1988;242(4877):423-6.

Colberre-Garapin et al. A new dominant hybrid selective marker for higher eukaryotic cells. J Mol Biol 150:1-14 (1981).

Garland et al. The use of Teflon cell culture bags to expand functionally active CD8+ cytotoxic T lymphocytes. J Immunol Meth 227(1-2):53-63 (1999).

Holliger, et al. Engineered antibody fragments and the rise of single domains. Nat Biotechnol. Sep. 2005;23(9):1126-36.

Jin, et al., The hyperactive Sleeping Beauty transposase SB100X improves the genetic modification of T cells to express a chimeric antigen receptor. Gene Ther. Sep. 2011; 18(9):849-56, doi: 10.1038/gt.2011.40. Epub Mar. 3, 2011.

Liberman, H.A. and Lachman, L., Eds., Pharmaceutical Dosage Forms, Marcel Decker, New York, N.Y., 1980.

PCT/US2018/036357 International Search Report and Written Opinion dated Oct. 3, 2018.

Remington: The Science and Practice of Pharmacy, Nineteenth Ed (Easton, Pa.: Mack Publishing Company, 1995).

Santerre et al. Expression of prokaryotic genes for hygromycin B and G418 resistance as dominant-selection markers in mouse L cells. Gene 30(1-3):147-156 (1984).

Ui-Tei et al. Sensitive assay of RNA interference in *Drosophila* and Chinese hamster cultured cells using firefly luciferase gene as target. FEBS Letters 479: 79-82 (2000).

Lelimousin et al., J. Am. Chem. Soc., 138:10611-10622 (2016).

Gowder et al., The Scientific World Journal (2014), 2014:971258.

Wang et al., Clinical Immunology (2014), 155:160-175.

Ahmed et al., J. Clin. Oncology (2015), 33:1688-1696.

(56) References Cited

OTHER PUBLICATIONS

Louis et al., Blood (2011), 118:6050-6056.
Beatty et al., Cancer Immunology Research (2014), 2:112-120.
Mardiros et al., Blood (2013), 122:3138-3148.
Johnson et al., Science Translational Medicine, 7:275ra22 a.
Berger et al., Cancer Immunology Research (2015), 3:206-216.
Chekmasova et al., Clin Cancer Res (2010) 16: 3594-3606.
O'Hear et al., Haematologica. (2015), 100:336-344.
Haso et al., Blood (2013) 122:1431 at Abstract.
Mendrola et al., J. Biol. Chem. (2002), 277:4704-4712.
Arkhipov et al., Cell (2013), 152:557-569.

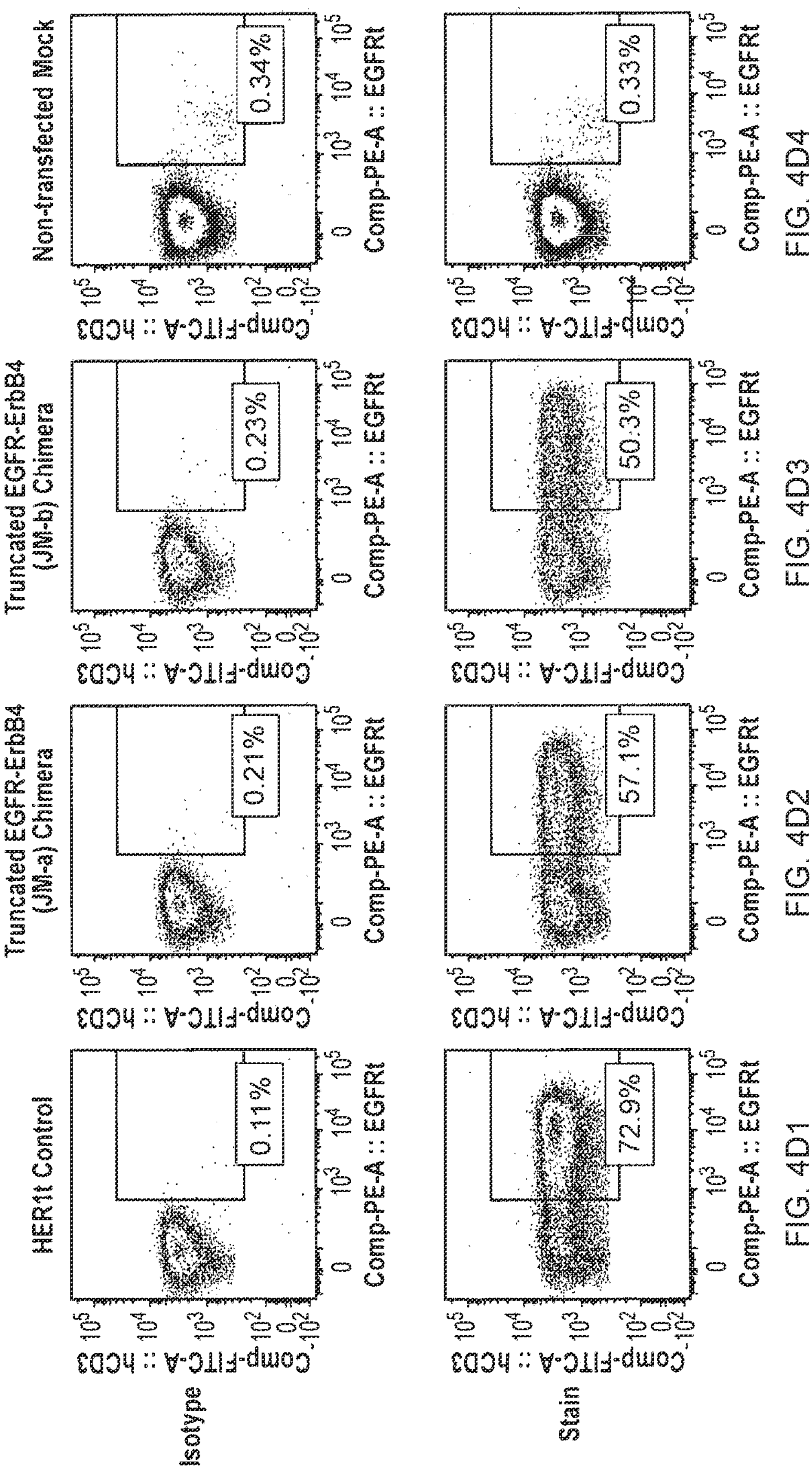
FIG. 4D1
FIG. 4D2
FIG. 4D3
FIG. 4D4

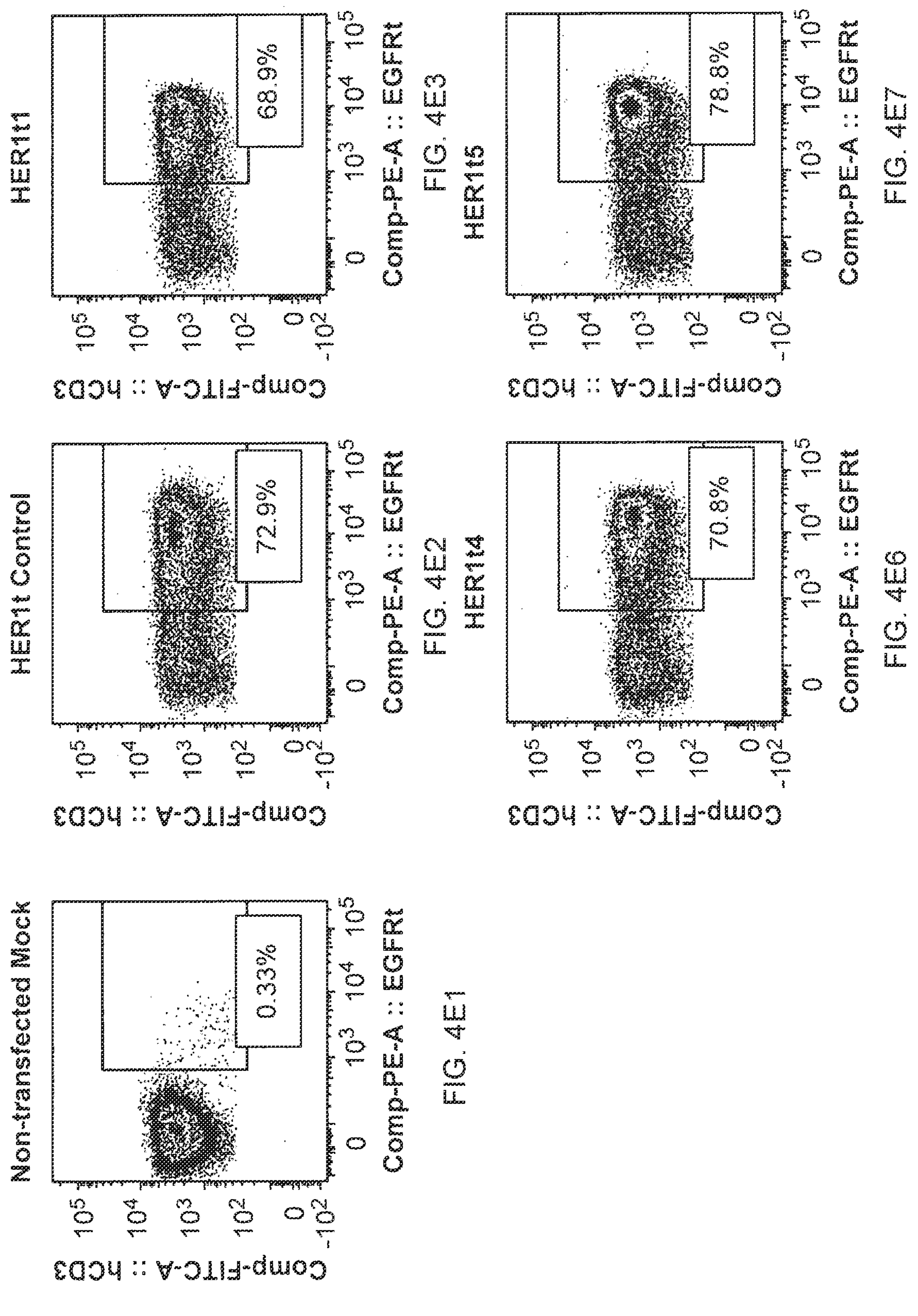
FIG. 4E1
FIG. 4E2
FIG. 4E3
FIG. 4E6
FIG. 4E7

HER1t2
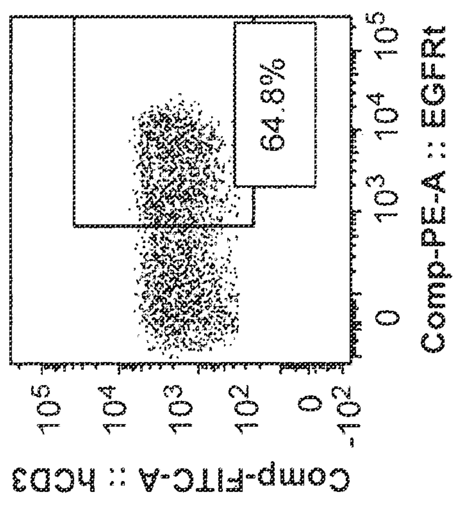
FIG. 4E4
HER1t3
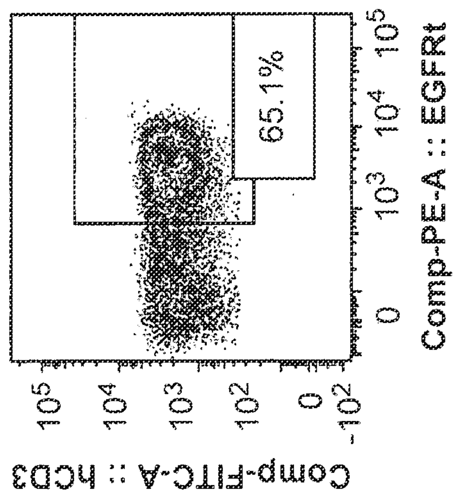
FIG. 4E5
HER1t6
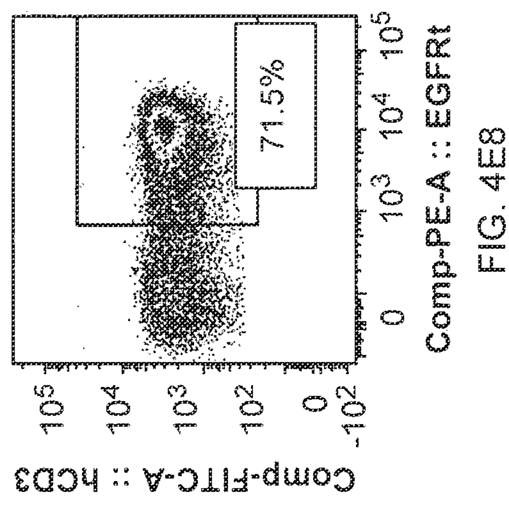
FIG. 4E8
HER1t7
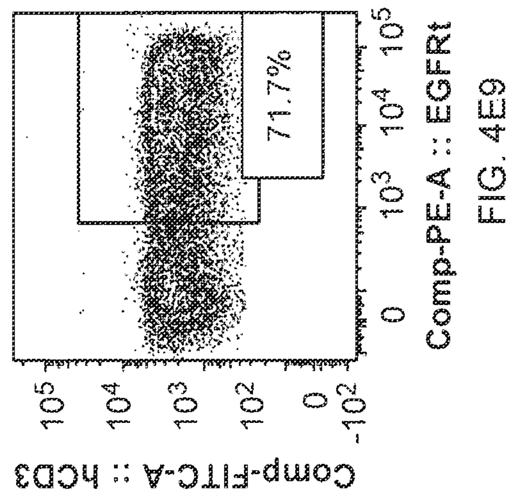
FIG. 4E9

SEQUENCE LISTING

```
<160> NUMBER OF SEQ ID NOS: 240

<210> SEQ ID NO 1
<211> LENGTH: 66
<212> TYPE: DNA
<213> ORGANISM: Unknown
<220> FEATURE:
<223> OTHER INFORMATION: Description of Unknown:
      GMCSFR alpha signal sequence

<400> SEQUENCE: 1

atgcttctcc tggtgacaag ccttctgctc tgtgagttac cacacccagc attcctcctg     60

atccca                                                                66
```

<210> SEQ ID NO 2
<211> LENGTH: 22
<212> TYPE: PRT
<213> ORGANISM: Unknown
<220> FEATURE:
<223> OTHER INFORMATION: Description of Unknown:
GMCSFR alpha signal sequence

<400> SEQUENCE: 2

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 3
<211> LENGTH: 60
<212> TYPE: DNA
<213> ORGANISM: Unknown
<220> FEATURE:
<223> OTHER INFORMATION: Description of Unknown:
Ig Kappa signal sequence

<400> SEQUENCE: 3

```
atgaggctcc ctgctcagct cctggggctg ctaatgctct gggtcccagg atccagtggg     60
```

<210> SEQ ID NO 4
<211> LENGTH: 20
<212> TYPE: PRT
<213> ORGANISM: Unknown
<220> FEATURE:
<223> OTHER INFORMATION: Description of Unknown:
Ig Kappa signal sequence

<400> SEQUENCE: 4

```
Met Arg Leu Pro Ala Gln Leu Leu Gly Leu Leu Met Leu Trp Val Pro
1               5                   10                  15

Gly Ser Ser Gly
            20
```

<210> SEQ ID NO 5
<211> LENGTH: 54
<212> TYPE: DNA
<213> ORGANISM: Unknown
<220> FEATURE:
<223> OTHER INFORMATION: Description of Unknown:
Immunoglobulin E signal sequence

<400> SEQUENCE: 5

```
atggattgga cctggattct gtttctggtg gccgctgcca caagagtgca cagc           54
```

<210> SEQ ID NO 6
<211> LENGTH: 18
<212> TYPE: PRT
<213> ORGANISM: Unknown
<220> FEATURE:
<223> OTHER INFORMATION: Description of Unknown:
Immunoglobulin E signal sequence

<400> SEQUENCE: 6

```
Met Asp Trp Thr Trp Ile Leu Phe Leu Val Ala Ala Ala Thr Arg Val
1               5                   10                  15

His Ser
```

<210> SEQ ID NO 7
<211> LENGTH: 63

<212> TYPE: DNA
<213> ORGANISM: Unknown
<220> FEATURE:
<223> OTHER INFORMATION: Description of Unknown:
CD8-alpha signal sequence

<400> SEQUENCE: 7
atggcgctgc ccgtgaccgc cttgctcctg ccgctggcct tgctgctcca cgccgccagg 60
ccg 63

<210> SEQ ID NO 8
<211> LENGTH: 21
<212> TYPE: PRT
<213> ORGANISM: Unknown
<220> FEATURE:
<223> OTHER INFORMATION: Description of Unknown:
CD8-alpha signal sequence

<400> SEQUENCE: 8

Met Ala Leu Pro Val Thr Ala Leu Leu Leu Pro Leu Ala Leu Leu Leu
1 5 10 15

His Ala Ala Arg Pro
20

<210> SEQ ID NO 9
<211> LENGTH: 63
<212> TYPE: DNA
<213> ORGANISM: Unknown
<220> FEATURE:
<223> OTHER INFORMATION: Description of Unknown:
TVB2(T21A) signal sequence

<400> SEQUENCE: 9
atgggcacca gcctcctctg ctggatggcc ctgtgtctcc tgggggcaga tcacgcagat 60
gct 63

<210> SEQ ID NO 10
<211> LENGTH: 21
<212> TYPE: PRT
<213> ORGANISM: Unknown
<220> FEATURE:
<223> OTHER INFORMATION: Description of Unknown:
TVB2(T21A) signal sequence

<400> SEQUENCE: 10

Met Gly Thr Ser Leu Leu Cys Trp Met Ala Leu Cys Leu Leu Gly Ala
1 5 10 15

Asp His Ala Asp Ala
20

<210> SEQ ID NO 11
<211> LENGTH: 72
<212> TYPE: DNA
<213> ORGANISM: Unknown
<220> FEATURE:
<223> OTHER INFORMATION: Description of Unknown:
CD52 signal sequence

<400> SEQUENCE: 11
atgaagcgct tcctcttcct cctactcacc atcagcctcc tggttatggt acagatacaa 60
actggactct ca 72

<210> SEQ ID NO 12
<211> LENGTH: 24

<212> TYPE: PRT
<213> ORGANISM: Unknown
<220> FEATURE:
<223> OTHER INFORMATION: Description of Unknown:
CD52 signal sequence

<400> SEQUENCE: 12

Met Lys Arg Phe Leu Phe Leu Leu Leu Thr Ile Ser Leu Leu Val Met
1 5 10 15

Val Gln Ile Gln Thr Gly Leu Ser
20

<210> SEQ ID NO 13
<211> LENGTH: 84
<212> TYPE: DNA
<213> ORGANISM: Unknown
<220> FEATURE:
<223> OTHER INFORMATION: Description of Unknown:
Low-affinity nerve growth factor receptor
(LNGFR, TNFRSF16) signal sequence

<400> SEQUENCE: 13
atgggggcag gtgccaccgg ccgcgccatg gacgggccgc gcctgctgct gttgctgctt 60
ctgggggtgt cccttggagg tgcc 84

<210> SEQ ID NO 14
<211> LENGTH: 28
<212> TYPE: PRT
<213> ORGANISM: Unknown
<220> FEATURE:
<223> OTHER INFORMATION: Description of Unknown:
Low-affinity nerve growth factor receptor
(LNGFR, TNFRSF16) signal sequence

<400> SEQUENCE: 14

Met Gly Ala Gly Ala Thr Gly Arg Ala Met Asp Gly Pro Arg Leu Leu
1 5 10 15

Leu Leu Leu Leu Leu Gly Val Ser Leu Gly Gly Ala
20 25

<210> SEQ ID NO 15
<211> LENGTH: 9
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15 ggaagcgga 9

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Gly Ser Gly
1

<210> SEQ ID NO 17
<211> LENGTH: 12
<212> TYPE: DNA

-continued

<213> ORGANISM: Artificial Sequence
<220> FEATURE:
<223> OTHER INFORMATION: Description of Artificial Sequence: Synthetic
oligonucleotide

<400> SEQUENCE: 17
agtggcagcg gc 12

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Ser Gly Ser Gly
1

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
ggcggaggcg gaagcggagg cggaggctcc ggcggaggcg gaagc 45

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Gly Gly Gly Gly Ser Gly Gly Gly Gly Ser Gly Gly Gly Gly Ser
1 5 10 15

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
ggtggcggtg gctcgggcgg tggtgggtcg ggtggcggcg gatctggtgg cggtggctcg 60

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Gly Gly Gly Gly Ser Gly Gly Gly Gly Ser Gly Gly Gly Gly Ser Gly
1 5 10 15

Gly Gly Gly Ser
20

<210> SEQ ID NO 23
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
ggcagcacct ccggcagcgg caagcctggc agcggcgagg gcagcaccaa gggc 54

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Gly Ser Thr Ser Gly Ser Gly Lys Pro Gly Ser Gly Glu Gly Ser Thr
1 5 10 15

Lys Gly

<210> SEQ ID NO 25
<211> LENGTH: 78
<212> TYPE: DNA
<213> ORGANISM: Unknown
<220> FEATURE:
<223> OTHER INFORMATION: Description of Unknown:
Glycophorin A (E91-R116) sequence

<400> SEQUENCE: 25
gagataacac tcattatttt tggggtgatg gctggtgtta ttggaacgat cctcttaatt 60
tcttacggta ttcgccga 78

<210> SEQ ID NO 26
<211> LENGTH: 26
<212> TYPE: PRT
<213> ORGANISM: Unknown
<220> FEATURE:
<223> OTHER INFORMATION: Description of Unknown:
Glycophorin A (E91-R116) sequence

<400> SEQUENCE: 26

Glu Ile Thr Leu Ile Ile Phe Gly Val Met Ala Gly Val Ile Gly Thr
1 5 10 15

Ile Leu Leu Ile Ser Tyr Gly Ile Arg Arg
20 25

<210> SEQ ID NO 27
<211> LENGTH: 69
<212> TYPE: DNA
<213> ORGANISM: Unknown
<220> FEATURE:
<223> OTHER INFORMATION: Description of Unknown:
Glycophorin A (I92-I114) sequence

<400> SEQUENCE: 27
ataacactca ttatttttgg ggtgatggct ggtgttattg gaacgatcct cttaatttct 60
tacggtatt 69

<210> SEQ ID NO 28

<211> LENGTH: 23
<212> TYPE: PRT
<213> ORGANISM: Unknown
<220> FEATURE:
<223> OTHER INFORMATION: Description of Unknown:
Glycophorin A (I92-I114) sequence

<400> SEQUENCE: 28

Ile Thr Leu Ile Ile Phe Gly Val Met Ala Gly Val Ile Gly Thr Ile
1 5 10 15

Leu Leu Ile Ser Tyr Gly Ile
20

<210> SEQ ID NO 29
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
ataacactca ttatttttgg ggtgatggct ggtgttattg gaacgatcct cttagccctg 60
ctcatctgg 69

<210> SEQ ID NO 30
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Ile Thr Leu Ile Ile Phe Gly Val Met Ala Gly Val Ile Gly Thr Ile
1 5 10 15

Leu Leu Ala Leu Leu Ile Trp
20

<210> SEQ ID NO 31
<211> LENGTH: 63
<212> TYPE: DNA
<213> ORGANISM: Unknown
<220> FEATURE:
<223> OTHER INFORMATION: Description of Unknown:
CD3 zeta (CD247) transmembrane domain sequence

<400> SEQUENCE: 31
ctctgctacc tgctggatgg aatcctcttc atctatggtg tcattctcac tgccttgttc 60
ctg 63

<210> SEQ ID NO 32
<211> LENGTH: 21
<212> TYPE: PRT
<213> ORGANISM: Unknown
<220> FEATURE:
<223> OTHER INFORMATION: Description of Unknown:
CD3 zeta (CD247) transmembrane domain sequence

<400> SEQUENCE: 32

Leu Cys Tyr Leu Leu Asp Gly Ile Leu Phe Ile Tyr Gly Val Ile Leu
1 5 10 15

Thr Ala Leu Phe Leu
20

<210> SEQ ID NO 33
<211> LENGTH: 84
<212> TYPE: DNA
<213> ORGANISM: Unknown
<220> FEATURE:
<223> OTHER INFORMATION: Description of Unknown:
CD8-alpha transmembrane domain sequence

<400> SEQUENCE: 33
atctacatct gggcccctct ggccggcacc tgtggcgtgc tgctgctgag cctggtcatc 60
accctgtact gcaaccaccg gaat 84

<210> SEQ ID NO 34
<211> LENGTH: 28
<212> TYPE: PRT
<213> ORGANISM: Unknown
<220> FEATURE:
<223> OTHER INFORMATION: Description of Unknown:
CD8-alpha transmembrane domain sequence

<400> SEQUENCE: 34

Ile Tyr Ile Trp Ala Pro Leu Ala Gly Thr Cys Gly Val Leu Leu Leu
1 5 10 15

Ser Leu Val Ile Thr Leu Tyr Cys Asn His Arg Asn
20 25

<210> SEQ ID NO 35
<211> LENGTH: 81
<212> TYPE: DNA
<213> ORGANISM: Unknown
<220> FEATURE:
<223> OTHER INFORMATION: Description of Unknown:
CD28 transmembrane domain sequence

<400> SEQUENCE: 35
ttttgggtgc tggtggtggt tggtggagtc ctggcttgct atagcttgct agtaacagtg 60
gcctttatta ttttctgggt g 81

<210> SEQ ID NO 36
<211> LENGTH: 27
<212> TYPE: PRT
<213> ORGANISM: Unknown
<220> FEATURE:
<223> OTHER INFORMATION: Description of Unknown:
CD28 transmembrane domain sequence

<400> SEQUENCE: 36

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 37
<211> LENGTH: 63
<212> TYPE: DNA
<213> ORGANISM: Unknown
<220> FEATURE:
<223> OTHER INFORMATION: Description of Unknown:
Cytotoxic T-lymphocyte protein 4 transmembrane domain sequence

<400> SEQUENCE: 37
ttcctcctct ggatccttgc agcagttagt tcggggttgt ttttttatag ctttctcctc 60
aca 63

<210> SEQ ID NO 38
<211> LENGTH: 21
<212> TYPE: PRT
<213> ORGANISM: Unknown
<220> FEATURE:
<223> OTHER INFORMATION: Description of Unknown:
Cytotoxic T-lymphocyte protein 4 transmembrane domain sequence

<400> SEQUENCE: 38

Phe Leu Leu Trp Ile Leu Ala Ala Val Ser Ser Gly Leu Phe Phe Tyr
1 5 10 15

Ser Phe Leu Leu Thr
20

<210> SEQ ID NO 39
<211> LENGTH: 66
<212> TYPE: DNA
<213> ORGANISM: Unknown
<220> FEATURE:
<223> OTHER INFORMATION: Description of Unknown:
Low-affinity nerve growth factor receptor
(LNGFR, TNFRSF16) transmembrane domain sequence

<400> SEQUENCE: 39
ctcatccctg tctattgctc catcctggct gctgtggttg tgggccttgt ggcctacata 60
gccttc 66

<210> SEQ ID NO 40
<211> LENGTH: 22
<212> TYPE: PRT
<213> ORGANISM: Unknown
<220> FEATURE:
<223> OTHER INFORMATION: Description of Unknown:
Low-affinity nerve growth factor receptor
(LNGFR, TNFRSF16) transmembrane domain sequence

<400> SEQUENCE: 40

Leu Ile Pro Val Tyr Cys Ser Ile Leu Ala Ala Val Val Val Gly Leu
1 5 10 15

Val Ala Tyr Ile Ala Phe
20

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
gcaacgaact tctctctcct aaaacaggct ggtgatgtgg aggagaatcc tggtcca 57

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Ala Thr Asn Phe Ser Leu Leu Lys Gln Ala Gly Asp Val Glu Glu Asn
1 5 10 15

Pro Gly Pro

<210> SEQ ID NO 43
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
cagtgtacta attatgctct cttgaaattg gctggagatg ttgagagcaa ccctggacct 60

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Gln Cys Thr Asn Tyr Ala Leu Leu Lys Leu Ala Gly Asp Val Glu Ser
1 5 10 15

Asn Pro Gly Pro
20

<210> SEQ ID NO 45
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
gagggcagag gaagtctgct aacatgcggt gacgtcgagg agaatcctgg acct 54

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Glu Gly Arg Gly Ser Leu Leu Thr Cys Gly Asp Val Glu Glu Asn Pro
1 5 10 15

Gly Pro

<210> SEQ ID NO 47
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
gtcaaacaga ccctaaactt tgatctgcta aaactggccg gggatgtgga aagtaatccc 60
ggcccc 66

<210> SEQ ID NO 48
<211> LENGTH: 22
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 48

Val Lys Gln Thr Leu Asn Phe Asp Leu Leu Lys Leu Ala Gly Asp Val
1 5 10 15

Glu Ser Asn Pro Gly Pro
20

<210> SEQ ID NO 49
<211> LENGTH: 570
<212> TYPE: DNA
<213> ORGANISM: Encephalomyocarditis virus

<400> SEQUENCE: 49 cccccctctcc ctcccccccc cctaacgtta ctggccgaag ccgcttggaa taaggccggt 60
gtgcgtttgt ctatatgtta ttttccacca tattgccgtc ttttggcaat gtgagggccc 120
ggaaacctgg ccctgtcttc ttgacgagca ttcctagggg tctttcccct ctcgccaaag 180
gaatgcaagg tctgttgaat gtcgtgaagg aagcagttcc tctggaagct tcttgaagac 240
aaacaacgtc tgtagcgacc ctttgcaggc agcggaaccc cccacctggc gacaggtgcc 300
tctgcggcca aaagccacgt gtataagata cacctgcaaa ggcggcacaa ccccagtgcc 360
acgttgtgag ttggatagtt gtggaaagag tcaaatggct ctcctcaagc gtattcaaca 420
aggggctgaa ggatgcccag aaggtacccc attgtatggg atctgatctg gggcctcggt 480
gcacatgctt tacatgtgtt tagtcgaggt taaaaaacgt ctaggccccc cgaaccacgg 540
ggacgtggtt ttcctttgaa aaacacgatc 570

<210> SEQ ID NO 50
<211> LENGTH: 1210
<212> TYPE: PRT
<213> ORGANISM: Unknown
<220> FEATURE:
<223> OTHER INFORMATION: Description of Unknown:
Epidermal growth factor receptor (EGFR) isoform a
precursor sequence

<400> SEQUENCE: 50

Met Arg Pro Ser Gly Thr Ala Gly Ala Ala Leu Leu Ala Leu Leu Ala
1 5 10 15

Ala Leu Cys Pro Ala Ser Arg Ala Leu Glu Glu Lys Lys Val Cys Gln
20 25 30

Gly Thr Ser Asn Lys Leu Thr Gln Leu Gly Thr Phe Glu Asp His Phe
35 40 45

Leu Ser Leu Gln Arg Met Phe Asn Asn Cys Glu Val Val Leu Gly Asn
50 55 60

Leu Glu Ile Thr Tyr Val Gln Arg Asn Tyr Asp Leu Ser Phe Leu Lys
65 70 75 80

Thr Ile Gln Glu Val Ala Gly Tyr Val Leu Ile Ala Leu Asn Thr Val
85 90 95

Glu Arg Ile Pro Leu Glu Asn Leu Gln Ile Ile Arg Gly Asn Met Tyr
100 105 110

Tyr Glu Asn Ser Tyr Ala Leu Ala Val Leu Ser Asn Tyr Asp Ala Asn
115 120 125

Lys Thr Gly Leu Lys Glu Leu Pro Met Arg Asn Leu Gln Glu Ile Leu
130 135 140

```
His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560
```

-continued

```
Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
```

```
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                 1015                 1020

Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185

Gly Ser  Thr Ala Glu Asn Ala  Glu Tyr Leu Arg Val  Ala Pro Gln
    1190                 1195                 1200

Ser Ser  Glu Phe Ile Gly Ala
    1205                 1210


<210> SEQ ID NO 51
<211> LENGTH: 1255
<212> TYPE: PRT
<213> ORGANISM: Unknown
<220> FEATURE:
<223> OTHER INFORMATION: Description of Unknown:
      Receptor tyrosine-protein kinase ErbB2 (HER2) isoform a
      precursor sequence

<400> SEQUENCE: 51

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110
```

-continued

```
Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525
```

-continued

```
Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
```

945 950 955 960

Ile Asp Ser Glu Cys Arg Pro Arg Phe Arg Glu Leu Val Ser Glu Phe
965 970 975

Ser Arg Met Ala Arg Asp Pro Gln Arg Phe Val Val Ile Gln Asn Glu
980 985 990

Asp Leu Gly Pro Ala Ser Pro Leu Asp Ser Thr Phe Tyr Arg Ser Leu
995 1000 1005

Leu Glu Asp Asp Asp Met Gly Asp Leu Val Asp Ala Glu Glu Tyr
1010 1015 1020

Leu Val Pro Gln Gln Gly Phe Phe Cys Pro Asp Pro Ala Pro Gly
1025 1030 1035

Ala Gly Gly Met Val His His Arg His Arg Ser Ser Ser Thr Arg
1040 1045 1050

Ser Gly Gly Gly Asp Leu Thr Leu Gly Leu Glu Pro Ser Glu Glu
1055 1060 1065

Glu Ala Pro Arg Ser Pro Leu Ala Pro Ser Glu Gly Ala Gly Ser
1070 1075 1080

Asp Val Phe Asp Gly Asp Leu Gly Met Gly Ala Ala Lys Gly Leu
1085 1090 1095

Gln Ser Leu Pro Thr His Asp Pro Ser Pro Leu Gln Arg Tyr Ser
1100 1105 1110

Glu Asp Pro Thr Val Pro Leu Pro Ser Glu Thr Asp Gly Tyr Val
1115 1120 1125

Ala Pro Leu Thr Cys Ser Pro Gln Pro Glu Tyr Val Asn Gln Pro
1130 1135 1140

Asp Val Arg Pro Gln Pro Pro Ser Pro Arg Glu Gly Pro Leu Pro
1145 1150 1155

Ala Ala Arg Pro Ala Gly Ala Thr Leu Glu Arg Pro Lys Thr Leu
1160 1165 1170

Ser Pro Gly Lys Asn Gly Val Val Lys Asp Val Phe Ala Phe Gly
1175 1180 1185

Gly Ala Val Glu Asn Pro Glu Tyr Leu Thr Pro Gln Gly Gly Ala
1190 1195 1200

Ala Pro Gln Pro His Pro Pro Pro Ala Phe Ser Pro Ala Phe Asp
1205 1210 1215

Asn Leu Tyr Tyr Trp Asp Gln Asp Pro Pro Glu Arg Gly Ala Pro
1220 1225 1230

Pro Ser Thr Phe Lys Gly Thr Pro Thr Ala Glu Asn Pro Glu Tyr
1235 1240 1245

Leu Gly Leu Asp Val Pro Val
1250 1255

<210> SEQ ID NO 52
<211> LENGTH: 1342
<212> TYPE: PRT
<213> ORGANISM: Unknown
<220> FEATURE:
<223> OTHER INFORMATION: Description of Unknown:
Receptor tyrosine-protein kinase ErbB3 (HER3) isoform 1
precursor sequence

<400> SEQUENCE: 52

Met Arg Ala Asn Asp Ala Leu Gln Val Leu Gly Leu Leu Phe Ser Leu
1 5 10 15

Ala Arg Gly Ser Glu Val Gly Asn Ser Gln Ala Val Cys Pro Gly Thr
20 25 30

```
Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445
```

-continued

```
Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
```

-continued

```
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu  Glu Glu Val Glu Leu  Glu Pro Glu
        995                 1000                1005

Leu Asp  Leu Asp Leu Asp Leu  Glu Ala Glu Glu Asp  Asn Leu Ala
    1010                1015                1020

Thr Thr  Thr Leu Gly Ser Ala  Leu Ser Leu Pro Val  Gly Thr Leu
    1025                1030                1035

Asn Arg  Pro Arg Gly Ser Gln  Ser Leu Leu Ser Pro  Ser Ser Gly
    1040                1045                1050

Tyr Met  Pro Met Asn Gln Gly  Asn Leu Gly Glu Ser  Cys Gln Glu
    1055                1060                1065

Ser Ala  Val Ser Gly Ser Ser  Glu Arg Cys Pro Arg  Pro Val Ser
    1070                1075                1080

Leu His  Pro Met Pro Arg Gly  Cys Leu Ala Ser Glu  Ser Ser Glu
    1085                1090                1095

Gly His  Val Thr Gly Ser Glu  Ala Glu Leu Gln Glu  Lys Val Ser
    1100                1105                1110

Met Cys  Arg Ser Arg Ser Arg  Ser Arg Ser Pro Arg  Pro Arg Gly
    1115                1120                1125

Asp Ser  Ala Tyr His Ser Gln  Arg His Ser Leu Leu  Thr Pro Val
    1130                1135                1140

Thr Pro  Leu Ser Pro Pro Gly  Leu Glu Glu Glu Asp  Val Asn Gly
    1145                1150                1155

Tyr Val  Met Pro Asp Thr His  Leu Lys Gly Thr Pro  Ser Ser Arg
    1160                1165                1170

Glu Gly  Thr Leu Ser Ser Val  Gly Leu Ser Ser Val  Leu Gly Thr
    1175                1180                1185

Glu Glu  Glu Asp Glu Asp Glu  Glu Tyr Glu Tyr Met  Asn Arg Arg
    1190                1195                1200

Arg Arg  His Ser Pro Pro His  Pro Pro Arg Pro Ser  Ser Leu Glu
    1205                1210                1215

Glu Leu  Gly Tyr Glu Tyr Met  Asp Val Gly Ser Asp  Leu Ser Ala
    1220                1225                1230

Ser Leu  Gly Ser Thr Gln Ser  Cys Pro Leu His Pro  Val Pro Ile
    1235                1240                1245

Met Pro  Thr Ala Gly Thr Thr  Pro Asp Glu Asp Tyr  Glu Tyr Met
    1250                1255                1260

Asn Arg  Gln Arg Asp Gly Gly  Gly Pro Gly Gly Asp  Tyr Ala Ala
    1265                1270                1275
```

Met Gly Ala Cys Pro Ala Ser Glu Gln Gly Tyr Glu Glu Met Arg
1280 1285 1290

Ala Phe Gln Gly Pro Gly His Gln Ala Pro His Val His Tyr Ala
1295 1300 1305

Arg Leu Lys Thr Leu Arg Ser Leu Glu Ala Thr Asp Ser Ala Phe
1310 1315 1320

Asp Asn Pro Asp Tyr Trp His Ser Arg Leu Phe Pro Lys Ala Asn
1325 1330 1335

Ala Gln Arg Thr
1340

<210> SEQ ID NO 53
<211> LENGTH: 1308
<212> TYPE: PRT
<213> ORGANISM: Unknown
<220> FEATURE:
<223> OTHER INFORMATION: Description of Unknown:
Receptor tyrosine-protein kinase ErbB4 (HER4) isoform
JM-a/CVT-1 precursor sequence

<400> SEQUENCE: 53

Met Lys Pro Ala Thr Gly Leu Trp Val Trp Val Ser Leu Leu Val Ala
1 5 10 15

Ala Gly Thr Val Gln Pro Ser Asp Ser Gln Ser Val Cys Ala Gly Thr
20 25 30

Glu Asn Lys Leu Ser Ser Leu Ser Asp Leu Glu Gln Gln Tyr Arg Ala
35 40 45

Leu Arg Lys Tyr Tyr Glu Asn Cys Glu Val Val Met Gly Asn Leu Glu
50 55 60

Ile Thr Ser Ile Glu His Asn Arg Asp Leu Ser Phe Leu Arg Ser Val
65 70 75 80

Arg Glu Val Thr Gly Tyr Val Leu Val Ala Leu Asn Gln Phe Arg Tyr
85 90 95

Leu Pro Leu Glu Asn Leu Arg Ile Ile Arg Gly Thr Lys Leu Tyr Glu
100 105 110

Asp Arg Tyr Ala Leu Ala Ile Phe Leu Asn Tyr Arg Lys Asp Gly Asn
115 120 125

Phe Gly Leu Gln Glu Leu Gly Leu Lys Asn Leu Thr Glu Ile Leu Asn
130 135 140

Gly Gly Val Tyr Val Asp Gln Asn Lys Phe Leu Cys Tyr Ala Asp Thr
145 150 155 160

Ile His Trp Gln Asp Ile Val Arg Asn Pro Trp Pro Ser Asn Leu Thr
165 170 175

Leu Val Ser Thr Asn Gly Ser Ser Gly Cys Gly Arg Cys His Lys Ser
180 185 190

Cys Thr Gly Arg Cys Trp Gly Pro Thr Glu Asn His Cys Gln Thr Leu
195 200 205

Thr Arg Thr Val Cys Ala Glu Gln Cys Asp Gly Arg Cys Tyr Gly Pro
210 215 220

Tyr Val Ser Asp Cys Cys His Arg Glu Cys Ala Gly Gly Cys Ser Gly
225 230 235 240

Pro Lys Asp Thr Asp Cys Phe Ala Cys Met Asn Phe Asn Asp Ser Gly
245 250 255

Ala Cys Val Thr Gln Cys Pro Gln Thr Phe Val Tyr Asn Pro Thr Thr
260 265 270

-continued

```
Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
    290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
        355                 360                 365

Leu Val Thr Gly Ile His Gly Asp Pro Tyr Asn Ala Ile Glu Ala Ile
    370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
            420                 425                 430

Ser Leu Leu Ile Leu Lys Gln Gln Gly Ile Thr Ser Leu Gln Phe Gln
        435                 440                 445

Ser Leu Lys Glu Ile Ser Ala Gly Asn Ile Tyr Ile Thr Asp Asn Ser
    450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
            500                 505                 510

Trp Gly Pro Gly Pro Asp Gln Cys Leu Ser Cys Arg Arg Phe Ser Arg
        515                 520                 525

Gly Arg Ile Cys Ile Glu Ser Cys Asn Leu Tyr Asp Gly Glu Phe Arg
    530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
        595                 600                 605

Asp Pro Asp Arg Glu Cys His Pro Cys His Pro Asn Cys Thr Gln Gly
    610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
                645                 650                 655

Val Ile Gly Gly Leu Phe Ile Leu Val Ile Val Gly Leu Thr Phe Ala
            660                 665                 670

Val Tyr Val Arg Arg Lys Ser Ile Lys Lys Lys Arg Ala Leu Arg Arg
        675                 680                 685

Phe Leu Glu Thr Glu Leu Val Glu Pro Leu Thr Pro Ser Gly Thr Ala
```

-continued

```
    690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
                725                 730                 735

Trp Val Pro Glu Gly Glu Thr Val Lys Ile Pro Val Ala Ile Lys Ile
            740                 745                 750

Leu Asn Glu Thr Thr Gly Pro Lys Ala Asn Val Glu Phe Met Asp Glu
        755                 760                 765

Ala Leu Ile Met Ala Ser Met Asp His Pro His Leu Val Arg Leu Leu
    770                 775                 780

Gly Val Cys Leu Ser Pro Thr Ile Gln Leu Val Thr Gln Leu Met Pro
785                 790                 795                 800

His Gly Cys Leu Leu Glu Tyr Val His Glu His Lys Asp Asn Ile Gly
                805                 810                 815

Ser Gln Leu Leu Leu Asn Trp Cys Val Gln Ile Ala Lys Gly Met Met
            820                 825                 830

Tyr Leu Glu Glu Arg Arg Leu Val His Arg Asp Leu Ala Ala Arg Asn
        835                 840                 845

Val Leu Val Lys Ser Pro Asn His Val Lys Ile Thr Asp Phe Gly Leu
    850                 855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
                885                 890                 895

Phe Thr His Gln Ser Asp Val Trp Ser Tyr Gly Val Thr Ile Trp Glu
            900                 905                 910

Leu Met Thr Phe Gly Gly Lys Pro Tyr Asp Gly Ile Pro Thr Arg Glu
        915                 920                 925

Ile Pro Asp Leu Leu Glu Lys Gly Glu Arg Leu Pro Gln Pro Pro Ile
    930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
                965                 970                 975

Met Ala Arg Asp Pro Gln Arg Tyr Leu Val Ile Gln Gly Asp Asp Arg
            980                 985                 990

Met Lys Leu Pro Ser Pro Asn Asp  Ser Lys Phe Phe Gln  Asn Leu Leu
        995                 1000                1005

Asp Glu  Glu Asp Leu Glu Asp  Met Met Asp Ala Glu  Glu Tyr Leu
    1010                1015                1020

Val Pro  Gln Ala Phe Asn Ile  Pro Pro Pro Ile Tyr  Thr Ser Arg
    1025                1030                1035

Ala Arg  Ile Asp Ser Asn Arg  Ser Glu Ile Gly His  Ser Pro Pro
    1040                1045                1050

Pro Ala  Tyr Thr Pro Met Ser  Gly Asn Gln Phe Val  Tyr Arg Asp
    1055                1060                1065

Gly Gly  Phe Ala Ala Glu Gln  Gly Val Ser Val Pro  Tyr Arg Ala
    1070                1075                1080

Pro Thr  Ser Thr Ile Pro Glu  Ala Pro Val Ala Gln  Gly Ala Thr
    1085                1090                1095

Ala Glu  Ile Phe Asp Asp Ser  Cys Cys Asn Gly Thr  Leu Arg Lys
    1100                1105                1110
```

Pro Val Ala Pro His Val Gln Glu Asp Ser Ser Thr Gln Arg Tyr
1115 1120 1125

Ser Ala Asp Pro Thr Val Phe Ala Pro Glu Arg Ser Pro Arg Gly
1130 1135 1140

Glu Leu Asp Glu Glu Gly Tyr Met Thr Pro Met Arg Asp Lys Pro
1145 1150 1155

Lys Gln Glu Tyr Leu Asn Pro Val Glu Glu Asn Pro Phe Val Ser
1160 1165 1170

Arg Arg Lys Asn Gly Asp Leu Gln Ala Leu Asp Asn Pro Glu Tyr
1175 1180 1185

His Asn Ala Ser Asn Gly Pro Pro Lys Ala Glu Asp Glu Tyr Val
1190 1195 1200

Asn Glu Pro Leu Tyr Leu Asn Thr Phe Ala Asn Thr Leu Gly Lys
1205 1210 1215

Ala Glu Tyr Leu Lys Asn Asn Ile Leu Ser Met Pro Glu Lys Ala
1220 1225 1230

Lys Lys Ala Phe Asp Asn Pro Asp Tyr Trp Asn His Ser Leu Pro
1235 1240 1245

Pro Arg Ser Thr Leu Gln His Pro Asp Tyr Leu Gln Glu Tyr Ser
1250 1255 1260

Thr Lys Tyr Phe Tyr Lys Gln Asn Gly Arg Ile Arg Pro Ile Val
1265 1270 1275

Ala Glu Asn Pro Glu Tyr Leu Ser Glu Phe Ser Leu Lys Pro Gly
1280 1285 1290

Thr Val Leu Pro Pro Pro Pro Tyr Arg His Arg Asn Thr Val Val
1295 1300 1305

<210> SEQ ID NO 54
<211> LENGTH: 1298
<212> TYPE: PRT
<213> ORGANISM: Unknown
<220> FEATURE:
<223> OTHER INFORMATION: Description of Unknown:
Receptor tyrosine-protein kinase ErbB4 (HER4) isoform JM-b
(isoform X7) precursor sequence

<400> SEQUENCE: 54

Met Lys Pro Ala Thr Gly Leu Trp Val Trp Val Ser Leu Leu Val Ala
1 5 10 15

Ala Gly Thr Val Gln Pro Ser Asp Ser Gln Ser Val Cys Ala Gly Thr
20 25 30

Glu Asn Lys Leu Ser Ser Leu Ser Asp Leu Glu Gln Gln Tyr Arg Ala
35 40 45

Leu Arg Lys Tyr Tyr Glu Asn Cys Glu Val Val Met Gly Asn Leu Glu
50 55 60

Ile Thr Ser Ile Glu His Asn Arg Asp Leu Ser Phe Leu Arg Ser Val
65 70 75 80

Arg Glu Val Thr Gly Tyr Val Leu Val Ala Leu Asn Gln Phe Arg Tyr
85 90 95

Leu Pro Leu Glu Asn Leu Arg Ile Ile Arg Gly Thr Lys Leu Tyr Glu
100 105 110

Asp Arg Tyr Ala Leu Ala Ile Phe Leu Asn Tyr Arg Lys Asp Gly Asn
115 120 125

Phe Gly Leu Gln Glu Leu Gly Leu Lys Asn Leu Thr Glu Ile Leu Asn
130 135 140

-continued

```
Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
    290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
        355                 360                 365

Leu Val Thr Gly Ile His Gly Asp Pro Tyr Asn Ala Ile Glu Ala Ile
    370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
            420                 425                 430

Ser Leu Leu Ile Leu Lys Gln Gln Gly Ile Thr Ser Leu Gln Phe Gln
        435                 440                 445

Ser Leu Lys Glu Ile Ser Ala Gly Asn Ile Tyr Ile Thr Asp Asn Ser
    450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
            500                 505                 510

Trp Gly Pro Gly Pro Asp Gln Cys Leu Ser Cys Arg Arg Phe Ser Arg
        515                 520                 525

Gly Arg Ile Cys Ile Glu Ser Cys Asn Leu Tyr Asp Gly Glu Phe Arg
    530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
```

-continued

```
                565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
        595                 600                 605

Asp Pro Asp Arg Glu Cys His Pro Cys His Pro Asn Cys Thr Gln Gly
    610                 615                 620

Cys Ile Gly Ser Ser Ile Glu Asp Cys Ile Gly Leu Met Asp Arg Thr
625                 630                 635                 640

Pro Leu Ile Ala Ala Gly Val Ile Gly Gly Leu Phe Ile Leu Val Ile
                645                 650                 655

Val Gly Leu Thr Phe Ala Val Tyr Val Arg Arg Lys Ser Ile Lys Lys
            660                 665                 670

Lys Arg Ala Leu Arg Arg Phe Leu Glu Thr Glu Leu Val Glu Pro Leu
        675                 680                 685

Thr Pro Ser Gly Thr Ala Pro Asn Gln Ala Gln Leu Arg Ile Leu Lys
    690                 695                 700

Glu Thr Glu Leu Lys Arg Val Lys Val Leu Gly Ser Gly Ala Phe Gly
705                 710                 715                 720

Thr Val Tyr Lys Gly Ile Trp Val Pro Glu Gly Glu Thr Val Lys Ile
                725                 730                 735

Pro Val Ala Ile Lys Ile Leu Asn Glu Thr Thr Gly Pro Lys Ala Asn
            740                 745                 750

Val Glu Phe Met Asp Glu Ala Leu Ile Met Ala Ser Met Asp His Pro
        755                 760                 765

His Leu Val Arg Leu Leu Gly Val Cys Leu Ser Pro Thr Ile Gln Leu
    770                 775                 780

Val Thr Gln Leu Met Pro His Gly Cys Leu Leu Glu Tyr Val His Glu
785                 790                 795                 800

His Lys Asp Asn Ile Gly Ser Gln Leu Leu Leu Asn Trp Cys Val Gln
                805                 810                 815

Ile Ala Lys Gly Met Met Tyr Leu Glu Glu Arg Arg Leu Val His Arg
            820                 825                 830

Asp Leu Ala Ala Arg Asn Val Leu Val Lys Ser Pro Asn His Val Lys
        835                 840                 845

Ile Thr Asp Phe Gly Leu Ala Arg Leu Leu Glu Gly Asp Glu Lys Glu
    850                 855                 860

Tyr Asn Ala Asp Gly Gly Lys Met Pro Ile Lys Trp Met Ala Leu Glu
865                 870                 875                 880

Cys Ile His Tyr Arg Lys Phe Thr His Gln Ser Asp Val Trp Ser Tyr
                885                 890                 895

Gly Val Thr Ile Trp Glu Leu Met Thr Phe Gly Gly Lys Pro Tyr Asp
            900                 905                 910

Gly Ile Pro Thr Arg Glu Ile Pro Asp Leu Leu Glu Lys Gly Glu Arg
        915                 920                 925

Leu Pro Gln Pro Pro Ile Cys Thr Ile Asp Val Tyr Met Val Met Val
    930                 935                 940

Lys Cys Trp Met Ile Asp Ala Asp Ser Arg Pro Lys Phe Lys Glu Leu
945                 950                 955                 960

Ala Ala Glu Phe Ser Arg Met Ala Arg Asp Pro Gln Arg Tyr Leu Val
                965                 970                 975

Ile Gln Gly Asp Asp Arg Met Lys Leu Pro Ser Pro Asn Asp Ser Lys
            980                 985                 990
```

Phe Phe Gln Asn Leu Leu Asp Glu Glu Asp Leu Glu Asp Met Met Asp
995 1000 1005

Ala Glu Glu Tyr Leu Val Pro Gln Ala Phe Asn Ile Pro Pro Pro
1010 1015 1020

Ile Tyr Thr Ser Arg Ala Arg Ile Asp Ser Asn Arg Ser Glu Ile
1025 1030 1035

Gly His Ser Pro Pro Pro Ala Tyr Thr Pro Met Ser Gly Asn Gln
1040 1045 1050

Phe Val Tyr Arg Asp Gly Gly Phe Ala Ala Glu Gln Gly Val Ser
1055 1060 1065

Val Pro Tyr Arg Ala Pro Thr Ser Thr Ile Pro Glu Ala Pro Val
1070 1075 1080

Ala Gln Gly Ala Thr Ala Glu Ile Phe Asp Asp Ser Cys Cys Asn
1085 1090 1095

Gly Thr Leu Arg Lys Pro Val Ala Pro His Val Gln Glu Asp Ser
1100 1105 1110

Ser Thr Gln Arg Tyr Ser Ala Asp Pro Thr Val Phe Ala Pro Glu
1115 1120 1125

Arg Ser Pro Arg Gly Glu Leu Asp Glu Glu Gly Tyr Met Thr Pro
1130 1135 1140

Met Arg Asp Lys Pro Lys Gln Glu Tyr Leu Asn Pro Val Glu Glu
1145 1150 1155

Asn Pro Phe Val Ser Arg Arg Lys Asn Gly Asp Leu Gln Ala Leu
1160 1165 1170

Asp Asn Pro Glu Tyr His Asn Ala Ser Asn Gly Pro Pro Lys Ala
1175 1180 1185

Glu Asp Glu Tyr Val Asn Glu Pro Leu Tyr Leu Asn Thr Phe Ala
1190 1195 1200

Asn Thr Leu Gly Lys Ala Glu Tyr Leu Lys Asn Asn Ile Leu Ser
1205 1210 1215

Met Pro Glu Lys Ala Lys Lys Ala Phe Asp Asn Pro Asp Tyr Trp
1220 1225 1230

Asn His Ser Leu Pro Pro Arg Ser Thr Leu Gln His Pro Asp Tyr
1235 1240 1245

Leu Gln Glu Tyr Ser Thr Lys Tyr Phe Tyr Lys Gln Asn Gly Arg
1250 1255 1260

Ile Arg Pro Ile Val Ala Glu Asn Pro Glu Tyr Leu Ser Glu Phe
1265 1270 1275

Ser Leu Lys Pro Gly Thr Val Leu Pro Pro Pro Pro Tyr Arg His
1280 1285 1290

Arg Asn Thr Val Val
1295

<210> SEQ ID NO 55
<211> LENGTH: 335
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile

```
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335


<210> SEQ ID NO 56
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300
```

ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420
acaataaact ggaaaaaact gtttgggacc tccggtcaga aaaccaaaat tataagcaac 480
agaggtgaaa acagctgcaa ggccacaggc caggtctgcc atgccttgtg ctcccccgag 540
ggctgctggg gcccggagcc cagggactgc gtctctggtg gcggtggctc gggcggtggt 600
gggtcgggtg gcggcggatc tggtggcggt ggctcgtttt gggtgctggt ggtggttggt 660
ggagtcctgg cttgctatag cttgctagta acagtggcct ttattatttt ctgggtgagg 720
agtaagagga gc 732

<210> SEQ ID NO 57
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Gly Gly Gly Gly Ser Gly Gly Gly Gly Ser Gly Gly Gly Gly Ser Gly
195 200 205

Gly Gly Gly Ser Phe Trp Val Leu Val Val Val Gly Gly Val Leu Ala
210 215 220

Cys Tyr Ser Leu Leu Val Thr Val Ala Phe Ile Ile Phe Trp Val Arg
225 230 235 240

Ser Lys Arg Ser

<210> SEQ ID NO 58
<211> LENGTH: 771
<212> TYPE: DNA

-continued

<213> ORGANISM: Artificial Sequence
<220> FEATURE:
<223> OTHER INFORMATION: Description of Artificial Sequence: Synthetic
      polynucleotide

<400> SEQUENCE: 58

```
cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc caggtctgcc atgccttgtg ctcccccgag     540

ggctgctggg gcccggagcc cagggactgc gtctcttgcc ggaatgtcag ccgaggcagg     600

gaatgcgtgg acaagggtgg cggtggctcg ggcggtggtg ggtcgggtgg cggcggatct     660

ggtggcggtg gctcgttttg ggtgctggtg gtggttggtg gagtcctggc ttgctatagc     720

ttgctagtaa cagtggcctt tattattttc tgggtgagga gtaagaggag c              771
```

<210> SEQ ID NO 59
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190
```

```
Cys Arg Asn Val Ser Arg Gly Arg Glu Cys Val Asp Lys Gly Gly Gly
        195                 200                 205

Gly Ser Gly Gly Gly Gly Ser Gly Gly Gly Gly Ser Gly Gly Gly Gly
    210                 215                 220

Ser Phe Trp Val Leu Val Val Val Gly Gly Val Leu Ala Cys Tyr Ser
225                 230                 235                 240

Leu Leu Val Thr Val Ala Phe Ile Ile Phe Trp Val Arg Ser Lys Arg
                245                 250                 255

Ser


<210> SEQ ID NO 60
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

cgcaaagtgt gtaacggaat aggtattggt gaatttaaag actcactctc cataaatgct     60

acgaatatta aacacttcaa aaactgcacc tccatcagtg gcgatctcca catcctgccg    120

gtggcattta ggggtgactc cttcacacat actcctcctc tggatccaca ggaactggat    180

attctgaaaa ccgtaaagga aatcacaggg tttttgctga ttcaggcttg gcctgaaaac    240

aggacggacc tccatgcctt tgagaaccta gaaatcatac gcggcaggac caagcaacat    300

ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctcttgcc ggaatgtcag ccgaggcagg    600

gaatgcgtgg acaagtgcaa ccttctggag ggtgagccaa gggagtttgt ggagaactct    660

gagtgcatac agggtggcgg tggctcgggc ggtggtgggt cgggtggcgg cggatctggt    720

ggcggtggct cgttttgggt gctggtggtg gttggtggag tcctggcttg ctatagcttg    780

ctagtaacag tggcctttat tattttctgg gtgaggagta agaggagc                 828


<210> SEQ ID NO 61
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80
```

```
Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Gly Gly Gly Gly Ser Gly Gly Gly Gly Ser Gly Gly Gly Gly Ser Gly
225                 230                 235                 240

Gly Gly Gly Ser Phe Trp Val Leu Val Val Val Gly Gly Val Leu Ala
                245                 250                 255

Cys Tyr Ser Leu Leu Val Thr Val Ala Phe Ile Ile Phe Trp Val Arg
            260                 265                 270

Ser Lys Arg Ser
        275
```

```
<210> SEQ ID NO 62
<211> LENGTH: 885
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc caggtctgcc atgccttgtg ctcccccgag     540

ggctgctggg gcccggagcc cagggactgc gtctcttgcc ggaatgtcag ccgaggcagg     600

gaatgcgtgg acaagtgcaa ccttctggag ggtgagccaa gggagtttgt ggagaactct     660

gagtgcatac agtgccaccc agagtgcctg cctcaggcca tgaacatcac ctgcacagga     720

cggggaccag acaactgtat ccagggcgga ggcggaagcg gaggcggagg ctccggcgga     780

ggcggaagct tttgggtgct ggtggtggtt ggtggagtcc tggcttgcta tagcttgcta     840
```

gtaacagtgg cctttattat tttctgggtg aggagtaaga ggagc 885

<210> SEQ ID NO 63
<211> LENGTH: 295
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys Cys Asn Leu
195 200 205

Leu Glu Gly Glu Pro Arg Glu Phe Val Glu Asn Ser Glu Cys Ile Gln
210 215 220

Cys His Pro Glu Cys Leu Pro Gln Ala Met Asn Ile Thr Cys Thr Gly
225 230 235 240

Arg Gly Pro Asp Asn Cys Ile Gln Gly Gly Gly Gly Ser Gly Gly Gly
245 250 255

Gly Ser Gly Gly Gly Gly Ser Phe Trp Val Leu Val Val Val Gly Gly
260 265 270

Val Leu Ala Cys Tyr Ser Leu Leu Val Thr Val Ala Phe Ile Ile Phe
275 280 285

Trp Val Arg Ser Lys Arg Ser
290 295

<210> SEQ ID NO 64
<211> LENGTH: 924
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
cgcaaagtgt gtaacggaat aggtattggt gaatttaaag actcactctc cataaatgct     60

acgaatatta aacacttcaa aaactgcacc tccatcagtg gcgatctcca catcctgccg    120

gtggcattta ggggtgactc cttcacacat actcctcctc tggatccaca ggaactggat    180

attctgaaaa ccgtaaagga aatcacaggg tttttgctga ttcaggcttg gcctgaaaac    240

aggacggacc tccatgcctt tgagaaccta gaaatcatac gcggcaggac caagcaacat    300

ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctcttgcc ggaatgtcag ccgaggcagg    600

gaatgcgtgg acaagtgcaa ccttctggag ggtgagccaa gggagtttgt ggagaactct    660

gagtgcatac agtgccaccc agagtgcctg cctcaggcca tgaacatcac ctgcacagga    720

cggggaccag acaactgtat ccagtgtgcc cactacattg acggccccca ctgcgtcaag    780

accggcggag gcggaagcgg aggcggaggc tccggcggag gcggaagctt ttgggtgctg    840

gtggtggttg gtggagtcct ggcttgctat agcttgctag taacagtggc ctttattatt    900

ttctgggtga ggagtaagag gagc                                           924
```

<210> SEQ ID NO 65
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
```

-continued

```
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Gly Gly Gly Gly Ser Gly Gly Gly Gly Ser Gly
            260                 265                 270

Gly Gly Gly Ser Phe Trp Val Leu Val Val Val Gly Gly Val Leu Ala
        275                 280                 285

Cys Tyr Ser Leu Leu Val Thr Val Ala Phe Ile Ile Phe Trp Val Arg
    290                 295                 300

Ser Lys Arg Ser
305


<210> SEQ ID NO 66
<211> LENGTH: 984
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc caggtctgcc atgccttgtg ctcccccgag     540

ggctgctggg gcccggagcc cagggactgc gtctcttgcc ggaatgtcag ccgaggcagg     600

gaatgcgtgg acaagtgcaa ccttctggag ggtgagccaa gggagtttgt ggagaactct     660

gagtgcatac agtgccaccc agagtgcctg cctcaggcca tgaacatcac ctgcacagga     720

cggggaccag acaactgtat ccagtgtgcc cactacattg acggccccca ctgcgtcaag     780

acctgcccgg caggagtcat gggagaaaac aacaccctgg tctggaagta cgcagacgcc     840

ggccatgtgt gccacctggg cggaggcgga agcggaggcg gaggctcctt ttgggtgctg     900

gtggtggttg gtggagtcct ggcttgctat agcttgctag taacagtggc ctttattatt     960

ttctgggtga ggagtaagag gagc                                            984


<210> SEQ ID NO 67
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 67

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys Cys Asn Leu
195 200 205

Leu Glu Gly Glu Pro Arg Glu Phe Val Glu Asn Ser Glu Cys Ile Gln
210 215 220

Cys His Pro Glu Cys Leu Pro Gln Ala Met Asn Ile Thr Cys Thr Gly
225 230 235 240

Arg Gly Pro Asp Asn Cys Ile Gln Cys Ala His Tyr Ile Asp Gly Pro
245 250 255

His Cys Val Lys Thr Cys Pro Ala Gly Val Met Gly Glu Asn Asn Thr
260 265 270

Leu Val Trp Lys Tyr Ala Asp Ala Gly His Val Cys His Leu Gly Gly
275 280 285

Gly Gly Ser Gly Gly Gly Gly Ser Phe Trp Val Leu Val Val Val Gly
290 295 300

Gly Val Leu Ala Cys Tyr Ser Leu Leu Val Thr Val Ala Phe Ile Ile
305 310 315 320

Phe Trp Val Arg Ser Lys Arg Ser
325

<210> SEQ ID NO 68
<211> LENGTH: 1032
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68
cgcaaagtgt gtaacggaat aggtattggt gaatttaaag actcactctc cataaatgct 60

-continued

```
acgaatatta aacacttcaa aaactgcacc tccatcagtg gcgatctcca catcctgccg    120
gtggcattta ggggtgactc cttcacacat actcctcctc tggatccaca ggaactggat    180
attctgaaaa ccgtaaagga aatcacaggg tttttgctga ttcaggcttg gcctgaaaac    240
aggacggacc tccatgcctt tgagaaccta gaaatcatac gcggcaggac caagcaacat    300
ggtcagtttt ctcttgcagt cgtcagcctg aacataacat ccttgggatt acgctccctc    360
aaggagataa gtgatggaga tgtgataatt tcaggaaaca aaaatttgtg ctatgcaaat    420
acaataaact ggaaaaaact gtttgggacc tccggtcaga aaaccaaaat tataagcaac    480
agaggtgaaa acagctgcaa ggccacaggc caggtctgcc atgccttgtg ctcccccgag    540
ggctgctggg gcccggagcc cagggactgc gtctcttgcc ggaatgtcag ccgaggcagg    600
gaatgcgtgg acaagtgcaa ccttctggag ggtgagccaa gggagtttgt ggagaactct    660
gagtgcatac agtgccaccc agagtgcctg cctcaggcca tgaacatcac ctgcacagga    720
cggggaccag acaactgtat ccagtgtgcc cactacattg acggccccca ctgcgtcaag    780
acctgcccgg caggagtcat gggagaaaac aacaccctgg tctggaagta cgcagacgcc    840
ggccatgtgt gccacctgtg ccatccaaac tgcacctacg gatgcactgg gccaggtctt    900
gaaggctgtc caggtggcgg tggcggcgga tctttttggg tgctggtggt ggttggtgga    960
gtcctggctt gctatagctt gctagtaaca gtggccttta ttattttctg ggtgaggagt   1020
aagaggagct aa                                                       1032
```

<210> SEQ ID NO 69
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
```

-continued

```
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Gly Gly Gly Gly Gly Gly Ser Phe Trp Val Leu Val Val Val Gly Gly
305                 310                 315                 320

Val Leu Ala Cys Tyr Ser Leu Leu Val Thr Val Ala Phe Ile Ile Phe
                325                 330                 335

Trp Val Arg Ser Lys Arg Ser
            340
```

<210> SEQ ID NO 70
<211> LENGTH: 786
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
atgaggctcc ctgctcagct cctggggctg ctaatgctct gggtcccagg atccagtggg     60

cgcaaagtgt gtaacggaat aggtattggt gaatttaaag actcactctc cataaatgct    120

acgaatatta aacacttcaa aaactgcacc tccatcagtg gcgatctcca catcctgccg    180

gtggcattta ggggtgactc cttcacacat actcctcctc tggatccaca ggaactggat    240

attctgaaaa ccgtaaagga aatcacaggg tttttgctga ttcaggcttg gcctgaaaac    300

aggacggacc tccatgcctt tgagaaccta gaaatcatac gcggcaggac caagcaacat    360

ggtcagtttt ctcttgcagt cgtcagcctg aacataacat ccttgggatt acgctccctc    420

aaggagataa gtgatggaga tgtgataatt tcaggaaaca aaaatttgtg ctatgcaaat    480

acaataaact ggaaaaaact gtttgggacc tccggtcaga aaaccaaaat tataagcaac    540

agaggtgaaa acagctgcaa ggccacaggc caggtctgcc atgccttgtg ctcccccgag    600

ggctgctggg gcccggagcc cagggactgc gtctctggtg gcggtggctc gggcggtggt    660

gggtcgggtg gcggcggatc tggtggcggt ggctcggaga taacactcat tatttttggg    720

gtgatggctg gtgttattgg aacgatcctc ttaatttctt acggtattcg ccgaggaggt    780

ggaagc                                                               786
```

<210> SEQ ID NO 71
<211> LENGTH: 262
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Met Arg Leu Pro Ala Gln Leu Leu Gly Leu Leu Met Leu Trp Val Pro
1 5 10 15

Gly Ser Ser Gly Arg Lys Val Cys Asn Gly Ile Gly Ile Gly Glu Phe
20 25 30

Lys Asp Ser Leu Ser Ile Asn Ala Thr Asn Ile Lys His Phe Lys Asn
35 40 45

Cys Thr Ser Ile Ser Gly Asp Leu His Ile Leu Pro Val Ala Phe Arg
50 55 60

Gly Asp Ser Phe Thr His Thr Pro Pro Leu Asp Pro Gln Glu Leu Asp
65 70 75 80

Ile Leu Lys Thr Val Lys Glu Ile Thr Gly Phe Leu Leu Ile Gln Ala
85 90 95

Trp Pro Glu Asn Arg Thr Asp Leu His Ala Phe Glu Asn Leu Glu Ile
100 105 110

Ile Arg Gly Arg Thr Lys Gln His Gly Gln Phe Ser Leu Ala Val Val
115 120 125

Ser Leu Asn Ile Thr Ser Leu Gly Leu Arg Ser Leu Lys Glu Ile Ser
130 135 140

Asp Gly Asp Val Ile Ile Ser Gly Asn Lys Asn Leu Cys Tyr Ala Asn
145 150 155 160

Thr Ile Asn Trp Lys Lys Leu Phe Gly Thr Ser Gly Gln Lys Thr Lys
165 170 175

Ile Ile Ser Asn Arg Gly Glu Asn Ser Cys Lys Ala Thr Gly Gln Val
180 185 190

Cys His Ala Leu Cys Ser Pro Glu Gly Cys Trp Gly Pro Glu Pro Arg
195 200 205

Asp Cys Val Ser Gly Gly Gly Gly Ser Gly Gly Gly Gly Ser Gly Gly
210 215 220

Gly Gly Ser Gly Gly Gly Gly Ser Glu Ile Thr Leu Ile Ile Phe Gly
225 230 235 240

Val Met Ala Gly Val Ile Gly Thr Ile Leu Leu Ile Ser Tyr Gly Ile
245 250 255

Arg Arg Gly Gly Gly Ser
260

<210> SEQ ID NO 72
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300
ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420

-continued

```
acaataaact ggaaaaaact gtttgggacc tccggtcaga aaaccaaaat tataagcaac    480

agaggtgaaa acagctgcaa ggccacaggc caggtctgcc atgccttgtg ctcccccgag    540

ggctgctggg gcccggagcc cagggactgc gtctctggtg gcggtggctc gggcggtggt    600

gggtcgggtg gcggcggatc tggtggcggt ggctcggaga taacactcat tatttttggg    660

gtgatggctg gtgttattgg aacgatcctc ttaatttctt acggtattcg ccgaggaggt    720

ggaagc                                                               726
```

<210> SEQ ID NO 73
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Gly Gly Gly Gly Ser Gly Gly Gly Gly Ser Gly Gly Gly Gly Ser Gly
        195                 200                 205

Gly Gly Gly Ser Glu Ile Thr Leu Ile Ile Phe Gly Val Met Ala Gly
    210                 215                 220

Val Ile Gly Thr Ile Leu Leu Ile Ser Tyr Gly Ile Arg Arg Gly Gly
225                 230                 235                 240

Gly Ser
```

<210> SEQ ID NO 74
<211> LENGTH: 777
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74
atgaggctcc ctgctcagct cctggggctg ctaatgctct gggtcccagg atccagtggg 60
cgcaaagtgt gtaacggaat aggtattggt gaatttaaag actcactctc cataaatgct 120
acgaatatta aacacttcaa aaactgcacc tccatcagtg gcgatctcca catcctgccg 180
gtggcattta ggggtgactc cttcacacat actcctcctc tggatccaca ggaactggat 240
attctgaaaa ccgtaaagga aatcacaggg tttttgctga ttcaggcttg gcctgaaaac 300
aggacggacc tccatgcctt tgagaaccta gaaatcatac gcggcaggac caagcaacat 360
ggtcagtttt ctcttgcagt cgtcagcctg aacataacat ccttgggatt acgctccctc 420
aaggagataa gtgatggaga tgtgataatt tcaggaaaca aaaatttgtg ctatgcaaat 480
acaataaact ggaaaaaact gtttgggacc tccggtcaga aaaccaaaat tataagcaac 540
agaggtgaaa acagctgcaa ggccacaggc caggtctgcc atgccttgtg ctcccccgag 600
ggctgctggg gcccggagcc cagggactgc gtctctggtg gcggtggctc gggcggtggt 660
gggtcgggtg gcggcggatc tggtggcggt ggctcgataa cactcattat ttttggggtg 720
atggctggtg ttattggaac gatcctctta atttcttacg gtattggagg tggaagc 777

<210> SEQ ID NO 75
<211> LENGTH: 259
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

Met Arg Leu Pro Ala Gln Leu Leu Gly Leu Leu Met Leu Trp Val Pro
1 5 10 15

Gly Ser Ser Gly Arg Lys Val Cys Asn Gly Ile Gly Ile Gly Glu Phe
20 25 30

Lys Asp Ser Leu Ser Ile Asn Ala Thr Asn Ile Lys His Phe Lys Asn
35 40 45

Cys Thr Ser Ile Ser Gly Asp Leu His Ile Leu Pro Val Ala Phe Arg
50 55 60

Gly Asp Ser Phe Thr His Thr Pro Pro Leu Asp Pro Gln Glu Leu Asp
65 70 75 80

Ile Leu Lys Thr Val Lys Glu Ile Thr Gly Phe Leu Leu Ile Gln Ala
85 90 95

Trp Pro Glu Asn Arg Thr Asp Leu His Ala Phe Glu Asn Leu Glu Ile
100 105 110

Ile Arg Gly Arg Thr Lys Gln His Gly Gln Phe Ser Leu Ala Val Val
115 120 125

Ser Leu Asn Ile Thr Ser Leu Gly Leu Arg Ser Leu Lys Glu Ile Ser
130 135 140

Asp Gly Asp Val Ile Ile Ser Gly Asn Lys Asn Leu Cys Tyr Ala Asn
145 150 155 160

Thr Ile Asn Trp Lys Lys Leu Phe Gly Thr Ser Gly Gln Lys Thr Lys
165 170 175

Ile Ile Ser Asn Arg Gly Glu Asn Ser Cys Lys Ala Thr Gly Gln Val
180 185 190

Cys His Ala Leu Cys Ser Pro Glu Gly Cys Trp Gly Pro Glu Pro Arg
195 200 205

Asp Cys Val Ser Gly Gly Gly Gly Ser Gly Gly Gly Gly Ser Gly Gly

```
    210                 215                 220

Gly Gly Ser Gly Gly Gly Gly Ser Ile Thr Leu Ile Ile Phe Gly Val
225                 230                 235                 240

Met Ala Gly Val Ile Gly Thr Ile Leu Leu Ile Ser Tyr Gly Ile Gly
                245                 250                 255

Gly Gly Ser


<210> SEQ ID NO 76
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc caggtctgcc atgccttgtg ctcccccgag     540

ggctgctggg gcccggagcc cagggactgc gtctctggtg gcggtggctc gggcggtggt     600

gggtcgggtg gcggcggatc tggtggcggt ggctcgataa cactcattat ttttggggtg     660

atggctggtg ttattggaac gatcctctta atttcttacg gtattggagg tggaagc        717


<210> SEQ ID NO 77
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125
```

```
Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Gly Gly Gly Gly Ser Gly Gly Gly Gly Ser Gly Gly Gly Gly Ser Gly
        195                 200                 205

Gly Gly Gly Ser Ile Thr Leu Ile Ile Phe Gly Val Met Ala Gly Val
    210                 215                 220

Ile Gly Thr Ile Leu Leu Ile Ser Tyr Gly Ile Gly Gly Gly Ser
225                 230                 235
```

<210> SEQ ID NO 78
<211> LENGTH: 777
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
atgaggctcc ctgctcagct cctggggctg ctaatgctct gggtcccagg atccagtggg      60

cgcaaagtgt gtaacggaat aggtattggt gaatttaaag actcactctc cataaatgct     120

acgaatatta aacacttcaa aaactgcacc tccatcagtg gcgatctcca catcctgccg     180

gtggcattta ggggtgactc cttcacacat actcctcctc tggatccaca ggaactggat     240

attctgaaaa ccgtaaagga aatcacaggg tttttgctga ttcaggcttg gcctgaaaac     300

aggacggacc tccatgcctt tgagaaccta gaaatcatac gcggcaggac caagcaacat     360

ggtcagtttt ctcttgcagt cgtcagcctg aacataacat ccttgggatt acgctccctc     420

aaggagataa gtgatggaga tgtgataatt tcaggaaaca aaaatttgtg ctatgcaaat     480

acaataaact ggaaaaaact gtttgggacc tccggtcaga aaaccaaaat tataagcaac     540

agaggtgaaa acagctgcaa ggccacaggc caggtctgcc atgccttgtg ctcccccgag     600

ggctgctggg gcccggagcc cagggactgc gtctctggtg gcggtggctc gggcggtggt     660

gggtcgggtg gcggcggatc tggtggcggt ggctcgataa cactcattat ttttggggtg     720

atggctggtg ttattggaac gatcctctta gccctgctca tctggggagg tggaagc        777
```

<210> SEQ ID NO 79
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Met Arg Leu Pro Ala Gln Leu Leu Gly Leu Leu Met Leu Trp Val Pro
1               5                   10                  15

Gly Ser Ser Gly Arg Lys Val Cys Asn Gly Ile Gly Ile Gly Glu Phe
            20                  25                  30

Lys Asp Ser Leu Ser Ile Asn Ala Thr Asn Ile Lys His Phe Lys Asn
        35                  40                  45
```

```
Cys Thr Ser Ile Ser Gly Asp Leu His Ile Leu Pro Val Ala Phe Arg
    50                  55                  60

Gly Asp Ser Phe Thr His Thr Pro Pro Leu Asp Pro Gln Glu Leu Asp
65                  70                  75                  80

Ile Leu Lys Thr Val Lys Glu Ile Thr Gly Phe Leu Leu Ile Gln Ala
                85                  90                  95

Trp Pro Glu Asn Arg Thr Asp Leu His Ala Phe Glu Asn Leu Glu Ile
            100                 105                 110

Ile Arg Gly Arg Thr Lys Gln His Gly Gln Phe Ser Leu Ala Val Val
        115                 120                 125

Ser Leu Asn Ile Thr Ser Leu Gly Leu Arg Ser Leu Lys Glu Ile Ser
    130                 135                 140

Asp Gly Asp Val Ile Ile Ser Gly Asn Lys Asn Leu Cys Tyr Ala Asn
145                 150                 155                 160

Thr Ile Asn Trp Lys Lys Leu Phe Gly Thr Ser Gly Gln Lys Thr Lys
                165                 170                 175

Ile Ile Ser Asn Arg Gly Glu Asn Ser Cys Lys Ala Thr Gly Gln Val
            180                 185                 190

Cys His Ala Leu Cys Ser Pro Glu Gly Cys Trp Gly Pro Glu Pro Arg
        195                 200                 205

Asp Cys Val Ser Gly Gly Gly Gly Ser Gly Gly Gly Gly Ser Gly Gly
    210                 215                 220

Gly Gly Ser Gly Gly Gly Gly Ser Ile Thr Leu Ile Ile Phe Gly Val
225                 230                 235                 240

Met Ala Gly Val Ile Gly Thr Ile Leu Leu Ala Leu Leu Ile Trp Gly
                245                 250                 255

Gly Gly Ser
```

```
<210> SEQ ID NO 80
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc caggtctgcc atgccttgtg ctcccccgag     540

ggctgctggg gcccggagcc cagggactgc gtctctggtg gcggtggctc gggcggtggt     600

gggtcgggtg gcggcggatc tggtggcggt ggctcgataa cactcattat ttttggggtg     660

atggctggtg ttattggaac gatcctctta gccctgctca tctggggagg tggaagc        717


<210> SEQ ID NO 81
<211> LENGTH: 239
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 81

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Gly Gly Gly Gly Ser Gly Gly Gly Gly Ser Gly Gly Gly Gly Ser Gly
195 200 205

Gly Gly Gly Ser Ile Thr Leu Ile Ile Phe Gly Val Met Ala Gly Val
210 215 220

Ile Gly Thr Ile Leu Leu Ala Leu Leu Ile Trp Gly Gly Gly Ser
225 230 235

<210> SEQ ID NO 82
<211> LENGTH: 771
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 82
atgaggctcc ctgctcagct cctggggctg ctaatgctct gggtcccagg atccagtggg 60
cgcaaagtgt gtaacggaat aggtattggt gaatttaaag actcactctc cataaatgct 120
acgaatatta aacacttcaa aaactgcacc tccatcagtg gcgatctcca catcctgccg 180
gtggcattta ggggtgactc cttcacacat actcctcctc tggatccaca ggaactggat 240
attctgaaaa ccgtaaagga aatcacaggg tttttgctga ttcaggcttg gcctgaaaac 300
aggacggacc tccatgcctt tgagaaccta gaaatcatac gcggcaggac caagcaacat 360
ggtcagtttt ctcttgcagt cgtcagcctg aacataacat ccttgggatt acgctccctc 420
aaggagataa gtgatggaga tgtgataatt tcaggaaaca aaaatttgtg ctatgcaaat 480
acaataaact ggaaaaaact gtttgggacc tccggtcaga aaaccaaaat tataagcaac 540
agaggtgaaa acagctgcaa ggccacaggc caggtctgcc atgccttgtg ctcccccgag 600
ggctgctggg gcccggagcc cagggactgc gtctctggtg gcggtggctc gggcggtggt 660
gggtcgggtg gcggcggatc tggtggcggt ggctcgctct gctacctgct ggatggaatc 720
ctcttcatct atggtgtcat tctcactgcc ttgttcctgg gaggtggaag c 771

<210> SEQ ID NO 83
<211> LENGTH: 257
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Met Arg Leu Pro Ala Gln Leu Leu Gly Leu Leu Met Leu Trp Val Pro
1 5 10 15

Gly Ser Ser Gly Arg Lys Val Cys Asn Gly Ile Gly Ile Gly Glu Phe
20 25 30

Lys Asp Ser Leu Ser Ile Asn Ala Thr Asn Ile Lys His Phe Lys Asn
35 40 45

Cys Thr Ser Ile Ser Gly Asp Leu His Ile Leu Pro Val Ala Phe Arg
50 55 60

Gly Asp Ser Phe Thr His Thr Pro Pro Leu Asp Pro Gln Glu Leu Asp
65 70 75 80

Ile Leu Lys Thr Val Lys Glu Ile Thr Gly Phe Leu Leu Ile Gln Ala
85 90 95

Trp Pro Glu Asn Arg Thr Asp Leu His Ala Phe Glu Asn Leu Glu Ile
100 105 110

Ile Arg Gly Arg Thr Lys Gln His Gly Gln Phe Ser Leu Ala Val Val
115 120 125

Ser Leu Asn Ile Thr Ser Leu Gly Leu Arg Ser Leu Lys Glu Ile Ser
130 135 140

Asp Gly Asp Val Ile Ile Ser Gly Asn Lys Asn Leu Cys Tyr Ala Asn
145 150 155 160

Thr Ile Asn Trp Lys Lys Leu Phe Gly Thr Ser Gly Gln Lys Thr Lys
165 170 175

Ile Ile Ser Asn Arg Gly Glu Asn Ser Cys Lys Ala Thr Gly Gln Val
180 185 190

Cys His Ala Leu Cys Ser Pro Glu Gly Cys Trp Gly Pro Glu Pro Arg
195 200 205

Asp Cys Val Ser Gly Gly Gly Gly Ser Gly Gly Gly Gly Ser Gly Gly
210 215 220

Gly Gly Ser Gly Gly Gly Gly Ser Leu Cys Tyr Leu Leu Asp Gly Ile
225 230 235 240

Leu Phe Ile Tyr Gly Val Ile Leu Thr Ala Leu Phe Leu Gly Gly Gly
245 250 255

Ser

<210> SEQ ID NO 84
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300
ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420
acaataaact ggaaaaaact gtttgggacc tccggtcaga aaaccaaaat tataagcaac 480
agaggtgaaa acagctgcaa ggccacaggc caggtctgcc atgccttgtg ctcccccgag 540
ggctgctggg gcccggagcc cagggactgc gtctctggtg gcggtggctc gggcggtggt 600
gggtcgggtg gcggcggatc tggtggcggt ggctcgctct gctacctgct ggatggaatc 660
ctcttcatct atggtgtcat tctcactgcc ttgttcctgg gaggtggaag c 711

<210> SEQ ID NO 85
<211> LENGTH: 237
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 85

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Gly Gly Gly Gly Ser Gly Gly Gly Gly Ser Gly Gly Gly Gly Ser Gly
195 200 205

Gly Gly Gly Ser Leu Cys Tyr Leu Leu Asp Gly Ile Leu Phe Ile Tyr

```
    210                 215                 220

Gly Val Ile Leu Thr Ala Leu Phe Leu Gly Gly Gly Ser
225                 230                 235


<210> SEQ ID NO 86
<211> LENGTH: 1077
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

atgcttctcc tggtgacaag ccttctgctc tgtgagttac cacacccagc attcctcctg     60

atcccacgca aagtgtgtaa cggaataggt attggtgaat ttaaagactc actctccata    120

aatgctacga atattaaaca cttcaaaaac tgcacctcca tcagtggcga tctccacatc    180

ctgccggtgg catttagggg tgactccttc acacatactc ctcctctgga tccacaggaa    240

ctggatattc tgaaaaccgt aaaggaaatc acagggtttt tgctgattca ggcttggcct    300

gaaaacagga cggacctcca tgcctttgag aacctagaaa tcatacgcgg caggaccaag    360

caacatggtc agtttctct tgcagtcgtc agcctgaaca taacatcctt gggattacgc    420

tccctcaagg agataagtga tggagatgtg ataatttcag gaaacaaaaa tttgtgctat    480

gcaaatacaa taaactggaa aaaactgttt gggacctccg gtcagaaaac caaaattata    540

agcaacagag gtgaaaacag ctgcaaggcc acaggccagg cctgccacca gctgtgcgcc    600

cgagggcact gctggggtcc agggcccacc cagtgtgtca actgcagcca gttccttcgg    660

ggccaggagt gcgtggagga atgccgagta ctgcaggggc tccccaggga gtatgtgaat    720

gccaggcact gtttgccgtg ccaccctgag tgtcagcccc agaatggctc agtgacctgt    780

tttggaccgg aggctgacca gtgtgtggcc tgtgcccact ataaggaccc tcccttctgc    840

gtggcccgct gccccagcgg tgtgaaacct gacctctcct acatgcccat ctggaagttt    900

ccagatgagg agggcgcatg ccagccttgc cccatcaact gcacccactc ctgtgtggac    960

ctggatgaca agggctgccc cgccgagcag agagccagcc ctctgacgtc catcatctct   1020

gcggtggttg gcattctgct ggtcgtggtc ttgggggtgg tctttgggat cctcatc      1077


<210> SEQ ID NO 87
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
```

-continued

```
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Ala Cys His Gln Leu Cys Ala Arg Gly His Cys Trp Gly Pro Gly
        195                 200                 205

Pro Thr Gln Cys Val Asn Cys Ser Gln Phe Leu Arg Gly Gln Glu Cys
    210                 215                 220

Val Glu Glu Cys Arg Val Leu Gln Gly Leu Pro Arg Glu Tyr Val Asn
225                 230                 235                 240

Ala Arg His Cys Leu Pro Cys His Pro Glu Cys Gln Pro Gln Asn Gly
                245                 250                 255

Ser Val Thr Cys Phe Gly Pro Glu Ala Asp Gln Cys Val Ala Cys Ala
            260                 265                 270

His Tyr Lys Asp Pro Pro Phe Cys Val Ala Arg Cys Pro Ser Gly Val
        275                 280                 285

Lys Pro Asp Leu Ser Tyr Met Pro Ile Trp Lys Phe Pro Asp Glu Glu
    290                 295                 300

Gly Ala Cys Gln Pro Cys Pro Ile Asn Cys Thr His Ser Cys Val Asp
305                 310                 315                 320

Leu Asp Asp Lys Gly Cys Pro Ala Glu Gln Arg Ala Ser Pro Leu Thr
                325                 330                 335

Ser Ile Ile Ser Ala Val Val Gly Ile Leu Leu Val Val Val Leu Gly
            340                 345                 350

Val Val Phe Gly Ile Leu Ile
        355
```

<210> SEQ ID NO 88
<211> LENGTH: 1011
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

```
cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480
```

```
agaggtgaaa acagctgcaa ggccacaggc caggcctgcc accagctgtg cgcccgaggg    540

cactgctggg gtccagggcc cacccagtgt gtcaactgca gccagttcct tcggggccag    600

gagtgcgtgg aggaatgccg agtactgcag ggctccccca gggagtatgt gaatgccagg    660

cactgtttgc cgtgccaccc tgagtgtcag ccccagaatg gctcagtgac ctgttttgga    720

ccggaggctg accagtgtgt ggcctgtgcc cactataagg accctccctt ctgcgtggcc    780

cgctgcccca gcggtgtgaa acctgacctc tcctacatgc ccatctggaa gtttccagat    840

gaggagggcg catgccagcc ttgccccatc aactgcaccc actcctgtgt ggacctggat    900

gacaagggct gccccgccga gcagagagcc agccctctga cgtccatcat ctctgcggtg    960

gttggcattc tgctggtcgt ggtcttgggg gtggtctttg ggatcctcat c            1011


<210> SEQ ID NO 89
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Ala Cys His Gln Leu
                165                 170                 175

Cys Ala Arg Gly His Cys Trp Gly Pro Gly Pro Thr Gln Cys Val Asn
            180                 185                 190

Cys Ser Gln Phe Leu Arg Gly Gln Glu Cys Val Glu Glu Cys Arg Val
        195                 200                 205

Leu Gln Gly Leu Pro Arg Glu Tyr Val Asn Ala Arg His Cys Leu Pro
    210                 215                 220

Cys His Pro Glu Cys Gln Pro Gln Asn Gly Ser Val Thr Cys Phe Gly
225                 230                 235                 240

Pro Glu Ala Asp Gln Cys Val Ala Cys Ala His Tyr Lys Asp Pro Pro
                245                 250                 255

Phe Cys Val Ala Arg Cys Pro Ser Gly Val Lys Pro Asp Leu Ser Tyr
```

-continued

```
            260                 265                 270

Met Pro Ile Trp Lys Phe Pro Asp Glu Glu Gly Ala Cys Gln Pro Cys
        275                 280                 285

Pro Ile Asn Cys Thr His Ser Cys Val Asp Leu Asp Asp Lys Gly Cys
    290                 295                 300

Pro Ala Glu Gln Arg Ala Ser Pro Leu Thr Ser Ile Ile Ser Ala Val
305                 310                 315                 320

Val Gly Ile Leu Leu Val Val Val Leu Gly Val Val Phe Gly Ile Leu
                325                 330                 335

Ile


<210> SEQ ID NO 90
<211> LENGTH: 1029
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

atgcttctcc tggtgacaag ccttctgctc tgtgagttac cacacccagc attcctcctg      60

atcccacgca aagtgtgtaa cggaataggt attggtgaat ttaaagactc actctccata     120

aatgctacga atattaaaca cttcaaaaac tgcacctcca tcagtggcga tctccacatc     180

ctgccggtgg catttagggg tgactccttc acacatactc ctcctctgga tccacaggaa     240

ctggatattc tgaaaaccgt aaaggaaatc acagggtttt tgctgattca ggcttggcct     300

gaaaacagga cggacctcca tgcctttgag aacctagaaa tcatacgcgg caggaccaag     360

caacatggtc agttttctct tgcagtcgtc agcctgaaca taacatcctt gggattacgc     420

tccctcaagg agataagtga tggagatgtg ataatttcag gaaacaaaaa tttgtgctat     480

gcaaatacaa taaactggaa aaaactgttt gggacctccg gtcagaaaac caaaattata     540

agcaacagag gtgaaaacag ctgcaaggcc acaggccagg cctgccacca gctgtgcgcc     600

cgagggcact gctggggtcc agggcccacc cagtgtgtca actgcagcca gttccttcgg     660

ggccaggagt gcgtggagga atgccgagta ctgcaggggc tccccaggga gtatgtgaat     720

gccaggcact gtttgccgtg ccaccctgag tgtcagcccc agaatggctc agtgacctgt     780

tttggaccgg aggctgacca gtgtgtggcc tgtgcccact ataaggaccc tcccttctgc     840

gtggcccgct gccccagcgg tgtgaaacct gacctctcct acatgcccat ctggaagttt     900

ccagatgagg agggcgcatg ccagccttgc cccatcaact gcacccactc ccctctgacg     960

tccatcatct ctgcggtggt tggcattctg ctggtcgtgg tcttgggggt ggtctttggg    1020

atcctcatc                                                            1029


<210> SEQ ID NO 91
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30
```

```
Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Ala Cys His Gln Leu Cys Ala Arg Gly His Cys Trp Gly Pro Gly
        195                 200                 205

Pro Thr Gln Cys Val Asn Cys Ser Gln Phe Leu Arg Gly Gln Glu Cys
    210                 215                 220

Val Glu Glu Cys Arg Val Leu Gln Gly Leu Pro Arg Glu Tyr Val Asn
225                 230                 235                 240

Ala Arg His Cys Leu Pro Cys His Pro Glu Cys Gln Pro Gln Asn Gly
                245                 250                 255

Ser Val Thr Cys Phe Gly Pro Glu Ala Asp Gln Cys Val Ala Cys Ala
            260                 265                 270

His Tyr Lys Asp Pro Pro Phe Cys Val Ala Arg Cys Pro Ser Gly Val
        275                 280                 285

Lys Pro Asp Leu Ser Tyr Met Pro Ile Trp Lys Phe Pro Asp Glu Glu
    290                 295                 300

Gly Ala Cys Gln Pro Cys Pro Ile Asn Cys Thr His Ser Pro Leu Thr
305                 310                 315                 320

Ser Ile Ile Ser Ala Val Val Gly Ile Leu Leu Val Val Val Leu Gly
                325                 330                 335

Val Val Phe Gly Ile Leu Ile
            340
```

<210> SEQ ID NO 92
<211> LENGTH: 963
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240
```

```
aggacggacc tccatgcctt tgagaaccta gaaatcatac gcggcaggac caagcaacat    300

ggtcagtttt ctcttgcagt cgtcagcctg aacataacat ccttgggatt acgctccctc    360

aaggagataa gtgatggaga tgtgataatt tcaggaaaca aaaatttgtg ctatgcaaat    420

acaataaact ggaaaaaact gtttgggacc tccggtcaga aaaccaaaat tataagcaac    480

agaggtgaaa acagctgcaa ggccacaggc caggcctgcc accagctgtg cgcccgaggg    540

cactgctggg gtccagggcc cacccagtgt gtcaactgca gccagttcct tcggggccag    600

gagtgcgtgg aggaatgccg agtactgcag gggctcccca gggagtatgt gaatgccagg    660

cactgtttgc cgtgccaccc tgagtgtcag ccccagaatg gctcagtgac ctgttttgga    720

ccggaggctg accagtgtgt ggcctgtgcc cactataagg accctccctt ctgcgtggcc    780

cgctgcccca gcggtgtgaa acctgacctc tcctacatgc ccatctggaa gtttccagat    840

gaggagggcg catgccagcc ttgccccatc aactgcaccc actcccctct gacgtccatc    900

atctctgcgg tggttggcat tctgctggtc gtggtcttgg gggtggtctt tgggatcctc    960

atc                                                                963
```

<210> SEQ ID NO 93
<211> LENGTH: 321
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Ala Cys His Gln Leu
                165                 170                 175

Cys Ala Arg Gly His Cys Trp Gly Pro Gly Pro Thr Gln Cys Val Asn
            180                 185                 190

Cys Ser Gln Phe Leu Arg Gly Gln Glu Cys Val Glu Glu Cys Arg Val
        195                 200                 205

Leu Gln Gly Leu Pro Arg Glu Tyr Val Asn Ala Arg His Cys Leu Pro
    210                 215                 220
```

```
Cys His Pro Glu Cys Gln Pro Gln Asn Gly Ser Val Thr Cys Phe Gly
225                 230                 235                 240

Pro Glu Ala Asp Gln Cys Val Ala Cys Ala His Tyr Lys Asp Pro Pro
                245                 250                 255

Phe Cys Val Ala Arg Cys Pro Ser Gly Val Lys Pro Asp Leu Ser Tyr
            260                 265                 270

Met Pro Ile Trp Lys Phe Pro Asp Glu Glu Gly Ala Cys Gln Pro Cys
        275                 280                 285

Pro Ile Asn Cys Thr His Ser Pro Leu Thr Ser Ile Ile Ser Ala Val
    290                 295                 300

Val Gly Ile Leu Leu Val Val Val Leu Gly Val Val Phe Gly Ile Leu
305                 310                 315                 320

Ile
```

<210> SEQ ID NO 94
<211> LENGTH: 1080
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94

```
atgcttctcc tggtgacaag ccttctgctc tgtgagttac cacacccagc attcctcctg     60

atcccacgca aagtgtgtaa cggaataggt attggtgaat ttaaagactc actctccata    120

aatgctacga atattaaaca cttcaaaaac tgcacctcca tcagtggcga tctccacatc    180

ctgccggtgg catttagggg tgactccttc acacatactc ctcctctgga tccacaggaa    240

ctggatattc tgaaaaccgt aaaggaaatc acagggtttt tgctgattca ggcttggcct    300

gaaaacagga cggacctcca tgcctttgag aacctagaaa tcatacgcgg caggaccaag    360

caacatggtc agttttctct tgcagtcgtc agcctgaaca taacatcctt gggattacgc    420

tccctcaagg agataagtga tggagatgtg ataatttcag gaaacaaaaa tttgtgctat    480

gcaaatacaa taaactggaa aaaactgttt gggacctccg gtcagaaaac caaaattata    540

agcaacagag gtgaaaacag ctgcaaggcc acaggccagg tgtgtgaccc actgtgctcc    600

tctgggggat gctggggccc aggccctggt cagtgcttgt cctgtcgaaa ttatagccga    660

ggaggtgtct gtgtgaccca ctgcaacttt ctgaatgggg agcctcgaga atttgcccat    720

gaggccgaat gcttctcctg ccacccggaa tgccaaccca tggagggcac tgccacatgc    780

aatggctcgg gctctgatac ttgtgctcaa tgtgcccatt ttcgagatgg gccccactgt    840

gtgagcagct gcccccatgg agtcctaggt gccaagggcc caatctacaa gtacccagat    900

gttcagaatg aatgtcggcc ctgccatgag aactgcaccc aggggtgtaa aggaccagag    960

cttcaagact gtttaggaca aacactggtg ctgatcggca aaacccatct gacaatggct   1020

ttgacagtga tagcaggatt ggtagtgatt ttcatgatgc tgggcggcac ttttctctac   1080
```

<210> SEQ ID NO 95
<211> LENGTH: 360
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

-continued

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys Asp Pro Leu Cys Ser Ser Gly Gly Cys Trp Gly Pro Gly
        195                 200                 205

Pro Gly Gln Cys Leu Ser Cys Arg Asn Tyr Ser Arg Gly Gly Val Cys
    210                 215                 220

Val Thr His Cys Asn Phe Leu Asn Gly Glu Pro Arg Glu Phe Ala His
225                 230                 235                 240

Glu Ala Glu Cys Phe Ser Cys His Pro Glu Cys Gln Pro Met Glu Gly
                245                 250                 255

Thr Ala Thr Cys Asn Gly Ser Gly Ser Asp Thr Cys Ala Gln Cys Ala
            260                 265                 270

His Phe Arg Asp Gly Pro His Cys Val Ser Ser Cys Pro His Gly Val
        275                 280                 285

Leu Gly Ala Lys Gly Pro Ile Tyr Lys Tyr Pro Asp Val Gln Asn Glu
    290                 295                 300

Cys Arg Pro Cys His Glu Asn Cys Thr Gln Gly Cys Lys Gly Pro Glu
305                 310                 315                 320

Leu Gln Asp Cys Leu Gly Gln Thr Leu Val Leu Ile Gly Lys Thr His
                325                 330                 335

Leu Thr Met Ala Leu Thr Val Ile Ala Gly Leu Val Val Ile Phe Met
            340                 345                 350

Met Leu Gly Gly Thr Phe Leu Tyr
        355                 360
```

<210> SEQ ID NO 96
<211> LENGTH: 1014
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 96

-continued

```
cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc caggtgtgtg acccactgtg ctcctctggg     540

ggatgctggg gcccaggccc tggtcagtgc ttgtcctgtc gaaattatag ccgaggaggt     600

gtctgtgtga cccactgcaa ctttctgaat ggggagcctc gagaatttgc ccatgaggcc     660

gaatgcttct cctgccaccc ggaatgccaa cccatggagg gcactgccac atgcaatggc     720

tcgggctctg atacttgtgc tcaatgtgcc cattttcgag atgggcccca ctgtgtgagc     780

agctgccccc atggagtcct aggtgccaag ggcccaatct acaagtaccc agatgttcag     840

aatgaatgtc ggccctgcca tgagaactgc acccaggggt gtaaaggacc agagcttcaa     900

gactgtttag gacaaacact ggtgctgatc ggcaaaaccc atctgacaat ggctttgaca     960

gtgatagcag gattggtagt gattttcatg atgctgggcg gcacttttct ctac          1014
```

<210> SEQ ID NO 97
<211> LENGTH: 338
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys Asp Pro Leu
                165                 170                 175
```

```
Cys Ser Ser Gly Gly Cys Trp Gly Pro Gly Pro Gly Gln Cys Leu Ser
            180                 185                 190

Cys Arg Asn Tyr Ser Arg Gly Gly Val Cys Val Thr His Cys Asn Phe
        195                 200                 205

Leu Asn Gly Glu Pro Arg Glu Phe Ala His Glu Ala Glu Cys Phe Ser
    210                 215                 220

Cys His Pro Glu Cys Gln Pro Met Glu Gly Thr Ala Thr Cys Asn Gly
225                 230                 235                 240

Ser Gly Ser Asp Thr Cys Ala Gln Cys Ala His Phe Arg Asp Gly Pro
                245                 250                 255

His Cys Val Ser Ser Cys Pro His Gly Val Leu Gly Ala Lys Gly Pro
            260                 265                 270

Ile Tyr Lys Tyr Pro Asp Val Gln Asn Glu Cys Arg Pro Cys His Glu
        275                 280                 285

Asn Cys Thr Gln Gly Cys Lys Gly Pro Glu Leu Gln Asp Cys Leu Gly
    290                 295                 300

Gln Thr Leu Val Leu Ile Gly Lys Thr His Leu Thr Met Ala Leu Thr
305                 310                 315                 320

Val Ile Ala Gly Leu Val Val Ile Phe Met Met Leu Gly Gly Thr Phe
                325                 330                 335

Leu Tyr
```

<210> SEQ ID NO 98
<211> LENGTH: 1101
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
atgcttctcc tggtgacaag ccttctgctc tgtgagttac cacacccagc attcctcctg     60

atcccacgca aagtgtgtaa cggaataggt attggtgaat ttaaagactc actctccata    120

aatgctacga atattaaaca cttcaaaaac tgcacctcca tcagtggcga tctccacatc    180

ctgccggtgg catttagggg tgactccttc acacatactc ctcctctgga tccacaggaa    240

ctggatattc tgaaaaccgt aaaggaaatc acagggtttt tgctgattca ggcttggcct    300

gaaaacagga cggacctcca tgcctttgag aacctagaaa tcatacgcgg caggaccaag    360

caacatggtc agttttctct tgcagtcgtc agcctgaaca taacatcctt gggattacgc    420

tccctcaagg agataagtga tggagatgtg ataatttcag gaaacaaaaa tttgtgctat    480

gcaaatacaa taaactggaa aaaactgttt gggacctccg gtcagaaaac caaaattata    540

agcaacagag gtgaaaacag ctgcaaggcc acaggccagg tgtgcaacca tctgtgttcc    600

agtgatggct gttggggacc tgggccagac caatgtctgt cgtgtcgccg cttcagtaga    660

ggaaggatct gcatagagtc ttgtaacctc tatgatggtg aatttcggga gtttgagaat    720

ggctccatct gtgtggagtg tgacccccag tgtgagaaga tggaagatgg cctcctcaca    780

tgccatggac cgggtcctga caactgtaca aagtgctctc attttaaaga tggcccaaac    840

tgtgtggaaa aatgtccaga tggcttacag gggcaaaca gtttcatttt caagtatgct     900

gatccagatc gggagtgcca cccatgccat ccaaactgca cccaagggtg taacggtccc    960

actagtcatg actgcattta ctacccatgg acgggccatt ccactttacc acaacatgct   1020

agaactcccc tgattgcagc tggagtaatt ggtgggctct tcattctggt cattgtgggt   1080
```

ctgacatttg ctgtttatgt t 1101

<210> SEQ ID NO 99
<211> LENGTH: 367
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 99

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys Asn His Leu Cys Ser Ser Asp Gly Cys Trp Gly Pro Gly
        195                 200                 205

Pro Asp Gln Cys Leu Ser Cys Arg Arg Phe Ser Arg Gly Arg Ile Cys
    210                 215                 220

Ile Glu Ser Cys Asn Leu Tyr Asp Gly Glu Phe Arg Glu Phe Glu Asn
225                 230                 235                 240

Gly Ser Ile Cys Val Glu Cys Asp Pro Gln Cys Glu Lys Met Glu Asp
                245                 250                 255

Gly Leu Leu Thr Cys His Gly Pro Gly Pro Asp Asn Cys Thr Lys Cys
            260                 265                 270

Ser His Phe Lys Asp Gly Pro Asn Cys Val Glu Lys Cys Pro Asp Gly
        275                 280                 285

Leu Gln Gly Ala Asn Ser Phe Ile Phe Lys Tyr Ala Asp Pro Asp Arg
    290                 295                 300

Glu Cys His Pro Cys His Pro Asn Cys Thr Gln Gly Cys Asn Gly Pro
305                 310                 315                 320

Thr Ser His Asp Cys Ile Tyr Tyr Pro Trp Thr Gly His Ser Thr Leu
                325                 330                 335

Pro Gln His Ala Arg Thr Pro Leu Ile Ala Ala Gly Val Ile Gly Gly
            340                 345                 350
```

Leu Phe Ile Leu Val Ile Val Gly Leu Thr Phe Ala Val Tyr Val
355 360 365

<210> SEQ ID NO 100
<211> LENGTH: 1035
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300
ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420
acaataaact ggaaaaaact gtttgggacc tccggtcaga aaaccaaaat tataagcaac 480
agaggtgaaa acagctgcaa ggccacaggc caggtgtgca accatctgtg ttccagtgat 540
ggctgttggg gacctgggcc agaccaatgt ctgtcgtgtc gccgcttcag tagaggaagg 600
atctgcatag agtcttgtaa cctctatgat ggtgaatttc gggagtttga gaatggctcc 660
atctgtgtgg agtgtgaccc ccagtgtgag aagatggaag atggcctcct cacatgccat 720
ggaccgggtc ctgacaactg tacaaagtgc tctcatttta aagatggccc aaactgtgtg 780
gaaaaatgtc cagatggctt acagggggca aacagtttca ttttcaagta tgctgatcca 840
gatcgggagt gccacccatg ccatccaaac tgcacccaag ggtgtaacgg tcccactagt 900
catgactgca tttactaccc atggacgggc cattccactt taccacaaca tgctagaact 960
cccctgattg cagctggagt aattggtggg ctcttcattc tggtcattgt gggtctgaca 1020
tttgctgttt atgtt 1035

<210> SEQ ID NO 101
<211> LENGTH: 345
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

-continued

```
Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys Asn His Leu
                165                 170                 175

Cys Ser Ser Asp Gly Cys Trp Gly Pro Gly Pro Asp Gln Cys Leu Ser
            180                 185                 190

Cys Arg Arg Phe Ser Arg Gly Arg Ile Cys Ile Glu Ser Cys Asn Leu
        195                 200                 205

Tyr Asp Gly Glu Phe Arg Glu Phe Glu Asn Gly Ser Ile Cys Val Glu
    210                 215                 220

Cys Asp Pro Gln Cys Glu Lys Met Glu Asp Gly Leu Leu Thr Cys His
225                 230                 235                 240

Gly Pro Gly Pro Asp Asn Cys Thr Lys Cys Ser His Phe Lys Asp Gly
                245                 250                 255

Pro Asn Cys Val Glu Lys Cys Pro Asp Gly Leu Gln Gly Ala Asn Ser
            260                 265                 270

Phe Ile Phe Lys Tyr Ala Asp Pro Asp Arg Glu Cys His Pro Cys His
        275                 280                 285

Pro Asn Cys Thr Gln Gly Cys Asn Gly Pro Thr Ser His Asp Cys Ile
    290                 295                 300

Tyr Tyr Pro Trp Thr Gly His Ser Thr Leu Pro Gln His Ala Arg Thr
305                 310                 315                 320

Pro Leu Ile Ala Ala Gly Val Ile Gly Gly Leu Phe Ile Leu Val Ile
                325                 330                 335

Val Gly Leu Thr Phe Ala Val Tyr Val
            340                 345
```

<210> SEQ ID NO 102
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
atgcttctcc tggtgacaag ccttctgctc tgtgagttac cacacccagc attcctcctg      60

atcccacgca aagtgtgtaa cggaataggt attggtgaat ttaaagactc actctccata     120

aatgctacga atattaaaca cttcaaaaac tgcacctcca tcagtggcga tctccacatc     180

ctgccggtgg catttagggg tgactccttc acacatactc ctcctctgga tccacaggaa     240

ctggatattc tgaaaaccgt aaaggaaatc acagggtttt tgctgattca ggcttggcct     300

gaaaacagga cggacctcca tgcctttgag aacctagaaa tcatacgcgg caggaccaag     360

caacatggtc agttttctct tgcagtcgtc agcctgaaca taacatcctt gggattacgc     420

tccctcaagg agataagtga tggagatgtg ataatttcag gaaacaaaaa tttgtgctat     480

gcaaatacaa taaactggaa aaaactgttt gggacctccg gtcagaaaac caaaattata     540

agcaacagag gtgaaaacag ctgcaaggcc acaggccagg tgtgcaacca tctgtgttcc     600
```

agtgatggct gttggggacc tgggccagac caatgtctgt cgtgtcgccg cttcagtaga 660
ggaaggatct gcatagagtc ttgtaacctc tatgatggtg aatttcggga gtttgagaat 720
ggctccatct gtgtggagtg tgacccccag tgtgagaaga tggaagatgg cctcctcaca 780
tgccatggac cgggtcctga caactgtaca aagtgctctc attttaaaga tggcccaaac 840
tgtgtggaaa aatgtccaga tggcttacag gggcaaaca gtttcatttt caagtatgct 900
gatccagatc gggagtgcca cccatgccat ccaaactgca cccaagggtg cataggctca 960
agtattgaag actgcatcgg cctgatggat agaactcccc tgattgcagc tggagtaatt 1020
ggtgggctct tcattctggt cattgtgggt ctgacatttg ctgtttatgt t 1071

<210> SEQ ID NO 103
<211> LENGTH: 357
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

Met Leu Leu Leu Val Thr Ser Leu Leu Leu Cys Glu Leu Pro His Pro
1 5 10 15

Ala Phe Leu Leu Ile Pro Arg Lys Val Cys Asn Gly Ile Gly Ile Gly
20 25 30

Glu Phe Lys Asp Ser Leu Ser Ile Asn Ala Thr Asn Ile Lys His Phe
35 40 45

Lys Asn Cys Thr Ser Ile Ser Gly Asp Leu His Ile Leu Pro Val Ala
50 55 60

Phe Arg Gly Asp Ser Phe Thr His Thr Pro Pro Leu Asp Pro Gln Glu
65 70 75 80

Leu Asp Ile Leu Lys Thr Val Lys Glu Ile Thr Gly Phe Leu Leu Ile
85 90 95

Gln Ala Trp Pro Glu Asn Arg Thr Asp Leu His Ala Phe Glu Asn Leu
100 105 110

Glu Ile Ile Arg Gly Arg Thr Lys Gln His Gly Gln Phe Ser Leu Ala
115 120 125

Val Val Ser Leu Asn Ile Thr Ser Leu Gly Leu Arg Ser Leu Lys Glu
130 135 140

Ile Ser Asp Gly Asp Val Ile Ile Ser Gly Asn Lys Asn Leu Cys Tyr
145 150 155 160

Ala Asn Thr Ile Asn Trp Lys Lys Leu Phe Gly Thr Ser Gly Gln Lys
165 170 175

Thr Lys Ile Ile Ser Asn Arg Gly Glu Asn Ser Cys Lys Ala Thr Gly
180 185 190

Gln Val Cys Asn His Leu Cys Ser Ser Asp Gly Cys Trp Gly Pro Gly
195 200 205

Pro Asp Gln Cys Leu Ser Cys Arg Arg Phe Ser Arg Gly Arg Ile Cys
210 215 220

Ile Glu Ser Cys Asn Leu Tyr Asp Gly Glu Phe Arg Glu Phe Glu Asn
225 230 235 240

Gly Ser Ile Cys Val Glu Cys Asp Pro Gln Cys Glu Lys Met Glu Asp
245 250 255

Gly Leu Leu Thr Cys His Gly Pro Gly Pro Asp Asn Cys Thr Lys Cys
260 265 270

Ser His Phe Lys Asp Gly Pro Asn Cys Val Glu Lys Cys Pro Asp Gly

```
        275                 280                 285

Leu Gln Gly Ala Asn Ser Phe Ile Phe Lys Tyr Ala Asp Pro Asp Arg
    290                 295                 300

Glu Cys His Pro Cys His Pro Asn Cys Thr Gln Gly Cys Ile Gly Ser
305                 310                 315                 320

Ser Ile Glu Asp Cys Ile Gly Leu Met Asp Arg Thr Pro Leu Ile Ala
                325                 330                 335

Ala Gly Val Ile Gly Gly Leu Phe Ile Leu Val Ile Val Gly Leu Thr
            340                 345                 350

Phe Ala Val Tyr Val
        355
```

<210> SEQ ID NO 104
<211> LENGTH: 1005
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 104

```
cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc caggtgtgca accatctgtg ttccagtgat     540

ggctgttggg gacctgggcc agaccaatgt ctgtcgtgtc gccgcttcag tagaggaagg     600

atctgcatag agtcttgtaa cctctatgat ggtgaatttc gggagtttga gaatggctcc     660

atctgtgtgg agtgtgaccc ccagtgtgag aagatggaag atggcctcct cacatgccat     720

ggaccgggtc ctgacaactg tacaaagtgc tctcatttta aagatggccc aaactgtgtg     780

gaaaaatgtc cagatggctt acagggggca aacagtttca ttttcaagta tgctgatcca     840

gatcgggagt gccacccatg ccatccaaac tgcacccaag ggtgcatagg ctcaagtatt     900

gaagactgca tcggcctgat ggatagaact cccctgattg cagctggagt aattggtggg     960

ctcttcattc tggtcattgt gggtctgaca tttgctgttt atgtt                    1005
```

<210> SEQ ID NO 105
<211> LENGTH: 335
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30
```

```
Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys Asn His Leu
                165                 170                 175

Cys Ser Ser Asp Gly Cys Trp Gly Pro Gly Pro Asp Gln Cys Leu Ser
            180                 185                 190

Cys Arg Arg Phe Ser Arg Gly Arg Ile Cys Ile Glu Ser Cys Asn Leu
        195                 200                 205

Tyr Asp Gly Glu Phe Arg Glu Phe Glu Asn Gly Ser Ile Cys Val Glu
    210                 215                 220

Cys Asp Pro Gln Cys Glu Lys Met Glu Asp Gly Leu Leu Thr Cys His
225                 230                 235                 240

Gly Pro Gly Pro Asp Asn Cys Thr Lys Cys Ser His Phe Lys Asp Gly
                245                 250                 255

Pro Asn Cys Val Glu Lys Cys Pro Asp Gly Leu Gln Gly Ala Asn Ser
            260                 265                 270

Phe Ile Phe Lys Tyr Ala Asp Pro Asp Arg Glu Cys His Pro Cys His
        275                 280                 285

Pro Asn Cys Thr Gln Gly Cys Ile Gly Ser Ser Ile Glu Asp Cys Ile
    290                 295                 300

Gly Leu Met Asp Arg Thr Pro Leu Ile Ala Ala Gly Val Ile Gly Gly
305                 310                 315                 320

Leu Phe Ile Leu Val Ile Val Gly Leu Thr Phe Ala Val Tyr Val
                325                 330                 335


<210> SEQ ID NO 106
<211> LENGTH: 891
<212> TYPE: DNA
<213> ORGANISM: Unknown
<220> FEATURE:
<223> OTHER INFORMATION: Description of Unknown:
      Full length CD20 sequence

<400> SEQUENCE: 106

atgacaacac ccagaaattc agtaaatggg actttcccgg cagagccaat gaaaggccct      60

attgctatgc aatctggtcc aaaaccactc ttcaggagga tgtcttcact ggtgggcccc     120

acgcaaagct tcttcatgag ggaatctaag actttggggg ctgtccagat tatgaatggg     180

ctcttccaca ttgccctggg gggtcttctg atgatcccag cagggatcta tgcacccatc     240

tgtgtgactg tgtggtaccc tctctgggga ggcattatgt atattatttc cggatcactc     300

ctggcagcaa cggagaaaaa ctccaggaag tgtttggtca aaggaaaaat gataatgaat     360
```

```
tcattgagcc tctttgctgc catttctgga atgattcttt caatcatgga catacttaat    420

attaaaattt cccatttttt aaaaatggag agtctgaatt ttattagagc tcacacacca    480

tatattaaca tatacaactg tgaaccagct aatccctctg agaaaaactc cccatctacc    540

caatactgtt acagcataca atctctgttc ttgggcattt tgtcagtgat gctgatcttt    600

gccttcttcc aggaacttgt aatagctggc atcgttgaga atgaatggaa aagaacgtgc    660

tccagaccca aatctaacat agttctcctg tcagcagaag aaaaaaaaga acagactatt    720

gaaataaaag aagaagtggt tggcctaact gaaacatctt cccaaccaaa gaatgaagaa    780

gacattgaaa ttattccaat ccaagaagag gaagaagaag aaacagagac gaactttcca    840

gaacctcccc aagatcagga atcctcacca atagaaaatg acagctctcc t             891
```

```
<210> SEQ ID NO 107
<211> LENGTH: 297
<212> TYPE: PRT
<213> ORGANISM: Unknown
<220> FEATURE:
<223> OTHER INFORMATION: Description of Unknown:
      Full length CD20 sequence

<400> SEQUENCE: 107

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
```

260 265 270

Glu Glu Thr Glu Thr Asn Phe Pro Glu Pro Pro Gln Asp Gln Glu Ser
275 280 285

Ser Pro Ile Glu Asn Asp Ser Ser Pro
290 295

<210> SEQ ID NO 108
<211> LENGTH: 789
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108
atgaccacac cacggaactc tgtgaatggc accttcccag cagagccaat gaagggacca 60
atcgcaatgc agagcggacc caagcctctg tttcggagaa tgagctccct ggtgggccca 120
acccagtcct tctttatgag agagtctaag acactgggcg ccgtgcagat catgaacgga 180
ctgttccaca tcgccctggg aggactgctg atgatcccag ccggcatcta cgcccctatc 240
tgcgtgaccg tgtggtaccc tctgtggggc ggcatcatgt atatcatctc cggctctctg 300
ctggccgcca cagagaagaa cagcaggaag tgtctggtga agggcaagat gatcatgaat 360
agcctgtccc tgtttgccgc catctctggc atgatcctga gcatcatgga catcctgaac 420
atcaagatca gccacttcct gaagatggag agcctgaact tcatcagagc ccacacccct 480
tacatcaaca tctataattg cgagcctgcc aacccatccg agaagaattc tccaagcaca 540
cagtactgtt attccatcca gtctctgttc ctgggcatcc tgtctgtgat gctgatcttt 600
gccttctttc aggagctggt catcgccggc atcgtggaga acgagtggaa gaggacctgc 660
agccgcccca agtccaatat cgtgctgctg tccgccgagg agaagaagga gcagacaatc 720
gagatcaagg aggaggtggt gggcctgacc gagacatcta gccagcctaa gaatgaggag 780
gatatcgag 789

<210> SEQ ID NO 109
<211> LENGTH: 263
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Met Thr Thr Pro Arg Asn Ser Val Asn Gly Thr Phe Pro Ala Glu Pro
1 5 10 15

Met Lys Gly Pro Ile Ala Met Gln Ser Gly Pro Lys Pro Leu Phe Arg
20 25 30

Arg Met Ser Ser Leu Val Gly Pro Thr Gln Ser Phe Phe Met Arg Glu
35 40 45

Ser Lys Thr Leu Gly Ala Val Gln Ile Met Asn Gly Leu Phe His Ile
50 55 60

Ala Leu Gly Gly Leu Leu Met Ile Pro Ala Gly Ile Tyr Ala Pro Ile
65 70 75 80

Cys Val Thr Val Trp Tyr Pro Leu Trp Gly Gly Ile Met Tyr Ile Ile
85 90 95

Ser Gly Ser Leu Leu Ala Ala Thr Glu Lys Asn Ser Arg Lys Cys Leu
100 105 110

-continued

```
Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu
            260
```

<210> SEQ ID NO 110
<211> LENGTH: 294
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110

```
atgataatga attcattgag cctctttgct gccatttctg gaatgattct ttcaatcatg      60

gacatactta atattaaaat ttcccatttt ttaaaaatgg agagtctgaa ttttattaga     120

gctcacacac catatattaa catatacaac tgtgaaccag ctaatccctc tgagaaaaac     180

tccccatcta cccaatactg ttacagcata caatctctgt tcttgggcat tttgtcagtg     240

atgctgatct ttgccttctt ccaggaactt gtaatagctg gcatcgttga gaat           294
```

<210> SEQ ID NO 111
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Met Ile Met Asn Ser Leu Ser Leu Phe Ala Ala Ile Ser Gly Met Ile
1               5                   10                  15

Leu Ser Ile Met Asp Ile Leu Asn Ile Lys Ile Ser His Phe Leu Lys
            20                  25                  30

Met Glu Ser Leu Asn Phe Ile Arg Ala His Thr Pro Tyr Ile Asn Ile
        35                  40                  45

Tyr Asn Cys Glu Pro Ala Asn Pro Ser Glu Lys Asn Ser Pro Ser Thr
    50                  55                  60

Gln Tyr Cys Tyr Ser Ile Gln Ser Leu Phe Leu Gly Ile Leu Ser Val
65                  70                  75                  80

Met Leu Ile Phe Ala Phe Phe Gln Glu Leu Val Ile Ala Gly Ile Val
                85                  90                  95
```

Glu Asn

<210> SEQ ID NO 112
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
atggccttac cagtgaccgc cttgctcctg ccgctggcct tgctgctcca cgccgccagg     60
ccgaaaattt cccatttttt aaaaatggag agtctgaatt ttattagagc tcacacacca    120
tatattaaca tatacaactg tgaaccagct aatccctctg agaaaaactc cccatctacc    180
caatactgtt acagcataca atctatctac atctgggcgc ccttggccgg gacttgtggg    240
gtccttctcc tgtcactggt tatcacc                                        267

<210> SEQ ID NO 113
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Ala Leu Pro Val Thr Ala Leu Leu Leu Pro Leu Ala Leu Leu Leu
1               5                   10                  15

His Ala Ala Arg Pro Lys Ile Ser His Phe Leu Lys Met Glu Ser Leu
            20                  25                  30

Asn Phe Ile Arg Ala His Thr Pro Tyr Ile Asn Ile Tyr Asn Cys Glu
        35                  40                  45

Pro Ala Asn Pro Ser Glu Lys Asn Ser Pro Ser Thr Gln Tyr Cys Tyr
    50                  55                  60

Ser Ile Gln Ser Ile Tyr Ile Trp Ala Pro Leu Ala Gly Thr Cys Gly
65                  70                  75                  80

Val Leu Leu Leu Ser Leu Val Ile Thr
                85

<210> SEQ ID NO 114
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
atgacaacac ccagaaattc agtaaatggg actttcccgg cagagccaat gaaaggccct     60
attgctatgc aatctggtcc aaaaccactc ttcaggagga tgtcttcact ggtgggcccc    120
acgcaaagct tcttcatgag ggaatctaag actttggggg ctgtccagat tatgaatggg    180
ctcttccaca ttgccctggg gggtcttctg atgatcccag cagggatcta tgcacccatc    240
tgtgtgactg tgtggtaccc tctctgggga ggcattatgt atattatttc cggatcactc    300
ctggcagcaa cggagaaaaa ctccaggaag tgtttggtca aaggaaaaat gataatgaat    360
tcattgagcc tctttgctgc catttctgga atgattcttt caatcatgga catacttaat    420
attaaaattt cccatttttt aaaaatggag agtctgaatt ttattagagc tcacacacca    480
tatattaaca tatacaactg tgaaccagct aatccctctg agaaaaactc cccatctacc 540
caatactgtt acagcataca atctctgttc ttgggcattt tgtcagtgat gctgatcttt 600
gccttcttcc aggaacttgt aatagctggc atcgttgaga at 642

<210> SEQ ID NO 115
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

Met Thr Thr Pro Arg Asn Ser Val Asn Gly Thr Phe Pro Ala Glu Pro
1 5 10 15

Met Lys Gly Pro Ile Ala Met Gln Ser Gly Pro Lys Pro Leu Phe Arg
20 25 30

Arg Met Ser Ser Leu Val Gly Pro Thr Gln Ser Phe Phe Met Arg Glu
35 40 45

Ser Lys Thr Leu Gly Ala Val Gln Ile Met Asn Gly Leu Phe His Ile
50 55 60

Ala Leu Gly Gly Leu Leu Met Ile Pro Ala Gly Ile Tyr Ala Pro Ile
65 70 75 80

Cys Val Thr Val Trp Tyr Pro Leu Trp Gly Gly Ile Met Tyr Ile Ile
85 90 95

Ser Gly Ser Leu Leu Ala Ala Thr Glu Lys Asn Ser Arg Lys Cys Leu
100 105 110

Val Lys Gly Lys Met Ile Met Asn Ser Leu Ser Leu Phe Ala Ala Ile
115 120 125

Ser Gly Met Ile Leu Ser Ile Met Asp Ile Leu Asn Ile Lys Ile Ser
130 135 140

His Phe Leu Lys Met Glu Ser Leu Asn Phe Ile Arg Ala His Thr Pro
145 150 155 160

Tyr Ile Asn Ile Tyr Asn Cys Glu Pro Ala Asn Pro Ser Glu Lys Asn
165 170 175

Ser Pro Ser Thr Gln Tyr Cys Tyr Ser Ile Gln Ser Leu Phe Leu Gly
180 185 190

Ile Leu Ser Val Met Leu Ile Phe Ala Phe Phe Gln Glu Leu Val Ile
195 200 205

Ala Gly Ile Val Glu Asn
210

<210> SEQ ID NO 116
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116
gtgactgtgt ggtaccctct ctggggaggc attatgtata ttatttccgg atcactcctg 60
gcagcaacgg agaaaaactc caggaagtgt ttggtcaaag gaaaaatgat aatgaattca 120
ttgagcctct ttgctgccat ttctggaatg attctttcaa tcatggacat acttaatatt 180
aaaatttccc attttttaaa aatggagagt ctgaatttta ttagagctca cacaccatat 240
attaacatat acaactgtga accagctaat ccctctgaga aaaactcccc atctacccaa 300
tactgttaca gcatacaatc tctgttcttg ggcattttgt cagtgatgct gatctttgcc 360
ttcttccagg aacttgtaat agctggcatc gttgagaat 399

<210> SEQ ID NO 117
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

Val Thr Val Trp Tyr Pro Leu Trp Gly Gly Ile Met Tyr Ile Ile Ser
1 5 10 15

Gly Ser Leu Leu Ala Ala Thr Glu Lys Asn Ser Arg Lys Cys Leu Val
20 25 30

Lys Gly Lys Met Ile Met Asn Ser Leu Ser Leu Phe Ala Ala Ile Ser
35 40 45

Gly Met Ile Leu Ser Ile Met Asp Ile Leu Asn Ile Lys Ile Ser His
50 55 60

Phe Leu Lys Met Glu Ser Leu Asn Phe Ile Arg Ala His Thr Pro Tyr
65 70 75 80

Ile Asn Ile Tyr Asn Cys Glu Pro Ala Asn Pro Ser Glu Lys Asn Ser
85 90 95

Pro Ser Thr Gln Tyr Cys Tyr Ser Ile Gln Ser Leu Phe Leu Gly Ile
100 105 110

Leu Ser Val Met Leu Ile Phe Ala Phe Phe Gln Glu Leu Val Ile Ala
115 120 125

Gly Ile Val Glu Asn
130

<210> SEQ ID NO 118
<211> LENGTH: 315
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118
gtgactgtgt ggtaccctct ctggggaggc attatgtata ttatttccgg atcactcctg 60
gcagcaacgg agaaaaactc caggaagtgt ttggtcaaag gaaaaatgat aatgaattca 120
ttgagcctct ttgctgccat ttctggaatg attctttcaa tcatggacat acttaatatt 180
aaaatttccc attttttaaa aatggagagt ctgaatttta ttagagctca cacaccatat 240
attaacatat acaactgtga accagctaat ccctctgaga aaaactcccc atctacccaa 300
tactgttaca gcata 315

<210> SEQ ID NO 119
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

Val Thr Val Trp Tyr Pro Leu Trp Gly Gly Ile Met Tyr Ile Ile Ser

-continued

```
1               5                   10                  15

Gly Ser Leu Leu Ala Ala Thr Glu Lys Asn Ser Arg Lys Cys Leu Val
            20                  25                  30

Lys Gly Lys Met Ile Met Asn Ser Leu Ser Leu Phe Ala Ala Ile Ser
        35                  40                  45

Gly Met Ile Leu Ser Ile Met Asp Ile Leu Asn Ile Lys Ile Ser His
    50                  55                  60

Phe Leu Lys Met Glu Ser Leu Asn Phe Ile Arg Ala His Thr Pro Tyr
65                  70                  75                  80

Ile Asn Ile Tyr Asn Cys Glu Pro Ala Asn Pro Ser Glu Lys Asn Ser
                85                  90                  95

Pro Ser Thr Gln Tyr Cys Tyr Ser Ile Gln Ser Leu Phe Leu Gly Ile
            100                 105                 110

Leu Ser Val Met Leu Ile Phe Ala Phe Phe Gln Glu Leu Val Ile Ala
        115                 120                 125

Gly Ile Val Glu Asn
    130
```

<210> SEQ ID NO 120
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120

```
ccatatatta acatatacaa ctgtgaacca gctaatccct ctgagaaaaa ctccccatct      60

acccaatact gttacagcat acaatcgggt ggcggcggat ctattgaagt tatgtatcct     120

cctccttacc tagacaatga gaagagcaat ggaaccatta tccatgtgaa agggaaacac     180

ctttgtccaa gtcccctatt tcccggacct tctaagccct tttgggtgct ggtggtggtt     240

ggtggagtcc tggcttgcta tagcttgcta gtaacagtgg cctttattat tttctgggtg     300

aggagtaaga ggagcaggct cctgcacagt gac                                  333
```

<210> SEQ ID NO 121
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

```
Pro Tyr Ile Asn Ile Tyr Asn Cys Glu Pro Ala Asn Pro Ser Glu Lys
1               5                   10                  15

Asn Ser Pro Ser Thr Gln Tyr Cys Tyr Ser Ile Gln Ser Gly Gly Gly
            20                  25                  30

Gly Ser Ile Glu Val Met Tyr Pro Pro Pro Tyr Leu Asp Asn Glu Lys
        35                  40                  45

Ser Asn Gly Thr Ile Ile His Val Lys Gly Lys His Leu Cys Pro Ser
    50                  55                  60

Pro Leu Phe Pro Gly Pro Ser Lys Pro Phe Trp Val Leu Val Val Val
65                  70                  75                  80

Gly Gly Val Leu Ala Cys Tyr Ser Leu Leu Val Thr Val Ala Phe Ile
                85                  90                  95

Ile Phe Trp Val Arg Ser Lys Arg Ser Arg Leu Leu His Ser Asp
```

100 105 110

<210> SEQ ID NO 122
<211> LENGTH: 435
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 122
ccatatatta acatatacaa ctgtgaacca gctaatccct ctgagaaaaa ctccccatct 60
acccaatact gttacagcat acaatcgggt ggcggcggat ctccatatat taacatatac 120
aactgtgaac cagctaatcc ctctgagaaa aactccccat ctacccaata ctgttacagc 180
atacaatcgg gtggcggcgg atctattgaa gttatgtatc ctcctcctta cctagacaat 240
gagaagagca atggaaccat tatccatgtg aaagggaaac acctttgtcc aagtccccta 300
tttcccggac cttctaagcc cttttgggtg ctggtggtgg ttggtggagt cctggcttgc 360
tatagcttgc tagtaacagt ggcctttatt attttctggg tgaggagtaa gaggagcagg 420
ctcctgcaca gtgac 435

<210> SEQ ID NO 123
<211> LENGTH: 145
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 123

Pro Tyr Ile Asn Ile Tyr Asn Cys Glu Pro Ala Asn Pro Ser Glu Lys
1 5 10 15

Asn Ser Pro Ser Thr Gln Tyr Cys Tyr Ser Ile Gln Ser Gly Gly Gly
20 25 30

Gly Ser Pro Tyr Ile Asn Ile Tyr Asn Cys Glu Pro Ala Asn Pro Ser
35 40 45

Glu Lys Asn Ser Pro Ser Thr Gln Tyr Cys Tyr Ser Ile Gln Ser Gly
50 55 60

Gly Gly Gly Ser Ile Glu Val Met Tyr Pro Pro Pro Tyr Leu Asp Asn
65 70 75 80

Glu Lys Ser Asn Gly Thr Ile Ile His Val Lys Gly Lys His Leu Cys
85 90 95

Pro Ser Pro Leu Phe Pro Gly Pro Ser Lys Pro Phe Trp Val Leu Val
100 105 110

Val Val Gly Gly Val Leu Ala Cys Tyr Ser Leu Leu Val Thr Val Ala
115 120 125

Phe Ile Ile Phe Trp Val Arg Ser Lys Arg Ser Arg Leu Leu His Ser
130 135 140

Asp
145

<210> SEQ ID NO 124
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 124
ccatatatta acatatacaa ctgtgaacca gctaatccct ctgagaaaaa ctccccatct 60
acccaatact gttacagcat acaatcgggt ggcggcggat ctccagcgcc gcgaccacca 120
acaccggcgc ccaccatcgc gtcgcagccc ctgtccctgc gcccagaggc gtgccggcca 180
gcggcggggg gcgcagtgca cacgaggggg ctggacttcg cctgtgatat ctacatctgg 240
gcgcccttgg ccgggacttg tggggtcctt ctcctgtcac tggttatcac cctttactgc 300
aaccacagga accgaagacg tgtttgcaaa tgtccccggc ctgtggtc 348

<210> SEQ ID NO 125
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Pro Tyr Ile Asn Ile Tyr Asn Cys Glu Pro Ala Asn Pro Ser Glu Lys
1 5 10 15

Asn Ser Pro Ser Thr Gln Tyr Cys Tyr Ser Ile Gln Ser Gly Gly Gly
20 25 30

Gly Ser Pro Ala Pro Arg Pro Pro Thr Pro Ala Pro Thr Ile Ala Ser
35 40 45

Gln Pro Leu Ser Leu Arg Pro Glu Ala Cys Arg Pro Ala Ala Gly Gly
50 55 60

Ala Val His Thr Arg Gly Leu Asp Phe Ala Cys Asp Ile Tyr Ile Trp
65 70 75 80

Ala Pro Leu Ala Gly Thr Cys Gly Val Leu Leu Leu Ser Leu Val Ile
85 90 95

Thr Leu Tyr Cys Asn His Arg Asn Arg Arg Arg Val Cys Lys Cys Pro
100 105 110

Arg Pro Val Val
115

<210> SEQ ID NO 126
<211> LENGTH: 300
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126
tgtgaaccag ctaatccctc tgagaaaaac tccccatcta cccaatactg ttcgggtggc 60
ggcggatcta ttgaagttat gtatcctcct ccttacctag acaatgagaa gagcaatgga 120
accattatcc atgtgaaagg gaaacacctt tgtccaagtc ccctatttcc cggaccttct 180
aagccctttt gggtgctggt ggtggttggt ggagtcctgg cttgctatag cttgctagta 240
acagtggcct ttattatttt ctgggtgagg agtaagagga gcaggctcct gcacagtgac 300

<210> SEQ ID NO 127
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

```
Cys Glu Pro Ala Asn Pro Ser Glu Lys Asn Ser Pro Ser Thr Gln Tyr
1               5                   10                  15

Cys Ser Gly Gly Gly Gly Ser Ile Glu Val Met Tyr Pro Pro Pro Tyr
            20                  25                  30

Leu Asp Asn Glu Lys Ser Asn Gly Thr Ile Ile His Val Lys Gly Lys
        35                  40                  45

His Leu Cys Pro Ser Pro Leu Phe Pro Gly Pro Ser Lys Pro Phe Trp
    50                  55                  60

Val Leu Val Val Val Gly Gly Val Leu Ala Cys Tyr Ser Leu Leu Val
65                  70                  75                  80

Thr Val Ala Phe Ile Ile Phe Trp Val Arg Ser Lys Arg Ser Arg Leu
                85                  90                  95

Leu His Ser Asp
            100
```

<210> SEQ ID NO 128
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
tgtgaaccag ctaatccctc tgagaaaaac tccccatcta cccaatactg ttcgggtggc     60

ggcggatctt gtgaaccagc taatccctct gagaaaaact ccccatctac ccaatactgt    120

tcgggtggcg gcggatctat tgaagttatg tatcctcctc cttacctaga caatgagaag    180

agcaatggaa ccattatcca tgtgaaaggg aaacaccttt gtccaagtcc cctatttccc    240

ggaccttcta agcccttttg ggtgctggtg gtggttggtg gagtcctggc ttgctatagc    300

ttgctagtaa cagtggcctt tattattttc tgggtgagga gtaagaggag caggctcctg    360

cacagtgac                                                            369
```

<210> SEQ ID NO 129
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Cys Glu Pro Ala Asn Pro Ser Glu Lys Asn Ser Pro Ser Thr Gln Tyr
1               5                   10                  15

Cys Ser Gly Gly Gly Gly Ser Cys Glu Pro Ala Asn Pro Ser Glu Lys
            20                  25                  30

Asn Ser Pro Ser Thr Gln Tyr Cys Ser Gly Gly Gly Gly Ser Ile Glu
        35                  40                  45

Val Met Tyr Pro Pro Pro Tyr Leu Asp Asn Glu Lys Ser Asn Gly Thr
    50                  55                  60

Ile Ile His Val Lys Gly Lys His Leu Cys Pro Ser Pro Leu Phe Pro
65                  70                  75                  80

Gly Pro Ser Lys Pro Phe Trp Val Leu Val Val Val Gly Gly Val Leu
                85                  90                  95

Ala Cys Tyr Ser Leu Leu Val Thr Val Ala Phe Ile Ile Phe Trp Val
            100                 105                 110
```

Arg Ser Lys Arg Ser Arg Leu Leu His Ser Asp
115 120

<210> SEQ ID NO 130
<211> LENGTH: 315
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130
tgtgaaccag ctaatccctc tgagaaaaac tccccatcta cccaatactg ttcgggtggc 60
ggcggatctc cagcgccgcg accaccaaca ccggcgccca ccatcgcgtc gcagcccctg 120
tccctgcgcc cagaggcgtg ccggccagcg gcgggggggcg cagtgcacac gagggggctg 180
gacttcgcct gtgatatcta catctgggcg cccttggccg ggacttgtgg ggtccttctc 240
ctgtcactgg ttatcaccct ttactgcaac cacaggaacc gaagacgtgt ttgcaaatgt 300
ccccggcctg tggtc 315

<210> SEQ ID NO 131
<211> LENGTH: 105
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

Cys Glu Pro Ala Asn Pro Ser Glu Lys Asn Ser Pro Ser Thr Gln Tyr
1 5 10 15

Cys Ser Gly Gly Gly Gly Ser Pro Ala Pro Arg Pro Pro Thr Pro Ala
20 25 30

Pro Thr Ile Ala Ser Gln Pro Leu Ser Leu Arg Pro Glu Ala Cys Arg
35 40 45

Pro Ala Ala Gly Gly Ala Val His Thr Arg Gly Leu Asp Phe Ala Cys
50 55 60

Asp Ile Tyr Ile Trp Ala Pro Leu Ala Gly Thr Cys Gly Val Leu Leu
65 70 75 80

Leu Ser Leu Val Ile Thr Leu Tyr Cys Asn His Arg Asn Arg Arg Arg
85 90 95

Val Cys Lys Cys Pro Arg Pro Val Val
100 105

<210> SEQ ID NO 132
<211> LENGTH: 729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132
atgaccacac cccggaactc cgtgaatggc accttccctg ccgagccaat gaagggccct 60
atcgccatgc agtctggccc aaagcccctg tttcggagaa tgagctccct ggtgggcccc 120
acccagagct tctttatgag ggagtccaag acactgggcg cctgcctggt gaagggcaag 180
atgatcatga actctctgag cctgttcgcc gccatctccg gcatgatcct gtctatcatg 240
gacatcctga acatcaagat ctctcacttc ctgaagatgg agagcctgaa cttcatccgg 300
gcccacaccc catacatcaa catctataat tgcgagcccg ccaaccctag cgagaagaat 360
tccccctcta cacagtactg ttatagcatc cagtccctgt tcctgggcat cctgtccgtg 420
atgctgatct ttgccttctt tcaggagctg gtcatcgccg gcatcgtgga gaacgagtgg 480
aagaggacct gttctcgccc taagagcaat atcgtgctgc tgagcgccga ggagaagaag 540
gagcagacaa tcgagatcaa ggaggaggtg gtgggcctga ccgagacatc tagccagcct 600
aagaatgagg aggatatcga gatcatccca atccaggagg aggaggagga ggagaccgag 660
acaaactttc cagagccccc tcaggaccag gagtcctctc caatcgagaa tgatagctcc 720
ccctgataa 729

<210> SEQ ID NO 133
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

Met Thr Thr Pro Arg Asn Ser Val Asn Gly Thr Phe Pro Ala Glu Pro
1 5 10 15

Met Lys Gly Pro Ile Ala Met Gln Ser Gly Pro Lys Pro Leu Phe Arg
20 25 30

Arg Met Ser Ser Leu Val Gly Pro Thr Gln Ser Phe Phe Met Arg Glu
35 40 45

Ser Lys Thr Leu Gly Ala Cys Leu Val Lys Gly Lys Met Ile Met Asn
50 55 60

Ser Leu Ser Leu Phe Ala Ala Ile Ser Gly Met Ile Leu Ser Ile Met
65 70 75 80

Asp Ile Leu Asn Ile Lys Ile Ser His Phe Leu Lys Met Glu Ser Leu
85 90 95

Asn Phe Ile Arg Ala His Thr Pro Tyr Ile Asn Ile Tyr Asn Cys Glu
100 105 110

Pro Ala Asn Pro Ser Glu Lys Asn Ser Pro Ser Thr Gln Tyr Cys Tyr
115 120 125

Ser Ile Gln Ser Leu Phe Leu Gly Ile Leu Ser Val Met Leu Ile Phe
130 135 140

Ala Phe Phe Gln Glu Leu Val Ile Ala Gly Ile Val Glu Asn Glu Trp
145 150 155 160

Lys Arg Thr Cys Ser Arg Pro Lys Ser Asn Ile Val Leu Leu Ser Ala
165 170 175

Glu Glu Lys Lys Glu Gln Thr Ile Glu Ile Lys Glu Glu Val Val Gly
180 185 190

Leu Thr Glu Thr Ser Ser Gln Pro Lys Asn Glu Glu Asp Ile Glu Ile
195 200 205

Ile Pro Ile Gln Glu Glu Glu Glu Glu Glu Thr Glu Thr Asn Phe Pro
210 215 220

Glu Pro Pro Gln Asp Gln Glu Ser Ser Pro Ile Glu Asn Asp Ser Ser
225 230 235 240

<210> SEQ ID NO 134
<211> LENGTH: 681
<212> TYPE: DNA
<213> ORGANISM: Artificial Sequence
<220> FEATURE:

-continued

<223> OTHER INFORMATION: Description of Artificial Sequence: Synthetic
polynucleotide

<400> SEQUENCE: 134
atgaccacac cacggaacag cgtgaatggc accttcccag cagagccaat gaagggacca 60
atcgcaatgc agtccggacc caagcctctg tttcggagaa tgagctccct ggtgggcccc 120
acccagtctt tctttatgag ggagagcaag acactgggcg cctgcctggt gaagggcaag 180
atgatcatga actccctgtc tctgttcgcc gccatcagcg gcatgatcct gtccatcatg 240
gacatcctga acatcaagat ctcccacttc ctgaagatgg agagcctgaa cttcatccgg 300
gcccacaccc cttacatcaa catctataat tgcgagcctg ccaacccatc tgagaagaat 360
agcccatcca cacagtactg ttattctatc cagagcctgt tcctgggcat cctgtccgtg 420
atgctgatct ttgccttctt tcaggagctg gtcatcgccg gcatcgtgga gaacgagtgg 480
aagaggacct gttcccgccc caagtctaat atcgtgctgc tgagcgccga ggagaagaag 540
gagcagacaa tcgagatcaa ggaggaggtg gtgggcctga ccgagacatc tagccagccc 600
aagaacgagg aggatatcga gatcatccct atccaggagg aggaggagga ggagaccgag 660
acaaattttc ctgagtgata a 681

<210> SEQ ID NO 135
<211> LENGTH: 225
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 135

Met Thr Thr Pro Arg Asn Ser Val Asn Gly Thr Phe Pro Ala Glu Pro
1 5 10 15

Met Lys Gly Pro Ile Ala Met Gln Ser Gly Pro Lys Pro Leu Phe Arg
20 25 30

Arg Met Ser Ser Leu Val Gly Pro Thr Gln Ser Phe Phe Met Arg Glu
35 40 45

Ser Lys Thr Leu Gly Ala Cys Leu Val Lys Gly Lys Met Ile Met Asn
50 55 60

Ser Leu Ser Leu Phe Ala Ala Ile Ser Gly Met Ile Leu Ser Ile Met
65 70 75 80

Asp Ile Leu Asn Ile Lys Ile Ser His Phe Leu Lys Met Glu Ser Leu
85 90 95

Asn Phe Ile Arg Ala His Thr Pro Tyr Ile Asn Ile Tyr Asn Cys Glu
100 105 110

Pro Ala Asn Pro Ser Glu Lys Asn Ser Pro Ser Thr Gln Tyr Cys Tyr
115 120 125

Ser Ile Gln Ser Leu Phe Leu Gly Ile Leu Ser Val Met Leu Ile Phe
130 135 140

Ala Phe Phe Gln Glu Leu Val Ile Ala Gly Ile Val Glu Asn Glu Trp
145 150 155 160

Lys Arg Thr Cys Ser Arg Pro Lys Ser Asn Ile Val Leu Leu Ser Ala
165 170 175

Glu Glu Lys Lys Glu Gln Thr Ile Glu Ile Lys Glu Glu Val Val Gly
180 185 190

Leu Thr Glu Thr Ser Ser Gln Pro Lys Asn Glu Glu Asp Ile Glu Ile
195 200 205

```
Ile Pro Ile Gln Glu Glu Glu Glu Glu Glu Thr Glu Thr Asn Phe Pro
    210                 215                 220

Glu
225
```

<210> SEQ ID NO 136
<211> LENGTH: 627
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
atgaccacac cccggaacag cgtgaatggc accttcccag ccgagcccat gaagggccct      60

atcgccatgc agtccggccc caagcctctg tttcggagaa tgagctccct ggtgggcccc     120

acccagtctt tctttatgag ggagagcaag acactgggcg cctgcctggt gaagggcaag     180

atgatcatga actccctgtc tctgttcgcc gccatcagcg gcatgatcct gtccatcatg     240

gacatcctga acatcaagat ctcccacttc ctgaagatgg agagcctgaa cttcatccgg     300

gcccacaccc catacatcaa catctataat tgcgagcctg ccaacccatc tgagaagaat     360

agcccctcca cacagtactg ttattctatc cagagcctgt tcctgggcat cctgtccgtg     420

atgctgatct ttgccttctt tcaggagctg gtcatcgccg gcatcgtgga gaacgagtgg     480

aagaggacct gttcccgccc taagtctaat atcgtgctgc tgagcgccga ggagaagaag     540

gagcagacaa tcgagatcaa ggaggaggtg gtgggcctga ccgagacatc tagccagcca     600

aagaatgagg aggatatcga gtgataa                                          627
```

<210> SEQ ID NO 137
<211> LENGTH: 207
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Cys Leu Val Lys Gly Lys Met Ile Met Asn
    50                  55                  60

Ser Leu Ser Leu Phe Ala Ala Ile Ser Gly Met Ile Leu Ser Ile Met
65                  70                  75                  80

Asp Ile Leu Asn Ile Lys Ile Ser His Phe Leu Lys Met Glu Ser Leu
                85                  90                  95

Asn Phe Ile Arg Ala His Thr Pro Tyr Ile Asn Ile Tyr Asn Cys Glu
            100                 105                 110

Pro Ala Asn Pro Ser Glu Lys Asn Ser Pro Ser Thr Gln Tyr Cys Tyr
        115                 120                 125

Ser Ile Gln Ser Leu Phe Leu Gly Ile Leu Ser Val Met Leu Ile Phe
    130                 135                 140

Ala Phe Phe Gln Glu Leu Val Ile Ala Gly Ile Val Glu Asn Glu Trp
145                 150                 155                 160
```

```
Lys Arg Thr Cys Ser Arg Pro Lys Ser Asn Ile Val Leu Leu Ser Ala
                165                 170                 175

Glu Glu Lys Lys Glu Gln Thr Ile Glu Ile Lys Glu Glu Val Val Gly
            180                 185                 190

Leu Thr Glu Thr Ser Ser Gln Pro Lys Asn Glu Glu Asp Ile Glu
        195                 200                 205


<210> SEQ ID NO 138
<211> LENGTH: 522
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

atgaccacac cccggaactc cgtgaatggc accttcccag ccgagcccat gaagggccct      60

atcgccatgc agtctggccc caagcctctg tttcggagaa tgagctccct ggtgggccct     120

acccagagct tctttatgag ggagtccaag acactgggcg cctgcctggt gaagggcaag     180

atgatcatga actctctgag cctgttcgcc gccatctccg gcatgatcct gtctatcatg     240

gacatcctga acatcaagat ctctcacttc ctgaagatgg agagcctgaa cttcatccgg     300

gcccacaccc catacatcaa catctataat tgcgagcctg ccaacccaag cgagaagaat     360

tccccctcta cacagtactg ttatagcatc cagtccctgt tcctgggcat cctgtccgtg     420

atgctgatct ttgccttctt tcaggagctg gtcatcgccg gcatcgtgga gaacgagtgg     480

aagaggacat gttctcgccc caagagcaat atcgtgtgat aa                        522


<210> SEQ ID NO 139
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Cys Leu Val Lys Gly Lys Met Ile Met Asn
    50                  55                  60

Ser Leu Ser Leu Phe Ala Ala Ile Ser Gly Met Ile Leu Ser Ile Met
65                  70                  75                  80

Asp Ile Leu Asn Ile Lys Ile Ser His Phe Leu Lys Met Glu Ser Leu
                85                  90                  95

Asn Phe Ile Arg Ala His Thr Pro Tyr Ile Asn Ile Tyr Asn Cys Glu
            100                 105                 110

Pro Ala Asn Pro Ser Glu Lys Asn Ser Pro Ser Thr Gln Tyr Cys Tyr
        115                 120                 125

Ser Ile Gln Ser Leu Phe Leu Gly Ile Leu Ser Val Met Leu Ile Phe
    130                 135                 140

Ala Phe Phe Gln Glu Leu Val Ile Ala Gly Ile Val Glu Asn Glu Trp
145                 150                 155                 160
```

Lys Arg Thr Cys Ser Arg Pro Lys Ser Asn Ile Val
165 170

<210> SEQ ID NO 140
<211> LENGTH: 591
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140
atgaccacac ccaggaacag cgtgtgcctg gtgaagggca agatgatcat gaatagcctg 60
tccctgttcg ccgccatctc tggcatgatc ctgagcatca tggacatcct gaacatcaag 120
atctcccact tcctgaagat ggagagcctg aacttcatcc gggcccacac cccatacatc 180
aacatctata attgcgagcc agccaacccc agcgagaaga attctcccag cacacagtac 240
tgttattcca tccagtctct gttcctgggc atcctgtccg tgatgctgat ctttgccttc 300
tttcaggagc tggtcatcgc cggcatcgtg gagaacgagt ggaagcggac ctgtagcaga 360
cctaagtcca atatcgtgct gctgtccgcc gaggagaaga aggagcagac aatcgagatc 420
aaggaggagg tggtgggcct gaccgagaca agctcccagc ccaagaacga ggaggatatc 480
gagatcatcc ctatccagga ggaggaggag gaggagaccg agacaaactt tccagagccc 540
cctcaggacc aggagtctag ccctatcgag aatgattcct ctccatgata a 591

<210> SEQ ID NO 141
<211> LENGTH: 195
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

Met Thr Thr Pro Arg Asn Ser Val Cys Leu Val Lys Gly Lys Met Ile
1 5 10 15

Met Asn Ser Leu Ser Leu Phe Ala Ala Ile Ser Gly Met Ile Leu Ser
20 25 30

Ile Met Asp Ile Leu Asn Ile Lys Ile Ser His Phe Leu Lys Met Glu
35 40 45

Ser Leu Asn Phe Ile Arg Ala His Thr Pro Tyr Ile Asn Ile Tyr Asn
50 55 60

Cys Glu Pro Ala Asn Pro Ser Glu Lys Asn Ser Pro Ser Thr Gln Tyr
65 70 75 80

Cys Tyr Ser Ile Gln Ser Leu Phe Leu Gly Ile Leu Ser Val Met Leu
85 90 95

Ile Phe Ala Phe Phe Gln Glu Leu Val Ile Ala Gly Ile Val Glu Asn
100 105 110

Glu Trp Lys Arg Thr Cys Ser Arg Pro Lys Ser Asn Ile Val Leu Leu
115 120 125

Ser Ala Glu Glu Lys Lys Glu Gln Thr Ile Glu Ile Lys Glu Glu Val
130 135 140

Val Gly Leu Thr Glu Thr Ser Ser Gln Pro Lys Asn Glu Glu Asp Ile
145 150 155 160

Glu Ile Ile Pro Ile Gln Glu Glu Glu Glu Glu Glu Thr Glu Thr Asn
165 170 175

```
Phe Pro Glu Pro Pro Gln Asp Gln Glu Ser Ser Pro Ile Glu Asn Asp
            180                 185                 190

Ser Ser Pro
        195


<210> SEQ ID NO 142
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142

ggacaaaacg acaccagcca aaccagcagc ccctca                              36


<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gln Asn Asp Thr Ser Gln Thr Ser Ser Pro Ser
1               5                   10


<210> SEQ ID NO 144
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144

atgaagcgct tcctcttcct cctactcacc atcagcctcc tggttatggt acagatacaa     60

actggactct caggacaaaa cgacaccagc caaaccagca gcccctcagg cagcacctcc    120

ggcagcggca agcctggcag cggcgagggc agcaccaagg gcggcggagg cggaagcgga    180

ggcggaggct ccaagccctt ctgggtgctg gtcgtggtcg gcggagtgct ggcctgttac    240

agcctgctgg tcaccgtggc cttcatcatc ttttgggtc                          279


<210> SEQ ID NO 145
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Gly Ser Thr Ser Gly Ser Gly Lys Pro Gly Ser Gly
        35                  40                  45

Glu Gly Ser Thr Lys Gly Gly Gly Gly Gly Ser Gly Gly Gly Gly Ser
    50                  55                  60

Lys Pro Phe Trp Val Leu Val Val Val Gly Gly Val Leu Ala Cys Tyr
65                  70                  75                  80
```

```
Ser Leu Leu Val Thr Val Ala Phe Ile Ile Phe Trp Val
                85                  90


<210> SEQ ID NO 146
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146

atgaagcgct tcctcttcct cctactcacc atcagcctcc tggttatggt acagatacaa     60

actggactct caggacaaaa cgacaccagc caaaccagca gcccctcagg cagcacctcc    120

ggcagcggca agcctggcag cggcgagggc agcaccaagg gcggccagaa tgatacatct    180

cagacttcat ctcctagcgg atccacttct ggttccggta aaccaggttc tggggaaggt    240

agtacaaaag gaggcggagg cggaagcgga ggcggaggct ccaagccctt ctgggtgctg    300

gtcgtggtcg gcggagtgct ggcctgttac agcctgctgg tcaccgtggc cttcatcatc    360

ttttgggtc                                                            369


<210> SEQ ID NO 147
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Gly Ser Thr Ser Gly Ser Gly Lys Pro Gly Ser Gly
        35                  40                  45

Glu Gly Ser Thr Lys Gly Gly Gln Asn Asp Thr Ser Gln Thr Ser Ser
    50                  55                  60

Pro Ser Gly Ser Thr Ser Gly Ser Gly Lys Pro Gly Ser Gly Glu Gly
65                  70                  75                  80

Ser Thr Lys Gly Gly Gly Gly Gly Ser Gly Gly Gly Gly Ser Lys Pro
                85                  90                  95

Phe Trp Val Leu Val Val Val Gly Gly Val Leu Ala Cys Tyr Ser Leu
            100                 105                 110

Leu Val Thr Val Ala Phe Ile Ile Phe Trp Val
        115                 120


<210> SEQ ID NO 148
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148

atgaagcgct tcctcttcct cctactcacc atcagcctcc tggttatggt acagatacaa     60

actggactct caggacaaaa cgacaccagc caaaccagca gcccctcagg cagcacctcc    120
```

-continued

```
ggcagcggca agcctggcag cggcgagggc agcaccaagg gcggccagaa tgatacatct    180

cagacttcat ctcctagcgg atccacttct ggttccggta aaccaggttc tggggaaggt    240

agtacaaaag gaggtcagaa cgacacttca cagacatcta gtccatccgg cagtacaagc    300

ggaagtggaa agcccggaag tggtgaggga tcaactaagg gtggcggagg cggaagcgga    360

ggcggaggct ccaagccctt ctgggtgctg gtcgtggtcg gcggagtgct ggcctgttac    420

agcctgctgg tcaccgtggc cttcatcatc ttttgggtc                           459


<210> SEQ ID NO 149
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Gly Ser Thr Ser Gly Ser Gly Lys Pro Gly Ser Gly
        35                  40                  45

Glu Gly Ser Thr Lys Gly Gly Gln Asn Asp Thr Ser Gln Thr Ser Ser
    50                  55                  60

Pro Ser Gly Ser Thr Ser Gly Ser Gly Lys Pro Gly Ser Gly Glu Gly
65                  70                  75                  80

Ser Thr Lys Gly Gly Gln Asn Asp Thr Ser Gln Thr Ser Ser Pro Ser
                85                  90                  95

Gly Ser Thr Ser Gly Ser Gly Lys Pro Gly Ser Gly Glu Gly Ser Thr
            100                 105                 110

Lys Gly Gly Gly Gly Gly Ser Gly Gly Gly Gly Ser Lys Pro Phe Trp
        115                 120                 125

Val Leu Val Val Val Gly Gly Val Leu Ala Cys Tyr Ser Leu Leu Val
    130                 135                 140

Thr Val Ala Phe Ile Ile Phe Trp Val
145                 150


<210> SEQ ID NO 150
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Gly Ser Thr Ser Gly Ser Gly Lys Pro Gly Ser Gly
        35                  40                  45

Glu Gly Ser Thr Lys Gly Gly Gln Asn Asp Thr Ser Gln Thr Ser Ser
    50                  55                  60

Pro Ser Gly Ser Thr Ser Gly Ser Gly Lys Pro Gly Ser Gly Glu Gly
65                  70                  75                  80
```

```
Ser Thr Lys Gly Gly Gln Asn Asp Thr Ser Gln Thr Ser Ser Pro Ser
                85                  90                  95

Gly Ser Thr Ser Gly Ser Gly Lys Pro Gly Ser Gly Glu Gly Ser Thr
            100                 105                 110

Lys Gly Gly Gly Gly Ser Gly Gly Gly Gly Ser Gly Gly Gly Gly Ser
        115                 120                 125

Gly Gly Gly Gly Ser Glu Ile Thr Leu Ile Ile Phe Gly Val Met Ala
    130                 135                 140

Gly Val Ile Gly Thr Ile Leu Leu Ile Ser Tyr Gly Ile Arg Arg Gly
145                 150                 155                 160

Gly Gly Ser


<210> SEQ ID NO 151
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Gly Ser Thr Ser Gly Ser Gly Lys Pro Gly Ser Gly
        35                  40                  45

Glu Gly Ser Thr Lys Gly Gly Gln Asn Asp Thr Ser Gln Thr Ser Ser
    50                  55                  60

Pro Ser Gly Ser Thr Ser Gly Ser Gly Lys Pro Gly Ser Gly Glu Gly
65                  70                  75                  80

Ser Thr Lys Gly Gly Gln Asn Asp Thr Ser Gln Thr Ser Ser Pro Ser
                85                  90                  95

Gly Ser Thr Ser Gly Ser Gly Lys Pro Gly Ser Gly Glu Gly Ser Thr
            100                 105                 110

Lys Gly Gly Gly Gly Ser Gly Gly Gly Gly Ser Gly Gly Gly Gly Ser
        115                 120                 125

Gly Gly Gly Gly Ser Ile Thr Leu Ile Ile Phe Gly Val Met Ala Gly
    130                 135                 140

Val Ile Gly Thr Ile Leu Leu Ala Leu Leu Ile Trp Gly Gly Gly Ser
145                 150                 155                 160


<210> SEQ ID NO 152
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Gly Ser Thr Ser Gly Ser Gly Lys Pro Gly Ser Gly
        35                  40                  45

Glu Gly Ser Thr Lys Gly Gly Gln Asn Asp Thr Ser Gln Thr Ser Ser
```

-continued 50 55 60

Pro Ser Gly Ser Thr Ser Gly Ser Gly Lys Pro Gly Ser Gly Glu Gly
65 70 75 80

Ser Thr Lys Gly Gly Gln Asn Asp Thr Ser Gln Thr Ser Ser Pro Ser
85 90 95

Gly Ser Thr Ser Gly Ser Gly Lys Pro Gly Ser Gly Glu Gly Ser Thr
100 105 110

Lys Gly Gly Gly Gly Ser Gly Gly Gly Gly Ser Gly Gly Gly Gly Ser
115 120 125

Gly Gly Gly Gly Ser Ile Thr Leu Ile Ile Phe Gly Val Met Ala Gly
130 135 140

Val Ile Gly Thr Ile Leu Leu Ala Leu Leu Ile Trp Gly Gly Gly Ser
145 150 155 160

<210> SEQ ID NO 153
<211> LENGTH: 1284
<212> TYPE: DNA
<213> ORGANISM: Unknown
<220> FEATURE:
<223> OTHER INFORMATION: Description of Unknown:
Low-affinity nerve growth factor receptor (LNGFR, TNFRSF16)
sequence

<400> SEQUENCE: 153
atgggggcag gtgccaccgg ccgcgccatg gacgggccgc gcctgctgct gttgctgctt 60
ctgggggtgt cccttggagg tgccaaggag gcatgcccca caggcctgta cacacacagc 120
ggtgagtgct gcaaagcctg caacctgggc gagggtgtgg cccagccttg tggagccaac 180
cagaccgtgt gtgagccctg cctggacagc gtgacgttct ccgacgtggt gagcgcgacc 240
gagccgtgca agccgtgcac cgagtgcgtg gggctccaga gcatgtcggc gccgtgcgtg 300
gaggccgacg acgccgtgtg ccgctgcgcc tacggctact accaggatga gacgactggg 360
cgctgcgagg cgtgccgcgt gtgcgaggcg ggctcgggcc tcgtgttctc ctgccaggac 420
aagcagaaca ccgtgtgcga ggagtgcccc gacggcacgt attccgacga ggccaaccac 480
gtggacccgt gcctgccctg caccgtgtgc gaggacaccg agcgccagct ccgcgagtgc 540
acacgctggg ccgacgccga gtgcgaggag atccctggcc gttggattac acggtccaca 600
cccccagagg gctcggacag cacagccccc agcacccagg agcctgaggc acctccagaa 660
caagacctca tagccagcac ggtggcaggt gtggtgacca cagtgatggg cagctcccag 720
cccgtggtga cccgaggcac caccgacaac ctcatccctg tctattgctc catcctggct 780
gctgtggttg tgggccttgt ggcctacata gccttcaaga ggtggaacag ctgcaagcag 840
aacaagcaag gagccaacag ccggccagtg aaccagacgc ccccaccaga gggagaaaaa 900
ctccacagcg acagtggcat ctccgtggac agccagagcc tgcatgacca gcagccccac 960
acgcagacag cctcgggcca ggccctcaag ggtgacggag gcctctacag cagcctgccc 1020
ccagccaagc gggaggaggt ggagaagctt ctcaacggct ctgcggggga cacctggcgg 1080
cacctggcgg gcgagctggg ctaccagccc gagcacatag actcctttac ccatgaggcc 1140
tgccccgttc gcgccctgct tgcaagctgg gccacccagg acagcgccac actggacgcc 1200
ctcctggccg ccctgcgccg catccagcga gccgacctcg tggagagtct gtgcagtgag 1260
tccactgcca catccccggt gtga 1284

<210> SEQ ID NO 154
<211> LENGTH: 427

<212> TYPE: PRT
<213> ORGANISM: Unknown
<220> FEATURE:
<223> OTHER INFORMATION: Description of Unknown:
Low-affinity nerve growth factor receptor (LNGFR, TNFRSF16)
sequence

<400> SEQUENCE: 154

Met Gly Ala Gly Ala Thr Gly Arg Ala Met Asp Gly Pro Arg Leu Leu
1 5 10 15

Leu Leu Leu Leu Leu Gly Val Ser Leu Gly Gly Ala Lys Glu Ala Cys
20 25 30

Pro Thr Gly Leu Tyr Thr His Ser Gly Glu Cys Cys Lys Ala Cys Asn
35 40 45

Leu Gly Glu Gly Val Ala Gln Pro Cys Gly Ala Asn Gln Thr Val Cys
50 55 60

Glu Pro Cys Leu Asp Ser Val Thr Phe Ser Asp Val Val Ser Ala Thr
65 70 75 80

Glu Pro Cys Lys Pro Cys Thr Glu Cys Val Gly Leu Gln Ser Met Ser
85 90 95

Ala Pro Cys Val Glu Ala Asp Asp Ala Val Cys Arg Cys Ala Tyr Gly
100 105 110

Tyr Tyr Gln Asp Glu Thr Thr Gly Arg Cys Glu Ala Cys Arg Val Cys
115 120 125

Glu Ala Gly Ser Gly Leu Val Phe Ser Cys Gln Asp Lys Gln Asn Thr
130 135 140

Val Cys Glu Glu Cys Pro Asp Gly Thr Tyr Ser Asp Glu Ala Asn His
145 150 155 160

Val Asp Pro Cys Leu Pro Cys Thr Val Cys Glu Asp Thr Glu Arg Gln
165 170 175

Leu Arg Glu Cys Thr Arg Trp Ala Asp Ala Glu Cys Glu Glu Ile Pro
180 185 190

Gly Arg Trp Ile Thr Arg Ser Thr Pro Pro Glu Gly Ser Asp Ser Thr
195 200 205

Ala Pro Ser Thr Gln Glu Pro Glu Ala Pro Pro Glu Gln Asp Leu Ile
210 215 220

Ala Ser Thr Val Ala Gly Val Val Thr Thr Val Met Gly Ser Ser Gln
225 230 235 240

Pro Val Val Thr Arg Gly Thr Thr Asp Asn Leu Ile Pro Val Tyr Cys
245 250 255

Ser Ile Leu Ala Ala Val Val Val Gly Leu Val Ala Tyr Ile Ala Phe
260 265 270

Lys Arg Trp Asn Ser Cys Lys Gln Asn Lys Gln Gly Ala Asn Ser Arg
275 280 285

Pro Val Asn Gln Thr Pro Pro Pro Glu Gly Glu Lys Leu His Ser Asp
290 295 300

Ser Gly Ile Ser Val Asp Ser Gln Ser Leu His Asp Gln Gln Pro His
305 310 315 320

Thr Gln Thr Ala Ser Gly Gln Ala Leu Lys Gly Asp Gly Gly Leu Tyr
325 330 335

Ser Ser Leu Pro Pro Ala Lys Arg Glu Glu Val Glu Lys Leu Leu Asn
340 345 350

Gly Ser Ala Gly Asp Thr Trp Arg His Leu Ala Gly Glu Leu Gly Tyr
355 360 365

Gln Pro Glu His Ile Asp Ser Phe Thr His Glu Ala Cys Pro Val Arg

-continued

```
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425


<210> SEQ ID NO 155
<211> LENGTH: 666
<212> TYPE: DNA
<213> ORGANISM: Unknown
<220> FEATURE:
<223> OTHER INFORMATION: Description of Unknown:
      LNGFR Extracellular Domain (K29-N250) sequence

<400> SEQUENCE: 155

aaggaggcat gccccacagg cctgtacaca cacagcggtg agtgctgcaa agcctgcaac     60

ctgggcgagg gtgtggccca gccttgtgga gccaaccaga ccgtgtgtga gccctgcctg    120

gacagcgtga cgttctccga cgtggtgagc gcgaccgagc cgtgcaagcc gtgcaccgag    180

tgcgtggggc tccagagcat gtcggcgccg tgcgtggagg ccgacgacgc cgtgtgccgc    240

tgcgcctacg gctactacca ggatgagacg actgggcgct gcgaggcgtg ccgcgtgtgc    300

gaggcgggct cgggcctcgt gttctcctgc caggacaagc agaacaccgt gtgcgaggag    360

tgccccgacg gcacgtattc cgacgaggcc aaccacgtgg acccgtgcct gccctgcacc    420

gtgtgcgagg acaccgagcg ccagctccgc gagtgcacac gctgggccga cgccgagtgc    480

gaggagatcc ctggccgttg gattacacgg tccacacccc cagagggctc ggacagcaca    540

gcccccagca cccaggagcc tgaggcacct ccagaacaag acctcatagc cagcacggtg    600

gcaggtgtgg tgaccacagt gatgggcagc tcccagcccg tggtgacccg aggcaccacc    660

gacaac                                                               666


<210> SEQ ID NO 156
<211> LENGTH: 222
<212> TYPE: PRT
<213> ORGANISM: Unknown
<220> FEATURE:
<223> OTHER INFORMATION: Description of Unknown:
      LNGFR Extracellular Domain (K29-N250) sequence

<400> SEQUENCE: 156

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
```

```
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
        195                 200                 205

Gly Ser Ser Gln Pro Val Val Thr Arg Gly Thr Thr Asp Asn
    210                 215                 220


<210> SEQ ID NO 157
<211> LENGTH: 558
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157

gagccctgcc tggacagcgt gacgttctcc gacgtggtga gcgcgaccga gccgtgcaag      60

ccgtgcaccg agtgcgtggg gctccagagc atgtcggcgc cgtgcgtgga ggccgacgac     120

gccgtgtgcc gctgcgccta cggctactac caggatgaga cgactgggcg ctgcgaggcg     180

tgccgcgtgt gcgaggcggg ctcgggcctc gtgttctcct gccaggacaa gcagaacacc     240

gtgtgcgagg agtgccccga cggcacgtat tccgacgagg ccaaccacgt ggacccgtgc     300

ctgccctgca ccgtgtgcga ggacaccgag cgccagctcc gcgagtgcac acgctgggcc     360

gacgccgagt gcgaggagat ccctggccgt tggattacac ggtccacacc cccagagggc     420

tcggacagca cagcccccag cacccaggag cctgaggcac ctccagaaca agacctcata     480

gccagcacgg tggcaggtgt ggtgaccaca gtgatgggca gctcccagcc cgtggtgacc     540

cgaggcacca ccgacaac                                                   558


<210> SEQ ID NO 158
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Pro Cys Leu Asp Ser Val Thr Phe Ser Asp Val Val Ser Ala Thr
1               5                   10                  15

Glu Pro Cys Lys Pro Cys Thr Glu Cys Val Gly Leu Gln Ser Met Ser
            20                  25                  30

Ala Pro Cys Val Glu Ala Asp Asp Ala Val Cys Arg Cys Ala Tyr Gly
        35                  40                  45

Tyr Tyr Gln Asp Glu Thr Thr Gly Arg Cys Glu Ala Cys Arg Val Cys
    50                  55                  60

Glu Ala Gly Ser Gly Leu Val Phe Ser Cys Gln Asp Lys Gln Asn Thr
65                  70                  75                  80

Val Cys Glu Glu Cys Pro Asp Gly Thr Tyr Ser Asp Glu Ala Asn His
                85                  90                  95
```

```
Val Asp Pro Cys Leu Pro Cys Thr Val Cys Glu Asp Thr Glu Arg Gln
            100                 105                 110

Leu Arg Glu Cys Thr Arg Trp Ala Asp Ala Glu Cys Glu Glu Ile Pro
        115                 120                 125

Gly Arg Trp Ile Thr Arg Ser Thr Pro Pro Glu Gly Ser Asp Ser Thr
    130                 135                 140

Ala Pro Ser Thr Gln Glu Pro Glu Ala Pro Pro Glu Gln Asp Leu Ile
145                 150                 155                 160

Ala Ser Thr Val Ala Gly Val Val Thr Thr Val Met Gly Ser Ser Gln
                165                 170                 175

Pro Val Val Thr Arg Gly Thr Thr Asp Asn
            180                 185
```

<210> SEQ ID NO 159
<211> LENGTH: 429
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159

```
cgctgcgcct acggctacta ccaggatgag acgactgggc gctgcgaggc gtgccgcgtg     60

tgcgaggcgg gctcgggcct cgtgttctcc tgccaggaca agcagaacac cgtgtgcgag    120

gagtgccccg acggcacgta ttccgacgag gccaaccacg tggacccgtg cctgccctgc    180

accgtgtgcg aggacaccga gcgccagctc cgcgagtgca cacgctgggc cgacgccgag    240

tgcgaggaga tccctggccg ttggattaca cggtccacac ccccagaggg ctcggacagc    300

acagccccca gcacccagga gcctgaggca cctccagaac aagacctcat agccagcacg    360

gtggcaggtg tggtgaccac agtgatgggc agctcccagc ccgtggtgac ccgaggcacc    420

accgacaac                                                            429
```

<210> SEQ ID NO 160
<211> LENGTH: 143
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 160

```
Arg Cys Ala Tyr Gly Tyr Tyr Gln Asp Glu Thr Thr Gly Arg Cys Glu
1               5                   10                  15

Ala Cys Arg Val Cys Glu Ala Gly Ser Gly Leu Val Phe Ser Cys Gln
            20                  25                  30

Asp Lys Gln Asn Thr Val Cys Glu Glu Cys Pro Asp Gly Thr Tyr Ser
        35                  40                  45

Asp Glu Ala Asn His Val Asp Pro Cys Leu Pro Cys Thr Val Cys Glu
    50                  55                  60

Asp Thr Glu Arg Gln Leu Arg Glu Cys Thr Arg Trp Ala Asp Ala Glu
65                  70                  75                  80

Cys Glu Glu Ile Pro Gly Arg Trp Ile Thr Arg Ser Thr Pro Pro Glu
                85                  90                  95

Gly Ser Asp Ser Thr Ala Pro Ser Thr Gln Glu Pro Glu Ala Pro Pro
            100                 105                 110

Glu Gln Asp Leu Ile Ala Ser Thr Val Ala Gly Val Val Thr Thr Val
```

```
        115                 120                 125

Met Gly Ser Ser Gln Pro Val Val Thr Arg Gly Thr Thr Asp Asn
    130                 135                 140
```

<210> SEQ ID NO 161
<211> LENGTH: 732
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 161

```
aaggaggcat gccccacagg cctgtacaca cacagcggtg agtgctgcaa agcctgcaac     60

ctgggcgagg gtgtggccca gccttgtgga gccaaccaga ccgtgtgtga gccctgcctg    120

gacagcgtga cgttctccga cgtggtgagc gcgaccgagc cgtgcaagcc gtgcaccgag    180

tgcgtggggc tccagagcat gtcggcgccg tgcgtggagg ccgacgacgc cgtgtgccgc    240

tgcgcctacg gctactacca ggatgagacg actgggcgct gcgaggcgtg ccgcgtgtgc    300

gaggcgggct cgggcctcgt gttctcctgc caggacaagc agaacaccgt gtgcgaggag    360

tgccccgacg gcacgtattc cgacgaggcc aaccacgtgg acccgtgcct gccctgcacc    420

gtgtgcgagg acaccgagcg ccagctccgc gagtgcacac gctgggccga cgccgagtgc    480

gaggagatcc ctggccgttg gattacacgg tccacacccc cagagggctc ggacagcaca    540

gcccccagca cccaggagcc tgaggcacct ccagaacaag acctcatagc cagcacggtg    600

gcaggtgtgg tgaccacagt gatgggcagc tcccagcccg tggtgacccg aggcaccacc    660

gacaacctca tccctgtcta ttgctccatc ctggctgctg tggttgtggg ccttgtggcc    720

tacatagcct tc                                                        732
```

<210> SEQ ID NO 162
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 162

```
Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140
```

Thr Glu Arg Gln Leu Arg Glu Cys Thr Arg Trp Ala Asp Ala Glu Cys
145 150 155 160

Glu Glu Ile Pro Gly Arg Trp Ile Thr Arg Ser Thr Pro Pro Glu Gly
165 170 175

Ser Asp Ser Thr Ala Pro Ser Thr Gln Glu Pro Glu Ala Pro Pro Glu
180 185 190

Gln Asp Leu Ile Ala Ser Thr Val Ala Gly Val Val Thr Thr Val Met
195 200 205

Gly Ser Ser Gln Pro Val Val Thr Arg Gly Thr Thr Asp Asn Leu Ile
210 215 220

Pro Val Tyr Cys Ser Ile Leu Ala Ala Val Val Val Gly Leu Val Ala
225 230 235 240

Tyr Ile Ala Phe

<210> SEQ ID NO 163
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

Lys Glu Ala Cys Pro Thr Gly Leu Tyr Thr His Ser Gly Glu Cys Cys
1 5 10 15

Lys Ala Cys Asn Leu Gly Glu Gly Val Ala Gln Pro Cys Gly Ala Asn
20 25 30

Gln Thr Val Cys Glu Pro Cys Leu Asp Ser Val Thr Phe Ser Asp Val
35 40 45

Val Ser Ala Thr Glu Pro Cys Lys Pro Cys Thr Glu Cys Val Gly Leu
50 55 60

Gln Ser Met Ser Ala Pro Cys Val Glu Ala Asp Asp Ala Val Cys Arg
65 70 75 80

Cys Ala Tyr Gly Tyr Tyr Gln Asp Glu Thr Thr Gly Arg Cys Glu Ala
85 90 95

Cys Arg Val Cys Glu Ala Gly Ser Gly Leu Val Phe Ser Cys Gln Asp
100 105 110

Lys Gln Asn Thr Val Cys Glu Glu Cys Pro Asp Gly Thr Tyr Ser Asp
115 120 125

Glu Ala Asn His Val Asp Pro Cys Leu Pro Cys Thr Val Cys Glu Asp
130 135 140

Thr Glu Arg Gln Leu Arg Glu Cys Thr Arg Trp Ala Asp Ala Glu Cys
145 150 155 160

Glu Glu Ile Pro Gly Arg Trp Ile Thr Arg Ser Thr Pro Pro Glu Gly
165 170 175

Ser Asp Ser Thr Ala Pro Ser Thr Gln Glu Pro Glu Ala Pro Pro Glu
180 185 190

Gln Asp Leu Ile Ala Ser Thr Val Ala Gly Val Val Thr Thr Val Met
195 200 205

Gly Ser Ser Gln Pro Val Val Thr Arg Gly Thr Thr Asp Asn Gly Gly
210 215 220

Gly Gly Ser Gly Gly Gly Gly Ser Gly Gly Gly Gly Ser Gly Gly Gly
225 230 235 240

Gly Ser Phe Trp Val Leu Val Val Val Gly Gly Val Leu Ala Cys Tyr
245 250 255

```
Ser Leu Leu Val Thr Val Ala Phe Ile Ile Phe Trp Val Arg Ser Lys
            260                 265                 270

Arg Ser


<210> SEQ ID NO 164
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Pro Cys Leu Asp Ser Val Thr Phe Ser Asp Val Val Ser Ala Thr
1               5                   10                  15

Glu Pro Cys Lys Pro Cys Thr Glu Cys Val Gly Leu Gln Ser Met Ser
            20                  25                  30

Ala Pro Cys Val Glu Ala Asp Asp Ala Val Cys Arg Cys Ala Tyr Gly
        35                  40                  45

Tyr Tyr Gln Asp Glu Thr Thr Gly Arg Cys Glu Ala Cys Arg Val Cys
    50                  55                  60

Glu Ala Gly Ser Gly Leu Val Phe Ser Cys Gln Asp Lys Gln Asn Thr
65                  70                  75                  80

Val Cys Glu Glu Cys Pro Asp Gly Thr Tyr Ser Asp Glu Ala Asn His
                85                  90                  95

Val Asp Pro Cys Leu Pro Cys Thr Val Cys Glu Asp Thr Glu Arg Gln
            100                 105                 110

Leu Arg Glu Cys Thr Arg Trp Ala Asp Ala Glu Cys Glu Glu Ile Pro
        115                 120                 125

Gly Arg Trp Ile Thr Arg Ser Thr Pro Pro Glu Gly Ser Asp Ser Thr
    130                 135                 140

Ala Pro Ser Thr Gln Glu Pro Glu Ala Pro Pro Glu Gln Asp Leu Ile
145                 150                 155                 160

Ala Ser Thr Val Ala Gly Val Val Thr Thr Val Met Gly Ser Ser Gln
                165                 170                 175

Pro Val Val Thr Arg Gly Thr Thr Asp Asn Gly Gly Gly Gly Ser Gly
            180                 185                 190

Gly Gly Gly Ser Gly Gly Gly Gly Ser Gly Gly Gly Gly Ser Phe Trp
        195                 200                 205

Val Leu Val Val Val Gly Gly Val Leu Ala Cys Tyr Ser Leu Leu Val
    210                 215                 220

Thr Val Ala Phe Ile Ile Phe Trp Val Arg Ser Lys Arg Ser
225                 230                 235


<210> SEQ ID NO 165
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Arg Cys Ala Tyr Gly Tyr Tyr Gln Asp Glu Thr Thr Gly Arg Cys Glu
1               5                   10                  15

Ala Cys Arg Val Cys Glu Ala Gly Ser Gly Leu Val Phe Ser Cys Gln
            20                  25                  30
```

```
Asp Lys Gln Asn Thr Val Cys Glu Glu Cys Pro Asp Gly Thr Tyr Ser
        35                  40                  45

Asp Glu Ala Asn His Val Asp Pro Cys Leu Pro Cys Thr Val Cys Glu
    50                  55                  60

Asp Thr Glu Arg Gln Leu Arg Glu Cys Thr Arg Trp Ala Asp Ala Glu
65                  70                  75                  80

Cys Glu Glu Ile Pro Gly Arg Trp Ile Thr Arg Ser Thr Pro Pro Glu
                85                  90                  95

Gly Ser Asp Ser Thr Ala Pro Ser Thr Gln Glu Pro Glu Ala Pro Pro
            100                 105                 110

Glu Gln Asp Leu Ile Ala Ser Thr Val Ala Gly Val Val Thr Thr Val
        115                 120                 125

Met Gly Ser Ser Gln Pro Val Val Thr Arg Gly Thr Thr Asp Asn Gly
    130                 135                 140

Gly Gly Gly Ser Gly Gly Gly Gly Ser Gly Gly Gly Gly Ser Gly Gly
145                 150                 155                 160

Gly Gly Ser Phe Trp Val Leu Val Val Val Gly Gly Val Leu Ala Cys
                165                 170                 175

Tyr Ser Leu Leu Val Thr Val Ala Phe Ile Ile Phe Trp Val Arg Ser
            180                 185                 190

Lys Arg Ser
        195
```

<210> SEQ ID NO 166
<211> LENGTH: 193
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

```
Arg Cys Ala Tyr Gly Tyr Tyr Gln Asp Glu Thr Thr Gly Arg Cys Glu
1               5                   10                  15

Ala Cys Arg Val Cys Glu Ala Gly Ser Gly Leu Val Phe Ser Cys Gln
            20                  25                  30

Asp Lys Gln Asn Thr Val Cys Glu Glu Cys Pro Asp Gly Thr Tyr Ser
        35                  40                  45

Asp Glu Ala Asn His Val Asp Pro Cys Leu Pro Cys Thr Val Cys Glu
    50                  55                  60

Asp Thr Glu Arg Gln Leu Arg Glu Cys Thr Arg Trp Ala Asp Ala Glu
65                  70                  75                  80

Cys Glu Glu Ile Pro Gly Arg Trp Ile Thr Arg Ser Thr Pro Pro Glu
                85                  90                  95

Gly Ser Asp Ser Thr Ala Pro Ser Thr Gln Glu Pro Glu Ala Pro Pro
            100                 105                 110

Glu Gln Asp Leu Ile Ala Ser Thr Val Ala Gly Val Val Thr Thr Val
        115                 120                 125

Met Gly Ser Ser Gln Pro Val Val Thr Arg Gly Thr Thr Asp Asn Gly
    130                 135                 140

Gly Gly Gly Ser Gly Gly Gly Gly Ser Gly Gly Gly Gly Ser Gly Gly
145                 150                 155                 160

Gly Gly Ser Glu Ile Thr Leu Ile Ile Phe Gly Val Met Ala Gly Val
                165                 170                 175

Ile Gly Thr Ile Leu Leu Ile Ser Tyr Gly Ile Arg Arg Gly Gly Gly
            180                 185                 190
```

Ser

<210> SEQ ID NO 167
<211> LENGTH: 190
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 167

Arg Cys Ala Tyr Gly Tyr Tyr Gln Asp Glu Thr Thr Gly Arg Cys Glu
1 5 10 15

Ala Cys Arg Val Cys Glu Ala Gly Ser Gly Leu Val Phe Ser Cys Gln
20 25 30

Asp Lys Gln Asn Thr Val Cys Glu Glu Cys Pro Asp Gly Thr Tyr Ser
35 40 45

Asp Glu Ala Asn His Val Asp Pro Cys Leu Pro Cys Thr Val Cys Glu
50 55 60

Asp Thr Glu Arg Gln Leu Arg Glu Cys Thr Arg Trp Ala Asp Ala Glu
65 70 75 80

Cys Glu Glu Ile Pro Gly Arg Trp Ile Thr Arg Ser Thr Pro Pro Glu
85 90 95

Gly Ser Asp Ser Thr Ala Pro Ser Thr Gln Glu Pro Glu Ala Pro Pro
100 105 110

Glu Gln Asp Leu Ile Ala Ser Thr Val Ala Gly Val Val Thr Thr Val
115 120 125

Met Gly Ser Ser Gln Pro Val Val Thr Arg Gly Thr Thr Asp Asn Gly
130 135 140

Gly Gly Gly Ser Gly Gly Gly Gly Ser Gly Gly Gly Gly Ser Gly Gly
145 150 155 160

Gly Gly Ser Ile Thr Leu Ile Ile Phe Gly Val Met Ala Gly Val Ile
165 170 175

Gly Thr Ile Leu Leu Ala Leu Leu Ile Trp Gly Gly Gly Ser
180 185 190

<210> SEQ ID NO 168
<211> LENGTH: 190
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 168

Arg Cys Ala Tyr Gly Tyr Tyr Gln Asp Glu Thr Thr Gly Arg Cys Glu
1 5 10 15

Ala Cys Arg Val Cys Glu Ala Gly Ser Gly Leu Val Phe Ser Cys Gln
20 25 30

Asp Lys Gln Asn Thr Val Cys Glu Glu Cys Pro Asp Gly Thr Tyr Ser
35 40 45

Asp Glu Ala Asn His Val Asp Pro Cys Leu Pro Cys Thr Val Cys Glu
50 55 60

Asp Thr Glu Arg Gln Leu Arg Glu Cys Thr Arg Trp Ala Asp Ala Glu
65 70 75 80

Cys Glu Glu Ile Pro Gly Arg Trp Ile Thr Arg Ser Thr Pro Pro Glu
85 90 95

```
Gly Ser Asp Ser Thr Ala Pro Ser Thr Gln Glu Pro Glu Ala Pro Pro
            100                 105                 110

Glu Gln Asp Leu Ile Ala Ser Thr Val Ala Gly Val Val Thr Thr Val
        115                 120                 125

Met Gly Ser Ser Gln Pro Val Val Thr Arg Gly Thr Thr Asp Asn Gly
    130                 135                 140

Gly Gly Gly Ser Gly Gly Gly Gly Ser Gly Gly Gly Gly Ser Gly Gly
145                 150                 155                 160

Gly Gly Ser Ile Thr Leu Ile Ile Phe Gly Val Met Ala Gly Val Ile
                165                 170                 175

Gly Thr Ile Leu Leu Ala Leu Leu Ile Trp Gly Gly Gly Ser
            180                 185                 190


<210> SEQ ID NO 169
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169

atggcgctgc ccgtgaccgc cttgctcctg ccgctggcct tgctgctcca cgccgccagg     60

ccggacatcc agatgacaca gactacatcc tccctgtctg cctctctggg agacagagtc    120

accatcagtt gcagggcaag tcaggacatt agtaaatatt taaattggta tcagcagaaa    180

ccagatggaa ctgttaaact cctgatctac catacatcaa gattacactc aggagtccca    240

tcaaggttca gtggcagtgg gtctggaaca gattattctc tcaccattag caatttggag    300

caggaagata ttgccactta cttttgccaa cagggtaata cgcttccgta cacgttcgga    360

ggggggacca agctggagat cacaggtggc ggtggctcgg gcggtggtgg gtcgggtggc    420

ggcggatctg aggtgaaact gcaggagtca ggacctggcc tggtggcgcc ctcacagagc    480

ctgtccgtca catgcactgt ctcaggggtc tcattacccg actatggtgt aagctggatt    540

cgccagcctc cacgaaaggg tctggagtgg ctgggagtaa tatggggtag tgaaaccaca    600

tactataatt cagctctcaa atccagactg accatcatca aggacaactc caagagccaa    660

gttttcttaa aaatgaacag tctgcaaact gatgacacag ccatttacta ctgtgccaaa    720

cattattact acggtggtag ctatgctatg gactactggg gccaaggaac ctcagtcacc    780

gtctcctcaa ccacgacgcc agcgccgcga ccaccaacac cggcgcccac catcgcgtcg    840

cagcccctgt ccctgcgccc agaggcgtgt agaccggctg caggtggagc agtgcacacg    900

agggggctgg acttcgcctg tgatatctac atctgggcgc ccttggccgg gacttgtggg    960

gtccttctcc tgtcactggt tatcaccctt tactgccgcg tcaagttcag caggagcgca   1020

gacgcccccg cgtacaagca gggccagaac cagctctata acgagctcaa tctaggacga   1080

agagaggagt acgatgtttt ggacaagaga cgtggccggg accctgagat ggggggaaag   1140

ccgagaagga agaaccctca ggaaggcctg tacaatgaac tgcagaaaga taagatggcg   1200

gaggcctaca gtgagattgg gatgaaaggc gagcgccgga ggggcaaggg gcacgatggc   1260

ctttaccagg gtctcagtac agccaccaag gacacctacg acgcccttca catgcaggcc   1320

ctgccccctc gc                                                       1332


<210> SEQ ID NO 170
<211> LENGTH: 444
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 170

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Val Lys Phe
                325                 330                 335

Ser Arg Ser Ala Asp Ala Pro Ala Tyr Lys Gln Gly Gln Asn Gln Leu
            340                 345                 350

Tyr Asn Glu Leu Asn Leu Gly Arg Arg Glu Glu Tyr Asp Val Leu Asp
        355                 360                 365

Lys Arg Arg Gly Arg Asp Pro Glu Met Gly Gly Lys Pro Arg Arg Lys
    370                 375                 380
```

-continued

```
Asn Pro Gln Glu Gly Leu Tyr Asn Glu Leu Gln Lys Asp Lys Met Ala
385                 390                 395                 400

Glu Ala Tyr Ser Glu Ile Gly Met Lys Gly Glu Arg Arg Arg Gly Lys
                405                 410                 415

Gly His Asp Gly Leu Tyr Gln Gly Leu Ser Thr Ala Thr Lys Asp Thr
            420                 425                 430

Tyr Asp Ala Leu His Met Gln Ala Leu Pro Pro Arg
        435                 440
```

<210> SEQ ID NO 171
<211> LENGTH: 1467
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 171

```
atggccttac cagtgaccgc cttgctcctg ccgctggcct tgctgctcca cgccgccagg     60

ccggacatcc agatgacaca gactacatcc tccctgtctg cctctctggg agacagagtc    120

accatcagtt gcagggcaag tcaggacatt agtaaatatt taaattggta tcagcagaaa    180

ccagatggaa ctgttaaact cctgatctac catacatcaa gattacactc aggagtccca    240

tcaaggttca gtggcagtgg gtctggaaca gattattctc tcaccattag caacctggag    300

caagaagata ttgccactta cttttgccaa cagggtaata cgcttccgta cacgttcgga    360

ggggggacca agctggagat cacaggcagc acctccggca gcggcaagcc tggcagcggc    420

gagggcagca ccaagggcga ggtgaaactg caggagtcag gacctggcct ggtggcgccc    480

tcacagagcc tgtccgtcac atgcactgtc tcaggggtct cattacccga ctatggtgta    540

agctggattc gccagcctcc acgaaagggt ctggagtggc tgggagtaat atggggtagt    600

gaaaccacat actataattc agctctcaaa tccagactga ccatcatcaa ggacaactcc    660

aagagccaag ttttcttaaa aatgaacagt ctgcaaactg atgacacagc catttactac    720

tgtgccaaac attattacta cggtggtagc tatgctatgg actactgggg ccaaggaacc    780

tcagtcaccg tctcctcaac cacgacgcca gcgccgcgac caccaacacc ggcgcccacc    840

atcgcgtcgc agcccctgtc cctgcgccca gaggcgtgcc ggccagcggc ggggggcgca    900

gtgcacacga gggggctgga cttcgcctgt gatatctaca tctgggcgcc cttggccggg    960

acttgtgggg tccttctcct gtcactggtt atcacccttt actgcaaacg gggcagaaag   1020

aaactcctgt atatattcaa acaaccattt atgagaccag tacaaactac tcaagaggaa   1080

gatggctgta gctgccgatt tccagaagaa gaagaaggag gatgtgaact gagagtgaag   1140

ttcagcagga gcgcagacgc ccccgcgtac aagcagggcc agaaccagct ctataacgag   1200

ctcaatctag gacgaagaga ggagtacgat gttttggaca agagacgtgg ccgggaccct   1260

gagatggggg gaaagccgag aaggaagaac cctcaggaag gcctgtacaa tgaactgcag   1320

aaagataaga tggcggaggc ctacagtgag attgggatga aaggcgagcg ccggaggggc   1380

aaggggcacg atggccttta ccagggtctc agtacagcca ccaaggacac ctacgacgcc   1440

cttcacatgc aggccctgcc ccctcgc                                       1467
```

<210> SEQ ID NO 172
<211> LENGTH: 489
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 172

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Ser Thr Ser Gly Ser Gly Lys Pro Gly Ser Gly Glu Gly Ser Thr
130 135 140

Lys Gly Glu Val Lys Leu Gln Glu Ser Gly Pro Gly Leu Val Ala Pro
145 150 155 160

Ser Gln Ser Leu Ser Val Thr Cys Thr Val Ser Gly Val Ser Leu Pro
165 170 175

Asp Tyr Gly Val Ser Trp Ile Arg Gln Pro Pro Arg Lys Gly Leu Glu
180 185 190

Trp Leu Gly Val Ile Trp Gly Ser Glu Thr Thr Tyr Tyr Asn Ser Ala
195 200 205

Leu Lys Ser Arg Leu Thr Ile Ile Lys Asp Asn Ser Lys Ser Gln Val
210 215 220

Phe Leu Lys Met Asn Ser Leu Gln Thr Asp Asp Thr Ala Ile Tyr Tyr
225 230 235 240

Cys Ala Lys His Tyr Tyr Tyr Gly Gly Ser Tyr Ala Met Asp Tyr Trp
245 250 255

Gly Gln Gly Thr Ser Val Thr Val Ser Ser Thr Thr Thr Pro Ala Pro
260 265 270

Arg Pro Pro Thr Pro Ala Pro Thr Ile Ala Ser Gln Pro Leu Ser Leu
275 280 285

Arg Pro Glu Ala Cys Arg Pro Ala Ala Gly Gly Ala Val His Thr Arg
290 295 300

Gly Leu Asp Phe Ala Cys Asp Ile Tyr Ile Trp Ala Pro Leu Ala Gly
305 310 315 320

Thr Cys Gly Val Leu Leu Leu Ser Leu Val Ile Thr Leu Tyr Cys Lys
325 330 335

Arg Gly Arg Lys Lys Leu Leu Tyr Ile Phe Lys Gln Pro Phe Met Arg
340 345 350

Pro Val Gln Thr Thr Gln Glu Glu Asp Gly Cys Ser Cys Arg Phe Pro
355 360 365

Glu Glu Glu Glu Gly Gly Cys Glu Leu Arg Val Lys Phe Ser Arg Ser
370 375 380

Ala Asp Ala Pro Ala Tyr Lys Gln Gly Gln Asn Gln Leu Tyr Asn Glu
385 390 395 400

Leu Asn Leu Gly Arg Arg Glu Glu Tyr Asp Val Leu Asp Lys Arg Arg
405 410 415

Gly Arg Asp Pro Glu Met Gly Gly Lys Pro Arg Arg Lys Asn Pro Gln
420 425 430

Glu Gly Leu Tyr Asn Glu Leu Gln Lys Asp Lys Met Ala Glu Ala Tyr
435 440 445

Ser Glu Ile Gly Met Lys Gly Glu Arg Arg Arg Gly Lys Gly His Asp
450 455 460

Gly Leu Tyr Gln Gly Leu Ser Thr Ala Thr Lys Asp Thr Tyr Asp Ala
465 470 475 480

Leu His Met Gln Ala Leu Pro Pro Arg
485

<210> SEQ ID NO 173
<211> LENGTH: 1455
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 173
atggcgctgc ccgtgaccgc cttgctcctg ccgctggcct tgctgctcca cgccgccagg 60
ccggacatcc agatgacaca gactacatcc tccctgtctg cctctctggg agacagagtc 120
accatcagtt gcagggcaag tcaggacatt agtaaatatt taaattggta tcagcagaaa 180
ccagatggaa ctgttaaact cctgatctac catacatcaa gattacactc aggagtccca 240
tcaaggttca gtggcagtgg gtctggaaca gattattctc tcaccattag caatttggag 300
caggaagata ttgccactta cttttgccaa cagggtaata cgcttccgta cacgttcgga 360
ggggggacca agctggagat cacaggtggc ggtggctcgg gcggtggtgg gtcgggtggc 420
ggcggatctg aggtgaaact gcaggagtca ggacctggcc tggtggcgcc ctcacagagc 480
ctgtccgtca catgcactgt ctcaggggtc tcattacccg actatggtgt aagctggatt 540
cgccagcctc cacgaaaggg tctggagtgg ctgggagtaa tatggggtag tgaaaccaca 600
tactataatt cagctctcaa atccagactg accatcatca aggacaactc caagagccaa 660
gttttcttaa aaatgaacag tctgcaaact gatgacacag ccatttacta ctgtgccaaa 720
cattattact acggtggtag ctatgctatg gactactggg gccaaggaac ctcagtcacc 780
gtctcctcaa ccacgacgcc agcgccgcga ccaccaacac cggcgcccac catcgcgtcg 840
cagcccctgt ccctgcgccc agaggcgtgt agaccggctg caggtggagc agtgcacacg 900
agggggctgg acttcgcctg tgatatctac atctgggcgc ccttggccgg gacttgtggg 960
gtccttctcc tgtcactggt tatcaccctt tactgcagga gtaagaggag caggctcctg 1020
cacagtgact acatgaacat gactccccgc cgccccgggc ccacccgcaa gcattaccag 1080
ccctatgccc caccacgcga cttcgcagcc tatcgctccc gcgtcaagtt cagcaggagc 1140
gcagacgccc ccgcgtacaa gcagggccag aaccagctct ataacgagct caatctagga 1200
cgaagagagg agtacgatgt tttggacaag agacgtggcc gggaccctga gatgggggga 1260
aagccgagaa ggaagaaccc tcaggaaggc ctgtacaatg aactgcagaa agataagatg 1320
gcggaggcct acagtgagat tgggatgaaa ggcgagcgcc ggaggggcaa ggggcacgat 1380
ggcctttacc agggtctcag tacagccacc aaggacacct acgacgccct tcacatgcag 1440
gccctgcccc ctcgc 1455

<210> SEQ ID NO 174
<211> LENGTH: 485
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 174

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Glu
130 135 140

Val Lys Leu Gln Glu Ser Gly Pro Gly Leu Val Ala Pro Ser Gln Ser
145 150 155 160

Leu Ser Val Thr Cys Thr Val Ser Gly Val Ser Leu Pro Asp Tyr Gly
165 170 175

Val Ser Trp Ile Arg Gln Pro Pro Arg Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ile Lys Asp Asn Ser Lys Ser Gln Val Phe Leu Lys
210 215 220

Met Asn Ser Leu Gln Thr Asp Asp Thr Ala Ile Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Arg Ser Lys Arg
325 330 335

Ser Arg Leu Leu His Ser Asp Tyr Met Asn Met Thr Pro Arg Arg Pro
340 345 350

Gly Pro Thr Arg Lys His Tyr Gln Pro Tyr Ala Pro Pro Arg Asp Phe

```
        355                 360                 365

Ala Ala Tyr Arg Ser Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485
```

<210> SEQ ID NO 175
<211> LENGTH: 2031
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 175

```
atgctgctgc tggtgaccag cctgctgctg tgtgagctgc cccaccccgc ctttctgctg     60
atccccgaca tccagatgac ccagaccacc tccagcctga gcgccagcct gggcgaccgg    120
gtgaccatca gctgccgggc cagccaggac atcagcaagt acctgaactg gtatcagcag    180
aagcccgacg gcaccgtcaa gctgctgatc taccacacca gccggctgca cagcggcgtg    240
cccagccggt ttagcggcag cggctccggc accgactaca gcctgaccat ctccaacctg    300
gagcaggagg acatcgccac ctacttttgc cagcagggca acacactgcc ctacaccttt    360
ggcggcggaa caaagctgga gatcaccggc agcacctccg gcagcggcaa gcctggcagc    420
ggcgagggca gcaccaaggg cgaggtgaag ctgcaggaga gcggccctgg cctggtggcc    480
cccagccaga gcctgagcgt gacctgtacc gtgtccggcg tgtccctgcc cgactacggc    540
gtgtcctgga tccggcagcc ccctaggaag ggcctggagt ggctgggcgt gatctggggc    600
agcgagacca cctactacaa cagcgccctg aagagccggc tgaccatcat caaggacaac    660
agcaagagcc aggtgttcct gaagatgaac agcctgcaga ccgacgacac cgccatctac    720
tactgtgcca agcactacta ctacggcggc agctacgcca tggactactg gggccagggc    780
accagcgtga ccgtgtccag cgagagcaag tacggccctc cctgcccccc ttgccctgcc    840
cccgagttcc tgggcggacc cagcgtgttc ctgttccccc ccaagcccaa ggacaccctg    900
atgatcagcc ggacccccga ggtgacctgt gtggtggtgg acgtgtccca ggaggacccc    960
gaggtccagt tcaactggta cgtggacggc gtggaggtgc acaacgccaa gaccaagccc   1020
cgggaggagc agttcaatag cacctaccgg gtggtgtccg tgctgaccgt gctgcaccag   1080
gactggctga acggcaagga atacaagtgt aaggtgtcca acaagggcct gcccagcagc   1140
atcgagaaaa ccatcagcaa ggccaagggc cagcctcggg agccccaggt gtacaccctg   1200
ccccctagcc aagaggagat gaccaagaat caggtgtccc tgacctgcct ggtgaagggc   1260
```

```
ttctacccca gcgacatcgc cgtggagtgg gagagcaacg gccagcccga gaacaactac   1320

aagaccaccc cccctgtgct ggacagcgac ggcagcttct tcctgtacag caggctgacc   1380

gtggacaaga gccggtggca ggagggcaac gtctttagct gctccgtgat gcacgaggcc   1440

ctgcacaacc actacaccca gaagagcctg tccctgagcc tgggcaagat gttctgggtg   1500

ctggtcgtgg tgggtggcgt gctggcctgc tacagcctgc tggtgacagt ggccttcatc   1560

atcttttggg tgaggagcaa gcggagcaga ggcggccaca gcgactacat gaacatgacc   1620

ccccggaggc ctggccccac ccggaagcac taccagccct acgcccctcc cagggacttc   1680

gccgcctacc ggagccgggt gaagttcagc cggagcgccg acgcccctgc ctaccagcag   1740

ggccagaacc agctgtacaa cgagctgaac ctgggccgga gggaggagta cgacgtgctg   1800

gacaagcgga gaggccggga ccctgagatg ggcggcaagc cccggagaaa gaaccctcag   1860

gagggcctgt ataacgaact gcagaaagac aagatggccg aggcctacag cgagatcggc   1920

atgaagggcg agcggcggag gggcaagggc cacgacggcc tgtaccaggg cctgagcacc   1980

gccaccaagg atacctacga cgccctgcac atgcaggccc tgccccccag a            2031
```

<210> SEQ ID NO 176
<211> LENGTH: 677
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220
```

```
Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Glu Ser Lys Tyr Gly
            260                 265                 270

Pro Pro Cys Pro Pro Cys Pro Ala Pro Glu Phe Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser Gln Glu Asp Pro
305                 310                 315                 320

Glu Val Gln Phe Asn Trp Tyr Val Asp Gly Val Glu Val His Asn Ala
                325                 330                 335

Lys Thr Lys Pro Arg Glu Glu Gln Phe Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Gly Leu Pro Ser Ser Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Gln Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Arg Leu Thr Val Asp Lys Ser
    450                 455                 460

Arg Trp Gln Glu Gly Asn Val Phe Ser Cys Ser Val Met His Glu Ala
465                 470                 475                 480

Leu His Asn His Tyr Thr Gln Lys Ser Leu Ser Leu Ser Leu Gly Lys
                485                 490                 495

Met Phe Trp Val Leu Val Val Val Gly Gly Val Leu Ala Cys Tyr Ser
            500                 505                 510

Leu Leu Val Thr Val Ala Phe Ile Ile Phe Trp Val Arg Ser Lys Arg
        515                 520                 525

Ser Arg Gly Gly His Ser Asp Tyr Met Asn Met Thr Pro Arg Arg Pro
    530                 535                 540

Gly Pro Thr Arg Lys His Tyr Gln Pro Tyr Ala Pro Pro Arg Asp Phe
545                 550                 555                 560

Ala Ala Tyr Arg Ser Arg Val Lys Phe Ser Arg Ser Ala Asp Ala Pro
                565                 570                 575

Ala Tyr Gln Gln Gly Gln Asn Gln Leu Tyr Asn Glu Leu Asn Leu Gly
            580                 585                 590

Arg Arg Glu Glu Tyr Asp Val Leu Asp Lys Arg Arg Gly Arg Asp Pro
        595                 600                 605

Glu Met Gly Gly Lys Pro Arg Arg Lys Asn Pro Gln Glu Gly Leu Tyr
    610                 615                 620

Asn Glu Leu Gln Lys Asp Lys Met Ala Glu Ala Tyr Ser Glu Ile Gly
625                 630                 635                 640

Met Lys Gly Glu Arg Arg Arg Gly Lys Gly His Asp Gly Leu Tyr Gln
```

645 650 655

Gly Leu Ser Thr Ala Thr Lys Asp Thr Tyr Asp Ala Leu His Met Gln
660 665 670

Ala Leu Pro Pro Arg
675

<210> SEQ ID NO 177
<211> LENGTH: 1131
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 177
aactgggtga atgtgatcag cgacctgaag aagatcgagg atctgatcca gagcatgcac 60
attgatgcca ccctgtacac agaatctgat gtgcacccta gctgtaaagt gaccgccatg 120 aagtgtttc tgctggagct gcaggtgatt tctctggaaa gcggagatgc ctctatccac 180
gacacagtgg agaatctgat catcctggcc aacaatagcc tgagcagcaa tggcaatgtg 240
acagagtctg gctgtaagga gtgtgaggag ctggaggaga agaacatcaa ggagtttctg 300
cagagctttg tgcacatcgt gcagatgttc atcaatacaa gctctggcgg aggatctgga 360
ggaggcggat ctggaggagg aggcagtgga ggcggaggat ctggcggagg atctctgcag 420
attacatgcc ctcctccaat gtctgtggag cacgccgata tttgggtgaa gtcctacagc 480
ctgtacagca gagagagata catctgcaac agcggcttta agagaaaggc cggcacctct 540
tctctgacag agtgcgtgct gaataaggcc acaaatgtgg cccactggac aacacctagc 600
ctgaagtgca ttagagatcc tgccctggtc caccagaggc ctgcccctcc atctacagtg 660
acaacagccg gagtgacacc tcagcctgaa tctctgagcc cttctggaaa agaacctgcc 720
gccagctctc ctagctctaa taataccgcc gccacaacag ccgccattgt gcctggatct 780
cagctgatgc ctagcaagtc tcctagcaca ggcacaacag agatcagcag ccacgaatct 840
tctcacggaa caccttctca gaccaccgcc aagaattggg agctgacagc ctctgcctct 900
caccagcctc caggagtgta tcctcagggc cactctgata caacagtggc catcagcaca 960
tctacagtgc tgctgtgtgg actgtctgcc gtgtctctgc tggcctgtta cctgaagtct 1020
agacagacac ctcctctggc ctctgtggag atggaggcca tggaagccct gcctgtgaca 1080
tggggaacaa gcagcagaga tgaggacctg gagaattgtt ctcaccacct g 1131

<210> SEQ ID NO 178
<211> LENGTH: 377
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 178

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

Thr Ser Ser Gly Gly Gly Ser Gly Gly Gly Gly Ser Gly Gly Gly Gly
115 120 125

Ser Gly Gly Gly Gly Ser Gly Gly Gly Ser Leu Gln Ile Thr Cys Pro
130 135 140

Pro Pro Met Ser Val Glu His Ala Asp Ile Trp Val Lys Ser Tyr Ser
145 150 155 160

Leu Tyr Ser Arg Glu Arg Tyr Ile Cys Asn Ser Gly Phe Lys Arg Lys
165 170 175

Ala Gly Thr Ser Ser Leu Thr Glu Cys Val Leu Asn Lys Ala Thr Asn
180 185 190

Val Ala His Trp Thr Thr Pro Ser Leu Lys Cys Ile Arg Asp Pro Ala
195 200 205

Leu Val His Gln Arg Pro Ala Pro Pro Ser Thr Val Thr Thr Ala Gly
210 215 220

Val Thr Pro Gln Pro Glu Ser Leu Ser Pro Ser Gly Lys Glu Pro Ala
225 230 235 240

Ala Ser Ser Pro Ser Ser Asn Asn Thr Ala Ala Thr Thr Ala Ala Ile
245 250 255

Val Pro Gly Ser Gln Leu Met Pro Ser Lys Ser Pro Ser Thr Gly Thr
260 265 270

Thr Glu Ile Ser Ser His Glu Ser Ser His Gly Thr Pro Ser Gln Thr
275 280 285

Thr Ala Lys Asn Trp Glu Leu Thr Ala Ser Ala Ser His Gln Pro Pro
290 295 300

Gly Val Tyr Pro Gln Gly His Ser Asp Thr Thr Val Ala Ile Ser Thr
305 310 315 320

Ser Thr Val Leu Leu Cys Gly Leu Ser Ala Val Ser Leu Leu Ala Cys
325 330 335

Tyr Leu Lys Ser Arg Gln Thr Pro Pro Leu Ala Ser Val Glu Met Glu
340 345 350

Ala Met Glu Ala Leu Pro Val Thr Trp Gly Thr Ser Ser Arg Asp Glu
355 360 365

Asp Leu Glu Asn Cys Ser His His Leu
370 375

<210> SEQ ID NO 179
<211> LENGTH: 841
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile

-continued

```
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Ile Tyr Ile Trp Ala Pro Leu Ala Gly Thr Cys Gly Val Leu
    290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Lys Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460
```

-continued

```
Leu Pro Pro Arg Glu Gly Arg Gly Ser Leu Leu Thr Cys Gly Asp Val
465                 470                 475                 480

Glu Glu Asn Pro Gly Pro Met Arg Leu Pro Ala Gln Leu Leu Gly Leu
                485                 490                 495

Leu Met Leu Trp Val Pro Gly Ser Ser Gly Arg Lys Val Cys Asn Gly
            500                 505                 510

Ile Gly Ile Gly Glu Phe Lys Asp Ser Leu Ser Ile Asn Ala Thr Asn
        515                 520                 525

Ile Lys His Phe Lys Asn Cys Thr Ser Ile Ser Gly Asp Leu His Ile
    530                 535                 540

Leu Pro Val Ala Phe Arg Gly Asp Ser Phe Thr His Thr Pro Pro Leu
545                 550                 555                 560

Asp Pro Gln Glu Leu Asp Ile Leu Lys Thr Val Lys Glu Ile Thr Gly
                565                 570                 575

Phe Leu Leu Ile Gln Ala Trp Pro Glu Asn Arg Thr Asp Leu His Ala
            580                 585                 590

Phe Glu Asn Leu Glu Ile Ile Arg Gly Arg Thr Lys Gln His Gly Gln
        595                 600                 605

Phe Ser Leu Ala Val Val Ser Leu Asn Ile Thr Ser Leu Gly Leu Arg
    610                 615                 620

Ser Leu Lys Glu Ile Ser Asp Gly Asp Val Ile Ile Ser Gly Asn Lys
625                 630                 635                 640

Asn Leu Cys Tyr Ala Asn Thr Ile Asn Trp Lys Lys Leu Phe Gly Thr
                645                 650                 655

Ser Gly Gln Lys Thr Lys Ile Ile Ser Asn Arg Gly Glu Asn Ser Cys
            660                 665                 670

Lys Ala Thr Gly Gln Val Cys His Ala Leu Cys Ser Pro Glu Gly Cys
        675                 680                 685

Trp Gly Pro Glu Pro Arg Asp Cys Val Ser Cys Arg Asn Val Ser Arg
    690                 695                 700

Gly Arg Glu Cys Val Asp Lys Cys Asn Leu Leu Glu Gly Glu Pro Arg
705                 710                 715                 720

Glu Phe Val Glu Asn Ser Glu Cys Ile Gln Cys His Pro Glu Cys Leu
                725                 730                 735

Pro Gln Ala Met Asn Ile Thr Cys Thr Gly Arg Gly Pro Asp Asn Cys
            740                 745                 750

Ile Gln Cys Ala His Tyr Ile Asp Gly Pro His Cys Val Lys Thr Cys
        755                 760                 765

Pro Ala Gly Val Met Gly Glu Asn Asn Thr Leu Val Trp Lys Tyr Ala
    770                 775                 780

Asp Ala Gly His Val Cys His Leu Cys His Pro Asn Cys Thr Tyr Gly
785                 790                 795                 800

Cys Thr Gly Pro Gly Leu Glu Gly Cys Pro Thr Asn Gly Pro Lys Ile
                805                 810                 815

Pro Ser Ile Ala Thr Gly Met Val Gly Ala Leu Leu Leu Leu Leu Val
            820                 825                 830

Val Ala Leu Gly Ile Gly Leu Phe Met
        835                 840
```

<210> SEQ ID NO 180
<211> LENGTH: 750
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 180

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser
225 230 235 240

Val Thr Val Ser Ser Thr Thr Thr Pro Ala Pro Arg Pro Pro Thr Pro
245 250 255

Ala Pro Thr Ile Ala Ser Gln Pro Leu Ser Leu Arg Pro Glu Ala Cys
260 265 270

Arg Pro Ala Ala Gly Gly Ala Val His Thr Arg Gly Leu Asp Phe Ala
275 280 285

Cys Asp Ile Tyr Ile Trp Ala Pro Leu Ala Gly Thr Cys Gly Val Leu
290 295 300

Leu Leu Ser Leu Val Ile Thr Leu Tyr Cys Lys Arg Gly Arg Lys Lys
305 310 315 320

Leu Leu Tyr Ile Phe Lys Gln Pro Phe Met Arg Pro Val Gln Thr Thr
325 330 335

Gln Glu Glu Asp Gly Cys Ser Cys Arg Phe Pro Glu Glu Glu Glu Gly
340 345 350

Gly Cys Glu Leu Arg Val Lys Phe Ser Arg Ser Ala Asp Ala Pro Ala
355 360 365

Tyr Lys Gln Gly Gln Asn Gln Leu Tyr Asn Glu Leu Asn Leu Gly Arg
370 375 380

Arg Glu Glu Tyr Asp Val Leu Asp Lys Arg Arg Gly Arg Asp Pro Glu
385 390 395 400

Met Gly Gly Lys Pro Arg Arg Lys Asn Pro Gln Glu Gly Leu Tyr Asn
405 410 415

Glu Leu Gln Lys Asp Lys Met Ala Glu Ala Tyr Ser Glu Ile Gly Met
420 425 430

Lys Gly Glu Arg Arg Arg Gly Lys Gly His Asp Gly Leu Tyr Gln Gly
435 440 445

Leu Ser Thr Ala Thr Lys Asp Thr Tyr Asp Ala Leu His Met Gln Ala
450 455 460

Leu Pro Pro Arg Glu Gly Arg Gly Ser Leu Leu Thr Cys Gly Asp Val
465 470 475 480

Glu Glu Asn Pro Gly Pro Met Arg Leu Pro Ala Gln Leu Leu Gly Leu
485 490 495

Leu Met Leu Trp Val Pro Gly Ser Ser Gly Arg Lys Val Cys Asn Gly
500 505 510

Ile Gly Ile Gly Glu Phe Lys Asp Ser Leu Ser Ile Asn Ala Thr Asn
515 520 525

Ile Lys His Phe Lys Asn Cys Thr Ser Ile Ser Gly Asp Leu His Ile
530 535 540

Leu Pro Val Ala Phe Arg Gly Asp Ser Phe Thr His Thr Pro Pro Leu
545 550 555 560

Asp Pro Gln Glu Leu Asp Ile Leu Lys Thr Val Lys Glu Ile Thr Gly
565 570 575

Phe Leu Leu Ile Gln Ala Trp Pro Glu Asn Arg Thr Asp Leu His Ala
580 585 590

Phe Glu Asn Leu Glu Ile Ile Arg Gly Arg Thr Lys Gln His Gly Gln
595 600 605

Phe Ser Leu Ala Val Val Ser Leu Asn Ile Thr Ser Leu Gly Leu Arg
610 615 620

Ser Leu Lys Glu Ile Ser Asp Gly Asp Val Ile Ile Ser Gly Asn Lys
625 630 635 640

Asn Leu Cys Tyr Ala Asn Thr Ile Asn Trp Lys Lys Leu Phe Gly Thr
645 650 655

Ser Gly Gln Lys Thr Lys Ile Ile Ser Asn Arg Gly Glu Asn Ser Cys
660 665 670

Lys Ala Thr Gly Gln Val Cys His Ala Leu Cys Ser Pro Glu Gly Cys
675 680 685

Trp Gly Pro Glu Pro Arg Asp Cys Val Ser Gly Gly Gly Gly Ser Gly
690 695 700

Gly Gly Gly Ser Gly Gly Gly Gly Ser Gly Gly Gly Gly Ser Phe Trp
705 710 715 720

Val Leu Val Val Val Gly Gly Val Leu Ala Cys Tyr Ser Leu Leu Val
725 730 735

Thr Val Ala Phe Ile Ile Phe Trp Val Arg Ser Lys Arg Ser
740 745 750

<210> SEQ ID NO 181
<211> LENGTH: 2814
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 181
gacatccaaa tgacacagac aaccagcagc ctctctgcca gtctgggaga tcgtgtgacc 60
atcagttgta gagcctcaca agatatttcc aaatacctaa actggtatca gcaaaaacca 120
gatggtacag tgaagttact gatctaccat actagccgtc ttcattccgg tgtgccttct 180
cgctttagcg ggtctggatc aggaacagat tacagtctca ccatcagcaa cctcgaacaa 240
gaagatatag ctacctattt ctgccagcag ggtaacactt tgccatatac cttcggagga 300
ggcacaaaac tggagatcac tggttctacc agtggaagcg gcaagcctgg ctccggtgaa 360
ggaagtacca aaggcgaagt gaagctgcaa gagtcaggtc caggtttggt agctcccagc 420
caatccctat ctgttacctg tacagtgtct ggtgtgtcac ttccagatta tggcgtgtca 480
tggataaggc agcccccacg aaaaggcctg gaatggttgg gggtgatctg gggatctgag 540
accacctact acaacagcgc cctgaaaagt cggctcacca tcatcaaaga caactccaag 600
tcacaagtgt ttcttaagat gaactcactt cagaccgacg acacagccat atactactgt 660
gctaaacatt actactatgg cggtagctat gccatggatt actggggtca aggtactagt 720
gtgacagtat catctgaatc aaagtatggc ccaccctgcc ccccttgtcc cgctcctgag 780
ttcctgggtg gtccctccgt attcctgttt ccacctaagc caaaagacac tctcatgatc 840
agcagaacac ctgaggtgac atgcgtcgta gttgatgtta gccaggagga ccccgaagtg 900
caatttaact ggtacgtaga cggtgtggaa gtgcataacg caaagaccaa gccacgtgaa 960
gagcagttta actccaccta ccgagtggtg tctgtgctca cagtcttaca tcaagattgg 1020
ctgaacggaa aagagtataa atgtaaagta tccaataagg gccttccctc tagcatcgaa 1080
aagactatct ccaaagccaa gggacagcca cgcgaaccac aggtgtatac tttacctcct 1140
tctcaagaag agatgaccaa gaaccaagta tctctgacgt gtttggtgaa ggggttctac 1200
ccctctgaca tcgcagtgga atgggaatca aacggtcaac ctgagaacaa ttacaaaacc 1260
accccacctg tgctggatag cgacggcagc ttctttctgt atagcaggct cacagtggat 1320
aaaagtcggt ggcaggaagg aaacgtattt agttgcagtg tgatgcacga ggccctccat 1380
aaccattata cccagaagtc actctcactt agtctgggta agatgttctg ggtgctcgtg 1440
gtcgtaggtg gagtgctggc ttgctactcc ctcttagtga ccgtggcttt tatcatcttc 1500
tgggtacgtt ccaaaaggtc ccgtggtggc cattcagatt acatgaatat gacccccaga 1560
cgaccaggcc caacaaggaa gcattatcaa ccttacgccc ctccccgaga ttttgcagct 1620
tatcgaagta gggtgaagtt cagccggtct gctgacgctc ctgcatacca gcaaggtcag 1680
aatcagttat acaatgagct aaatctagga cgacgcgaag aatatgatgt gctggacaaa 1740
cgacgtggca gggaccctga aatgggtggc aagccaagaa ggaagaaccc acaagagggt 1800
ctgtacaacg agttgcagaa agacaagatg gcagaggcct actccgagat cggaatgaaa 1860
ggagagaggc ggaggggtaa aggacatgac ggtctttacc agggcctgag cacagctact 1920
aaagatacct acgacgccct ccacatgcag gctttgcccc cacgagctac caattttagt 1980
ctgttgaaac aagctggaga tgtcgaggaa aatccaggcc caatgcgact tcctgctcaa 2040
ctgctgggtc tgctcatgct gtgggttcct ggaagcagtg gccgaaaggt ctgcaacggc 2100
atcggtatcg gcgaatttaa ggatagtcta tctatcaacg ctaccaatat taagcatttt 2160
aagaactgca cgtctatttc cggcgacttg cacatcctcc ctgttgcatt tcggggtgat 2220
agtttcaccc ataccccccc tctcgatcca caagaactgg acattcttaa aaccgttaaa 2280
gaaataacag gttttctcct catccaggca tggcccgaga ataggacaga tcttcacgca 2340
tttgaaaacc tcgaaatcat cagagggagg accaaacagc atggtcagtt tagtctcgca 2400
gtggtgtctc tgaacatcac ttctttaggg cttcgatcac ttaaggaaat ctctgacggt 2460
gatgtaatca tcagcggtaa caagaacctg tgctacgcta acacgatcaa ctggaagaag 2520
ctgtttggca caagcggcca gaaaaccaag atcattagta ataggggcga gaatagctgt 2580
aaagcaaccg ggcaagtgtg tcacgctctg tgttctcccg agggatgttg gggacctgaa 2640
ccaagagact gcgttagtgg aggggggggc tctggtggcg gaggatctgg cggaggcgga 2700
agcggaggcg gggggagctt ctgggtgctc gtggtcgtag gaggggtgct ggcctgttac 2760
tctctactcg taactgttgc tttcatcata ttctgggtcc gaagtaagcg tagc 2814

<210> SEQ ID NO 182
<211> LENGTH: 938
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser
225 230 235 240

Val Thr Val Ser Ser Glu Ser Lys Tyr Gly Pro Pro Cys Pro Pro Cys
245 250 255

Pro Ala Pro Glu Phe Leu Gly Gly Pro Ser Val Phe Leu Phe Pro Pro
260 265 270

Lys Pro Lys Asp Thr Leu Met Ile Ser Arg Thr Pro Glu Val Thr Cys
275 280 285

-continued

```
Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys Met Phe Trp Val Leu Val
465                 470                 475                 480

Val Val Gly Gly Val Leu Ala Cys Tyr Ser Leu Leu Val Thr Val Ala
                485                 490                 495

Phe Ile Ile Phe Trp Val Arg Ser Lys Arg Ser Arg Gly Gly His Ser
            500                 505                 510

Asp Tyr Met Asn Met Thr Pro Arg Arg Pro Gly Pro Thr Arg Lys His
        515                 520                 525

Tyr Gln Pro Tyr Ala Pro Pro Arg Asp Phe Ala Ala Tyr Arg Ser Arg
    530                 535                 540

Val Lys Phe Ser Arg Ser Ala Asp Ala Pro Ala Tyr Gln Gln Gly Gln
545                 550                 555                 560

Asn Gln Leu Tyr Asn Glu Leu Asn Leu Gly Arg Arg Glu Glu Tyr Asp
                565                 570                 575

Val Leu Asp Lys Arg Arg Gly Arg Asp Pro Glu Met Gly Gly Lys Pro
            580                 585                 590

Arg Arg Lys Asn Pro Gln Glu Gly Leu Tyr Asn Glu Leu Gln Lys Asp
        595                 600                 605

Lys Met Ala Glu Ala Tyr Ser Glu Ile Gly Met Lys Gly Glu Arg Arg
    610                 615                 620

Arg Gly Lys Gly His Asp Gly Leu Tyr Gln Gly Leu Ser Thr Ala Thr
625                 630                 635                 640

Lys Asp Thr Tyr Asp Ala Leu His Met Gln Ala Leu Pro Pro Arg Ala
                645                 650                 655

Thr Asn Phe Ser Leu Leu Lys Gln Ala Gly Asp Val Glu Glu Asn Pro
            660                 665                 670

Gly Pro Met Arg Leu Pro Ala Gln Leu Leu Gly Leu Leu Met Leu Trp
        675                 680                 685

Val Pro Gly Ser Ser Gly Arg Lys Val Cys Asn Gly Ile Gly Ile Gly
    690                 695                 700

Glu Phe Lys Asp Ser Leu Ser Ile Asn Ala Thr Asn Ile Lys His Phe
```

```
705                 710                 715                 720

Lys Asn Cys Thr Ser Ile Ser Gly Asp Leu His Ile Leu Pro Val Ala
                725                 730                 735

Phe Arg Gly Asp Ser Phe Thr His Thr Pro Pro Leu Asp Pro Gln Glu
            740                 745                 750

Leu Asp Ile Leu Lys Thr Val Lys Glu Ile Thr Gly Phe Leu Leu Ile
        755                 760                 765

Gln Ala Trp Pro Glu Asn Arg Thr Asp Leu His Ala Phe Glu Asn Leu
    770                 775                 780

Glu Ile Ile Arg Gly Arg Thr Lys Gln His Gly Gln Phe Ser Leu Ala
785                 790                 795                 800

Val Val Ser Leu Asn Ile Thr Ser Leu Gly Leu Arg Ser Leu Lys Glu
                805                 810                 815

Ile Ser Asp Gly Asp Val Ile Ile Ser Gly Asn Lys Asn Leu Cys Tyr
            820                 825                 830

Ala Asn Thr Ile Asn Trp Lys Lys Leu Phe Gly Thr Ser Gly Gln Lys
        835                 840                 845

Thr Lys Ile Ile Ser Asn Arg Gly Glu Asn Ser Cys Lys Ala Thr Gly
    850                 855                 860

Gln Val Cys His Ala Leu Cys Ser Pro Glu Gly Cys Trp Gly Pro Glu
865                 870                 875                 880

Pro Arg Asp Cys Val Ser Gly Gly Gly Gly Ser Gly Gly Gly Gly Ser
                885                 890                 895

Gly Gly Gly Gly Ser Gly Gly Gly Gly Ser Phe Trp Val Leu Val Val
            900                 905                 910

Val Gly Gly Val Leu Ala Cys Tyr Ser Leu Leu Val Thr Val Ala Phe
        915                 920                 925

Ile Ile Phe Trp Val Arg Ser Lys Arg Ser
    930                 935


<210> SEQ ID NO 183
<211> LENGTH: 959
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Met Arg Leu Pro Ala Gln Leu Leu Gly Leu Leu Met Leu Trp Val Pro
1               5                   10                  15

Gly Ser Ser Gly Arg Lys Val Cys Asn Gly Ile Gly Ile Gly Glu Phe
            20                  25                  30

Lys Asp Ser Leu Ser Ile Asn Ala Thr Asn Ile Lys His Phe Lys Asn
        35                  40                  45

Cys Thr Ser Ile Ser Gly Asp Leu His Ile Leu Pro Val Ala Phe Arg
    50                  55                  60

Gly Asp Ser Phe Thr His Thr Pro Pro Leu Asp Pro Gln Glu Leu Asp
65                  70                  75                  80

Ile Leu Lys Thr Val Lys Glu Ile Thr Gly Phe Leu Leu Ile Gln Ala
                85                  90                  95

Trp Pro Glu Asn Arg Thr Asp Leu His Ala Phe Glu Asn Leu Glu Ile
            100                 105                 110

Ile Arg Gly Arg Thr Lys Gln His Gly Gln Phe Ser Leu Ala Val Val
        115                 120                 125
```

```
Ser Leu Asn Ile Thr Ser Leu Gly Leu Arg Ser Leu Lys Glu Ile Ser
    130                 135                 140

Asp Gly Asp Val Ile Ile Ser Gly Asn Lys Asn Leu Cys Tyr Ala Asn
145                 150                 155                 160

Thr Ile Asn Trp Lys Lys Leu Phe Gly Thr Ser Gly Gln Lys Thr Lys
                165                 170                 175

Ile Ile Ser Asn Arg Gly Glu Asn Ser Cys Lys Ala Thr Gly Gln Val
            180                 185                 190

Cys His Ala Leu Cys Ser Pro Glu Gly Cys Trp Gly Pro Glu Pro Arg
        195                 200                 205

Asp Cys Val Ser Gly Gly Gly Gly Ser Gly Gly Gly Gly Ser Gly Gly
    210                 215                 220

Gly Gly Ser Gly Gly Gly Gly Ser Phe Trp Val Leu Val Val Val Gly
225                 230                 235                 240

Gly Val Leu Ala Cys Tyr Ser Leu Leu Val Thr Val Ala Phe Ile Ile
                245                 250                 255

Phe Trp Val Arg Ser Lys Arg Ser Ala Thr Asn Phe Ser Leu Leu Lys
            260                 265                 270

Gln Ala Gly Asp Val Glu Glu Asn Pro Gly Pro Met Ala Leu Pro Val
        275                 280                 285

Thr Ala Leu Leu Leu Pro Leu Ala Leu Leu Leu His Ala Ala Arg Pro
    290                 295                 300

Asp Ile Gln Met Thr Gln Thr Thr Ser Ser Leu Ser Ala Ser Leu Gly
305                 310                 315                 320

Asp Arg Val Thr Ile Ser Cys Arg Ala Ser Gln Asp Ile Ser Lys Tyr
                325                 330                 335

Leu Asn Trp Tyr Gln Gln Lys Pro Asp Gly Thr Val Lys Leu Leu Ile
            340                 345                 350

Tyr His Thr Ser Arg Leu His Ser Gly Val Pro Ser Arg Phe Ser Gly
        355                 360                 365

Ser Gly Ser Gly Thr Asp Tyr Ser Leu Thr Ile Ser Asn Leu Glu Gln
    370                 375                 380

Glu Asp Ile Ala Thr Tyr Phe Cys Gln Gln Gly Asn Thr Leu Pro Tyr
385                 390                 395                 400

Thr Phe Gly Gly Gly Thr Lys Leu Glu Ile Thr Gly Ser Thr Ser Gly
                405                 410                 415

Ser Gly Lys Pro Gly Ser Gly Glu Gly Ser Thr Lys Gly Glu Val Lys
            420                 425                 430

Leu Gln Glu Ser Gly Pro Gly Leu Val Ala Pro Ser Gln Ser Leu Ser
        435                 440                 445

Val Thr Cys Thr Val Ser Gly Val Ser Leu Pro Asp Tyr Gly Val Ser
    450                 455                 460

Trp Ile Arg Gln Pro Pro Arg Lys Gly Leu Glu Trp Leu Gly Val Ile
465                 470                 475                 480

Trp Gly Ser Glu Thr Thr Tyr Tyr Asn Ser Ala Leu Lys Ser Arg Leu
                485                 490                 495

Thr Ile Ile Lys Asp Asn Ser Lys Ser Gln Val Phe Leu Lys Met Asn
            500                 505                 510

Ser Leu Gln Thr Asp Asp Thr Ala Ile Tyr Tyr Cys Ala Lys His Tyr
        515                 520                 525

Tyr Tyr Gly Gly Ser Tyr Ala Met Asp Tyr Trp Gly Gln Gly Thr Ser
    530                 535                 540

Val Thr Val Ser Ser Glu Ser Lys Tyr Gly Pro Pro Cys Pro Pro Cys
```

545 550 555 560

Pro Ala Pro Glu Phe Leu Gly Gly Pro Ser Val Phe Leu Phe Pro Pro
565 570 575

Lys Pro Lys Asp Thr Leu Met Ile Ser Arg Thr Pro Glu Val Thr Cys
580 585 590

Val Val Val Asp Val Ser Gln Glu Asp Pro Glu Val Gln Phe Asn Trp
595 600 605

Tyr Val Asp Gly Val Glu Val His Asn Ala Lys Thr Lys Pro Arg Glu
610 615 620

Glu Gln Phe Asn Ser Thr Tyr Arg Val Val Ser Val Leu Thr Val Leu
625 630 635 640

His Gln Asp Trp Leu Asn Gly Lys Glu Tyr Lys Cys Lys Val Ser Asn
645 650 655

Lys Gly Leu Pro Ser Ser Ile Glu Lys Thr Ile Ser Lys Ala Lys Gly
660 665 670

Gln Pro Arg Glu Pro Gln Val Tyr Thr Leu Pro Pro Ser Gln Glu Glu
675 680 685

Met Thr Lys Asn Gln Val Ser Leu Thr Cys Leu Val Lys Gly Phe Tyr
690 695 700

Pro Ser Asp Ile Ala Val Glu Trp Glu Ser Asn Gly Gln Pro Glu Asn
705 710 715 720

Asn Tyr Lys Thr Thr Pro Pro Val Leu Asp Ser Asp Gly Ser Phe Phe
725 730 735

Leu Tyr Ser Arg Leu Thr Val Asp Lys Ser Arg Trp Gln Glu Gly Asn
740 745 750

Val Phe Ser Cys Ser Val Met His Glu Ala Leu His Asn His Tyr Thr
755 760 765

Gln Lys Ser Leu Ser Leu Ser Leu Gly Lys Met Phe Trp Val Leu Val
770 775 780

Val Val Gly Gly Val Leu Ala Cys Tyr Ser Leu Leu Val Thr Val Ala
785 790 795 800

Phe Ile Ile Phe Trp Val Arg Ser Lys Arg Ser Arg Gly Gly His Ser
805 810 815

Asp Tyr Met Asn Met Thr Pro Arg Arg Pro Gly Pro Thr Arg Lys His
820 825 830

Tyr Gln Pro Tyr Ala Pro Pro Arg Asp Phe Ala Ala Tyr Arg Ser Arg
835 840 845

Val Lys Phe Ser Arg Ser Ala Asp Ala Pro Ala Tyr Gln Gln Gly Gln
850 855 860

Asn Gln Leu Tyr Asn Glu Leu Asn Leu Gly Arg Arg Glu Glu Tyr Asp
865 870 875 880

Val Leu Asp Lys Arg Arg Gly Arg Asp Pro Glu Met Gly Gly Lys Pro
885 890 895

Arg Arg Lys Asn Pro Gln Glu Gly Leu Tyr Asn Glu Leu Gln Lys Asp
900 905 910

Lys Met Ala Glu Ala Tyr Ser Glu Ile Gly Met Lys Gly Glu Arg Arg
915 920 925

Arg Gly Lys Gly His Asp Gly Leu Tyr Gln Gly Leu Ser Thr Ala Thr
930 935 940

Lys Asp Thr Tyr Asp Ala Leu His Met Gln Ala Leu Pro Pro Arg
945 950 955

<210> SEQ ID NO 184

<211> LENGTH: 763
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 184

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Lys Pro Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Asn His Arg Asn
305                 310                 315                 320

Arg Ser Lys Arg Ser Arg Gly Gly His Ser Asp Tyr Met Asn Met Thr
                325                 330                 335

Pro Arg Arg Pro Gly Pro Thr Arg Lys His Tyr Gln Pro Tyr Ala Pro
            340                 345                 350

Pro Arg Asp Phe Ala Ala Tyr Arg Ser Arg Val Lys Phe Ser Arg Ser
        355                 360                 365

Ala Asp Ala Pro Ala Tyr Gln Gln Gly Gln Asn Gln Leu Tyr Asn Glu
```

```
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg Arg Ala Lys Arg Ser Gly Ser
465                 470                 475                 480

Gly Glu Gly Arg Gly Ser Leu Leu Thr Cys Gly Asp Val Glu Glu Asn
                485                 490                 495

Pro Gly Pro Met Arg Leu Pro Ala Gln Leu Leu Gly Leu Leu Met Leu
            500                 505                 510

Trp Val Pro Gly Ser Ser Gly Arg Lys Val Cys Asn Gly Ile Gly Ile
        515                 520                 525

Gly Glu Phe Lys Asp Ser Leu Ser Ile Asn Ala Thr Asn Ile Lys His
    530                 535                 540

Phe Lys Asn Cys Thr Ser Ile Ser Gly Asp Leu His Ile Leu Pro Val
545                 550                 555                 560

Ala Phe Arg Gly Asp Ser Phe Thr His Thr Pro Pro Leu Asp Pro Gln
                565                 570                 575

Glu Leu Asp Ile Leu Lys Thr Val Lys Glu Ile Thr Gly Phe Leu Leu
            580                 585                 590

Ile Gln Ala Trp Pro Glu Asn Arg Thr Asp Leu His Ala Phe Glu Asn
        595                 600                 605

Leu Glu Ile Ile Arg Gly Arg Thr Lys Gln His Gly Gln Phe Ser Leu
    610                 615                 620

Ala Val Val Ser Leu Asn Ile Thr Ser Leu Gly Leu Arg Ser Leu Lys
625                 630                 635                 640

Glu Ile Ser Asp Gly Asp Val Ile Ile Ser Gly Asn Lys Asn Leu Cys
                645                 650                 655

Tyr Ala Asn Thr Ile Asn Trp Lys Lys Leu Phe Gly Thr Ser Gly Gln
            660                 665                 670

Lys Thr Lys Ile Ile Ser Asn Arg Gly Glu Asn Ser Cys Lys Ala Thr
        675                 680                 685

Gly Gln Val Cys His Ala Leu Cys Ser Pro Glu Gly Cys Trp Gly Pro
    690                 695                 700

Glu Pro Arg Asp Cys Val Ser Gly Gly Gly Gly Ser Gly Gly Gly Gly
705                 710                 715                 720

Ser Gly Gly Gly Gly Ser Gly Gly Gly Gly Ser Phe Trp Val Leu Val
                725                 730                 735

Val Val Gly Gly Val Leu Ala Cys Tyr Ser Leu Leu Val Thr Val Ala
            740                 745                 750

Phe Ile Ile Phe Trp Val Arg Ser Lys Arg Ser
        755                 760
```

<210> SEQ ID NO 185
<211> LENGTH: 2553
<212> TYPE: DNA
<213> ORGANISM: Artificial Sequence -continued
<220> FEATURE:
<223> OTHER INFORMATION: Description of Artificial Sequence: Synthetic
      polynucleotide

<400> SEQUENCE: 185

```
gacatacaga tgactcagac aacaagtagc ttgtccgcat ccctgggcga tagagtgacc      60
atcagttgtc gagcatccca agatatatcc aagtacttaa actggtatca gcagaagcca     120
gatggcaccg tcaagctgct aatctaccac acaagtaggc tccacagcgg agtgcctagc     180
cgattctctg gttctggttc tggcacagac tattccctaa ccatcagcaa cctggagcaa     240
gaggacattg caacatattt ttgccagcag ggcaacacac tgccatatac ctttggaggc     300
gggaccaagc tggaaatcac cggtagtacg agtggttctg gaaaacctgg ttctggcgaa     360
ggtagtacta aaggagaggt gaaacttcaa gagagtggcc ctggcttggt ggccccttct     420
caaagtttga gcgtgacctg cacagtaagt ggcgtcagcc tgccagatta cggagtcagt     480
tggattcgcc agcctccaag gaagggcctt gaatggctgg gcgtaatctg gggtccgaa      540
accacctatt acaactccgc acttaagagc cgtttaacca tcatcaaaga caacagcaag     600
agtcaggtct ttctcaaaat gaatagtctg caaacggacg acaccgctat ctactattgt     660
gccaagcact actactatgg tggctcctac gctatggatt actggggaca aggaacaagc     720
gtgacagtgt caagtactac cacacctgct ccccgtcctc caacccccgc tcctactatt     780
gccagtcaac cactgtctct taggcccgag gcatgtaggc cagcagcagg cggggctgtg     840
catacccgag gtctcgactt cgcctgcgac atatatatct gggcccctct ggctggcact     900
tgtggggtcc tcctcctgag tctcgtgatc actctgtatt gtaaacgtgg gcgaaagaag     960
ctcctttaca tcttcaagca acccttcatg aggcctgtac agaccacgca ggaggaggac    1020
gggtgtagtt gccgattccc cgaagaggaa gaaggcggtt gcgagcttcg agtgaaattc    1080
agtaggagtg ctgacgcacc agcatataag cagggccaga accaattata caacgagctg    1140
aacctcggac gaagggaaga gtatgatgtg ctggataagc gcagaggccg tgatccagaa    1200
atgggcggca aacctcgtcg gaaaaatcca caagaggggc tatacaacga attgcagaaa    1260
gacaaaatgg cagaggccta ttctgaaatc ggcatgaagg gcgaacgacg aagaggtaag    1320
ggtcatgacg gcctgtatca aggtctctct accgccacaa aggacactta cgatgcttta    1380
cacatgcagg ctctccctcc cagacaatgc accaactacg ctctattgaa gttggcagga    1440
gatgtggaat ccaaccccgg tcctatgcgt ctacctgccc agctgcttgg gctcctgatg    1500
ctgtgggtcc ccggcagcag tggtagaaaa gtatgtaacg gcataggtat cggtgaattt    1560
aaggactcac taagcatcaa cgccacaaac atcaagcact ttaagaactg tacctctatt    1620
agcggagact tacacatcct gccagtcgca tttcgaggag acagtttcac ccacactcca    1680
cctctcgatc ctcaggaatt agacattctt aaaacagtta aggaaatcac tggatttctt    1740
cttatccagg cctggccaga aaatagaaca gacctgcacg ctttcgagaa ccttgaaata    1800
atacgaggca ggaccaaaca gcatggccaa tttagtttgg ctgtagtctc cttgaacatc    1860
acttcccttg gcctaaggtc tttgaaggaa atcagtgacg gagacgtgat tatcagcggg    1920
aacaagaacc tctgttacgc aaacacaatc aactggaaga agctctttgg caccagcggc    1980
cagaagacaa agatcatttc taaccgagga gagaacagtt gtaaggcaac aggacaagtg    2040
tgccacgctt tgtgcagccc cgagggatgt tggggtcctg agccacgtga ttgtgtctct    2100
tgccggaacg tcagcagagg tagagaatgt gtggataagt gcaacctcct ggaaggggag    2160
cctcgtgagt tcgtggagaa ctccgaatgt atccagtgtc atccagaatg cctgccccag    2220
```

gccatgaaca taacatgtac aggacgcggc ccagacaact gcatacagtg cgcccactac 2280
attgatggcc cccattgcgt aaagacttgt cctgctggag tcatgggcga aaataacacc 2340
ctggtgtgga agtacgccga cgctggccat gtatgtcatc tgtgtcatcc taattgcacc 2400
tatggctgca ctggccccgg ccttgaagga tgccccggcg gtggaggagg aggctctttc 2460
tgggtcctcg tggtggtggg aggcgtgctg gcctgctatt ccttgctggt cacggtcgcc 2520
ttcattattt tctgggtgag atctaaaaga agc 2553

<210> SEQ ID NO 186
<211> LENGTH: 851
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 186

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Ile Tyr Ile Trp Ala Pro Leu Ala Gly Thr Cys Gly Val Leu
```

```
    290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Lys Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg Gln Cys Thr Asn Tyr Ala Leu Leu Lys Leu Ala Gly
465                 470                 475                 480

Asp Val Glu Ser Asn Pro Gly Pro Met Arg Leu Pro Ala Gln Leu Leu
                485                 490                 495

Gly Leu Leu Met Leu Trp Val Pro Gly Ser Ser Gly Arg Lys Val Cys
            500                 505                 510

Asn Gly Ile Gly Ile Gly Glu Phe Lys Asp Ser Leu Ser Ile Asn Ala
        515                 520                 525

Thr Asn Ile Lys His Phe Lys Asn Cys Thr Ser Ile Ser Gly Asp Leu
    530                 535                 540

His Ile Leu Pro Val Ala Phe Arg Gly Asp Ser Phe Thr His Thr Pro
545                 550                 555                 560

Pro Leu Asp Pro Gln Glu Leu Asp Ile Leu Lys Thr Val Lys Glu Ile
                565                 570                 575

Thr Gly Phe Leu Leu Ile Gln Ala Trp Pro Glu Asn Arg Thr Asp Leu
            580                 585                 590

His Ala Phe Glu Asn Leu Glu Ile Ile Arg Gly Arg Thr Lys Gln His
        595                 600                 605

Gly Gln Phe Ser Leu Ala Val Val Ser Leu Asn Ile Thr Ser Leu Gly
    610                 615                 620

Leu Arg Ser Leu Lys Glu Ile Ser Asp Gly Asp Val Ile Ile Ser Gly
625                 630                 635                 640

Asn Lys Asn Leu Cys Tyr Ala Asn Thr Ile Asn Trp Lys Lys Leu Phe
                645                 650                 655

Gly Thr Ser Gly Gln Lys Thr Lys Ile Ile Ser Asn Arg Gly Glu Asn
            660                 665                 670

Ser Cys Lys Ala Thr Gly Gln Val Cys His Ala Leu Cys Ser Pro Glu
        675                 680                 685

Gly Cys Trp Gly Pro Glu Pro Arg Asp Cys Val Ser Cys Arg Asn Val
    690                 695                 700

Ser Arg Gly Arg Glu Cys Val Asp Lys Cys Asn Leu Leu Glu Gly Glu
705                 710                 715                 720
```

```
Pro Arg Glu Phe Val Glu Asn Ser Glu Cys Ile Gln Cys His Pro Glu
                725                 730                 735

Cys Leu Pro Gln Ala Met Asn Ile Thr Cys Thr Gly Arg Gly Pro Asp
            740                 745                 750

Asn Cys Ile Gln Cys Ala His Tyr Ile Asp Gly Pro His Cys Val Lys
        755                 760                 765

Thr Cys Pro Ala Gly Val Met Gly Glu Asn Asn Thr Leu Val Trp Lys
    770                 775                 780

Tyr Ala Asp Ala Gly His Val Cys His Leu Cys His Pro Asn Cys Thr
785                 790                 795                 800

Tyr Gly Cys Thr Gly Pro Gly Leu Glu Gly Cys Pro Gly Gly Gly Gly
                805                 810                 815

Gly Gly Ser Phe Trp Val Leu Val Val Val Gly Gly Val Leu Ala Cys
            820                 825                 830

Tyr Ser Leu Leu Val Thr Val Ala Phe Ile Ile Phe Trp Val Arg Ser
        835                 840                 845

Lys Arg Ser
    850


<210> SEQ ID NO 187
<211> LENGTH: 761
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
```

-continued

```
    210                 215                 220

Tyr Tyr Gly Gly Ser Tyr Ala Met Asp Tyr Trp Gly Gln Gly Thr Ser
225                 230                 235                 240

Val Thr Val Ser Ser Lys Pro Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Asn His Arg Asn
305                 310                 315                 320

Arg Ser Lys Arg Ser Arg Gly Gly His Ser Asp Tyr Met Asn Met Thr
                325                 330                 335

Pro Arg Arg Pro Gly Pro Thr Arg Lys His Tyr Gln Pro Tyr Ala Pro
            340                 345                 350

Pro Arg Asp Phe Ala Ala Tyr Arg Ser Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg Arg Ala Lys Arg Ser Gly Ser
465                 470                 475                 480

Gly Glu Gly Arg Gly Ser Leu Leu Thr Cys Gly Asp Val Glu Glu Asn
                485                 490                 495

Pro Gly Pro Met Arg Leu Pro Ala Gln Leu Leu Gly Leu Leu Met Leu
            500                 505                 510

Trp Val Pro Gly Ser Ser Gly Arg Lys Val Cys Asn Gly Ile Gly Ile
        515                 520                 525

Gly Glu Phe Lys Asp Ser Leu Ser Ile Asn Ala Thr Asn Ile Lys His
    530                 535                 540

Phe Lys Asn Cys Thr Ser Ile Ser Gly Asp Leu His Ile Leu Pro Val
545                 550                 555                 560

Ala Phe Arg Gly Asp Ser Phe Thr His Thr Pro Pro Leu Asp Pro Gln
                565                 570                 575

Glu Leu Asp Ile Leu Lys Thr Val Lys Glu Ile Thr Gly Phe Leu Leu
            580                 585                 590

Ile Gln Ala Trp Pro Glu Asn Arg Thr Asp Leu His Ala Phe Glu Asn
        595                 600                 605

Leu Glu Ile Ile Arg Gly Arg Thr Lys Gln His Gly Gln Phe Ser Leu
    610                 615                 620

Ala Val Val Ser Leu Asn Ile Thr Ser Leu Gly Leu Arg Ser Leu Lys
625                 630                 635                 640
```

Glu Ile Ser Asp Gly Asp Val Ile Ile Ser Gly Asn Lys Asn Leu Cys
645 650 655

Tyr Ala Asn Thr Ile Asn Trp Lys Lys Leu Phe Gly Thr Ser Gly Gln
660 665 670

Lys Thr Lys Ile Ile Ser Asn Arg Gly Glu Asn Ser Cys Lys Ala Thr
675 680 685

Gly Gln Val Cys His Ala Leu Cys Ser Pro Glu Gly Cys Trp Gly Pro
690 695 700

Glu Pro Arg Asp Cys Val Ser Gly Gly Gly Gly Ser Gly Gly Gly Gly
705 710 715 720

Ser Gly Gly Gly Gly Ser Gly Gly Gly Gly Ser Glu Ile Thr Leu Ile
725 730 735

Ile Phe Gly Val Met Ala Gly Val Ile Gly Thr Ile Leu Leu Ile Ser
740 745 750

Tyr Gly Ile Arg Arg Gly Gly Gly Ser
755 760

<210> SEQ ID NO 188
<211> LENGTH: 750
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser

```
225                 230                 235                 240

Val Thr Val Ser Ser Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Ile Tyr Ile Trp Ala Pro Leu Ala Gly Thr Cys Gly Val Leu
    290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Lys Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg Gln Cys Thr Asn Tyr Ala Leu Leu Lys Leu Ala Gly
465                 470                 475                 480

Asp Val Glu Ser Asn Pro Gly Pro Met Arg Leu Pro Ala Gln Leu Leu
                485                 490                 495

Gly Leu Leu Met Leu Trp Val Pro Gly Ser Ser Gly Arg Lys Val Cys
            500                 505                 510

Asn Gly Ile Gly Ile Gly Glu Phe Lys Asp Ser Leu Ser Ile Asn Ala
        515                 520                 525

Thr Asn Ile Lys His Phe Lys Asn Cys Thr Ser Ile Ser Gly Asp Leu
    530                 535                 540

His Ile Leu Pro Val Ala Phe Arg Gly Asp Ser Phe Thr His Thr Pro
545                 550                 555                 560

Pro Leu Asp Pro Gln Glu Leu Asp Ile Leu Lys Thr Val Lys Glu Ile
                565                 570                 575

Thr Gly Phe Leu Leu Ile Gln Ala Trp Pro Glu Asn Arg Thr Asp Leu
            580                 585                 590

His Ala Phe Glu Asn Leu Glu Ile Ile Arg Gly Arg Thr Lys Gln His
        595                 600                 605

Gly Gln Phe Ser Leu Ala Val Val Ser Leu Asn Ile Thr Ser Leu Gly
    610                 615                 620

Leu Arg Ser Leu Lys Glu Ile Ser Asp Gly Asp Val Ile Ile Ser Gly
625                 630                 635                 640

Asn Lys Asn Leu Cys Tyr Ala Asn Thr Ile Asn Trp Lys Lys Leu Phe
                645                 650                 655
```

Gly Thr Ser Gly Gln Lys Thr Lys Ile Ile Ser Asn Arg Gly Glu Asn
660 665 670

Ser Cys Lys Ala Thr Gly Gln Val Cys His Ala Leu Cys Ser Pro Glu
675 680 685

Gly Cys Trp Gly Pro Glu Pro Arg Asp Cys Val Ser Gly Gly Gly Gly
690 695 700

Ser Gly Gly Gly Gly Ser Gly Gly Gly Gly Ser Gly Gly Gly Gly Ser
705 710 715 720

Glu Ile Thr Leu Ile Ile Phe Gly Val Met Ala Gly Val Ile Gly Thr
725 730 735

Ile Leu Leu Ile Ser Tyr Gly Ile Arg Arg Gly Gly Gly Ser
740 745 750

<210> SEQ ID NO 189
<211> LENGTH: 758
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 189

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser
225 230 235 240

Val Thr Val Ser Ser Lys Pro Thr Thr Thr Pro Ala Pro Arg Pro Pro
245 250 255

Thr Pro Ala Pro Thr Ile Ala Ser Gln Pro Leu Ser Leu Arg Pro Glu

```
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Asn His Arg Asn
305                 310                 315                 320

Arg Ser Lys Arg Ser Arg Gly Gly His Ser Asp Tyr Met Asn Met Thr
                325                 330                 335

Pro Arg Arg Pro Gly Pro Thr Arg Lys His Tyr Gln Pro Tyr Ala Pro
            340                 345                 350

Pro Arg Asp Phe Ala Ala Tyr Arg Ser Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg Arg Ala Lys Arg Ser Gly Ser
465                 470                 475                 480

Gly Glu Gly Arg Gly Ser Leu Leu Thr Cys Gly Asp Val Glu Glu Asn
                485                 490                 495

Pro Gly Pro Met Arg Leu Pro Ala Gln Leu Leu Gly Leu Leu Met Leu
            500                 505                 510

Trp Val Pro Gly Ser Ser Gly Arg Lys Val Cys Asn Gly Ile Gly Ile
        515                 520                 525

Gly Glu Phe Lys Asp Ser Leu Ser Ile Asn Ala Thr Asn Ile Lys His
    530                 535                 540

Phe Lys Asn Cys Thr Ser Ile Ser Gly Asp Leu His Ile Leu Pro Val
545                 550                 555                 560

Ala Phe Arg Gly Asp Ser Phe Thr His Thr Pro Pro Leu Asp Pro Gln
                565                 570                 575

Glu Leu Asp Ile Leu Lys Thr Val Lys Glu Ile Thr Gly Phe Leu Leu
            580                 585                 590

Ile Gln Ala Trp Pro Glu Asn Arg Thr Asp Leu His Ala Phe Glu Asn
        595                 600                 605

Leu Glu Ile Ile Arg Gly Arg Thr Lys Gln His Gly Gln Phe Ser Leu
    610                 615                 620

Ala Val Val Ser Leu Asn Ile Thr Ser Leu Gly Leu Arg Ser Leu Lys
625                 630                 635                 640

Glu Ile Ser Asp Gly Asp Val Ile Ile Ser Gly Asn Lys Asn Leu Cys
                645                 650                 655

Tyr Ala Asn Thr Ile Asn Trp Lys Lys Leu Phe Gly Thr Ser Gly Gln
            660                 665                 670

Lys Thr Lys Ile Ile Ser Asn Arg Gly Glu Asn Ser Cys Lys Ala Thr
        675                 680                 685
```

Gly Gln Val Cys His Ala Leu Cys Ser Pro Glu Gly Cys Trp Gly Pro
    690                 695                 700

Glu Pro Arg Asp Cys Val Ser Gly Gly Gly Gly Ser Gly Gly Gly Gly
705                 710                 715                 720

Ser Gly Gly Gly Gly Ser Gly Gly Gly Gly Ser Ile Thr Leu Ile Ile
                725                 730                 735

Phe Gly Val Met Ala Gly Val Ile Gly Thr Ile Leu Leu Ile Ser Tyr
            740                 745                 750

Gly Ile Gly Gly Gly Ser
        755

<210> SEQ ID NO 190
<211> LENGTH: 747
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala

```
        275                 280                 285

Cys Asp Ile Tyr Ile Trp Ala Pro Leu Ala Gly Thr Cys Gly Val Leu
    290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Lys Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg Gln Cys Thr Asn Tyr Ala Leu Leu Lys Leu Ala Gly
465                 470                 475                 480

Asp Val Glu Ser Asn Pro Gly Pro Met Arg Leu Pro Ala Gln Leu Leu
                485                 490                 495

Gly Leu Leu Met Leu Trp Val Pro Gly Ser Ser Gly Arg Lys Val Cys
            500                 505                 510

Asn Gly Ile Gly Ile Gly Glu Phe Lys Asp Ser Leu Ser Ile Asn Ala
        515                 520                 525

Thr Asn Ile Lys His Phe Lys Asn Cys Thr Ser Ile Ser Gly Asp Leu
    530                 535                 540

His Ile Leu Pro Val Ala Phe Arg Gly Asp Ser Phe Thr His Thr Pro
545                 550                 555                 560

Pro Leu Asp Pro Gln Glu Leu Asp Ile Leu Lys Thr Val Lys Glu Ile
                565                 570                 575

Thr Gly Phe Leu Leu Ile Gln Ala Trp Pro Glu Asn Arg Thr Asp Leu
            580                 585                 590

His Ala Phe Glu Asn Leu Glu Ile Ile Arg Gly Arg Thr Lys Gln His
        595                 600                 605

Gly Gln Phe Ser Leu Ala Val Val Ser Leu Asn Ile Thr Ser Leu Gly
    610                 615                 620

Leu Arg Ser Leu Lys Glu Ile Ser Asp Gly Asp Val Ile Ile Ser Gly
625                 630                 635                 640

Asn Lys Asn Leu Cys Tyr Ala Asn Thr Ile Asn Trp Lys Lys Leu Phe
                645                 650                 655

Gly Thr Ser Gly Gln Lys Thr Lys Ile Ile Ser Asn Arg Gly Glu Asn
            660                 665                 670

Ser Cys Lys Ala Thr Gly Gln Val Cys His Ala Leu Cys Ser Pro Glu
        675                 680                 685

Gly Cys Trp Gly Pro Glu Pro Arg Asp Cys Val Ser Gly Gly Gly Gly
    690                 695                 700
```

Ser Gly Gly Gly Gly Ser Gly Gly Gly Gly Ser Gly Gly Gly Gly Ser
705 710 715 720

Ile Thr Leu Ile Ile Phe Gly Val Met Ala Gly Val Ile Gly Thr Ile
725 730 735

Leu Leu Ile Ser Tyr Gly Ile Gly Gly Gly Ser
740 745

<210> SEQ ID NO 191
<211> LENGTH: 758
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser
225 230 235 240

Val Thr Val Ser Ser Lys Pro Thr Thr Thr Pro Ala Pro Arg Pro Pro
245 250 255

Thr Pro Ala Pro Thr Ile Ala Ser Gln Pro Leu Ser Leu Arg Pro Glu
260 265 270

Ala Cys Arg Pro Ala Ala Gly Gly Ala Val His Thr Arg Gly Leu Asp
275 280 285

Phe Ala Cys Asp Ile Tyr Ile Trp Ala Pro Leu Ala Gly Thr Cys Gly
290 295 300

Val Leu Leu Leu Ser Leu Val Ile Thr Leu Tyr Cys Asn His Arg Asn

-continued

```
305                 310                 315                 320

Arg Ser Lys Arg Ser Arg Gly Gly His Ser Asp Tyr Met Asn Met Thr
                325                 330                 335

Pro Arg Arg Pro Gly Pro Thr Arg Lys His Tyr Gln Pro Tyr Ala Pro
            340                 345                 350

Pro Arg Asp Phe Ala Ala Tyr Arg Ser Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg Arg Ala Lys Arg Ser Gly Ser
465                 470                 475                 480

Gly Glu Gly Arg Gly Ser Leu Leu Thr Cys Gly Asp Val Glu Glu Asn
                485                 490                 495

Pro Gly Pro Met Arg Leu Pro Ala Gln Leu Leu Gly Leu Leu Met Leu
            500                 505                 510

Trp Val Pro Gly Ser Ser Gly Arg Lys Val Cys Asn Gly Ile Gly Ile
        515                 520                 525

Gly Glu Phe Lys Asp Ser Leu Ser Ile Asn Ala Thr Asn Ile Lys His
    530                 535                 540

Phe Lys Asn Cys Thr Ser Ile Ser Gly Asp Leu His Ile Leu Pro Val
545                 550                 555                 560

Ala Phe Arg Gly Asp Ser Phe Thr His Thr Pro Pro Leu Asp Pro Gln
                565                 570                 575

Glu Leu Asp Ile Leu Lys Thr Val Lys Glu Ile Thr Gly Phe Leu Leu
            580                 585                 590

Ile Gln Ala Trp Pro Glu Asn Arg Thr Asp Leu His Ala Phe Glu Asn
        595                 600                 605

Leu Glu Ile Ile Arg Gly Arg Thr Lys Gln His Gly Gln Phe Ser Leu
    610                 615                 620

Ala Val Val Ser Leu Asn Ile Thr Ser Leu Gly Leu Arg Ser Leu Lys
625                 630                 635                 640

Glu Ile Ser Asp Gly Asp Val Ile Ile Ser Gly Asn Lys Asn Leu Cys
                645                 650                 655

Tyr Ala Asn Thr Ile Asn Trp Lys Lys Leu Phe Gly Thr Ser Gly Gln
            660                 665                 670

Lys Thr Lys Ile Ile Ser Asn Arg Gly Glu Asn Ser Cys Lys Ala Thr
        675                 680                 685

Gly Gln Val Cys His Ala Leu Cys Ser Pro Glu Gly Cys Trp Gly Pro
    690                 695                 700

Glu Pro Arg Asp Cys Val Ser Gly Gly Gly Gly Ser Gly Gly Gly Gly
705                 710                 715                 720

Ser Gly Gly Gly Gly Ser Gly Gly Gly Gly Ser Ile Thr Leu Ile Ile
                725                 730                 735
```

```
Phe Gly Val Met Ala Gly Val Ile Gly Thr Ile Leu Leu Ala Leu Leu
            740                 745                 750

Ile Trp Gly Gly Gly Ser
        755


<210> SEQ ID NO 192
<211> LENGTH: 747
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Ile Tyr Ile Trp Ala Pro Leu Ala Gly Thr Cys Gly Val Leu
    290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
```

-continued

```
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Lys Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg Gln Cys Thr Asn Tyr Ala Leu Leu Lys Leu Ala Gly
465                 470                 475                 480

Asp Val Glu Ser Asn Pro Gly Pro Met Arg Leu Pro Ala Gln Leu Leu
                485                 490                 495

Gly Leu Leu Met Leu Trp Val Pro Gly Ser Ser Gly Arg Lys Val Cys
            500                 505                 510

Asn Gly Ile Gly Ile Gly Glu Phe Lys Asp Ser Leu Ser Ile Asn Ala
        515                 520                 525

Thr Asn Ile Lys His Phe Lys Asn Cys Thr Ser Ile Ser Gly Asp Leu
    530                 535                 540

His Ile Leu Pro Val Ala Phe Arg Gly Asp Ser Phe Thr His Thr Pro
545                 550                 555                 560

Pro Leu Asp Pro Gln Glu Leu Asp Ile Leu Lys Thr Val Lys Glu Ile
                565                 570                 575

Thr Gly Phe Leu Leu Ile Gln Ala Trp Pro Glu Asn Arg Thr Asp Leu
            580                 585                 590

His Ala Phe Glu Asn Leu Glu Ile Ile Arg Gly Arg Thr Lys Gln His
        595                 600                 605

Gly Gln Phe Ser Leu Ala Val Val Ser Leu Asn Ile Thr Ser Leu Gly
    610                 615                 620

Leu Arg Ser Leu Lys Glu Ile Ser Asp Gly Asp Val Ile Ile Ser Gly
625                 630                 635                 640

Asn Lys Asn Leu Cys Tyr Ala Asn Thr Ile Asn Trp Lys Lys Leu Phe
                645                 650                 655

Gly Thr Ser Gly Gln Lys Thr Lys Ile Ile Ser Asn Arg Gly Glu Asn
            660                 665                 670

Ser Cys Lys Ala Thr Gly Gln Val Cys His Ala Leu Cys Ser Pro Glu
        675                 680                 685

Gly Cys Trp Gly Pro Glu Pro Arg Asp Cys Val Ser Gly Gly Gly Gly
    690                 695                 700

Ser Gly Gly Gly Gly Ser Gly Gly Gly Gly Ser Gly Gly Gly Gly Ser
705                 710                 715                 720

Ile Thr Leu Ile Ile Phe Gly Val Met Ala Gly Val Ile Gly Thr Ile
                725                 730                 735

Leu Leu Ala Leu Leu Ile Trp Gly Gly Gly Ser
            740                 745
```

<210> SEQ ID NO 193
<211> LENGTH: 666
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 193

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

Thr Ser Ser Gly Gly Gly Ser Gly Gly Gly Gly Ser Gly Gly Gly Gly
115 120 125

Ser Gly Gly Gly Gly Ser Gly Gly Gly Ser Leu Gln Ile Thr Cys Pro
130 135 140

Pro Pro Met Ser Val Glu His Ala Asp Ile Trp Val Lys Ser Tyr Ser
145 150 155 160

Leu Tyr Ser Arg Glu Arg Tyr Ile Cys Asn Ser Gly Phe Lys Arg Lys
165 170 175

Ala Gly Thr Ser Ser Leu Thr Glu Cys Val Leu Asn Lys Ala Thr Asn
180 185 190

Val Ala His Trp Thr Thr Pro Ser Leu Lys Cys Ile Arg Asp Pro Ala
195 200 205

Leu Val His Gln Arg Pro Ala Pro Pro Ser Thr Val Thr Thr Ala Gly
210 215 220

Val Thr Pro Gln Pro Glu Ser Leu Ser Pro Ser Gly Lys Glu Pro Ala
225 230 235 240

Ala Ser Ser Pro Ser Ser Asn Asn Thr Ala Ala Thr Thr Ala Ala Ile
245 250 255

Val Pro Gly Ser Gln Leu Met Pro Ser Lys Ser Pro Ser Thr Gly Thr
260 265 270

Thr Glu Ile Ser Ser His Glu Ser Ser His Gly Thr Pro Ser Gln Thr
275 280 285

Thr Ala Lys Asn Trp Glu Leu Thr Ala Ser Ala Ser His Gln Pro Pro
290 295 300

Gly Val Tyr Pro Gln Gly His Ser Asp Thr Thr Val Ala Ile Ser Thr
305 310 315 320

Ser Thr Val Leu Leu Cys Gly Leu Ser Ala Val Ser Leu Leu Ala Cys
325 330 335

Tyr Leu Lys Ser Arg Gln Thr Pro Pro Leu Ala Ser Val Glu Met Glu
340 345 350

Ala Met Glu Ala Leu Pro Val Thr Trp Gly Thr Ser Ser Arg Asp Glu

```
        355                 360                 365

Asp Leu Glu Asn Cys Ser His His Leu Arg Ala Lys Arg Gly Ser Gly
    370                 375                 380

Glu Gly Arg Gly Ser Leu Leu Thr Cys Gly Asp Val Glu Glu Asn Pro
385                 390                 395                 400

Gly Pro Met Arg Leu Pro Ala Gln Leu Leu Gly Leu Leu Met Leu Trp
                405                 410                 415

Val Pro Gly Ser Ser Gly Arg Lys Val Cys Asn Gly Ile Gly Ile Gly
            420                 425                 430

Glu Phe Lys Asp Ser Leu Ser Ile Asn Ala Thr Asn Ile Lys His Phe
        435                 440                 445

Lys Asn Cys Thr Ser Ile Ser Gly Asp Leu His Ile Leu Pro Val Ala
    450                 455                 460

Phe Arg Gly Asp Ser Phe Thr His Thr Pro Pro Leu Asp Pro Gln Glu
465                 470                 475                 480

Leu Asp Ile Leu Lys Thr Val Lys Glu Ile Thr Gly Phe Leu Leu Ile
                485                 490                 495

Gln Ala Trp Pro Glu Asn Arg Thr Asp Leu His Ala Phe Glu Asn Leu
            500                 505                 510

Glu Ile Ile Arg Gly Arg Thr Lys Gln His Gly Gln Phe Ser Leu Ala
        515                 520                 525

Val Val Ser Leu Asn Ile Thr Ser Leu Gly Leu Arg Ser Leu Lys Glu
    530                 535                 540

Ile Ser Asp Gly Asp Val Ile Ile Ser Gly Asn Lys Asn Leu Cys Tyr
545                 550                 555                 560

Ala Asn Thr Ile Asn Trp Lys Lys Leu Phe Gly Thr Ser Gly Gln Lys
                565                 570                 575

Thr Lys Ile Ile Ser Asn Arg Gly Glu Asn Ser Cys Lys Ala Thr Gly
            580                 585                 590

Gln Val Cys His Ala Leu Cys Ser Pro Glu Gly Cys Trp Gly Pro Glu
        595                 600                 605

Pro Arg Asp Cys Val Ser Gly Gly Gly Gly Ser Gly Gly Gly Gly Ser
    610                 615                 620

Gly Gly Gly Gly Ser Gly Gly Gly Gly Ser Phe Trp Val Leu Val Val
625                 630                 635                 640

Val Gly Gly Val Leu Ala Cys Tyr Ser Leu Leu Val Thr Val Ala Phe
                645                 650                 655

Ile Ile Phe Trp Val Arg Ser Lys Arg Ser
            660                 665


<210> SEQ ID NO 194
<211> LENGTH: 971
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45
```

```
Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Glu Ser Lys Tyr Gly Pro Pro Cys Pro Pro Cys
                245                 250                 255

Pro Ala Pro Glu Phe Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys Met Phe Trp Val Leu Val
```

-continued 465 470 475 480

Val Val Gly Gly Val Leu Ala Cys Tyr Ser Leu Leu Val Thr Val Ala
485 490 495

Phe Ile Ile Phe Trp Val Arg Ser Lys Arg Ser Arg Gly Gly His Ser
500 505 510

Asp Tyr Met Asn Met Thr Pro Arg Arg Pro Gly Pro Thr Arg Lys His
515 520 525

Tyr Gln Pro Tyr Ala Pro Pro Arg Asp Phe Ala Ala Tyr Arg Ser Arg
530 535 540

Val Lys Phe Ser Arg Ser Ala Asp Ala Pro Ala Tyr Gln Gln Gly Gln
545 550 555 560

Asn Gln Leu Tyr Asn Glu Leu Asn Leu Gly Arg Arg Glu Glu Tyr Asp
565 570 575

Val Leu Asp Lys Arg Arg Gly Arg Asp Pro Glu Met Gly Gly Lys Pro
580 585 590

Arg Arg Lys Asn Pro Gln Glu Gly Leu Tyr Asn Glu Leu Gln Lys Asp
595 600 605

Lys Met Ala Glu Ala Tyr Ser Glu Ile Gly Met Lys Gly Glu Arg Arg
610 615 620

Arg Gly Lys Gly His Asp Gly Leu Tyr Gln Gly Leu Ser Thr Ala Thr
625 630 635 640

Lys Asp Thr Tyr Asp Ala Leu His Met Gln Ala Leu Pro Pro Arg Ala
645 650 655

Thr Asn Phe Ser Leu Leu Lys Gln Ala Gly Asp Val Glu Glu Asn Pro
660 665 670

Gly Pro Met Thr Thr Pro Arg Asn Ser Val Asn Gly Thr Phe Pro Ala
675 680 685

Glu Pro Met Lys Gly Pro Ile Ala Met Gln Ser Gly Pro Lys Pro Leu
690 695 700

Phe Arg Arg Met Ser Ser Leu Val Gly Pro Thr Gln Ser Phe Phe Met
705 710 715 720

Arg Glu Ser Lys Thr Leu Gly Ala Val Gln Ile Met Asn Gly Leu Phe
725 730 735

His Ile Ala Leu Gly Gly Leu Leu Met Ile Pro Ala Gly Ile Tyr Ala
740 745 750

Pro Ile Cys Val Thr Val Trp Tyr Pro Leu Trp Gly Gly Ile Met Tyr
755 760 765

Ile Ile Ser Gly Ser Leu Leu Ala Ala Thr Glu Lys Asn Ser Arg Lys
770 775 780

Cys Leu Val Lys Gly Lys Met Ile Met Asn Ser Leu Ser Leu Phe Ala
785 790 795 800

Ala Ile Ser Gly Met Ile Leu Ser Ile Met Asp Ile Leu Asn Ile Lys
805 810 815

Ile Ser His Phe Leu Lys Met Glu Ser Leu Asn Phe Ile Arg Ala His
820 825 830

Thr Pro Tyr Ile Asn Ile Tyr Asn Cys Glu Pro Ala Asn Pro Ser Glu
835 840 845

Lys Asn Ser Pro Ser Thr Gln Tyr Cys Tyr Ser Ile Gln Ser Leu Phe
850 855 860

Leu Gly Ile Leu Ser Val Met Leu Ile Phe Ala Phe Phe Gln Glu Leu
865 870 875 880

Val Ile Ala Gly Ile Val Glu Asn Glu Trp Lys Arg Thr Cys Ser Arg
885 890 895

Pro Lys Ser Asn Ile Val Leu Leu Ser Ala Glu Glu Lys Lys Glu Gln
900 905 910

Thr Ile Glu Ile Lys Glu Glu Val Val Gly Leu Thr Glu Thr Ser Ser
915 920 925

Gln Pro Lys Asn Glu Glu Asp Ile Glu Ile Ile Pro Ile Gln Glu Glu
930 935 940

Glu Glu Glu Glu Thr Glu Thr Asn Phe Pro Glu Pro Pro Gln Asp Gln
945 950 955 960

Glu Ser Ser Pro Ile Glu Asn Asp Ser Ser Pro
965 970

<210> SEQ ID NO 195
<211> LENGTH: 937
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 195

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser
225 230 235 240

Val Thr Val Ser Ser Glu Ser Lys Tyr Gly Pro Pro Cys Pro Pro Cys
245 250 255

Pro Ala Pro Glu Phe Leu Gly Gly Pro Ser Val Phe Leu Phe Pro Pro
260 265 270

Lys Pro Lys Asp Thr Leu Met Ile Ser Arg Thr Pro Glu Val Thr Cys

-continued

```
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys Met Phe Trp Val Leu Val
465                 470                 475                 480

Val Val Gly Gly Val Leu Ala Cys Tyr Ser Leu Leu Val Thr Val Ala
                485                 490                 495

Phe Ile Ile Phe Trp Val Arg Ser Lys Arg Ser Arg Gly Gly His Ser
            500                 505                 510

Asp Tyr Met Asn Met Thr Pro Arg Arg Pro Gly Pro Thr Arg Lys His
        515                 520                 525

Tyr Gln Pro Tyr Ala Pro Pro Arg Asp Phe Ala Ala Tyr Arg Ser Arg
    530                 535                 540

Val Lys Phe Ser Arg Ser Ala Asp Ala Pro Ala Tyr Gln Gln Gly Gln
545                 550                 555                 560

Asn Gln Leu Tyr Asn Glu Leu Asn Leu Gly Arg Arg Glu Glu Tyr Asp
                565                 570                 575

Val Leu Asp Lys Arg Arg Gly Arg Asp Pro Glu Met Gly Gly Lys Pro
            580                 585                 590

Arg Arg Lys Asn Pro Gln Glu Gly Leu Tyr Asn Glu Leu Gln Lys Asp
        595                 600                 605

Lys Met Ala Glu Ala Tyr Ser Glu Ile Gly Met Lys Gly Glu Arg Arg
    610                 615                 620

Arg Gly Lys Gly His Asp Gly Leu Tyr Gln Gly Leu Ser Thr Ala Thr
625                 630                 635                 640

Lys Asp Thr Tyr Asp Ala Leu His Met Gln Ala Leu Pro Pro Arg Ala
                645                 650                 655

Thr Asn Phe Ser Leu Leu Lys Gln Ala Gly Asp Val Glu Glu Asn Pro
            660                 665                 670

Gly Pro Met Thr Thr Pro Arg Asn Ser Val Asn Gly Thr Phe Pro Ala
        675                 680                 685

Glu Pro Met Lys Gly Pro Ile Ala Met Gln Ser Gly Pro Lys Pro Leu
    690                 695                 700
```

```
Phe Arg Arg Met Ser Ser Leu Val Gly Pro Thr Gln Ser Phe Phe Met
705                 710                 715                 720

Arg Glu Ser Lys Thr Leu Gly Ala Val Gln Ile Met Asn Gly Leu Phe
                725                 730                 735

His Ile Ala Leu Gly Gly Leu Leu Met Ile Pro Ala Gly Ile Tyr Ala
            740                 745                 750

Pro Ile Cys Val Thr Val Trp Tyr Pro Leu Trp Gly Gly Ile Met Tyr
        755                 760                 765

Ile Ile Ser Gly Ser Leu Leu Ala Ala Thr Glu Lys Asn Ser Arg Lys
    770                 775                 780

Cys Leu Val Lys Gly Lys Met Ile Met Asn Ser Leu Ser Leu Phe Ala
785                 790                 795                 800

Ala Ile Ser Gly Met Ile Leu Ser Ile Met Asp Ile Leu Asn Ile Lys
                805                 810                 815

Ile Ser His Phe Leu Lys Met Glu Ser Leu Asn Phe Ile Arg Ala His
            820                 825                 830

Thr Pro Tyr Ile Asn Ile Tyr Asn Cys Glu Pro Ala Asn Pro Ser Glu
        835                 840                 845

Lys Asn Ser Pro Ser Thr Gln Tyr Cys Tyr Ser Ile Gln Ser Leu Phe
    850                 855                 860

Leu Gly Ile Leu Ser Val Met Leu Ile Phe Ala Phe Phe Gln Glu Leu
865                 870                 875                 880

Val Ile Ala Gly Ile Val Glu Asn Glu Trp Lys Arg Thr Cys Ser Arg
                885                 890                 895

Pro Lys Ser Asn Ile Val Leu Leu Ser Ala Glu Glu Lys Lys Glu Gln
            900                 905                 910

Thr Ile Glu Ile Lys Glu Glu Val Val Gly Leu Thr Glu Thr Ser Ser
        915                 920                 925

Gln Pro Lys Asn Glu Glu Asp Ile Glu
    930                 935


<210> SEQ ID NO 196
<211> LENGTH: 888
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
```

-continued

```
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Glu Ser Lys Tyr Gly Pro Pro Cys Pro Pro Cys
                245                 250                 255

Pro Ala Pro Glu Phe Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys Met Phe Trp Val Leu Val
465                 470                 475                 480

Val Val Gly Gly Val Leu Ala Cys Tyr Ser Leu Leu Val Thr Val Ala
                485                 490                 495

Phe Ile Ile Phe Trp Val Arg Ser Lys Arg Ser Arg Gly Gly His Ser
            500                 505                 510

Asp Tyr Met Asn Met Thr Pro Arg Arg Pro Gly Pro Thr Arg Lys His
        515                 520                 525

Tyr Gln Pro Tyr Ala Pro Pro Arg Asp Phe Ala Ala Tyr Arg Ser Arg
    530                 535                 540
```

Val Lys Phe Ser Arg Ser Ala Asp Ala Pro Ala Tyr Gln Gln Gly Gln
545 550 555 560

Asn Gln Leu Tyr Asn Glu Leu Asn Leu Gly Arg Arg Glu Glu Tyr Asp
565 570 575

Val Leu Asp Lys Arg Arg Gly Arg Asp Pro Glu Met Gly Gly Lys Pro
580 585 590

Arg Arg Lys Asn Pro Gln Glu Gly Leu Tyr Asn Glu Leu Gln Lys Asp
595 600 605

Lys Met Ala Glu Ala Tyr Ser Glu Ile Gly Met Lys Gly Glu Arg Arg
610 615 620

Arg Gly Lys Gly His Asp Gly Leu Tyr Gln Gly Leu Ser Thr Ala Thr
625 630 635 640

Lys Asp Thr Tyr Asp Ala Leu His Met Gln Ala Leu Pro Pro Arg Ala
645 650 655

Thr Asn Phe Ser Leu Leu Lys Gln Ala Gly Asp Val Glu Glu Asn Pro
660 665 670

Gly Pro Met Thr Thr Pro Arg Asn Ser Val Asn Gly Thr Phe Pro Ala
675 680 685

Glu Pro Met Lys Gly Pro Ile Ala Met Gln Ser Gly Pro Lys Pro Leu
690 695 700

Phe Arg Arg Met Ser Ser Leu Val Gly Pro Thr Gln Ser Phe Phe Met
705 710 715 720

Arg Glu Ser Lys Thr Leu Gly Ala Val Gln Ile Met Asn Gly Leu Phe
725 730 735

His Ile Ala Leu Gly Gly Leu Leu Met Ile Pro Ala Gly Ile Tyr Ala
740 745 750

Pro Ile Cys Val Thr Val Trp Tyr Pro Leu Trp Gly Gly Ile Met Tyr
755 760 765

Ile Ile Ser Gly Ser Leu Leu Ala Ala Thr Glu Lys Asn Ser Arg Lys
770 775 780

Cys Leu Val Lys Gly Lys Met Ile Met Asn Ser Leu Ser Leu Phe Ala
785 790 795 800

Ala Ile Ser Gly Met Ile Leu Ser Ile Met Asp Ile Leu Asn Ile Lys
805 810 815

Ile Ser His Phe Leu Lys Met Glu Ser Leu Asn Phe Ile Arg Ala His
820 825 830

Thr Pro Tyr Ile Asn Ile Tyr Asn Cys Glu Pro Ala Asn Pro Ser Glu
835 840 845

Lys Asn Ser Pro Ser Thr Gln Tyr Cys Tyr Ser Ile Gln Ser Leu Phe
850 855 860

Leu Gly Ile Leu Ser Val Met Leu Ile Phe Ala Phe Phe Gln Glu Leu
865 870 875 880

Val Ile Ala Gly Ile Val Glu Asn
885

<210> SEQ ID NO 197
<211> LENGTH: 848
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 197

Met Lys Arg Phe Leu Phe Leu Leu Leu Thr Ile Ser Leu Leu Val Met

-continued

```
1               5                   10                  15

Val Gln Ile Gln Thr Gly Leu Ser Gly Gln Asn Asp Thr Ser Gln Thr
            20                  25                  30

Ser Ser Pro Ser Gly Ser Thr Ser Gly Ser Gly Lys Pro Gly Ser Gly
        35                  40                  45

Glu Gly Ser Thr Lys Gly Gly Gln Asn Asp Thr Ser Gln Thr Ser Ser
    50                  55                  60

Pro Ser Gly Ser Thr Ser Gly Ser Gly Lys Pro Gly Ser Gly Glu Gly
65                  70                  75                  80

Ser Thr Lys Gly Gly Gln Asn Asp Thr Ser Gln Thr Ser Ser Pro Ser
                85                  90                  95

Gly Ser Thr Ser Gly Ser Gly Lys Pro Gly Ser Gly Glu Gly Ser Thr
            100                 105                 110

Lys Gly Gly Gly Gly Gly Ser Gly Gly Gly Gly Ser Lys Pro Phe Trp
        115                 120                 125

Val Leu Val Val Val Gly Gly Val Leu Ala Cys Tyr Ser Leu Leu Val
    130                 135                 140

Thr Val Ala Phe Ile Ile Phe Trp Val Ala Thr Asn Phe Ser Leu Leu
145                 150                 155                 160

Lys Gln Ala Gly Asp Val Glu Glu Asn Pro Gly Pro Met Ala Leu Pro
                165                 170                 175

Val Thr Ala Leu Leu Leu Pro Leu Ala Leu Leu Leu His Ala Ala Arg
            180                 185                 190

Pro Asp Ile Gln Met Thr Gln Thr Thr Ser Ser Leu Ser Ala Ser Leu
        195                 200                 205

Gly Asp Arg Val Thr Ile Ser Cys Arg Ala Ser Gln Asp Ile Ser Lys
    210                 215                 220

Tyr Leu Asn Trp Tyr Gln Gln Lys Pro Asp Gly Thr Val Lys Leu Leu
225                 230                 235                 240

Ile Tyr His Thr Ser Arg Leu His Ser Gly Val Pro Ser Arg Phe Ser
                245                 250                 255

Gly Ser Gly Ser Gly Thr Asp Tyr Ser Leu Thr Ile Ser Asn Leu Glu
            260                 265                 270

Gln Glu Asp Ile Ala Thr Tyr Phe Cys Gln Gln Gly Asn Thr Leu Pro
        275                 280                 285

Tyr Thr Phe Gly Gly Gly Thr Lys Leu Glu Ile Thr Gly Ser Thr Ser
    290                 295                 300

Gly Ser Gly Lys Pro Gly Ser Gly Glu Gly Ser Thr Lys Gly Glu Val
305                 310                 315                 320

Lys Leu Gln Glu Ser Gly Pro Gly Leu Val Ala Pro Ser Gln Ser Leu
                325                 330                 335

Ser Val Thr Cys Thr Val Ser Gly Val Ser Leu Pro Asp Tyr Gly Val
            340                 345                 350

Ser Trp Ile Arg Gln Pro Pro Arg Lys Gly Leu Glu Trp Leu Gly Val
        355                 360                 365

Ile Trp Gly Ser Glu Thr Thr Tyr Tyr Asn Ser Ala Leu Lys Ser Arg
    370                 375                 380

Leu Thr Ile Ile Lys Asp Asn Ser Lys Ser Gln Val Phe Leu Lys Met
385                 390                 395                 400

Asn Ser Leu Gln Thr Asp Asp Thr Ala Ile Tyr Tyr Cys Ala Lys His
                405                 410                 415

Tyr Tyr Tyr Gly Gly Ser Tyr Ala Met Asp Tyr Trp Gly Gln Gly Thr
            420                 425                 430
```

```
Ser Val Thr Val Ser Ser Glu Ser Lys Tyr Gly Pro Pro Cys Pro Pro
        435                 440                 445

Cys Pro Ala Pro Glu Phe Leu Gly Gly Pro Ser Val Phe Leu Phe Pro
    450                 455                 460

Pro Lys Pro Lys Asp Thr Leu Met Ile Ser Arg Thr Pro Glu Val Thr
465                 470                 475                 480

Cys Val Val Val Asp Val Ser Gln Glu Asp Pro Glu Val Gln Phe Asn
                485                 490                 495

Trp Tyr Val Asp Gly Val Glu Val His Asn Ala Lys Thr Lys Pro Arg
            500                 505                 510

Glu Glu Gln Phe Asn Ser Thr Tyr Arg Val Val Ser Val Leu Thr Val
        515                 520                 525

Leu His Gln Asp Trp Leu Asn Gly Lys Glu Tyr Lys Cys Lys Val Ser
    530                 535                 540

Asn Lys Gly Leu Pro Ser Ser Ile Glu Lys Thr Ile Ser Lys Ala Lys
545                 550                 555                 560

Gly Gln Pro Arg Glu Pro Gln Val Tyr Thr Leu Pro Pro Ser Gln Glu
                565                 570                 575

Glu Met Thr Lys Asn Gln Val Ser Leu Thr Cys Leu Val Lys Gly Phe
            580                 585                 590

Tyr Pro Ser Asp Ile Ala Val Glu Trp Glu Ser Asn Gly Gln Pro Glu
        595                 600                 605

Asn Asn Tyr Lys Thr Thr Pro Pro Val Leu Asp Ser Asp Gly Ser Phe
    610                 615                 620

Phe Leu Tyr Ser Arg Leu Thr Val Asp Lys Ser Arg Trp Gln Glu Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Leu Gly Lys Met Phe Trp Val Leu
            660                 665                 670

Val Val Val Gly Gly Val Leu Ala Cys Tyr Ser Leu Leu Val Thr Val
        675                 680                 685

Ala Phe Ile Ile Phe Trp Val Arg Ser Lys Arg Ser Arg Gly Gly His
    690                 695                 700

Ser Asp Tyr Met Asn Met Thr Pro Arg Arg Pro Gly Pro Thr Arg Lys
705                 710                 715                 720

His Tyr Gln Pro Tyr Ala Pro Pro Arg Asp Phe Ala Ala Tyr Arg Ser
                725                 730                 735

Arg Val Lys Phe Ser Arg Ser Ala Asp Ala Pro Ala Tyr Gln Gln Gly
            740                 745                 750

Gln Asn Gln Leu Tyr Asn Glu Leu Asn Leu Gly Arg Arg Glu Glu Tyr
        755                 760                 765

Asp Val Leu Asp Lys Arg Arg Gly Arg Asp Pro Glu Met Gly Gly Lys
    770                 775                 780

Pro Arg Arg Lys Asn Pro Gln Glu Gly Leu Tyr Asn Glu Leu Gln Lys
785                 790                 795                 800

Asp Lys Met Ala Glu Ala Tyr Ser Glu Ile Gly Met Lys Gly Glu Arg
                805                 810                 815

Arg Arg Gly Lys Gly His Asp Gly Leu Tyr Gln Gly Leu Ser Thr Ala
            820                 825                 830

Thr Lys Asp Thr Tyr Asp Ala Leu His Met Gln Ala Leu Pro Pro Arg
        835                 840                 845
```

<210> SEQ ID NO 198
<211> LENGTH: 910
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 198

```
Met Arg Leu Pro Ala Gln Leu Leu Gly Leu Leu Met Leu Trp Val Pro
1               5                   10                  15

Gly Ser Ser Gly Arg Cys Ala Tyr Gly Tyr Tyr Gln Asp Glu Thr Thr
            20                  25                  30

Gly Arg Cys Glu Ala Cys Arg Val Cys Glu Ala Gly Ser Gly Leu Val
        35                  40                  45

Phe Ser Cys Gln Asp Lys Gln Asn Thr Val Cys Glu Glu Cys Pro Asp
    50                  55                  60

Gly Thr Tyr Ser Asp Glu Ala Asn His Val Asp Pro Cys Leu Pro Cys
65                  70                  75                  80

Thr Val Cys Glu Asp Thr Glu Arg Gln Leu Arg Glu Cys Thr Arg Trp
                85                  90                  95

Ala Asp Ala Glu Cys Glu Glu Ile Pro Gly Arg Trp Ile Thr Arg Ser
            100                 105                 110

Thr Pro Pro Glu Gly Ser Asp Ser Thr Ala Pro Ser Thr Gln Glu Pro
        115                 120                 125

Glu Ala Pro Pro Glu Gln Asp Leu Ile Ala Ser Thr Val Ala Gly Val
    130                 135                 140

Val Thr Thr Val Met Gly Ser Ser Gln Pro Val Val Thr Arg Gly Thr
145                 150                 155                 160

Thr Asp Asn Gly Gly Gly Gly Ser Gly Gly Gly Gly Ser Gly Gly Gly
                165                 170                 175

Gly Ser Gly Gly Gly Gly Ser Phe Trp Val Leu Val Val Val Gly Gly
            180                 185                 190

Val Leu Ala Cys Tyr Ser Leu Leu Val Thr Val Ala Phe Ile Ile Phe
        195                 200                 205

Trp Val Arg Ser Lys Arg Ser Ala Thr Asn Phe Ser Leu Leu Lys Gln
    210                 215                 220

Ala Gly Asp Val Glu Glu Asn Pro Gly Pro Met Ala Leu Pro Val Thr
225                 230                 235                 240

Ala Leu Leu Leu Pro Leu Ala Leu Leu Leu His Ala Ala Arg Pro Asp
                245                 250                 255

Ile Gln Met Thr Gln Thr Thr Ser Ser Leu Ser Ala Ser Leu Gly Asp
            260                 265                 270

Arg Val Thr Ile Ser Cys Arg Ala Ser Gln Asp Ile Ser Lys Tyr Leu
        275                 280                 285

Asn Trp Tyr Gln Gln Lys Pro Asp Gly Thr Val Lys Leu Leu Ile Tyr
    290                 295                 300

His Thr Ser Arg Leu His Ser Gly Val Pro Ser Arg Phe Ser Gly Ser
305                 310                 315                 320

Gly Ser Gly Thr Asp Tyr Ser Leu Thr Ile Ser Asn Leu Glu Gln Glu
                325                 330                 335

Asp Ile Ala Thr Tyr Phe Cys Gln Gln Gly Asn Thr Leu Pro Tyr Thr
            340                 345                 350

Phe Gly Gly Gly Thr Lys Leu Glu Ile Thr Gly Ser Thr Ser Gly Ser
        355                 360                 365
```

```
Gly Lys Pro Gly Ser Gly Glu Gly Ser Thr Lys Gly Glu Val Lys Leu
    370                 375                 380

Gln Glu Ser Gly Pro Gly Leu Val Ala Pro Ser Gln Ser Leu Ser Val
385                 390                 395                 400

Thr Cys Thr Val Ser Gly Val Ser Leu Pro Asp Tyr Gly Val Ser Trp
                405                 410                 415

Ile Arg Gln Pro Pro Arg Lys Gly Leu Glu Trp Leu Gly Val Ile Trp
            420                 425                 430

Gly Ser Glu Thr Thr Tyr Tyr Asn Ser Ala Leu Lys Ser Arg Leu Thr
        435                 440                 445

Ile Ile Lys Asp Asn Ser Lys Ser Gln Val Phe Leu Lys Met Asn Ser
    450                 455                 460

Leu Gln Thr Asp Asp Thr Ala Ile Tyr Tyr Cys Ala Lys His Tyr Tyr
465                 470                 475                 480

Tyr Gly Gly Ser Tyr Ala Met Asp Tyr Trp Gly Gln Gly Thr Ser Val
                485                 490                 495

Thr Val Ser Ser Glu Ser Lys Tyr Gly Pro Pro Cys Pro Pro Cys Pro
            500                 505                 510

Ala Pro Glu Phe Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser Gln Glu Asp Pro Glu Val Gln Phe Asn Trp Tyr
545                 550                 555                 560

Val Asp Gly Val Glu Val His Asn Ala Lys Thr Lys Pro Arg Glu Glu
                565                 570                 575

Gln Phe Asn Ser Thr Tyr Arg Val Val Ser Val Leu Thr Val Leu His
            580                 585                 590

Gln Asp Trp Leu Asn Gly Lys Glu Tyr Lys Cys Lys Val Ser Asn Lys
        595                 600                 605

Gly Leu Pro Ser Ser Ile Glu Lys Thr Ile Ser Lys Ala Lys Gly Gln
    610                 615                 620

Pro Arg Glu Pro Gln Val Tyr Thr Leu Pro Pro Ser Gln Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Arg Leu Thr Val Asp Lys Ser Arg Trp Gln Glu Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Leu Gly Lys Met Phe Trp Val Leu Val Val
                725                 730                 735

Val Gly Gly Val Leu Ala Cys Tyr Ser Leu Leu Val Thr Val Ala Phe
            740                 745                 750

Ile Ile Phe Trp Val Arg Ser Lys Arg Ser Arg Gly Gly His Ser Asp
        755                 760                 765

Tyr Met Asn Met Thr Pro Arg Arg Pro Gly Pro Thr Arg Lys His Tyr
    770                 775                 780
```

```
Gln Pro Tyr Ala Pro Pro Arg Asp Phe Ala Ala Tyr Arg Ser Arg Val
785                 790                 795                 800

Lys Phe Ser Arg Ser Ala Asp Ala Pro Ala Tyr Gln Gln Gly Gln Asn
                805                 810                 815

Gln Leu Tyr Asn Glu Leu Asn Leu Gly Arg Arg Glu Glu Tyr Asp Val
            820                 825                 830

Leu Asp Lys Arg Arg Gly Arg Asp Pro Glu Met Gly Gly Lys Pro Arg
        835                 840                 845

Arg Lys Asn Pro Gln Glu Gly Leu Tyr Asn Glu Leu Gln Lys Asp Lys
    850                 855                 860

Met Ala Glu Ala Tyr Ser Glu Ile Gly Met Lys Gly Glu Arg Arg Arg
865                 870                 875                 880

Gly Lys Gly His Asp Gly Leu Tyr Gln Gly Leu Ser Thr Ala Thr Lys
                885                 890                 895

Asp Thr Tyr Asp Ala Leu His Met Gln Ala Leu Pro Pro Arg
            900                 905                 910


<210> SEQ ID NO 199
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199

cgcaaagtgt gtaacggaat aggtattggt gaatttaaag actcactctc cataaatgct      60

acgaatatta aacacttcaa aaactgcacc tccatcagtg gcgatctcca catcctgccg     120

gtggcattta ggggtgactc cttcacacat actcctcctc tggatccaca ggaactggat     180

attctgaaaa ccgtaaagga aatcacaggg tttttgctga ttcaggcttg gcctgaaaac     240

aggacggacc tccatgcctt tgagaaccta gaaatcatac gcggcaggac caagcaacat     300

ggtcagtttt ctcttgcagt cgtcagcctg aacataacat ccttgggatt acgctccctc     360

aaggagataa gtgatggaga tgtgataatt tcaggaaaca aaaatttgtg ctatgcaaat     420

acaataaact ggaaaaaact gtttgggacc tccggtcaga aaaccaaaat tataagcaac     480

agaggtgaaa acagctgcaa ggccacaggc cag                                  513


<210> SEQ ID NO 200
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80
```

-continued

```
Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln
                165                 170
```

<210> SEQ ID NO 201
<211> LENGTH: 423
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 201

```
gtctgccatg ccttgtgctc ccccgagggc tgctggggcc cggagcccag ggactgcgtc     60

tcttgccgga atgtcagccg aggcagggaa tgcgtggaca agtgcaacct tctggagggt    120

gagccaaggg agtttgtgga gaactctgag tgcatacagt gccacccaga gtgcctgcct    180

caggccatga acatcacctg cacaggacgg ggaccagaca actgtatcca gtgtgcccac    240

tacattgacg gcccccactg cgtcaagacc tgcccggcag gagtcatggg agaaaacaac    300

accctggtct ggaagtacgc agacgccggc catgtgtgcc acctgtgcca tccaaactgc    360

acctacggat gcactgggcc aggtcttgaa ggctgtccaa cgaatgggcc taagatcccg    420

tcc                                                                   423
```

<210> SEQ ID NO 202
<211> LENGTH: 141
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 202

```
Val Cys His Ala Leu Cys Ser Pro Glu Gly Cys Trp Gly Pro Glu Pro
1               5                   10                  15

Arg Asp Cys Val Ser Cys Arg Asn Val Ser Arg Gly Arg Glu Cys Val
            20                  25                  30

Asp Lys Cys Asn Leu Leu Glu Gly Glu Pro Arg Glu Phe Val Glu Asn
        35                  40                  45

Ser Glu Cys Ile Gln Cys His Pro Glu Cys Leu Pro Gln Ala Met Asn
    50                  55                  60

Ile Thr Cys Thr Gly Arg Gly Pro Asp Asn Cys Ile Gln Cys Ala His
65                  70                  75                  80

Tyr Ile Asp Gly Pro His Cys Val Lys Thr Cys Pro Ala Gly Val Met
                85                  90                  95

Gly Glu Asn Asn Thr Leu Val Trp Lys Tyr Ala Asp Ala Gly His Val
            100                 105                 110

Cys His Leu Cys His Pro Asn Cys Thr Tyr Gly Cys Thr Gly Pro Gly
        115                 120                 125
```

```
Leu Glu Gly Cys Pro Thr Asn Gly Pro Lys Ile Pro Ser
    130                 135                 140


<210> SEQ ID NO 203
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Val Cys His Ala Leu Cys Ser Pro Glu Gly Cys Trp Gly Pro Glu Pro
1               5                   10                  15

Arg Asp Cys Val Ser
            20


<210> SEQ ID NO 204
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Val Cys His Ala Leu Cys Ser Pro Glu Gly Cys Trp Gly Pro Glu Pro
1               5                   10                  15

Arg Asp Cys Val Ser Cys Arg Asn Val Ser Arg Gly Arg Glu Cys Val
            20                  25                  30

Asp Lys


<210> SEQ ID NO 205
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Val Cys His Ala Leu Cys Ser Pro Glu Gly Cys Trp Gly Pro Glu Pro
1               5                   10                  15

Arg Asp Cys Val Ser Cys Arg Asn Val Ser Arg Gly Arg Glu Cys Val
            20                  25                  30

Asp Lys Cys Asn Leu Leu Glu Gly Glu Pro Arg Glu Phe Val Glu Asn
        35                  40                  45

Ser Glu Cys Ile Gln
    50


<210> SEQ ID NO 206
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Val Cys His Ala Leu Cys Ser Pro Glu Gly Cys Trp Gly Pro Glu Pro
1               5                   10                  15

Arg Asp Cys Val Ser Cys Arg Asn Val Ser Arg Gly Arg Glu Cys Val
            20                  25                  30
```

Asp Lys Cys Asn Leu Leu Glu Gly Glu Pro Arg Glu Phe Val Glu Asn
35 40 45

Ser Glu Cys Ile Gln Cys His Pro Glu Cys Leu Pro Gln Ala Met Asn
50 55 60

Ile Thr Cys Thr Gly Arg Gly Pro Asp Asn Cys Ile Gln
65 70 75

<210> SEQ ID NO 207
<211> LENGTH: 90
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 207

Val Cys His Ala Leu Cys Ser Pro Glu Gly Cys Trp Gly Pro Glu Pro
1 5 10 15

Arg Asp Cys Val Ser Cys Arg Asn Val Ser Arg Gly Arg Glu Cys Val
20 25 30

Asp Lys Cys Asn Leu Leu Glu Gly Glu Pro Arg Glu Phe Val Glu Asn
35 40 45

Ser Glu Cys Ile Gln Cys His Pro Glu Cys Leu Pro Gln Ala Met Asn
50 55 60

Ile Thr Cys Thr Gly Arg Gly Pro Asp Asn Cys Ile Gln Cys Ala His
65 70 75 80

Tyr Ile Asp Gly Pro His Cys Val Lys Thr
85 90

<210> SEQ ID NO 208
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 208

Val Cys His Ala Leu Cys Ser Pro Glu Gly Cys Trp Gly Pro Glu Pro
1 5 10 15

Arg Asp Cys Val Ser Cys Arg Asn Val Ser Arg Gly Arg Glu Cys Val
20 25 30

Asp Lys Cys Asn Leu Leu Glu Gly Glu Pro Arg Glu Phe Val Glu Asn
35 40 45

Ser Glu Cys Ile Gln Cys His Pro Glu Cys Leu Pro Gln Ala Met Asn
50 55 60

Ile Thr Cys Thr Gly Arg Gly Pro Asp Asn Cys Ile Gln Cys Ala His
65 70 75 80

Tyr Ile Asp Gly Pro His Cys Val Lys Thr Cys Pro Ala Gly Val Met
85 90 95

Gly Glu Asn Asn Thr Leu Val Trp Lys Tyr Ala Asp Ala Gly His Val
100 105 110

Cys His Leu
115

<210> SEQ ID NO 209
<211> LENGTH: 133
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 209

Val Cys His Ala Leu Cys Ser Pro Glu Gly Cys Trp Gly Pro Glu Pro
1 5 10 15

Arg Asp Cys Val Ser Cys Arg Asn Val Ser Arg Gly Arg Glu Cys Val
20 25 30

Asp Lys Cys Asn Leu Leu Glu Gly Glu Pro Arg Glu Phe Val Glu Asn
35 40 45

Ser Glu Cys Ile Gln Cys His Pro Glu Cys Leu Pro Gln Ala Met Asn
50 55 60

Ile Thr Cys Thr Gly Arg Gly Pro Asp Asn Cys Ile Gln Cys Ala His
65 70 75 80

Tyr Ile Asp Gly Pro His Cys Val Lys Thr Cys Pro Ala Gly Val Met
85 90 95

Gly Glu Asn Asn Thr Leu Val Trp Lys Tyr Ala Asp Ala Gly His Val
100 105 110

Cys His Leu Cys His Pro Asn Cys Thr Tyr Gly Cys Thr Gly Pro Gly
115 120 125

Leu Glu Gly Cys Pro
130

<210> SEQ ID NO 210
<211> LENGTH: 312
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 210

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser
305                 310

<210> SEQ ID NO 211
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

<210> SEQ ID NO 212
<211> LENGTH: 205
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 212

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys
195 200 205

<210> SEQ ID NO 213
<211> LENGTH: 224
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 213

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp

```
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220


<210> SEQ ID NO 214
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln
                245


<210> SEQ ID NO 215
<211> LENGTH: 261
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 215

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr
            260

<210> SEQ ID NO 216
<211> LENGTH: 286
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 216

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

```
Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu
        275                 280                 285


<210> SEQ ID NO 217
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125
```

-continued

```
Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300


<210> SEQ ID NO 218
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Lys Ile Ser His Phe Leu Lys Met Glu Ser Leu Asn Phe Ile Arg Ala
1               5                   10                  15

His Thr Pro Tyr Ile Asn Ile Tyr Asn Cys Glu Pro Ala Asn Pro Ser
            20                  25                  30

Glu Lys Asn Ser Pro Ser Thr Gln Tyr Cys Tyr Ser Ile Gln Ser
        35                  40                  45


<210> SEQ ID NO 219
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Pro Tyr Ile Asn Ile Tyr Asn Cys Glu Pro Ala Asn Pro Ser Glu Lys
1               5                   10                  15

Asn Ser Pro Ser Thr Gln Tyr Cys Tyr Ser Ile Gln Ser
            20                  25


<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 220

Cys Glu Pro Ala Asn Pro Ser Glu Lys Asn Ser Pro Ser Thr Gln Tyr
1               5                   10                  15

Cys

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Gly Gly Gly Ser
1               5

<210> SEQ ID NO 222
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 "Gly Gly Gly
      Gly Ser" repeating units

<400> SEQUENCE: 222

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ser Gly Gly Gly Gly Ser
1               5

<210> SEQ ID NO 224
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Gly Gly Ser
1

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 225

Glu Ser Lys Tyr Gly Pro Pro Cys Pro Pro Cys Pro
1               5                   10

<210> SEQ ID NO 226
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ser Gly Gly Gly Ser Gly Gly Gly Gly Ser Gly Gly Gly Gly Ser Gly
1               5                   10                  15

Gly Gly Gly Ser Gly Gly Gly Ser Leu Gln
            20                  25

<210> SEQ ID NO 227
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Arg Ala Lys Arg Gly Ser Gly Glu Gly Arg Gly Ser Leu Leu Thr Cys
1               5                   10                  15

Gly Asp Val Glu Glu Asn Pro Gly Pro
            20                  25

<210> SEQ ID NO 228
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Arg Ala Lys Arg Ser Gly Ser Gly Glu Gly Arg Gly Ser Leu Leu Thr
1               5                   10                  15

Cys Gly Asp Val Glu Glu Asn Pro Gly Pro
            20                  25

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 229

Asp Xaa Glu Xaa Asn Pro Gly Pro
1               5

<210> SEQ ID NO 230
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 230

Arg Ala Lys Arg
1

<210> SEQ ID NO 231
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 231
agagctaaga gg 12

<210> SEQ ID NO 232
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 232
cgtgcaaagc gt 12

<210> SEQ ID NO 233
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Arg Ala Lys Arg Ala Pro Val Lys Gln Thr Leu Asn Phe Asp Leu Leu
1 5 10 15

Lys Leu Ala Gly Asp Val Glu Ser Asn Pro Gly Pro
20 25

<210> SEQ ID NO 234
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 234
agagccaaga gggcaccggt gaaacagact ttgaattttg accttctgaa gttggcagga 60
gacgttgagt ccaaccctgg gccc 84

<210> SEQ ID NO 235
<211> LENGTH: 22
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 235

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 236
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ggaagcggag ctactaactt cagcctgctg aagcaggctg gagacgtgga ggagaaccct     60
ggacct                                                                66

<210> SEQ ID NO 237
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Arg Ala Lys Arg Ala Pro Val Lys Gln Gly Ser Gly Ala Thr Asn Phe
1               5                   10                  15

Ser Leu Leu Lys Gln Ala Gly Asp Val Glu Glu Asn Pro Gly Pro
            20                  25                  30

<210> SEQ ID NO 238
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
cgtgcaaagc gtgcaccggt gaaacaggga agcggagcta ctaacttcag cctgctgaag     60
caggctggag acgtggagga gaaccctgga cct                                  93

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:

-continued

```
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MISC_FEATURE
<222> LOCATION: (1)..(10)
<223> OTHER INFORMATION: This sequence may encompass 2-5 "Xaa Pro"
      repeating units

<400> SEQUENCE: 239

Xaa Pro Xaa Pro Xaa Pro Xaa Pro Xaa Pro
1               5                   10


<210> SEQ ID NO 240
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(26)
<223> OTHER INFORMATION: This region may encompass 2-5 "Glu Ala Ala Ala
      Lys" repeating units

<400> SEQUENCE: 240

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25
```

EXPRESSION OF NOVEL CELL TAGS

CROSS-REFERENCE TO RELATED APPLICATION

The present application is a division of U.S. application Ser. No. 16/001,759, filed Jun. 6, 2018, which in turn claims the benefit of U.S. Provisional Patent Application No. 62/516,639 filed Jun. 7, 2017, both of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on May 30, 2018, is named 50471-708_601_SL.txt and is 464,445 bytes in size.

BACKGROUND OF THE DISCLOSURE

Cell therapies offer the promise of treating diseases that cannot be treated adequately by conventional pharmaceuticals. Blood transfusions were the first type of cell therapy to treat hematological malignancies. Recent advances in cell isolation, induction and gene transfer technologies has allowed for genetic modification of various cell types (primary and immortalized) for treatment of variety of diseases e.g. cancer, cardiovascular, dermatological, neurological, and ophthalmological diseases. In many cases, it is critical to enrich for genetically modified cell therapy product to achieve necessary purity to allow for expansion of select cells of therapeutic interest and/or eliminate non-genetically modified or other cell types prior to infusion in patients. In addition, adoptive cell immunotherapy using for example, cytokines, chimeric antigen receptors (CAR) and T-cell receptors (TCR) has shown great promise to successfully direct killing of tumor cells. While this innovative technology is promising, the administration of modified immune cells into tumor bearing individuals has not been without safety issues, for instance toxicity, tumor lysis and cytokine release syndrome (i.e., "cytokine storm") in the case of CAR-T cell therapy. In order to take full advantage of the therapeutic potential offered by adoptive T cell immunotherapy techniques, it is imperative that side effects such as cytokine storm be controlled during therapy.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Provided are polypeptide constructs and polynucleotides which can be expressed in cells to address one or more of the above deficiencies.

Provided is a polypeptide construct and polynucleotide encoding the polypeptide construct, the polypeptide construct comprising a truncated variant of a natural polypeptide. In some embodiments, the polypeptide construct can further comprise a transmembrane domain or a fragment thereof, a signal peptide and/or a peptide linker. Also provided herein are engineered cells expressing the polynucleotides and polypeptide constructs. The engineered cells can express the polypeptide constructs at the cell surface thereby providing for a cell marker (or "cell tag") which in some embodiments uniquely identifies the engineered cells.

Further provided herein is a polypeptide construct and polynucleotide encoding the polypeptide construct, the polypeptide construct comprising a truncated variant of a natural polypeptide and a transmembrane domain. In certain embodiments, the truncated variant comprises an extracellular domain or portion thereof and a transmembrane domain or portion thereof. In some embodiments, the polypeptide construct can comprise a transmembrane domain and a truncated variant derived from different natural proteins. In some cases, the truncated variant transmembrane domain of a polypeptide construct is a single-pass transmembrane domain. In other cases, the transmembrane domain of a polypeptide construct is a multiple-pass transmembrane domain.

Provided herein is a polypeptide construct and a polynucleotide encoding the polypeptide construct, the polypeptide construct including a transmembrane dimerization domain capable of coupling a cell surface polypeptide (e.g., a truncated variant fused to the transmembrane domain) at the cell surface to a second cell surface polypeptide. In certain embodiments, the coupling of cell surface polypeptides via a transmembrane dimerization domain can amplify a signal originating at the cell surface polypeptides relative to a non-dimerized configuration.

Still further provided herein is a polypeptide construct and a polynucleotide encoding the polypeptide construct, the polypeptide construct comprising domains or fragments thereof which originate from different natural proteins. In some embodiments, a polypeptide construct described herein can comprise a truncated variant of a natural polypeptide, a transmembrane domain, an optional peptide linker connecting the truncated variant to the transmembrane domain, and a signal peptide directing the polypeptide construct to a cell surface. For example, in some embodiments, a polypeptide construct contains a truncated variant or fragment thereof which is derived from a different natural protein than a transmembrane domain or fragment thereof fused either directly or indirectly to the truncated variant or fragment thereof. In some embodiments, a particular domain (e.g. extracellular domain) of a polypeptide construct described herein is chimeric and contains amino acid sequences derived from different natural proteins.

In some cases provided are methods and compositions comprising a polypeptide construct including a cell surface polypeptide and a trans-membrane dimerization domain, wherein the trans-membrane dimerization domain induces dimerization of the cell surface polypeptide and the cell surface polypeptide binds a predetermined antibody or a variant or fragment thereof. Also provided herein are polynucleotide sequences encoding a polypeptide construct described herein.

Provided herein are methods and compositions comprising cell tags that include truncated variants of polypeptides, such as HER1, CD20, LNGFR and CD52. In some cases, the truncated variants of the polypeptides do not bind an endogenous receptor. The disclosed truncated non-immunogenic polypeptides can be used as cell tags for example as a cell marker, depletion marker or kill tag.

Provided herein are compositions comprising engineered cells that express polypeptide constructs or polynucleotides as described herein. In some cases, the engineered cells further express at least one of a chimeric antigen receptor (CAR), a T-cell receptor (TCR) and/or a cytokine.

Provided herein are methods of regulating activity of genetically engineered cells in a subject (e.g., undergoing immunotherapy), comprising providing to the subject genetically engineered cells encoding a polynucleotide construct disclosed herein, and further providing to the subject a predetermined binding partner that binds and regulates the activity of the cells. Also provided are systems and kits for use in the methods.

Provided is a polypeptide construct comprising a cell surface polypeptide and a trans-membrane dimerization domain, wherein said trans-membrane dimerization domain induces dimerization of said cell surface polypeptide, and wherein said cell surface polypeptide binds a predetermined antibody or a variant or fragment thereof.

In some embodiments, said cell surface polypeptide comprises at least one of a HER1 polypeptide, a LNGFR polypeptide, a CD20 polypeptide and a CD52 polypeptide. In some cases, said cell surface polypeptide comprises a HER1 polypeptide, and said HER 1 polypeptide comprises a polypeptide sequence which has at least 70%, 75%, 80%, 85%, 90%, 95%, 99% or 99.5% identity to a sequence shown in SEQ ID Nos:211, 212, 213, 214, 215, 216 or 217. In some instances, said HER1 polypeptide comprises a polypeptide sequence comprising a sequence shown in SEQ ID NOs: 211, 212, 213, 214, 215, 216 or 217.

In some embodiments, said cell surface polypeptide comprises a CD20 polypeptide, and said CD20 polypeptide comprises a polypeptide sequence which has at least 70%, 75%, 80%, 85%, 90%, 95%, 99% or 99.5% identity to a sequence shown in SEQ ID NO:218, SEQ ID NO:219 or SEQ ID NO:220. In some cases said CD20 polypeptide comprises a polypeptide sequence comprising a sequence shown in SEQ ID NO:218, SEQ ID NO:219 or SEQ ID NO:220.

In some embodiments, said cell surface polypeptide comprises a LNGFR polypeptide, and said LNGFR polypeptide comprises a polypeptide sequence which has at least 70%, 75%, 80%, 85%, 90%, 95%, 99% or 99.5% identity to a sequence shown in SEQ ID NO:156, SEQ ID NO:158 or SEQ ID NO:160. In some cases said cell surface polypeptide comprises a LNGFR polypeptide, and said LNGFR polypeptide comprises a polypeptide sequence which has at least 70%, 75%, 80%, 85%, 90%, 95%, 99% or 99.5% identity to a sequence shown in SEQ ID NO:156, SEQ ID NO:158 or SEQ ID NO:160.

In some instances, said cell surface polypeptide does not bind an endogenous receptor. In some cases, said trans-membrane dimerization domain can form either a homodimer or a heterodimer with a complementary dimerization domain. In some instances, said trans-membrane dimerization domain comprises at least one cysteine residue. In some embodiments, said trans-membrane dimerization domain comprises a glycophorin A transmembrane domain or fragment or variant thereof, a glycophorin A-integrin β3 chimeric transmembrane domain or fragment or variant thereof or a CD3 zeta transmembrane domain. In some cases, such a cell surface polypeptide comprises at least a HER1 polypeptide.

In some cases, said polypeptide construct is expressed in an engineered cell. In some embodiments, said engineered cell is an animal cell. In some instances, said animal cell is a human cell. In some embodiments, said human cell is a T cell or NK cell. In some cases, said engineered cell further comprises a Sleeping Beauty transposase.

In some instances, said engineered cell further expresses at least one additional exogenous polypeptide. In some cases, said engineered cell further expresses at least one exogenous receptor polypeptide or fragment thereof. In some instances, said engineered cell further expresses at least one of a chimeric antigen receptor (CAR), a T-cell receptor (TCR) and a cytokine. In some embodiments, said engineered cell further expresses at least one CAR and wherein said CAR binds at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72, EGFRvIII, CD123 and VEGF-R2.

In some cases, said engineered cell further expresses at least one recombinant cytokine. In some instances, said recombinant cytokine comprises at least one of IL-15, mbIL-15, IL-2, IL-12, and IL-21. In some embodiments, said polypeptide construct is encoded by a polynucleotide incorporated into said engineered cell by genome editing. In some cases, said genome editing comprises use of at least a site specific serine recombinase system. In some instances, said polypeptide construct comprises a linker that fuses said cell surface polypeptide to said trans-membrane dimerization domain. In some cases, a polypeptide homo-dimer or heterodimer comprises the polypeptide construct.

Provided is a polynucleotide encoding a polypeptide construct comprising a non-immunogenic cell surface polypeptide fused to a trans-membrane dimerization domain, wherein said trans-membrane dimerization domain induces dimerization of said cell surface polypeptide. In some embodiments, said cell surface polypeptide does not bind an endogenous receptor. In some cases, said cell surface polypeptide does not contain any endogenous signaling or trafficking functions.

In some instances, said polynucleotide comprises at least one sequence encoding at least one heterologous gene. In some embodiments, said at least one heterologous gene is modulated by an inducible promoter. In some cases said at least one heterologous gene comprises at least one of a chimeric antigen receptor (CAR), a T-cell receptor (TCR) and a cytokine. In some embodiments, said at least one heterologous gene comprises said CAR, and wherein said CAR binds at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72, EGFRvIII, CD123 and VEGF-R2.

In some embodiments, said at least one heterologous gene comprises a cytokine. In some cases, said cytokine comprises at least one of IL-15, IL-2, IL-12, IL-21, and a fusion of IL-15 and IL-15Rα. In some embodiments, said cytokine is in secreted form. In some instances, said cytokine is in membrane bound form.

In some embodiments, said polynucleotide comprises at least one sequence comprising a polypeptide linker selected from the group consisting of 2A, GSG-2A, GSG linker (SEQ ID NO: 16), SGSG linker (SEQ ID NO: 18), furinlink variants and derivatives thereof. In some embodiments, said 2A linker is a p2A linker a T2A linker, F2A linker or E2A linker.

In some instances, said polypeptide construct acts as a tag to enrich cells, select cells, or induce cell death in cells expressing said cell surface molecule. In some cases, said cell surface polypeptide comprises at least one of a HER1 polypeptide, a LNGFR polypeptide, a CD20 polypeptide and a CD52 polypeptide. In some embodiments, said trans-membrane dimerization domain comprises a glycophorin A transmembrane domain or fragment or variant thereof, a glycophorin A-integrin β3 chimeric transmembrane domain or fragment or variant thereof, or a CD3 zeta transmembrane domain.

In some cases, a vector comprises the polynucleotide. In some instances, said vector is a lentivirus vector, a retroviral vector, or a non-viral vector. In some embodiments, the non-viral vector is a Sleeping Beauty transposon. In some cases, said polynucleotide is incorporated into an engineered cell by genome editing. In some cases, said genome editing comprises use of at least a site specific serine recombinase system.

Provided is a method of regulating activity of genetically engineered cells in a subject comprising: providing to said subject an amount of genetically engineered cells encoding a polypeptide construct comprising a cell surface polypeptide fused to a trans-membrane dimerization domain, wherein said trans-membrane dimerization domain induces dimerization of said cell surface polypeptide, and wherein said cell surface polypeptide binds a predetermined binding partner or a variant or fragment thereof; and providing to said subject said predetermined binding partner in an amount sufficient to bind and thereby regulating activity of said genetically engineered cells.

In some embodiments, said cell surface polypeptide is a non-immunogenic polypeptide. In some embodiments, said cell surface polypeptide comprises at least one of a HER1 polypeptide, a LNGFR polypeptide, a CD20 polypeptide and a CD52 polypeptide. In some instances, said cell surface polypeptide does not bind an endogenous receptor. In some cases, said trans-membrane dimerization domain can form either a homodimer or a heterodimer with a complementary dimerization domain. In some embodiments, said trans-membrane dimerization domain comprises at least one cysteine residue. In some instances, said trans-membrane dimerization domain comprises a glycophorin A transmembrane domain or fragment or variant thereof, a glycophorin A-integrin β3 chimeric transmembrane domain or fragment or variant thereof, or a CD3 zeta transmembrane domain.

In some cases, said binding partner comprises an antibody, or cell surface polypeptide binding region thereof. In some embodiments, said antibody comprises at least one of: monoclonal antibody, scFv, scFab, diabody, and camelid antibody. In some instances, said antibody comprises at least one of: rituximab, cetuximab, alemtuzumab, panitumumab and necitumumab.

In some cases, said genetically engineered cells comprise at least one of: T cells and NK cells. In some embodiments, at least one of said genetically engineered cells further expresses at least one additional exogenous polypeptide. In some instances, at least one of said genetically engineered cells further expresses at least one of a chimeric antigen receptor (CAR), a T-cell receptor (TCR) and a cytokine. In some cases, at least one of said genetically engineered cells further expresses at least one CAR and wherein said CAR binds at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72, EGFRvIII, CD123 and VEGF-R2.

In some embodiments, at least one of said genetically engineered cells further expresses at least one recombinant cytokine. In some instances, said recombinant cytokine comprises at least one of IL-15, mbIL-15, IL-2, IL-12, and IL-21. In some cases, said predetermined binding partner is provided in an amount sufficient to cause a reduction in at least one symptom associated with a cytokine storm or a systemic inflammatory response. In some embodiments, said predetermined binding partner is provided in an amount sufficient to cause a reduction in at least one symptom associated with tumor lysis syndrome. In some instances, said polypeptide construct is encoded by a polynucleotide incorporated into said engineered cells by genome editing. In some cases, said genome editing comprises use of at least a site specific serine recombinase system.

Provided is a polynucleotide encoding a truncated non-immunogenic CD20 polypeptide that binds an anti-CD20 antibody, wherein said truncated non-immunogenic CD20 polypeptide does not bind an endogenous receptor.

In some embodiments, said CD20 polypeptide comprises a polypeptide sequence which has at least 70%, 75%, 80%, 85%, 90%, 95%, 99% or 99.5% identity to the sequence shown in SEQ ID NO:109. In some cases, said CD20 polypeptide comprises a polypeptide sequence comprising the sequence of SEQ ID NO:109. In some instances, said CD20 polypeptide binds said anti-CD20 antibody with at least 50%, 60%, 70%, 80% or 90% the binding efficiency as native CD20. In some embodiments, said anti-CD20 antibody comprises at least one of: rituximab, cetuximab, tositumomab, veltuzumab, afutuzumab, blontuvetmab and obinutuzumab.

Provided is a polynucleotide encoding a truncated non-immunogenic HER1 polypeptide consisting of at least a HER1 Domain III or fragment thereof, and a truncated HER1 Domain IV, wherein said HER1 polypeptide binds an anti-HER1 antibody, and wherein said HER1 polypeptide is expressed in an engineered cell.

In some embodiments, said truncated HER1 Domain IV comprises a truncation of at least 10%, 15%, 20%, 25%, 30%, 35%, 40%, 45% or 50% of said HER1 Domain IV.

In some cases, said truncated HER1 Domain IV comprises a polypeptide sequence which has at least 70%, 75%, 80%, 85%, 90%, 95%, 99% or 99.5% identity to a sequence shown in SEQ ID NOs:203, 204, 205, 206, 207, 208 or 209. In some instances, said truncated HER1 Domain IV comprises a polypeptide sequence comprising a sequence shown in SEQ ID NOs: 203, 204, 205, 206, 207, 208 or 209. In some embodiments, said HER1 Domain III or fragment thereof comprises a polypeptide sequence which has at least 70%, 75%, 80%, 85%, 90%, 95%, 99% or 99.5% identity to the sequence shown in SEQ ID NO:200. In some cases, said HER1 Domain III comprises a polypeptide sequence comprising the sequence shown in SEQ ID NO:200.

In some instances, said polynucleotide further encodes a CD28 trans-membrane domain and a peptide linker for coupling said HER1 polypeptide to said CD28 trans-membrane domain. In some cases, said polynucleotide encodes a polypeptide construct comprising a polypeptide sequence comprising the sequence shown in SEQ ID NO:57. In some embodiments, said anti-HER1 antibody comprises at least one of: rituximab, cetuximab, futuximab, depatuxizumab, imgatuzumab, laprituximab, matuzumab, necitumumab, nimotuzumab, panitumumab, and zalutumumab.

Provided is a polynucleotide encoding a truncated non-immunogenic CD52 polypeptide that binds an anti-CD52 antibody, wherein said truncated non-immunogenic CD52 polypeptide does not bind an endogenous receptor, and wherein said non-immunogenic CD52 polypeptide is expressed in an engineered cell.

In some cases, said CD52 polypeptide comprises a polypeptide sequence which has at least 70%, 75%, 80%, 85%, 90%, 95%, 99% or 99.5% identity to the sequence shown in SEQ ID NO:143. In some instances, said CD52 polypeptide comprises a polypeptide sequence comprising the sequence shown in SEQ ID NO:143.

In some embodiments, a polynucleotide is expressed in a cell further comprising at least one sequence encoding at least one heterologous gene. In some embodiments, said at least one heterologous gene is modulated by an inducible promoter. In some instances, said at least one heterologous gene comprises at least one of a chimeric antigen receptor (CAR), a T-cell receptor (TCR) and a cytokine. In some embodiments, said at least one heterologous gene comprises a CAR, and wherein said CAR binds at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72, EGFRvIII, CD123 and VEGF-R2.

In some embodiments, said at least one heterologous gene comprises a cytokine. In some embodiments, said cytokine comprises at least one of IL-15, IL-2, IL-12, IL-21, and a fusion of IL-15 and IL-15Rα. In some cases, said cytokine is in secreted form. In some instances, said cytokine is in membrane bound form.

In some embodiments, a vector comprises said polynucleotide. In some cases, said vector is a lentivirus vector, a retroviral vector, or a non-viral vector. In some instances, said non-viral vector is a Sleeping Beauty transposon. In some embodiments, said polynucleotide is incorporated into an engineered cell by genome editing. In some instances, said genome editing comprises use of at least a site specific serine recombinase system. In some cases, an engineered cell encodes the polynucleotide. In some cases, the engineered cell is a T cell or an NK cell. In some cases, the polynucleotide encodes a polypeptide.

Further provided herein is a method of treating cancer comprising administering to a subject an effective amount of an engineered cell comprising a polynucleotide. In some embodiments, the method further comprises administering at least one binding partner capable of binding to a polypeptide expressed on said engineered cell. In some cases, said binding partner is an antibody.

Provided herein is a method of regulating activity of genetically engineered cells in a subject comprising providing to said subject an amount of genetically engineered cells encoding a polypeptide construct comprising a cell surface polypeptide which is a chimeric polypeptide comprising a first truncated non-immunogenic polypeptide and a second truncated non-immunogenic polypeptide, and wherein said cell surface polypeptide binds at least one predetermined binding partner or a variant or fragment thereof; and providing to said subject said predetermined binding partner in an amount sufficient to bind and thereby regulating activity of said genetically engineered cells.

In some embodiments, said first truncated non-immunogenic polypeptide comprises a fragment or derivative of a member of the EGFR family. In some cases, said second truncated non-immunogenic polypeptide comprises a fragment or derivative of a member of the EGFR family. In some instances, said first truncated non-immunogenic polypeptide comprises a HER1 polypeptide. In some embodiments, said HER1 polypeptide comprises a polypeptide sequence which has at least 70%, 75%, 80%, 85%, 90%, 95%, 99% or 99.5% identity to a sequence shown in SEQ ID NOs:211, 212, 213, 214, 215, 216 or 217. In some embodiments, said HER1 polypeptide comprises a polypeptide sequence comprising a sequence shown in SEQ ID NOs: 211, 212, 213, 214, 215, 216 or 217. In some cases, said HER1 polypeptide comprises a polypeptide sequence comprising the sequence shown in SEQ ID NO:211.

In some cases, said second truncated non-immunogenic polypeptide comprises at least one of a HER2 polypeptide, an ErbB3 polypeptide and an ErbB4 polypeptide. In some embodiments, said polypeptide construct comprises a polypeptide sequence which has at least 70%, 75%, 80%, 85%, 90%, 95%, 99% or 99.5% identity to a sequence shown in SEQ ID NO:89, SEQ ID NO:93, SEQ ID NO:97, SEQ ID NO:101 or SEQ ID NO:105.

In some embodiments, said at least one predetermined binding partner binds said HER1 polypeptide. In some instances, said at least one predetermined binding partner comprises at least one of rituximab, cetuximab, futuximab, depatuxizumab, imgatuzumab, laprituximab, matuzumab, necitumumab, nimotuzumab, panitumumab, and zalutumumab. In some cases, said at least one predetermined binding partner further includes a second predetermined binding partner that binds said second truncated non-immunogenic polypeptide. In some cases, said second truncated non-immunogenic polypeptide is a HER2 polypeptide, and said second predetermined binding partner is pertuzumab.

In some instances, said polypeptide construct further comprises a signal peptide. In some instances, said polypeptide construct further comprises a trans-membrane domain. In some embodiments, said trans-membrane domain comprises a trans-membrane dimerization domain. In some cases, said trans-membrane dimerization domain comprises a glycophorin A transmembrane domain, a glycophorin A-integrin β3 chimeric transmembrane domain or a CD3 zeta transmembrane domain. In some cases, said trans-membrane dimerization domain comprises a polypeptide sequence which has at least 70%, 75%, 80%, 85%, 90%, 95%, 99% or 99.5% identity to a sequence shown in SEQ ID NO:26, SEQ ID NO:28, SEQ ID NO:30 or SEQ ID NO:32. In some embodiments, said trans-membrane dimerization domain comprises a polypeptide sequence comprising a sequence shown in SEQ ID NO:26, SEQ ID NO:28, SEQ ID NO:30 or SEQ ID NO:32.

In some instances, said first truncated non-immunogenic polypeptide comprises a CD20 polypeptide. In some embodiments, said CD20 polypeptide comprises a polypeptide sequence which has at least 70%, 75%, 80%, 85%, 90%, 95%, 99% or 99.5% identity to a sequence shown in SEQ ID NO:218, SEQ ID NO:219 or SEQ ID NO:220. In some cases, said CD20 polypeptide comprises a polypeptide sequence comprising a sequence shown in SEQ ID NO:218, SEQ ID NO:219 or SEQ ID NO:220. In some embodiments, said at least one predetermined binding partner comprises at least one of: rituximab, tositumomab, veltuzumab, afutuzumab, blontuvetmab and obinutuzumab.

Provided is a polypeptide construct comprising a truncated non-immunogenic HER1 polypeptide consisting of a HER1 Domain III and a truncated HER1 Domain IV, wherein said HER1 polypeptide binds an anti-HER1 antibody; a CD28 trans-membrane domain; and a peptide linker for coupling said HER1 polypeptide to said CD28 transmembrane domain; wherein said polypeptide construct is expressed in an engineered cell.

In some embodiments, said HER1 Domain III comprises a polypeptide sequence comprising the sequence shown in SEQ ID NO:200 and said HER1 Domain IV comprises a polypeptide sequence comprising the sequence shown in SEQ ID NO:203. In some instances, said CD28 transmembrane domain comprises a polypeptide sequence comprising the sequence shown in SEQ ID NO:36 and said peptide linker comprises a G4S peptide linker (SEQ ID NO: 221). In some cases, said G4S peptide linker (SEQ ID NO: 221) comprises a polypeptide sequence comprising the sequence shown in SEQ ID NO:22. In some embodiments, said polypeptide construct comprises a polypeptide sequence comprising the sequence shown in SEQ ID NO:57.

In some cases, said anti-HER1 antibody comprises at least one of rituximab, cetuximab, futuximab, depatuxizumab, imgatuzumab, laprituximab, matuzumab, necitumumab, nimotuzumab, panitumumab, and zalutumumab.

Provided is a polypeptide construct comprising a truncated non-immunogenic CD20 polypeptide, wherein said CD20 polypeptide binds an anti-CD20 antibody; wherein said polypeptide construct is expressed in an engineered cell.

In some embodiments, said polypeptide construct has at least 70%, 75%, 80%, 85%, 90%, 95%, 99% or 99.5% identity to the sequence shown in SEQ ID NO:109. In some cases, said polypeptide construct comprises a polypeptide sequence comprising the sequence shown in SEQ ID NO:109. In some instances, said anti-CD20 antibody comprises at least one of: rituximab, tositumomab, veltuzumab, afutuzumab, blontuvetmab and obinutuzumab.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 4D1 shows expression of truncated HER1 (HER1t) polypeptide expressed in human donor PBMCs transfected with HER1t and stained with an ant-HER1t antibody ("stain") compared to isotype control ("isotype"). FIG. 4D2 shows expression of HER1t expressed in human donor PBMCs transfected with truncated EGFR-Erb4 (JM-a) corresponding to SEQ ID NO: 101 and stained with an anti-HER1t antibody ("stain") compared to isotype control ("isotype"). FIG. 4D3 shows expression of HER1t expressed in human donor PBMCs transfected with truncated EGFR-ErbB4 (JM-b) corresponding to SEQ ID NO: 105 and stained with an anti-HER1t antibody ("stain") compared to isotype control ("isotype"). FIG. 4D4 shows expression of HER 1t in mock cells that have not been transfected with HER1t and stained with an anti-HER1t antibody ("stain") compared to isotype control ("isotype").

FIG. 4E1 shows expression of HER1t in mock cells that have not been transfected with HER1t. FIG. 4E2 shows expression of HER1t in human donor PBMCs transfected with HER1t. FIG. 4E3 shows expression of HER1t in human donor PBMCs transfected with HER1t1 corresponding to SEQ ID NO: 57. FIG. 4F4 shows expression of HER1t in human donor PBMCs transfected with HER12 corresponding to SEQ ID NO: 59. FIG. 4E5 shows expression of HER1t in human donor PBMCs transfected with HER1t3 corresponding to SEQ ID NO: 61. FIG. 4E6 shows expression of HER1t in human donor PBMCs transfected with HER1 t4 corresponding to SEQ ID NO: 63. FIG. 4E7 shows expression of HER 1 t in human donor PBMCs transfected with HER1t5 corresponding to SEQ ID NO: 65. FIG. 4E8 shows expression of HER1t in human donor PBMCs transfected with HER1t6 corresponding to SEQ ID NO:67. FIG. 4E9 shows expression of HER1t in human donor PBMCs transfected with HER1t7 corresponding to SEQ ID NO: 69.

FIG. 6 shows cetuximab- and alemtuzumab-mediated ADCC activity (expressed as % specific killing; y-axis) in NK cells (left), CD16 NK cells (middle), and CD16 NK cells transfected with CAR and HER1t1 (right). Cetuximab showed specific ADCC in presence of HER1t1.

FIG. 8 shows a Western blot analysis showing expression of HER1t1 cell tag in genetically modified SUP-T1 cell lines. Lane 1: IP antibody only; Lane 2: Jurkat cells only; Lane 3: SUPT1/HER1t1 (high levels of HER1t1); Lane 4: SUPT1/HER1t1 (low levels of HER1t1); Lane 5: A431 cells expressing full-length HER1; Lane 6: Marker. Bold arrow points to protein pulled down by cetuximab in all lines except A431. HER1t1 corresponds to SEQ ID NO:57.

DETAILED DESCRIPTION OF THE DISCLOSURE

Figure 1A:
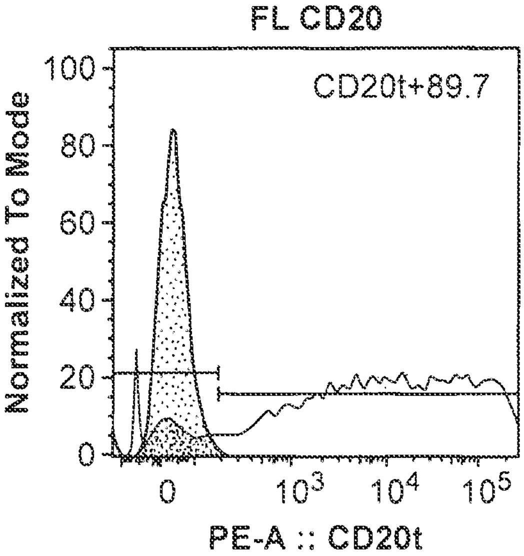
FIG. 1A shows expression levels of full-length CD20 cell tag (corresponding to SEQ ID NO: 107) in HEK-293T cells as detected by flow cytometry using rituximab compared to a control cell tag.
Figure 1B:
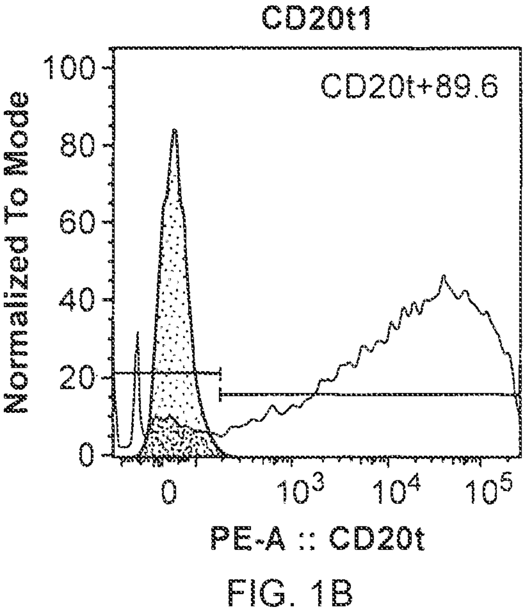
FIG. 1B shows expression levels of a truncated CD20 (CD20t, corresponding to SEQ ID NO: 109) in HEK-293T cells as detected by flow cytometry using rituxirnab compared to a control cell tag.
Figure 1C:
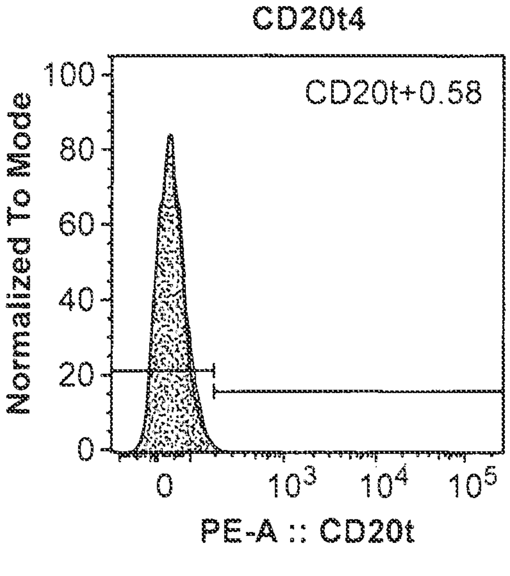
FIG. 1C shows expression levels of a truncated CD20 (CD20t4, corresponding to SEQ ID NO: 115) in HEK-293T cells as detected by flow cytometry using rituxinab compared to a control cell tag.
Figure 1D:
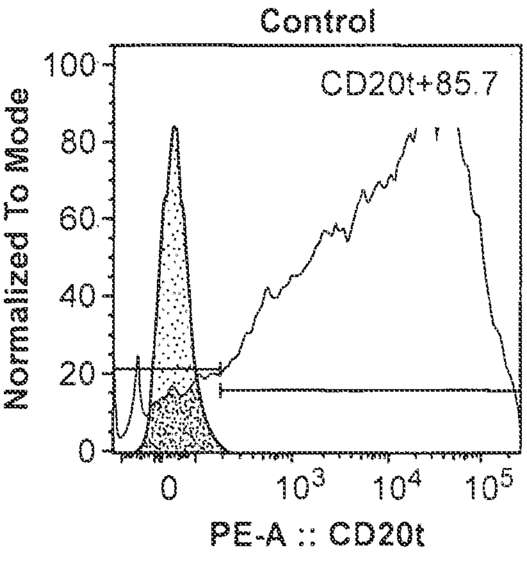
FIG. 1D depicts the control. Shaded areas denote mock-transfected control cells whereas non-shaded areas denote expression of cell tags from transfected cells. Each transfection was performed in triplicate.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the invention may be described in the context of a single embodiment, the features may also be provided separately or in any suitable combination. Conversely, although the invention may be described herein in the context of separate embodiments for clarity, the invention may also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the inventions.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

By "isolated" is meant the removal of a nucleic acid from its natural environment. By "purified" is meant that a given nucleic acid, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins may be formulated with diluents or adjuvants and still for practical purposes be isolated. For example, nucleic acids typically are mixed with an acceptable carrier or diluent when used for introduction into cells.

"Polynucleotide" or "oligonucleotide" as used herein refers to a polymeric form of nucleotides of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

"Polypeptide" is used interchangeably with the terms "polypeptides" and "protein(s)," and refers to a polymer of amino acid residues. A "mature protein" is a protein which is full-length and which, optionally, includes glycosylation or other modifications typical for the protein in a given cellular environment.

Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides described herein in an engineered cell can be associated with post-translational modifications of one or more amino acids of the polypeptide constructs. Non-limiting examples of post-translational modifications include phosphorylation, acylation including acetylation and formylation, glycosylation (including N-linked and β-linked), amidation, hydroxylation, alkylation including methylation and ethylation, ubiquitylation, addition of pyrrolidone carboxylic acid, formation of disulfide bridges, sulfation, myristoylation, palmitoylation, isoprenylation, farnesylation, geranylation, glypiation, lipoylation and iodination.

"Antibody" as used herein refers to monoclonal or polyclonal antibodies. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

"Antigen recognition moiety or domain" refers to a molecule or portion of a molecule that specifically binds to an antigen. In some embodiments, the antigen recognition moiety is an antibody, antibody like molecule or fragment thereof and the antigen is a tumor antigen.

"Antibody like molecules" may be for example proteins that are members of the Ig-superfamily which are able to selectively bind a partner. MHC molecules and T cell receptors are such molecules. In some embodiments the antibody-like molecule is a TCR. In some embodiments the TCR has been modified to increase its MHC binding affinity.

The terms "fragment of an antibody," "antibody fragment," "functional fragment of an antibody," and "antigen-binding portion" are used interchangeably herein to mean one or more fragments or portions of an antibody that retain the ability to specifically bind to an antigen (see, generally, Holliger et al., Nat. Biotech., 23(9):1126-1129 (2005)). The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CHI domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., Science, 242: 423-426 (1988); Huston et al., Proc. Natl. Acad. Sci. USA, 85: 5879-5883 (1988); and Osbourn et al., Nat. Biotechnol., 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Pat. No. 8,603,950.

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology.

The terms "identical" or "sequence identity" in the context of two nucleic acid sequences or amino acid sequences of polypeptides refers to the residues in the two sequences which are the same when aligned for maximum correspondence over a specified comparison window. In some embodiments, a polypeptide herein is at least 60%, 65%, 70%, 75%, 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first, they are transcribed from DNA to RNA, and the RNA produced is then reverse transcribed to DNA. This copied DNA is then inserted at a new position into the genome. The reverse transcription step is catalyzed by a reverse transcriptase, which may be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons may be identified by short direct repeats which may be created by the staggered cut in the target DNA and filling in by DNA polymerase, followed by a series of inverted repeats important for the TE excision by transposase. Cut-and-paste TEs may be duplicated if their transposition takes place during S phase of the cell cycle when a donor site has already been replicated, but a target site has not yet been replicated. Transposition can be classified as either "autonomous" or "non-autonomous" in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism. In some embodiments, the transposase's catalytic activity can be utilized to move gene(s) from a vector to the genome.

The nucleic acid sequences and vectors disclosed or contemplated herein may be introduced into a cell by "transfection," "transformation," "nucleofection" or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)); and nucleofection (Trompeter et al., J. Immunol. Methods 274:245-256 (2003). Phage or viral vectors can be introduced into host cells, after growth of infectious particles in suitable packaging cells, many of which are commercially available.

"Tumor antigen" as used herein refers to any antigenic substance produced or overexpressed in tumor cells. It may, for example, trigger an immune response in the host. Alternatively, for purposes of this disclosure, tumor antigens may be proteins that are expressed by both healthy and tumor cells but because they identify a certain tumor type, are a suitable therapeutic target.

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter.

The term "promoter activity" refers to the extent of expression of nucleotide sequence that is operably linked to the promoter whose activity is being measured. Promoter activity may be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In some embodiments, the inducible promoter is part of a genetic switch.

The term "enhancer," as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

"Coding sequence" as used herein refers to a segment of a polynucleotide that codes for a polypeptide. The region or sequence is bounded nearer the 5' end by a start codon and nearer the 3' end with a stop codon. Coding sequences may also be referred to as open reading frames.

"Operably linked" as used herein refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers may be located upstream, downstream or embedded within the coding regions of the DNA sequence. A DNA for a signal sequence is operably linked to DNA coding for a polypeptide if the signal sequence is expressed as a pre-protein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "induction" refers to an increase in nucleic acid sequence transcription, promoter activity and/or expression brought about by a transcriptional regulator, relative to some basal level of transcription.

A "target" gene or "heterologous" gene, or "gene of interest (GOI)" refers to a gene introduced into the host cell by gene transfer.

"Recombinase" as used herein refers to a group of enzymes that can facilitate site-specific recombination between defined sites, where the sites are physically separated on a single DNA molecule or where the sites reside on separate DNA molecules. The DNA sequences of the defined recombination sites are not necessarily identical. Initiation of recombination depends on protein-DNA interaction, within the group there are a large number of proteins that catalyze phage integration and excision (e.g., X integrase, ϕC31), resolution of circular plasmids (e.g., Tn3, gamma delta, Cre, Flp), DNA inversion for expression of alternate genes (e.g., Hin, Gin, Pin), assembly of genes during development (e.g., *Anabaena* nitrogen fixation genes), and transposition (e.g., IS607 transposon). Most site-specific recombinases fall into one of the two families, based on evolutionary and mechanistic relatedness. These are λ integrase family or tyrosine recombinases (e.g., Cre, Flp, Xer D) and resolvase/integrase family or serine recombinase family (e.g., ϕC31, TP901-1, Tn3, gamma delta).

"Recombination attachment sites" are specific polynucleotide sequences that are recognized by the recombinase enzymes described herein. Typically, two different sites are involved (termed "complementary sites"), one present in the target nucleic acid (e.g., a chromosome or episome of a eukaryote or prokaryote) and another on the nucleic acid that is to be integrated at the target recombination site. The terms "attB" and "attP," which refer to attachment (or recombination) sites originally from a bacterial target and a phage donor, respectively, are used herein although recombination sites for particular enzymes may have different names. The recombination sites typically include left and right arms separated by a core or spacer region. Thus, an attB recombination site consists of BOB', where B and B' are the left and right arms, respectively, and O is the core region. Similarly, attP is POP', where P and P' are the arms and O is again the core region. Upon recombination between the attB and attP sites, and concomitant integration of a nucleic acid at the target, the recombination sites that flank the integrated DNA are referred to as "attL" and "attR." The attL and attR sites, using the terminology above, thus consist of BOP' and POB", respectively. In some representations herein, the "O" is omitted and attB and attP, for example, are designated as BB' and PP', respectively.

The term "gene editing" or "genome editing" refers to the insertion, deletion or replacement of nucleotides of DNA in the genome of a living organism. Typically genome editing uses engineered nucleases which can create site-specific double-stranded breaks at a pre-determined location of the genome. The present disclosure contemplates any means for editing genomes. Non-limiting examples of genome editing techniques include CRISPR, Argonaute and AttSite site-specific serine recombinase systems. Herein a "CRISPR gene editing system" of "CRISPR system" refers to any RNA-guided Cas protein-mediated process for targeting a change in DNA sequence to a specific region of a genome. Herein "Argonaute gene editing system" refers to any single-stranded DNA guided Argonaute endonuclease-mediated process for targeting a change in DNA sequence to a specific region of a genome. Herein "AttSite gene editing system" or "site-specific serine recombinase gene editing system" or "site specific serine recombinase system" refer to any process that involves providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP) or a bacterial genomic recombination attachment site (attB), the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP and when the first recombination attachment site is attP, the second recombination attachment site is attB. Examples of embodiments of an AttSite serine recombinase system are provided in U.S. Pat. No. 9,034,650, all of which is incorporated herein by reference.

The terms "endogenous" as used herein in reference to a molecule such as a polynucleotide or polypeptide refers to the naturally occurring form of the molecule which can be found in a wildtype cell or organism. A molecule which is found in an organism endogenously can be contrasted with an engineered molecule as described herein which typically does not occur naturally. For example, an engineered molecule can comprise a variant of a naturally occurring polypeptide or polynucleotide. In some embodiments, the variant of a naturally occurring polypeptide is a truncated variant of a naturally occurring polypeptide. Herein the term "truncated variant" refers to a protein or polypeptide which is missing one or more sequences of amino acids and/or domains relative to the endogenous version of the protein or polypeptide. For example, a truncated variant incorporated into a polypeptide construct described herein can be missing a sequence of amino acids which corresponds to a domain (e.g., intracellular signaling domain, transmembrane domain, ligand binding domain, etc) normally present in the endogenous protein. The natural version of the truncated polypeptide can be derived from any organism, including mammalian species such as mice, rats, rabbits and humans. Engineered polynucleotides and polypeptides described herein can be expressed in an engineered cell. Herein an engineered cell is a cell which has been modified from its natural or endogenous state. An example of an engineered cell is a cell described herein which has been modified (e.g., by transfection of a polynucleotide into the cell) to encode a truncated variant of a natural polypeptide or a truncated variant of a natural polynucleotide.

Polypeptide Constructs

Disclosed herein are polypeptide constructs, polynucleotides encoding the same, engineered cells harboring and/or expressing the polypeptide constructs and polynucleotides and methods of regulating activity of the engineered cells. Engineered cells as described herein can include immune effector cells engineered to encode and to express cytokines, chimeric antigen receptors and T-cell receptors.

Herein the term "regulating" or "regulation" when used with reference to engineered cells or polypeptide constructs expressed therein, refers generally to a regulation of the activity or amount of the engineered cells after administration to a subject. In some embodiments, regulating activity of engineered cells refers to a depletion of the engineered cells in a subject. In some embodiments, regulating activity of the engineered cells refers to depletion of some engineered cells in a subject as a result of administering to the subject an amount of an antibody or binding partner that binds a polypeptide construct expressed on the engineered cells. In some embodiments, regulating activity of the engineered cells refers to a depletion of the engineered cells as a result of activating cell death via binding of an antibody or binding partner to a polypeptide construct described herein expressed on or associated with said engineered cell. In some embodiments, regulating activity of the engineered cells refers to activating an ADCC or CDC pathway in the engineered cells.

The polypeptides, polynucleotides and engineered cells disclosed herein collectively represent a suite of therapeutic tools which can be used to improve the efficacy of conventional immunotherapies, and in particular adoptive cell therapies. For example, engineered cells described herein can encode and express a polypeptide construct at the cell surface as a novel cell tag. A cell tag can in some embodiments function as a cell marker which labels, marks or flags a cell expressing the cell tag as an engineered cell. In embodiments where the cell tag has been engineered to lack epitopes recognized by endogenous proteins, such a cell tag can function to uniquely distinguish an engineered cell from other cells in an organism, for example during adoptive cell immunotherapy.

In other examples, the polypeptides, polynucleotides and engineered cells described herein can be used to minimize or eliminate toxicities of immunotherapy in subjects where safety is a concern (e.g. due to a potential for onset of cytokine storm). The cell tags described herein can include one or more epitopes recognized by an antibody introduced during immunotherapy to thereby induce a cellular mechanism that will slow therapeutic output and/or mitigate possible side effects of therapy. In some embodiments, the antibody binds to the epitope to induce antibody-dependent cell-mediated cytotoxicity (ADCC) and/or complement-dependent cytotoxicity (CDC). Accordingly, the cell tags described herein can provide for a depletion marker or "kill tag" unique to engineered cells allowing practitioners to control therapeutic output and thereby optimize efficacy and safety of therapy.

The immunotherapeutic arsenal described herein improves upon conventional immunotherapy by providing the potential for control over adoptive cell therapeutic interventions. In some embodiments, engineered cells can be sensitized to cell depletion strategies by expressing a polypeptide construct capable of dimerizing or multimerizing at the surface of engineered cells. Such dimerized or multimerized polypeptides can be used to amplify a depletion signal and thereby rapidly downregulate or eliminate the engineered immune cell therapy in subjects who are prone to or are experiencing side effects related to therapy. The administration of engineered cells expressing a dimerizing or multimerizing polypeptide construct can provide for further control and optimization over cell depletion interventions. In further embodiments, implementation of the polynucleotide constructs disclosed herein as a part of a "kill switch" (or "suicide switch") system employing an inducible promoter can allow for control over when a particular polypeptide construct is expressed, thereby conferring additional control points over immunotherapy at both the transcriptional and post-translational levels.

In another embodiment, the cell tags described herein can be used to enrich for engineered cells that specifically express such cell tags. For example, the cell tags can be used to enrich for certain engineered cells to isolate certain engineered cells that only express such cell tags to achieve necessary purity to allow for expansion of select cells of therapeutic interest. Various methods such as FACs, column purification or magnetic beads based methods can be utilized as appropriate.

The polypeptide constructs disclosed herein can comprise one or more domains or specific fragments thereof. Typically the polypeptide construct can comprise a signal peptide sequence, an extracellular domain, a peptide linker and a transmembrane domain, each of which functions to confer a particular desired property to the polypeptide construct. For example, the polypeptide construct can include a signal peptide to post-translationally direct the polypeptide construct to the cell surface; a transmembrane domain to anchor the polypeptide domain to the cell; an extracellular portion, which can include a truncated variant of a natural polypeptide; and a peptide linker connecting the transmembrane domain to the extracellular portion. In some embodiments, the peptide linker functions as an extracellular peptide extension to position the extracellular portion of the polypeptide in the extracellular matrix and thereby make it available to confer cell tag functionality (e.g., to present or to extend an epitope to allow access to bind an antibody). In certain embodiments, one or more of the above domains may not be present in the polypeptide construct. For example, a polypeptide construct described herein can be engineered to lack a peptide linker domain. In other embodiments, a polypeptide construct comprises one or more domains derived from different proteins (i.e., the polypeptide construct is chimeric).

Herein the term "extracellular" when used with reference to a portion of a polypeptide construct refers to the amino acids of the polypeptide which are positioned on the exterior of the cell membrane. In some embodiments, the extracellular portion can be referred to as a cell surface polypeptide. Typically a portion (e.g., distal portion) of a cell surface polypeptide extends or protrudes distally into the extracellular space from the plasma membrane of a cell. In some instances, the extending portion may be bound and thereby recognized by an antibody or antigen-recognizing polypeptide that has a structure complementary to and specific for the structure of the extending portion. A cell surface polypeptide can encompass polypeptides or fragments thereof which occur naturally at the surface of the cell as well as polypeptides or fragments thereof which are not found naturally at the cell surface (e.g., a truncated variant of a natural polypeptide).

The extracellular portion or cell surface polypeptide can include a truncated variant of a natural polypeptide. The truncated variant can for example, extend from the exterior of the plasma membrane (e.g. via a linker connected to or adjacent to the transmembrane domain) into the extracellular space. In certain embodiments, the truncated variant is missing amino acids which in the natural version of the polypeptide contribute to an intracellular domain and/or a transmembrane domain. The truncated variant can be modified from an endogenous polypeptide in any way to produce an extracellular portion of a cell tag. For example, the truncated variant can be modified to reduce or eliminate amino acids which normally function to comprise an epitope in the extracellular domain which can be recognized by an endogenous protein, such as an antigen or receptor. By removing amino acids which normally interface (e.g., in cell signaling pathways) with extracellular molecules, the truncated variant can be made unreactive or immunologically/epitopically silent at the cell surface, or reduced or minimized in its reactivity or binding with endogenous molecules. Any modification to a natural polypeptide to remove natural epitopes is contemplated herein, including truncation of all or part of an extracellular domain, and removal of one or more amino acids which form part of an epitope, or are post-translationally modified to form part of an epitope.

Although a truncated variant described herein can be epitopically silent with respect to endogenous signaling pathways, the truncated variant can include one or more epitopes which are capable of being recognized by a molecule (e.g., antibody) that does not normally contact a surface of a cell corresponding to an engineered cell described herein. In some embodiments, an antibody or binding partner specific for an epitope of the truncated variant is introduced exogenously (e.g., during immunotherapy using adopted cells). In this respect, an epitope of the truncated variant capable of being recognized by an introduced antibody or fragment thereof can be referred to as dormant or quiescent. That is, a cell tag incorporated at the cell surface of an engineered cell used for adoptive immunotherapy can contain an epitope which lies dormant until the proper molecule is introduced into a subject to trigger or activate the cell tag (i.e., via recognition of the epitope). Such an epitope does not interfere with the therapeutic output of the engineered cells where therapy is proceeding as desired (i.e., the epitope remains silent or quiescent), but embodies a trigger which can be activated to downregulate cellular output where for any reason the immunotherapy needs to be subdued. The present disclosure contemplates the use of any antibody or small molecule which is capable of recognizing an epitope of a cell tag to suppress the therapeutic output of an engineered cell expressing the tag via elimination of such cells (e.g., via ADCC or CDC). Non-limiting examples of antibodies which can be used to recognize an epitope of an extracellular domain (e.g., truncated variant) of a cell tag include rituximab, cetuximab, gefitinib, erlotinib, afatinib, brigatinib, icotinib, osimertinib, panitumumab, zalutumumab, nimotuzumab, matuzumab, afutuzumab, blontuvetmab, obinutuzumab, ibritumomab tiuxetan, tositumomab, ofatumumab, ocaratuzumab, ocrelizumab, TRU-015 (Trubion), veltuzumab (IMMU-106), alemtuzumab, ANT1034, HI 186(Bio Rad), YTH34.5 (Bio Rad) and YTH66.9HL (Bio-Rad), trastuzumab and pertuzumab.

Another example of a modification which can be made to an endogenous polypeptide to produce a truncated variant as contemplated herein is to remove one or more amino acids which normally contribute to or participate in intracellular signaling and/or trafficking pathways. Truncation of an endogenous polypeptide to remove signaling domains reinforces the function of a cell tag as a dormant, inducible cell marker which in its dormant state does not interfere with cellular function (e.g. in adopted cells during adoptive cell therapy).

In some embodiments, the cell surface polypeptide of the polypeptide construct can comprise a truncated variant of a receptor tyrosine kinase. Non-limiting examples include a truncated variant of a receptor from the EGF receptor family (e.g., a truncated variant of HER1), PDGF receptor family, VEGF receptor family, insulin receptor family, FGF receptor family, Trk receptor family and Eph receptor family. In other embodiments, the cell surface polypeptide can comprise a truncated variant of a CD protein (e.g., CD20 or CD52) or a truncated variant of LNFGR (CD271).

In certain embodiments, the cell surface polypeptide of the cell tag can include a truncated variant which has been modified to remove a transmembrane domain and intracellular signaling portion of the natural or endogenous polypeptide. The truncation of the transmembrane domain and intracellular signaling portion frees the cell surface or extracellular portion of the polypeptide from its endogenous context, for example making it available for incorporation into a chimeric polypeptide construct that includes the cell surface polypeptide fused to a transmembrane domain (e.g., via a linker) derived from a different natural protein. Such chimeric polypeptide constructs in turn can confer the cell surface polypeptide (e.g., truncated variant) with altered activity or characteristics compared to the endogenous version of the polypeptide. In some embodiments, a cell surface polypeptide is capable of dimerizing when expressed in a chimeric polypeptide construct.

The present disclosure contemplates that multiple different polypeptide constructs can be expressed in the same engineered cell. For example, a cell disclosed herein can express multiple polypeptide constructs that differ in the identity of the cell surface polypeptide and/or transmembrane domain.

A polypeptide construct described herein can include a cell surface polypeptide comprising a truncated variant of a natural polypeptide, a transmembrane domain fused to the cell surface polypeptide, optionally a linker connecting the truncated variant to the transmembrane domain, and a signal peptide directing the cell tag to a cell surface of an engineered cell.

Signal Peptide

A signal peptide is a sequence of amino acids typically located at the N-terminus of a newly synthesized protein or polypeptide which directs the protein or polypeptide to the cell surface. In some embodiments, the signal peptide directs the polypeptide to the cell surface to be inserted (e.g., via a transmembrane domain) into the cellular membrane. In some embodiments, a polypeptide construct described herein is synthesized with the signal peptide, but then post-translationally processed to cleave the signal peptide such that the mature polypeptide construct lacks the signal peptide amino acid sequence. In other embodiments, the signal peptide sequence is not cleaved and remains in the mature polypeptide construct.

The present disclosure provides for a polypeptide construct comprising any known or unknown signal peptide capable of directing and/or trafficking the polypeptide construct to the cell surface. For example, in some embodiments, a polypeptide construct comprises a signal sequence corresponding to the signal peptide of GMCSFRα, Ig Kappa, Immunoglobulin E, CD8α, TVB2 (T21A), CD52 or Low-affinity nerve growth factor receptor (LNGFR, TNFRSF16).

In embodiments, the signal peptide is encoded by a polynucleotide comprising a nucleotide sequence which has at least 70%, 75%, 80%, 85%, 90%, 95%, 99%, or 100% identity with a nucleotide sequence selected from the list consisting of SEQ ID NO:1; SEQ ID NO:3; SEQ ID NO:5; SEQ ID NO:7; SEQ ID NO:9; SEQ ID NO:11; or SEQ ID NO:13. In embodiments, the signal peptide comprises an amino acid sequence which has at least 70%, 75%, 80%, 85%, 90%, 95%, 99%, or 100% identity with an amino acid sequence selected from the list consisting of SEQ ID NO:2; SEQ ID NO:4; SEQ ID NO:6; SEQ ID NO:8; SEQ ID NO:10; SEQ ID NO:12; and SEQ ID NO:14.

Peptide Linker

A polypeptide construct described herein can comprise a peptide linker to connect a domain or fragment thereof of the polypeptide construct to a different domain or fragment thereof of the polypeptide construct. In some embodiments, a peptide linker connects the transmembrane domain of the polypeptide construct to a cell surface polypeptide (e.g. truncated variant of a natural polypeptide) of the polypeptide construct. For example, a polypeptide construct can comprise a peptide linker comprising a GSG linker (SEQ ID NO: 16), SGSG linker (SEQ ID NO: 18), (G4S)3 linker (SEQ ID NO: 20), (G4S)4 linker (SEQ ID NO: 22) and/or a Whitlow linker.

Provided herein is a peptide linker of any length or size to link a transmembrane domain to a cell surface polypeptide (e.g. truncated variant). For example, in some embodiments, a peptide linker is sized to maintain the distance between the truncated variant and the transmembrane domain at about the same distance as occurs between the natural non-truncated version of the polypeptide and its endogenous transmembrane domain. In embodiments, truncated variants as described herein are linked to a transmembrane domain via different size G4S linkers (G4S)n, wherein n=0, 1, 2, 3, 4, 5 (SEQ ID NO: 222), to maintain the "natural" distance between the HER1t and the transmembrane protein. For example, where two different truncated variants of the same natural polypeptide are of different lengths, the smaller-length truncated variant may be compensated by a larger sized linker in order to position both truncated variants at approximately the same distance from the cell surface.

In certain embodiments, a peptide linker can be used to link together domains or portions thereof other than a transmembrane domain. For example, a peptide linker can connect two protein moieties of the cell surface polypeptide. In some cases, the cell surface polypeptide can be chimeric and comprise truncated variants from multiple natural polypeptides which can be connected via a peptide linker. An example is a polypeptide construct comprising HER1t together with one or more truncated variants of another member of the EGFR family (e.g., HER2, ErbB3 and ErbB4). In other cases, the cell surface polypeptide can comprise a concatemer of two or more copies of a truncated variant connected via a peptide linker (e.g. SEQ ID NO: 123 comprising two copies of a CD20 truncated polypeptide linked via an SGS linker).

In embodiments, the peptide linker is encoded by a polynucleotide comprising a nucleotide sequence which has at least 70%, 75%, 80%, 85%, 90%, 95%, 99%, or 100% identity to a nucleotide sequence selected from the list consisting of SEQ ID NO:15; SEQ ID NO:17; SEQ ID NO:19; SEQ ID NO:21; and SEQ ID NO:23. In embodiments, the peptide linker comprises an amino acid sequence which has at least 70%, 75%, 80%, 85%, 90%, 95%, 99%, or 100% identity to an amino acid sequence selected from the list consisting of SEQ ID NO:16; SEQ ID NO:18; SEQ ID NO:20; SEQ ID NO:22; and SEQ ID NO:24.

Transmembrane Domain

A polypeptide construct described herein can include a transmembrane domain that can be inserted into a plasma membrane to anchor the polypeptide construct at the cell surface. The present disclosure provides for a polypeptide construct comprising one or more of any known or unknown transmembrane domains or fragments thereof. In some embodiments, the transmembrane domain of the polypeptide construct can comprise a transmembrane domain derived from and/or homologous to one or more natural proteins. In some embodiments, the transmembrane domain of the polypeptide construct comprises an amino acid sequence corresponding to the transmembrane domain of a single natural protein. In some embodiments, the transmembrane domain of the polypeptide construct comprises a chimeric transmembrane domain comprising amino acid sequences derived from two or more natural proteins.

A polypeptide construct described herein can comprise a transmembrane domain which is single-pass or multi-pass. CD8a is an example of a protein having a single-pass transmembrane domain. In some embodiments, a polypeptide construct disclosed herein comprises a transmembrane domain corresponding to and/or homologous to a transmembrane domain or fragment thereof from the CD8a protein. In embodiments, the transmembrane domain of the polypeptide construct is encoded by a polynucleotide comprising a nucleotide sequence which has at least 70%, 75%, 80%, 85%, 90%, 95%, 99%, or 100% identity to a nucleotide sequence of SEQ ID NO:33. In embodiments, the transmembrane domain comprises an amino acid sequence which has at least 70%, 75%, 80%, 85%, 90%, 95%, 99%, or 100% identity to an amino acid sequence of SEQ ID NO:34.

An example of a multi-pass protein is CD28. In some embodiments, the transmembrane domain of a polypeptide construct can comprise a transmembrane domain corresponding to and/or homologous to a transmembrane domain or fragment thereof from the CD28 protein. In embodiments, the transmembrane domain of the polypeptide construct is encoded by a polynucleotide comprising a nucleotide sequence which has at least 70%, 75%, 80%, 85%, 90%, 95%, 99%, or 100% identity to a nucleotide sequence of SEQ ID NO:35. In embodiments, the transmembrane domain comprises an amino acid sequence which has at least 70%, 75%, 80%, 85%, 90%, 95%, 99%, or 100% identity to an amino acid sequence of SEQ ID NO:36.

In some embodiments, the transmembrane domain is a transmembrane dimerization domain. Herein "transmembrane dimerization domain" refers to a transmembrane domain or fragment thereof that is capable of physically interacting or "dimerizing" within the plasma membrane of a cell with a second transmembrane domain or fragment thereof. Typically the transmembrane dimerization domain is comprised within a first polypeptide construct which dimerizes via the transmembrane dimerization domain with a second polypeptide. Where a transmembrane dimerization domain of a first polypeptide is fused at its distal (extracellular oriented) end to a first cell surface polypeptide, and a transmembrane dimerization domain of a second polypeptide is fused at its distal end to a second cell surface polypeptide, physical interaction of the first and second transmembrane domains within the cell membrane can result in the dimerization of the first and second cell surface polypeptides. In some embodiments, the transmembrane domain can multimerize to from a trimer, a tetramer or a multimer.

In certain embodiments, a transmembrane dimerization domain induces dimerization of cell surface polypeptides without the requirement for any extracellular inducing agent (e.g., ligand or antibody specific for an epitope of the cell surface polypeptide). For example, a transmembrane dimerization domain can induce dimerization of a cell surface polypeptide by spontaneously physically interacting or coupling with a second transmembrane dimerization domain within the cell membrane of a cell. It will thus be understood that a cell expressing a polypeptide construct described herein can display dimerized cell surface polypeptides on a cell surface of the cell prior to the administration of any extracellular cell surface binding agent comprising an antibody, protein, ligand or molecule described herein. Dimerization of cell surface polypeptides via a transmembrane dimerization domain can leverage a cell expressing such a polypeptide construct towards an enhanced cellular response when the dimerized cell surface polypeptides contact and recognize a ligand or antibody. For example, where a polypeptide construct comprises a cell surface polypeptide comprising HER1t, a pair of HER1t cell surface polypeptides can be dimerized prior to or at the time of contact with a CDC- or ADCC-inducing agent such as cetuximab. As a result of the dimerized configuration of the cetuximab-binding cell surface polypeptides, administration of the binding agent at times of distress (e.g. during a cytokine storm) can amplify the cytotoxic effect thereby increasing the likelihood that a cell will be killed. In some embodiments, an agent that binds to a cell surface polypeptide (e.g. dimerized cell surface polypeptide) to induce a cellular response in an engineered cell expressing a polypeptide construct disclosed herein is provided exogenously and/or does not exist endogenously. The present disclosure provides for a transmembrane dimerization domain to facilitate dimerization of any cell surface polypeptide, including truncated variants of natural polypeptides, such as HER1t, LNGFRt, CD20t and CD52t.

In some embodiments, a transmembrane dimerization domain can form a covalent link with a second transmembrane domain to induce dimerization of the cell surface polypeptide. In some embodiments, the covalent connection is in the form of a disulfide bond formed between cysteine amino acids present in each of the adjacent transmembrane domains. In other embodiments, a transmembrane dimerization domain within the cell membrane can form a non-covalent connection with a second transmembrane domain to induce dimerization of the cell surface polypeptide.

A polypeptide construct described herein can have a transmembrane dimerization domain that physically interacts with another transmembrane dimerization domain. In such cases, the first and second transmembrane dimerization domains of the respective first and second polypeptide constructs can either have the same amino acid sequence (i.e., homodimer with respect to the transmembrane dimerization domain) or different amino acid sequences (i.e., heterodimer with respect to the transmembrane dimerization domain). In certain embodiments, each respective transmembrane dimerization domain of a dimerized polypeptide pair comprises at least one cysteine residue that mediates formation of a disulfide bridge between corresponding cysteine residues in the first and second transmembrane dimerization domains.

The transmembrane domain of a polypeptide construct can comprise an amino acid sequence corresponding to and/or homologous to an amino acid sequence of the protein glycophorin A. In some embodiments, a glycophorin A amino acid sequence incorporated into a polypeptide construct described herein includes the transmembrane domain or fragment thereof of glycophorin A. In some embodiments, the transmembrane domain of the polypeptide construct can include one or more amino acids that normally flank the glycophorin A transmembrane domain. In some embodiments, a polypeptide construct comprising all or part of a glycophorin A transmembrane domain is capable of dimerizing (e.g., homodimerizing) with a second polypeptide construct comprising all or part of a glycophorin A transmembrane domain. In such cases, the amino acid sequence incorporated from glycophorin A into the polypeptide construct can define a transmembrane dimerization domain. For example, the glycophorin A dimerization domain can comprise the dimerization motif GXXXG.

In some embodiments, a polypeptide construct comprises a transmembrane domain including at least amino acids E91-R116 of glycophorin A. In some embodiments, a polypeptide construct comprises a transmembrane domain including at least amino acids I92-I114 of glycophorin A. In embodiments, a polypeptide construct comprises a transmembrane domain corresponding to a glycophorin A domain or fragment thereof encoded by a polynucleotide comprising a nucleotide sequence which has at least 70%, 75%, 80%, 85%, 90%, 95%, 99%, or 100% identity to a nucleotide sequence selected from the list consisting of SEQ ID NO:25 and SEQ ID NO:27. In embodiments, the polypeptide construct comprises a transmembrane domain corresponding to a glycophorin A domain or portion thereof which has at least 70%, 75%, 80%, 85%, 90%, 95%, 99%, or 100% identity to an amino acid sequence selected from the list consisting of SEQ ID NO:26 and SEQ ID NO:28.

A polypeptide construct described herein can include a transmembrane domain which is a chimera of amino acid sequences from two or more natural polypeptides. For example, the transmembrane domain can include an amino acid sequence corresponding to a glycophorin A domain or portion thereof linked or fused to an amino acid sequence from a second protein. In some embodiments, such a chimeric transmembrane domain is capable of dimerization with a second transmembrane domain (e.g., chimeric or non-chimeric) and thus embodies a transmembrane dimerization domain. For example, an amino acid sequence corresponding to a glycophorin A transmembrane domain or fragment thereof can be fused to an amino acid sequence corresponding to a domain or fragment thereof of integrin β3 to form a chimeric transmembrane domain of a polypeptide construct. In some embodiments, the polypeptide construct comprises a transmembrane domain comprising amino acids I92-L109 of glycophorin A fused to amino acids A737-W741 of integrin β3. In embodiments, a polypeptide construct comprises a transmembrane domain corresponding to a glycophorin A-integrin β3 chimeric sequence encoded by a polynucleotide comprising a nucleotide sequence which has at least 70%, 75%, 80%, 85%, 90%, 95%, 99%, or 100% identity with the nucleotide sequence of SEQ ID NO:29. In embodiments, the polypeptide construct comprises a transmembrane domain which has at least 70%, 75%, 80%, 85%, 90%, 95%, 99%, or 100% identity with the amino acid sequence of SEQ ID NO:30.

The transmembrane domain of a polypeptide construct can comprise an amino acid sequence corresponding to and/or homologous to an amino acid sequence within a transmembrane domain of the CD3 zeta chain. In some embodiments, a polypeptide construct comprising a transmembrane domain or fragment thereof of a CD3 zeta chain is capable of dimerizing (e.g., homodimerizing) with a second polypeptide construct comprising a transmembrane domain or fragment thereof of a CD3 zeta chain transmembrane domain. In such cases, the amino acid sequence corresponding to the CD3 zeta chain transmembrane domain can define a transmembrane dimerization domain. In some embodiments, the polypeptide construct comprises a transmembrane domain encoded by a polynucleotide comprising a nucleotide sequence which has at least 70%, 75%, 80%, 85%, 90%, 95%, 99%, or 100% identity to a nucleotide sequence of SEQ ID NO:31. In other embodiments, the transmembrane domain is encoded by a polynucleotide comprising the nucleotide sequence of SEQ ID NO:31. In embodiments, the polypeptide construct comprises a transmembrane domain which has at least 70%, 75%, 80%, 85%, 90%, 95%, 99%, or 100% identity to an amino acid sequence of SEQ ID NO:32.

In other embodiments, the transmembrane domain of a polynucleotide construct herein can comprise an amino acid sequence corresponding to and/or homologous to a transmembrane domain or fragment thereof from the proteins CTLA4 (cytotoxic T-lymphocyte protein 4) and/or LNGFR (TNFRSF16). For example, the polypeptide construct can comprise a transmembrane domain encoded by a polynucleotide comprising a nucleotide sequence which has at least 70%, 75%, 80%, 85%, 90%, 95%, 99%, or 100% identity to a nucleotide sequence selected from the list consisting of SEQ ID NO:37 and SEQ ID NO 39. In embodiments, the polypeptide construct comprises a transmembrane domain which has at least 70%, 75%, 80%, 85%, 90%, 95%, 99%, or 100% identity to an amino acid sequence selected from the list consisting of SEQ ID NO: 38 and SEQ ID NO: 40.

Truncated Variants

A polypeptide construct described herein can comprise a cell surface polypeptide linked to the transmembrane domain. In certain embodiments, the cell surface polypeptide comprises a truncated variant of a natural polypeptide. Herein a wide variety of natural polypeptides are provided as a precursor or substrate to produce a truncated variant incorporated into a polypeptide construct. Each natural polypeptide precursor can further be subject to multiple different truncations to yield a large number of possible truncated variants for use in the polypeptide constructs described herein.

Examples of precursors include epidermal growth factor receptor (EGFR or HER1) isoform a precursor (e.g., SEQ ID NO:50); receptor tyrosine protein kinase ErbB2 (HER2) isoform a precursor (e.g., SEQ ID NO:51); receptor tyrosine-protein kinase ErbB3 (HER3) isoform 1 precursor (e.g., SEQ ID NO:52), receptor tyrosine protein kinase ErbB4 (HER4) isoform JM-a/CVT-1 precursor (e.g., SEQ ID NO:53), receptor tyrosine protein kinase ErbB4 (HER4) isoform JM-b isoform X7 (e.g., SEQ ID NO:54), CD20 precursor (e.g., SEQ ID NO:108), CD52 precursor, and LNGFR precursor (e.g., SEQ ID NO:154).

In certain embodiments, the cell surface polypeptide comprises a truncated HER1 polypeptide (herein designated HER1t or EGFRt). Natural HER1 includes an extracellular region comprising Domain I, II, III and IV, a transmembrane domain, and an intracellular tyrosine kinase and regulatory region. Certain antibodies capable of inducing ADCC (e.g., panitumumab and cetuximab) are known to bind to Domain III of endogenous HER1.

Provided herein are polypeptide constructs comprising HER1 polypeptides which are truncated for any amino acids, domains or fragments of endogenous HER1. Herein a HER1 polypeptide can comprise a HER1t polypeptide. In some embodiments, a HER1 polypeptide consists of or consists essentially of a HER t polypeptide. In other embodiments, a HER1 polypeptide can comprise a HER1t polypeptide in addition to other HER1 domains (e.g. a HER1 transmembrane domain). In embodiments, a HER1 polypeptide can lack an intracellular domain or fragment thereof normally found in HER1, including the tyrosine kinase domain and regulatory region. In some embodiments, the HER1 polypeptide can lack a transmembrane domain or fragment thereof normally found in HER1. In some embodiments, the HER1 polypeptide can lack an extracellular domain or fragment thereof normally found in HER1, including all or part of Domain I, Domain II and Domain IV normally found in HER1.

In some embodiments, a cell surface polypeptide comprises a HER1t polypeptide lacking a fragment of Domain III normally found in HER1. In some embodiments, the HER1t polypeptide consists of or consists essentially of all or a part of Domain III of the endogenous HER1 protein. In some embodiments, the HER1t polypeptide consists of or consists essentially of all of Domain III of the endogenous HER1 protein. In an embodiment, HER1t Domain III incorporated into the cell surface polypeptide is encoded by a polynucleotide comprising a nucleotide sequence which has at least 70%, 75%, 80%, 85%, 90%, 95%, 99%, or 100% identity to a nucleotide sequence of SEQ ID NO:199. In an embodiment, HER1t Domain III incorporated into the cell surface polypeptide has at least 70%, 75%, 80%, 85%, 90%, 95%, 99%, or 100% identity to an amino acid sequence of SEQ ID NO:200.

In some embodiments, a HER1t polypeptide incorporated into the cell surface polypeptide comprises Domain IV or a fragment thereof of endogenous HER1. An endogenous HER1 Domain IV can be encoded by a polynucleotide comprising a nucleotide sequence which has at least 70%, 75%, 80%, 85%, 90%, 95%, 99%, or 100% identity to a nucleotide sequence of SEQ ID NO:201. In an embodiment, an endogenous HER1t Domain IV has at least 70%, 75%, 80%, 85%, 90%, 95%, 99%, or 100% identity to an amino acid sequence of SEQ ID NO:202. In other embodiments, the HER1t polypeptide incorporated into a cell surface polypeptide can comprise a truncated Domain IV. The HER1t truncated Domain IV can comprise a truncation of at least 10%, 15%, 20%, 25%, 30%, 35%, 40%, 45%, 50%, 55%, 60%, 65%, 70%, 75%, 80%, 85%, 90%, 95%, or 100% of Domain IV of natural HER1. In an embodiment, the HER1t truncated Domain IV incorporated into the cell surface polypeptide has at least 70%, 75%, 80%, 85%, 90%, 95%, 99%, or 100% identity to an amino acid sequence selected from the list consisting of SEQ ID NO:203, SEQ ID NO: SEQ ID NO:204, SEQ ID NO:205, SEQ ID NO:206, SEQ ID NO:207 SEQ ID NO:208, and SEQ ID NO:209.

A polypeptide construct described herein can comprise a HER1t polypeptide comprising HER1 Domain III and Domain IV. In an embodiment, a HER1t polypeptide comprises HER1 Domain III and Domain IV having at least 70%, 75%, 80%, 85%, 90%, 95%, 99%, or 100% identity to the amino acid sequence of SEQ ID NO:210.

A polypeptide construct described herein can comprise a HER1t polypeptide comprising HER1 Domain III and a fragment of Domain IV. In an embodiment, a HER1t polypeptide has at least 70%, 75%, 80%, 85%, 90%, 95%, 99%, or 100% identity to an amino acid sequence selected from the list consisting of SEQ ID NO:211, SEQ ID NO:212, SEQ ID NO:213, SEQ ID NO:214, SEQ ID NO:215, SEQ ID NO:216, and SEQ ID NO:217.

Natural HER1 also contains multiple disulfide bond pairs in Domain IV. In some embodiments, the HER1t truncated Domain IV can comprise truncation at positions to preserve disulfide bond pairs. In further embodiments, HER1t variants as described herein are linked to a transmembrane domain via different size G4S linkers (G4S)n, wherein n=0, 1, 2, 3, 4, 5 (SEQ ID NO: 222), to maintain the "natural" distance between the HER1t and the transmembrane protein. In further embodiments, 7 residue linker between domain IV and EGFR transmembrane domain can be further removed as this linker plays a role in dimerization of EGFR receptors, which leads to EGF ligand activation.

A HER1t polypeptide incorporated into a cell surface polypeptide described herein can include an epitope that can be recognized by an exogenously introduced binding partner or antibody. In some embodiments, a HER1t polypeptide can incorporate a cetuximab-binding domain in order to facilitate targeted depletion of cells expressing a polypeptide construct described herein. Depletion can be due for example to cell death resulting from CDC and/or ADCC. Non-limiting examples of molecules which can be endogenously introduced to bind to and/or recognize an epitope on a cell surface polypeptide comprising HER1t can include cetuximab, gefitinib, erlotinib, afatinib, brigatinib, icotinib, osimertinib, panitumumab, zalutumumab, nimotuzumab, and matuzumab. In various embodiments, the antibody can be a monoclonal antibody, scFv, scFab, diabody, or camelid antibody. In another embodiment, the antibody can be conjugated to a drug or a toxin.

Figure 4A:
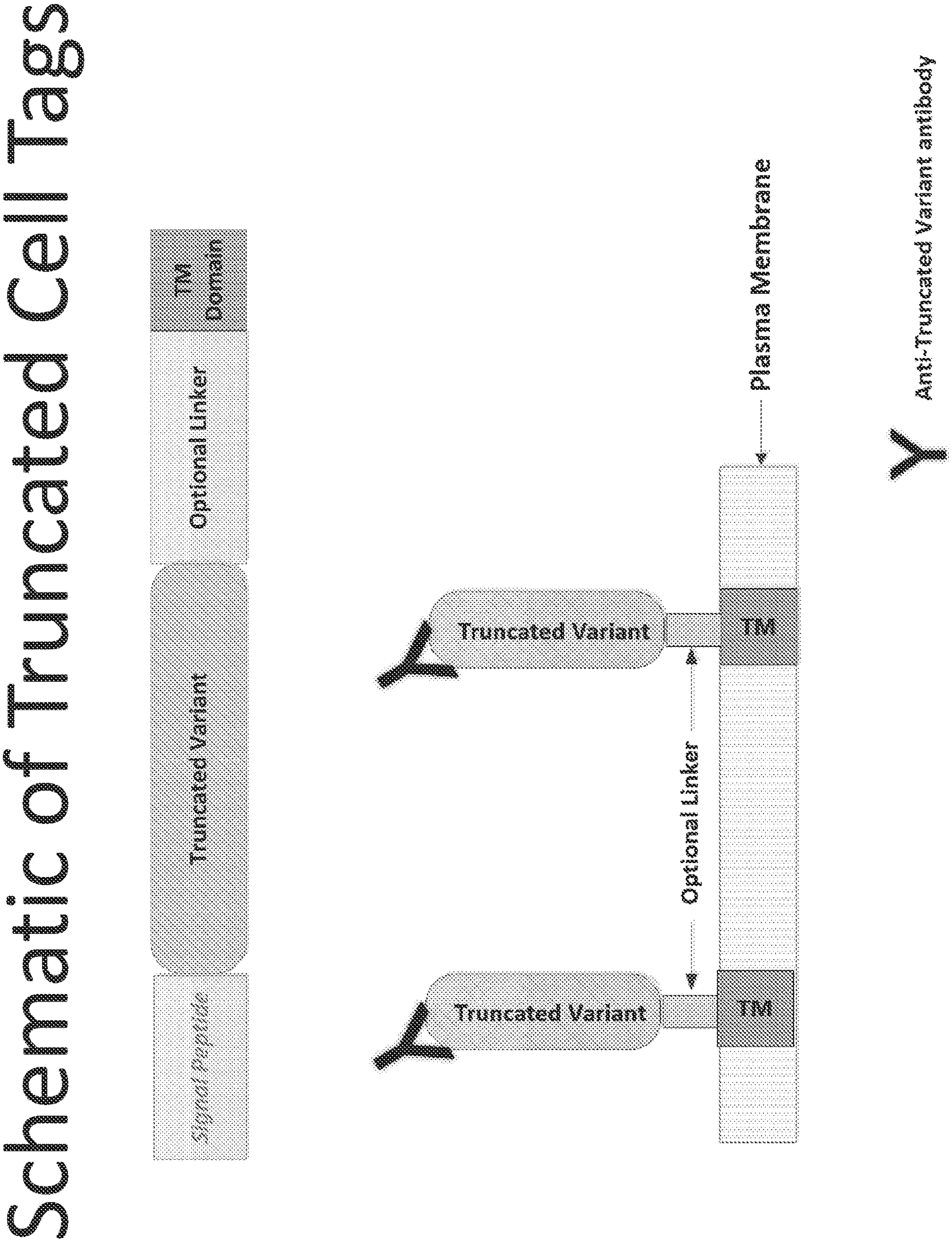
FIG. 4A is a schematic diagram illustrating embodiments of a polypeptide construct described herein. The top panel shows an embodiment of a polypeptide construct comprising a signal peptide for directing the polypeptide construct to the cell surface, truncated variant of a natural polypeptide, an optional linker, and a transmembrane (TM) domain. The bottom panel illustrates an embodiment of a polypeptide construct expressed in an engineered cell described herein. The polypeptide construct is anchored to the cell surface by a transmembrane (TM) domain, which is fused to an extracellular-oriented truncated variant via an optional peptide linker. In the embodiment shown, the linker serves as an extension to direct and extend the truncated variant from cell surface, thus optimizing binding of an antibody or binding partner (represented by anti-truncated variant antibody) to an epitope of the truncated variant.
Figure 4B:
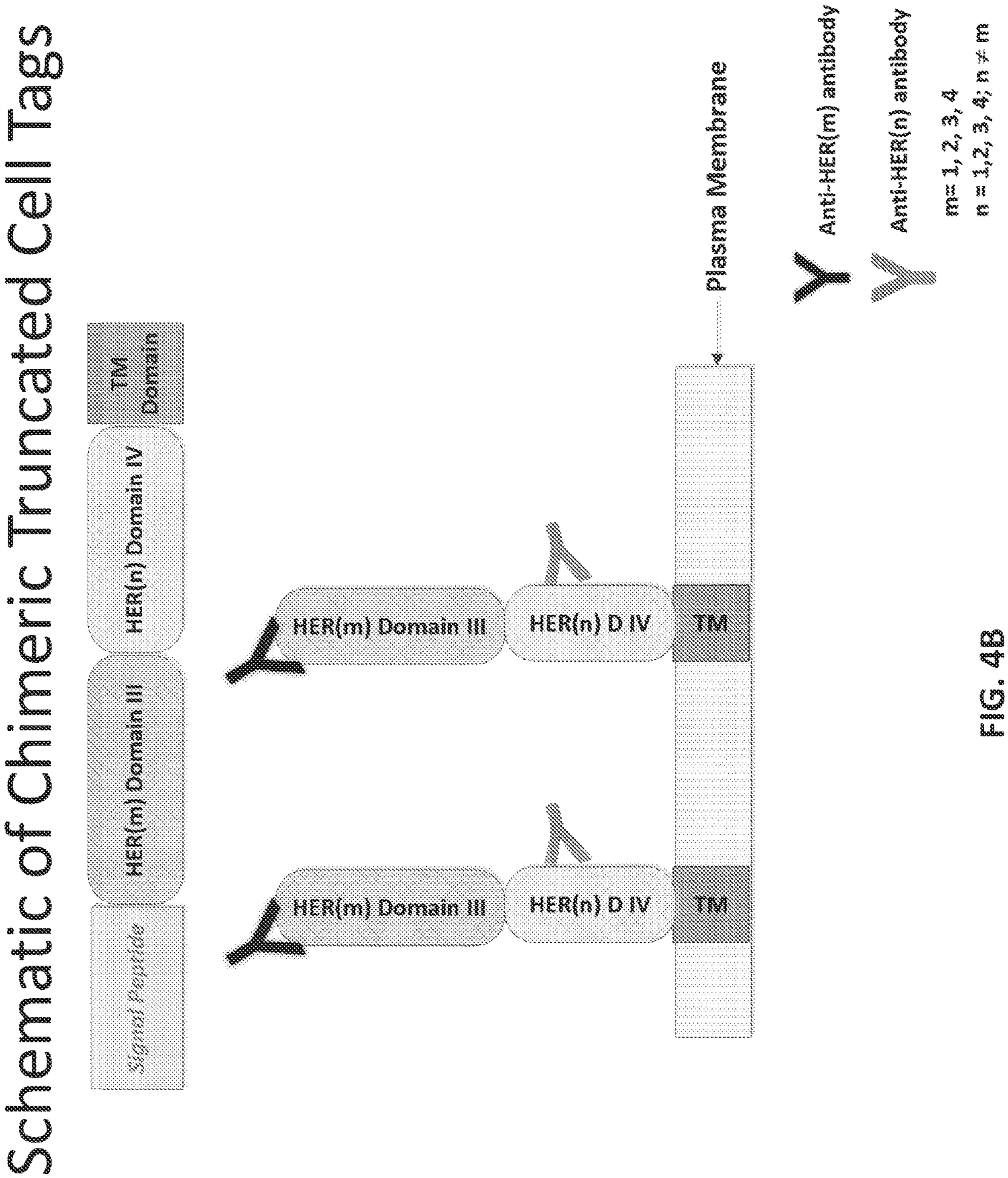
FIG. 4B is a schematic diagram illustrating an embodiment of a polypeptide construct described herein. The truncated variant and optional linker from FIG. 4A are replaced in FIG. 4*b* by a HER(m) Domain III and HER(n) Domain IV, where m and n represent any member of the EGFR/HER family including HER1, HER2, ErbB3 and ErbB4 (i.e., m=1-4 and n=1-4, but n≠m). In the embodiment shown, each of the HER(m) Domain III and HER(n) Domain IV present different epitopes which are recognized by different antibodies (i.e., Anti-HER(m) and Anti-HER(n) antibody, respectively).
Figure 4C:
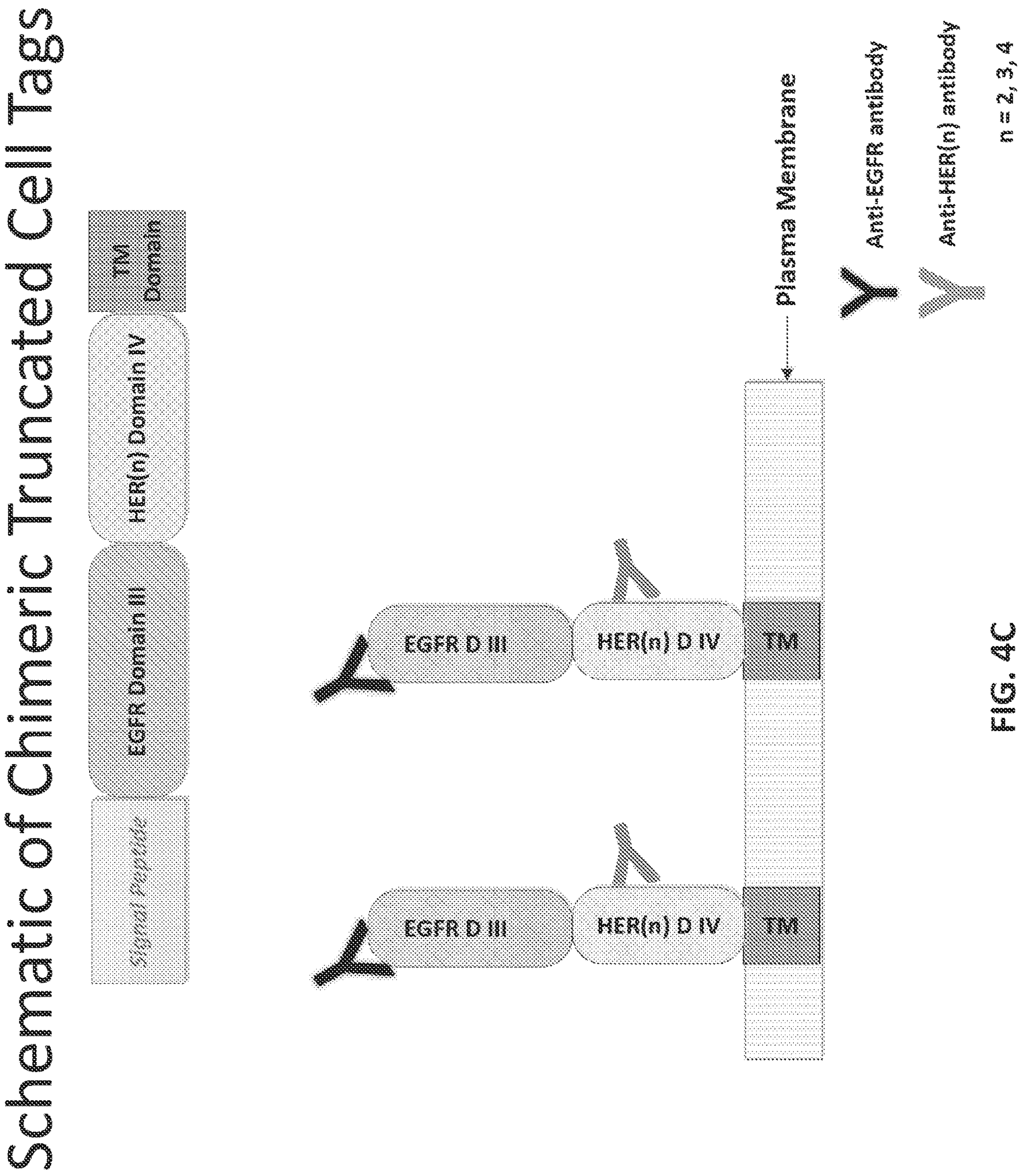
FIG. 4C is a schematic diagram illustrating a specific embodiment in which the HER(m) Domain III of FIG. 4B corresponds to an EGFR Domain III, recognized by an Anti-EGFR antibody, which is fused to Domain IV of either HER2, ErbB3 or ErbB4 at c-terminus followed by a TM domain.

A cell surface polypeptide incorporated into a polypeptide construct described herein can comprise truncated variants of multiple different natural polypeptides. For example, the cell surface polypeptide can comprise a polypeptide chimera comprising multiple truncated polypeptides from the EGFR family. FIG. 4B illustrates an embodiment of a polypeptide construct conferring cell tag functionality, wherein the cell surface polypeptide comprises Domain III from one member of the HER/EGFR family (HER(m)) and Domain IV or a fragment thereof from a different member of the HER/EGFR family (HER(n)). Provided herein are chimeric cell surface polypeptides comprising any combination of extracellular domains from two or more of EGFR/HER1, HER2, ErbB3 and ErbB4. FIG. 4C depicts the specific case where Domain III is derived from EGFR/HER1. An advantage of such chimeric cell surface polypeptides is that each individual truncation can remove epitopes from the respective natural polypeptide which are prone to binding endogenous molecules, while preserving an epitope which can be recognized by an exogenously introduced antibody during adoptive cell therapy. For example, where the chimeric cell surface polypeptide comprises Domain III from EGFR and Domain IV from HER2, engineered cells expressing the polypeptide can be susceptible to both the antibodies cetuximab (recognizing Domain III of EGFR) and trastuzumab (recognizing Domain IV of HER2). Thus, the chimeric cell surface polypeptides described herein provide a further mechanism to control immune cell behavior during immunotherapy, by providing for binding sites for multiple antibiotics/binding partners. For example, in a circumstance where a subject experiencing side effects during adoptive cell therapy does not respond to an administered antibiotic (e.g., cetuximab) targeting an epitope on one of the truncated variants in the chimeric cell surface polypeptide, a different antibody (e.g., trastuzumab) can be administered to the subject to target the same engineered cell via a different epitope on the other truncated variant of the chimeric cell surface polypeptide.

In some embodiments, a chimeric cell surface polypeptide can be fused to a transmembrane domain which is homologous to an EGFR family member. For example, the transmembrane domain can correspond to a transmembrane domain from EGFR/HER1, HER2, ErbB3 or ErbB4. In other embodiments, the transmembrane domain can be homologous to a non-EGFR transmembrane domain, including a transmembrane domain corresponding to SEQ ID NO:26, SEQ ID NO:28, SEQ ID NO:30, SEQ ID NO:32, SEQ ID NO:34, SEQ ID NO:36, SEQ ID NO:38 and SEQ ID NO:40.

In some embodiments, a chimeric cell surface polypeptide can comprise a chimera of a HER1t polypeptide and a truncated HER2 (HER2t) polypeptide or fragment thereof. For example, the polypeptide construct can comprise a HER1t/EGFRt polypeptide comprising HER1 Domain III and a HER2t polypeptide comprising a HER2 Domain IV and HER2 transmembrane domain. In an embodiment, the EGFR-HER2 chimeric cell surface polypeptide fused to the HER2 transmembrane domain can be encoded by a polynucleotide comprising a nucleotide sequence having at least 70%, 75%, 80%, 85%, 90%, 95%, 99% or 100% identity to a nucleotide sequence selected from the group consisting of SEQ ID NO:88 and SEQ ID NO:92 (delta 16). In an embodiment, the EGFR-HER2 chimeric cell surface polypeptide fused to the HER2 transmembrane domain has at least 70%, 75%, 80%, 85%, 90%, 95%, 99% or 100% identity to an amino acid sequence selected from the group consisting of SEQ ID NO:89 and SEQ ID NO:93 (delta 16).

In some embodiments, a chimeric cell surface polypeptide can comprise a chimera of a HER1t polypeptide and a truncated ErbB3 (ErbB3t) polypeptide or fragment thereof. For example, the polypeptide construct can comprise a HER1t/EGFRt polypeptide comprising HER1 Domain III and an ErbB3t polypeptide comprising an ErbB3 Domain IV and ErbB3 transmembrane domain. In an embodiment, the EGFR-ErbB3 chimeric cell surface polypeptide fused to the ErbB3 transmembrane domain can be encoded by a polynucleotide comprising a nucleotide sequence having at least 70%, 75%, 80%, 85%, 90%, 95%, 99% or 100% identity to the nucleotide sequence of SEQ ID NO:96. In an embodiment, the EGFR-ErbB3 chimeric cell surface polypeptide fused to the ErbB3 transmembrane domain has at least 70%, 75%, 80%, 85%, 90%, 95%, 99% or 100% identity to the amino acid sequence of SEQ ID NO:97.

In some embodiments, a chimeric cell surface polypeptide can comprise a chimera of a HER1t polypeptide and a truncated ErbB4 (ErbB4t) polypeptide or fragment thereof. For example, the polypeptide construct can comprise a HER1t/EGFRt polypeptide comprising Domain III and an ErbB4t polypeptide comprising ErbB4 Domain IV and ErbB4 transmembrane domain. In some embodiments, an ErbB4t polypeptide can comprise a JM-a extracellular juxtamembrane domain encoded by the ErbB4 JM-a alternative transcript. In some embodiments, an ErbB4t polypeptide can comprise a JM-b extracellular juxtamembrane domain encoded by the ErbB4 JM-b alternative transcript. In an embodiment, the chimeric cell surface polypeptide fused to the ErbB4 transmembrane domain can be encoded by a polynucleotide comprising a nucleotide sequence having at least 70%, 75%, 80%, 85%, 90%, 95%, 99% or 100% identity to s nucleotide sequence selected from the list consisting of SEQ ID NO:100 (EGFR-ErbB4 (JM-a)) and SEQ ID NO:104 (EGFR-ErbB4 (JM-b)). In an embodiment, the EGFR-ErbB4 chimeric cell surface polypeptide fused to the ErbB4 transmembrane domain has at least 70%, 75%, 80%, 85%, 90%, 95%, 99% or 100% identity to the amino acid sequence selected from the list consisting of SEQ ID NO:101 (EGFR-ErbB4 (JM-a)) and SEQ ID NO:105 (EGFR-ErbB4 (JM-b)).

A polypeptide construct described herein can comprise any combination of signal peptide, cell surface polypeptide comprising a HER1t polypeptide (e.g., comprising only HER1t or a chimeric polypeptide comprising HER1t), transmembrane domain and optionally a linker. For example, a polypeptide construct can comprise a cell surface polypeptide comprising a HER1t polypeptide or a chimeric polypeptide comprising HER1t linked or fused to a derivative or fragment of a CD28 transmembrane domain via a linker (e.g., one or more (e.g., 1-4) copies of (G4S (SEQ ID NO: 221))). In some embodiments, the cell surface polypeptide can include a HER1t polypeptide encoded by a polynucleotide comprising a nucleotide sequence having at least 70%, 75%, 80%, 85%, 90%, 95%, 99% or 100% identity to a nucleotide sequence selected from the list consisting of SEQ ID NO:56 (HER1t1); SEQ ID NO:58 (HER1t2); SEQ ID NO:60 (HER1t3); SEQ ID NO:62 (HER1t4); SEQ. ID NO:64 (HER1t5); SEQ ID NO:66 (HER1t6); SEQ ID NO:68 (HER1t7); SEQ ID NO:72 (HER1t8); SEQ ID NO:76 (HER1t9); SEQ ID NO:80 (HER1t10); and SEQ ID NO:84 (HER1t11). In some embodiments, the cell surface polypeptide can include a HER1t polypeptide comprising an amino acid sequence having at least 70%, 75%, 80%, 85%, 90%, 95%, 99% or 100% identity to an amino acid sequence selected from the list consisting of SEQ ID NO:55 (HER1t); SEQ ID NO:57 (HER1t1); SEQ ID NO:59 (HER1t2); SEQ ID NO:61 (HER1t3); SEQ. ID NO:63 (HER1t4); SEQ ID NO:65 (HER1t5); SEQ ID NO:67 (HER1t6); SEQ ID NO:69 (HER1t7); SEQ ID NO:73(HER1t8); SEQ ID NO:77 (HER1t9); SEQ ID NO:81 (HER1t10); and SEQ ID NO:85 (HER1t11).

In some embodiments, a polypeptide construct can comprise a signal peptide, a cell surface polypeptide comprising a HER1t polypeptide or a chimeric polypeptide comprising a HER1t polypeptide, a transmembrane domain comprising a transmembrane dimerization domain, and a linker to connect the transmembrane domain and cell surface polypeptide. For example, a polypeptide construct can comprise an Ig Kappa signal peptide, a particular truncated variant of HER1, a linker (e.g. (G4S)4 (SEQ ID NO: 22)) and a transmembrane dimerization domain (e.g., comprising I92-I114 of glycophorin A or the transmembrane domain from CD3 zeta). In embodiments, a polypeptide construct comprising a HER1t polypeptide and a transmembrane dimerization domain is encoded by a polynucleotide comprising a nucleotide sequence which has at least 70%, 75%, 80%, 85%, 90%, 95%, 99%, or 100% identity to a nucleotide sequence selected from the list consisting of SEQ ID NO:70 (glycophorin A; HER1t8); SEQ ID NO:74 (glycophorin A; HER1t9); SEQ ID NO:78 (glycophorin A; HER1t10); and SEQ ID NO:82 (CD3 zeta; HER1t11). In embodiments, a polypeptide construct comprising a HER1t polypeptide and a transmembrane dimerization domain comprises an amino acid sequence which has at least 70%, 75%, 80%, 85%, 90%, 95%, 99%, or 100% identity to an amino acid sequence selected from the list consisting of SEQ ID NO:71 (glycophorin A; HER1t8); SEQ ID NO:75 (glycophorin A; HER1t9); SEQ ID NO:79 (glycophorin A; HERtl10); and SEQ ID NO:83 (CD3 zeta; HER1t11).

In another embodiment, a polypeptide construct can comprise a cell surface polypeptide comprising a HER1t-HER2t chimera linked to a HER2 transmembrane domain. The truncated HER1t-HER2t chimera and transmembrane domain can be further connected to a signal peptide (e.g., GMCSFRα) which directs the polypeptide construct to the cell surface. In an embodiment, the polypeptide construct is encoded by a polynucleotide having at least 70%, 75%, 80%, 85%, 90%, 95%, 99%, or 100% identity to a nucleotide sequence selected from the list consisting of SEQ ID NO:86 and SEQ ID NO:90 (delta 16). In an embodiment, the polypeptide construct has an amino acid sequence having at least 70%, 75%, 80%, 85%, 90%, 95%, 99%, or 100% identity to an amino acid sequence selected from the list consisting of SEQ ID NO:87 and SEQ ID NO:91 (delta 16).

In another example, a polypeptide construct can comprise a cell surface polypeptide comprising a HER1t-ErbB3t chimera linked to an ErbB3 transmembrane domain. In an embodiment, the HER1t-ErbB3t chimera and transmembrane domain is further connected to a signal peptide (e.g., GMCSFRα) which directs the polypeptide construct to the cell surface. In an embodiment, the polypeptide construct is encoded by a polynucleotide having at least 70%, 75%, 80%, 85%, 90%, 95%, 99%, or 100% identity to a nucleotide sequence of SEQ ID NO:94. In an embodiment, the polypeptide construct has an amino acid sequence having at least 70%, 75%, 80%, 85%, 90%, 95%, 99%, or 100% identity to the amino acid sequence of SEQ ID NO:95.

In still another example, a polypeptide construct can comprise a cell surface polypeptide comprising a HER1t-ErbB4t chimera linked to an ErbB4 transmembrane domain. In an embodiment, the HER1t-ErbB4t chimera and transmembrane domain is further connected to a signal peptide (e.g., GMCSFRα) which directs the polypeptide construct to the cell surface. In an embodiment, the polypeptide construct is encoded by a polynucleotide having at least 70%, 75%, 80%, 85%, 90%, 95%, 99%, or 100% identity to a nucleotide sequence selected from the list consisting of SEQ ID NO:98 (JM-a variant) and SEQ ID NO:102 (JM-b variant). In an embodiment, the polypeptide construct has an amino acid sequence having at least 70%, 75%, 80%, 85%, 90%, 95%, 99%, or 100% identity to an amino acid sequence selected from the list consisting of SEQ ID NO:99 (JM-a variant) and SEQ ID NO:103 (JM-b variant).

A polypeptide construct comprising a HER1t polypeptide can comprise any signal peptide capable of directing the polypeptide construct to the cell surface. For example, a cell surface polypeptide comprising a HER1t polypeptide (e.g., comprising an amino acid sequence which has at least 70%, 75%, 80%, 85%, 90%, 95%, 99%, or 100% identity to an amino acid sequence selected from the list consisting of SEQ ID NO:200, SEQ ID NO:210, SEQ ID NO:211, SEQ ID NO:212, SEQ ID NO:213, SEQ ID NO:214, SEQ ID NO:215, SEQ ID NO:216 and SEQ ID NO:217) can be fused to a signal peptide comprising an amino acid sequence which has at least 70%, 75%, 80%, 85%, 90%, 95%, 99%, or 100% identity to an amino acid sequence selected from the list consisting of SEQ ID NO:2 (GMCSFRα), SEQ ID NO:4 (Ig Kappa), SEQ ID NO:6 (Immunoglobulin E), SEQ ID NO:8 (CD8α), SEQ ID NO:10 (TVB2), SEQ ID NO:12 (CD52) or SEQ ID NO:14 (LNFGR).

A polypeptide construct comprising a HER1t polypeptide can comprise any transmembrane domain, including a transmembrane domain that does not comprise a dimerization domain. For example, a cell surface polypeptide comprising a HER1t polypeptide (e.g., comprising an amino acid sequence which has at least 70%, 75%, 80%, 85%, 90%, 95%, 99%, or 100% identity to an amino acid sequence selected from the list consisting of SEQ ID NO:200, SEQ ID NO:210, SEQ ID NO:211, SEQ ID NO:212, SEQ ID NO:213, SEQ ID NO:214, SEQ ID NO:215, SEQ ID NO:216 and SEQ ID NO:217) can be linked to a transmembrane domain comprising an amino acid sequence which has at least 70%, 75%, 80%, 85%, 90%, 95%, 99%, or 100% identity to an amino acid sequence selected from the list consisting of SEQ ID NO:26 (glycophorin A E91-R116), SEQ ID NO:28 (glycophorin A I92-I114), SEQ ID NO:30 (glycophorin A(192-L109).integrin β3 (A737-W741), SEQ ID NO:32 (CD3 zeta chain), SEQ ID NO: 34 (CD8α), SEQ ID NO:36 (CD28), SEQ ID NO:38 (CTLA4) and SEQ ID NO:40 (LNGFR).

A polypeptide construct comprising a HER1t polypeptide can comprise any peptide linker (or in some embodiments no peptide linker). For example, a cell surface polypeptide comprising HER1t (e.g., comprising an amino acid sequence which has at least 70%, 75%, 80%, 85%, 90%, 95%, 99%, or 100% identity to an amino acid sequence selected from the list consisting of SEQ ID NO:200, SEQ ID NO:210, SEQ ID NO:211, SEQ ID NO:212, SEQ ID NO:213, SEQ ID NO:214, SEQ ID NO:215, SEQ ID NO:216 and SEQ ID NO:217) can be fused to a peptide linker comprising an amino acid sequence which has at least 70%, 75%, 80%, 85%, 90%, 95%, 99%, or 100% identity to an amino acid sequence selected from the list consisting of SEQ ID NO:16 (GSG), SEQ ID NO:18 (SGSG), SEQ ID NO:20 ((G4S)3), SEQ ID NO:22 ((G4S)4) and SEQ ID NO:24 (Whitlow).

A cell surface polypeptide can incorporate a truncated CD polypeptide. For example, the cell surface polypeptide can include a truncated CD20 polypeptide (herein designated CD20t). The natural CD20 polypeptide is a multi-pass transmembrane protein encoded by a membrane-spanning 4-domains subfamily A member 1 (MS4A1) gene. In certain embodiments full-length CD20 can be encoded by a polynucleotide comprising the nucleotide sequence of SEQ ID NO:106, and full-length CD20 amino acid sequence can correspond to the amino acid sequence of SEQ ID NO:107. In some embodiments, CD20 comprises 4 transmembrane domain passes encompassing amino acids 57-78, 85-105, 121-141, and 189-209. In some embodiments, CD20 comprises 2 extracellular domains encompassing amino acids 79-84 and 142-188. In some embodiments, CD20 comprises 3 cytoplasmic domains encompassing amino acids 1-56, 106-120 and 210-297.

Provided herein are polypeptide constructs comprising CD20 polypeptides which are truncated for any amino acids, domains or fragments of endogenous CD20. Herein a CD20 polypeptide can comprise a CD20t polypeptide. In some embodiments, a CD20 polypeptide consists of or consists essentially of a CD20t polypeptide. In other embodiments, a CD20 polypeptide can comprise a CD20t polypeptide in addition to another CD20 domain or portion thereof (e.g. a CD20 transmembrane domain and/or cytoplasmic domain). For example, a CD20 polypeptide can be truncated for an intracellular cytoplasmic (e.g. signaling) domain or portion thereof, a transmembrane (e.g. helical) domain or portion thereof, and/or an extracellular domain or portion thereof. In some embodiments, a CD20 polypeptide can be missing multiple domains or multiple portions of a domain relative to the wildtype polypeptide. In an embodiment, a CD20 polypeptide comprises M1-E263 of endogenous CD20 (SEQ ID NO:109; CD20t1), M117-N214 of endogenous CD20 (SEQ ID NO:111 (CD20t2), M1-N214 of endogenous CD20 (SEQ ID NO:115; CD20t4), V82-N214 of endogenous CD20 (SEQ ID NO: 117; CD205), or V82-I186 of endogenous CD20 (SEQ ID NO:119, CD20t6).

In an embodiment, a CD20t polypeptide can comprise an extracellular domain or fragment thereof. In an embodiment, a CD20t polypeptide has at least 70%, 75%, 80%, 85%, 90%, 95%, 99%, or 100% identity to an amino acid sequence selected from the list consisting of SEQ ID NO:218, SEQ ID NO:219 and SEQ ID NO:220. In some embodiments, a CD20t polypeptide can be linked to a transmembrane domain or fragment thereof. In an embodiment, a polypeptide construct comprises a CD20t polypeptide linked to a CD20 transmembrane domain. In some embodiments, a polypeptide construct comprising a CD20t polypeptide linked to a CD20 transmembrane domain is encoded by a polynucleotide comprising a nucleotide sequence having at least 70%, 75%, 80%, 85%, 90%, 95%, 99% or 100% identity to a nucleotide sequence selected from the list consisting of SEQ ID NO:108 (CD20t1 encoding M1-E263); SEQ ID NO:110 (CD20t2 encoding M117-N214); SEQ ID NO:114 (CD20t4 encoding M1-N214); SEQ ID NO: 116 (CD20t5 encoding V82-N214); SEQ ID NO: 118 (CD20t6 encoding V82-I186); SEQ ID NO:132 (CD20t13 encoding M1-A54 and CI11-P297); SEQ ID NO:134 (CD20t14 encoding M1-A54 and CI11-E281); SEQ ID NO:136 (CD20t15 encoding M1-A54 and CI11-E263); SEQ ID NO:138 (CD20t16 encoding M1-A54 and CI11-V228); and SEQ ID NO:140 (CD20t17 encoding M1-V8 and C111-P297). In an embodiment, a polypeptide construct comprising a CD20t polypeptide linked to a CD20 transmembrane domain can comprise an amino acid sequence having at least 70%, 75%, 80%, 85%, 90%, 95%, 99% or 100% identity to an amino acid sequence selected from the list consisting of SEQ ID NO:109 (CD20t1: M1-E263); SEQ ID NO:111 (CD20t2: M117-N214); SEQ ID NO: 115 (CD20t4: M1-N214); SEQ ID NO:117 (CD20t5: V82-N214); SEQ ID NO:119 (CD20t6: V82-I186); SEQ ID NO:133 (CD20t13: M1-A54 and C111-P297); SEQ ID NO:135 (CD20t14: M1-A54 and C111-E281); SEQ ID NO:137 (CD20t15: M1-A54 and CI11-E263); SEQ ID NO:139 (CD20t16: M1-A54 and CI11-V228); and SEQ ID NO:141 (CD20t17: M1-V8 and C111-P297).

In some embodiments, a CD20t polypeptide can retain at least one copy of a rituximab-binding mimotope of endogenous CD20, as described in Philip et al., (2014), "A highly compact epitope-based marker/suicide gene for easier and safer T-cell therapy," Blood: 124: 1277-1287. In some embodiments, one or more copies of a rituximab-binding epitope of CD20t can be fused to one or more CD-34-derived amino acid sequences, such as the amino-terminal 40 amino acids of CD34 which facilitate binding of an anti-CD34 monoclonal antibody. In some embodiments, a CD20t polypeptide can have multiple domains removed, or a portion of multiple domains removed.

A cell surface polypeptide incorporating a CD20t polypeptide can include an epitope that can be recognized by an exogenously introduced antibody or binding partner. For example, a CD20t polypeptide included in the cell surface polypeptide can incorporate a rituximab-binding domain in order to facilitate targeted depletion of cells expressing a polypeptide construct described herein (e.g., via CDC and/or antibody-dependent cellular cytotoxicity ADCC). Non-limiting examples of antibodies which can be used to bind to an epitope of a cell surface polypeptide comprising a CD20t polypeptide include rituximab, hOUBM3/6, afutuzumab, blontuvetmab, obinutuzumab, ibritumomab tiuxetan, tositumomab, ofatumumab, ocaratuzumab, ocrelizumab, TRU-015 (Trubion) and veltuzumab (IMMU-106). In various embodiments, the antibody can be a monoclonal antibody, scFv, scFab, diabody, or camelid antibody. In other embodiments, the antibody can be conjugated to a drug or a toxin. In some embodiments, the CD20t polypeptide includes an epitope found in an extracellular domain of endogenous CD20. In some embodiments, an epitope of the CD20t polypeptide includes amino acids 170-185 of endogenous CD20. In some embodiments, an epitope of the CD20t polypeptide includes amino acids 170-173 and 182-185 of endogenous CD20.

In further embodiments, a cell surface polypeptide comprising a CD20t polypeptide is chimeric for a truncated variant of one or more additional polypeptides. For example, a chimeric cell surface polypeptide can comprise a CD20t polypeptide and a truncated CD8a (CD8at) polypeptide.

A cell surface polypeptide can further comprise multiple CD20t linked sequences together as a concatemer. For example, a cell surface polypeptide can comprise the same CD20t amino acid sequence repeated in succession, or different CD20t variants connected together. In some embodiments, CD20t amino acid sequences are linked together in the cell surface polypeptide by a peptide linker. In an embodiment, an SGS or SG4S linker (SEQ ID NO: 223) can be used to link together repeating CD20 amino acid sequences in a cell surface polypeptide (e.g., see SEQ ID NO:123 (SGS linker) and SEQ ID NO:129 (SG4S linker (SEQ ID NO: 223)), which further comprise the cell surface polypeptide linked to a CD28 transmembrane domain by an SG4S linker (SEQ ID NO: 223).

A polypeptide construct described herein can comprise any combination of signal peptide, cell surface polypeptide comprising a CD20t polypeptide (e.g., comprising only CD20t or a CD20t chimera), transmembrane domain and optionally a linker. For example, a polypeptide construct can comprise an SG4S linker (SEQ ID NO: 223) which connects or fuses a cell surface polypeptide comprising a CD20t polypeptide to a transmembrane domain. In certain embodiments, a transmembrane domain is derived from or homologous to a transmembrane domain or fragment thereof from CD20, CD28 or CD8α. In an embodiment, a polypeptide construct comprising CD20t is encoded by a polynucleotide comprising a nucleotide sequence selected from the list consisting of SEQ ID NO:112 (CD20t3 encoding CD20t (K142-S188) and CD8a (I183-T203) transmembrane domain); SEQ ID NO:120 (CD20t7 encoding CD20t (P160-Q187), an SG4S linker (SEQ ID NO: 223) and CD28 (I96-D172) transmembrane domain); SEQ ID NO:122 (CD20t8 encoding a CD20t-concatemer (P160-Q187 separated by an SGS linker), SG4S linker (SEQ ID NO: 223) and CD28 (I96-D172) transmembrane domain); SEQ ID NO:124 (CD20t9 encoding CD20t (P160-Q187), an SG4S linker (SEQ ID NO: 223) and a CD8a (P120-V201) transmembrane domain); SEQ ID NO:126 (CD20t10 encoding CD20t (C167-C183), an SG4S linker (SEQ ID NO: 223) and a CD28 (I96-D172) transmembrane domain; SEQ ID NO: 128 (CD20t11 encoding a CD20 concatemer (C167-C183 separated by an SG4S linker (SEQ ID NO: 223)), an SG4S linker (SEQ ID NO: 223) and a CD28 (I96-D172) transmembrane domain; and SEQ ID NO: 130 (CD20t12 encoding CD20t (C167-C183), an SG4S linker (SEQ ID NO: 223) and a CD8a (P120-V201) transmembrane domain). In an embodiment, a polypeptide construct comprising CD20t comprises an amino acid sequence selected from the list consisting of SEQ ID NO:113 (CD20t3; CD20t (K142-S188) and CD8a (I183-T203) transmembrane domain); SEQ ID NO:121 (CD20t7 encoding CD20t (P160-Q187), an SG4S linker (SEQ ID NO: 223) and CD28 (I96-D172) transmembrane domain); SEQ ID NO:123 (CD20t8 encoding a CD20t-concatemer (P160-Q187 separated by an SGS linker), SG4S linker (SEQ ID NO: 223) and CD28 (I96-D172) transmembrane domain); SEQ ID NO:125 (CD20t9 encoding CD20t (P160-Q187), an SG4S linker (SEQ ID NO: 223) and a CD8a (P120-V201) transmembrane domain); SEQ ID NO:127 (CD20t10 encoding CD20t (C167-C183), an SG4S linker (SEQ ID NO: 223) and a CD28 (I96-D172) transmembrane domain; SEQ ID NO: 129 (CD20t11 encoding a CD20 concatemer (C167-C183 separated by an SG4S linker (SEQ ID NO: 223)), an SG4S linker (SEQ ID NO: 223) and a CD28 (I96-D172) transmembrane domain; and SEQ ID NO:131 (CD20t12 encoding CD20t (C167-C183), an SG4S linker (SEQ ID NO: 223) and a CD8a (P120-V201) transmembrane domain).

A polypeptide construct comprising a CD20t polypeptide can comprise any signal peptide capable of directing the polypeptide construct to the cell surface. For example, a polypeptide construct comprising a CD20t polypeptide (e.g., a polypeptide which comprises an amino acid sequence selected from the list consisting of SEQ ID NO:218, SEQ ID NO:219 and SEQ ID NO:220) can be fused to a signal peptide comprising an amino acid sequence which has at least 70%, 75%, 80%, 85%, 90%, 95%, 99%, or 100% identity to an amino acid sequence selected from the list consisting of SEQ ID NO:2 (GMCSFRα), SEQ ID NO:4 (IG Kappa), SEQ ID NO:6 (Immunoglobulin E), SEQ ID NO:8 (CD8α), SEQ ID NO:10 (TVB2), SEQ ID NO:12 (CD52) or SEQ ID NO:14 (LNFGR).

A polypeptide construct comprising a CD20t polypeptide can comprise any transmembrane domain, including a transmembrane domain that comprises a dimerization domain or does not comprise a dimerization domain. For example, a polypeptide construct comprising a CD20t polypeptide (e.g., a polypeptide which comprises an amino acid sequence selected from the list consisting of SEQ ID NO:218, SEQ ID NO:219 and SEQ ID NO:220) can be fused to a transmembrane domain comprising an amino acid sequence which has at least 70%, 75%, 80%, 85%, 90%, 95%, 99%, or 100% identity to an amino acid sequence selected from the list consisting of SEQ ID NO:26 (glycophorin A E91-R116), SEQ ID NO:28 (glycophorin A I92-I114), SEQ ID NO:30 (glycophorin A (I92-L109).integrin β3 (A737-W741), SEQ ID NO:32 (CD3 zeta chain), SEQ ID NO: 34 (CD8α), SEQ ID NO:36 (CD28), SEQ ID NO:38 (CTLA4) and SEQ ID NO:40 (LNGFR). Polypeptide constructs comprising CD20t can further comprise transmembrane domains derived from or homologous to CD28 and/or CD8α.

A polypeptide construct comprising a CD20t polypeptide can comprise any peptide linker (or in some embodiments no peptide linker). For example, a polypeptide construct comprising a CD20t polypeptide (e.g., a polypeptide which comprises an amino acid sequence selected from the list consisting of SEQ ID NO:218, SEQ ID NO:219 and SEQ ID NO:220) can be fused to a peptide linker comprising an amino acid sequence which has at least 70%, 75%, 80%, 85%, 90%, 95%, 99%, or 100% identity to an amino acid sequence selected from the list consisting of SEQ ID NO:16 (GSG), SEQ ID NO:18 (SGSG), SEQ ID NO:20 ((G4S)3), SEQ ID NO:22 ((G4S)4) and SEQ ID NO:24 (Whitlow).

Another example of a CD polypeptide which can be truncated and incorporated into a cell tag described herein is CD52. CD52 occurs endogenously in humans as a peptide of 12 amino acids linked at its C-terminus to a glycosylphosphatidylinositol (GPI) anchor. In some embodiments, glycophosphatidylinositol (GPI) can be used to anchor the polypeptides described herein to the cell surface.

Provided herein are polypeptide constructs comprising CD52 polypeptides which are truncated for any amino acids, domains or fragments of endogenous CD52. Herein a CD52 polypeptide can comprise a truncated CD52 (CD52t) polypeptide. In some embodiments, a CD52 polypeptide consists of or consists essentially of a cell surface polypeptide comprising a CD52t polypeptide. In other embodiments, a CD52 polypeptide can comprise a cell surface polypeptide comprising a CD52t polypeptide in addition to other CD52 domains (e.g. a CD52 signal peptide).

Herein are provided polypeptide constructs which comprise a cell surface polypeptide comprising a truncated CD52t polypeptide. In some embodiments, a CD52t polypeptide is linked to a CD52 signal peptide for directing the truncated variant to the cell surface. In some embodiments, a cell surface polypeptide comprising a CD52t polypeptide can incorporate one or more epitopes that can be recognized by an exogenously introduced antibody or binding partner. For example, a CD52t polypeptide can incorporate one or more alemtuzumab-binding domains and thereby facilitate targeted depletion of cells expressing a polypeptide construct described herein. In some embodiments, targeted depletion can result from alemtuzumab-mediated CDC and/or ADCC, or another cellular mechanism which mediates the cytotoxic effects of alemtuzumab recognition. Non-limiting examples of anti-CD52 molecules which can recognize a cell surface polypeptide comprising a CD52t polypeptide include alemtuzumab, ANT1034, HI 186(Bio Rad), YTH34.5 (Bio Rad) and YTH66.9HL (Bio-Rad). In various embodiments, the antibody can be a monoclonal antibody, scFv, scFab, diabody, or camelid antibody. In an embodiment, a polynucleotide sequence encoding a CD52 epitope comprises a nucleotide sequence which has at least 70%, 75%, 80%, 85%, 90%, 95%, 99%, or 100% identity to the nucleotide sequence of SEQ ID NO:142. In an embodiment, a CD52 epitope has at least 70%, 75%, 80%, 85%, 90%, 95%, 99%, or 100% identity to the amino acid sequence of SEQ ID NO:143.

A polypeptide construct described herein can have multiple epitopes which can be recognized by an antibody or binding partner. For example, in the case of a CD52t polypeptide, a polypeptide construct comprising a CD52t polypeptide can comprise multiple epitopes specific for a binding partner (e.g., alemtuzumab). In an embodiment, a CD52t polypeptide comprises multiple copies (e.g., at least two copies, at least three copies, at least four copies, at least five copies, at least six copies, or at least ten copies) of the amino acid sequence shown in SEQ ID NO:143. Each copy or repeat of the amino acid sequence can be separated in a polypeptide construct by a linker (e.g., Whitlow linker). In an embodiment, a polypeptide construct comprises a CD52 signal peptide linked to one or more copies of a CD52t polypeptide fused to a Whitlow linker, which is linked (e.g. via one or more copies of a (G4S) linker (SEQ ID NO: 221)) to a transmembrane domain (e.g., CD28 transmembrane domain or a fragment thereof). In an embodiment, a polypeptide construct comprising a CD52t polypeptide is encoded by a polynucleotide which has at least 70%, 75%, 80%, 85%, 90%, 95%, 99%, or 100% identity to a nucleotide sequence selected from the list consisting of SEQ ID NO:144 (CD52t1; encoding one copy of an epitope/linker,), SEQ ID NO:146 (CD52t2; encoding two copies of an epitope/linker), and SEQ ID NO:148 (CD52t3; encoding three copies of an epitope/linker). In an embodiment, a polypeptide comprising a CD52t polypeptide has at least 70%, 75%, 80%, 85%, 90%, 95%, 99%, or 100% identity to an amino acid sequence selected from the list consisting of SEQ ID NO:145 (CD52t1; encoding one copy of an epitope/linker,), SEQ ID NO:147 (CD52t2; encoding two copies of an epitope/linker), and SEQ ID NO:149 (CD52t3; encoding three copies of an epitope/linker)

A polypeptide construct comprising a CD52t polypeptide can comprise any transmembrane domain, including a transmembrane domain that comprises a dimerization domain or does not comprise a dimerization domain. For example, a cell surface polypeptide comprising a CD52t polypeptide can be fused via a linker (e.g. 3×GS linker (SEQ ID NO: 224)) to a transmembrane domain comprising a transmembrane dimerization domain (e.g. derived from or homologous to a transmembrane domain of glycophorin A or glycophorin A-integrin β3). In an embodiment, a polypeptide construct comprising a CD52t polypeptide has at least 70%, 75%, 80%, 85%, 90%, 95%, 99%, or 100% identity to an amino acid sequence selected from the list consisting of SEQ ID NO:150 (CD52t4; CD52 signal peptide, 3×GS peptide linker (SEQ ID NO: 224) and glycophorin A transmembrane domain), SEQ ID NO:151 (CD52t5; CD52 signal peptide, 3×GS peptide linker (SEQ ID NO: 224) and glycophorin A transmembrane domain), and SEQ ID NO: 152 (CD52t6; CD52 signal peptide, 3×GS linker (SEQ ID NO: 224) and glycophorin A-integrin β3 transmembrane domain).

In embodiments, a polypeptide construct comprising a CD52t polypeptide (e.g., SEQ ID NO:143, which can be linked to a CD52 signal peptide to give rise to an amino acid sequence which has at least 70%, 75%, 80%, 85%, 90%, 95%, 99%, or 100% identity to an amino acid sequence selected from the list consisting of SEQ ID NO:145, SEQ ID NO:147, and SEQ ID NO:149) can be linked to a transmembrane domain comprising an amino acid sequence which has at least 70%, 75%, 80%, 85%, 90%, 95%, 99%, or 100% identity to an amino acid sequence selected from the list consisting of SEQ ID NO:26 (glycophorin A E91-R116), SEQ ID NO:28 (glycophorin A I92-I114), SEQ ID NO:30 (glycophorin A(I92-L109).integrin β3 (A737-W741), SEQ ID NO:32 (CD3 zeta chain), SEQ ID NO: 34 (CD8α), SEQ ID NO:36 (CD28), SEQ ID NO:38 (CTLA4) and SEQ ID NO:40 (LNGFR).

A polypeptide construct comprising a CD52t polypeptide can comprise any signal peptide capable of directing the polypeptide construct to the cell surface. In an embodiment, a CD52t polypeptide is linked to a signal peptide of CD52 (e.g., the polypeptide construct comprises an amino acid sequence which has at least 70%, 75%, 80%, 85%, 90%, 95%, 99%, or 100% identity to the amino acid sequence selected from the list consisting of SEQ ID NO:145, SEQ ID NO:147, and SEQ ID NO:149). In some embodiments, a polypeptide construct comprises a CD52t polypeptide (e.g., SEQ ID NO:143) linked to a signal peptide comprising an amino acid sequence which has at least 70%, 75%, 80%, 85%, 90%, 95%, 99%, or 100% identity to an amino acid sequence selected from the list consisting of SEQ ID NO:2 (GMCSFRα), SEQ ID NO:4 (IG Kappa), SEQ ID NO:6 (Immunoglobulin E), SEQ ID NO:8 (CD8), SEQ ID NO:10 (TVB2), SEQ ID NO:12 (CD52) or SEQ ID NO:14 (LNFGR).

A polypeptide construct comprising a CD52t polypeptide can comprise any peptide linker (or in some embodiments no peptide linker). For example, a cell surface polypeptide comprising CD52t (e.g., comprising an amino acid sequence which has at least 70%, 75%, 80%, 85%, 90%, 95%, 99%, or 100% identity to the amino acid sequence of SEQ ID NO:143) can be fused to a peptide linker comprising an amino acid sequence which has at least 70%, 75%, 80%, 85%, 90%, 95%, 99%, or 100% identity to an amino acid sequence selected from the list consisting of SEQ ID NO:16 (GSG), SEQ ID NO:18 (SGSG), SEQ ID NO:20 ((G4S)3), SEQ ID NO:22 ((G4S)4) and SEQ ID NO:24 (Whitlow).

In other embodiments, the cell surface polypeptide can include a truncated version of a polypeptide from the tumor necrosis factor (TNF) receptor superfamily. For example, LNGFR is a single-pass type I transmembrane glycoprotein having an extracellular domain exhibiting a folded structure due in part to disulfide bond formation between cysteine residues of the protein. In an embodiment, a polynucleotide encoding LNGFR or a portion thereof comprises a nucleotide sequence having at least 70%, 75%, 80%, 85%, 90%, 95%, 99%, or 100% identity to a nucleotide sequence selected from the list consisting of SEQ ID NO:153, SEQ ID NO: 155 (encoding K29-N250 of the LNGFR extracellular domain), SEQ ID NO: 157 (encoding E65-N250 including cysteine residues 2,3,4 capable of forming disulfide bonds), and SEQ ID NO: 159 (encoding R108-N250 including cysteine residues 3,4 capable of forming disulfide bonds). In an embodiment, LNGFR has at least 70%, 75%, 80%, 85%, 90%, 95%, 99%, or 100% identity to an amino acid sequence selected from the list consisting of SEQ ID NO:154, SEQ ID NO: 156 (comprising K29-N250 of the LNGFR extracellular domain), SEQ ID NO: 158 (comprising E65-N250 including cysteine residues 2,3,4 capable of forming disulfide bonds), and SEQ ID NO: 160 (comprising R108-N250 including cysteine residues 3,4 capable of forming disulfide bonds).

Provided herein are polypeptide constructs comprising LNGFR polypeptides which are truncated for any amino acids, domains or fragments of endogenous LNGFR. Herein an LNGFR polypeptide can comprise an LNGFRt polypeptide. In some embodiments, an LNGFR polypeptide consists of or consists essentially of a cell surface polypeptide comprising an LNGFRt polypeptide. In other embodiments, an LNGFR polypeptide can comprise a cell surface polypeptide comprising an LNGFRt polypeptide in addition to other LNGFR domains (e.g. an LNGFR transmembrane domain).

A polypeptide construct can comprise a truncated LNGFR (herein LNGFRt) polypeptide with any domain or fragment thereof truncated relative to the wildtype protein. For example, an LNGFRt polypeptide can be truncated for one or more of the transmembrane domain or a portion thereof, the intracellular domain or a portion thereof, or the extracellular domain or a portion thereof. In some embodiments, an LNGFRt polypeptide can be truncated for one or more TNFR-Cys repeats that form a natural binding domain for its ligands (e.g., NGF, BDNF, NTF3 and NTF4). In an embodiment, a polypeptide construct comprises an LNGFRt polypeptide comprising the entire extracellular domain (SEQ ID NO:156). In an embodiment, a polypeptide construct comprising an LNGFRt polypeptide is fused to an LNGFR transmembrane domain. In an embodiment, a polynucleotide encoding an LNGFRt polypeptide linked to an LNGFR transmembrane domain comprises a nucleotide sequence having at least 70%, 75%, 80%, 85%, 90%, 95%, 99%, or 100% identity to the nucleotide sequence of SEQ ID NO:161 (LNGFRt1). In an embodiment, an LNGFRt polypeptide linked to an LNGFR transmembrane domain has at least 70%, 75%, 80%, 85%, 90%, 95%, 99%, or 100% identity to the amino acid sequence of SEQ ID NO:162 (LNGFRt1).

A polypeptide construct comprising an LNGFRt polypeptide can comprise any transmembrane domain, including a transmembrane domain that comprises a dimerization domain or does not comprise a dimerization domain. For example, a polypeptide construct can comprise an LNGFRt polypeptide linked to an LNGFR transmembrane domain or a fragment thereof. In other embodiments, a LNGFRt polypeptide can be fused (e.g., via a linker) to a transmembrane domain or fragment thereof derived from a different polypeptide, including a transmembrane domain capable of dimerization. In an embodiment, a polypeptide construct comprising an LNGFRt polypeptide has at least 70%, 75%, 80%, 85%, 90%, 95%, 99%, or 100% identity to an amino acid sequence selected from the list consisting of SEQ ID NO:163 (LNGFRt2; entire LNGFR extracellular domain; GS linker and CD28 transmembrane domain); SEQ ID NO:164 (LNGFRt3; fragment of LNGFR extracellular domain including cysteine residues 2-4, a GS peptide linker and a CD28 transmembrane domain), SEQ ID NO: 165 (LNGFRt3; fragment of LNGFR extracellular domain including cysteine residues 3-4, a GS peptide linker and a CD28 transmembrane domain); SEQ ID NO:166 (LNGFRt5; fragment of LNGFR extracellular domain including cysteine residues 3-4, GS linker and glycophorin A transmembrane domain), SEQ ID NO: 167 (LNGFRt6; fragment of LNGFR extracellular domain including cysteine residues 3-4, GS linker and glycophorin A transmembrane domain); and SEQ ID NO: 168 (LNGFRt7; fragment of LNGFR extracellular domain comprising cysteine residues 3-4, GS linker and glycophorin A-integrin β3 transmembrane domain).

In some embodiments, a polypeptide construct comprising an LNGFRt polypeptide can be fused to a transmembrane domain comprising an amino acid sequence which has at least 70%, 75%, 80%, 85%, 90%, 95%, 99%, or 100% identity to an amino acid sequence selected from the list consisting of SEQ ID NO:26 (glycophorin A E91-R116), SEQ ID NO:28 (glycophorin A I92-I114), SEQ ID NO:30 (glycophorin A(192-L109).integrin β3 (A737-W741), SEQ ID NO:32 (CD3 zeta chain), SEQ ID NO: 34 (CD8α), SEQ ID NO:36 (CD28), SEQ ID NO:38 (CTLA4) and SEQ ID NO:40 (LNGFR).

A polypeptide construct comprising an LNGFRt polypeptide can comprise any signal peptide capable of directing the polypeptide construct to the cell surface. For example, a cell surface polypeptide comprising an LNGFRt polypeptide can be fused to a signal peptide comprising an amino acid sequence which has at least 70%, 75%, 80%, 85%, 90%, 95%, 99%, or 100% identity to an amino acid sequence selected from the list consisting of SEQ ID NO:2 (GMCSFRα), SEQ ID NO:4 (IG Kappa), SEQ ID NO:6 (Immunoglobulin E), SEQ ID NO:8 (CD8α), SEQ ID NO:10 (TVB2), SEQ ID NO:12 (CD52) or SEQ ID NO:14 (LNFGR).

A polypeptide construct comprising an LNGFRt polypeptide can comprise any peptide linker (or in some embodiments no peptide linker). For example, a cell surface polypeptide comprising an LNGFRt polypeptide can be fused to a peptide linker comprising an amino acid sequence which has at least 70%, 75%, 80%, 85%, 90%, 95%, 99%, or 100% identity to an amino acid sequence selected from the list consisting of SEQ ID NO:16 (GSG), SEQ ID NO:18 (SGSG), SEQ ID NO:20 ((G4S)3), SEQ ID NO:22 ((G4S)4) and SEQ ID NO:24 (Whitlow).

Polynucleotide Constructs
Vector

The polypeptide constructs described herein can be encoded by one or more polynucleotides incorporated into an engineered cell via a vector. Herein an "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors may contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors may be capable of directly expressing nucleic acid sequence products encoded therein without ligation or integration of the vector into host cell DNA sequences.

A vector also can comprise a "selectable marker gene." The term "selectable marker gene," as used herein, refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., Proc. Natl. Acad. Sci. USA, 77: 3567 (1980); O'Hare et al., Proc. Natl. Acad. Sci. USA, 78: 1527 (1981); Mulligan & Berg, Proc. Natl. Acad. Sci. USA, 78: 2072 (1981); Colberre-Garapin et al., J. Mol. Biol., 150:1 (1981); Santerre et al., Gene, 30: 147 (1984); Kent et al., Science, 237: 901-903 (1987); Wigler et al., Cell, 11: 223 (1977); Szybalska & Szybalski, Proc. Natl. Acad. Sci. USA, 48: 2026 (1962); Lowy et al., Cell, 22: 817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Provided herein is a polypeptide construct which can comprise a signal peptide, a transmembrane domain, a cell surface polypeptide comprising a truncated variant of a natural polypeptide, and optionally a peptide linker connecting the transmembrane domain to the cell surface polypeptide. For example, FIG. 4A illustrates an embodiment of a polypeptide construct having cell tag functionality. The truncated variant extends into the extracellular matrix via a peptide linker connecting to the transmembrane domain. The truncated variant can include one or more epitopes for an anti-truncated variant antibody (e.g., exogenously added) which can recognize and bind to the truncated variant/cell tag. In some embodiments, binding of the antibody to the truncated variant can result in cell depletion (e.g., via ADCC), which can be beneficial for example during adoptive cell therapy where the cell has been engineered to express one or more additional molecules such as a cytokine, TCR and/or CAR. In some embodiments, different polypeptide constructs comprise a constant transmembrane domain and signal peptide, but vary in the identity of the truncated variant incorporated into the polypeptide construct. For example, different polypeptide constructs can comprise different truncated variants of the same natural polypeptide.

Where two polypeptide constructs incorporate different truncated variants of the same natural polypeptide, the polypeptide constructs may further differ based on the presence/absence of a peptide linker in the polypeptide construct or the length of the peptide linker. In some embodiments, the peptide linker of each polypeptide construct is sized to maintain a relatively constant distance between the distal end of the particular truncated variant and the cell surface.

Provided herein are polynucleotides and methods for using the polynucleotides to facilitate the construction of polypeptide constructs for use during immunotherapy. In certain embodiments, a polynucleotide can comprise a vector comprising a sequence encoding a signal peptide and a transmembrane domain (e.g. either comprising or lacking a transmembrane dimerization domain). The vector can provide for the cloning of an insert between the signal peptide and the transmembrane domain, such that the insert comprises a nucleotide sequence encoding a particular truncated variant and optionally a peptide linker. Alternatively, vectors can be provided that comprise a polynucleotide encoding a signal peptide, a particular truncated variant and optionally a linker, and provide for the insertion of a nucleotide sequence encoding a transmembrane domain adjacent to the coding sequence for the truncated variant or linker. By providing for a series of vectors that maintain as constant a particular domain or domains in a resultant polypeptide construct, but allow for the swapping in and out of a domain that may be variable between polypeptide constructs, the present disclosure facilitates the production of polypeptide constructs comprising any combination of signal peptide, truncated variant, transmembrane domain and linker.

Vector Modications

A polynucleotide vector useful for the methods and compositions described herein can be a good manufacturing practices (GMP) compatible vector. For example, a GMP vector may be purer than a non-GMP vector. In some cases, purity can be measured by bioburden. For example, bioburden can be the presence or absence of aerobes, anaerobes, sporeformers, fungi, or combinations thereof in a vector composition. In some cases, a pure vector can be endotoxin low or endotoxin free. Purity can also be measured by double-stranded primer-walking sequencing. Plasmid identity can be a source of determining purity of a vector. A GMP vector of the invention can be from 10% to 99% more pure than a non-GMP vector. A GMP vector can be from 10%, 15%, 20%, 25%, 30%, 35%, 40%, 45%, 50%, 55%, 60%, 65%, 70%, 75%, 80%, 85%, 90%, 95%, 96%, 97%, 98%, or 99% more pure than a non-GMP vector as measured by the presence of bioburden, endotoxin, sequencing, or combinations thereof.

In some cases, a terminator sequence at the end of the first gene program is used. A terminator sequence can ensure that a transcript is terminating prior to initiating a second gene program. For example, an expression vectors may contain sequences necessary for the termination of transcription and for stabilizing an mRNA. Such sequences are commonly available from the 5' and, occasionally 3', untranslated regions of eukaryotic or viral DNAs or cDNAs. These regions can contain nucleotide segments transcribed as polyadenylated fragments in the untranslated portion of the mRNA. Cells comprising the expression vector are grown under conditions that provide for expression of the desired polypeptide, either in vivo or in vitro.

In some cases, a spacer sequence can be used at the end of a first polypeptide encoded by a polynucleotide in a vector. In other cases, a spacer sequence can be used at the end of a second gene in a vector. A spacer sequence can also be used following a first gene and a second gene in a vector.

These vectors can be used to express a polypeptide encoded by a gene, or portion of a gene of interest. A gene of portion or a gene can be inserted by using any method, viral or non-viral. For example; a method can be a non-viral based technique.

Additional Features Encoded by Constructs

The polynucleotides disclosed herein can encode one or more proteins in addition to or alongside the polynucleotide constructs described above. For example, in some embodiments the polypeptide constructs can be linked to a chimeric antigen receptor (CAR), a T-cell receptor (TCR) and/or a cytokine.

Chimeric Receptors

Some embodiments described herein include a polynucleotide which encodes a chimeric receptor expressed on the surface of the cell. In some instances, the chimeric receptor comprises an antigen binding region that enables recognition and binding to an antigen, for instance, a tumor antigen such as a tumor-associated antigen or a tumor-specific antigen. In some instances, the antigen binding region comprises an antibody or binding fragment, for example, an Fab, an Fab', an F(ab')2, an F(ab')3, an scFv, an sc(Fv)2, a dsFv, a diabody, a minibody, and a nanobody or binding fragments thereof. In some cases, the antigen binding region comprises an scFv. In some cases, the chimeric receptor comprises an scFv (e.g., a chimeric antigen receptor (CAR)). In some instances, the chimeric antigen receptor comprises a pattern-recognition receptor. In other cases, the chimeric receptor comprises an engineered T-cell receptor (TCR).

Chimeric Antigen Receptors (CARs)

In some embodiments, a cell expressing a polypeptide construct described herein also expresses one or more chimeric antigen receptors (CARs).

A chimeric antigen receptor (CAR) as described herein, is an engineered receptor which grafts an exogenous specificity onto an immune effector cell. In some instances, a CAR comprises an extracellular domain (ectodomain) that comprises an antigen binding domain, a stalk region, a transmembrane domain and an intracellular (endodomain) domain. In some instances, the intracellular domain further comprises one or more intracellular signaling domains. In some instances, a CAR described herein comprises an antigen binding domain, a stalk region, a transmembrane domain, one or more costimulatory domains, and a signaling domain for T-cell activation.

In embodiments, the CAR of the present disclosure comprises a target-specific binding element otherwise referred to as an antigen-binding moiety. In embodiments, the CAR of the present disclosure is engineered to target a tumor antigen of interest by way of engineering a desired antigen-binding moiety that specifically binds to a predetermined antigen on a tumor cell. In the context of the present disclosure, “tumor antigen” or “hyperproliferative disorder antigen” or “antigen associated with a hyperproliferative disorder,” refers to antigens that are common to specific hyperproliferative disorders such as cancer.

An antigen binding domain can comprise complementary determining regions of a monoclonal antibody, variable regions of a monoclonal antibody, and/or antigen binding fragments thereof. A complementarity determining region (CDR) is a short amino acid sequence found in the variable domains of antigen receptor (e.g., immunoglobulin and T-cell receptor) proteins that assumes a structure that complements the structure of an antigen and therefore provides the receptor with its specificity for that particular antigen. Each polypeptide chain of an antigen receptor can contain three CDRs (CDR1, CDR2, and CDR3). In some instances, an antigen binding domain comprises F(ab')2, Fab', Fab, Fv, or scFv. In some cases, an antigen binding domain is a scFv. In some cases, an antigen binding domain is a Fab. In some cases, an antigen binding domain is a Fab'. In some cases, an antigen binding domain is F(ab')2. In some cases, an antigen binding domain is a Fv.

In some embodiments, a CAR described herein comprises an antigen binding domain that binds to an epitope on CD19, CD20, CD33, CD44, BCMA, CD123, EGFRvIII, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72 or VEGF-R2. In some embodiments, a CAR described herein comprises an antigen binding domain that binds to an epitope on CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72, EGFRvIII, CD123 and VEGF-R2. In some embodiments, a CAR described herein comprises an antigen binding domain that binds to an epitope on CD19 or CD33. In some instances, a CAR described herein comprises an antigen binding domain that binds to an epitope on CD19. In some cases, a CAR described herein comprises an antigen binding domain that binds to an epitope on CD33. In further embodiments, a CAR or a chimeric receptor or antigen binding polypeptide described herein comprises an autoantigen or an antigen binding region that binds to an epitope on HLA-A2, myelin oligodendrocyte glycoprotein (MOG), factor VIII (FVIII), MAdCAM1, SDF1, or collagen type II.

In some embodiments, the polynucleotides, polypeptides and methods described herein can be used for the treatment of a hyperproliferative disease, such as a cancer, an autoimmune disease or for the treatment of an infection, such as a viral, bacterial or parasitic infection. In some aspects, the antigen is an antigen that is elevated in cancer cells, in autoimmune cells or in cells that are infected by a virus, bacteria or parasite. Pathogens that may be targeted include, without limitation, *Plasmodium*, trypanosome, *Aspergillus, Candida*, Hepatitis A, Hepatitis B, Hepatitis C, HSV, HPV, RSV, EBV, CMV, JC virus, BK virus, or Ebola pathogens. Autoimmune diseases can include graft-versus-host disease, rheumatoid arthritis, lupus, celiac disease, Crohn's disease, Sjogren Syndrome, polymyalgia rheumatic, multiple sclerosis, neuromyelitis optica, ankylosing spondylitis, Type 1 diabetes, alopecia areata, vasculitis, temporal arteritis, bullous pemphigoid, psoriasis, pemphigus vulgaris, or autoimmune uveitis.

The pathogen recognized by a CAR may be essentially any kind of pathogen, but in some embodiments the pathogen is a fungus, bacteria, or virus. Exemplary viral pathogens include those of the families of Adenoviridae, Epstein-Barr virus (EBV), Cytomegalovirus (CMV), Respiratory Syncytial Virus (RSV), JC virus, BK virus, HPV, HSV, HHV family of viruses, Hepatitis family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and Stachybotrys. Exemplary pathogenic bacteria include *Streptococcus, Pseudomonas, Shigella, Campylobacter, Staphylococcus, Helicobacter, E. coli, Rickettsia, Bacillus, Bordetella, Chlamydia*, Spirochetes, and *Salmonella*. In some embodiments the pathogen receptor Dectin-1 may be used to generate a CAR that recognizes the carbohydrate structure on the cell wall of fungi such as *Aspergillus*. In another embodiment, CARs can be made based on an antibody recognizing viral determinants (e.g., the glycoproteins from CMV and Ebola) to interrupt viral infections and pathology.

In some embodiments, a "stalk" region, or a "spacer" or "hinge" region, is used to link the antigen-binding domain to the transmembrane domain. In some instances, a "stalk domain" or "stalk region" comprise any oligonucleotide- or polypeptide that functions to link the transmembrane domain to, either the extracellular domain or, the cytoplasmic domain in the polypeptide chain. In some embodiments, it is flexible enough to allow the antigen-binding domain to orient in different directions to facilitate antigen recognition. In some instances, the stalk region comprises the hinge region from IgG1. In alternative instances, the stalk region comprises the CH2CH3 region of immunoglobulin and optionally portions of CD3. In some cases, the stalk region comprises a CD8a hinge region, an IgG4-Fc 12 amino acid hinge region (ESKYGPPCPPCP (SEQ ID NO: 225)) or IgG4 hinge regions as described in WO/2016/073755.

The transmembrane domain can be derived from either a natural or a synthetic source. Where the source is natural, the domain can be derived from any membrane-bound or transmembrane protein. Suitable transmembrane domains can include the transmembrane region(s) of alpha, beta or zeta chain of the T-cell receptor, or a transmembrane region from CD28, CD3 epsilon, CD3ζ, CD45, CD4, CD5, CD8α, CD9, CD16, CD22, CD33, CD37, CD64, CD80, CD86, CD134, CD137 or CD154. Alternatively the transmembrane domain can be synthetic, and can comprise hydrophobic residues such as leucine and valine. In some embodiments, a triplet of phenylalanine, tryptophan and valine is found at one or both termini of a synthetic transmembrane domain. Optionally, a short oligonucleotide or polypeptide linker, in some embodiments, between 2 and 10 amino acids in length may form the linkage between the transmembrane domain and the cytoplasmic signaling domain of a CAR. In some embodiments, the linker is a glycine-serine linker. In some embodiments, the transmembrane domain comprises a CD8a transmembrane domain or a CD3ζtransmembrane domain. In some embodiments, the transmembrane domain comprises a CD8a transmembrane domain. In other embodiments, the transmembrane domain comprises a CD3ζtransmembrane domain. In still other embodiments, the transmembrane domain comprises a transmembrane dimerization domain.

The intracellular domain can comprise one or more costimulatory domains. Exemplary costimulatory domains include, but are not limited to, CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD27, CD28, 4-1BB (CD137), ICOS, OX40 (CD134) or fragment or combination thereof. In some instances, a CAR described herein comprises one or more, or two or more of costimulatory domains selected from CD8, CD28, 4-1BB (CD137), or fragment or combination thereof. In some instances, a CAR described herein comprises one or more, or two or more of costimulatory domains selected from CD28, 4-1BB (CD137), or fragment or combination thereof. In some instances, a CAR described herein comprises costimulatory domains CD28 and 4-1BB (CD137) or their respective fragments thereof. In some instances, a CAR described herein comprises costimulatory domains CD28 and OX40 (CD134) or their respective fragments thereof. In some instances, a CAR described herein comprises costimulatory domains CD8 and CD28 or their respective fragments thereof. In some instances, a CAR described herein comprises costimulatory domains CD28 or a fragment thereof. In some instances, a CAR described herein comprises costimulatory domains 4-1BB (CD137) or a fragment thereof. In some instances, a CAR described herein comprises costimulatory domains OX40 (CD134) or a fragment thereof. In some instances, a CAR described herein comprises costimulatory domains CD8 or a fragment thereof.

The intracellular signaling domain, also known as cytoplasmic domain, of the CAR of the present disclosure, is responsible for activation of at least one of the normal effector functions of the immune cell in which the CAR has been placed. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal. In some embodiments, the intracellular domain further comprises a signaling domain for T-cell activation. In some instances, the signaling domain for T-cell activation comprises a domain derived from TCR zeta, FcR gamma, FcR beta, CD3 gamma, CD3 delta, CD3 epsilon, CD5, CD22, CD79a, CD79b or CD66d. In some cases, the signaling domain for T-cell activation comprises a domain derived from CD3ζ.

The term "functional portion," when used in reference to a CAR, refers to any part or fragment of the CAR of the present disclosure, which part or fragment retains the biological activity of the CAR of which it is a part (the parent CAR). In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

The term "functional variant," as used herein, refers to a polypeptide, or a protein having substantial or significant sequence identity or similarity to the reference polypeptide, and retains the biological activity of the reference polypeptide of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 80% identical, about 90% identical, about 95% identical, or about 99% identical to the nucleic acid sequence encoding the parent CAR.

The polynucleotide constructs disclosed herein can be co-expressed in an engineered cell with a CAR. In some embodiments, a polypeptide construct and CAR can be encoded by a single transcript. An advantage of encoding a polypeptide construct comprising a truncated variant and a CAR in the same transcript is that an engineered cell manufacturing the CAR protein is also likely to have also manufactured the polypeptide construct. Accordingly, where intervention is required during immunotherapy to diminish CAR expression (e.g., to mitigate side effects of therapy), an engineered cell co-expressing the polypeptide constructs with the CAR can be primed to respond in a relatively short time frame to the administration of exogenous antibodies that target the cell tags conferred by the truncated variants disclosed herein.

CD19-Specific CARs

CD19 is a cell surface glycoprotein of the immunoglobulin superfamily. In some instances, CD19 has been detected in solid tumors such as pancreatic cancer, liver cancer, and prostate cancer.

In some embodiments, the antigen binding moiety of a CAR described herein, is specific to CD19. A CD19-specific CAR, when expressed on the cell surface, may redirect the specificity of T cells to human CD19. In embodiments, the antigen binding domain comprises a single chain antibody fragment (scFv) comprising a variable domain light chain (VL) and variable domain heavy chain (VH) of a target antigen specific monoclonal anti-CD19 antibody joined by a flexible linker, such as a glycine-serine linker or a Whitlow linker. In embodiments, the scFv are SJ25C1 and/or FMC63. In embodiments, the scFv is humanized. In some embodiments, the antigen binding moiety may comprise VH and VL that are directionally linked, for example, from N to C terminus, VH-linker-VL or VL-linker-VH.

In some embodiments, described herein include a CD19-specific CAR, in which the antigen binding domain comprises a scFv that binds CD19. In some instances, the antigen binding domain recognizes an epitope on CD19.

In some embodiments, the antigen binding domain recognizes an epitope on CD19 that is also recognized by JCAR014, JCAR015, JCAR017, or 19-28z CAR (Juno Therapeutics). In some embodiments, described herein include a CD19-specific CAR-T cell, in which the antigen binding domain recognizes an epitope on CD19 that is also recognized by JCAR014, JCAR015, JCAR017, or 19-28z CAR (Juno Therapeutics). In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by JCAR014, JCAR015, JCAR017, or 19-28z CAR (Juno Therapeutics). In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, a CD19-specific CAR-T cell described herein comprises an anti-CD19 antibody described in US20160152723.

In some embodiments, the antigen binding domain recognizes an epitope on CD19 that is also recognized by KTE-C19 (Kite Pharma, Inc.). In some embodiments, described herein include a CD19-specific CAR-T cell, in which the antigen binding domain recognizes an epitope on CD19 that is also recognized by KTE-C19. In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by KTE-C19. In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, a CD19-specific CAR-T cell described herein comprises an anti-CD19 antibody described in WO2015187528 or fragment or derivative thereof.

In some embodiments, the antigen binding domain recognizes an epitope on CD19 that is also recognized by CTL019 (Novartis). In some embodiments, described herein include a CD19-specific CAR-T cell, in which the antigen binding domain recognizes an epitope on CD19 that is also recognized by CTL019. In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by CTL019. In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ. In some embodiments, the antigen binding domain recognizes an epitope on CD19 that is also recognized by UCART19 (Cellectis). In some embodiments, described herein include a CD19-specific CAR-T cell, in which the antigen binding domain recognizes an epitope on CD19 that is also recognized by UCART19. In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by UCART19. In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, the antigen binding domain recognizes an epitope on CD19 that is also recognized by BPX-401 (Bellicum). In some embodiments, described herein include a CD19-specific CAR-T cell, in which the antigen binding domain recognizes an epitope on CD19 that is also recognized by BPX-401. In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by BPX-401. In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some cases, the antigen binding domain recognizes an epitope on CD19 that is also recognized by blinatumomab (Amgen), coltuximabravtansine (ImmunoGen Inc/Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed). In some instances, the CD19-specific CAR further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

Some embodiments described herein include a CD19-specific CAR-T cell, in which the antigen binding domain comprises a F(ab')2, Fab', Fab, Fv, or scFv. In some instances, the antigen binding domain recognizes an epitope on CD19. In some cases, the antigen binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed). In some instances, the CD19-specific CAR-T cell further comprises a transmembrane domain selected from a CD8a transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some cases, a CD19-specific CAR-T cell described herein comprise a scFv antigen binding domain, and the antigen binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed). In some instances, the CD19-specific CAR-T cell further comprises a transmembrane domain selected from a CD8alpha transmembrane domain or a CD3ζtransmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In an embodiment, a polynucleotide encoding a CAR comprises a nucleotide sequence which has at least 70%, 75%, 80%, 85%, 90%, 95%, 99%, or 100% identity to a nucleotide sequence selected from the list consisting of SEQ ID NO:169 (encoding CD19-CD3ζCAR), SEQ ID NO: 171 (encoding CD19-CD137-CD3ζCAR), SEQ ID NO: 173 (encoding CD19-CD28-CD3ζCAR), and SEQ ID NO:175 (encoding CD19-CD28-CDI CAR further comprising an IgG4 Fc spacer). In an embodiment, an amino acid sequence comprising a CAR has at least 70%, 75%, 80%, 85%, 90%, 95%, 99%, or 100% identity to an amino acid sequence selected from the list consisting of SEQ ID NO:170 (CD19-CD3ζCAR), SEQ ID NO: 172 (CD19-CD137-CD3ζCAR), SEQ ID NO: 174 (CD19-CD28-CD3ζCAR), and SEQ ID NO:176 (CD19-CD28-CD3ζCAR further comprising an IgG4 Fc spacer).

In some embodiments, a polynucleotide disclosed herein can comprise a codon-optimized cDNA sequence encoding an anti-CD19 CAR and a cleavable T2A linker connecting to a cell surface polypeptide (e.g. HER1t). For example a cytotoxic T lymphocyte can be engineered to express a CD19-specific chimeric antigen receptor (CAR) that signals via a cytoplasmic costimulatory (CD28) domain fused to the cytoplasmic CD3-ζ domain. This polypeptide can further incorporate a C-terminal 2A cleavable linker followed by for example an extracellular cell tag comprising, in some embodiments, truncated human HER1 (HER1t), truncated CD20 (CD20t), truncated CD52 (CD52t), or truncated LNGFR (LNGFRt). In other embodiments, a polypeptide can comprise a polypeptide construct comprising a truncated variant preceding a CD19-specific CAR (e.g. via a P2A cleavable linker).

The present disclosure provides for polynucleotides and polypeptides encoding a CAR and any polypeptide construct described herein. In an embodiment, a polypeptide construct incorporating an anti-CD19 CAR, cleavable T2A linker and cell surface polypeptide is encoded by a polynucleotide comprising a nucleotide sequence having at least 70%, 75%, 80%, 85%, 90%, 95%, 99%, or 100% identity to a nucleotide sequence selected from the list consisting of SEQ ID NO:181 (CD19-CD28-CD3ζCAR.P2A.Ig Kappa signal peptide.HER1t1 from SEQ ID NO: 56) and SEQ ID NO:185 (CD19-CD137-CD3ζCAR.E2A.Ig Kappa signal peptide.HER1t7 from SEQ ID NO:68).

In an embodiment, a polypeptide construct incorporating an anti-CD19 CAR, cleavable T2Alinker and cell surface polypeptide has at least 70%, 75%, 80%, 85%, 90%, 95%, 99%, or 100% identity to an amino acid sequence selected from the list consisting of SEQ ID NO:179 (CD19-CD137-CD3ζCAR.T2A.Ig Kappa signal peptide.HER1t from SEQ ID NO:55), SEQ ID NO:180 (CD19-CD137-CD3ζCAR.T2A.Ig Kappa signal peptide.HER1t from SEQ ID NO:55), SEQ ID NO:182 (CD19-CD28-CD3ζCAR.P2A.Ig Kappa signal peptide.HER1t1 from SEQ ID NO: 57), SEQ ID NO:183 (Ig Kappa signal peptide.HER1t1.P2A.CD8a signal peptide.CD19-CD28-CD3ζCAR, where the HER1t1 is from SEQ ID NO:57), SEQ ID NO:184 (CD19-CD28-CD3ζCAR.Furin-T2A.Ig Kappa signal peptide.HER1t1 from SEQ ID NO:57), SEQ ID NO:186 (CD19-CD137-CD3ζCAR.E2A.Ig Kappa signal peptide.HER1t7 from SEQ ID NO:69), SEQ ID NO:187 (CD19-CD28-CD3ζCAR.Furin-T2A.Ig Kappa signal peptide.HER1t8 from SEQ ID NO:73), SEQ ID NO:188 (CD19-CD137-CD3ζ CAR.E2A.Ig Kappa signal peptide.HER1t8 from SEQ ID NO:73), SEQ ID NO:189 (CD19-CD28-CD3ζCAR.Furin-T2A.Ig Kappa signal peptide.HER1t9 from SEQ ID NO:77), SEQ ID NO:190 (CD19-CD137-CD3ζCAR.E2A.Ig Kappa signal peptide.HER1t9 from SEQ ID NO:77), SEQ ID NO:191 (CD19-CD28-CD3ζCAR.Furin-T2A.Ig Kappa signal peptide.HER1t10 from SEQ ID NO:81), SEQ ID NO:192 (CD19-CD137-CD3ζCAR.E2A.Ig Kappa signal peptide.HER1t10 from SEQ ID NO:81), SEQ ID NO:194 (CD19-CD28-CD3ζCAR.P2A.CD20), SEQ ID NO:195 (CD19-CD28-CD3ζCAR.P2A.CD20t1 from SEQ ID NO:109), SEQ ID NO:196 (CD19-CD28-CD3ζCAR.P2A.CD20t4 from SEQ ID NO:115), SEQ ID NO:197 (CD52t3.P2A.CD8a signal peptide.CD19-CD28-CD3ζCAR, where CD52t3 is from SEQ ID NO:149), and SEQ ID NO:198 (Ig Kappa signal peptide.LNGFRt4.P2A.CD8a signal peptide.CD19-CD28-CD3ζCAR, where LNGFRt4 is from SEQ ID NO:165).

Engineered T-cell Receptor (TCR)

In some embodiments, the chimeric receptor encoded by a polynucleotide described herein, comprises an engineered T-cell receptor. The T cell receptor (TCR) is composed of two chains (αβ or γδ) that pair on the surface of the T cell to form a heterodimeric receptor. In some instances, the αβ TCR is expressed on most T cells in the body and is known to be involved in the recognition of specific MHC-restricted antigens. Each α and β chain are composed of two domains: a constant domain (C) which anchors the protein to the cell membrane and is associated with invariant subunits of the CD3 signaling apparatus; and a variable domain (V) that confers antigen recognition through six loops, referred to as complementarity determining regions (CDRs). In some instances, each of the V domains comprises three CDRs; e.g., CDR1, CDR2 and CDR3 with CDR3 as the hypervariable region. These CDRs interact with a complex formed between an antigenic peptide bound to a protein encoded by the major histocompatibility complex (pepMHC) (e.g., HLA-A, HLA-B, HLA-C, HLA-DPAI, HLA-DPB1, HLA-DQAI, HLA-DQB1, HLA-DRA, or HLA-DRB1 complex). In some instances, the constant domain further comprises a joining region that connects the constant domain to the variable domain. In some cases, the beta chain further comprises a short diversity region which makes up part of the joining region.

In some cases, such TCR are reactive to specific tumor antigen, e.g. NY-ESO, Mage A3, Titin. In other cases, such TCR are reactive to specific neoantigens expressed within a patient's tumor (i.e. patient-specific, somatic, non-synonymous mutations expressed by tumors). In some cases, engineered TCRs can be affinity-enhanced.

In some embodiments, a TCR is described using the International Immunogenetics (IMGT) TCR nomenclature, and links to the IMGT public database of TCR sequences. For example, there can be several types of alpha chain variable (Vα) regions and several types of beta chain variable (Vβ) regions distinguished by their framework, CDR1, CDR2, and CDR3 sequences. As such, a Vα type can be referred to in IMGT nomenclature by a unique TRAV number. For example, "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. Similarly, "TRBV5-I" defines a TCR Vβ region having unique framework and CDR1 and CDR2 sequences, but with only a partly defined CDR3 sequence.

In some cases, the beta chain diversity region is referred to in IMGT nomenclature by the abbreviation TRBD.

In some instances, the unique sequences defined by the IMGT nomenclature are widely known and accessible to those working in the TCR field. For example, they can be found in the IMGT public database and in "T cell Receptor Factsbook", (2001) LeFranc and LeFranc, Academic Press, ISBN 0-12-441352-8.

In some embodiments, an ap heterodimeric TCR is, for example, transfected as full length chains having both cytoplasmic and transmembrane domains. In some cases, the TCRs contain an introduced disulfide bond between residues of the respective constant domains, as described, for example, in WO 2006/000830.

In some instances, TCRs described herein are in single chain format, for example see WO 2004/033685. Single chain formats include αβ TCR polypeptides of the Vα-L-Vβ, Vβ-L-Vα, Vα-Cα-L-Vβ, Vα-L-Vβ-Cβ, Vα-Cα-L-Vβ-Cβ types, wherein Vα and Vβ are TCR α and β variable regions respectively, Cα and Cβ are TCR α and β constant regions respectively, and L is a linker sequence. In certain embodiments single chain TCRs of the present disclosure may have an introduced disulfide bond between residues of the respective constant domains, as described in WO 2004/033685.

The TCR described herein may be associated with a detectable label, a therapeutic agent or a PK modifying moiety.

Exemplary detectable labels for diagnostic purposes include, but are not limited to, fluorescent labels, radiolabels, enzymes, nucleic acid probes and contrast reagents.

The present disclosure provides for polynucleotides and polypeptides encoding a TCR and any polypeptide construct described herein. In some embodiments, a polynucleotide disclosed herein can comprise a codon-optimized cDNA sequence encoding a TCR and a cleavable T2A linker connecting to a cell surface polypeptide (e.g. HER 1t). For example a cytotoxic T lymphocyte can be engineered to express a TCR polypeptide that further incorporates a C-terminal 2A cleavable linker followed by for example an extracellular cell tag comprising, in some embodiments, truncated human HER1 (HER1t), truncated CD20 (CD20t), truncated CD52 (CD52t), or truncated LNGFR (LNGFRt). In other embodiments, a polypeptide can comprise a polypeptide construct comprising a truncated variant preceding a TCR (e.g. linked via a P2A cleavable linker).

Cytokines

Provided herein are polynucleotides encoding polypeptide cell tags and a cytokine, or variant or derivative thereof, and methods and systems incorporating the same. Cytokine is a category of small proteins between about 5-20 kDa that are involved in cell signaling. In some embodiments, the cytokines can be membrane bound or secreted. In other embodiments, the cytokines can be intracellular. In some instances, cytokines include chemokines, interferons, interleukins, colony-stimulating factors or tumor necrosis factors. In some embodiments, chemokines play a role as a chemoattractant to guide the migration of cells, and is classified into four subfamilies: CXC, CC, CX3C, and XC. Non-limiting exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17; the XC subfamily: XCL1 and XCL2; and the CX3C subfamily CX3CL1.

Interferons (IFNs) comprise interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes including IFNA1, IFNA2, IFNA4, IFNA5, IFNA6, IFNA7, IFNA8, IFNA10, IFNA13, IFNA14, IFNA16, IFNA17, and IFNA21.

Interleukins are expressed by leukocytes or white blood cells and they promote the development and differentiation of T and B lymphocytes and hematopoietic cells. Exemplary interleukines include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36.

In some embodiments, an interleukin comprises mbIL-15. In some embodiments, a mbIL-15 is a membrane-bound chimeric IL-15 which can be co-expressed with a modified effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rαthrough a linker. In some instances, the mbIL-15 is as described in Hurton et al., "Tethered IL-15 augments antitumor activity and promotes a stem-cell memory subset in tumor-specific T cells," PNAS 2016. In an embodiment, mbIL-15 is encoded by a polynucleotide comprising a nucleotide sequence having at least 70%, 75%, 80%, 85%, 90%, 95%, 99%, or 100% identity to the nucleotide sequence of SEQ ID NO:177. In an embodiment, mbIL-15 has at least 70%, 75%, 80%, 85%, 90%, 95%, 99%, or 100% identity to the amino acid sequence of SEQ ID NO:178.

In another aspect, the interleukin can comprise IL-12. In some embodiments, the IL-12 is a single chain IL-12 (scIL-12), protease sensitive IL-12, destabilized IL-12, membrane bound IL-12, intercalated IL-12. In some instances, the IL-12 variants are as described in WO2015/095249, WO2016/048903, WO2017/062953, all of which is incorporated by reference in their entireties.

Tumor necrosis factors (TNFs) are a group of cytokines that modulate apoptosis. In some instances, there are about 19 members within the TNF family, including, not limited to, TNFα, lymphotoxin-alpha (LT-alpha), lymphotoxin-beta (LT-beta), T cell antigen gp39 (CD40L), CD27L, CD30L, FASL, 4-1BBL, OX40L, and TNF-related apoptosis inducing ligand (TRAIL).

Colony-stimulating factors (CSFs) are secreted glycoproteins that interact with receptor proteins on the surface of hemopoietic stem cells, which subsequently modulates cell proliferation and differentiation into specific kind of blood cells. In some instances, a CSF comprises macrophage colony-stimulating factor, granulocyte macrophage colony-stimulating factor (GM-CSF), granulocyte colony-stimulating factor (G-CSF) or promegapoietin.

In some embodiments, the cytokine is a membrane-bound cytokine, which is co-expressed with a chimeric antigen receptor and/or a TCR described herein.

In some embodiments, one or more methods described herein further comprise administration of a cytokine. In some instances, the cytokine comprises a chemokine, an interferon, an interleukin, a colony-stimulating factor or a tumor necrosis factor. In some instances, one or more methods described herein further comprise administration of a cytokine selected from a chemokine, an interferon, an interleukin, a colony-stimulating factor or a tumor necrosis factor. In some instances, one or more methods described herein further comprise administration of a cytokine selected from IL2, IL7, IL12, IL15, IL21, IFNγ or TNF-α.

In some embodiments, a polynucleotide disclosed herein can comprise a codon-optimized cDNA sequence encoding a cytokine and a cleavable T2A linker connecting to a cell surface polypeptide (e.g. HER1t). For example a cytotoxic T lymphocyte can be engineered to express a polypeptide comprising a cytokine and further incorporating a 2A cleavable linker followed by for example an extracellular cell tag comprising, in some embodiments, truncated human HER 1 (HER1t), truncated CD20 (CD20t), truncated CD52 (CD52t), or truncated LNGFR (LNGFRt). In other embodiments, a polypeptide can comprise a polypeptide construct comprising a truncated variant preceding a cytokine (e.g. linked via a P2A cleavable linker).

The present disclosure provides for polynucleotides and polypeptides encoding a cytokine and any polypeptide construct described herein. In an embodiment, a polypeptide construct incorporating a cytokine, cleavable T2A linker and cell surface polypeptide is has at least 70%, 75%, 80%, 85%, 90%, 95%, 99%, or 100% identity to the amino acid sequence of SEQ ID NO:193 (membrane bound IL-15T2A.HER1t1 from SEQ ID NO:57).

IRES and Linkers

Also disclosed are constructs comprising linkers and IRES elements to facilitate the expression and functionality of the polynucleotides and polypeptides described herein.

IRES Element

The term "internal ribosome entry site (IRES)" as used herein can be intended to mean internal ribosomal entry site. In a vector comprising an IRES sequence, a first gene can be translated by a cap-dependent, ribosome scanning, mechanism with its own 5'-UTR, whereas translation of a subsequent gene can be accomplished by direct recruitment of a ribosome to an IRES in a cap-independent manner. An IRES sequence can allow eukaryotic ribosomes to bind and begin translation without binding to a 5' capped end. An IRES sequence can allow expression of multiple genes from one transcript (Mountford and Smith 1995).

The term "CAP" or "cap" as used herein refers to a modified nucleotide, generally a 7-methyl guanosine, linked 3' to 5' (7meG-ppp-G), to the 5' end of a eukaryotic mRNA, that serves as a required element in the normal translation initiation pathway during expression of protein from that mRNA.

In certain cases, an IRES region can be derived from a virus, such as picornavirus, encephalomyocarditis virus, hepatitis C virus IRES sequence. In other cases, an IRES sequence can be derived from an encephalomyocarditis virus. The term "EMCV" or "encephalomyocarditis virus" as used herein refers to any member isolate or strain of the encephalomyocarditis virus species of the genus of the family Picornaviridae. Examples are: EMCV-R (Rueckert) strain virus, Columbia-SK virus. In some cases, a cellular IRES element, such as eukaryotic initiation factor 4G, immunoglobulin heavy chain binding protein, c-myc proto-oncogene, vascular endothelial growth factor, fibroblast growth factor-1 IRES, or any combination or modification thereof can be used. In some cases, a cellular IRES can have increased gene expression when compared to a viral IRES.

An IRES sequence of viral, cellular or a combination thereof can be utilized in a vector. An IRES can be from encephalomyocarditis (EMCV) or poliovirus (PV). In some cases, an IRES element is selected from a group consisting of Poliovirus (PV), Encephalomyelitis virus (EMCV), Foot-and-mouth disease virus (FMDV), Porcine teschovirus-1 (PTV-1), Aichivirus (AiV), Seneca Valley virus (SVV), Hepatitis C virus (HCV), Classical swine fever virus (CSFV), Human immunodeficiency virus-2 (HIV-2), Human immunodeficiency virus-1 (HIV-1), Moloney murine leukemia virus (MoMLV), Feline immunodeficiency virus (FIV), Mouse mammary tumor virus (MMTV), Human cytomegalovirus latency (pUL138), Epstein-Barr virus (EBNA-1), Herpes virus Marek's disease (MDV RLORF9), SV40 polycistronic 19S (SV40 19S), *Rhopalosiphum padi* virus (RhPV), Cricket paralysis virus (CrPV), Ectropis obliqua picorna-like virus (EoPV), *Plautia stali* intestine virus (PSIV), *Triatoma* virus (TrV), Bee paralysis dicistrovirus (IAPV, KBV), Black currant reversion virus (BRV), *Pelargonium* flower break virus (PFBV), Hibiscus chlorotic ringspot virus (HCRSV), Crucifer-infecting tobamovirus (CrTMV), Potato leaf roll polerovirus (PLRV), Tobacco etch virus (TEV), Giardiavirus (GLV), *Leishmania* RNA virus-1 (LRV-1), and combinations or modifications thereof. In some cases, an IRES is selected from a group consisting of Apaf-1, XIAP, HIAP2/c-IAP1, DAP5, Bcl-2, c-myc, CAT-1, INR, Differentiation LEF-1, PDGF2, HIF-1a, VEGF, FGF2, BiP, BAG-1, CIRP, p53, SHMT1, PITSLREp58, CDK1, Rpr, hid, hsp70, grim, skl, Antennapedia, dFoxO, dInR, Adh-Adhr, HSP101, ADH, URE-2, GPR1, NCE102, YMR181a, MSN1, BOIl, FLO8, GIC1, and any combination or modification thereof.

In certain embodiments, a IRES is an EMCV IRES comprising a nucleotide sequence having at least 70%, 75%, 80%, 85%, 90%, 95%, 99%, 99.5% or 100% identity with the nucleotide sequence of SEQ ID NO:49.

When an IRES element is included between two open reading frames (ORFs), initiation of translation can occur by a canonical 5'-m7GpppN cap-dependent mechanism in a first ORF and a cap-independent mechanism in a second ORF downstream of the IRES element.

In some cases, genes can be linked by an internal ribosomal entry site (IRES). An IRES can allow simultaneous expression of multiple genes. For example, an IRES sequence can permit production of multiple proteins from a single mRNA transcript. A ribosomes can bind to an IRES in a 5'-cap independent manner and initiate translation.

In some cases, an IRES sequence can be or can be about 500 base pairs. An IRES sequence can be from 300 base pairs to 1000 base pairs. For example, an IRES can be 300, 350, 400, 450, 500, 550, 600, 650, 700, 750, 800, 850, 900, 950, or 1000 base pairs long.

In some cases, expression of a downstream gene within a vector comprising an IRES sequence can be reduced. For example, a gene following an IRES sequence can have reduced expression over a gene preceding an IRES sequence. Reduced expression can be from 1% to 99% reduction over a preceding gene.

Linkers

In some embodiments, a polynucleotide linker can be utilized in a polynucleotide described herein. A polynucleotide linker can be a double-stranded segment of DNA containing desired restriction sites that may be added to create end structures that are compatible with a vector comprising a polynucleotide described herein. In some cases, a polynucleotide linker can be useful for modifying vectors comprising polynucleotides described herein. For example, a vector modification comprising a polynucleotide linker can be a change in a multiple cloning site, or the addition of a poly-histidine tail. Polynucleotide linkers can also be used to adapt the ends of blunt insert DNA for cloning into a vector cleaved with a restriction enzyme with cohesive end termini. The use of polynucleotide linkers can be more efficient than a blunt ligation into a vector and can provide a method of releasing an insert from a vector in downstream applications. In some cases an insert can be a polynucleotide sequence encoding polypeptides useful for therapeutic applications.

A polynucleotide linker can be an oligomer. A polynucleotide linker can be a DNA double strand, single strand, or a combination thereof. In some cases, a linker can be RNA. A polynucleotide linker can be ligated into a vector comprising a polynucleotide described herein by a T4 ligase in some cases. To facilitate a ligation an excess of polynucleotide linkers can be added to a composition comprising an insert and a vector. In some cases, an insert and vector are pre-treated before a linker is introduced. For example, pre-treatment with a methylase can prevent unwanted cleavage of insert DNA.

In embodiments, a polynucleotide linker comprises a nucleotide sequence having at least 70%, 75%, 80%, 85%, 90%, 95%, 99%, 99.5% or 100% identity with the nucleotide sequence of porcine teschovirus-1 2A region (P2A) (SEQ ID NO:41); equine rhinitis A virus 2A region (E2A) (SEQ ID NO:43); Thosea asigna virus 2A region (T2A) (SEQ ID NO:45); or foot-and-mouth disease virus 2A region (F2A) (SEQ ID NO:47).

In certain embodiments, two or more polypeptides encoded by a polynucleotide described herein can be separated by an intervening sequence encoding an intervening linker polypeptide. Herein the term "intervening linker polypeptide" referring to an amino acid sequence separating two or more polypeptides encoded by a polynucleotide is distinguished from the term "peptide linker" which refers to the sequence of amino acids which is optionally included in a polypeptide construct disclosed herein to connect the transmembrane domain to the cell surface polypeptide (e.g. comprising a truncated variant of a natural polypeptide). In certain cases, the intervening linker polypeptide is a cleavage-susceptible intervening linker polypeptide. In some embodiments, polypeptides of interest are expressed as fusion proteins linked by a cleavage-susceptible intervening linker polypeptide. In certain embodiments, cleavage-susceptible intervening linker polypeptide(s) can be any one or more of: Ff2A, T2A, p2A, 2A, GSG-p2A, GSG linker (SEQ ID NO: 16), and furin link variants.

In embodiments, an intervening linker polypeptide comprises an amino acid sequence having at least 70%, 75%, 80%, 85%, 90%, 95%, 99%, 99.5% or 100% identity with the amino acid sequence of porcine teschovirus-1 2A region (P2A) (SEQ ID NO:41); equine rhinitis A virus 2A region (E2A) (SEQ ID NO:44); Thosea asigna virus 2A region (T2A) (SEQ ID NO:46); or foot-and-mouth disease virus 2A region (F2A) (SEQ ID NO:48).

In some cases, a viral 2A sequence can be used. 2A elements can be shorter than IRES, having from 5 to 100 base pairs. In some cases, a 2A sequence can have 5, 10, 15, 20, 25, 30, 35, 40, 45, 50, 55, 60, 65, 70, 75, 80, 85, 90, or 100 nucleotides in length. 2A linked genes can be expressed in one single open reading frame and "self-cleavage" can occur co-translationally between the last two amino acids, GP, at the C-terminus of the 2A polypeptide, giving rise to equal amounts of co-expressed proteins.

A viral 2A sequence can be about 20 amino acids. In some cases, a viral 2A sequence can contain a consensus motif Asp-Vαl/Ile-Glu-X-Asn-Pro-Gly-Pro (SEQ ID NO: 229). A consensus motif sequence can act co-translationally. For example, formation of a normal peptide bond between a glycine and proline residue can be prevented, which can result in ribosomal skipping and cleavage of a nascent polypeptide. This effect can produce multiple genes at equimolar levels.

A 2A peptide can allow translation of multiple proteins in a single open reading frame into a polypeptide that can be subsequently cleaved into individual polypeptide through a ribosome-skipping mechanism (Funston, Kallioinen et al. 2008). In some embodiments, a 2A sequence can include: Ff2A, T2A, p2A, 2A, T2A, E2A, F2A, and BmCPV2A, BmIFV2A, and any combination thereof.

In some cases, a vector can comprise an IRES sequence and a 2A polynucleotide linker sequence. In other cases, expression of multiple genes linked with 2A peptides can be facilitated by a spacer sequence (GSG (SEQ ID NO: 16)) ahead of the 2A peptides. In some cases, constructs can combine a spacers, linkers, adaptors, promotors, or combinations thereof. For example, a construct can have a spacer (SGSG (SEQ ID NO: 18) or GSG (SEQ ID NO: 16)) and furin intervening polypeptide linker (R-A-K—R (SEQ ID NO: 230)) cleavage site with different 2A peptides. A spacer can be an I-Ceui. In some cases, a linker can be engineered. For example, a linker can be designed to comprise chemical characteristics such as hydrophobicity. In some cases, at least two linker sequences can produce the same protein. In other cases, multiple linkers can be used in a vector.

In certain cases, an intervening linker polypeptide can-comprise an amino acid sequence "RAKR (SEQ ID NO: 230)". In certain cases, a Furin intervening linkerpolypeptide can be encoded by a polynucleotide sequence comprising "AGAGCTAAGAGG (SEQ ID NO: 231)."

In certain cases, an intervening linker polypeptide can be a linker comprising a sequence disclosed in the table below:

TABLE 1

| Linker amino acid sequences | | |
|---|---|---|
| SEQ ID No. | Linker Name | Sequence (N- to C- terminus) |
| 230 | Furinlink1 | RAKR |
| 233 | Fmdv | RAKRAPVKQTLNFDLLKLAGDVESNPGP |
| 42 | p2a | ATNFSLLKQAGDVEENPGP |
| 235 | GSG-p2a | GSGATNFSLLKQAGDVEENPGP |
| 237 | fp2a | RAKRAPVKQGSGATNFSLLKQAGDVEENPGP |
| 16 | GSG linker | GSG |
| 18 | SGSG linker | SGSG |
| 24 | Whitlow | GSTSGSGKPGSGEGSTKG |
| 226 | Linker | SGGGSGGGGSGGGGSGGGGSGGGSLQ |
| 227 | Furin-GSG-T2A | RAKRGSGEGRGSLLTCGDVEENPGP |
| 228 | Furin-SGSG-T2A | RAKRSGSGEGRGSLLTCGDVEENPGP |
| 42 | Porcine teschovirus-1 2A region (P2A) | ATNFSLLKQAGDVEENPGP |
| 44 | Equine rhinitis A virus 2A region (E2A) | QCTNYALLKLAGDVESNPGP |
| 48 | Foot-and-mouth disease virus 2A region (F2A) | VKQTLNFDLLKLAGDVESNPGP |

In some embodiments, a linker can be utilized in a polynucleotide described herein. A linker can be a flexible linker, a rigid linker, an in vivo cleavable linker, or any combination thereof. In some cases, a linker may link functional domains together (as in flexible and rigid linkers) or releasing free functional domain in vivo as in in vivo cleavable linkers.

In some embodiments, polynucleotide linkers and intervening linker polypeptides can improve biological activity, increase expression yield, and achieve desirable pharmacokinetic profiles.

In some cases, an intervening linker polypeptide sequence described herein can include a flexible linker. Flexible linkers can be applied when a joined domain requires a certain degree of movement or interaction. Flexible linkers can be composed of small, non-polar (e.g., Gly) or polar (e.g., Ser or Tbr) amino acids. A flexible linker can have sequences consisting primarily of stretches of Gly and Ser residues ("GS" linker). An example of a flexible linker can have the sequence of (Gly-Gly-Gly-Gly-Ser)n (SEQ ID NO: 221; e.g., SEQ ID NO: 20 or 22). By adjusting the copy number "n", the length of this exemplary GS linker can be optimized to achieve appropriate separation of functional domains, or to maintain necessary inter-domain interactions. Besides GS linkers, other flexible linkers can be utilized for recombinant fusion proteins. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein domains. In addition, although flexible linkers may not have rigid structures, they can serve as a passive linker to keep a distance between functional domains. The length of a flexible linker can be adjusted to allow for proper folding or to achieve optimal biological activity of the fusion proteins.

An intervening linker polypeptide described herein can further include a rigid linker in some cases. A rigid linker can be utilized to maintain a fixed distance between domains of a polypeptide. Examples of rigid linkers can be: Alpha helix-forming linkers, Pro-rich sequence, (XP)n, x-Pro backbone (SEQ ID NO: 239), A(EAAAK)nA (SEQ ID NO: 240) (n=2-5), to name a few. Rigid linkers can exhibit relatively stiff structures by adopting α-helical structures or by containing multiple Pro residues in some cases.

An intervening linker polypeptide described herein can be cleavable in some cases. In other cases an intervening linker polypeptide is not cleavable. Linkers that are not cleavable may covalently join functional domains together to act as one molecule throughout an in vivo process or an ex vivo process. An intervening linker polypeptide can also be cleavable in vivo. A cleavable intervening linker polypeptide can for example be introduced to release free functional domains in vivo. An intervening linker polypeptide can be cleaved by for example the presence of reducing reagents and proteases. For example, a reduction of a disulfide bond may be utilized to produce a cleavable intervening linker polypeptide. In the case of a disulfide intervening linker polypeptide, a cleavage event through disulfide exchange with a thiol, such as glutathione, could produce a cleavage. In other cases, an in vivo cleavage of a intervening linker polypeptide in a recombinant fusion protein may also be carried out by proteases that can be expressed in vivo under pathological conditions (e.g. cancer or inflammation), in specific cells or tissues, or constrained within certain cellular compartments. In some cases, a cleavable intervening linker polypeptide may allow for targeted cleavage. For example, the specificity of many proteases can offer slower cleavage of a intervening linker polypeptide in constrained compartments. A cleavable intervening linker polypeptide can also comprise hydrazone, peptides, disulfide, or thioesther. For example, a hydrazone can confer serum stability. In other cases, a hydrazone can allow for cleavage in an acidic compartment. An acidic compartment can have a pH up to about 7. A linker can also include a thioether. A thioether can be nonreducible and/or can be designed for intracellular proteolytic degradation.

A linker can be an engineered linker. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker.

In some embodiments are polynucleotides encoding a polypeptide construct comprising a furin polypeptide and a 2A polypeptide, wherein the furin polypeptide and the 2A polypeptide are connected by an intervening linker polypeptide comprising at least three hydrophobic amino acids. In some cases, at least three hydrophobic amino acids are selected from the list consisting of glycine (Gly)(G), alanine (Ala)(A), valine (Val)(V), leucine (Lu)(L), isoleucine (Ile)(I), proline (Pro)(P), phenylalanine (Phe)(F), methionine (Met)(M), tryptophan (Trp)(W).

Expression of Polypeptide Constructs

In some embodiments, the polynucleotides and polypeptides described herein can be constitutively expressed, for example using the constitutive promoters of viral and non-viral delivery systems (see below). In other embodiments, the polypeptide constructs, polynucleotides and methods provided herein can be implemented in a gene switch system. The term "gene switch" refers to the combination of a response element associated with a promoter, and for instance, an EcR based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems may include ligand inducible heterologous gene expression systems.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., 1992; No et al., 1996). Later, Suhr et al., 1998 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the first polypeptide with the second polypeptide thereby resulting in dimerization of the DNA binding domain and the transactivation domain. Since the DNA binding and transactivation domains reside on two different molecules, the background activity in the absence of ligand is greatly reduced.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptorJ0 (LXRO), steroid hormone receptor like protein (RLD-1), liver x receptor (LXR), liver x receptor a (LXRa), farnesoid x receptor (FXR), receptor interacting protein 14 (RIP-14), and farnesol receptor (HRR-1).

In some cases, an inducible promoter can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919 each of which is incorporated by reference in its entirety.

Modified Effector Cells

Provided are effector cells modified to express one or more polypeptide constructs capable of functioning in the effector cells as cell tags.

"T cell" or "T lymphocyte" as used herein is a type of lymphocyte that plays a central role in cell-mediated immunity. They may be distinguished from other lymphocytes, such as B cells and natural killer cells (NK cells), by the presence of a T-cell receptor (TCR) on the cell surface.

In some embodiments, modified effector cells are modified immune cells that comprise T cells and/or natural killer cells. T cells or T lymphocytes are a subtype of white blood cells that are involved in cell-mediated immunity. Exemplary T cells include T helper cells, cytotoxic T cells, TH17 cells, stem memory T cells (TSCM), naïve T cells, memory T cells, effector T cells, regulatory T cells, or natural killer T cells.

T helper cells (TH cells) assist other white blood cells in immunologic processes, including maturation of B cells into plasma cells and memory B cells, and activation of cytotoxic T cells and macrophages. In some instances, TH cells are known as CD4+ T cells due to expression of the CD4 glycoprotein on the cell surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate different types of immune responses. Signaling from the APC directs T cells into particular subtypes. In some embodiments herein, secreted cytokines can be recombinant.

Cytotoxic T cells (TC cells or CTLs) destroy virus-infected cells and tumor cells, and are also implicated in transplant rejection. These cells are also known as CD8+ T cells since they express the CD8 glycoprotein on their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise subtypes: stem memory T cells (TSCM), central memory T cells (TCM cells) and two types of effector memory T cells (TEM cells and TEMRA cells). Memory cells may be either CD4+ or CD8+. Memory T cells may express the cell surface proteins CD45RO, CD45RA and/or CCR7.

Regulatory T cells (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

Natural killer T cells (NKT cells) bridge the adaptive immune system with the innate immune system. Unlike conventional T cells that recognize peptide antigens presented by major histocompatibility complex (MHC) molecules, NKT cells recognize glycolipid antigen presented by a molecule called CDld. Once activated, these cells can perform functions ascribed to both Th and Tc cells (i.e., cytokine production and release of cytolytic/cell killing molecules). They are also able to recognize and eliminate some tumor cells and cells infected with herpes viruses.

Natural killer (NK) cells are a type of cytotoxic lymphocyte of the innate immune system. In some instances, NK cells provide a first line defense against viral infections and/or tumor formation. NK cells can detect MHC presented on infected or cancerous cells, triggering cytokine release, and subsequently induce lysis and apoptosis. NK cells can further detect stressed cells in the absence of antibodies and/or MHC, thereby allowing a rapid immune response.

Viral Based Delivery Systems

The present disclosure also provides delivery systems, such as viral-based systems, in which a nucleic acid described herein is inserted. Representative viral expression vectors include, but are not limited to, adeno-associated viral vectors, adenovirus-based vectors (e.g., the adenovirus-based Per.C6 system available from Crucell, Inc. (Leiden, The Netherlands)), lentivirus-based vectors (e.g., the lentiviral-based pLPI from Life Technologies (Carlsbad, Calif.)), retroviral vectors (e.g., the pFB-ERV plus pCFB-EGSH), and herpes virus-based vectors. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In an additional embodiment, the viral vector is an adeno-associated viral vector. In a further embodiment, the viral vector is a retroviral vector. In general, and in embodiments, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNATM5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

Another example of a suitable promoter is human elongation growth factor 1 alpha 1 (hEF1a1). In embodiments, the vector construct comprising the CARs and/or TCRs of the present disclosure comprises hEF1a1 functional variants.

However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR or TCR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neomycin resistance gene (neo) and ampicillin resistance gene and the like. In some embodiments, a truncated epidermal growth factor receptor (HER1t) tag may be used as a selectable marker gene.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the vectors comprise a hEF1a1 promoter to drive expression of transgenes, a bovine growth hormone polyA sequence to enhance transcription, a woodchuck hepatitis virus posttranscriptional regulatory element (WPRE), as well as LTR sequences derived from the pFUGW plasmid.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5: 505-10 (1991)). However, compositions that have different structures in solution than the normal vesicular structure are also encompassed. For example, the lipids may assume a micellar structure or merely exist as non-uniform aggregates of lipid molecules. Also contemplated are lipofectamine-nucleic acid complexes.

Non-Viral Based Delivery Systems

In some instances, polynucleotides encoding cell tags described herein can also be introduced into T cells using non-viral based delivery systems, such as the "Sleeping Beauty (SB) Transposon System," which refers a synthetic DNA transposon system for introducing DNA sequences into the chromosomes of vertebrates. Some exemplary embodiments of the system are described, for example, in U.S. Pat. Nos. 6,489,458 and 8,227,432. The Sleeping Beauty transposon system is composed of a Sleeping Beauty (SB) transposase and a SB transposon. In embodiments, the Sleeping Beauty transposon system can include the SB11 transposon system, the SB100X transposon system, or the SB110 transposon system.

DNA transposons translocate from one DNA site to another in a simple, cut-and-paste manner. Transposition is a precise process in which a defined DNA segment is excised from one DNA molecule and moved to another site in the same or different DNA molecule or genome. As do other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, for instance a DNA or mRNA source, in which case the transposon becomes a non-autonomous element. Non-autonomous transposons are most useful as genetic tools because after insertion they cannot independently continue to excise and re-insert. SB transposons envisaged to be used as non-viral vectors for introduction of genes into genomes of vertebrate animals and for gene therapy. Briefly, the Sleeping Beauty (SB) system (Hackett et al., Mol Ther 18:674-83, (2010)) was adapted to genetically modify the T cells (Cooper et al., Blood 105:1622-31, (2005)). This involved two steps: (i) the electro-transfer of DNA plasmids expressing a SB transposon [i.e., chimeric antigen receptor (CAR) to redirect T-cell specificity (Jin et al., Gene Ther 18:849-56, (2011); Kebriaei et al., Hum Gene Ther 23:444-50, (2012)) and SB transposase and (ii) the propagation and expansion of T cells stably expressing integrants on designer artificial antigen-presenting cells (AaPC) derived from the K562 cell line (also known as AaPCs (Activating and Propagating Cells). In one embodiment, the SB transposon system includes coding sequence encoding membrane boundIL-15 and/or a chimeric antigen receptor. Such systems are described for example in Singh et al., Cancer Res (8):68 (2008). Apr. 15, 2008 and Maiti et al., J Immunother. 36(2): 112-123 (2013), incorporated herein by reference in their entireties. In certain embodiments, the DNA plasmid expressing a SB transposon comprising a CAR or TCR and a cytokine and polypeptide cell tag are electroporated into an effector cell which is then infused into a patient without further propagation and expansion.

In some embodiments, a polynucleotide encoding a CAR or a TCR or a cytokine and one or more polypeptide cell tag(s) in a modified effector cell described herein is encoded in one or more transposon DNA plasmid vectors, and the SB transposase is encoded in a separate vector. In embodiments, the polypeptide cell tag is encoded in a transposon DNA plasmid vector, a CAR or TCR or cytokine is encoded in a second transposon DNA plasmid vector, and the SB transposase is encoded in a third DNA plasmid vector. In some embodiments, the CAR or TCR and cytokine and polypeptide cell tag is encoded in a single transposon.

In some embodiments, the polypeptides described herein provides a safety mechanism by allowing for depletion of infused CAR-T cells through administering FDA approved antibodies or any antibody that recognizes a polypeptide construct to induce a cell depletion pathway. In some embodiments, HER1t variants described herein provide a safety mechanism by binding to introduced cetuximab and allowing for cell depletion. In some embodiments, CD20t variants also provide a safety mechanism by allowing for depletion of infused CAR-T cells through administering FDA-approved rituximab therapy.

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, molecular assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the present disclosure.

In embodiments, a modified effector cell described herein and other genetic elements are delivered to a cell using the SB11 transposon system, the SB100X transposon system, the SB110 transposon system, the piggyBac transposon system (see, e.g., Wilson et al, "PiggyBac Transposon-mediated Gene Transfer in Human Cells," Molecular Therapy 15:139-145 (2007), incorporated herein by reference in its entirety) and/or the piggyBac transposon system (see, e.g., Mitra et al., "Functional characterization of piggyBac from the bat *Myotis lucifugus* unveils an active mammalian DNA transposon," Proc. Natl. Acad. Sci USA 110:234-239 (2013). Additional transposases and transposon systems are provided in U.S. Pat. Nos.; 6,489,458; 6,613, 752, 7,148,203; 7,985,739; 8,227,432; 9,228,180; U.S. Patent Publn. No. 2011/0117072; Mates et al., Nat Genet, 41(6):753-61 (2009). doi: 10.1038/ng.343. Epub 2009 May 3, Gene Ther., 18(9):849-56 (2011). doi: 10.1038/gt2011.40. Epub 2011 Mar 31 and in Ivics et al., Cell. 91(4):501-10, (1997), each of which is incorporated herein by reference in their entirety. Additional suitable non-viral systems can include integrating expression vectors, which may randomly integrate into the host cell's DNA, or may include a recombination site to enable the specific recombination between the expression vector and the host cell's chromosome. Targeted integration of transgenes into predefined genetic loci is a desirable goal for many applications. First, a first recombination site for a site-specific recombinase is inserted at a genomic site, either at a random or at a predetermined location. Subsequently, the cells are transfected with a plasmid carrying the gene or DNA of interest and the second recombination site and a source for recombinase (expression plasmid, RNA, protein, or virus-expressing recombinase). Recombination between the first and second recombination sites leads to integration of plasmid DNA.

Such integrating expression vectors may utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein may be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant is a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

Also provided herein is a system for integrating heterologous genes in a host cell, said system comprising one or more gene expression cassettes. In some instances, the system includes a first gene expression cassette comprising a first polynucleotide encoding a first polypeptide construct. In other instances, the system can include a second gene expression cassette comprising a second polynucleotide encoding a second polypeptide construct. In yet other instances, the system can include a third gene expression cassette. In one embodiment, the system includes recombinant attachment sites; and a serine recombinase; such that upon contacting said host cell with at least said first gene expression cassette, in the presence of said serine recombinase, said heterologous genes are integrated in said host cell.

In some instances, the system further comprises a ligand; such that upon contacting said host cell, in the presence of said ligand, said heterologous gene are expressed in said host cell. In one instance, the system also includes recombinant attachment sites. In some instances, one recombination attachment site is a phage genomic recombination attachment site (attP) or a bacterial genomic recombination attachment site (attB). In one instance, the host cell is an eukaryotic cell. In another instance, the host cell is a human cell. In further instances, the host cell is a T cell or NK cell.

In one embodiment, the heterologous gene in the system described above comprises a CAR. In some embodiments, the CAR binds at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72, EGFRvIII, CD123 and VEGF-R2.

In another embodiment, the system includes a heterologous gene comprising a cytokine. In some instances, the cytokine comprises at least one of IL-15, IL-2, IL-12, IL-21, and a fusion of IL-15 and IL-15Rα. In some embodiments, the system includes a heterologous gene comprising at least one cell tag described herein. In some embodiments, said cell tag comprises at least one of a HER1 polypeptide, a LNGFR polypeptide, a CD20 polypeptide and a CD52 polypeptide. In some embodiments, the mbIL-15 is encoded with a cell tag. Examples of cell tags can include truncated: HER1 polypeptide, LNGFR polypeptide, CD20 polypeptide, CD52 polypeptide or any other appropriate cell tags for use as a depletion or kill switch, or enrichment marker.

In further embodiments, said system is contained in one or more vectors. In one instance, the system is contained in one vector. In one instance, the first gene expression cassette, the second gene expression cassette, and the recombinant attachment sites are contained in one vector. In one instance, the first gene expression cassette, the second gene expression cassette, the third gene expression cassette and the recombinant attachment sites are contained in one vector. In another instance, the serine recombinase is SF370. In other instances, the serine recombinase is in a separate vector.

The recombinases can be introduced into a target cell before, concurrently with, or after the introduction of a targeting vector. The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components described above are useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed).

Recombinases for use in the practice of the present invention can be produced recombinantly or purified as previously described. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, Proc. Nat. Acad. Sci. 95:5505-5510, 1998.)

In one embodiment, the recombinases can be introduced into the eukaryotic cells that contain the recombination attachment sites at which recombination is desired by any suitable method. Methods of introducing functional proteins, e.g., by microinjection or other methods, into cells are well known in the art. Introduction of purified recombinase protein ensures a transient presence of the protein and its function, which is often a preferred embodiment. Alternatively, a gene encoding the recombinase can be included in an expression vector used to transform the cell, in which the recombinase-encoding polynucleotide is operably linked to a promoter which mediates expression of the polynucleotide in the eukaryotic cell. The recombinase polypeptide can also be introduced into the eukaryotic cell by messenger RNA that encodes the recombinase polypeptide. It is generally preferred that the recombinase be present for only such time as is necessary for insertion of the nucleic acid fragments into the genome being modified. Thus, the lack of permanence associated with most expression vectors is not expected to be detrimental. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide. In other embodiments, the recombinase gene is introduced into a transgenic eukaryotic organism. Transgenic cells or animals can be made that express a recombinase constitutively or under cell-specific, tissue-specific, developmental-specific, organelle-specific, or small molecule-inducible or repressible promoters. The recombinases can be also expressed as a fusion protein with other peptides, proteins, nuclear localizing signal peptides, signal peptides, or organelle-specific signal peptides (e.g., mitochondrial or chloroplast transit peptides to facilitate recombination in mitochondria or chloroplast).

For example, a recombinase may be from the Integrase or Resolvase families. The Integrase family of recombinases has over one hundred members and includes, for example, FLP, Cre, and lambda integrase. The Integrase family, also referred to as the tyrosine family or the lambda integrase family, uses the catalytic tyrosine's hydroxyl group for a nucleophilic attack on the phosphodiester bond of the DNA. Typically, members of the tyrosine family initially nick the DNA, which later forms a double strand break. Examples of tyrosine family integrases include Cre, FLP, SSV1, and lambda (λ) integrase. In the resolvase family, also known as the serine recombinase family, a conserved serine residue forms a covalent link to the DNA target site (Grindley, et al., (2006) Ann Rev Biochem 16:16).

In one embodiment, the recombinase is an isolated polynucleotide sequence comprising a nucleic acid sequence that encodes a recombinase selecting from the group consisting of a SPβc2 recombinase, a SF370.1 recombinase, a Bxb1 recombinase, an A118 recombinase and a ϕRv1 recombinase. Examples of serine recombinases are described in detail in U.S. Pat. No. 9,034,652, hereby incorporated by reference in its entirety.

In one embodiment, a method for site-specific recombination comprises providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB Further embodiments provide for the introduction of a site-specific recombinase into a cell whose genome is to be modified. One embodiment relates to a method for obtaining site-specific recombination in an eukaryotic cell comprises providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP) or a bacterial genomic recombination attachment site (attB), the second recombination attachment site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB. In an embodiment the recombinase is selected from the group consisting of an A118 recombinase, a SF370.1 recombinase, a SPβc2 recombinase, a ϕRv1 recombinase, and a Bxb1 recombinase. In one embodiment the recombination results in integration.

Immune Effector Cell Sources

In certain aspects, the embodiments described herein include methods of making and/or expanding the antigen-specific redirected immune effector cells (e.g., T-cells, NK-cell or NK T-cells) that comprises transfecting the cells with an expression vector containing a DNA (or RNA) construct encoding the polypeptide construct, then, optionally, stimulating the cells with feeder cells, recombinant antigen, or an antibody to the receptor to cause the cells to proliferate. In certain aspects, the cell (or cell population) engineered to express a CAR or TCR is a stem cell, iPS cell, immune effector cell or a precursor of these cells.

Sources of immune effector cells can include both allogeneic and autologous sources. In some cases immune effector cells may be differentiated from stem cells or induced pluripotent stem cells (iPSCs). Thus, cell for engineering according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells such as T cells derived from human peripheral blood mononuclear cells (PBMC). PBMCs can be collected from the peripheral blood or after stimulation with G-CSF (Granulocyte colony stimulating factor) from the bone marrow, or umbilical cord blood. Following transfection or transduction (e.g., with a CAR expression construct), the cells may be immediately infused or may be cryo-preserved. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells. The recombinant T cells may be expanded by stimulation with IL-2, or other cytokines that bind the common gamma-chain (e.g., IL-7, IL-12, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be further selected with the use of magnetic bead based isolation methods and/or fluorescence activated cell sorting technology and further cultured with the AaPCs. In a further aspect, the genetically modified cells may be cryopreserved.

T cells can also be obtained from a number of sources, including peripheral blood, bone marrow, lymph node tissue, cord blood, thymus tissue, tissue from a site of infection, ascites, pleural effusion, spleen tissue, and tumor (tumor-infiltrating lymphocytes). In certain embodiments of the present disclosure, any number of T cell lines available in the art, may be used. In certain embodiments of the present disclosure, T cells can be obtained from a unit of blood collected from a subject using any number of techniques known to the skilled artisan, such as Ficoll® separation. In embodiments, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the present disclosure, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL® gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. In another embodiment, CD14+ cells are depleted from the T-cell population. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this disclosure. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is 5×106/ml. In other embodiments, the concentration used can be from about 1×105/ml to 1×106/ml, and any integer value in between.

In other embodiments, the cells may be incubated on a rotator for varying lengths of time at varying speeds at either 2-10° C. or at room temperature.

T cells for stimulation can also be frozen after a washing step. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present disclosure.

Also contemplated in the context of the present disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, (1991); Henderson et al., Immun 73:316-321, (1991); Bierer et al., Curr. Opin. Immun 5:763-773, (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present disclosure, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

In certain embodiments T cells comprising polynucleotides and polypeptides described herein can optionally, be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

"Adoptive T cell transfer" refers to the isolation and ex vivo expansion of tumor specific T cells to achieve greater number of T cells than what could be obtained by vaccination alone or the patient's natural tumor response. The tumor specific T cells are then infused into patients with cancer in an attempt to give their immune system the ability to overwhelm remaining tumor via T cells which can attack and kill cancer. There are many forms of adoptive T cell therapy being used for cancer treatment; culturing tumor infiltrating lymphocytes or TIL, isolating and expanding one particular T cell or clone, and even using T cells that have been engineered to potently recognize and attack tumors.

In some cases, T cells described herein are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, (1998); Haanen et al., J. Exp. Med. 190(9):13191328, (1999); Garland et al., J. Immunol Meth. 227(1-2):53-63, (1999)).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present disclosure.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In certain aspects of the present disclosure, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present disclosure, more anti-CD28 antibody is bound to the particles than anti-CD3 antibody, i.e., the ratio of CD3:CD28 is less than one. In certain embodiments of the present disclosure, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In embodiments, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one ratio being at least 1:1 particles per T cell. In one embodiment, a ratio of particles to cells of 1:1 or less is used. In one particular embodiment, the particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present disclosure. In particular, ratios will vary depending on particle size and on cell size and type.

In further embodiments of the present disclosure, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, 104 to 109 T cells) and beads (for example, DYNABEADS® M-450 CD3/CD28 T paramagnetic beads at a ratio of 1:1, or MACS® MicroBeads from Miltenyi Biotec) are combined in a buffer, for example, PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present disclosure, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-. gamma., IL-4, IL-7, GM-CSF, IL-10, IL-12, IL-15, TGFbeta, and TNF-alpha or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, alpha-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In some cases, immune effector cells of the embodiments (e.g., T-cells) are co-cultured with activating and propagating cells (AaPCs), to aid in cell expansion. AaPCs can also be referred to as artificial Antigen Presenting cells (aAPCs). For example, antigen presenting cells (APCs) are useful in preparing therapeutic compositions and cell therapy products of the embodiments. In one aspect, the AaPCs may be genetically modified K562 cells. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009, each of which is incorporated by reference. In yet a further aspect of the embodiments, culturing the genetically modified CAR cells comprises culturing the genetically modified CAR cells in the presence of dendritic cells or activating and propagating cells (AaPCs) that stimulate expansion of the CAR-expressing immune effector cells. In still further aspects, the AaPCs comprise a CAR-binding antibody or fragment thereof expressed on the surface of the AaPCs. The AaPCs may comprise additional molecules that activate or co-stimulate T-cells in some cases. The additional molecules may, in some cases, comprise membrane-bound Cy cytokines. In yet still further aspects, the AaPCs are inactivated or irradiated, or have been tested for and confirmed to be free of infectious material. In still further aspects, culturing the transgenic CAR cells in the presence of AaPCs comprises culturing the transgenic CAR cells in a medium comprising soluble cytokines, such as IL-15, IL-21 and/or IL-2. The cells may be cultured at a ratio of about 10:1 to about 1:10; about 3:1 to about 1:5; about 1:1 to about 1:3 (immune effector cells to AaPCs); or any range derivable therein. For example, the co-culture of T cells and AaPCs can be at a ratio of about 1:1, about 1:2 or about 1:3.

In one aspect, the AaPCs may express CD137L. In some aspects, the AaPCs can further express the antigen that is targeted by the CAR cell. In other aspects, the AaPCs may further express CD19, CD64, CD86, or mIL15. In certain aspects, the AaPCs may express at least one anti-CD3 antibody clone, such as, for example, OKT3 and/or UCHT1. In one aspect, the AaPCs may be treated (e.g. irradiated or mytomycin C) to eliminate their growth potential. In one aspect, the AaPCs may have been tested for and confirmed to be free of infectious material. Methods for producing such AaPCs are known in the art. In one aspect, culturing the CAR-modified T cell population with AaPCs may comprise culturing the cells at a ratio of about 10:1 to about 1:10; about 3:1 to about 1:5; about 1:1 to about 1:3 (T cells to AaPCs); or any range derivable therein. For example, the co-culture of T cells and AaPCs can be at a ratio of about 1:1, about 1:2 or about 1:3. In one aspect, the culturing step may further comprise culturing with an aminobisphosphonate (e.g., zoledronic acid).

In a further aspect, the population of CAR-T cells is cultured and/or stimulated for no more than 7, 14, 21, 28, 35 42 days, 49, 56, 63 or 70 days. In some embodiments, the population of CAR-T cells is cultured and/or stimulated for at least 0, 2, 4, 6, 8, 10, 12, 14, 16, 18, 20, 22, 24, 26, 28, 30 or more days. In some embodiments, the population of CAR-T cells is cultured and/or stimulated for at least 5, 10, 15, 20, 25, 30, 35, 40, 45, 50, 55, 60 or more days. In some embodiments, the population of CAR-T cells is cultured and/or stimulated for at least 7, 14, 21, 28, 35, 42, 49, 56, 63 or more days. In other embodiments, a stimulation includes the co-culture of the CAR-T cells with AaPCs to promote the growth of CAR positive T cells. In another aspect, the population of genetically modified CAR cells is stimulated for not more than: 1× stimulation, 2× stimulation, 3× stimulation, 4× stimulation, 5× stimulation, 5× stimulation, 6× stimulation, 7× stimulation, 8× stimulation, 9× stimulation or 10× stimulation. In some instances, the genetically modified cells are not cultured ex vivo in the presence of AaPCs. In some specific instances, the method of the embodiment further comprises enriching the cell population for CAR-expressing immune effector cells (e.g., T-cells) after the transfection and/or culturing step. The enriching may comprise fluorescence-activated cell sorting (FACS) and sorting for CAR-expressing cells. In a further aspect, the sorting for CAR-expressing cells comprises use of a CAR-binding antibody. The enriching may also comprise depletion of CD56+ cells. In yet still a further aspect of the embodiment, the method further comprises cryopreserving a sample of the population of genetically modified CAR cells.

In some cases, AaPCs are incubated with a peptide of an optimal length that allows for direct binding of the peptide to the MHC molecule without additional processing. Alternatively, the cells can express an antigen of interest (i.e., in the case of MHC-independent antigen recognition). Furthermore, in some cases, APCs can express an antibody that binds to either a specific CAR polypeptide or to CAR polypeptides in general (e.g., a universal activating and propagating cell (uAPC). Such methods are disclosed in WO/2014/190273, which is incorporated herein by reference. In addition to peptide-MHC molecules or antigens of interest, the AaPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, ThI differentiation, short-term T-cell survival, and cytokine secretion such as interleukin (IL)-2. Adhesion molecules can include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001, incorporated herein by reference.

Cells selected to become AaPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become AaPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, AaPCs preferably retain the deficiencies and poikilothermic properties that were possessed by the cells prior to their modification to generate the AaPCs. Exemplary AaPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g., Schneider 1972 Illustrative methods for the preparation, growth, and culture of Schneider 2 cells, are provided in U.S. Pat. Nos. 6,225,042, 6,355,479, and 6,362,001.

In one embodiment, AaPCs are also subjected to a freeze-thaw cycle. In an exemplary freeze-thaw cycle, the AaPCs may be frozen by contacting a suitable receptacle containing the AaPCs with an appropriate amount of liquid nitrogen, solid carbon dioxide (i.e., dry ice), or similar low-temperature material, such that freezing occurs rapidly. The frozen APCs are then thawed, either by removal of the AaPCs from the low-temperature material and exposure to ambient room temperature conditions, or by a facilitated thawing process in which a lukewarm water bath or warm hand is employed to facilitate a shorter thawing time. Additionally, AaPCs may be frozen and stored for an extended period of time prior to thawing. Frozen AaPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing AaPCs that undergo the freeze-thaw cycle, or are essentially removed, such as by transfer of AaPCs to media that is essentially devoid of such preservatives.

In further embodiments, xenogenic nucleic acid and nucleic acid endogenous to the AaPCs, may be inactivated by crosslinking, so that essentially no cell growth, replication or expression of nucleic acid occurs after the inactivation. In one embodiment, AaPCs are inactivated at a point subsequent to the expression of exogenous MHC and assisting molecules, presentation of such molecules on the surface of the AaPCs, and loading of presented MHC molecules with selected peptide or peptides. Accordingly, such inactivated and selected peptide loaded AaPCs, while rendered essentially incapable of proliferating or replicating, retain selected peptide presentation function. Preferably, the crosslinking also yields AaPCs that are essentially free of contaminating microorganisms, such as bacteria and viruses, without substantially decreasing the antigen-presenting cell function of the AaPCs. Thus crosslinking maintains the important AaPC functions of while helping to alleviate concerns about safety of a cell therapy product developed using the AaPCs. For methods related to crosslinking and AaPCs, see for example, U.S. Patent Application Publication No. 20090017000, which is incorporated herein by reference.

In certain embodiments there are further provided an engineered antigen presenting cell (APC). Such cells may be used, for example, as described above, to propagate immune effector cells ex vivo. In further aspects, engineered APCs may, themselves be administered to a patient and thereby stimulate expansion of immune effector cells in vivo. Engineered APCs of the embodiments may, themselves, be used as a therapeutic agent. In other embodiments, the engineered APCs can used as a therapeutic agent that can stimulate activation of endogenous immune effector cells specific for a target antigen and/or to increase the activity or persistence of adoptively transferred immune effector cells specific to a target antigen.

As used herein the term “engineered APC” refers to cell(s) that comprises at least a first transgene, wherein the first transgene encodes a HLA. Such engineered APCs may further comprise a second transgene for expression of an antigen, such that the antigen is presented at the surface on the APC in complex with the HLA. In some aspects, the engineered APC can be a cell type that presented antigens (e.g., a dendritic cell). In further aspects, engineered APC can be produced from a cell type that does not normally present antigens, such a T-cell or T-cell progenitor (referred to as “T-APC”). Thus, in some aspects, an engineered APC of the embodiments comprises a first transgene encoding a target antigen and a second transgene encoding a human leukocyte antigen (HLA), such that the HLA is expressed on the surface of the engineered APC in complex with an epitope of the target antigen. In certain specific aspects, the HLA expressed in the engineered APC is HLA-A2.

In some aspects, an engineered APC of the embodiments may further comprise at least a third transgene encoding co-stimulatory molecule. The co-stimulatory molecule may be a co-stimulatory cytokine that may be a membrane-bound Cy cytokine. In certain aspects, the co-stimulatory cytokine is IL-15, such as membrane-bound IL-15. In some further aspects, an engineered APC may comprise an edited (or deleted) gene. For example, an inhibitory gene, such as PD-1, LIM-3, CTLA-4 or a TCR, can be edited to reduce or eliminate expression of the gene. An engineered APC of the embodiments may further comprise a transgene encoding any target antigen of interest. For example, the target antigen can be an infectious disease antigen or a tumor-associated antigen (TAA).

Point Care

In one embodiment of the present disclosure, the immune effector cells described herein are modified at a point care site. In some cases, the point care site is at a hospital or at a facility (e.g., a medical facility) near a subject in need of treatment. The subject undergoes apheresis and peripheral blood mononuclear cells (PBMCs) or a sub population of PBMC can be enriched for example, by elutriation or Ficoll separation. Enriched PBMC or a subpopulation of PBMC can be cryopreserved in any appropriate cryopreservation solution prior to further processing. In one instance, the elutriation process is performed using a buffer solution containing human serum albumin. Immune effector cells, such as T cells can be isolated by selection methods described herein. In one instance, the selection method for T cells includes beads specific for CD3 and CD8 on T cells. In one case, the beads can be paramagnetic beads. The harvested immune effector cells can be cryopreserved in any appropriate cryopreservation solution prior to modification. The immune effector cells can be thawed up to 24 hours, 36 hours, 48 hours. 72 hours or 96 hours ahead of infusion. The thawed cells can be placed in cell culture buffer, for example in cell culture buffer (e.g. RPMI) supplemented with fetal bovine serum (FBS) or placed in a buffer that includes cytokines such as IL-2 and IL-21, prior to modification. In another aspect, the harvested immune effector cells can be modified immediately without the need for cryopreservation.

In some cases, the immune effector cells are modified by engineering/introducing a chimeric receptor, one or more cell tag(s) described herein, and/or cytokine into the immune effector cells and then rapidly infused into a subject. In some cases, the sources of immune effector cells can include both allogeneic and autologous sources. In one case, the immune effector cells can be T cells or NK cells. In one case, the chimeric receptor can be a CD19 CAR. In another case, the chimeric receptor can be a CD33 CAR. In a further case, the chimeric receptor can be a MUC16 CAR. In another case, the cytokine can be mbIL-15. In one case, the mbIL-15 is of SEQ ID NO: 178, or variant or fragment thereof. In one case, the cell tag can be SEQ ID NO: 57. In yet another case, expression of mbIL-15 is modulated by ligand inducible gene-switch expression systems described herein. For example, a ligand such as veledimex can be delivered to the subject to modulate the expression of mbIL-15. In another aspect, veledimex is provided at 5 mg, 10 mg, 15 mg, 20 mg, 30 mg, 40 mg, 50 mg, 60 mg, 70 mg, 80 mg, 90 mg or 100 mg. In a further aspect, lower doses of veledimex are provided, for example, 0.5 mg, 1 mg, 5 mg, 10 mg, 15 mg or 20 mg. In one embodiment, veledimex is administered to the subject 0, 1, 2, 3, 4, 5, 6, 7, 8, 9, 10, 11, 12, 13, 14, 15, 16, 17, 18, 19, 20, or 21 days prior to infusion of the modified immune effector cells. In a further embodiment, veledimex is administered about once every 12 hours, about once every 24 hours, about once every 36 hours or about once every 48 hours, for an effective period of time to a subject post infusion of the modified immune effector cells. In one embodiment, an effective period of time for veledimex administration is about: 7, 8, 9, 10, 11, 12, 13, 14, 15, 16, 17, 18, 19, 20, 21, 22, 23, 24, 25, 26, 27, 28, 29, 30 days. In other embodiments, veledimex can be re-administered after a rest period, after a drug holiday or when the subject experiences a relapse.

In certain cases, where an adverse effect on a subject is observed or when treatment is not needed, the cell tag can be activated, for example via cetuximab, for conditional in vivo ablation of modified immune effector cells comprising cell tags such as truncated epidermal growth factor receptor tags (HER1t variants) as described herein.

In some embodiments, such immune effectors cells are modified by the constructs through electroporation. In one instance, electroporation is performed with electroporators such as Lonza's Nucleofector™ electroporators. In other embodiments, the vector comprising the above-mentioned constructs is a non-viral or viral vector. In one case, the non-viral vector includes a Sleeping Beauty transposon-transposase system. In one instance, the immune effector cells are electroporated using a specific sequence. For example, the immune effector cells can be electroporated with one transposon followed by the DNA encoding the transposase followed by a second transposon. In another instance, the immune effector cells can be electroporated with all transposons and transposase at the same time. In another instance, the immune effector cells can be electroporated with a transposase followed by both transposons or one transposon at a time. While undergoing sequential electroporation, the immune effector cells may be rested for a period of time prior to the next electroporation step.

In some cases, the modified immune effector cells do not undergo a propagation and activation step. In some cases, the modified immune effector cells do not undergo an incubation or culturing step (e.g. ex vivo propagation). In certain cases, the modified immune effector cells are placed in a buffer that includes IL-2 and IL21 prior to infusion. In other instances, the modified immune effector cells are placed or rested in cell culture buffer, for example in cell culture buffer (e.g. RPMI) supplemented with fetal bovine serum (FBS) prior to infusion. Prior to infusion, the modified immune effector cells can be harvested, washed and formulated in saline buffer in preparation for infusion into the subject.

In one instance, the subject has been lymphodepleted prior to infusion. In other instances, lymphodepletion is not required and the modified immune effector cells are rapidly infused into the subject. Exemplary lymphodepletion regimens are listed in Tables 2 and 3 below:

TABLE 2

| Regimen 1 | |
|---|---|
| D-6 | Admit/IV Hydration |
| D-5 | Fludarabine 25 mg/m2, Cyclophosphamide 250 mg/m2 |
| D-4 | Fludarabine 25 mg/m2, Cyclophosphamide 250 mg/m2 |
| D-3 | Fludarabine 25 mg/m2 IV, Cyclophosphamide 250 mg/m2 |
| D-2 | REST |
| D-1 | REST |
| D-0 | T-cell infusion |

TABLE 3

| Regimen 2 | |
|---|---|
| D-6 | Admit/IV Hydration |
| D-5 | Fludarabine 30 mg/m2, Cyclophosphamide 500 mg/m2 |
| D-4 | Fludarabine 30 mg/m2, Cyclophosphamide 500 mg/m2 |
| D-3 | Fludarabine 30 mg/m2 IV, Cyclophosphamide 500 mg/m2 |
| D-2 | REST |
| D-1 | REST |
| D-0 | T-cell infusion |

In a further instance, the subject undergoes minimal lymphodepletion. Minimal lymphodepletion herein refers to a reduced lymphodepletion protocol such that the subject can be infused within 1 day, 2 days or 3 days following the lymphodepletion regimen. In one instance, a reduced lymphodepletion protocol can include lower doses of fludarabine and/or cyclophosphamide. In another instance, a reduced lymphodepletion protocol can include a shortened period of lymphodepletion, for example 1 day or 2 days.

In one embodiment, the immune effector cells are modified by engineering/introducing a chimeric receptor and a cytokine into said immune effector cells and then rapidly infused into a subject. In other cases, the immune effector cells are modified by engineering/introducing a chimeric receptor and a cytokine into said cells and then infused within at least: 0, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 hours into a subject. In other cases, immune effector cells are modified by engineering/introducing a chimeric receptor and a cytokine into the immune effector cells and then infused in 0 days, <1 day, <2 days, <3 days, <4 days, <5 days, <6 days or <7 days into a subject.

In some embodiments, an amount of modified effector cells is administered to a subject in need thereof and the amount is determined based on the efficacy and the potential of inducing a cytokine-associated toxicity. In another embodiment, the modified effector cells are $CAR^+$ and CD3+ cells. In some cases, an amount of modified effector cells comprises about 104 to about $10^9$ modified effector cells/kg. In some cases, an amount of modified effector cells comprises about $10^4$ to about $10^5$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises $>10^4$ but $\leq 10^5$ modified effector cells/kg. In some cases, an amount of modified effector cells comprises $>10^5$ but $\leq 10^6$ modified effector cells/kg. In some cases, an amount of modified effector cells comprises $>10^6$ but $\leq 10^7$ modified effector cells/kg. In one embodiment, a lower dose $>10^2$ but $\leq 10^4$ modified effector cells/kg may be infused.

In one embodiment, the modified immune effector cells are targeted to the cancer via regional delivery directly to the tumor tissue. For example, in ovarian cancer, the modified immune effector cells can be delivered intraperitoneally (IP) to the abdomen or peritoneal cavity. Such IP delivery can be performed via a port or pre-existing port placed for delivery of chemotherapy drugs. Other methods of regional delivery of modified immune effector cells can include catheter infusion into resection cavity, ultrasound guided intratumoral injection, hepatic artery infusion or intrapleural delivery.

In one embodiment, a subject in need thereof, can begin therapy with a first dose of modified immune effector cells delivered via IP followed by a second dose of modified immune effector cells delivered via IV. In a further embodiment, the second dose of modified immune effector cells can be followed by subsequent doses which can be delivered via IV or IP. In one embodiment, the duration between the first and second or further subsequent dose can be about: 0, 1, 2,3,4, 5, 6, 7, 8, 9, 10, 11, 12, 13, 14, 15, 16, 17, 18, 19, 20, 21, 22, 23, 24, 25, 26, 27, 28, 29, 30 days. In one embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In another embodiment, the duration between the first and second or further subsequent dose can be about: 0, 1, 2, 3, 4, 5, 6, 7, 8, 9 or 10 years.

In another embodiment, a catheter can be placed at the tumor or metastasis site for further administration of 1, 2, 3, 4, 5, 6, 7, 8, 9, 10 doses of modified immune effector cells. In some cases, doses of modified effector cells can comprise about $10^2$to about 109 modified effector cells/kg. In cases where toxicity is observed, doses of modified effector cells can comprise about $10^2$ to about $10^5$ modified effector cells/kg. In some cases, doses of modified effector cells can start at about $10^2$ modified effector cells/kg and subsequent doses can be increased to about: $10^4$, $10^5$, $10^6$, $10^7$, 10 or 109 modified effector cells/kg.

In other embodiments, a method of stimulating the proliferation and/or survival of engineered cells comprises obtaining a sample of cells from a subject, and transfecting cells of the sample of cells with one or more polynucleotides that comprise one or more transposons. In one embodiment, the transposons encode a chimeric antigen receptor (CAR), a cytokine, one or more cell tags, and a transposase effective to integrate said one or more polynucleotides into the genome of said cells, to provide a population of engineered cells. In an embodiment, the transposons encode a chimeric antigen receptor (CAR), a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In one instance, lymphodepletion is not required prior to administration of the engineered cells to a subject.

In one instance, a method of in vivo propagation of engineered cells comprises obtaining a sample of cells from a subject, and transfecting cells of the sample of cells with one or more polynucleotides that comprise one or more transposons. In one embodiment, the transposon(s) comprising a chimeric antigen receptor (CAR), a cytokine, one or more cell tags; and a transposase effective to integrate said one or more polynucleotides into the genome of said cells are electroporated into the sample of cells, to provide a population of engineered cells. In a further embodiment, the transposons encode a chimeric antigen receptor (CAR), a cytokine, one or more cell tags, gene switch polypeptides for ligand-inducible control of the cytokine and a transposase effective to integrate said one or more polynucleotides into the genome of said cells, to provide a population of engineered cells. In an embodiment, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain. In some embodiments, the first gene switch polypeptide and the second gene switch polypeptide are connected by a linker. In another embodiment, a single transposon can comprise a chimeric antigen receptor (CAR), a cytokine, one or more cell tags such as HER1t or any variants described herein. In one instance, lymphodepletion is not required prior to administration of the engineered cells to a subject.

In another embodiment, a method of enhancing in vivo persistence of engineered cells in a subject in need thereof comprises obtaining a sample of cells from a subject, and transfecting cells of the sample of cells with one or more polynucleotides that comprise one or more transposons. In one embodiment, the transposon(s) comprising a chimeric antigen receptor (CAR), a cytokine, one or more cell tags; and a transposase effective to integrate said one or more polynucleotides into the genome of said cells are electroporated into the sample of cells, to provide a population of engineered cells. In another embodiment, a single transposon can comprise a chimeric antigen receptor (CAR), a cytokine, one or more cell tags such as HER1t or any variants described herein. In some cases, one or more transposons encode a chimeric antigen receptor (CAR), a cytokine, one or more cell tags, gene switch polypeptides for ligand-inducible control of the cytokine and a transposase effective to integrate the DNA into the genome of said cells, to provide a population of engineered cells. In some cases, the gene switch polypeptides comprise i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and the second gene switch polypeptide are connected by a linker. In one instance, lymphodepletion is not required prior to administration of the engineered cells to a subject.

In another embodiment, a method of treating a subject with a solid tumor comprises obtaining a sample of cells from a subject, transfecting cells of the sample with one or more polynucleotides that comprise one or more transposons, and administering the population of engineered cells to the subject. In one instance, lymphodepletion is not required prior to administration of the engineered cells to a subject. In some cases, the one or more transposons encode a chimeric antigen receptor (CAR), a cytokine, one or more cell tags, and a transposase effective to integrate the DNA into the genome of the cells. In some cases, the one or more transposons encode a chimeric antigen receptor (CAR), a cytokine, one or more cell tags, gene switch polypeptides for ligand-inducible control of the cytokine and a transposase effective to integrate the DNA into the genome of the cells. In some cases, the gene switch polypeptides comprise: i) a first gene switch polypeptide that comprises a DNA binding domain fused to a first nuclear receptor ligand binding domain, and ii) a second gene switch polypeptide that comprises a transactivation domain fused to a second nuclear receptor ligand binding domain, wherein the first gene switch polypeptide and second gene switch polypeptide are connected by a linker. In some cases, the cells are transfected via electroporation. In some cases, the polynucleotides encoding the gene switch polypeptides are modulated by a promoter. In some cases, the promoter is a tissue-specific promoter or an EF1A promoter or functional variant thereof. In some cases, the tissue-specific promoter comprises a T cell specific response element or an NFAT response element. In some cases, the cytokine comprises at least one of IL-1, IL-2, IL-15, IL-12, IL-21, a fusion of IL-15, IL-15R or an IL-15 variant. In some cases, the cytokine is in secreted form. In some cases, the cytokine is in membrane-bound form. In some cases, the cells are NK cells, NKT cells, T-cells or T-cell progenitor cells. In some cases, the cells are administered to a subject (e.g. by infusing the subject with the engineered cells). In some cases, the method further comprises administering an effective amount of a ligand (e.g. veledimex) to induce expression of the cytokine. In some cases, the CAR is capable of binding at least one of CD19, CD33, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, MUC-16, h5T4, PSMA, TAG-72, EGFRvIII, CD123 and VEGF-R2. In some cases, the transposase is salmonid-type TcI-like transposase. In some cases, the transposase is SB11 or SB100×transposase. In other cases, the transposase is PiggyBac. In some cases, the cell tag comprise at least one of a HER1t1.

Indications

In some embodiments, disclosed herein are methods of administering a modified effector cell encoding a polynucleotide described herein to a subject having a disorder, for instance cancer or an infectious disease. In some cases, the cancer is a cancer associated with an expression of CD19, CD20, CD33, CD44, BCMA, CD123, EGFRvIII, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72 or VEGF-R2.

In some embodiments, disclosed herein are methods of administering a polynucleotide, polypeptide or a modified effector cell encoding a polynucleotide described herein, to a subject having a cancer associated with an overexpression of CD19. In some embodiments, disclosed herein are methods of administering a modified effector cell to a subject having a cancer associated with an overexpression of CD33. In some embodiments, disclosed herein are methods of administering a modified effector cell to a subject having a cancer associated with an overexpression of CD44, BCMA, CD123, EGFRvIII, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, MUC-1, MUC-16, MAGE-A1, h5T4, PSMA, TAG-72 or VEGF-R2. In some cases, the cancer is a metastatic cancer. In other cases, the cancer is a relapsed or refractory cancer.

In some cases, a cancer is a solid tumor or a hematologic malignancy. In some instances, the cancer is a solid tumor. In other instances, the cancer is a hematologic malignancy. In some cases, the cancer is a metastatic cancer. In some cases, the cancer is a relapsed or refractory cancer.

In some instances, the cancer is a solid tumor. Exemplary solid tumors include, but are not limited to, anal cancer, appendix cancer; bile duct cancer (i.e., cholangiocarcinoma); bladder cancer, brain tumor, breast cancer, cervical cancer; colon cancer, cancer of Unknown Primary (CUP); esophageal cancer, eye cancer, fallopian tube cancer, gastroenterological cancer; kidney cancer, liver cancer; lung cancer; medulloblastoma; melanoma; oral cancer, ovarian cancer; pancreatic cancer, parathyroid disease; penile cancer, pituitary tumor, prostate cancer; rectal cancer, skin cancer, stomach cancer, testicular cancer, throat cancer; thyroid cancer; uterine cancer, vaginal cancer, or vulvar cancer.

In some instances, the cancer is a hematologic malignancy. In some cases, a hematologic malignancy comprises a lymphoma, a leukemia, a myeloma, or a B-cell malignancy. In some cases, a hematologic malignancy comprises a lymphoma, a leukemia or a myeloma. In some instances, exemplary hematologic malignancies include chronic lymphocytic leukemia (CLL), small lymphocytic lymphoma (SLL), high risk CLL, non-CLUSLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the hematologic malignancy comprises a myeloid leukemia. In some embodiments, the hematologic malignancy comprises acute myeloid leukemia (AML) or chronic myeloid leukemia (CML).

In some instances, disclosed herein are methods of administering to a subject having a hematologic malignancy selected from chronic lymphocytic leukemia (CLL), small lymphocytic lymphoma (SLL), high risk CLL, non-CLUSLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis a modified effector cell described herein. In some instances, disclosed herein are methods of administering to a subject having a hematologic malignancy selected from AML or CML a modified effector cell to the subject.

In other cases, disclosed herein are methods of administering to a subject having an infection due to an infectious disease. An infectious disease can be a disease resulting from a bacterial, viral or fungi infection. In other instances, exemplary viral pathogens include those of the families of Adenoviridae, Epstein-Barr virus (EBV), Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and Stachybotrys. Exemplary pathogenic bacteria include *Streptococcus, Pseudomonas, Shigella, Campylobacter, Staphylococcus, Helicobacter, E. coli, Rickettsia, Bacillus, Bordetella, Chlamydia*, Spirochetes, and *Salmonella.*

Modified Effector Cell Doses

In some embodiments, an amount of modified effector cells is administered to a subject in need thereof and the amount is determined based on the efficacy and the potential of inducing a cytokine-associated toxicity. In some cases, an amount of modified immune effector cells comprises about $10^2$ to about $10^9$ modified immune effector cells/kg. In some cases, an amount of modified immune effector cells comprises about $10^3$ to about $10^9$ modified immune effector cells/kg. In some cases, an amount of modified immune effector cells comprises about $10^4$ to about $10^9$ modified immune effector cells/kg. In some cases, an amount of modified effector cells comprises about $10^5$ to about $10^9$ modified effector cells/kg. In some cases, an amount of modified effector cells comprises about $10^5$ to about $10^8$ modified effector cells/kg. In some cases, an amount of modified effector cells comprises about $10^5$ to about $10^7$ modified effector cells/kg. In some cases, an amount of modified effector cells comprises about $10^6$ to about $10^9$ modified effector cells/kg. In some cases, an amount of modified effector cells comprises about $10^6$ to about $10^8$ modified effector cells/kg. In some cases, an amount of modified effector cells comprises about $10^7$ to about $10^9$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises about $10^7$to about $10^8$ modified effector cells/kg. In some cases, an amount of modified effector cells comprises about $10^8$ to about $10^9$ modified effector cells/kg. In some instances, an amount of modified effector cells comprises about $10^9$ modified effector cells/kg. In some instances, an amount of modified effector cells comprises about $10^8$ modified effector cells/kg. In some instances, an amount of modified effector cells comprises about $10^7$ modified effector cells/kg. In some instances, an amount of modified effector cells comprises about $10^6$ modified effector cells/kg. In some instances, an amount of modified effector cells comprises about $10^5$ modified effector cells/kg.

In some embodiments, the modified effector cells are modified T cells. In some instances, the modified T cells are CAR-T cells. In some cases, an amount of CAR-T cells comprises about $10^2$ to about I10 CAR-T cells/kg. In some cases, an amount of CAR-T cells comprises about $10^5$ to about $10^9$ CAR-T cells/kg. In some cases, an amount of CAR-T cells comprises about $10^5$ to about 108 CAR-T cells/kg. In some cases, an amount of CAR-T cells comprises about $10^5$ to about $10^7$ CAR-T cells/kg. In some cases, an amount of CAR-T cells comprises about $10^6$ to about $10^9$ CAR-T cells/kg. In some cases, an amount of CAR-T cells comprises about $10^6$ to about 108 CAR-T cells/kg. In some cases, an amount of CAR-T cells comprises about $10^7$to about $10^9$ CAR-T cells/kg. In some cases, an amount of CAR-T cells comprises about $10^5$ to about $10^6$ CAR-T cells/kg. In some cases, an amount of CAR-T cells comprises about $10^6$ to about $10^7$ CAR-T cells/kg. In some cases, an amount of CAR-T cells comprises about $10^7$to about $10^8$ CAR-T cells/kg. In some cases, an amount of CAR-T cells comprises about 108 to about $10^9$ CAR-T cells/kg. In some instances, an amount of CAR-T cells comprises about $10^9$ CAR-T cells/kg. In some instances, an amount of CAR-T cells comprises about $10^8$ CAR-T cells/kg. In some instances, an amount of CAR-T cells comprises about 10' CAR-T cells/kg. In some instances, an amount of CAR-T cells comprises about $10^6$ CAR-T cells/kg. In some instances, an amount of CAR-T cells comprises about $10^5$ CAR-T cells/kg.

In some embodiments, the CAR-T cells are CD19-specific CAR-T cells. In some cases, an amount of CD19-specific CAR-T cells comprises about $10^2$ to about $10^9$ CAR-T cells/kg. In some embodiments, the CAR-T cells are CD19-specific CAR-T cells. In some cases, an amount of CD19-specific CAR-T cells comprises about 103 to about $10^9$ CAR-T cells/kg. In some embodiments, the CAR-T cells are CD19-specific CAR-T cells. In some cases, an amount of CD19-specific CAR-T cells comprises about $10^4$ to about $10^9$ CAR-T cells/kg. In some cases, an amount of CD19-specific CAR-T cells comprises about $10^5$ to about $10^9$ CAR-T cells/kg. In some cases, an amount of CD19-specific CAR-T cells comprises about $10^5$ to about 108 CAR-T cells/kg. In some cases, an amount of CD19-specific CAR-T cells comprises about $10^5$ to about $10^7$ CAR-T cells/kg. In some cases, an amount of CD19-specific CAR-T cells comprises about $10^6$ to about $10^9$ CAR-T cells/kg. In some cases, an amount of CD19-specific CAR-T cells comprises about $10^6$ to about 108 CAR-T cells/kg. In some cases, an amount of CD19-specific CAR-T cells comprises about $10^7$ to about $10^9$ CAR-T cells/kg. In some cases, an amount of CD19-specific CAR-T cells comprises about $10^5$ to about $10^6$ CAR-T cells/kg. In some cases, an amount of CD19-specific CAR-T cells comprises about $10^6$ to about $10^7$ CAR-T cells/kg. In some cases, an amount of CD19-specific CAR-T cells comprises about $10^7$ to about 108 CAR-T cells/kg. In some cases, an amount of CD19-specific CAR-T cells comprises about $10^8$ to about $10^9$ CAR-T cells/kg. In some instances, an amount of CD19-specific CAR-T cells comprises about $10^9$ CAR-T cells/kg. In some instances, an amount of CD19-specific CAR-T cells comprises about $10^8$ CAR-T cells/kg. In some instances, an amount of CD19-specific CAR-T cells comprises about $10^7$ CAR-T cells/kg. In some instances, an amount of CD19-specific CAR-T cells comprises about $10^6$ CAR-T cells/kg. In some instances, an amount of CD19-specific CAR-T cells comprises about $10^5$ CAR-T cells/kg. In some instances, an amount of CD19-specific CAR-T cells comprises about $10^4$ CAR-T cells/kg. In some instances, an amount of CD19-specific CAR-T cells comprises about 103 CAR-T cells/kg. In some instances, an amount of CD19-specific CAR-T cells comprises about $10^2$ CAR-T cells/kg.

In some embodiments, the modified T cells are engineered TCR T-cells. In some cases, an amount of engineered TCR T− cells comprises about $10^2$ to about $10^9$ TCR cells/kg. In some cases, an amount of engineered TCR T− cells comprises about 103 to about $10^9$ TCR cells/kg. In some cases, an amount of engineered TCR T− cells comprises about $10^4$ to about $10^9$ TCR cells/kg. In some cases, an amount of engineered TCR T− cells comprises about $10^5$ to about $10^9$ TCR cells/kg. In some cases, an amount of engineered TCR cells comprises about $10^5$ to about $10^8$ TCR cells/kg. In some cases, an amount of engineered TCR cells comprises about $10^5$ to about $10^7$ TCR cells/kg. In some cases, an amount of engineered TCR cells comprises about $10^6$ to about $10^9$ TCR cells/kg. In some cases, an amount of engineered TCR cells comprises about $10^6$ to about $10^8$ TCR cells/kg. In some cases, an amount of engineered TCR cells comprises about $10^7$ to about $10^9$ TCR cells/kg. In some cases, an amount of engineered TCR cells comprises about $10^5$ to about $10^6$ TCR cells/kg. In some cases, an amount of engineered TCR cells comprises about $10^6$ to about $10^7$ TCR cells/kg. In some cases, an amount of engineered TCR cells comprises about $10^7$ to about $10^8$ TCR cells/kg. In some cases, an amount of engineered TCR cells comprises about $10^8$ to about $10^9$ TCR cells/kg. In some instances, an amount of engineered TCR cells comprises about $10^9$ TCR cells/kg. In some instances, an amount of engineered TCR cells comprises about $10^8$ TCR cells/kg. In some instances, an amount of engineered TCR cells comprises about $10^7$ TCR cells/kg. In some instances, an amount of engineered TCR cells comprises about $10^6$ TCR cells/kg. In some instances, an amount of engineered TCR cells comprises about $10^5$ TCR cells/kg. In some instances, an amount of engineered TCR cells comprises about $10^4$ TCR cells/kg. In some instances, an amount of engineered TCR cells comprises about $10^3$ TCR cells/kg. In some instances, an amount of engineered TCR cells comprises about $10^2$ TCR cells/kg.

Pharmaceutical Compositions and Dosage Forms

In some embodiments, disclosed herein are compositions comprising a polynucleotide or polypeptide disclosed herein for administration in a subject. In some instances, are modified effector cell compositions encoding a polynucleotide or polypeptide disclosed herein, and optionally containing a cytokine and/or an additional therapeutic agent. In some instances, also included herein are vectors encoding polypeptide constructs for expressing cell tags for modification of an effector cell.

In some instances, pharmaceutical compositions of a modified effector cell or a vector encoding polypeptide constructs and a chimeric antigen receptor are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intra-articular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Proliferative disease" as referred to herein means a unifying concept that excessive proliferation of cells and turnover of cellular matrix contribute significantly to the pathogenesis of several diseases, including cancer is presented.

"Patient" as used herein refers to a mammalian subject diagnosed with or suspected of having or developing a physiological condition, for instance a cancer or an autoimmune condition or an infection. In some embodiments, the term "patient" refers to a mammalian subject with a higher than average likelihood of developing cancer. Exemplary patients may be humans, apes, dogs, pigs, cattle, cats, horses, goats, sheep, rodents and other mammalians that can benefit from the therapies disclosed herein. Exemplary human patients can be male and/or female.

"Administering" is referred to herein as providing the compositions of the present disclosure to a patient. By way of example and not limitation, composition administration, e.g., injection, may be performed by intravenous (i.v.) injection, sub-cutaneous (s.c.) injection, intradermal (i.d.) injection, intraperitoneal (i.p.) injection, or intramuscular (i.m.) injection. One or more such routes may be employed.

Parenteral administration can be, for example, by bolus injection or by gradual perfusion over time. Alternatively, or concurrently, administration may be by the oral route. Additionally, administration may also be by surgical deposition of a bolus or pellet of cells, or positioning of a medical device.

"A patient in need thereof" or "subject in need thereof" is referred to herein as a patient or subject diagnosed with or suspected of having a disease or disorder, for instance, but not restricted to a proliferative disorder such as cancer. In one embodiment, the patient or subject has or is likely to develop solid tumors or leukemia. In some embodiments leukemia can be, for instance, acute lymphoblastic leukemia (ALL), acute myeloid leukemia (AML), chronic lymphocytic leukemia (CLL) and chronic myeloid leukemia (CML).

The compositions of the present disclosure may comprises host cells expressing the inventive nucleic acid sequences, or a vector comprising the inventive nucleic acid sequence, in an amount that is effective to treat or prevent proliferative disorders. As used herein, the terms "treatment," "treating," and the like refer to obtaining a desired pharmacologic and/or physiologic effect. In embodiments, the effect is therapeutic, i.e., the effect partially or completely cures a disease and/or adverse symptom attributable to the disease. To this end, the inventive method comprises administering a "therapeutically effective amount" of the composition comprising the host cells expressing the inventive nucleic acid sequence, or a vector comprising the inventive nucleic acid sequences.

A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the inventive nucleic acid sequences to elicit a desired response in the individual.

Alternatively, the pharmacologic and/or physiologic effect may be "prophylactic," i.e., the effect completely or partially prevents a disease or symptom thereof.

A "prophylactically effective amount" refers to an amount effective, at dosages and for periods of time necessary, to achieve a desired prophylactic result (e.g., prevention of disease onset).

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpynrolidone/vinyl acetate copolymer, crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and an anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween @ 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68@, F88@, and F10$^8$@, which are block copolymers of ethylene oxide and propylene oxide); and poloxamines (e.g., Tetronic 908@, also known as Poloxamine 908@, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include cells encoding polypeptide constructs expressing one or more of the truncated non-immunogenic polypeptides described herein (e.g., CD20 or CD52). Optionally, the cells may additionally contain one or more heterologous genes, for example a gene encoding a CAR, T-cell receptor and/or a cytokine. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

SEQUENCES

Provided below is a representative list of certain sequences included in embodiments provided herein.

| Sequence Name | SEQ ID NO | Sequence |
|---|---|---|
| GMCSFR alpha signal peptide (nt) | 1 | atgcttctcctggtgacaagccttctgctctgtgagttaccacacccagcattcctcct gatccca |
| GMCSFR alpha signal peptide (aa) | 2 | MLLLVTSLLLCELPHPAFLLIP |
| Ig Kappa signal peptide (nt) | 3 | atgaggctccctgctcagctcctggggctgctaatgctctgggtcccaggatccagtgg g |
| Ig Kappa signal peptide (aa) | 4 | MRLPAQLLGLLMLWVPGSSG |
| Immunoglobulin E signal peptide (nt) | 5 | atggattggacctggattctgtttctggtggccgctgccacaagagtgcacagc |
| Immunoglobulin E signal peptide (aa) | 6 | MDWTWILFLVAAATRVHS |
| CD8α signal peptide (nt) | 7 | atggcgctgcccgtgaccgccttgctcctgccgctggccttgctgctccacgccgccag gccg |
| CD8α signal peptide (aa) | 8 | MALPVTALLLPLALLLHAARP |
| TVB2(T21A) signal peptide (nt) | 9 | atgggcaccagcctcctctgctggatggccctgtgtctcctgggggcagatcacgcaga tgct |
| TVB2(T21A) signal peptide (aa) | 10 | MGTSLLCWMALCLLGADHADA |
| CD52 signal peptide (nt) | 11 | atgaagcgcttcctcttcctcctactcaccatcagcctcctggttatggtacagataca aactggactctca |
| CD52 signal peptide (aa) | 12 | MKRFLFLLLTISLLVMVQIQTGLS |
| Low-affinity nerve growth factor receptor (LNGFR, TNFRSF16) signal peptide (nt) | 13 | atgggggcaggtgccaccggccgcgccatggacgggccgcgcctgctgctgttgctgct tctgggggtgtcccttggaggtgcc |

-continued

| Sequence Name | SEQ ID NO | Sequence |
|---|---|---|
| Low-affinity nerve growth factor receptor (LNGFR, TNFRSF16) signal peptide (aa) | 14 | MGAGATGRAMDGPRLLLLLLLGVSLGGA |
| GSG linker (nt) | 15 | ggaagcgga |
| GSG linker (aa) | 16 | GSG |
| SGSG linker (nt) | 17 | agtggcagcggc |
| SGSG linker (aa) | 18 | SGSG |
| (G4S)3 Linker (nt) | 19 | ggcggaggcggaagcggaggcggaggctccggcggaggcggaagc |
| (G4S)3 Linker (aa) | 20 | GGGGSGGGGSGGGGS |
| (G4S)4 Linker (nt) | 21 | Ggtggcggtggctcgggcggtggtgggtcgggtggcggcggatctggtggcggtggctc g |
| (G4S)4 Linker (aa) | 22 | GGGGSGGGGSGGGGSGGGGS |
| Whitlow Linker (nt) | 23 | ggcagcacctccggcagcggcaagcctggcagcggcgagggcagcaccaagggc |
| Whitlow Linker (aa) | 24 | GSTSGSGKPGSGEGSTKG |
| Glycophorin A (E91-R116) (nt) | 25 | gagataacactcattatttttggggtgatggctggtgttattggaacgatcctcttaat ttcttacggtattcgccga |
| Glycophorin A (E91-R116) (aa) | 26 | EITLIIFGVMAGVIGTILLISYGIRR |
| Glycophorin A (192-I114) (nt) | 27 | ataacactcattatttttggggtgatggctggtgttattggaacgatcctcttaatttc ttacggtatt |
| Glycophorin A (192-I114) (aa) | 28 | ITLIIFGVMAGVIGTILLISYGI |
| Glycophorin A (I92-L109). Integrin B3 (A737-W741) chimera (nt) | 29 | ataacactcattatttttggggtgatggctggtgttattggaacgatcctcttagccct gctcatctgg |
| Glycophorin A (I92-L109). Integrin B3 (A737-W741) chimera (aa) | 30 | ITLIIFGVMAGVIGTILLALLIW |
| CD3 zeta (CD247) transmembrane domain (nt) | 31 | ctctgctacctgctggatggaatcctcttcatctatggtgtcattctcactgccttgtt cctg |
| CD3 zeta (CD247) transmembrane domain (aa) | 32 | LCYLLDGILFIYGVILTALFL |
| CD8α transmembrane domain (nt) | 33 | atctacatctgggcccctctggccggcacctgtggcgtgctgctgctgagcctggtcat caccctgtactgcaaccaccggaat |
| CD8α transmembrane domain (aa) | 34 | IYIWAPLAGTCGVLLLSLVITLYCNHRN |
| CD28 transmembrane domain (nt) | 35 | ttttgggtgctggtggtggttggtggagtcctggcttgctatagcttgctagtaacagt ggcctttattattttctgggtg |

-continued

| Sequence Name | SEQ ID NO | Sequence |
|---|---|---|
| CD28 transmembrane domain (aa) | 36 | FWVLVVVGGVLACYSLLVTVAFIIFWV |
| Cytotoxic T-lymphocyte protein 4 transmembrane domain (nt) | 37 | ttcctcctctggatccttgcagcagttagttcggggttgtttttttatagctttctcct caca |
| Cytotoxic T-lymphocyte protein 4 transmembrane domain (aa) | 38 | FLLWILAAVSSGLFFYSFLLT |
| Low-affinity nerve growth factor receptor (LNGFR, TNFRSF16) transmembrane domain (nt) | 39 | ctcatccctgtctattgctccatcctggctgctgtggttgtgggccttgtggcctacat agccttc |
| Low-affinity nerve growth factor receptor (LNGFR, TNFRSF16) transmembrane domain (aa) | 40 | LIPVYCSILAAVVVGLVAYIAF |
| Porcine teschovirus-1 2A region (P2A) (nt) | 41 | gcaacgaacttctctctcctaaaacaggctggtgatgtggaggagaatcctggtcca |
| Porcine teschovirus-1 2A region (P2A) (aa) | 42 | ATNFSLLKQAGDVEENPGP |
| Equine rhinitis A virus 2A region (E2A) (nt) | 43 | cagtgtactaattatgctctcttgaaattggctggagatgttgagagcaaccctggacc t |
| Equine rhinitis A virus 2A region (E2A) (aa) | 44 | QCTNYALLKLAGDVESNPGP |
| *Thosea asigna* virus 2A region (T2A) (nt) | 45 | gagggcagaggaagtctgctaacatgcggtgacgtcgaggagaatcctggacct |
| *Thosea asigna* virus 2A region (T2A) (aa) | 46 | EGRGSLLTCGDVEENPGP |
| Foot- and -mouth disease virus 2A region (F2A) (nt) | 47 | gtcaaacagaccctaaactttgatctgctaaaactggccggggatgtggaaagtaatcc cggcccc |
| Foot-and-mouth disease virus 2A region (F2A) (aa) | 48 | VKQTLNFDLLKLAGDVESNPGP |
| EMCV IRES (nt) | 49 | ccccctctccctccccccccccctaacgttactggccgaagccgcttggaataaggccgg tgtgcgtttgtctatatgttattttccaccatattgccgtcttttggcaatgtgagggc ccggaaacctggccctgtcttcttgacgagcattcctaggggtctttcccctctcgcca aaggaatgcaaggtctgttgaatgtcgtgaaggaagcagttcctctggaagcttcttga agacaaacaacgtctgtagcgaccctttgcaggcagcggaaccccccacctggcgacag |

-continued

| Sequence Name | SEQ ID NO | Sequence |
|---|---|---|
| | | gtgcctctgcggccaaaagccacgtgtataagatacacctgcaaaggcggcacaacccc<br>agtgccacgttgtgagttggatagttgtggaaagagtcaaatggctctcctcaagcgta<br>ttcaacaaggggctgaaggatgcccagaaggtaccccattgtatgggatctgatctggg<br>gcctcggtgcacatgctttacatgtgtttagtcgaggttaaaaaacgtctaggccccc<br>gaaccacggggacgtggttttcctttgaaaaacacgatc |
| Epidermal growth factor receptor (EGFR) isoform a precursor (aa) | 50 | MRPSGTAGAALLALLAALCPASRALEEKKVCQGTSNKLTQLGTFEDHFLSLQRMFNNCE<br>VVLGNLEITYVQRNYDLSFLKTIQEVAGYVLIALNTVERIPLENLQIIRGNMYYENSYA<br>LAVLSNYDANKTGLKELPMRNLQEILHGAVRFSNNPALCNVESIQWRDIVSSDFLSNMS<br>MDFQNHLGSCQKCDPSCPNGSCWGAGEENCQKLTKIICAQQCSGRCRGKSPSDCCHNQC<br>AAGCTGPRESDCLVCRKFRDEATCKDTCPPLMLYNPTTYQMDVNPEGKYSFGATCVKKC<br>PRNYVVTDHGSCVRACGADSYEMEEDGVRKCKKCEGPCRKVCNGIGIGEFKDSLSINAT<br>NIKHFKNCTSISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVIISGNKNLCYA<br>NTINWKKLFGTSGQKTKIISNRGENSCKATGQVCHALCSPEGCWGPEPRDCVSCRNVSR<br>GRECVDKCNLLEGEPREFVENSECIQCHPECLPQAMNITCTGRGPDNCIQCAHYIDGPH<br>CVKTCPAGVMGENNTLVWKYADAGHVCHLCHPNCTYGCTGPGLEGCPTNGPKIPSIATG<br>MVGALLLLLVVALGIGLFMRRRHIVRKRTLRRLLQERELVEPLTPSGEAPNQALLRILK<br>ETEFKKIKVLGSGAFGTVYKGLWIPEGEKVKIPVAIKELREATSPKANKEILDEAYVMA<br>SVDNPHVCRLLGICLTSTVQLITQLMPFGCLLDYVREHKDNIGSQYLLNWCVQIAKGMN<br>YLEDRRLVHRDLAARNVLVKTPQHVKITDFGLAKLLGAEEKEYHAEGGKVPIKWMALES<br>ILHRIYTHQSDVWSYGVTVWELMTFGSKPYDGIPASEISSILEKGERLPQPPICTIDVY<br>MIMVKCWMIDADSRPKFRELIIEFSKMARDPQRYLVIQGDERMHLPSPTDSNFYRALMD<br>EEDMDDVVDADEYLIPQQGFFSSPSTSRTPLLSSLSATSNNSTVACIDRNGLQSCPIKE<br>DSFLQRYSSDPTGALTEDSIDDTFLPVPEYINQSVPKRPAGSVQNPVYHNQPLNPAPSR<br>DPHYQDPHSTAVGNPEYLNTVQPTCVNSTFDSPAHWAQKGSHQISLDNPDYQQDFFPKE<br>AKPNGIFKGSTAENAEYLRVAPQSSEFIGA |
| Receptor tyrosine-protein kinase ErbB2 (HER2) isoform a precursor (aa) | 51 | MELAALCRWGLLLALLPPGAASTQVCTGTDMKLRLPASPETHLDMLRHLYQGCQVVQGN<br>LELTYLPTNASLSFLQDIQEVQGYVLIAHNQVRQVPLQRLRIVRGTQLFEDNYALAVLD<br>NGDPLNNTTPVTGASPGGLRELQLRSLTEILKGGVLIQRNPQLCYQDTILWKDIFHKNN<br>QLALTLIDTNRSRACHPCSPMCKGSRCWGESSEDCQSLTRTVCAGGCARCKGPLPTDCC<br>HEQCAAGCTGPKHSDCLACLHFNHSGICELHCPALVTYNTDTFESMPNPEGRYTFGASC<br>VTACPYNYLSTDVGSCTLVCPLHNQEVTAEDGTQRCEKCSKPCARVCYGLGMEHLREVR<br>AVTSANIQEFAGCKKIFGSLAFLPESFDGDPASNTAPLQPEQLQVFETLEEITGYLYIS<br>AWPDSLPDLSVFQNLQVIRGRILHNGAYSLTLQGLGISWLGLRSLRELGSGLALIHHNT<br>HLCFVHTVPWDQLFRNPHQALLHTANRPEDECVGEGLACHQLCARGHCWGPGPTQCVNC<br>SQFLRGQECVEECRVLQGLPREYVNARHCLPCHPECQPQNGSVTCFGPEADQCVACAHY<br>KDPPFCVARCPSGVKPDLSYMPIWKFPDEEGACQPCPINCTHSCVDLDDKGCPAEQRAS<br>PLTSIISAVVGILLVVVLGVVFGILIKRRQQKIRKYTMRRLLQETELVEPLTPSGAMPN<br>QAQMRILKETELRKVKVLGSGAFGTVYKGIWIPDGENVKIPVAIKVLRENTSPKANKEI<br>LDEAYVMAGVGSPYVSRLLGICLTSTVQLVTQLMPYGCLLDHVRENRGRLGSQDLLNWC<br>MQIAKGMSYLEDVRLVHRDLAARNVLVKSPNHVKITDFGLARLLDIDETEYHADGGKVP<br>IKWMALESILRRRFTHQSDVWSYGVTVWELMTFGAKPYDGIPAREIPDLLEKGERLPQP<br>PICTIDVYMIMVKCWMIDSECRPRFRELVSEFSRMARDPQRFVVIQNEDLGPASPLDST<br>FYRSLLEDDDMGDLVDAEEYLVPQQGFFCPDPAPGAGGMVHHRHRSSSTRSGGGDLTLG<br>LEPSEEEAPRSPLAPSEGAGSDVFDGDLGMGAAKGLQSLPTHDPSPLQRYSEDPTVPL<br>PSETDGYVAPLTCSPQPEYVNQPDVRPQPPSPREGPLPAARPAGATLERPKTLSPGKNG<br>VVKDVFAFGGAVENPEYLTPQGGAAPQPHPPPAFSPAFDNLYYWDQDPPERGAPPSTFK<br>GTPTAENPEYLGLDVPV |
| Receptor tyrosine-protein kinase ErbB3 (HER3) isoform 1 precursor (aa) | 52 | MRANDALQVLGLLFSLARGSEVGNSQAVCPGTLNGLSVTGDAENQYQTLYKLYERCEVV<br>MGNLEIVLTGHNADLSFLQWIREVTGYVLVAMNEFSTLPLPNLRVVRGTQVYDGKFAIF<br>VMLNYNTNSSHALRQLRLTQLTEILSGGVYIEKNDKLCHMDTIDWRDIVRDRDAEIVVK<br>DNGRSCPPCHEVCKGRCWGPGSEDCQTLTKTICAPQCNGHCFGPNPNQCCHDECAGGCS<br>GPQDTDCFACRHFNDSGACVPRCPQPLVYNKLTFQLEPNPHTKYQYGGVCVASCPHNFV<br>VDQTSCVRACPPDKMEVDKNGLKMCEPCGGLCPKACEGTGSGSRFQTVDSSNIDGFVNC<br>TKILGNLDFLITGLNGDPWHKIPALDPEKLNVFRTVREITGYLNIQSWPPHMHNFSVFS<br>NLTTIGGRSLYNRGFSLLIMKNLNVTSLGFRSLKEISAGRIYISANRQLCYHHSLNWTK<br>VLRGPTEERLDIKHNRPRRDCVAEGKVCDPLCSSGGCWGPGPGQCLSCRNYSRGGVCVT<br>HCNFLNGEPREFAHEAECFSCHPECQPMEGTATCNGSGSDTCAQCAHFRDGPHCVSSCP<br>HGVLGAKGPIYKYPDVQNECRPCHENCTQGCKGPELQDCLGQTLVLIGKTHLTMALTVI<br>AGLVVIFMMLGGTFLYWRGRRIQNKRAMRRYLERGESIEPLDPSEKANKVL<br>ARIFKETELRKLKVLGSGVFGTVHKGVWIPEGESIKIPVCIKVIEDKSGRQSFQAVTDH<br>MLAIGSLDHAHIVRLLGLCPGSSLQLVTQYLPLGSLLDHVRQHRGALGPQLLLNWGVQI<br>AKGMYYLEEHGMVHRNLAARNVLLKSPSQVQVADFGVADLLPPDDKQLLYSEAKTPIKW<br>MALESIHFGKYTHQSDVWSYGVTVWELMTFGAEPYAGLRLAEVPDLLEKGERLAQPQIC<br>TIDVYMVMVKCWMIDENIRPTFKELANEFTRMARDPPRYLVIKRESGPGIAPGPEPHGL<br>TNKKLEEVELEPELDLDLDLEAEEDNLATTTLGSALSLPVGTLNRPRGSQSLLSP<br>SSGYMPMNQGNLGESCQESAVSGSSERCPRPVSLHPMPRGCLASESSEGHVTGSEAELQ<br>EKVSMCRSRSRSRSPRPRGDSAYHSQRHSLLTPVTPLSPPGLEEEDVNGYVMPDTHLKG<br>TPSSREGTLSSVGLSSVLGTEEEDEDEEYEYMNRRRRHSPPHPPRPSSLEELGYEYMDV<br>GSDLSASLGSTQSCPLHPVPIMPTAGTTPDEDYEYMNRQRDGGGPGGDYAAMGACPASE<br>QGYEEMRAFQGPGHQAPHVHYARLKTLRSLEATDSAFDNPDYWHSRLFPKANAQRT |

-continued

| Sequence Name | SEQ ID NO | Sequence |
|---|---|---|
| Receptor tyrosine-protein kinase ErbB4 (HER4) isoform JM-a/CVT-1 precursor (aa) | 53 | MKPATGLWVWVSLLVAAGTVQPSDSQSVCAGTENKLSSLSDLEQQYRALRKYYENCEVV<br>MGNLEITSIEHNRDLSFLRSVREVTGYVLVALNQFRYLPLENLRIIRGTKLYEDRYALA<br>IFLNYRKDGNFGLQELGLKNLTEILNGGVYVDQNKFLCYADTIHWQDIVRNPWPSNLTL<br>VSTNGSSGCGRCHKSCTGRCWGPTENHCQTLTRTVCAEQCDGRCYGPYVSDCCHRECAG<br>GCSGPKDTDCFACMNFNDSGACVTQCPQTFVYNPTTFQLEHNFNAKYTYGAFCVKKCPH<br>NFVVDSSSCVRACPSSKMEVEENGIKMCKPCTDICPKACDGIGTGSLMSAQTVDS<br>SNIDKFINCTKINGNLIFLVTGIHGDPYNAIEAIDPEKLNVFRTVREITGFLNIQSWPP<br>NMTDFSVFSNLVTIGGRVLYSGLSLLILKQQGITSLQFQSLKEISAGNIYITDNSNLCY<br>YHTINWTTLFSTINQRIVIRDNRKAENCTAEGMVCNHLCSSDGCWGPGPDQCLSCRRFS<br>RGRICIESCNLYDGEFREFENGSICVECDPQCEKMEDGLLTCHGPGPDNCTKCSHFKDG |
| | 54 | PNCVEKCPDGLQGANSFIFKYADPDRECHPCHPNCTQGCNGPTSHDCIYYPWTGHSTLP<br>QHARTPLIAAGVIGGLFILVIVGLTFAVYVRRKSIKKKRALRRFLETELVEPLTP<br>SGTAPNQAQLRILKETELKRVKVLGSGAFGTVYKGIWVPEGETVKIPVAIKILNETTGP<br>KANVEFMDEALIMASMDHPHLVRLLGVCLSPTIQLVTQLMPHGCLLEYVHEHKDNIGSQ<br>LLLNWCVQIAKGMMYLEERRLVHRDLAARNVLVKSPNHVKITDFGLARLLEGDEKEYNA<br>DGGKMPIKWMALECIHYRKFTHQSDVWSYGVTIWELMTFGGKPYDGIPTREIPDLLEKG<br>ERLPQPPICTIDVYMVMVKCWMIDADSRPKFKELAAEFSRMARDPQRYLVIQGDDRMKL<br>PSPNDSKFFQNLLDEEDLEDMMDAEEYLVPQAFNIPPPIYTSRARIDSNRSEIGH<br>SPPPAYTPMSGNQFVYRDGGFAAEQGVSVPYRAPTSTIPEAPVAQGATAEIFDDSCCNG<br>TLRKPVAPHVQEDSSTQRYSADPTVFAPERSPRGELDEEGYMTPMRDKPKQEYLNPVEE<br>NPFVSRRKNGDLQALDNPEYHNASNGPPKAEDEYVNEPLYLNTFANTLGKAEYLKNNIL<br>SMPEKAKKAFDNPDYWNHSLPPRSTLQHPDYLQEYSTKYFYKQNGRIRPIVAENPEYLS<br>EFSLKPGTVLPPPPYRHRNTVV<br>MKPATGLWVWVSLLVAAGTVQPSDSQSVCAGTENKLSSLSDLEQQYRALRKYYENCEVV<br>MGNLEITSIEHNRDLSFLRSVREVTGYVLVALNQFRYLPLENLRIIRGTKLYEDRYALA<br>IFLNYRKDGNFGLQELGLKNLTEILNGGVYVDQNKFLCYADTIHWQDIVRNPWPSNLTL<br>VSTNGSSGCGRCHKSCTGRCWGPTENHCQTLTRTVCAEQCDGRCYGPYVSDCCHRECAG<br>GCSGPKDTDCFACMNFNDSGACVTQCPQTFVYNPTTFQLEHNFNAKYTYGAFCVKKCPH |
| Receptor tyrosine-protein kinase ErbB4 (HER4) isoform JM-b (isoform X7) precursor (aa) | | NFVVDSSSCVRACPSSKMEVEENGIKMCKPCTDICPKACDGIGTGSLMSAQTVDSSNID<br>KFINCTKINGNLIFLVTGIHGDPYNAIEAIDPEKLNVFRTVREITGFLNIQSWPPNMTD<br>FSVFSNLVTIGGRVLYSGLSLLILKQQGITSLQFQSLKEISAGNIYITDNSNLCYYHTI<br>NWTTLFSTINQRIVIRDNRKAENCTAEGMVCNHLCSSDGCWGPGPDQCLSCRRFSRGRI<br>CIESCNLYDGEFREFENGSICVECDPQCEKMEDGLLTCHGPGPDNCTKCSHFKDGPNCV<br>EKCPDGLQGANSFIFKYADPDRECHPCHPNCTQGCIGSSIEDCIGLMDRTPLIAAGVIG<br>GLFILVIVGLTFAVYVRRKSIKKKRALRRFLETELVEPLTPSGTAPNQAQLRILKETEL<br>KRVKVLGSGAFGTVYKGIWVPEGETVKIPVAIKILNETTGPKANVEFMDEALIMASMDH<br>PHLVRLLGVCLSPTIQLVTQLMPHGCLLEYVHEHKDNIGSQLLLNWCVQIAKGMMYLEE<br>RRLVHRDLAARNVLVKSPNHVKITDFGLARLLEGDEKEYNADGGKMPIKWMALECIHYR<br>KFTHQSDVWSYGVTIWELMTFGGKPYDGIPTREIPDLLEKGERLPQPPICTIDVYMVMV<br>KCWMIDADSRPKFKELAAEFSRMARDPQRYLVIQGDDRMKLPSPNDSKFFQNLLDEEDL<br>EDMMDAEEYLVPQAFNIPPPIYTSRARIDSNRSEIGHSPPPAYTPMSGNQFVYRDGGFA<br>AEQGVSVPYRAPTSTIPEAPVAQGATAEIFDDSCCNGTLRKPVAPHVQEDSSTQRYSAD<br>PTVFAPERSPRGELDEEGYMTPMRDKPKQEYLNPVEENPFVSRRKNGDLQALDNPEYHN<br>ASNGPPKAEDEYVNEPLYLNTFANTLGKAEYLKNNILSMPEKAKKAFDNPDYWNHSLPP<br>RSTLQHPDYLQEYSTKYFYKQNGRIRPIVAENPEYLSEFSLKPGTVLPPPPYRHRNTVV |
| Truncated EGFR (huEGFRt) (Her1t) (aa) | 55 | RKVCNGIGIGEFKDSLSINATNIKHFKNCTSISGDLHILPVAFRGDSFTH<br>TPPLDPQELDILKTVKEITGFLLIQAWPENRTDLHAFENLEIIRGRTKQH<br>GQFSLAVVSLNITSLGLRSLKEISDGDVIISGNKNLCYANTINWKKLFGT<br>SGQKTKIISNRGENSCKATGQVCHALCSPEGCWGPEPRDCVSCRNVSRGR<br>ECVDKCNLLEGEPREFVENSECIQCHPECLPQAMNITCTGRGPDNCIQCA<br>HYIDGPHCVKTCPAGVMGENNTLVWKYADAGHVCHLCHPNCTYGCTGPGL<br>EGCPTNGPKIPSIATGMVGALLLLLVVALGIGLFM |
| EGFR truncated design 1 (Her1 truncated design 1) (HER1t1) (nt) | 56 | Cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctctggtggcggtggctc<br>gggcggtggtgggtcgggtggcggcggatctggtggcggtggctcgttttgggtgctgg<br>tggtggttggtggagtcctggcttgctatagcttgctagtaacagtggcctttattatt<br>ttctgggtgaggagtaagaggagc |
| EGFR truncated design 1 (Her1 truncated design 1) (HER1t1) (aa) | 57 | RKVCNGIGIGEFKDSLSINATNIKHFKNCTSISGDLHILPVAFRGDSFTH<br>TPPLDPQELDILKTVKEITGFLLIQAWPENRTDLHAFENLEIIRGRTKQH<br>GQFSLAVVSLNITSLGLRSLKEISDGDVIISGNKNLCYANTINWKKLFGT<br>SGQKTKIISNRGENSCKATGQVCHALCSPEGCWGPEPRDCVSGGGGSGGG<br>GSGGGGSGGGGSFWVLVVVGGVLACYSLLVTVAFIIFWVRSKRS |

-continued

| Sequence Name | SEQ ID NO | Sequence |
|---|---|---|
| EGFR truncated design 2 (Her1 truncated design 2) (HER1t2) (nt) | 58 | Cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctcttgccggaatgtcag<br>ccgaggcagggaatgcgtggacaagggtggcggtggctcgggcggtggtgggtcgggtg<br>gcggcggatctggtggcggtggctcgttttgggtgctggtggtggttggtggagtcctg<br>gcttgctatagcttgctagtaacagtggcctttattattttctgggtgaggagtaagag<br>gagc |
| EGFR truncated design 2 (Her1 truncated design 2) (HER1t2) (aa) | 59 | RKVCNGIGIGEFKDSLSINATNIKHFKNCT<br>SISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVII<br>SGNKNLCYANTINWKKLFGTSGQKTKIISNRGENSCKATGQVCHALCSPE<br>GCWGPEPRDCVSCRNVSRGRECVDKGGGGSGGGGSGGGGSGGGGSFWVLV<br>VVGGVLACYSLLVTVAFIIFWVRSKRS |
| EGFR truncated design 3 (Her1 truncated design 3) (HER1t3) (nt) | 60 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctcttgccggaatgtcag<br>ccgaggcagggaatgcgtggacaagtgcaaccttctggagggtgagccaagggagtttg<br>tggagaactctgagtgcatacagggtggcggtggctcgggcggtggtgggtcgggtggc<br>ggcggatctggtggcggtggctcgttttgggtgctggtggtggttggtggagtcctggc<br>ttgctatagcttgctagtaacagtggcctttattattttctgggtgaggagtaagagga<br>gc |
| EGFR truncated design 3 (Her1 truncated design 3) (HER1t3) (aa) | 61 | RKVCNGIGIGEFKDSLSINATNIKHFKNCT<br>SISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVII<br>SGNKNLCYANTINWKKLFGTSGQKTKIISNRGENSCKATGQVCHALCSPE<br>GCWGPEPRDCVSCRNVSRGRECVDKCNLLEGEPREFVENSECIQGGGGSG<br>GGGSGGGGSGGGGSFWVLVVVGGVLACYSLLVTVAFIIFWVRSKRS |
| EGFR truncated design 4 (Her1 truncated design 4) (HER1t4) (nt) | 62 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctcttgccggaatgtcag<br>ccgaggcagggaatgcgtggacaagtgcaaccttctggagggtgagccaagggagtttg<br>tggagaactctgagtgcatacagtgccacccagagtgcctgcctcaggccatgaacatc<br>acctgcacaggacggggaccagacaactgtatccagggcggaggcggaagcggaggcgg<br>aggctccggcggaggcggaagcttttgggtgctggtggtggttggtggagtcctggctt<br>gctatagcttgctagtaacagtggcctttattattttctgggtgaggagtaagaggagc |
| EGFR truncated design 4 (Her1 truncated design 4) (HER1t4) (aa) | 63 | RKVCNGIGIGEFKDSLSINATNIKHFKNCT<br>SISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVII<br>SGNKNLCYANTINWKKLFGTSGQKTKIISNRGENSCKATGQVCHALCSPE<br>GCWGPEPRDCVSCRNVSRGRECVDKCNLLEGEPREFVENSECIQCHPECL<br>PQAMNITCTGRGPDNCIQGGGGSGGGGGGGSFWVLVVVGGVLACYSLL<br>VTVAFIIFWVRSKRS |
| EGFR truncated design 5 (Her1 truncated design 5) (HER1t5) (nt) | 64 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta |

-continued

| Sequence Name | SEQ ID NO | Sequence |
|---|---|---|
| | | tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctcttgccggaatgtcag<br>ccgaggcagggaatgcgtggacaagtgcaaccttctggagggtgagccaagggagtttg<br>tggagaactctgagtgcatacagtgccacccagagtgcctgcctcaggccatgaacatc<br>acctgcacaggacggggaccagacaactgtatccagtgtgcccactacattgacggccc<br>ccactgcgtcaagaccggcggaggcggaagcggaggcggaggctccggcggaggcggaa<br>gcttttgggtgctggtggtggttggtggagtcctggcttgctatagcttgctagtaaca<br>gtggcctttattattttctgggtgaggagtaagaggagc |
| EGFR truncated design 5 (Her1 truncated design 5) (HER1t5) (aa) | 65 | RKVCNGIGIGEFKDSLSINATNIKHFKNCT<br>SISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVII<br>SGNKNLCYANTINWKKLFGTSGQKTKIISNRGENSCKATGQVCHALCSPE<br>GCWGPEPRDCVSCRNVSRGRECVDKCNLLEGEPREFVENSECIQCHPECL<br>PQAMNITCTGRGPDNCIQCAHYIDGPHCVKTGGGGSGGGGSGGGGSFWVL<br>VVVGGVLACYSLLVTVAFIIFWVRSKRS |
| EGFR truncated design 6 (Her1 truncated design 6) (HER1t6) (nt) | 66 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctcttgccggaatgtcag<br>ccgaggcagggaatgcgtggacaagtgcaaccttctggagggtgagccaagggagtttg<br>tggagaactctgagtgcatacagtgccacccagagtgcctgcctcaggccatgaacatc<br>acctgcacaggacggggaccagacaactgtatccagtgtgcccactacattgacggccc<br>ccactgcgtcaagacctgcccggcaggagtcatgggagaaaacaacaccctggtctgga<br>agtacgcagacgccggccatgtgtgccacctgggcggaggcggaagcggaggcggaggc<br>tcctttttgggtgctggtggtggttggtggagtcctggcttgctatagcttgctagtaac<br>agtggcctttattattttctgggtgaggagtaagaggagc |
| EGFR truncated design 6 (Her1 truncated design 6) (HER1t6) (aa) | 67 | RKVCNGIGIGEFKDSLSINATNIKHFKNCT<br>SISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVII<br>SGNKNLCYANTINWKKLFGTSGQKTKIISNRGENSCKATGQVCHALCSPE<br>GCWGPEPRDCVSCRNVSRGRECVDKCNLLEGEPREFVENSECIQCHPECL<br>PQAMNITCTGRGPDNCIQCAHYIDGPHCVKTCPAGVMGENNTLVWKYADA<br>GHVCHLGGGGSGGGGSFWVLVVVGGVLACYSLLVTVAFIIFWVRSKRS |
| EGFR truncated design 7 (Her1 truncated design 7) (HER1t7) (nt) | 68 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctcttgccggaatgtcag<br>ccgaggcagggaatgcgtggacaagtgcaaccttctggagggtgagccaagggagtttg<br>tggagaactctgagtgcatacagtgccacccagagtgcctgcctcaggccatgaacatc<br>acctgcacaggacggggaccagacaactgtatccagtgtgcccactacattgacggccc<br>ccactgcgtcaagacctgcccggcaggagtcatgggagaaaacaacaccctggtctgga<br>agtacgcagacgccggccatgtgtgccacctgtgccatccaaactgcacctacggatgc<br>actgggccaggtcttgaaggctgtccaggtggcggtggcggcggatctttttgggtgct<br>ggtggtggttggtggagtcctggcttgctatagcttgctagtaacagtggcctttatta<br>ttttctgggtgaggagtaagaggagctaa |
| EGFR truncated design 7 (Her1 truncated design 7) (HER1t7) (aa) | 69 | RKVCNGIGIGEFKDSLSINATNIKHFKNCT<br>SISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVII<br>SGNKNLCYANTINWKKLFGTSGQKTKIISNRGENSCKATGQVCHALCSPE<br>GCWGPEPRDCVSCRNVSRGRECVDKCNLLEGEPREFVENSECIQCHPECL<br>PQAMNITCTGRGPDNCIQCAHYIDGPHCVKTCPAGVMGENNTLVWKYADA<br>GHVCHLCHPNCTYGCTGPGLEGCPGGGGGGSFWVLVVVGGVLACYSLLVT<br>VAFIIFWVRSKRS* |
| EGFR truncated design 8 (Her1 truncated design 8) (HER1t8) Ig | 70 | atgaggctccctgctcagctcctggggctgctaatgctctgggtcccaggatccagtgg<br>gcgcaaagtgtgtaacggaataggtattggtgaatttaaagactcactctccataaatg<br>ctacgaatattaaacacttcaaaaactgcacctccatcagtggcgatctccacatcctg<br>ccggtggcatttaggggtgactccttcacacatactcctcctctggatccacaggaact |

-continued

| Sequence Name | SEQ ID NO | Sequence |
|---|---|---|
| Kappa Signal Peptide (nt) | | ggatattctgaaaaccgtaaaggaaatcacagggtttttgctgattcaggcttggcctg<br>aaaacaggacggacctccatgcctttgagaacctagaaatcatacgcggcaggaccaag<br>caacatggtcagttttctcttgcagtcgtcagcctgaacataacatccttgggattacg<br>ctccctcaaggagataagtgatggagatgtgataatttcaggaaacaaaaatttgtgct<br>atgcaaatacaataaactggaaaaaactgtttgggacctccggtcagaaaaccaaaatt<br>ataagcaacagaggtgaaaacagctgcaaggccacaggccaggtctgccatgccttgtg<br>ctcccccgagggctgctggggcccggagcccagggactgcgtctctggtggcggtggct<br>cgggcggtggtgggtcgggtggcggcggatctggtggcggtggctcggagataacactc<br>attatttttggggtgatggctggtgttattggaacgatcctcttaatttcttacggtat<br>tcgccgaggaggtggaagc |
| EGFR truncated design 8 (Her1 truncated design 8) (HER1t8) Ig Kappa Signal Peptide (aa) | 71 | MRLPAQLLGLLMLWVPGSSGRKVCNGIGIGEFKDSLSINATNIKHFKNCT<br>SISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVII<br>SGNKNLCYANTINWKKLFGTSGQKTKIISNRGENSCKATGQVCHALCSPE<br>GCWGPEPRDCVSGGGGSGGGGSGGGGSGGGGSEITLIIFGVMAGVIGTIL<br>LISYGIRRGGGS |
| EGFR truncated design 8 (Her1 truncated design 8) (HER1t8) (nt) | 72 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctctggtggcggtggctc<br>gggcggtggtgggtcgggtggcggcggatctggtggcggtggctcggagataacactca<br>ttatttttggggtgatggctggtgttattggaacgatcctcttaatttcttacggtatt<br>cgccgaggaggtggaagc |
| EGFR truncated design 8 (Her1 truncated design 8) (HER1t8) (aa) | 73 | RKVCNGIGIGEFKDSLSINATNIKHFKNCTSISGDLHILPVAFRGDSFTHTPPLDPQEL<br>DILKTVKEITGFLLIQAWPENRTDLHAFENLEIIRGRTKQHGQFSLAVVSLNITSLGLR<br>SLKEISDGDVIISGNKNLCYANTINWKKLFGTSGQKTKIISNRGENSCKATGQVCHALC<br>SPEGCWGPEPRDCVSGGGGSGGGGSGGGGSGGGGSEITLIIFGVMAGVIGTILLISYGI<br>RRGGGS |
| EGFR truncated design 9 (Her1 truncated design 9) (HER1t9) with Ig Kappa Signal Peptide (nt) | 74 | atgaggctccctgctcagctcctggggctgctaatgctctgggtcccaggatccagtgg<br>gcgcaaagtgtgtaacggaataggtattggtgaatttaaagactcactctccataaatg<br>ctacgaatattaaacacttcaaaaactgcacctccatcagtggcgatctccacatcctg<br>ccggtggcatttaggggtgactccttcacacatactcctcctctggatccacaggaact<br>ggatattctgaaaaccgtaaaggaaatcacagggtttttgctgattcaggcttggcctg<br>aaaacaggacggacctccatgcctttgagaacctagaaatcatacgcggcaggaccaag<br>caacatggtcagttttctcttgcagtcgtcagcctgaacataacatccttgggattacg<br>ctccctcaaggagataagtgatggagatgtgataatttcaggaaacaaaaatttgtgct<br>atgcaaatacaataaactggaaaaaactgtttgggacctccggtcagaaaaccaaaatt<br>ataagcaacagaggtgaaaacagctgcaaggccacaggccaggtctgccatgccttgtg<br>ctcccccgagggctgctggggcccggagcccagggactgcgtctctggtggcggtggct<br>cgggcggtggtgggtcgggtggcggcggatctggtggcggtggctcgataacactcatt<br>atttttggggtgatggctggtgttattggaacgatcctcttaatttcttacggtattgg<br>aggtggaagc |
| EGFR truncated design 9 (Her1 truncated design 9) (HER1t9) with Ig Kappa Signal Peptide (aa) | 75 | MRLPAQLLGLLMLWVPGSSGRKVCNGIGIGEFKDSLSINATNIKHFKNCT<br>SISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVII<br>SGNKNLCYANTINWKKLFGTSGQKTKIISNRGENSCKATGQVCHALCSPE<br>GCWGPEPRDCVSGGGGSGGGGSGGGGSGGGGSITLIIFGVMAGVIGTILL<br>ISYGIGGGS |
| EGFR truncated design 9 (Her1 truncated design 9) (HER1t9) (nt) | 76 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctctggtggcggtggctc<br>gggcggtggtgggtcgggtggcggcggatctggtggcggtggctcgataacactcatta<br>tttttggggtgatggctggtgttattggaacgatcctcttaatttcttacggtattgga<br>ggtggaagc |
| EGFR truncated design 9 (Her1 | 77 | RKVCNGIGIGEFKDSLSINATNIKHFKNCTSISGDLHILPVAFRGDSFTHTPPLDPQEL<br>DILKTVKEITGFLLIQAWPENRTDLHAFENLEIIRGRTKQHGQFSLAVVSLNITSLGLR |

-continued

| Sequence Name | SEQ ID NO | Sequence |
|---|---|---|
| truncated design 9) (HER1t9) (aa) | | SLKEISDGDVIISGNKNLCYANTINWKKLFGTSGQKTKIISNRGENSCKATGQVCHALC<br>SPEGCWGPEPRDCVSGGGGSGGGGSGGGGSGGGGSITLIIFGVMAGVIGTILLISYGIG<br>GGS |
| EGFR truncated design 10 (Her1 truncated design 10) (HER1t10) with Ig Kappa Signal Peptide (nt) | 78 | atgaggctccctgctcagctcctggggctgctaatgctctgggtcccaggatccagtgg<br>gcgcaaagtgtgtaacggaataggtattggtgaatttaaagactcactctccataaatg<br>ctacgaatattaaacacttcaaaaactgcacctccatcagtggcgatctccacatcctg<br>ccggtggcatttaggggtgactccttcacacatactcctcctctggatccacaggaact<br>ggatattctgaaaaccgtaaaggaaatcacagggtttttgctgattcaggcttggcctg<br>aaaacaggacggacctccatgcctttgagaacctagaaatcatacgcggcaggaccaag<br>caacatggtcagttttctcttgcagtcgtcagcctgaacataacatccttgggattacg<br>ctccctcaaggagataagtgatggagatgtgataatttcaggaaacaaaaatttgtgct<br>atgcaaatacaataaactggaaaaaactgtttgggacctccggtcagaaaaccaaaatt<br>ataagcaacagaggtgaaaacagctgcaaggccacaggccaggtctgccatgccttgtg<br>ctcccccgagggctgctggggcccggagcccagggactgcgtctctggtggcggtggct<br>cgggcggtggtgggtcgggtggcggcggatctggtggcggtggctcgataacactcatt<br>atttttggggtgatggctggtgttattggaacgatcctcttagccctgctcatctgggg<br>aggtggaagc |
| EGFR truncated design 10 (Her1 truncated design 10) (HER1t10) with Ig Kappa Signal Peptide (aa) | 79 | MRLPAQLLGLLMLWVPGSSGRKVCNGIGIGEFKDSLSINATNIKHFKNCT<br>SISGDLHILPVAFRGDSFTHTPPLDPQELDILKTVKEITGFLLIQAWPEN<br>RTDLHAFENLEIIRGRTKQHGQFSLAVVSLNITSLGLRSLKEISDGDVII<br>SGNKNLCYANTINWKKLFGTSGQKTKIISNRGENSCKATGQVCHALCSPE<br>GCWGPEPRDCVSGGGGSGGGGSGGGGSGGGGSITLIIFGVMAGVIGTILL<br>ALLIWGGGS |
| EGFR truncated design 10 (Her1 truncated design 10) (HER1t10) (nt) | 80 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtctgccatgccttgtgc<br>tcccccgagggctgctggggcccggagcccagggactgcgtctctggtggcggtggctc<br>gggcggtggtgggtcgggtggcggcggatctggtggcggtggctcgataacactcatta<br>tttttggggtgatggctggtgttattggaacgatcctcttagccctgctcatctgggga<br>ggtggaagc |
| EGFR truncated design 10 (Her1 truncated design 10) (HER1t10) (aa) | 81 | RKVCNGIGIGEFKDSLSINATNIKHFKNCTSISGDLHILPVAFRGDSFTHTPPLDPQEL<br>DILKTVKEITGFLLIQAWPENRTDLHAFENLEIIRGRTKQHGQFSLAVVSLNITSLGLR<br>SLKEISDGDVIISGNKNLCYANTINWKKLFGTSGQKTKIISNRGENSCKATGQVCHALC<br>SPEGCWGPEPRDCVSGGGGSGGGGSGGGGSGGGGSITLIIFGVMAGVIGTILLALLIWG<br>GGS |
| EGFR truncated design 11 (Her1 truncated design 11) (HER1t11) with Ig Kappa Signal Peptide (nt) | 82 | atgaggctccctgctcagctcctggggctgctaatgctctgggtcccaggatccagtgg<br>gcgcaaagtgtgtaacggaataggtattggtgaatttaaagactcactctccataaatg<br>ctacgaatattaaacacttcaaaaactgcacctccatcagtggcgatctccacatcctg<br>ccggtggcatttaggggtgactccttcacacatactcctcctctggatccacaggaact<br>ggatattctgaaaaccgtaaaggaaatcacagggtttttgctgattcaggcttggcctg<br>aaaacaggacggacctccatgcctttgagaacctagaaatcatacgcggcaggaccaag<br>caacatggtcagttttctcttgcagtcgtcagcctgaacataacatccttgggattacg<br>ctccctcaaggagataagtgatggagatgtgataatttcaggaaacaaaaatttgtgct<br>atgcaaatacaataaactggaaaaaactgtttgggacctccggtcagaaaaccaaaatt<br>ataagcaacagaggtgaaaacagctgcaaggccacaggccaggtctgccatgccttgtg<br>ctcccccgagggctgctggggcccggagcccagggactgcgtctctggtggcggtggct<br>cgggcggtggtgggtcgggtggcggcggatctggtggcggtggctcgctctgctacctg<br>ctggatggaatcctcttcatctatggtgtcattctcactgccttgttcctgggaggtgg<br>aagc |
| EGFR truncated design 11 (Her1 truncated design 11) (HER1t11) with Ig Kappa Signal Peptide (aa) | 83 | MRLPAQLLGLLMLWVPGSSGRKVCNGIGIGEFKDSLSINATNIKHFKNCTSISGDLHIL<br>PVAFRGDSFTHTPPLDPQELDILKTVKEITGFLLIQAWPENRTDLHAFENLEIIRGRTK<br>QHGQFSLAVVSLNITSLGLRSLKEISDGDVIISGNKNLCYANTINWKKLFGTSGQKTKI<br>ISNRGENSCKATGQVCHALCSPEGCWGPEPRDCVSGGGGSGGGGSGGGGSGGGGSLCYL<br>LDGILFIYGVILTALFLGGGS |
| EGFR truncated design 11 (Her1 truncated design 11) (HER1t11) (nt) | 84 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc |

-continued

| Sequence Name | SEQ ID NO | Sequence |
|---|---|---|
| | | tccctcaaggagataagtgatggagatgtgataatttcaggaaacaaaaatttgtgcta tgcaaatacaataaactggaaaaaactgtttgggacctccggtcagaaaaccaaaatta taagcaacagaggtgaaaacagctgcaaggccacaggccaggtctgccatgccttgtgc tcccccgagggctgctggggcccggagcccagggactgcgtctctggtggcggtggctc gggcggtggtgggtcgggtggcggcggatctggtggcggtggctcgctctgctacctgc tggatggaatcctcttcatctatggtgtcattctcactgccttgttcctgggaggtgga agc |
| EGFR truncated design 11 (Her1 truncated design 11) (HER1t11) (aa) | 85 | RKVCNGIGIGEFKDSLSINATNIKHFKNCTSISGDLHILPVAFRGDSFTHTPPLDPQEL DILKTVKEITGFLLIQAWPENRTDLHAFENLEIIRGRTKQHGQFSLAVVSLNITSLGLR SLKEISDGDVIISGNKNLCYANTINWKKLFGTSGQKTKIISNRGENSCKATGQVCHALC SPEGCWGPEPRDCVSGGGGSGGGGSGGGGSGGGGSLCYLLDGILFIYGVILTALFLGGG S |
| Truncated EGFR-HER2 Chimera with GMCSFR alpha signal peptide (nt) | 86 | atgcttctcctggtgacaagccttctgctctgtgagttaccacacccagcattcctcct gatcccacgcaaagtgtgtaacggaataggtattggtgaatttaaagactcactctcca taaatgctacgaatattaaacacttcaaaaactgcacctccatcagtggcgatctccac atcctgccggtggcatttaggggtgactccttcacacatactcctcctctggatccaca ggaactggatattctgaaaaccgtaaaggaaatcacagggtttttgctgattcaggctt ggcctgaaaacaggacggacctccatgcctttgagaacctagaaatcatacgcggcagg accaagcaacatggtcagttttctcttgcagtcgtcagcctgaacataacatccttggg attacgctccctcaaggagataagtgatggagatgtgataatttcaggaaacaaaaatt tgtgctatgcaaatacaataaactggaaaaaactgtttgggacctccggtcagaaaacc aaaattataagcaacagaggtgaaaacagctgcaaggccacaggccaggcctgccacca gctgtgcgcccgagggcactgctggggtccagggcccacccagtgtgtcaactgcagcc agttccttcggggccaggagtgcgtggaggaatgccgagtactgcaggggctccccagg gagtatgtgaatgccaggcactgtttgccgtgccaccctgagtgtcagccccagaatgg ctcagtgacctgttttggaccggaggctgaccagtgtgtggcctgtgcccactataagg accctcccttctgcgtggcccgctgccccagcggtgtgaaacctgacctctcctacatg cccatctggaagtttccagatgaggagggcgcatgccagccttgccccatcaactgcac ccactcctgtgtggacctggatgacaagggctgccccgccgagcagagagccagccctc tgacgtccatcatctctgcggtggttggcattctgctggtcgtggtcttggggggtggtc tttgggatcctcatc |
| Truncated EGFR-HER2 Chimera with GMCSFR alpha signal peptide (aa) | 87 | MLLLVTSLLLCELPHPAFLLIPRKVCNGIGIGEFKDSLSINATNIKHFKN CTSISGDLHILPVAFRGDSFTHTPPLDPQELDILKTVKEITGFLLIQAWP ENRTDLHAFENLEIIRGRTKQHGQFSLAVVSLNITSLGLRSLKEISDGDV IISGNKNLCYANTINWKKLFGTSGQKTKIISNRGENSCKATGQACHQLCA RGHCWGPGPTQCVNCSQFLRGQECVEECRVLQGLPREYVNARHCLPCHPE CQPQNGSVTCFGPEADQCVACAHYKDPPFCVARCPSGVKPDLSYMPIWKF PDEEGACQPCPINCTHSCVDLDDKGCPAEQRASPLTSIISAVVGILLVVV LGVVFGILI |
| Truncated EGFR-HER2 Chimera (nt) | 88 | cgcaaagtgtgtaacggaataggtattggtgaatttaaagactcactctccataaatgc tacgaatattaaacacttcaaaaactgcacctccatcagtggcgatctccacatcctgc cggtggcatttaggggtgactccttcacacatactcctcctctggatccacaggaactg gatattctgaaaaccgtaaaggaaatcacagggtttttgctgattcaggcttggcctga aaacaggacggacctccatgcctttgagaacctagaaatcatacgcggcaggaccaagc aacatggtcagttttctcttgcagtcgtcagcctgaacataacatccttgggattacgc tccctcaaggagataagtgatggagatgtgataatttcaggaaacaaaaatttgtgcta tgcaaatacaataaactggaaaaaactgtttgggacctccggtcagaaaaccaaaatta taagcaacagaggtgaaaacagctgcaaggccacaggccaggcctgccaccagctgtgc gcccgagggcactgctggggtccagggcccacccagtgtgtcaactgcagccagttcct tcggggccaggagtgcgtggaggaatgccgagtactgcaggggctccccagggagtatg tgaatgccaggcactgtttgccgtgccaccctgagtgtcagccccagaatggctcagtg acctgttttggaccggaggctgaccagtgtgtggcctgtgcccactataaggaccctcc cttctgcgtggcccgctgccccagcggtgtgaaacctgacctctcctacatgcccatct ggaagtttccagatgaggagggcgcatgccagccttgccccatcaactgcacccactcc tgtgtggacctggatgacaagggctgccccgccgagcagagagccagccctctgacgtc catcatctctgcggtggttggcattctgctggtcgtggtcttggggggtggtctttggga tcctcatc |
| Truncated EGFR-HER2 Chimera (aa) | 89 | RKVCNGIGIGEFKDSLSINATNIKHFKN CTSISGDLHILPVAFRGDSFTHTPPLDPQELDILKTVKEITGFLLIQAWP ENRTDLHAFENLEIIRGRTKQHGQFSLAVVSLNITSLGLRSLKEISDGDV IISGNKNLCYANTINWKKLFGTSGQKTKIISNRGENSCKATGQACHQLCA RGHCWGPGPTQCVNCSQFLRGQECVEECRVLQGLPREYVNARHCLPCHPE CQPQNGSVTCFGPEADQCVACAHYKDPPFCVARCPSGVKPDLSYMPIWKF PDEEGACQPCPINCTHSCVDLDDKGCPAEQRASPLTSIISAVVGILLVVV LGVVFGILI |

-continued

| Sequence Name | SEQ ID NO | Sequence |
|---|---|---|
| Truncated EGFR-HER2 (delta 16) Chimera with GMCSFR alpha signal peptide (nt) | 90 | atgcttctcctggtgacaagccttctgctctgtgagttaccacacccagcattcctcct<br>gatcccacgcaaagtgtgtaacggaataggtattggtgaatttaaagactcactctcca<br>taaatgctacgaatattaaacacttcaaaaactgcacctccatcagtggcgatctccac<br>atcctgccggtggcatttaggggtgactccttcacacatactcctcctctggatccaca<br>ggaactggatattctgaaaaccgtaaaggaaatcacagggtttttgctgattcaggctt<br>ggcctgaaaacaggacggacctccatgcctttgagaacctagaaatcatacgcggcagg<br>accaagcaacatggtcagttttctcttgcagtcgtcagcctgaacataacatccttggg<br>attacgctccctcaaggagataagtgatggagatgtgataatttcaggaaacaaaaatt<br>tgtgctatgcaaatacaataaactggaaaaaactgtttgggacctccggtcagaaaacc<br>aaaattataagcaacagaggtgaaaacagctgcaaggccacaggccaggcctgccacca<br>gctgtgcgcccgagggcactgctggggtccagggcccacccagtgtgtcaactgcagcc<br>agttccttcggggccaggagtgcgtggaggaatgccgagtactgcaggggctccccagg<br>gagtatgtgaatgccaggcactgtttgccgtgccaccctgagtgtcagccccagaatgg<br>ctcagtgacctgttttggaccggaggctgaccagtgtgtggcctgtgcccactataagg<br>accctcccttctgcgtggcccgctgccccagcggtgtgaaacctgacctctcctacatg<br>cccatctggaagtttccagatgaggagggcgcatgccagccttgccccatcaactgcac<br>ccactcccctctgacgtccatcatctctgcggtggttggcattctgctggtcgtggtct<br>tgggggtggtctttgggatcctcatc |
| Truncated EGFR-HER2 (delta 16) Chimera with GMCSFR alpha signal peptide (aa) | 91 | MLLLVTSLLLCELPHPAFLLIPRKVCNGIGIGEFKDSLSINATNIKHFKN<br>CTSISGDLHILPVAFRGDSFTHTPPLDPQELDILKTVKEITGFLLIQAWP<br>ENRTDLHAFENLEIIRGRTKQHGQFSLAVVSLNITSLGLRSLKEISDGDV<br>IISGNKNLCYANTINWKKLFGTSGQKTKIISNRGENSCKATGQACHQLCA<br>RGHCWGPGPTQCVNCSQFLRGQECVEECRVLQGLPREYVNARHCLPCHPE<br>CQPQNGSVTCFGPEADQCVACAHYKDPPFCVARCPSGVKPDLSYMPIWKF<br>PDEEGACQPCPINCTHSPLTSIISAVVGILLVVVLGVVFGILI |
| Truncated EGFR-HER2 (delta 16) (nt) | 92 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggcctgccaccagctgtgc<br>gcccgagggcactgctggggtccagggcccacccagtgtgtcaactgcagccagttcct<br>tcggggccaggagtgcgtggaggaatgccgagtactgcaggggctccccagggagtatg<br>tgaatgccaggcactgtttgccgtgccaccctgagtgtcagccccagaatggctcagtg<br>acctgttttggaccggaggctgaccagtgtgtggcctgtgcccactataaggaccctcc<br>cttctgcgtggcccgctgccccagcggtgtgaaacctgacctctcctacatgcccatct<br>ggaagtttccagatgaggagggcgcatgccagccttgccccatcaactgcacccactcc<br>cctctgacgtccatcatctctgcggtggttggcattctgctggtcgtggtcttgggggt<br>ggtctttgggatcctcatc |
| Truncated EGFR-HER2 (delta 16) (aa) | 93 | RKVCNGIGIGEFKDSLSINATNIKHFKN<br>CTSISGDLHILPVAFRGDSFTHTPPLDPQELDILKTVKEITGFLLIQAWP<br>ENRTDLHAFENLEIIRGRTKQHGQFSLAVVSLNITSLGLRSLKEISDGDV<br>IISGNKNLCYANTINWKKLFGTSGQKTKIISNRGENSCKATGQACHQLCA<br>RGHCWGPGPTQCVNCSQFLRGQECVEECRVLQGLPREYVNARHCLPCHPE<br>CQPQNGSVTCFGPEADQCVACAHYKDPPFCVARCPSGVKPDLSYMPIWKF<br>PDEEGACQPCPINCTHSPLTSIISAVVGILLVVVLGVVFGILI |
| Truncated EGFR-ErbB3 Chimera with GMCSFR alpha signal peptide (nt) | 94 | atgcttctcctggtgacaagccttctgctctgtgagttaccacacccagcattcctcct<br>gatcccacgcaaagtgtgtaacggaataggtattggtgaatttaaagactcactctcca<br>taaatgctacgaatattaaacacttcaaaaactgcacctccatcagtggcgatctccac<br>atcctgccggtggcatttaggggtgactccttcacacatactcctcctctggatccaca<br>ggaactggatattctgaaaaccgtaaaggaaatcacagggtttttgctgattcaggctt<br>ggcctgaaaacaggacggacctccatgcctttgagaacctagaaatcatacgcggcagg<br>accaagcaacatggtcagttttctcttgcagtcgtcagcctgaacataacatccttggg<br>attacgctccctcaaggagataagtgatggagatgtgataatttcaggaaacaaaaatt<br>tgtgctatgcaaatacaataaactggaaaaaactgtttgggacctccggtcagaaaacc<br>aaaattataagcaacagaggtgaaaacagctgcaaggccacaggccaggtgtgtgaccc<br>actgtgctcctctggggggatgctggggcccaggccctggtcagtgcttgtcctgtcgaa<br>attatagccgaggaggtgtctgtgtgacccactgcaactttctgaatggggagcctcga<br>gaatttgcccatgaggccgaatgcttctcctgccacccggaatgccaacccatggaggg<br>cactgccacatgcaatggctcgggctctgatacttgtgctcaatgtgcccattttcgag<br>atgggccccactgtgtgagcagctgcccccatggagtcctaggtgccaagggcccaatc<br>tacaagtacccagatgttcagaatgaatgtcggccctgccatgagaactgcacccaggg<br>gtgtaaaggaccagagcttcaagactgtttaggacaaacactggtgctgatcggcaaaa<br>cccatctgacaatggctttgacagtgatagcaggattggtagtgattttcatgatgctg<br>ggcggcacttttctctac |
| Truncated EGFR-ErbB3 Chimera with GMCSFR | 95 | MLLLVTSLLLCELPHPAFLLIPRKVCNGIGIGEFKDSLSINATNIKHFKN<br>CTSISGDLHILPVAFRGDSFTHTPPLDPQELDILKTVKEITGFLLIQAWP<br>ENRTDLHAFENLEIIRGRTKQHGQFSLAVVSLNITSLGLRSLKEISDGDV |

-continued

| Sequence Name | SEQ ID NO | Sequence |
|---|---|---|
| alpha signal peptide (aa) | | IISGNKNLCYANTINWKKLFGTSGQKTKIISNRGENSCKATGQVCDPLCS<br>SGGCWGPGPGQCLSCRNYSRGGVCVTHCNFLNGEPREFAHEAECFSCHPE<br>CQPMEGTATCNGSGSDTCAQCAHFRDGPHCVSSCPHGVLGAKGPIYKYPD<br>VQNECRPCHENCTQGCKGPELQDCLGQTLVLIGKTHLTMALTVIAGLVVI<br>FMMLGGTFLY |
| Truncated EGFR-ErbB3 Chimera (nt) | 96 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtgtgtgacccactgtgc<br>tcctctggggggatgctggggcccaggccctggtcagtgcttgtcctgtcgaaattatag<br>ccgaggaggtgtctgtgtgacccactgcaactttctgaatggggagcctcgagaatttg<br>cccatgaggccgaatgcttctcctgccacccggaatgccaacccatggagggcactgcc<br>acatgcaatggctcgggctctgatacttgtgctcaatgtgcccattttcgagatgggcc<br>ccactgtgtgagcagctgcccccatggagtcctaggtgccaagggcccaatctacaagt<br>acccagatgttcagaatgaatgtcggccctgccatgagaactgcacccaggggtgtaaa<br>ggaccagagcttcaagactgtttaggacaaacactggtgctgatcggcaaaacccatct<br>gacaatggctttgacagtgatagcaggattggtagtgattttcatgatgctgggcggca<br>cttttctctac |
| Truncated EGFR-ErbB3 Chimera (aa) | 97 | RKVCNGIGIGEFKDSLSINATNIKHFKN<br>CTSISGDLHILPVAFRGDSFTHTPPLDPQELDILKTVKEITGFLLIQAWP<br>ENRTDLHAFENLEIIRGRTKQHGQFSLAVVSLNITSLGLRSLKEISDGDV<br>IISGNKNLCYANTINWKKLFGTSGQKTKIISNRGENSCKATGQVCDPLCS<br>SGGCWGPGPGQCLSCRNYSRGGVCVTHCNFLNGEPREFAHEAECFSCHPE<br>CQPMEGTATCNGSGSDTCAQCAHFRDGPHCVSSCPHGVLGAKGPIYKYPD<br>VQNECRPCHENCTQGCKGPELQDCLGQTLVLIGKTHLTMALTVIAGLVVI<br>FMMLGGTFLY |
| Truncated EGFR-ErbB4 (JM-a) Chimera with GMCSFR alpha signal peptide (nt) | 98 | atgcttctcctggtgacaagccttctgctctgtgagttaccacacccagcattcctcct<br>gatcccacgcaaagtgtgtaacggaataggtattggtgaatttaaagactcactctcca<br>taaatgctacgaatattaaacacttcaaaaactgcacctccatcagtggcgatctccac<br>atcctgccggtggcatttaggggtgactccttcacacatactcctcctctggatccaca<br>ggaactggatattctgaaaaccgtaaaggaaatcacagggtttttgctgattcaggctt<br>ggcctgaaaacaggacggacctccatgcctttgagaacctagaaatcatacgcggcagg<br>accaagcaacatggtcagttttctcttgcagtcgtcagcctgaacataacatccttggg<br>attacgctccctcaaggagataagtgatggagatgtgataatttcaggaaacaaaaatt<br>tgtgctatgcaaatacaataaactggaaaaaactgtttgggacctccggtcagaaaacc<br>aaaattataagcaacagaggtgaaaacagctgcaaggccacaggccaggtgtgcaacca<br>tctgtgttccagtgatggctgttggggacctgggccagaccaatgtctgtcgtgtcgcc<br>gcttcagtagaggaaggatctgcatagagtcttgtaacctctatgatggtgaatttcgg<br>gagtttgagaatggctccatctgtgtggagtgtgacccccagtgtgagaagatggaaga<br>tggcctcctcacatgccatggaccgggtcctgacaactgtacaaagtgctctcatttta<br>aagatggcccaaactgtgtggaaaaatgtccagatggcttacaggggggcaaacagtttc<br>attttcaagtatgctgatccagatcgggagtgccacccatgccatccaaactgcaccca<br>agggtgtaacggtcccactagtcatgactgcatttactacccatggacgggccattcca<br>ctttaccacaacatgctagaactcccctgattgcagctggagtaattggtgggctcttc<br>attctggtcattgtgggtctgacatttgctgtttatgtt |
| Truncated EGFR-ErbB4 (JM-a) Chimera with GMCSFR alpha signal peptide (aa) | 99 | MLLLVTSLLLCELPHPAFLLIPRKVCNGIGIGEFKDSLSINATNIKHFKNCTSISGDLH<br>ILPVAFRGDSFTH<br>TPPLDPQELDILKTVKEITGFLLIQAWPENRTDLHAFENLEIIRGRTKQH<br>GQFSLAVVSLNITSLGLRSLKEISDGDVIISGNKNLCYANTINWKKLFGT<br>SGQKTKIISNRGENSCKATGQVCNHLCSSDGCWGPGPDQCLSCRRFSRGR<br>ICIESCNLYDGEFREFENGSICVECDPQCEKMEDGLLTCHGPGPDNCTKC<br>SHFKDGPNCVEKCPDGLQGANSFIFKYADPDRECHPCHPNCTQGCNGPTS<br>HDCIYYPWTGHSTLPQHARTPLIAAGVIGGLFILVIVGLTFAVYV |
| Truncated EGFR-ErbB4 (JM-a) Chimera (nt) | 100 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccaggtgtgcaaccatctgtgt<br>tccagtgatggctgttggggacctgggccagaccaatgtctgtcgtgtcgccgcttcag<br>tagaggaaggatctgcatagagtcttgtaacctctatgatggtgaatttcgggagtttg<br>agaatggctccatctgtgtggagtgtgacccccagtgtgagaagatggaagatggcctc<br>ctcacatgccatggaccgggtcctgacaactgtacaaagtgctctcattttaaagatgg |

-continued

| Sequence Name | SEQ ID NO | Sequence |
|---|---|---|
| | | cccaaactgtgtggaaaaatgtccagatggcttacagggggcaaacagtttcattttca agtatgctgatccagatcgggagtgccacccatgccatccaaactgcacccaagggtgt aacggtcccactagtcatgactgcatttactacccatggacgggccattccactttacc acaacatgctagaactcccctgattgcagctggagtaattggtgggctcttcattctgg tcattgtgggtctgacatttgctgtttatgtt |
| Truncated EGFR-ErbB4 (JM-a) Chimera (aa) | 101 | RKVCNGIGIGEFKDSLSINATNIKHFKNCTSISGDLHILPVAFRGDSFTH TPPLDPQELDILKTVKEITGFLLIQAWPENRTDLHAFENLEIIRGRTKQH GQFSLAVVSLNITSLGLRSLKEISDGDVIISGNKNLCYANTINWKKLFGT SGQKTKIISNRGENSCKATGQVCNHLCSSDGCWGPGPDQCLSCRRFSRGR ICIESCNLYDGEFREFENGSICVECDPQCEKMEDGLLTCHGPGPDNCTKC SHFKDGPNCVEKCPDGLQGANSFIFKYADPDRECHPCHPNCTQGCNGPTS HDCIYYPWTGHSTLPQHARTPLIAAGVIGGLFILVIVGLTFAVYV |
| Truncated EGFR-ErbB4 (JM-b) Chimera with GMCSFR alpha signal peptide (nt) | 102 | atgcttctcctggtgacaagccttctgctctgtgagttaccacacccagcattcctcct gatcccacgcaaagtgtgtaacggaataggtattggtgaatttaaagactcactctcca taaatgctacgaatattaaacacttcaaaaactgcacctccatcagtggcgatctccac atcctgccggtggcatttaggggtgactccttcacacatactcctcctctggatccaca ggaactggatattctgaaaaccgtaaaggaaatcacagggtttttgctgattcaggctt ggcctgaaaacaggacggacctccatgcctttgagaacctagaaatcatacgcggcagg accaagcaacatggtcagttttctcttgcagtcgtcagcctgaacataacatccttggg attacgctccctcaaggagataagtgatggagatgtgataatttcaggaaacaaaaatt tgtgctatgcaaatacaataaactggaaaaaactgtttgggacctccggtcagaaaacc aaaattataagcaacagaggtgaaaacagctgcaaggccacaggccaggtgtgcaacca tctgtgttccagtgatggctgttggggacctgggccagaccaatgtctgtcgtgtcgcc gcttcagtagaggaaggatctgcatagagtcttgtaacctctatgatggtgaatttcgg gagtttgagaatggctccatctgtgtggagtgtgacccccagtgtgagaagatggaaga tggcctcctcacatgccatggaccgggtcctgacaactgtacaaagtgctctcatttta aagatggcccaaactgtgtggaaaaatgtccagatggcttacagggggcaaacagtttc attttcaagtatgctgatccagatcgggagtgccacccatgccatccaaactgcaccca agggtgcataggctcaagtattgaagactgcatcggcctgatggatagaactcccctga ttgcagctggagtaattggtgggctcttcattctggtcattgtgggtctgacatttgct gtttatgtt |
| Truncated EGFR-ErbB4 (JM-b) Chimera with GMCSFR alpha signal peptide (aa) | 103 | MLLLVTSLLLCELPHPAFLLIPRKVCNGIGIGEFKDSLSINATNIKHFKNCTSISGDLH ILPVAFRGDSFTH TPPLDPQELDILKTVKEITGFLLIQAWPENRTDLHAFENLEIIRGRTKQH GQFSLAVVSLNITSLGLRSLKEISDGDVIISGNKNLCYANTINWKKLFGT SGQKTKIISNRGENSCKATGQVCNHLCSSDGCWGPGPDQCLSCRRFSRGR ICIESCNLYDGEFREFENGSICVECDPQCEKMEDGLLTCHGPGPDNCTKC SHFKDGPNCVEKCPDGLQGANSFIFKYADPDRECHPCHPNCTQGCIGSSI EDCIGLMDRTPLIAAGVIGGLFILVIVGLTFAVYV |
| Truncated EGFR-ErbB4 (JM-b) Chimera (nt) | 104 | Cgcaaagtgtgtaacggaataggtattggtgaatttaaagactcactctccataaatgc tacgaatattaaacacttcaaaaactgcacctccatcagtggcgatctccacatcctgc cggtggcatttaggggtgactccttcacacatactcctcctctggatccacaggaactg gatattctgaaaaccgtaaaggaaatcacagggtttttgctgattcaggcttggcctga aaacaggacggacctccatgcctttgagaacctagaaatcatacgcggcaggaccaagc aacatggtcagttttctcttgcagtcgtcagcctgaacataacatccttgggattacgc tccctcaaggagataagtgatggagatgtgataatttcaggaaacaaaaatttgtgcta tgcaaatacaataaactggaaaaaactgtttgggacctccggtcagaaaaccaaaatta taagcaacagaggtgaaaacagctgcaaggccacaggccaggtgtgcaaccatctgtgt tccagtgatggctgttggggacctgggccagaccaatgtctgtcgtgtcgccgcttcag tagaggaaggatctgcatagagtcttgtaacctctatgatggtgaatttcgggagtttg agaatggctccatctgtgtggagtgtgacccccagtgtgagaagatggaagatggcctc ctcacatgccatggaccgggtcctgacaactgtacaaagtgctctcattttaaagatgg cccaaactgtgtggaaaaatgtccagatggcttacagggggcaaacagtttcattttca agtatgctgatccagatcgggagtgccacccatgccatccaaactgcacccaagggtgc ataggctcaagtattgaagactgcatcggcctgatggatagaactcccctgattgcagc tggagtaattggtgggctcttcattctggtcattgtgggtctgacatttgctgtttatg tt |
| Truncated EGFR-ErbB4 (JM-b) Chimera (aa) | 105 | RKVCNGIGIGEFKDSLSINATNIKHFKNCTSISGDLHILPVAFRGDSFTH TPPLDPQELDILKTVKEITGFLLIQAWPENRTDLHAFENLEIIRGRTKQH GQFSLAVVSLNITSLGLRSLKEISDGDVIISGNKNLCYANTINWKKLFGT SGQKTKIISNRGENSCKATGQVCNHLCSSDGCWGPGPDQCLSCRRFSRGR ICIESCNLYDGEFREFENGSICVECDPQCEKMEDGLLTCHGPGPDNCTKC SHFKDGPNCVEKCPDGLQGANSFIFKYADPDRECHPCHPNCTQGCIGSSI EDCIGLMDRTPLIAAGVIGGLFILVIVGLTFAVYV |
| Full length CD20 (nt) | 106 | Atgacaacacccagaaattcagtaaatgggactttcccggcagagccaatgaaaggccc tattgctatgcaatctggtccaaaaccactcttcaggaggatgtcttcactggtgggcc ccacgcaaagcttcttcatgagggaatctaagactttgggggctgtccagattatgaat gggctcttccacattgccctggggggtcttctgatgatcccagcagggatctatgcacc catctgtgtgactgtgtggtaccctctctggggaggcattatgtatattatttccggat cactcctggcagcaacggagaaaaactccaggaagtgtttggtcaaaggaaaaatgata |

-continued

| Sequence Name | SEQ ID NO | Sequence |
|---|---|---|
| | | atgaattcattgagcctctttgctgccatttctggaatgattctttcaatcatggacat acttaatattaaaatttcccatttttttaaaaatggagagtctgaattttattagagctc acacaccatatattaacatatacaactgtgaaccagctaatccctctgagaaaaactcc ccatctacccaatactgttacagcatacaatctctgttcttgggcattttgtcagtgat gctgatctttgccttcttccaggaacttgtaatagctggcatcgttgagaatgaatgga aaagaacgtgctccagacccaaatctaacatagttctcctgtcagcagaagaaaaaaaa gaacagactattgaaataaaagaagaagtggttgggctaactgaaacatcttcccaacc aaagaatgaagaagacattgaaattattccaatccaagaagaggaagaagaagaaacag agacgaactttccagaacctccccaagatcaggaatcctcaccaatagaaaatgacagc tctcct |
| Full length CD20 (aa) | 107 | MTTPRNSVNGTFPAEPMKGPIAMQSGPKPLFRRMSSLVGPTQSFFMRESK TLGAVQIMNGLFHIALGGLLMIPAGIYAPICVTVWYPLWGGIMYIISGSL LAATEKNSRKCLVKGKMIMNSLSLFAAISGMILSIMDILNIKISHFLKME SLNFIRAHTPYINIYNCEPANPSEKNSPSTQYCYSIQSLFLGILSVMLIF AFFQELVIAGIVENEWKRTCSRPKSNIVLLSAEEKKEQTIEIKEEVVGLT ETSSQPKNEEDIEIIPIQEEEEEETETNFPEPPQDQESSPIENDSSP |
| Truncated CD20 design 1 (CD20t1) [CD20(M1-E263] (nt) | 108 | atgaccacaccacggaactctgtgaatggcaccttcccagcagagccaatgaagggacc aatcgcaatgcagagcggacccaagcctctgtttcggagaatgagctccctggtgggcc caacccagtccttctttatgagagagtctaagacactgggcgccgtgcagatcatgaac ggactgttccacatcgccctgggaggactgctgatgatcccagccggcatctacgcccc tatctgcgtgaccgtgtggtaccctctgtggggcggcatcatgtatatcatctccggct ctctgctggccgccacagagaagaacagcaggaagtgtctggtgaagggcaagatgatc atgaatagcctgtccctgtttgccgccatctctggcatgatcctgagcatcatggacat cctgaacatcaagatcagccacttcctgaagatggagagcctgaacttcatcagagccc acaccccttacatcaacatctataattgcgagcctgccaacccatccgagaagaattct ccaagcacacagtactgttattccatccagtctctgttcctgggcatcctgtctgtgat gctgatctttgccttctttcaggagctggtcatcgccggcatcgtggagaacgagtgga agaggacctgcagccgccccaagtccaatatcgtgctgctgtccgccgaggagaagaag gagcagacaatcgagatcaaggaggaggtggtgggcctgaccgagacatctagccagcc taagaatgaggaggatatcgag |
| Truncated CD20 design 1 (CD20t1) [CD20(M1-E263] (aa) | 109 | MTTPRNSVNGTFPAEPMKGPIAMQSGPKPLFRRMSSLVGPTQSFFMRESK TLGAVQIMNGLFHIALGGLLMIPAGIYAPICVTVWYPLWGGIMYIISGSL LAATEKNSRKCLVKGKMIMNSLSLFAAISGMILSIMDILNIKISHFLKME SLNFIRAHTPYINIYNCEPANPSEKNSPSTQYCYSIQSLFLGILSVMLIF AFFQELVIAGIVENEWKRTCSRPKSNIVLLSAEEKKEQTIEIKEEVVGLT ETSSQPKNEEDIE |
| Truncated CD20 design 2 (CD20t2) CD20(M117-N214) (nt) | 110 | atgataatgaattcattgagcctctttgctgccatttctggaatgattctttcaatcat ggacatacttaatattaaaatttcccatttttttaaaaatggagagtctgaattttatta gagctcacacaccatatattaacatatacaactgtgaaccagctaatccctctgagaaa aactccccatctacccaatactgttacagcatacaatctctgttcttgggcattttgtc agtgatgctgatctttgccttcttccaggaacttgtaatagctggcatcgttgagaat |
| Truncated CD20 design 2 (CD20t2) CD20(M117-N214) (aa) | 111 | MIMNSLSLFAAISGMILSIMDILNIKISHFLKMESLNFIRAHTPYINIYN CEPANPSEKNSPSTQYCYSIQSLFLGILSVMLIFAFFQELVIAGIVEN |
| Truncated CD20 design 3 (CD20t3)CD20(K142-S188).CD8a(I183-T203) (nt) | 112 | atggccttaccagtgaccgccttgctcctgccgctggccttgctgctccacgccgccag gccgaaaatttcccatttttttaaaaatggagagtctgaattttattagagctcacacac catatattaacatatacaactgtgaaccagctaatccctctgagaaaaactccccatct acccaatactgttacagcatacaatctatctacatctgggcgcccttggccgggacttg tggggtccttctcctgtcactggttatcacc |
| Truncated CD20 design 3 (CD20t3)CD20(K142-S188).CD8a (I183-T203) (aa) | 113 | MALPVTALLLPLALLLHAARPKISHFLKMESLNFIRAHTPYINIYNCEPA NPSEKNSPSTQYCYSIQSIYIWAPLAGTCGVLLLSLVIT |
| Truncated CD20 design 4 (CD20t4) CD20(M1-N214) (nt) | 114 | atgacaacacccagaaattcagtaaatgggactttcccggcagagccaatgaaaggccc tattgctatgcaatctggtccaaaaccactcttcaggaggatgtcttcactggtgggcc ccacgcaaagcttcttcatgagggaatctaagactttgggggctgtccagattatgaat gggctcttccacattgccctggggggtcttctgatgatcccagcagggatctatgcacc catctgtgtgactgtgtggtaccctctctggggaggcattatgtatattatttccggat cactcctggcagcaacggagaaaaactccaggaagtgtttggtcaaaggaaaaatgata atgaattcattgagcctctttgctgccatttctggaatgattctttcaatcatggacat acttaatattaaaatttcccatttttttaaaaatggagagtctgaattttattagagctc acacaccatatattaacatatacaactgtgaaccagctaatccctctgagaaaaactcc ccatctacccaatactgttacagcatacaatctctgttcttgggcattttgtcagtgat gctgatctttgccttcttccaggaacttgtaatagctggcatcgttgagaat |

-continued

| Sequence Name | SEQ ID NO | Sequence |
|---|---|---|
| Truncated CD20 design 4 (CD20t4) CD20(M1-N214) (aa) | 115 | MTTPRNSVNGTFPAEPMKGPIAMQSGPKPLFRRMSSLVGPTQSFFMRESK TLGAVQIMNGLFHIALGGLLMIPAGIYAPICVTVWYPLWGGIMYIISGSL LAATEKNSRKCLVKGKMIMNSLSLFAAISGMILSIMDILNIKISHFLKME SLNFIRAHTPYINIYNCEPANPSEKNSPSTQYCYSIQSLFLGILSVMLIF AFFQELVIAGIVEN |
| Truncated CD20 design 5 (CD2015) CD20(V82-N214) (nt) | 116 | gtgactgtgtggtaccctctctggggaggcattatgtatattatttccggatcactcct ggcagcaacggagaaaaactccaggaagtgtttggtcaaaggaaaaatgataatgaatt cattgagcctctttgctgccatttctggaatgattctttcaatcatggacatacttaat attaaaatttcccatttttttaaaaatggagagtctgaattttattagagctcacacacc atatattaacatatacaactgtgaaccagctaatccctctgagaaaaactccccatcta cccaatactgttacagcatacaatctctgttcttgggcattttgtcagtgatgctgatc tttgccttcttccaggaacttgtaatagctggcatcgttgagaat |
| Truncated CD20 design 5 (CD20t5) CD20(V82-N214) (aa) | 117 | VTVWYPLWGGIMYIISGSLLAATEKNSRKCLVKGKMIMNSLSLFAAISGM ILSIMDILNIKISHFLKMESLNFIRAHTPYINIYNCEPANPSEKNSPSTQ YCYSIQSLFLGILSVMLIFAFFQELVIAGIVEN |
| Truncated CD20 design 6 (CD20t6) CD20(V82-I186) (nt) | 118 | Gtgactgtgtggtaccctctctggggaggcattatgtatattatttccggatcactcct ggcagcaacggagaaaaactccaggaagtgtttggtcaaaggaaaaatgataatgaatt cattgagcctctttgctgccatttctggaatgattctttcaatcatggacatacttaat attaaaatttcccatttttttaaaaatggagagtctgaattttattagagctcacacacc atatattaacatatacaactgtgaaccagctaatccctctgagaaaaactccccatcta cccaatactgttacagcata |
| Truncated CD20 design 6 (CD20t6) CD20(V82-I186) (aa) | 119 | VTVWYPLWGGIMYIISGSLLAATEKNSRKCLVKGKMIMNSLSLFAAISGM ILSIMDILNIKISHFLKMESLNFIRAHTPYINIYNCEPANPSEKNSPSTQ YCYSIQSLFLGILSVMLIFAFFQELVIAGIVEN |
| Truncated CD20 design 7 (CD20t7) CD20(P160-Q187).SG4S linker.CD28(I196-D172) (nt) | 120 | ccatatattaacatatacaactgtgaaccagctaatccctctgagaaaaactccccatc tacccaatactgttacagcatacaatcgggtggcggcggatctattgaagttatgtatc ctcctccttacctagacaatgagaagagcaatggaaccattatccatgtgaaagggaaa cacctttgtccaagtcccctatttcccggaccttctaagcccttttgggtgctggtggt ggttggtggagtcctggcttgctatagcttgctagtaacagtggcctttattattttct gggtgaggagtaagaggagcaggctcctgcacagtgac |
| Truncated CD20 design 7 (CD20t7) CD20(P160-Q187).SG4S linker.CD28(I96-D172 (aa) | 121 | PYINIYNCEPANPSEKNSPSTQYCYSIQSGGGGSIEVMYPPPYLDNEKSNGTIIHVKGK HLCPSPLFPGPSKPFWVLVVVGGVLACYSLLVTVAFIIFWVRSKRSRLLHSD |
| Truncated CD20 design 8 (CD2018) CD20(P160-Q187). SGSlinker.hCD20 (P160-Q187).SG4S linker.CD28(I96-D172) (nt) | 122 | ccatatattaacatatacaactgtgaaccagctaatccctctgagaaaaactccccatc tacccaatactgttacagcatacaatcgggtggcggcggatctccatatattaacatat acaactgtgaaccagctaatccctctgagaaaaactccccatctacccaatactgttac agcatacaatcgggtggcggcggatctattgaagttatgtatcctcctccttacctaga caatgagaagagcaatggaaccattatccatgtgaaagggaaacacctttgtccaagtc ccctatttcccggaccttctaagcccttttgggtgctggtggtggttggtggagtcctg gcttgctatagcttgctagtaacagtggcctttattattttctgggtgaggagtaagag gagcaggctcctgcacagtgac |
| Truncated CD20 design 8 (CD20t8) CD20(P160-Q187).SGS linker.hCD20(P160-Q187).SG4S linker.CD28(I96-D172) (aa) | 123 | PYINIYNCEPANPSEKNSPSTQYCYSIQSGGGGSPYINIYNCEPANPSEKNSPSTQYCY SIQSGGGGSIEVMYPPPYLDNEKSNGTIIHVKGKHLCPSPLFPGPSKPFWVLVVVGGVL ACYSLLVTVAFIIFWVRSKRSRLLHSD |
| Truncated CD20 design 9 (CD20t9) CD20(P160-Q187).SG4S linker.CD8a (P120-V201) (nt) | 124 | ccatatattaacatatacaactgtgaaccagctaatccctctgagaaaaactccccatc tacccaatactgttacagcatacaatcgggtggcggcggatctccagcgccgcgaccac caacaccggcgcccaccatcgcgtcgcagcccctgtccctgcgcccagaggcgtgccgg ccagcggcggggggcgcagtgcacacgagggggctggacttcgcctgtgatatctacat ctgggcgcccttggccgggacttgtggggtccttctcctgtcactggttatcaccctttt actgcaaccacaggaaccgaagacgtgtttgcaaatgtccccggcctgtggtc |

-continued

| Sequence Name | SEQ ID NO | Sequence |
|---|---|---|
| Truncated CD20 design 9 (CD20t9) CD20(P160-Q187).SG4S linker.CD8a (P120-V201) (aa) | 125 | PYINIYNCEPANPSEKNSPSTQYCYSIQSGGGGSPAPRPPTPAPTIASQPLSLRPEACR PAAGGAVHTRGLDFACDIYIWAPLAGTCGVLLLSLVITLYCNHRNRRRVCKCPRPVV |
| Truncated CD20 design 10 (CD20t10) CD20(C167-C183).SG4S linker.CD28 (I96-D172) (nt) | 126 | tgtgaaccagctaatccctctgagaaaaactccccatctacccaatactgttcgggtgg cggcggatctattgaagttatgtatcctcctccttacctagacaatgagaagagcaatg gaaccattatccatgtgaaagggaaacacctttgtccaagtcccctatttcccggacct tctaagcccttttgggtgctggtggtggttggtggagtcctggcttgctatagcttgct agtaacagtggcctttattattttctgggtgaggagtaagaggagcaggctcctgcaca gtgac |
| Truncated CD20 design 10 (CD20t10) CD20(C167-C183).SG4S linker.CD28 (I96-D172) (aa) | 127 | CEPANPSEKNSPSTQYCSGGGGSIEVMYPPPYLDNEKSNGTIIHVKGKHLCPSPLFPGP SKPFWVLVVVGGVLACYSLLVTVAFIIFWVRSKRSRLLHSD |
| Truncated CD20 design 11 (CD20t11) CD20(C167-C183).SG4S linker.CD20 (C167-C183).SG4S linker CD28 (I96-D172) (nt) | 128 | tgtgaaccagctaatccctctgagaaaaactccccatctacccaatactgttcgggtgg cggcggatcttgtgaaccagctaatccctctgagaaaaactccccatctacccaatact gttcgggtggcggcggatctattgaagttatgtatcctcctccttacctagacaatgag aagagcaatggaaccattatccatgtgaaagggaaacacctttgtccaagtcccctatt tcccggaccttctaagcccttttgggtgctggtggtggttggtggagtcctggcttgct atagcttgctagtaacagtggcctttattattttctgggtgaggagtaagaggagcagg ctcctgcacagtgac |
| Truncated CD20 design 11 (CD20t11) CD20(C167-C183).SG4S linker.CD20 (C1671-C183).SG4S inker.CD28 (I96-D172) (aa) | 129 | CEPANPSEKNSPSTQYCSGGGGSCEPANPSEKNSPSTQYCSGGGGSIEVMYPPPYLDNE KSNGTIIHVKGKHLCPSPLFPGPSKPFWVLVVVGGVLACYSLLVTVAFIIFWVRSKRSR LLHSD |
| Truncated CD20 design 12 (CD20t12) CD20(C167-C183).SG4S linker.CD8a (P120-V201) (nt) | 130 | tgtgaaccagctaatccctctgagaaaaactccccatctacccaatactgttcgggtgg cggcggatctccagcgccgcgaccaccaacaccggcgcccaccatcgcgtcgcagcccc tgtccctgcgcccagaggcgtgccggccagcggcggggggcgcagtgcacacgaggggg ctggacttcgcctgtgatatctacatctgggcgcccttggccgggacttgtggggtcct tctcctgtcactggttatcaccctttactgcaaccacaggaaccgaagacgtgtttgca aatgtccccggcctgtggtc |
| Truncated CD20 design 12 (CD20t12) CD20(C167-C183).SG4S linker.CD8a (P120-V201) (aa) | 131 | CEPANPSEKNSPSTQYCSGGGGSPAPRPPTPAPTIASQPLSLRPEACRPAAGGAVHTRG LDFACDIYIWAPLAGTCGVLLLSLVITLYCNHRNRRRVCKCPRPVV |
| Truncated CD20 design 13 (CD20t13) CD20v1 [CD20(M1-A54).CD20 (C111-P297] (nt) | 132 | atgaccacaccccggaactccgtgaatggcaccttccctgccgagccaatgaagggccc tatcgccatgcagtctggcccaaagcccctgtttcggagaatgagctccctggtgggcc ccacccagagcttctttatgagggagtccaagacactgggcgcctgcctggtgaagggc aagatgatcatgaactctctgagcctgttcgccgccatctccggcatgatcctgtctat catggacatcctgaacatcaagatctctcacttcctgaagatggagagcctgaacttca tccgggcccacaccccatacatcaacatctataattgcgagcccgccaaccctagcgag aagaattcccccctctacacagtactgttatagcatccagtccctgttcctgggcatcct gtccgtgatgctgatctttgccttctttcaggagctggtcatcgccggcatcgtggaga acgagtggaagaggacctgttctcgccctaagagcaatatcgtgctgctgagcgccgag gagaagaaggagcagacaatcgagatcaaggaggaggtggtgggcctgaccgagacatc tagccagcctaagaatgaggaggatatcgagatcatcccaatccaggaggaggaggagg aggagaccgagacaaactttccagagccccctcaggaccaggagtcctctccaatcgag aatgatagctcccccctgataa |
| Truncated CD20 design 13 | 133 | MTTPRNSVNGTFPAEPMKGPIAMQSGPKPLFRRMSSLVGPTQSFFMRESKTLGACLVKG KMIMNSLSLFAAISGMILSIMDILNIKISHFLKMESLNFIRAHTPYINIYNCEPANPSE |

-continued

| Sequence Name | SEQ ID NO | Sequence |
|---|---|---|
| (CD20t13) CD20v1 [CD20(M1- A54).CD20(C111- P297] (aa) | | KNSPSTQYCYSIQSLFLGILSVMLIFAFFQELVIAGIVENEWKRTCSRPKSNIVLLSAE<br>EKKEQTIEIKEEVVGLTETSSQPKNEEDIEIIPIQEEEEEETETNFPEPPQDQESSPIE<br>NDSS |
| Truncated CD20 design 14 (CD20t14) CD20v1 (delta 281-297/ wildtype) [CD20(M1- A54).CD20(C111- E281] (nt) | 134 | atgaccacaccacggaacagcgtgaatggcaccttcccagcagagccaatgaagggacc<br>aatcgcaatgcagtccggacccaagcctctgtttcggagaatgagctccctggtgggcc<br>ccacccagtctttctttatgagggagagcaagacactgggcgcctgcctggtgaagggc<br>aagatgatcatgaactccctgtctctgttcgccgccatcagcggcatgatcctgtccat<br>catggacatcctgaacatcaagatctcccacttcctgaagatggagagcctgaacttca<br>tccgggcccacaccccttacatcaacatctataattgcgagcctgccaacccatctgag<br>aagaatagcccatccacacagtactgttattctatccagagcctgttcctgggcatcct<br>gtccgtgatgctgatctttgccttctttcaggagctggtcatcgccggcatcgtggaga<br>acgagtggaagaggacctgttcccgccccaagtctaatatcgtgctgctgagcgccgag<br>gagaagaaggagcagacaatcgagatcaaggaggaggtggtgggcctgaccgagacatc<br>tagccagcccaagaacgaggaggatatcgagatcatccctatccaggaggaggaggagg<br>aggagaccgagacaaattttcctgagtgataa |
| Truncated CD20 design 14 (CD20t14) CD20v1 (delta 281-297/ wildtype) [CD20(M1- A54).CD20(C111- E281] (aa) | 135 | MTTPRNSVNGTFPAEPMKGPIAMQSGPKPLFRRMSSLVGPTQSFFMRESKTLGACLVKG<br>KMIMNSLSLFAAISGMILSIMDILNIKISHFLKMESLNFIRAHTPYINIYNCEPANPSE<br>KNSPSTQYCYSIQSLFLGILSVMLIFAFFQELVIAGIVENEWKRTCSRPKSNIVLLSAE<br>EKKEQTIEIKEEVVGLTETSSQPKNEEDIEIIPIQEEEEEETETNFPE |
| Truncated CD20 design 15 (CD20t15) CD20v1 (delta 263-297/ wildtype)_2 [CD20(M1- A54).CD20(C111- E263] (nt) | 136 | atgaccacaccccggaacagcgtgaatggcaccttcccagccgagcccatgaagggccc<br>tatcgccatgcagtccggccccaagcctctgtttcggagaatgagctccctggtgggcc<br>ccacccagtctttctttatgagggagagcaagacactgggcgcctgcctggtgaagggc<br>aagatgatcatgaactccctgtctctgttcgccgccatcagcggcatgatcctgtccat<br>catggacatcctgaacatcaagatctcccacttcctgaagatggagagcctgaacttca<br>tccgggcccacaccccatacatcaacatctataattgcgagcctgccaacccatctgag<br>aagaatagcccctccacacagtactgttattctatccagagcctgttcctgggcatcct<br>gtccgtgatgctgatctttgccttctttcaggagctggtcatcgccggcatcgtggaga<br>acgagtggaagaggacctgttcccgccctaagtctaatatcgtgctgctgagcgccgag<br>gagaagaaggagcagacaatcgagatcaaggaggaggtggtgggcctgaccgagacatc<br>tagccagccaaagaatgaggaggatatcgagtgataa |
| Truncated CD20 design 15 (CD20t15) CD20v1 (delta 263-297/ wildtype)_2 [CD20(M1- A54 .CD20(C111- E263] (aa) | 137 | MTTPRNSVNGTFPAEPMKGPIAMQSGPKPLFRRMSSLVGPTQSFFMRESKTLGACLVKG<br>KMIMNSLSLFAAISGMILSIMDILNIKISHFLKMESLNFIRAHTPYINIYNCEPANPSE<br>KNSPSTQYCYSIQSLFLGILSVMLIFAFFQELVIAGIVENEWKRTCSRPKSNIVLLSAE<br>EKKEQTIEIKEEVVGLTETSSQPKNEEDIE |
| Truncated CD20 design 16 (CD20t16) CD20v1 (delta 245-297/ wildtype ) [CD20(M1- A54).CD20(C111- V228] (nt) | 138 | atgaccacaccccggaactccgtgaatggcaccttcccagccgagcccatgaagggccc<br>tatcgccatgcagtctggccccaagcctctgtttcggagaatgagctccctggtgggcc<br>ctacccagagcttctttatgagggagtccaagacactgggcgcctgcctggtgaagggc<br>aagatgatcatgaactctctgagcctgttcgccgccatctccggcatgatcctgtctat<br>catggacatcctgaacatcaagatctctcacttcctgaagatggagagcctgaacttca<br>tccgggcccacaccccatacatcaacatctataattgcgagcctgccaacccaagcgag<br>aagaattcccctctacacagtactgttatagcatccagtccctgttcctgggcatcct<br>gtccgtgatgctgatctttgccttctttcaggagctggtcatcgccggcatcgtggaga<br>acgagtggaagaggacatgttctcgccccaagagcaatatcgtgtgataa |
| Truncated CD20 design 16 (CD20t16) CD20v1 (delta 245-297/ wildtype) [CD20(M1- A54).CD20(C111- V228] (aa) | 139 | MTTPRNSVNGTFPAEPMKGPIAMQSGPKPLFRRMSSLVGPTQSFFMRESKTLGACLVKG<br>KMIMNSLSLFAAISGMILSIMDILNIKISHFLKMESLNFIRAHTPYINIYNCEPANPSE<br>KNSPSTQYCYSIQSLFLGILSVMLIFAFFQELVIAGIVENEWKRTCSRPKSNIV |

-continued

| Sequence Name | SEQ ID NO | Sequence |
|---|---|---|
| Truncated CD20 design 17 (CD20t17) CD20v2 [CD20(M1-V8).CD20(C111-P297 (nt) | 140 | atgaccacacccaggaacagcgtgtgcctggtgaagggcaagatgatcatgaatagcct gtccctgttcgccgccatctctggcatgatcctgagcatcatggacatcctgaacatca agatctcccacttcctgaagatggagagcctgaacttcatccgggcccacaccccatac atcaacatctataattgcgagccagccaaccccagcgagaagaattctcccagcacaca gtactgttattccatccagtctctgttcctgggcatcctgtccgtgatgctgatctttg ccttctttcaggagctggtcatcgccggcatcgtggagaacgagtggaagcggacctgt agcagacctaagtccaatatcgtgctgctgtccgccgaggagaagaaggagcagacaat cgagatcaaggaggaggtggtgggcctgaccgagacaagctcccagcccaagaacgagg aggatatcgagatcatccctatccaggaggaggaggaggaggagacgagacaaacttt ccagagcccccctcaggaccaggagtctagccctatcgagaatgattcctctccatgata a |
| Truncated CD20 design 17 (CD20t17) CD20v2 [CD20(M1-V8).CD20(C111-P297] (aa) | 141 | MTTPRNSVCLVKGKMIMNSLSLFAAISGMILSIMDILNIKISHFLKMESLNFIRAHTPY INIYNCEPANPSEKNSPSTQYCYSIQSLFLGILSVMLIFAFFQELVIAGIVENEWKRTC SRPKSNIVLLSAEEKKEQTIEIKEEVVGLTETSSQPKNEEDIEIIPIQEEEEEETETNF PEPPQDQESSPIENDSSP |
| CD52 (G25-S36) (CAMPATH-1 antigen) (nt) | 142 | ggacaaaacgacaccagccaaaccagcagcccctca |
| CD52 (G25-S36) (CAMPATH-1 antigen) (aa) | 143 | GQNDTSQTSSPS |
| Truncated CD52 Design 1 (CD52t1) with CD52 signal peptide (nt) | 144 | atgaagcgcttcctcttcctcctactcaccatcagcctcctggttatggtacagataca aactggactctcaggacaaaacgacaccagccaaaccagcagcccctcaggcagcacct ccggcagcggcaagcctggcagcggcgagggcagcaccaagggcggcggaggcggaagc ggaggcggaggctccaagcccttctgggtgctggtcgtggtcggcggagtgctggcctg ttacagcctgctggtcaccgtggccttcatcatcttttgggtc |
| Truncated CD52 Design 1 (CD52t1) with CD52 signal peptide (aa) | 145 | MKRFLFLLLTISLLVMVQIQTGLSGQNDTSQTSSPSGSTSGSGKPGSGEG STKGGGGGSGGGGSKPFWVLVVVGGVLACYSLLVTVAFIIFWV |
| Truncated CD52 Design 2 (CD52t2) with CD52 signal peptide (nt) | 146 | atgaagcgcttcctcttcctcctactcaccatcagcctcctggttatggtacagataca aactggactctcaggacaaaacgacaccagccaaaccagcagcccctcaggcagcacct ccggcagcggcaagcctggcagcggcgagggcagcaccaagggcggccagaatgataca tctcagacttcatctcctagcggatccacttctggttccggtaaaccaggttctgggga aggtagtacaaaaggaggcggaggcggaagcggaggcggaggctccaagcccttctggg tgctggtcgtggtcggcggagtgctggcctgttacagcctgctggtcaccgtggccttc atcatcttttgggtc |
| Truncated CD52 Design 2 (CD52t2) with CD52 signal peptide (aa) | 147 | MKRFLFLLLTISLLVMVQIQTGLSGQNDTSQTSSPSGSTSGSGKPGSGEG STKGGQNDTSQTSSPSGSTSGSGKPGSGEGSTKGGGGGSGGGGSKPFWVL VVVGGVLACYSLLVTVAFIIFWV |
| Truncated CD52 Design 3 (CD52t3) with CD52 signal peptide (nt) | 148 | atgaagcgcttcctcttcctcctactcaccatcagcctcctggttatggtacagataca aactggactctcaggacaaaacgacaccagccaaaccagcagcccctcaggcagcacct ccggcagcggcaagcctggcagcggcgagggcagcaccaagggcggccagaatgataca tctcagacttcatctcctagcggatccacttctggttccggtaaaccaggttctgggga aggtagtacaaaaggaggtcagaacgacacttcacagacatctagtccatccggcagta caagcggaagtggaaagcccggaagtggtgagggatcaactaagggtggcggaggcgga agcggaggcggaggctccaagcccttctgggtgctggtcgtggtcggcggagtgctggc ctgttacagcctgctggtcaccgtggccttcatcatcttttgggtc |
| Truncated CD52 Design 3 (CD52t3) with CD52 signal peptide (aa) | 149 | MKRFLFLLLTISLLVMVQIQTGLSGQNDTSQTSSPSGSTSGSGKPGSGEG STKGGQNDTSQTSSPSGSTSGSGKPGSGEGSTKGGQNDTSQTSSPSGSTS GSGKPGSGEGSTKGGGGGSGGGGSKPFWVLVVVGGVLACYSLLVTVAFII FWV |
| Truncated CD52 Design 4 (CD52t4) with CD52 signal peptide (aa) | 150 | MKRFLFLLLTISLLVMVQIQTGLSGQNDTSQTSSPSGSTSGSGKPGSGEG STKGGQNDTSQTSSPSGSTSGSGKPGSGEGSTKGGQNDTSQTSSPSGSTS GSGKPGSGEGSTKGGGGSGGGGSGGGGSGGGGSEITLIIFGVMAGVIGTI LLISYGIRRGGGS |

-continued

| Sequence Name | SEQ ID NO | Sequence |
|---|---|---|
| Truncated CD52 Design 5 (CD52t5) with CD52 signal peptide (aa) | 151 | MKRFLFLLLTISLLVMVQIQTGLSGQNDTSQTSSPSGSTSGSGKPGSGEG<br>STKGGQNDTSQTSSPSGSTSGSGKPGSGEGSTKGGQNDTSQTSSPSGSTS<br>GSGKPGSGEGSTKGGGGSGGGGSGGGGSGGGGSITLIIFGVMAGVIGTIL<br>LALLIWGGGS |
| Truncated CD52 Design 6 (CD52t6) with CD52 signal peptide (aa) | 152 | MKRFLFLLLTISLLVMVQIQTGLSGQNDTSQTSSPSGSTSGSGKPGSGEG<br>STKGGQNDTSQTSSPSGSTSGSGKPGSGEGSTKGGQNDTSQTSSPSGSTS<br>GSGKPGSGEGSTKGGGGGGGGSGGGGSGGGGSITLIIFGVMAGVIGTIL<br>LALLIWGGGS |
| Low-affinity nerve growth factor receptor (LNGFR, TNFRSF16) (nt) | 153 | atgggggcaggtgccaccggccgcgccatggacgggccgcgcctgctgctgttgctgct<br>tctgggggtgtcccttggaggtgccaaggaggcatgccccacaggcctgtacacacaca<br>gcggtgagtgctgcaaagcctgcaacctgggcgagggtgtggcccagccttgtggagcc<br>aaccagaccgtgtgtgagccctgcctggacagcgtgacgttctccgacgtggtgagcgc<br>gaccgagccgtgcaagccgtgcaccgagtgcgtggggctccagagcatgtcggcgccgt<br>gcgtggaggccgacgacgccgtgtgccgctgcgcctacggctactaccaggatgagacg<br>actgggcgctgcgaggcgtgccgcgtgtgcgaggcgggctcgggcctcgtgttctcctg<br>ccaggacaagcagaacaccgtgtgcgaggagtgccccgacggcacgtattccgacgagg<br>ccaaccacgtggacccgtgcctgccctgcaccgtgtgcgaggacaccgagcgccagctc<br>cgcgagtgcacacgctgggccgacgccgagtgcgaggagatccctggccgttggattac<br>acggtccacacccccagagggctcggacagcacagcccccagcacccaggagcctgagg<br>cacctccagaacaagacctcatagccagcacggtggcaggtgtggtgaccacagtgatg<br>ggcagctcccagcccgtggtgacccgaggcaccaccgacaacctcatccctgtctattg<br>ctccatcctggctgctgtggttgtgggccttgtggcctacatagccttcaagaggtgga<br>acagctgcaagcagaacaagcaaggagccaacagccggccagtgaaccagacgcccca<br>ccagagggagaaaaactccacagcgacagtggcatctccgtggacagccagagcctgca<br>tgaccagcagccccacacgcagacagcctcgggccaggccctcaagggtgacggaggcc<br>tctacagcagcctgcccccagccaagcgggaggaggtggagaagcttctcaacggctct<br>gcgggggacacctggcggcacctggcgggcgagctgggctaccagcccgagcacataga<br>ctcctttacccatgaggcctgccccgttcgcgccctgcttgcaagctgggccacccagg<br>acagcgccacactggacgccctcctggccgccctgcgccgcatccagcgagccgacctc<br>gtggagagtctgtgcagtgagtccactgccacatccccggtgtga |
| Low-affinity nerve growth factor receptor (LNGFR, TNFRSF16) (aa) | 154 | MGAGATGRAMDGPRLLLLLLLGVSLGGAKEACPTGLYTHSGECCKACNLGEGVAQPCGA<br>NQTVCEPCLDSVTFSDVVSATEPCKPCTECVGLQSMSAPCVEADDAVCRCAYGYYQDET<br>TGRCEACRVCEAGSGLVFSCQDKQNTVCEECPDGTYSDEANHVDPCLPCTVCEDTERQL<br>RECTRWADAECEEIPGRWITRSTPPEGSDSTAPSTQEPEAPPEQDLIASTVAGVVTTVM<br>GSSQPVVTRGTTDNLIPVYCSILAAVVVGLVAYIAFKRWNSCKQNKQGANSRPVNQTPP<br>PEGEKLHSDSGISVDSQSLHDQQPHTQTASGQALKGDGGLYSSLPPAKREEVEKLLNGS<br>AGDTWRHLAGELGYQPEHIDSFTHEACPVRALLASWATQDSATLDALLAALRRIQRADL<br>VESLCSESTATSPV |
| LNGFR Extracellular Domain (K29-N250) (nt) | 15! | aaggaggcatgccccacaggcctgtacacacacagcggtgagtgctgcaaagcctgcaa<br>cctgggcgagggtgtggcccagccttgtggagccaaccagaccgtgtgtgagccctgcc<br>tggacagcgtgacgttctccgacgtggtgagcgcgaccgagccgtgcaagccgtgcacc<br>gagtgcgtggggctccagagcatgtcggcgccgtgcgtggaggccgacgacgccgtgtg<br>ccgctgcgcctacggctactaccaggatgagacgactgggcgctgcgaggcgtgccgcg<br>tgtgcgaggcgggctcgggcctcgtgttctcctgccaggacaagcagaacaccgtgtgc<br>gaggagtgccccgacggcacgtattccgacgaggccaaccacgtggacccgtgcctgcc<br>ctgcaccgtgtgcgaggacaccgagcgccagctccgcgagtgcacacgctgggccgacg<br>ccgagtgcgaggagatccctggccgttggattacacggtccacacccccagagggctcg<br>gacagcacagcccccagcacccaggagcctgaggcacctccagaacaagacctcatagc<br>cagcacggtggcaggtgtggtgaccacagtgatgggcagctcccagcccgtggtgaccc<br>gaggcaccaccgacaac |
| LNGFR Extracellular Domain (K29-N250) (aa) | 156 | KEACPTGLYTHSGECCKACNLGEGVAQPCGANQTVCEPCLDSVTFSDVVS<br>ATEPCKPCTECVGLQSMSAPCVEADDAVCRCAYGYYQDETTGRCEACRVC<br>EAGSGLVFSCQDKQNTVCEECPDGTYSDEANHVDPCLPCTVCEDTERQLR<br>ECTRWADAECEEIPGRWITRSTPPEGSDSTAPSTQEPEAPPEQDLIASTV<br>AGVVTTVMGSSQPVVTRGTTDN |
| LNGFR Cys 2,3,4 (E65-N250) (nt) | 157 | Gagccctgcctggacagcgtgacgttctccgacgtggtgagcgcgaccgagccgtgcaa<br>gccgtgcaccgagtgcgtggggctccagagcatgtcggcgccgtgcgtggaggccgacg<br>acgccgtgtgccgctgcgcctacggctactaccaggatgagacgactgggcgctgcgag<br>gcgtgccgcgtgtgcgaggcgggctcgggcctcgtgttctcctgccaggacaagcagaa<br>caccgtgtgcgaggagtgccccgacggcacgtattccgacgaggccaaccacgtggacc<br>cgtgcctgccctgcaccgtgtgcgaggacaccgagcgccagctccgcgagtgcacacgc<br>tgggccgacgccgagtgcgaggagatccctggccgttggattacacggtccacaccccc<br>agagggctcggacagcacagcccccagcacccaggagcctgaggcacctccagaacaag<br>acctcatagccagcacggtggcaggtgtggtgaccacagtgatgggcagctcccagccc<br>gtggtgacccgaggcaccaccgacaac |

-continued

| Sequence Name | SEQ ID NO | Sequence |
|---|---|---|
| LNGFR Cys 2,3,4 (E65-N250) (aa) | 158 | EPCLDSVTFSDVVSATEPCKPCTECVGLQSMSAPCVEADDAVCRCAYGYY QDETTGRCEACRVCEAGSGLVFSCQDKQNTVCEECPDGTYSDEANHVDPC LPCTVCEDTERQLRECTRWADAECEEIPGRWITRSTPPEGSDSTAPSTQE PEAPPEQDLIASTVAGVVTTVMGSSQPVVTRGTTDN |
| LNGFR Cys3,4 (R108-N250) (nt) | 159 | cgctgcgcctacggctactaccaggatgagacgactgggcgctgcgaggcgtgccgcgt gtgcgaggcgggctcgggcctcgtgttctcctgccaggacaagcagaacaccgtgtgcg aggagtgccccgacggcacgtattccgacgaggccaaccacgtggacccgtgcctgccc tgcaccgtgtgcgaggacaccgagcgccagctccgcgagtgcacacgctgggccgacgc cgagtgcgaggagatccctggccgttggattacacggtccacacccccagagggctcgg acagcacagcccccagcacccaggagcctgaggcacctccagaacaagacctcatagcc agcacggtggcaggtgtggtgaccacagtgatgggcagctcccagcccgtggtgacccg aggcaccaccgacaac |
| LNGFR Cys3,4 (R108-N250) (aa) | 160 | RCAYGYYQDETTGRCEACRVCEAGSGLVFSCQDKQNTVCEECPDGTYSDE ANHVDPCLPCTVCEDTERQLRECTRWADAECEEIPGRWITRSTPPEGSDS TAPSTQEPEAPPEQDLIASTVAGVVTTVMGSSQPVVTRGTTDN |
| Truncated LNGFR design 1 (LNGFRt1) (nt) | 161 | aaggaggcatgccccacaggcctgtacacacacagcggtgagtgctgcaaagcctgcaa cctgggcgagggtgtggcccagccttgtggagccaaccagaccgtgtgtgagccctgcc tggacagcgtgacgttctccgacgtggtgagcgcgaccgagccgtgcaagccgtgcacc gagtgcgtggggctccagagcatgtcggcgccgtgcgtggaggccgacgacgccgtgtg ccgctgcgcctacggctactaccaggatgagacgactgggcgctgcgaggcgtgccgcg tgtgcgaggcgggctcgggcctcgtgttctcctgccaggacaagcagaacaccgtgtgc gaggagtgccccgacggcacgtattccgacgaggccaaccacgtggacccgtgcctgcc ctgcaccgtgtgcgaggacaccgagcgccagctccgcgagtgcacacgctgggccgacg ccgagtgcgaggagatccctggccgttggattacacggtccacacccccagagggctcg gacagcacagcccccagcacccaggagcctgaggcacctccagaacaagacctcatagc cagcacggtggcaggtgtggtgaccacagtgatgggcagctcccagcccgtggtgaccc gaggcaccaccgacaacctcatccctgtctattgctccatcctggctgctgtggttgtg ggccttgtggcctacatagccttc |
| Truncated LNGFR design 1 (LNGFRt1) (aa) | 162 | KEACPTGLYTHSGECCKACNLGEGVAQPCGANQTVCEPCLDSVTFSDVVS ATEPCKPCTECVGLQSMSAPCVEADDAVCRCAYGYYQDETTGRCEACRVC EAGSGLVFSCQDKQNTVCEECPDGTYSDEANHVDPCLPCTVCEDTERQLR ECTRWADAECEEIPGRWITRSTPPEGSDSTAPSTQEPEAPPEQDLIASTV AGVVTTVMGSSQPVVTRGTTDNLIPVYCSILAAVVVGLVAYIAF |
| Truncated LNGFR design 2 (LNGFRt2) (aa) | 163 | KEACPTGLYTHSGECCKACNLGEGVAQPCGANQTVCEPCLDSVTFSDVVS ATEPCKPCTECVGLQSMSAPCVEADDAVCRCAYGYYQDETTGRCEACRVC EAGSGLVFSCQDKQNTVCEECPDGTYSDEANHVDPCLPCTVCEDTERQLR ECTRWADAECEEIPGRWITRSTPPEGSDSTAPSTQEPEAPPEQDLIASTV AGVVTTVMGSSQPVVTRGTTDNGGGGSGGGGSGGGGSGGGGSFWVLVVVG GVLACYSLLVTVAFIIFWVRSKRS |
| Truncated LNGFR design 3 (LNGFRt3) (aa) | 164 | EPCLDSVTFSDVVSATEPCKPCTECVGLQSMSAPCVEADDAVCRCAYGYY QDETTGRCEACRVCEAGSGLVFSCQDKQNTVCEECPDGTYSDEANHVDPC LPCTVCEDTERQLRECTRWADAECEEIPGRWITRSTPPEGSDSTAPSTQE PEAPPEQDLIASTVAGVVTTVMGSSQPVVTRGTTDNGGGGGGGGSGGGG SGGGGSFWVLVVVGGVLACYSLLVTVAFIIFWVRSKRS |
| Truncated LNGFR design 4 (LNGFRt4) (aa) | 165 | RCAYGYYQDETTGRCEACRVCEAGSGLVFSCQDKQNTVCEECPDGTYSDE ANHVDPCLPCTVCEDTERQLRECTRWADAECEEIPGRWITRSTPPEGSDS TAPSTQEPEAPPEQDLIASTVAGVVTTVMGSSQPVVTRGTTDNGGGGSGG GGSGGGGSGGGGSFWVLVVVGGVLACYSLLVTVAFIIFWVRSKRS |
| Truncated LNGFR design 5 (LNGFRt5) (aa) | 166 | RCAYGYYQDETTGRCEACRVCEAGSGLVFSCQDKQNTVCEECPDGTYSDE ANHVDPCLPCTVCEDTERQLRECTRWADAECEEIPGRWITRSTPPEGSDS TAPSTQEPEAPPEQDLIASTVAGVVTTVMGSSQPVVTRGTTDNGGGGSGG GGSGGGGGGGGSEITLIIFGVMAGVIGTILLISYGIRRGGGS |
| Truncated LNGFR design 6 (LNGFRt6) (aa) | 167 | RCAYGYYQDETTGRCEACRVCEAGSGLVFSCQDKQNTVCEECPDGTYSDE ANHVDPCLPCTVCEDTERQLRECTRWADAECEEIPGRWITRSTPPEGSDS TAPSTQEPEAPPEQDLIASTVAGVVTTVMGSSQPVVTRGTTDNGGGGSGG GGSGGGGSGGGGSITLIIFGVMAGVIGTILLALLIWGGGS |
| Truncated LNGFR design 7 (LNGFRt7) (aa) | 168 | RCAYGYYQDETTGRCEACRVCEAGSGLVFSCQDKQNTVCEECPDGTYSDE ANHVDPCLPCTVCEDTERQLRECTRWADAECEEIPGRWITRSTPPEGSDS TAPSTQEPEAPPEQDLIASTVAGVVTTVMGSSQPVVTRGTTDNGGGGSGG GGSGGGGSGGGGSITLIIFGVMAGVIGTILLALLIWGGGS |
| CD19-CD3ζ CAR (nt) | 169 | atggcgctgcccgtgaccgccttgctcctgccgctggccttgctgctccacgccgccag gccggacatccagatgacacagactacatcctccctgtctgcctctctgggagacagag tcaccatcagttgcagggcaagtcaggacattagtaaatatttaaattggtatcagcag aaaccagatggaactgttaaactcctgatctaccatacatcaagattacactcaggagt cccatcaaggttcagtggcagtgggtctggaacagattattctctcaccattagcaatt |

-continued

| Sequence Name | SEQ ID NO | Sequence |
|---|---|---|
| | | tggagcaggaagatattgccacttacttttgccaacagggtaatacgcttccgtacacg<br>ttcggaggggggaccaagctggagatcacaggtggcggtggctcgggcggtggtgggtc<br>gggtggcggcggatctgaggtgaaactgcaggagtcaggacctggcctggtggcgccct<br>cacagagcctgtccgtcacatgcactgtctcaggggtctcattacccgactatggtgta<br>agctggattcgccagcctccacgaaagggtctggagtggctgggagtaatatggggtag<br>tgaaaccacatactataattcagctctcaaatccagactgaccatcatcaaggacaact<br>ccaagagccaagttttcttaaaaatgaacagtctgcaaactgatgacacagccatttac<br>tactgtgccaaacattattactacggtggtagctatgctatggactactggggccaagg<br>aacctcagtcaccgtctcctcaaccacgacgccagcgccgcgaccaccaacaccggcgc<br>ccaccatcgcgtcgcagcccctgtccctgcgcccagaggcgtgtagaccggctgcaggt<br>ggagcagtgcacacgagggggctggacttcgcctgtgatatctacatctgggcgccctt<br>ggccgggacttgtggggtccttctcctgtcactggttatcaccctttactgccgcgtca<br>agttcagcaggagcgcagacgcccccgcgtacaagcagggccagaaccagctctataac<br>gagctcaatctaggacgaagagaggagtacgatgttttggacaagagacgtggccggga<br>ccctgagatgggggggaaagccgagaaggaagaaccctcaggaaggcctgtacaatgaac<br>tgcagaaagataagatggcggaggcctacagtgagattgggatgaaaggcgagcgccgg<br>aggggcaaggggcacgatggcctttaccagggtctcagtacagccaccaaggacaccta<br>cgacgcccttcacatgcaggccctgccccctcgc |
| CD19-CD3ζ CAR<br>(aa) | 170 | MALPVTALLLPLALLLHAARPDIQMTQTTSSLSASLGDRVTISCRASQDI<br>SKYLNWYQQKPDGTVKLLIYHTSRLHSGVPSRFSGSGSGTDYSLTISNLE<br>QEDIATYFCQQGNTLPYTFGGGTKLEITGGGGSGGGGSGGGGSEVKLQES<br>GPGLVAPSQSLSVTCTVSGVSLPDYGVSWIRQPPRKGLEWLGVIWGSETT<br>YYNSALKSRLTIIKDNSKSQVFLKMNSLQTDDTAIYYCAKHYYYGGSYAM<br>DYWGQGTSVTVSSTTTPAPRPPTPAPTIASQPLSLRPEACRPAAGGAVHT<br>RGLDFACDIYIWAPLAGTCGVLLLSLVITLYCRVKFSRSADAPAYKQGQN<br>QLYNELNLGRREEYDVLDKRRGRDPEMGGKPRRKNPQEGLYNELQKDKMA<br>EAYSEIGMKGERRRGKGHDGLYQGLSTATKDTYDALHMQALPPR |
| CD19-CD137-CD3ζ<br>CAR (nt) | 171 | atggccttaccagtgaccgccttgctcctgccgctggccttgctgctccacgccgccag<br>gccggacatccagatgacacagactacatcctccctgtctgcctctctgggagacagag<br>tcaccatcagttgcagggcaagtcaggacattagtaaatatttaaattggtatcagcag<br>aaaccagatggaactgttaaactcctgatctaccatacatcaagattacactcaggagt<br>cccatcaaggttcagtggcagtgggtctggaacagattattctctcaccattagcaacc<br>tggagcaagaagatattgccacttacttttgccaacagggtaatacgcttccgtacacg<br>ttcggaggggggaccaagctggagatcacaggcagcacctccggcagcggcaagcctgg<br>cagcggcgagggcagcaccaagggcgaggtgaaactgcaggagtcaggacctggcctgg<br>tggcgccctcacagagcctgtccgtcacatgcactgtctcaggggtctcattacccgac<br>tatggtgtaagctggattcgccagcctccacgaaagggtctggagtggctgggagtaat<br>atggggtagtgaaaccacatactataattcagctctcaaatccagactgaccatcatca<br>aggacaactccaagagccaagttttcttaaaaatgaacagtctgcaaactgatgacaca<br>gccatttactactgtgccaaacattattactacggtggtagctatgctatggactactg<br>gggccaaggaacctcagtcaccgtctcctcaaccacgacgccagcgccgcgaccaccaa<br>caccggcgcccaccatcgcgtcgcagcccctgtccctgcgcccagaggcgtgccggcca<br>gcggcggggggcgcagtgcacacgagggggctggacttcgcctgtgatatctacatctg<br>ggcgcccttggccgggacttgtggggtccttctcctgtcactggttatcaccctttact<br>gcaaacggggcagaaagaaactcctgtatatattcaaacaaccatttatgagaccagta<br>caaactactcaagaggaagatggctgtagctgccgatttccagaagaagaagaaggagg<br>atgtgaactgagagtgaagttcagcaggagcgcagacgcccccgcgtacaagcagggcc<br>agaaccagctctataacgagctcaatctaggacgaagagaggagtacgatgttttggac<br>aagagacgtggccgggaccctgagatggggggaaagccgagaaggaagaaccctcagga<br>aggcctgtacaatgaactgcagaaagataagatggcggaggcctacagtgagattggga<br>tgaaaggcgagcgccggaggggcaaggggcacgatggcctttaccagggtctcagtaca<br>gccaccaaggacacctacgacgcccttcacatgcaggccctgccccctcgc |
| CD19-CD137-CDζ<br>CAR (aa) | 172 | MALPVTALLLPLALLLHAARPDIQMTQTTSSLSASLGDRVTISCRASQDI<br>SKYLNWYQQKPDGTVKLLIYHTSRLHSGVPSRFSGSGSGTDYSLTISNLE<br>QEDIATYFCQQGNTLPYTFGGGTKLEITGSTSGSGKPGSGEGSTKGEVKL<br>QESGPGLVAPSQSLSVTCTVSGVSLPDYGVSWIRQPPRKGLEWLGVIWGS<br>ETTYYNSALKSRLTIIKDNSKSQVFLKMNSLQTDDTAIYYCAKHYYYGGS<br>YAMDYWGQGTSVTVSSTTTPAPRPPTPAPTIASQPLSLRPEACRPAAGGA<br>VHTRGLDFACDIYIWAPLAGTCGVLLLSLVITLYCKRGRKKLLYIFKQPF<br>MRPVQTTQEEDGCSCRFPEEEEGGCELRVKFSRSADAPAYKQGQNQLYNE<br>LNLGRREEYDVLDKRRGRDPEMGGKPRRKNPQEGLYNELQKDKMAEAYSE<br>IGMKGERRRGKGHDGLYQGLSTATKDTYDALHMQALPPR |
| CD19-CD28-CD3ζ<br>CAR (nt) | 173 | atggcgctgcccgtgaccgccttgctcctgccgctggccttgctgctccacgccgccag<br>gccggacatccagatgacacagactacatcctccctgtctgcctctctgggagacagag<br>tcaccatcagttgcagggcaagtcaggacattagtaaatatttaaattggtatcagcag<br>aaaccagatggaactgttaaactcctgatctaccatacatcaagattacactcaggagt<br>cccatcaaggttcagtggcagtgggtctggaacagattattctctcaccattagcaatt<br>tggagcaggaagatattgccacttacttttgccaacagggtaatacgcttccgtacacg<br>ttcggaggggggaccaagctggagatcacaggtggcggtggctcgggcggtggtgggtc<br>gggtggcggcggatctgaggtgaaactgcaggagtcaggacctggcctggtggcgccct<br>cacagagcctgtccgtcacatgcactgtctcaggggtctcattacccgactatggtgta<br>agctggattcgccagcctccacgaaagggtctggagtggctgggagtaatatggggtag |

-continued

| Sequence Name | SEQ ID NO | Sequence |
|---|---|---|
| | | tgaaaccacatactataattcagctctcaaatccagactgaccatcatcaaggacaact<br>ccaagagccaagttttcttaaaaatgaacagtctgcaaactgatgacacagccatttac<br>tactgtgccaaacattattactacggtggtagctatgctatggactactggggccaagg<br>aacctcagtcaccgtctcctcaaccacgacgccagcgccgcgaccaccaacaccggcgc<br>ccaccatcgcgtcgcagcccctgtccctgcgcccagaggcgtgtagaccggctgcaggt<br>ggagcagtgcacacgagggggctggacttcgcctgtgatatctacatctgggcgccctt<br>ggccgggacttgtggggtccttctcctgtcactggttatcaccctttactgcaggagta<br>agaggagcaggctcctgcacagtgactacatgaacatgactccccgccgccccgggccc<br>acccgcaagcattaccagccctatgccccaccacgcgacttcgcagcctatcgctcccg<br>cgtcaagttcagcaggagcgcagacgcccccgcgtacaagcagggccagaaccagctct<br>ataacgagctcaatctaggacgaagagaggagtacgatgttttggacaagagacgtggc<br>cgggaccctgagatgggggggaaagccgagaaggaagaaccctcaggaaggcctgtacaa<br>tgaactgcagaaagataagatggcggaggcctacagtgagattgggatgaaaggcgagc<br>gccggaggggcaaggggcacgatggcctttaccagggtctcagtacagccaccaaggac<br>acctacgacgcccttcacatgcaggccctgccccctcgc |
| CD19-CD28-CD3ζ CAR (aa) | 174 | MALPVTALLLPLALLLHAARPDIQMTQTTSSLSASLGDRVTISCRASQDI<br>SKYLNWYQQKPDGTVKLLIYHTSRLHSGVPSRFSGSGSGTDYSLTISNLE<br>QEDIATYFCQQGNTLPYTFGGGTKLEITGGGGSGGGGSGGGGSEVKLQES<br>GPGLVAPSQSLSVTCTVSGVSLPDYGVSWIRQPPRKGLEWLGVIWGSETT<br>YYNSALKSRLTIIKDNSKSQVFLKMNSLQTDDTAIYYCAKHYYYGGSYAM<br>DYWGQGTSVTVSSTTTPAPRPPTPAPTIASQPLSLRPEACRPAAGGAVHT<br>RGLDFACDIYIWAPLAGTCGVLLLSLVITLYCRSKRSRLLHSDYMNMTPR<br>RPGPTRKHYQPYAPPRDFAAYRSRVKFSRSADAPAYKQGQNQLYNELNLG<br>RREEYDVLDKRRGRDPEMGGKPRRKNPQEGLYNELQKDKMAEAYSEIGMK<br>GERRRGKGHDGLYQGLSTATKDTYDALHMQALPPR |
| CD19-CD28-CD3ζ CAR (nt) | 175 | atgctgctgctggtgaccagcctgctgctgtgtgagctgccccaccccgcctttctgct<br>gatccccgacatccagatgacccagaccacctccagcctgagcgccagcctgggcgacc<br>gggtgaccatcagctgccgggccagccaggacatcagcaagtacctgaactggtatcag<br>cagaagcccgacggcaccgtcaagctgctgatctaccacaccagccggctgcacagcgg<br>cgtgcccagccggtttagcggcagcggctccggcaccgactacagcctgaccatctcca<br>acctggagcaggaggacatcgccacctacttttgccagcagggcaacacactgccctac<br>acctttggcggcggaacaaagctggagatcaccggcagcacctccggcagcggcaagcc<br>tggcagcggcgagggcagcaccaagggcgaggtgaagctgcaggagagcggccctggcc<br>tggtggcccccagccagagcctgagcgtgacctgtaccgtgtccggcgtgtccctgccc<br>gactacggcgtgtcctggatccggcagccccctaggaagggcctggagtggctgggcgt<br>gatctggggcagcgagaccacctactacaacagcgccctgaagagccggctgaccatca<br>tcaaggacaacagcaagagccaggtgttcctgaagatgaacagcctgcagaccgacgac<br>accgccatctactactgtgccaagcactactactacggcggcagctacgccatggacta<br>ctggggccagggcaccagcgtgaccgtgtccagcgagagcaagtacggccctccctgcc<br>ccccttgccctgcccccgagttcctgggcggacccagcgtgttcctgttccccccaag<br>cccaaggacaccctgatgatcagccggacccccgaggtgacctgtgtggtggtggacgt<br>gtcccaggaggaccccgaggtccagttcaactggtacgtggacggcgtggaggtgcaca<br>acgccaagaccaagccccgggaggagcagttcaatagcacctaccgggtggtgtccgtg<br>ctgaccgtgctgcaccaggactggctgaacggcaaggaatacaagtgtaaggtgtccaa<br>caagggcctgcccagcagcatcgagaaaaccatcagcaaggccaagggccagcctcggg<br>agccccaggtgtacaccctgcccccctagccaagaggagatgaccaagaatcaggtgtcc<br>ctgacctgcctggtgaagggcttctaccccagcgacatcgccgtggagtgggagagcaa<br>cggccagcccgagaacaactacaagaccaccccccctgtgctggacagcgacggcagct<br>tcttcctgtacagcaggctgaccgtggacaagagccggtggcaggagggcaacgtcttt<br>agctgctccgtgatgcacgaggccctgcacaaccactacacccagaagagcctgtccct<br>gagcctgggcaagatgttctgggtgctggtcgtggtgggtggcgtgctggcctgctaca<br>gcctgctggtgacagtggccttcatcatcttttgggtgaggagcaagcggagcagaggc<br>ggccacagcgactacatgaacatgacccccccggaggcctggccccacccggaagcacta<br>ccagccctacgcccctcccagggacttcgccgcctaccggagccgggtgaagttcagcc<br>ggagcgccgacgcccctgcctaccagcagggccagaaccagctgtacaacgagctgaac<br>ctgggccggagggaggagtacgacgtgctggacaagcggagaggccgggaccctgagat<br>gggcggcaagccccggagaaagaaccctcaggagggcctgtataacgaactgcagaaag<br>acaagatggccgaggcctacagcgagatcggcatgaagggcgagcggcggaggggcaag<br>ggccacgacggcctgtaccagggcctgagcaccgccaccaaggatacctacgacgccct<br>gcacatgcaggccctgccccccaga |
| CD19-CD28-CD3ζ CAR (aa) | 176 | MLLLVTSLLLCELPHPAFLLIPDIQMTQTTSSLSASLGDRVTISCRASQD<br>ISKYLNWYQQKPDGTVKLLIYHTSRLHSGVPSRFSGSGSGTDYSLTISNL<br>EQEDIATYFCQQGNTLPYTFGGGTKLEITGSTSGSGKPGSGEGSTKGEVK<br>LQESGPGLVAPSQSLSVTCTVSGVSLPDYGVSWIRQPPRKGLEWLGVIWG<br>SETTYYNSALKSRLTIIKDNSKSQVFLKMNSLQTDDTAIYYCAKHYYYGG<br>SYAMDYWGQGTSVTVSSESKYGPPCPPCPAPEFLGGPSVFLFPPKPKDTL<br>MISRTPEVTCVVVDVSQEDPEVQFNWYVDGVEVHNAKTKPREEQFNSTYR<br>VVSVLTVLHQDWLNGKEYKCKVSNKGLPSSIEKTISKAKGQPREPQVYTL<br>PPSQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSLGKMFWV |

-continued

| Sequence Name | SEQ ID NO | Sequence |
|---|---|---|
| | | LVVVGGVLACYSLLVTVAFIIFWVRSKRSRGGHSDYMNMTPRRPGPTRKH<br>YQPYAPPRDFAAYRSRVKFSRSADAPAYQQGQNQLYNELNLGRREEYDVL<br>DKRRGRDPEMGGKPRRKNPQEGLYNELQKDKMAEAYSEIGMKGERRRGKG<br>HDGLYQGLSTATKDTYDALHMQALPPR |
| Membrane bound Interleukin-15 (IL-15.Linker.IL-15Rα) (nt) | 177 | aactgggtgaatgtgatcagcgacctgaagaagatcgaggatctgatccagagcatgca<br>cattgatgccaccctgtacacagaatctgatgtgcaccctagctgtaaagtgaccgcca<br>tgaagtgttttctgctggagctgcaggtgatttctctggaaagcggagatgcctctatc<br>cacgacacagtggagaatctgatcatcctggccaacaatagcctgagcagcaatggcaa<br>tgtgacagagtctggctgtaaggagtgtgaggagctggaggagaagaacatcaaggagt<br>ttctgcagagctttgtgcacatcgtgcagatgttcatcaatacaagctctggcggagga<br>tctggaggaggcggatctggaggaggaggcagtggaggcggaggatctggcggaggatc<br>tctgcagattacatgccctcctccaatgtctgtggagcacgccgatatttgggtgaagt<br>cctacagcctgtacagcagagagagatacatctgcaacagcggctttaagagaaaggcc<br>ggcacctcttctctgacagagtgcgtgctgaataaggccacaaatgtggcccactggac<br>aacacctagcctgaagtgcattagagatcctgccctggtccaccagaggcctgcccctc<br>catctacagtgacaacagccggagtgacacctcagcctgaatctctgagcccttctgga<br>aaagaacctgccgccagctctcctagctctaataataccgccgccacaacagccgccat<br>tgtgcctggatctcagctgatgcctagcaagtctcctagcacaggcacaacagagatca<br>gcagccacgaatcttctcacggaacaccttctcagaccaccgccaagaattgggagctg<br>acagcctctgcctctcaccagcctccaggagtgtatcctcagggccactctgatacaac<br>agtggccatcagcacatctacagtgctgctgtgtggactgtctgccgtgtctctgctgg<br>cctgttacctgaagtctagacagacacctcctctggcctctgtggagatggaggccatg<br>gaagccctgcctgtgacatggggaacaagcagcagagatgaggacctggagaattgttc<br>tcaccacctg |
| Membrane bound Interleukin-15 (IL-15.Linker.IL-15Rα) (aa) | 178 | NWVNVISDLKKIEDLIQSMHIDATLYTESDVHPSCKVTAMKCFLLELQVISLESGDASI<br>HDTVENLIILANNSLSSNGNVTESGCKECEELEEKNIKEFLQSFVHIVQMFINTSSGGG<br>SGGGGGSGGGSGGGGSGGGSLQITCPPPMSVEHADIWVKSYSLYSRERYICNSGFKRKA<br>GTSSL<br>TECVLNKATNVAHWTTPSLKCIRDPALVHQRPAPPSTVTTAGVTPQPESLSPSGKEPAA<br>SSPSSNNTAATTAAIVPGSQLMPSKSPSTGTTEISSHESSHGTPSQTTAKNWELTASAS<br>HQPPGVYPQGHSDTTVAISTSTVLLCGLSAVSLLACYLKSRQTPPLASVEMEAMEALPV<br>TWGTSSRDEDLENCSHHL |
| CD19-CD137-CD3 CAR.T2A.Ig Kappa signal peptide.HER1t (aa) | 179 | DIQMTQTTSSLSASLGDRVTISCRASQDISKYLNWYQQKPDGTVKLLIYHTSRLHSGVP<br>SRFSGSGSGTDYSLTISNLEQEDIATYFCQQGNTLPYTFGGGTKLEITGSTSGSGKPGS<br>GEGSTKGEVKLQESGPGLVAPSQSLSVTCTVSGVSLPDYGVSWIRQPPRKGLEWLGVIW<br>GSETTYYNSALKSRLTIIKDNSKSQVFLKMNSLQTDDTAIYYCAKHYYYGGSYAMDYWG<br>QGTSVTVSSTTTPAPRPPTPAPTIASQPLSLRPEACRPAAGGAVHTRGLDFACDIYIWA<br>PLAGTCGVLLLSLVITLYCKRGRKKLLYIFKQPFMRPVQTTQEEDGCSCRFPEEEEGGC<br>ELRVKFSRSADAPAYKQGQNQLYNELNLGRREEYDVLDKRRGRDPEMGGKPRRKNPQEG<br>LYNELQKDKMAEAYSEIGMKGERRRGKGHDGLYQGLSTATKDTYDALHMQALPPREGRG<br>SLLTCGDVEENPGPMRLPAQLLGLLMLWVPGSSGRKVCNGIGIGEFKDSLSINATNIKH<br>FKNCTSISGDLHILPVAFRGDSFTHTPPLDPQELDILKTVKEITGFLLIQAWPENRTDL<br>HAFENLEIIRGRTKQHGQFSLAVVSLNITSLGLRSLKEISDGDVIISGNKNLCYANTIN<br>WKKLFGTSGQKTKIISNRGENSCKATGQVCHALCSPEGCWGPEPRDCVSCRNVSRGREC<br>VDKCNLLEGEPREFVENSECIQCHPECLPQAMNITCTGRGPDNCIQCAHYIDGPHCVKT<br>CPAGVMGENNTLVWKYADAGHVCHLCHPNCTYGCTGPGLEGCPTNGPKIPSIATGMVGA<br>LLLLLVVALGIGLFM |
| CD19-CD137-CD3ζ CAR.T2A.Ig Kappa signal peptide.HER1t (aa) | 180 | DIQMTQTTSSLSASLGDRVTISCRASQDISKYLNWYQQKPDGTVKLLIYHTSRLHSGVP<br>SRFSGSGSGTDYSLTISNLEQEDIATYFCQQGNTLPYTFGGGTKLEITGSTSGSGKPGS<br>GEGSTKGEVKLQESGPGLVAPSQSLSVTCTVSGVSLPDYGVSWIRQPPRKGLEWLGVIW<br>GSETTYYNSALKSRLTIIKDNSKSQVFLKMNSLQTDDTAIYYCAKHYYYGGSYAMDYWG<br>QGTSVTVSSTTTPAPRPPTPAPTIASQPLSLRPEACRPAAGGAVHTRGLDFACDIYIWA<br>PLAGTCGVLLLSLVITLYCKRGRKKLLYIFKQPFMRPVQTTQEEDGCSCRFPEEEEGGC<br>ELRVKFSRSADAPAYKQGQNQLYNELNLGRREEYDVLDKRRGRDPEMGGKPRRKNPQEG<br>LYNELQKDKMAEAYSEIGMKGERRRGKGHDGLYQGLSTATKDTYDALHMQALPPREGRG<br>SLLTCGDVEENPGPMRLPAQLLGLLMLWVPGSSGRKVCNGIGIGEFKDSLSINATNIKH<br>FKNCTSISGDLHILPVAFRGDSFTHTPPLDPQELDILKTVKEITGFLLIQAWPENRTDL<br>HAFENLEIIRGRTKQHGQFSLAVVSLNITSLGLRSLKEISDGDVIISGNKNLCYANTIN<br>WKKLFGTSGQKTKIISNRGENSCKATGQVCHALCSPEGCWGPEPRDCVSGGGGSGGGGS<br>GGGGSGGGGSFWVLVVVGGVLACYSLLVTVAFIIFWVRSKRS |
| CD19-CD28-CD3ζ CAR.P2A.Ig Kappa signal peptide.HER1t1 (nt) | 181 | gacatccaaatgacacagacaaccagcagcctctctgccagtctgggagatcgtgtgac<br>catcagttgtagagcctcacaagatatttccaaatacctaaactggtatcagcaaaaac<br>cagatggtacagtgaagttactgatctaccatactagccgtcttcattccggtgtgcct<br>tctcgctttagcgggtctggatcaggaacagattacagtctcaccatcagcaacctcga<br>acaagaagatatagctacctatttctgccagcagggtaacactttgccatataccttcg<br>gaggaggcacaaaactggagatcactggttctaccagtggaagcggcaagcctggctcc<br>ggtgaaggaagtaccaaaggcgaagtgaagctgcaagagtcaggtccaggtttggtagc<br>tcccagccaatccctatctgttacctgtacagtgtctggtgtgtcacttccagattatg<br>gcgtgtcatggataaggcagcccccacgaaaaggcctggaatggttgggggtgatctgg<br>ggatctgagaccacctactacaacagcgccctgaaaagtcggctcaccatcatcaaaga<br>caactccaagtcacaagtgtttcttaagatgaactcacttcagaccgacgacacagcca |

-continued

| Sequence Name | SEQ ID NO | Sequence |
|---|---|---|
| | | tatactactgtgctaaacattactactatggcggtagctatgccatggattactggggt<br>caaggtactagtgtgacagtatcatctgaatcaaagtatggcccaccctgcccccttg<br>tcccgctcctgagttcctgggtggtccctccgtattcctgtttccacctaagccaaaag<br>acactctcatgatcagcagaacacctgaggtgacatgcgtcgtagttgatgttagccag<br>gaggaccccgaagtgcaatttaactggtacgtagacggtgtggaagtgcataacgcaaa<br>gaccaagccacgtgaagagcagtttaactccacctaccgagtggtgtctgtgctcacag<br>tcttacatcaagattggctgaacggaaaagagtataaatgtaaagtatccaataagggc<br>cttccctctagcatcgaaaagactatctccaaagccaagggacagccacgcgaaccaca<br>ggtgtatactttacctccttctcaagaagagatgaccaagaaccaagtatctctgacgt<br>gtttggtgaaggggttctacccctctgacatcgcagtggaatgggaatcaaacggtcaa<br>cctgagaacaattacaaaaccaccccacctgtgctggatagcgacggcagcttctttct<br>gtatagcaggctcacagtggataaaagtcggtggcaggaaggaaacgtatttagttgca<br>gtgtgatgcacgaggccctccataaccattatacccagaagtcactctcacttagtctg<br>ggtaagatgttctgggtgctcgtggtcgtaggtggagtgctggcttgctactccctctt<br>agtgaccgtggcttttatcatcttctgggtacgttccaaaaggtcccgtggtggccatt<br>cagattacatgaatatgacccccagacgaccaggcccaacaaggaagcattatcaacct<br>tacgcccctccccgagattttgcagcttatcgaagtagggtgaagttcagccggtctgc<br>tgacgctcctgcataccagcaaggtcagaatcagttatacaatgagctaaatctaggac<br>gacgcgaagaatatgatgtgctggacaaacgacgtggcagggaccctgaaatgggtggc<br>aagccaagaaggaagaacccacaagagggtctgtacaacgagttgcagaaagacaagat<br>ggcagaggcctactccgagatcggaatgaaaggagagaggcggaggggtaaaggacatg<br>acggtctttaccagggcctgagcacagctactaaagatacctacgacgccctccacatg<br>caggctttgcccccacgagctaccaattttagtctgttgaaacaagctggagatgtcga<br>ggaaaatccaggcccaatgcgacttcctgctcaactgctgggtctgctcatgctgtggg<br>ttcctggaagcagtggccgaaaggtctgcaacggcatcggtatcggcgaatttaaggat<br>agtctatctatcaacgctaccaatattaagcattttaagaactgcacgtctatttccgg<br>cgacttgcacatcctccctgttgcatttcggggtgatagtttcacccatacccccccctc<br>tcgatccacaagaactggacattcttaaaaccgttaaagaaataacaggttttctcctc<br>atccaggcatggcccgagaataggacagatcttcacgcatttgaaaacctcgaaatcat<br>cagagggaggaccaaacagcatggtcagtttagtctcgcagtggtgtctctgaacatca<br>cttctttagggcttcgatcacttaaggaaatctctgacggtgatgtaatcatcagcggt<br>aacaagaacctgtgctacgctaacacgatcaactggaagaagctgtttggcacaagcgg<br>ccagaaaaccaagatcattagtaataggggcgagaatagctgtaaagcaaccgggcaag<br>tgtgtcacgctctgtgttctcccgagggatgttggggacctgaaccaagagactgcgtt<br>agtggagggggggctctggtggcggaggatctggcggaggcggaagcggaggcggggg<br>gagcttctgggtgctcgtggtcgtaggaggggtgctggcctgttactctctactcgtaa<br>ctgttgctttcatcatattctgggtccgaagtaagcgtagc |
| CD19-CD28-CD3ζ CAR.P2A.Ig Kappa signal peptide.HER1t1 (aa) | 182 | DIQMTQTTSSLSASLGDRVTISCRASQDISKYLNWYQQKPDGTVKLLIYHTSRLHSGVP<br>SRFSGSGSGTDYSLTISNLEQEDIATYFCQQGNTLPYTFGGGTKLEITGSTSGSGKPGS<br>GEGSTKGEVKLQESGPGLVAPSQSLSVTCTVSGVSLPDYGVSWIRQPPRKGLEWLGVIW<br>GSETTYYNSALKSRLTIIKDNSKSQVFLKMNSLQTDDTAIYYCAKHYYYGGSYAMDYWG<br>QGTSVTVSSESKYGPPCPPCPAPEFLGGPSVFLFPPKPKDTLMISRTPEVTCVVVDVSQ<br>EDPEVQFNWYVDGVEVHNAKTKPREEQFNSTYRVVSVLTVLHQDWLNGKEYKCKVSNKG<br>LPSSIEKTISKAKGQPREPQVYTLPPSQEEMTKNQVSLTCLVKGFYPSDIAVEWESNGQ<br>PENNYKTTPPVLDSDGSFFLYSRLTVDKSRWQEGNVFSCSVMHEALHNHYTQKSLSLSL<br>GKMFWVLVVVGGVLACYSLLVTVAFIIFWVRSKRSRGGHSDYMNMTPRRPGPTRKHYQP<br>YAPPRDFAAYRSRVKFSRSADAPAYQQGQNQLYNELNLGRREEYDVLDKRRGRDPEMGG<br>KPRRKNPQEGLYNELQKDKMAEAYSEIGMKGERRRGKGHDGLYQGLSTATKDTYDALHM<br>QALPPRATNFSLLKQAGDVEENPGPMRLPAQLLGLLMLWVPGSSGRKVCNGIGIGEFKD<br>SLSINATNIKHFKNCTSISGDLHILPVAFRGDSFTHTPPLDPQELDILKTVKEITGFLL<br>IQAWPENRTDLHAFENLEIIRGRTKQHGQFSLAVVSLNITSLGLRSLKEISDGDVIISG<br>NKNLCYANTINWKKLFGTSGQKTKIISNRGENSCKATGQVCHALCSPEGCWGPEPRDCV<br>SGGGGGGGSGGGGSGGGGSFWVLVVVGGVLACYSLLVTVAFIIFWVRSKRS |
| Ig Kappa signal peptide.HER1t1. P2A.CD8α signal peptide.CD19-CD28-CD3ζ CAR (aa) | 183 | MRLPAQLLGLLMLWVPGSSGRKVCNGIGIGEFKDSLSINATNIKHFKNCTSISGDLHIL<br>PVAFRGDSFTHTPPLDPQELDILKTVKEITGFLLIQAWPENRTDLHAFENLEIIRGRTK<br>QHGQFSLAVVSLNITSLGLRSLKEISDGDVIISGNKNLCYANTINWKKLFGTSGQKTKI<br>ISNRGENSCKATGQVCHALCSPEGCWGPEPRDCVSGGGGSGGGGSGGGGSGGGGSFWVL<br>VVVGGVLACYSLLVTVAFIIFWVRSKRSATNFSLLKQAGDVEENPGPMALPVTALLLPL<br>ALLLHAARPDIQMTQTTSSLSASLGDRVTISCRASQDISKYLNWYQQKPDGTVKLLIYH<br>TSRLHSGVPSRFSGSGSGTDYSLTISNLEQEDIATYFCQQGNTLPYTFGGGTKLEITGS<br>TSGSGKPGSGEGSTKGEVKLQESGPGLVAPSQSLSVTCTVSGVSLPDYGVSWIRQPPRK<br>GLEWLGVIWGSETTYYNSALKSRLTIIKDNSKSQVFLKMNSLQTDDTAIYYCAKHYYYG<br>GSYAMDYWGQGTSVTVSSESKYGPPCPPCPAPEFLGGPSVFLFPPKPKDTLMISRTPEV<br>TCVVVDVSQEDPEVQFNWYVDGVEVHNAKTKPREEQFNSTYRVVSVLTVLHQDWLNGKE<br>YKCKVSNKGLPSSIEKTISKAKGQPREPQVYTLPPSQEEMTKNQVSLTCLVKGFYPSDI<br>AVEWESNGQPENNYKTTPPVLDSDGSFFLYSRLTVDKSRWQEGNVFSCSVMHEALHNHY<br>TQKSLSLSLGKMFWVLVVVGGVLACYSLLVTVAFIIFWVRSKRSRGGHSDYMNMTPRRP<br>GPTRKHYQPYAPPRDFAAYRSRVKFSRSADAPAYQQGQNQLYNELNLGRREEYDVLDKR<br>RGRDPEMGGKPRRKNPQEGLYNELQKDKMAEAYSEIGMKGERRRGKGHDGLYQGLSTAT<br>KDTYDALHMQALPPR |
| CD19-CD28-CD35 CAR.Furin-T2A.Ig Kappa signal | 184 | DIQMTQTTSSLSASLGDRVTISCRASQDISKYLNWYQQKPDGTVKLLIYHTSRLHSGVP<br>SRFSGSGSGTDYSLTISNLEQEDIATYFCQQGNTLPYTFGGGTKLEITGSTSGSGKPGS<br>GEGSTKGEVKLQESGPGLVAPSQSLSVTCTVSGVSLPDYGVSWIRQPPRKGLEWLGVIW |

-continued

| Sequence Name | SEQ ID NO | Sequence |
|---|---|---|
| peptide.HER1t1 (aa) | | GSETTYYNSALKSRLTIIKDNSKSQVFLKMNSLQTDDTAIYYCAKHYYYGGSYAMDYWG QGTSVTVSSKPTTTPAPRPPTPAPTIASQPLSLRPEACRPAAGGAVHTRGLDFACDIYI WAPLAGTCGVLLLSLVITLYCNHRNRSKRSRGGHSDYMNMTPRRPGPTRKHYQPYAPPR DFAAYRSRVKFSRSADAPAYQQGQNQLYNELNLGRREEYDVLDKRRGRDPEMGGKPRRK NPQEGLYNELQKDKMAEAYSEIGMKGERRRGKGHDGLYQGLSTATKDTYDALHMQALPP RRAKRSGSGEGRGSLLTCGDVEENPGPMRLPAQLLGLLMLWVPGSSGRKVCNGIGIGEF KDSLSINATNIKHFKNCTSISGDLHILPVAFRGDSFTHTPPLDPQELDILKTVKEITGF LLIQAWPENRTDLHAFENLEIIRGRTKQHGQFSLAVVSLNITSLGLRSLKEISDGDVII SGNKNLCYANTINWKKLFGTSGQKTKIISNRGENSCKATGQVCHALCSPEGCWGPEPRD CVSGGGGSGGGGSGGGGSGGGGSFWVLVVVGGVLACYSLLVTVAFIIFWVRSKRS |
| CD19-CD137-CD3ζ CAR.E2A.Ig Kappa signal peptide.HER1t7 (nt) | 185 | gacatacagatgactcagacaacaagtagcttgtccgcatccctgggcgatagagtgac catcagttgtcgagcatcccaagatatatccaagtacttaaactggtatcagcagaagc cagatggcaccgtcaagctgctaatctaccacacaagtaggctccacagcggagtgcct agccgattctctggttctggttctggcacagactattccctaaccatcagcaacctgga gcaagaggacattgcaacatattttgccagcagggcaacacactgccatatacctttg gaggcgggaccaagctggaaatcaccggtagtacgagtggttctggaaaacctggttct ggcgaaggtagtactaaaggagaggtgaaacttcaagagagtggccctggcttggtggc cccttctcaaagtttgagcgtgacctgcacagtaagtggcgtcagcctgccagattacg gagtcagttggattcgccagcctccaaggaagggccttgaatggctgggcgtaatctgg gggtccgaaaccacctattacaactccgcacttaagagccgtttaaccatcatcaaaga caacagcaagagtcaggtctttctcaaaatgaatagtctgcaaacggacgacaccgcta tctactattgtgccaagcactactactatggtggctcctacgctatggattactgggga caaggaacaagcgtgacagtgtcaagtactaccacacctgctccccgtcctccaacccc cgctcctactattgccagtcaaccactgtctcttaggcccgaggcatgtaggccagcag caggcggggctgtgcatacccgaggtctcgacttcgcctgcgacatatatatctgggcc cctctggctggcacttgtggggtcctcctcctgagtctcgtgatcactctgtattgtaa acgtgggcgaaagaagctcctttacatcttcaagcaacccttcatgaggcctgtacaga ccacgcaggaggaggacgggtgtagttgccgattccccgaagaggaagaaggcggttgc gagcttcgagtgaaattcagtaggagtgctgacgcaccagcatataagcagggccagaa ccaattatacaacgagctgaacctcggacgaagggaagagtatgatgtgctggataagc gcagaggccgtgatccagaaatgggcggcaaacctcgtcggaaaaatccacaagagggg ctatacaacgaattgcagaaagacaaaatggcagaggcctattctgaaatcggcatgaa gggcgaacgacgaagaggtaagggtcatgacggcctgtatcaaggtctctctaccgcca caaaggacacttacgatgctttacacatgcaggctctccctcccagacaatgcaccaac tacgctctattgaagttggcaggagatgtggaatccaaccccggtcctatgcgtctacc tgcccagctgcttgggctcctgatgctgtgggtccccggcagcagtggtagaaaagtat gtaacggcataggtatcggtgaatttaaggactcactaagcatcaacgccacaaacatc aagcactttaagaactgtacctctattagcggagacttacacatcctgccagtcgcatt tcgaggagacagtttcacccacactccacctctcgatcctcaggaattagacattctta aaacagttaaggaaatcactggatttcttcttatccaggcctggccagaaaatagaaca gacctgcacgctttcgagaaccttgaaataatacgaggcaggaccaaacagcatggcca atttagtttggctgtagtctccttgaacatcacttcccttggcctaaggtctttgaagg aaatcagtgacggagacgtgattatcagcgggaacaagaacctctgttacgcaaacaca atcaactggaagaagctctttggcaccagcggccagaagacaaagatcatttctaaccg aggagagaacagttgtaaggcaacaggacaagtgtgccacgctttgtgcagccccgagg gatgttggggtcctgagccacgtgattgtgtctcttgccggaacgtcagcagaggtaga gaatgtgtggataagtgcaacctcctggaaggggagcctcgtgagttcgtggagaactc cgaatgtatccagtgtcatccagaatgcctgccccaggccatgaacataacatgtacag gacgcggcccagacaactgcatacagtgcgcccactacattgatggcccccattgcgta aagacttgtcctgctggagtcatgggcgaaaataacaccctggtgtggaagtacgccga cgctggccatgtatgtcatctgtgtcatcctaattgcacctatggctgcactggccccg gccttgaaggatgccccggcggtggaggaggaggctctttctgggtcctcgtggtggtg ggaggcgtgctggcctgctattccttgctggtcacggtcgccttcattattttctgggt gagatctaaaagaagc |
| CD19-CD137-CD3ζ CAR.E2A.Ig Kappa signal peptide.HER1t7 (aa) | 186 | DIQMTQTTSSLSASLGDRVTISCRASQDISKYLNWYQQKPDGTVKLLIYHTSRLHSGVP SRFSGSGSGTDYSLTISNLEQEDIATYFCQQGNTLPYTFGGGTKLEITGSTSGSGKPGS GEGSTKGEVKLQESGPGLVAPSQSLSVTCTVSGVSLPDYGVSWIRQPPRKGLEWLGVIW GSETTYYNSALKSRLTIIKDNSKSQVFLKMNSLQTDDTAIYYCAKHYYYGGSYAMDYWG QGTSVTVSSTTTPAPRPPTPAPTIASQPLSLRPEACRPAAGGAVHTRGLDFACDIYIWA PLAGTCGVLLLSLVITLYCKRGRKKLLYIFKQPFMRPVQTTQEEDGCSCRFPEEEEGGC ELRVKFSRSADAPAYKQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPRQCTN YALLKLAGDVESNPGPMRLPAQLLGLLMLWVPGSSGRKVCNGIGIGEFKDSLSINATNI KHFKNCTSISGDLHILPVAFRGDSFTHTPPLDPQELDILKTVKEITGFLLIQAWPENRT DLHAFENLEIIRGRTKQHGQFSLAVVSLNITSLGLRSLKEISDGDVIISGNKNLCYANT INWKKLFGTSGQKTKIISNRGENSCKATGQVCHALCSPEGCWGPEPRDCVSCRNVSRGR ECVDKCNLLEGEPREFVENSECIQCHPECLPQAMNITCTGRGPDNCIQCAHYIDGPHCV KTCPAGVMGENNTLVWKYADAGHVCHLCHPNCTYGCTGPGLEGCPGGGGGGSFWVLVVV GGVLACYSLLVTVAFIIFWVRSKRS |

-continued

| Sequence Name | SEQ ID NO | Sequence |
|---|---|---|
| CD19-CD28-CD3ζ CAR.Furin-T2A.Ig Kappa signal peptide.HER1t8 (aa) | 187 | DIQMTQTTSSLSASLGDRVTISCRASQD<br>ISKYLNWYQQKPDGTVKLLIYHTSRLHSGVPSRFSGSGSGTDYSLTISNL<br>EQEDIATYFCQQGNTLPYTFGGGTKLEITGSTSGSGKPGSGEGSTKGEVK<br>LQESGPGLVAPSQSLSVTCTVSGVSLPDYGVSWIRQPPRKGLEWLGVIWG<br>SETTYYNSALKSRLTIIKDNSKSQVFLKMNSLQTDDTAIYYCAKHYYYGG<br>SYAMDYWGQGTSVTVSSKPTTTPAPRPPTPAPTIASQPLSLRPEACRPAA<br>GGAVHTRGLDFACDIYIWAPLAGTCGVLLLSLVITLYCNHRNRSKRSRGG<br>HSDYMNMTPRRPGPTRKHYQPYAPPRDFAAYRSRVKFSRSADAPAYQQGQ<br>NQLYNELNLGRREEYDVLDKRRGRDPEMGGKPRRKNPQEGLYNELQKDKM<br>AEAYSEIGMKGERRRGKGHDGLYQGLSTATKDTYDALHMQALPPRRAKRS<br>GSGEGRGSLLTCGDVEENPGPMRLPAQLLGLLMLWVPGSSGRKVCNGIGI<br>GEFKDSLSINATNIKHFKNCTSISGDLHILPVAFRGDSFTHTPPLDPQEL<br>DILKTVKEITGFLLIQAWPENRTDLHAFENLEIIRGRTKQHGQFSLAVVS<br>LNITSLGLRSLKEISDGDVIISGNKNLCYANTINWKKLFGTSGQKTKIIS<br>NRGENSCKATGQVCHALCSPEGCWGPEPRDCVSGGGGSGGGGSGGGGSGG<br>GGSEITLIIFGVMAGVIGTILLISYGIRRGGGS |
| CD19-CD137-CD3ζ CAR.E2A.Ig Kappa signal peptide. HER1t8 (aa) | 188 | DIQMTQTTSSLSASLGDRVTISCRASQDISKYLNWYQQKPDGTVKLLIYHTSRLHSGVP<br>SRFSGSGSGTDYSLTISNLEQEDIATYFCQQGNTLPYTFGGGTKLEITGSTSGSGKPGS<br>GEGSTKGEVKLQESGPGLVAPSQSLSVTCTVSGVSLPDYGVSWIRQPPRKGLEWLGVIW<br>GSETTYYNSALKSRLTIIKDNSKSQVFLKMNSLQTDDTAIYYCAKHYYYGGSYAMDYWG<br>QGTSVTVSSTTTPAPRPPTPAPTIASQPLSLRPEACRPAAGGAVHTRGLDFACDIYIWA<br>PLAGTCGVLLLSLVITLYCKRGRKKLLYIFKQPFMRPVQTTQEEDGCSCRFPEEEEGGC<br>ELRVKFSRSADAPAYKQGQNQLYNELNLGRREEYDVLDKRRGRDPEMGGKPRRKNPQEG<br>LYNELQKDKMAEAYSEIGMKGERRRGKGHDGLYQGLSTATKDTYDALHMQALPPRQCTN<br>YALLKLAGDVESNPGPMRLPAQLLGLLMLWVPGSSGRKVCNGIGIGEFKDSLSINATNI<br>KHFKNCTSISGDLHILPVAFRGDSFTHTPPLDPQELDILKTVKEITGFLLIQAWPENRT<br>DLHAFENLEIIRGRTKQHGQFSLAVVSLNITSLGLRSLKEISDGDVIISGNKNLCYANT<br>INWKKLFGTSGQKTKIISNRGENSCKATGQVCHALCSPEGCWGPEPRDCVSGGGGSGGG<br>GSGGGGSGGGGSEITLIIFGVMAGVIGTILLISYGIRRGGGS |
| CD19-CD28-CD3ζ CAR.Furin-T2A.Ig Kappa signal peptide.HER1t9 (aa) | 189 | DIQMTQTTSSLSASLGDRVTISCRASQD<br>ISKYLNWYQQKPDGTVKLLIYHTSRLHSGVPSRFSGSGSGTDYSLTISNL<br>EQEDIATYFCQQGNTLPYTFGGGTKLEITGSTSGSGKPGSGEGSTKGEVK<br>LQESGPGLVAPSQSLSVTCTVSGVSLPDYGVSWIRQPPRKGLEWLGVIWG<br>SETTYYNSALKSRLTIIKDNSKSQVFLKMNSLQTDDTAIYYCAKHYYYGG<br>SYAMDYWGQGTSVTVSSKPTTTPAPRPPTPAPTIASQPLSLRPEACRPAA<br>GGAVHTRGLDFACDIYIWAPLAGTCGVLLLSLVITLYCNHRNRSKRSRGG<br>HSDYMNMTPRRPGPTRKHYQPYAPPRDFAAYRSRVKFSRSADAPAYQQGQ<br>NQLYNELNLGRREEYDVLDKRRGRDPEMGGKPRRKNPQEGLYNELQKDKM<br>AEAYSEIGMKGERRRGKGHDGLYQGLSTATKDTYDALHMQALPPRRAKRS<br>GSGEGRGSLLTCGDVEENPGPMRLPAQLLGLLMLWVPGSSGRKVCNGIGI<br>GEFKDSLSINATNIKHFKNCTSISGDLHILPVAFRGDSFTHTPPLDPQEL<br>DILKTVKEITGFLLIQAWPENRTDLHAFENLEIIRGRTKQHGQFSLAVVS<br>LNITSLGLRSLKEISDGDVIISGNKNLCYANTINWKKLFGTSGQKTKIIS<br>NRGENSCKATGQVCHALCSPEGCWGPEPRDCVSGGGGSGGGGSGGGGSGG<br>GGSITLIIFGVMAGVIGTILLISYGIGGGS |
| CD19-CD137-CD3ζ CAR.E2A.Ig Kappa signal peptide.HER1t9 (aa) | 190 | DIQMTQTTSSLSASLGDRVTISCRASQDISKYLNWYQQKPDGTVKLLIYHTSRLHSGVP<br>SRFSGSGSGTDYSLTISNLEQEDIATYFCQQGNTLPYTFGGGTKLEITGSTSGSGKPGS<br>GEGSTKGEVKLQESGPGLVAPSQSLSVTCTVSGVSLPDYGVSWIRQPPRKGLEWLGVIW<br>GSETTYYNSALKSRLTIIKDNSKSQVFLKMNSLQTDDTAIYYCAKHYYYGGSYAMDYWG<br>QGTSVTVSSTTTPAPRPPTPAPTIASQPLSLRPEACRPAAGGAVHTRGLDFACDIYIWA<br>PLAGTCGVLLLSLVITLYCKRGRKKLLYIFKQPFMRPVQTTQEEDGCSCRFPEEEEGGC<br>ELRVKFSRSADAPAYKQGQNQLYNELNLGRREEYDVLDKRRGRDPEMGGKPRRKNPQEG<br>LYNELQKDKMAEAYSEIGMKGERRRGKGHDGLYQGLSTATKDTYDALHMQALPPRQCTN<br>YALLKLAGDVESNPGPMRLPAQLLGLLMLWVPGSSGRKVCNGIGIGEFKDSLSINATNI<br>KHFKNCTSISGDLHILPVAFRGDSFTHTPPLDPQELDILKTVKEITGFLLIQAWPENRT<br>DLHAFENLEIIRGRTKQHGQFSLAVVSLNITSLGLRSLKEISDGDVIISGNKNLCYANT<br>INWKKLFGTSGQKTKIISNRGENSCKATGQVCHALCSPEGCWGPEPRDCVSGGGGSGGG<br>GSGGGGSGGGGSITLIIFGVMAGVIGTILLISYGIGGGS |
| CD19-CD28-CD3ζ CAR.Furin-T2A.Ig Kappa signal peptide.HER1t10 (aa) | 191 | DIQMTQTTSSLSASLGDRVTISCRASQD<br>ISKYLNWYQQKPDGTVKLLIYHTSRLHSGVPSRFSGSGSGTDYSLTISNL<br>EQEDIATYFCQQGNTLPYTFGGGTKLEITGSTSGSGKPGSGEGSTKGEVK<br>LQESGPGLVAPSQSLSVTCTVSGVSLPDYGVSWIRQPPRKGLEWLGVIWG<br>SETTYYNSALKSRLTIIKDNSKSQVFLKMNSLQTDDTAIYYCAKHYYYGG<br>SYAMDYWGQGTSVTVSSKPTTTPAPRPPTPAPTIASQPLSLRPEACRPAA<br>GGAVHTRGLDFACDIYIWAPLAGTCGVLLLSLVITLYCNHRNRSKRSRGG<br>HSDYMNMTPRRPGPTRKHYQPYAPPRDFAAYRSRVKFSRSADAPAYQQGQ<br>NQLYNELNLGRREEYDVLDKRRGRDPEMGGKPRRKNPQEGLYNELQKDKM<br>AEAYSEIGMKGERRRGKGHDGLYQGLSTATKDTYDALHMQALPPRRAKRS<br>GSGEGRGSLLTCGDVEENPGPMRLPAQLLGLLMLWVPGSSGRKVCNGIGI<br>GEFKDSLSINATNIKHFKNCTSISGDLHILPVAFRGDSFTHTPPLDPQEL<br>DILKTVKEITGFLLIQAWPENRTDLHAFENLEIIRGRTKQHGQFSLAVVS<br>LNITSLGLRSLKEISDGDVIISGNKNLCYANTINWKKLFGTSGQKTKIIS |

-continued

| Sequence Name | SEQ ID NO | Sequence |
|---|---|---|
| | | NRGENSCKATGQVCHALCSPEGCWGPEPRDCVSGGGGSGGGGSGGGGSGG GGSITLIIFGVMAGVIGTILLALLIWGGGS |
| CD19-CD137-CD3ζ CAR.E2A.Ig Kappa signal peptide.HER1t10 (aa) | 192 | DIQMTQTTSSLSASLGDRVTISCRASQDISKYLNWYQQKPDGTVKLLIYHTSRLHSGVP SRFSGSGSGTDYSLTISNLEQEDIATYFCQQGNTLPYTFGGGTKLEITGSTSGSGKPGS GEGSTKGEVKLQESGPGLVAPSQSLSVTCTVSGVSLPDYGVSWIRQPPRKGLEWLGVIW GSETTYYNSALKSRLTIIKDNSKSQVFLKMNSLQTDDTAIYYCAKHYYYGGSYAMDYWG QGTSVTVSSTTTPAPRPPTPAPTIASQPLSLRPEACRPAAGGAVHTRGLDFACDIYIWA PLAGTCGVLLLSLVITLYCKRGRKKLLYIFKQPFMRPVQTTQEEDGCSCRFPEEEEGGC ELRVKFSRSADAPAYKQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPRQCTN YALLKLAGDVESNPGPMRLPAQLLGLLMLWVPGSSGRKVCNGIGIGEFKDSLSINATNI KHFKNCTSISGDLHILPVAFRGDSFTHTPPLDPQELDILKTVKEITGFLLIQAWPENRT DLHAFENLEIIRGRTKQHGQFSLAVVSLNITSLGLRSLKEISDGDVIISGNKNLCYANT INWKKLFGTSGQKTKIISNRGENSCKATGQVCHALCSPEGCWGPEPRDCVSGGGGSGGG GSGGGGSGGGGSITLIIFGVMAGVIGTILLALLIWGGGS* |
| Membrane bound IL-15.T2A.HER1t1 (aa) | 193 | NWVNVISDLKKIEDLIQSMHIDATLYTESDVHPSCKVTAMKCFLLELQVISLESGDASI HDTVENLIILANNSLSSNGNVTESGCKECEELEEKNIKEFLQSFVHIVQMFINTSSGGG SGGGGSGGGGSGGGGSGGGSLQITCPPPMSVEHADIWVKSYSLYSRERYICNSGFKRKA GTSSL TECVLNKATNVAHWTTPSLKCIRDPALVHQRPAPPSTVTTAGVTPQPESLSPSGKEPAA SSPSSNNTAATTAAIVPGSQLMPSKSPSTGTTEISSHESSHGTPSQTTAKNWELTASAS HQPPGVYPQGHSDTTVAISTSTVLLCGLSAVSLLACYLKSRQTPPLASVEMEAMEALPV TWGTSSRDEDLENCSHHLRAKRGSGEGRGSLLTCGDVEENPGPMRLPAQLLGLLMLWVP GSSGRKVCNGIGIGEFKDSLSINATNIKHFKNCTSISGDLHILPVAFRGDSFTHTPPLD PQELDILKTVKEITGFLLIQAWPENRTDLHAFENLEIIRGRTKQHGQFSLAVVSLNITS LGLRSLKEISDGDVIISGNKNLCYANTINWKKLFGTSGQKTKIISNRGENSCKATGQVC HALCSPEGCWGPEPRDCVSGGGGSGGGGSGGGGSGGGGSFWVLVVVGGVLACYSLLVTV AFIIFWVRSKRS |
| CD19-CD28-CD3ζ CAR.P2A.CD20 (aa) | 194 | DIQMTQTTSSLSASLGDRVTISCRASQDISKYLNWYQQKPDGTVKLLIYHTSRLHSGVP SRFSGSGSGTDYSLTISNLEQEDIATYFCQQGNTLPYTFGGGTKLEITGSTSGSGKPGS GEGSTKGEVKLQESGPGLVAPSQSLSVTCTVSGVSLPDYGVSWIRQPPRKGLEWLGVIW GSETTYYNSALKSRLTIIKDNSKSQVFLKMNSLQTDDTAIYYCAKHYYYGGSYAMDYWG QGTSVTVSSESKYGPPCPPCPAPEFLGGPSVFLFPPKPKDTLMISRTPEVTCVVVDVSQ EDPEVQFNWYVDGVEVHNAKTKPREEQFNSTYRVVSVLTVLHQDWLNGKEYKCKVSNKG LPSSIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKSLSLSL GKMFWVLVVVGGVLACYSLLVTVAFIIFWVRSKRSRGGHSDYMNMTPRRPGPTRKHYQP YAPPRDFAAYRSRVKFSRSADAPAYQQGQNQLYNELNLGRREEYDVLDKRRGRDPEMGG KPRRKNPQEGLYNELQKDKMAEAYSEIGMKGERRRGKGHDGLYQGLSTATKDTYDALHM QALPPRATNFSLLKQAGDVEENPGPMTTPRNSVNGTFPAEPMKGPIAMQSGPKPLFRRM SSLVGPTQSFFMRESKTLGAVQIMNGLFHIALGGLLMIPAGIYAPICVTVWYPLWGGIM YIISGSLLAATEKNSRKCLVKGKMIMNSLSLFAAISGMILSIMDILNIKISHFLKMESL NFIRAHTPYINIYNCEPANPSEKNSPSTQYCYSIQSLFLGILSVMLIFAFFQELVIAGI VENEWKRTCSRPKSNIVLLSAEEKKEQTIEIKEEVVGLTETSSQPKNEEDIEIIPIQEE EEEETETNFPEPPQDQESSPIENDSSP |
| CD19-CD28-CD3ζ CAR.P2A.CD20t1 (aa) | 195 | DIQMTQTTSSLSASLGDRVTISCRASQDISKYLNWYQQKPDGTVKLLIYHTSRLHSGVP SRFSGSGSGTDYSLTISNLEQEDIATYFCQQGNTLPYTFGGGTKLEITGSTSGSGKPGS GEGSTKGEVKLQESGPGLVAPSQSLSVTCTVSGVSLPDYGVSWIRQPPRKGLEWLGVIW GSETTYYNSALKSRLTIIKDNSKSQVFLKMNSLQTDDTAIYYCAKHYYYGGSYAMDYWG QGTSVTVSSESKYGPPCPPCPAPEFLGGPSVFLFPPKPKDTLMISRTPEVTCVVVDVSQ EDPEVQFNWYVDGVEVHNAKTKPREEQFNSTYRVVSVLTVLHQDWLNGKEYKCKVSNKG LPSSIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKSLSLSL GKMFWVLVVVGGVLACYSLLVTVAFIIFWVRSKRSRGGHSDYMNMTPRRPGPTRKHYQP YAPPRDFAAYRSRVKFSRSADAPAYQQGQNQLYNELNLGRREEYDVLDKRRGRDPEMGG KPRRKNPQEGLYNELQKDKMAEAYSEIGMKGERRRGKGHDGLYQGLSTATKDTYDALHM QALPPRATNFSLLKQAGDVEENPGPMTTPRNSVNGTFPAEPMKGPIAMQSGPKPLFRRM SSLVGPTQSFFMRESKTLGAVQIMNGLFHIALGGLLMIPAGIYAPICVTVWYPLWGGIM YIISGSLLAATEKNSRKCLVKGKMIMNSLSLFAAISGMILSIMDILNIKISHFLKMESL NFIRAHTPYINIYNCEPANPSEKNSPSTQYCYSIQSLFLGILSVMLIFAFFQELVIAGI VENEWKRTCSRPKSNIVLLSAEEKKEQTIEIKEEVVGLTETSSQPKNEEDIE |
| CD19-CD28-CD3ζ CAR.P2A.CD20t4 (aa) | 196 | DIQMTQTTSSLSASLGDRVTISCRASQDISKYLNWYQQKPDGTVKLLIYHTSRLHSGVP SRFSGSGSGTDYSLTISNLEQEDIATYFCQQGNTLPYTFGGGTKLEITGSTSGSGKPGS GEGSTKGEVKLQESGPGLVAPSQSLSVTCTVSGVSLPDYGVSWIRQPPRKGLEWLGVIW GSETTYYNSALKSRLTIIKDNSKSQVFLKMNSLQTDDTAIYYCAKHYYYGGSYAMDYWG QGTSVTVSSESKYGPPCPPCPAPEFLGGPSVFLFPPKPKDTLMISRTPEVTCVVVDVSQ EDPEVQFNWYVDGVEVHNAKTKPREEQFNSTYRVVSVLTVLHQDWLNGKEYKCKVSNKG LPSSIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKSLSLSL GKMFWVLVVVGGVLACYSLLVTVAFIIFWVRSKRSRGGHSDYMNMTPRRPGPTRKHYQP YAPPRDFAAYRSRVKFSRSADAPAYQQGQNQLYNELNLGRREEYDVLDKRRGRDPEMGG |

-continued

| Sequence Name | SEQ ID NO | Sequence |
|---|---|---|
| | | KPRRKNPQEGLYNELQKDKMAEAYSEIGMKGERRRGKGHDGLYQGLSTATKDTYDALHM<br>QALPPRATNFSLLKQAGDVEENPGPMTTPRNSVNGTFPAEPMKGPIAMQSGPKPLFRRM<br>SSLVGPTQSFFMRESKTLGAVQIMNGLFHIALGGLLMIPAGIYAPICVTVWYPLWGGIM<br>YIISGSLLAATEKNSRKCLVKGKMIMNSLSLFAAISGMILSIMDILNIKISHFLKMESL<br>NFIRAHTPYINIYNCEPANPSEKNSPSTQYCYSIQSLFLGILSVMLIFAFFQELVIAGI<br>VEN |
| CD52t3.P2A.CD8α signal peptide.CD19-CD28-CD3ζ CAR (aa) | 197 | MKRFLFLLLTISLLVMVQIQTGLSGQNDTSQTSSPSGSTSGSGKPGSGEGSTKGGQNDT<br>SQTSSPSGSTSGSGKPGSGEGSTKGGQNDTSQTSSPSGSTSGSGKPGSGEGSTKGGGGG<br>SGGGGSKPFWVLVVVGGVLACYSLLVTVAFIIFWVATNFSLLKQAGDVEENPGPMALPV<br>TALLLPLALLLHAARPDIQMTQTTSSLSASLGDRVTISCRASQDISKYLNWYQQKPDGT<br>VKLLIYHTSRLHSGVPSRFSGSGSGTDYSLTISNLEQEDIATYFCQQGNTLPYTFGGGT<br>KLEITGSTSGSGKPGSGEGSTKGEVKLQESGPGLVAPSQSLSVTCTVSGVSLPDYGVSW<br>IRQPPRKGLEWLGVIWGSETTYYNSALKSRLTIIKDNSKSQVFLKMNSLQTDDTAIYYC<br>AKHYYYGGSYAMDYWGQGTSVTVSSESKYGPPCPPCPAPEFLGGPSVFLFPPKPKDTLM<br>ISRTPEVTCVVVDVSQEDPEVQFNWYVDGVEVHNAKTKPREEQFNSTYRVVSVLTVLHQ<br>DWLNGKEYKCKVSNKGLPSSIEKTISKAKGQPREPQVYTLPPSQEEMTKNQVSLTCLVK<br>GFYPSDIAVEWESNGQPENNYKTTPPVLDSDGSFFLYSRLTVDKSRWQEGNVFSCSVMH<br>EALHNHYTQKSLSLSLGKMFWVLVVVGGVLACYSLLVTVAFIIFWVRSKRSRGGHSDYM<br>NMTPRRPGPTRKHYQPYAPPRDFAAYRSRVKFSRSADAPAYQQGQNQLYNELNLGRREE<br>YDVLDKRRGRDPEMGGKPRRKNPQEGLYNELQKDKMAEAYSEIGMKGERRRGKGHDGLY<br>QGLSTATKDTYDALHMQALPPR |
| Ig Kappa signal peptide.LNGFRt4. P2A.CD8α signal peptide.CD19-CD28-CD3ζ CAR (aa) | 198 | MRLPAQLLGLLMLWVPGSSGRCAYGYYQDETTGRCEACRVCEAGSGLVFSCQDKQNTVC<br>EECPDGTYSDEANHVDPCLPCTVCEDTERQLRECTRWADAECEEIPGRWITRSTPPEGS<br>DSTAPSTQEPEAPPEQDLIASTVAGVVTTVMGSSQPVVTRGTTDNGGGGSGGGGSGGGG<br>SGGGGSFWVLVVVGGVLACYSLLVTVAFIIFWVRSKRSATNFSLLKQAGDVEENPGPMA<br>LPVTALLLPLALLLHAARPDIQMTQTTSSLSASLGDRVTISCRASQDISKYLNWYQQKP<br>DGTVKLLIYHTSRLHSGVPSRFSGSGSGTDYSLTISNLEQEDIATYFCQQGNTLPYTFG<br>GGTKLEITGSTSGSGKPGSGEGSTKGEVKLQESGPGLVAPSQSLSVTCTVSGVSLPDYG<br>VSWIRQPPRKGLEWLGVIWGSETTYYNSALKSRLTIIKDNSKSQVFLKMNSLQTDDTAI<br>YYCAKHYYYGGSYAMDYWGQGTSVTVSSESKYGPPCPPCPAPEFLGGPSVFLFPPKPKD<br>TLMISRTPEVTCVVVDVSQEDPEVQFNWYVDGVEVHNAKTKPREEQFNSTYRVVSVLTV<br>LHQDWLNGKEYKCKVSNKGLPSSIEKTISKAKGQPREPQVYTLPPSQEEMTKNQVSLTC<br>LVKGFYPSDIAVEWESNGQPENNYKTTPPVLDSDGSFFLYSRLTVDKSRWQEGNVFSCS<br>VMHEALHNHYTQKSLSLSLGKMFWVLVVVGGVLACYSLLVTVAFIIFWVRSKRSRGGHS<br>DYMNMTPRRPGPTRKHYQPYAPPRDFAAYRSRVKFSRSADAPAYQQGQNQLYNELNLGR<br>REEYDVLDKRRGRDPEMGGKPRRKNPQEGLYNELQKDKMAEAYSEIGMKGERRRGKGHD<br>GLYQGLSTATKDTYDALHMQALPPR |
| Epidermal growth factor receptor (EGFR) Domain III [(R310-Q480) of mature protein OR (R334-Q504) of proprotein] (nt) | 199 | cgcaaagtgtgtaacggaataggtattggtgaatttaaagactcactctccataaatgc<br>tacgaatattaaacacttcaaaaactgcacctccatcagtggcgatctccacatcctgc<br>cggtggcatttaggggtgactccttcacacatactcctcctctggatccacaggaactg<br>gatattctgaaaaccgtaaaggaaatcacagggtttttgctgattcaggcttggcctga<br>aaacaggacggacctccatgcctttgagaacctagaaatcatacgcggcaggaccaagc<br>aacatggtcagttttctcttgcagtcgtcagcctgaacataacatccttgggattacgc<br>tccctcaaggagataagtgatggagatgtgataatttcaggaaacaaaaatttgtgcta<br>tgcaaatacaataaactggaaaaaactgtttgggacctccggtcagaaaaccaaaatta<br>taagcaacagaggtgaaaacagctgcaaggccacaggccag |
| Epidermal growth factor receptor (EGFR) Domain III [(R310-Q480) of mature protein OR (R334-Q504) of proprotein] (aa) | 200 | RKVCNGIGIGEFKDSLSINATNIKHFKNCTSISGDLHILPVAFRGDSFTHTPPLDPQEL<br>DILKTVKEITGFLLIQAWPENRTDLHAFENLEIIRGRTKQHGQFSLAVVSLNITSLGLR<br>SLKEISDGDVIISGNKNLCYANTINWKKLFGTSGQKTKIISNRGENSCKATGQ |
| Epidermal growth factor receptor (EGFR) Domain IV [(V481-S621) of mature protein OR (V505-S645) of proprotein] (nt) | 201 | gtctgccatgccttgtgctcccccgagggctgctggggcccggagcccagggactgcgt<br>ctcttgccggaatgtcagccgaggcagggaatgcgtggacaagtgcaaccttctggagg<br>gtgagccaagggagtttgtggagaactctgagtgcatacagtgccacccagagtgcctg<br>cctcaggccatgaacatcacctgcacaggacggggaccagacaactgtatccagtgtgc<br>ccactacattgacggcccccactgcgtcaagacctgcccggcaggagtcatgggagaaa<br>acaacaccctggtctggaagtacgcagacgccggccatgtgtgccacctgtgccatcca<br>aactgcacctacggatgcactgggccaggtcttgaaggctgtccaacgaatgggcctaa<br>gatcccgtcc |
| Epidermal growth factor receptor (EGFR) Domain IV [(V481-S621) of mature protein OR (V505-S645) of proprotein] (aa) | 202 | VCHALCSPEGCWGPEPRDCVSCRNVSRGRECVDKCNLLEGEPREFVENSECIQCHPECL<br>PQAMNITCTGRGPDNCIQCAHYIDGPHCVKTCPAGVMGENNTLVWKYADAGHVCHLCHP<br>NCTYGCTGPGLEGCPTNGPKIPS |

-continued

| Sequence Name | SEQ ID NO | Sequence |
|---|---|---|
| HER1t1 Domain IV | 203 | VCHALCSPEGCWGPEPRDCVS |
| HER1t2 Domain IV | 204 | VCHALCSPEGCWGPEPRDCVSCRNVSRGRECVDK |
| HER1t3 Domain IV | 205 | VCHALCSPEGCWGPEPRDCVSCRNVSRGRECVDKCNLLEGEPREFVENSECIQ |
| HER1t4 Domain IV | 206 | VCHALCSPEGCWGPEPRDCVSCRNVSRGRECVDKCNLLEGEPREFVENSECIQCHPECL PQAMNITCTGRGPDNCIQ |
| HER1t5 Domain IV | 207 | VCHALCSPEGCWGPEPRDCVSCRNVSRGRECVDKCNLLEGEPREFVENSECIQCHPECL PQAMNITCTGRGPDNCIQCAHYIDGPHCVKT |
| HER1t6 Domain IV | 208 | VCHALCSPEGCWGPEPRDCVSCRNVSRGRECVDKCNLLEGEPREFVENSECIQCHPECL PQAMNITCTGRGPDNCIQCAHYIDGPHCVKTCPAGVMGENNTLVWKYADAGHVCHL |
| HER1t7 Domain IV | 209 | VCHALCSPEGCWGPEPRDCVSCRNVSRGRECVDKCNLLEGEPREFVENSECIQCHPECL PQAMNITCTGRGPDNCIQCAHYIDGPHCVKTCPAGVMGENNTLVWKYADAGHVCHLCHP NCTYGCTGPGLEGCP |
| HER1t Domain III/IV | 210 | RKVCNGIGIGEFKDSLSINATNIKHFKNCTSISGDLHILPVAFRGDSFTH TPPLDPQELDILKTVKEITGFLLIQAWPENRTDLHAFENLEIIRGRTKQH GQFSLAVVSLNITSLGLRSLKEISDGDVIISGNKNLCYANTINWKKLFGT SGQKTKIISNRGENSCKATGQVCHALCSPEGCWGPEPRDCVSCRNVSRGR ECVDKCNLLEGEPREFVENSECIQCHPECLPQAMNITCTGRGPDNCIQCA HYIDGPHCVKTCPAGVMGENNTLVWKYADAGHVCHLCHPNCTYGCTGPGL EGCPTNGPKIPS |
| HER1t1 Domain III/IV | 211 | RKVCNGIGIGEFKDSLSINATNIKHFKNCTSISGDLHILPVAFRGDSFTH TPPLDPQELDILKTVKEITGFLLIQAWPENRTDLHAFENLEIIRGRTKQH GQFSLAVVSLNITSLGLRSLKEISDGDVIISGNKNLCYANTINWKKLFGT SGQKTKIISNRGENSCKATGQVCHALCSPEGCWGPEPRDCVS |
| HER1t2 Domain III/IV | 212 | RKVCNGIGIGEFKDSLSINATNIKHFKNCT SISGDLHILPVAFRGDSFTHTPPLDPQELDILKTVKEITGFLLIQAWPEN RTDLHAFENLEIIRGRTKQHGQFSLAVVSLNITSLGLRSLKEISDGDVII SGNKNLCYANTINWKKLFGTSGQKTKIISNRGENSCKATGQVCHALCSPE GCWGPEPRDCVSCRNVSRGRECVDK |
| HER1t3 Domain III/IV | 213 | RKVCNGIGIGEFKDSLSINATNIKHFKNCT SISGDLHILPVAFRGDSFTHTPPLDPQELDILKTVKEITGFLLIQAWPEN RTDLHAFENLEIIRGRTKQHGQFSLAVVSLNITSLGLRSLKEISDGDVII SGNKNLCYANTINWKKLFGTSGQKTKIISNRGENSCKATGQVCHALCSPE GCWGPEPRDCVSCRNVSRGRECVDKCNLLEGEPREFVENSECIQ |
| HER1t4 Domain III/IV | 214 | RKVCNGIGIGEFKDSLSINATNIKHFKNCT SISGDLHILPVAFRGDSFTHTPPLDPQELDILKTVKEITGFLLIQAWPEN RTDLHAFENLEIIRGRTKQHGQFSLAVVSLNITSLGLRSLKEISDGDVII SGNKNLCYANTINWKKLFGTSGQKTKIISNRGENSCKATGQVCHALCSPE GCWGPEPRDCVSCRNVSRGRECVDKCNLLEGEPREFVENSECIQCHPECL PQAMNITCTGRGPDNCIQ |
| HER1t5 Domain III/IV | 215 | RKVCNGIGIGEFKDSLSINATNIKHFKNCT SISGDLHILPVAFRGDSFTHTPPLDPQELDILKTVKEITGFLLIQAWPEN RTDLHAFENLEIIRGRTKQHGQFSLAVVSLNITSLGLRSLKEISDGDVII SGNKNLCYANTINWKKLFGTSGQKTKIISNRGENSCKATGQVCHALCSPE GCWGPEPRDCVSCRNVSRGRECVDKCNLLEGEPREFVENSECIQCHPECL PQAMNITCTGRGPDNCIQCAHYIDGPHCVKT |
| HER1t6 Domain III/IV | 216 | RKVCNGIGIGEFKDSLSINATNIKHFKNCT SISGDLHILPVAFRGDSFTHTPPLDPQELDILKTVKEITGFLLIQAWPEN RTDLHAFENLEIIRGRTKQHGQFSLAVVSLNITSLGLRSLKEISDGDVII SGNKNLCYANTINWKKLFGTSGQKTKIISNRGENSCKATGQVCHALCSPE GCWGPEPRDCVSCRNVSRGRECVDKCNLLEGEPREFVENSECIQCHPECL PQAMNITCTGRGPDNCIQCAHYIDGPHCVKTCPAGVMGENNTLVWKYADA GHVCHL |

-continued

| Sequence Name | SEQ ID NO | Sequence |
|---|---|---|
| HER1t7 Domain III/IV | 217 | RKVCNGIGIGEFKDSLSINATNIKHFKNCT SISGDLHILPVAFRGDSFTHTPPLDPQELDILKTVKEITGFLLIQAWPEN RTDLHAFENLEIIRGRTKQHGQFSLAVVSLNITSLGLRSLKEISDGDVII SGNKNLCYANTINWKKLFGTSGQKTKIISNRGENSCKATGQVCHALCSPE GCWGPEPRDCVSCRNVSRGRECVDKCNLLEGEPREFVENSECIQCHPECL PQAMNITCTGRGPDNCIQCAHYIDGPHCVKTCPAGVMGENNTLVWKYADA GHVCHLCHPNCTYGCTGPGLEGCP |
| CD20t3 EC Domain 142-188 | 218 | KISHFLKMESLNFIRAHTPYINIYNCEPANPSEKNSPSTQYCYSIQS |
| CD20t7 EC Domain P160-Q187 | 219 | PYINIYNCEPANPSEKNSPSTQYCYSIQS |
| CD20t10 EC Domain C167-C183 | 220 | CEPANPSEKNSPSTQYC |
| Linker | 221 | G4S linker |
| linker | 222 | (G4S)n, wherein n = 0, 1, 2, 3, 4, 5 |
| Linker | 223 | SG4S linker |
| Linker | 224 | 3xGS linker |
| Linker | 225 | ESKYGPPCPPCP |
| Linker | 226 | SGGGSGGGGSGGGGSGGGGSGGGSLQ |
| Furin-GSG-T2A | 227 | RAKRGSGEGRGSLLTCGDVEENPGP |
| Furin-SGSG-T2A | 228 | RAKRSGSGEGRGSLLTCGDVEENPGP |
| Linker | 229 | Asp-Val/Ile-Glu-X-Asn-Pro-Gly-Pro |
| Furinlink1 | 230 | RAKR |
| Linker | 231 | AGAGCTAAGAGG |
| Furinlink1 | 232 | CGTGCAAAGCGT |
| Fmdv | 233 | RAKRAPVKQTLNFDLLKLAGDVESNPGP |
| Fmdv | 234 | AGAGCCAAGAGGGCACCGGTGAAACAGACTTTGAATTTTGACCTTCTGAAGTTGGCAGG AGACGTTGAGTCCAACCCTGGGCCC |
| GSG-p2a | 235 | GSGATNFSLLKQAGDVEENPGP |
| GSG-p2a | 236 | GGAAGCGGAGCTACTAACTTCAGCCTGCTGAAGCAGGCTGGAGACGTGGAGGAGAACCC TGGACCT |
| fp2a | 237 | RAKRAPVKQGSGATNFSLLKQAGDVEENPGP |
| fp2a | 238 | CGTGCAAAGCGTGCACCGGTGAAACAGGGAAGCGGAGCTACTAACTTCAGCCTGCTGAA GCAGGCTGGAGACGTGGAGGAGAACCCTGGACCT |
| Linker | 239 | (XP)n (n = 2-5) |
| linker | 240 | A(EAAAK) nA (n = 2-5) |

EXAMPLES

These examples are provided for illustrative purposes only and not to limit the scope of the claims provided herein.

Example 1. Expression and Activity of Truncated CD20 (CD20t) Polypeptide Construct as a Cell Tag HEK-293T cells were transfected with wild-type CD20, truncated CD20 cell tags as well as a positive control for anti-CD20 antibody rituximab. Expression was measured by flowcytometry using rituximab. As shown in FIG. 1, CD20 truncation variant CD20t1 (SEQ ID NO:$10^9$) exhibited robust expression when detected by rituximab relative to variant CD20t4 (SEQ ID NO:115). These data indicate that only specific truncations in the CD20 endogenous polypeptide may be compatible with the use of CD20t as a cell tag.

Figure 2:
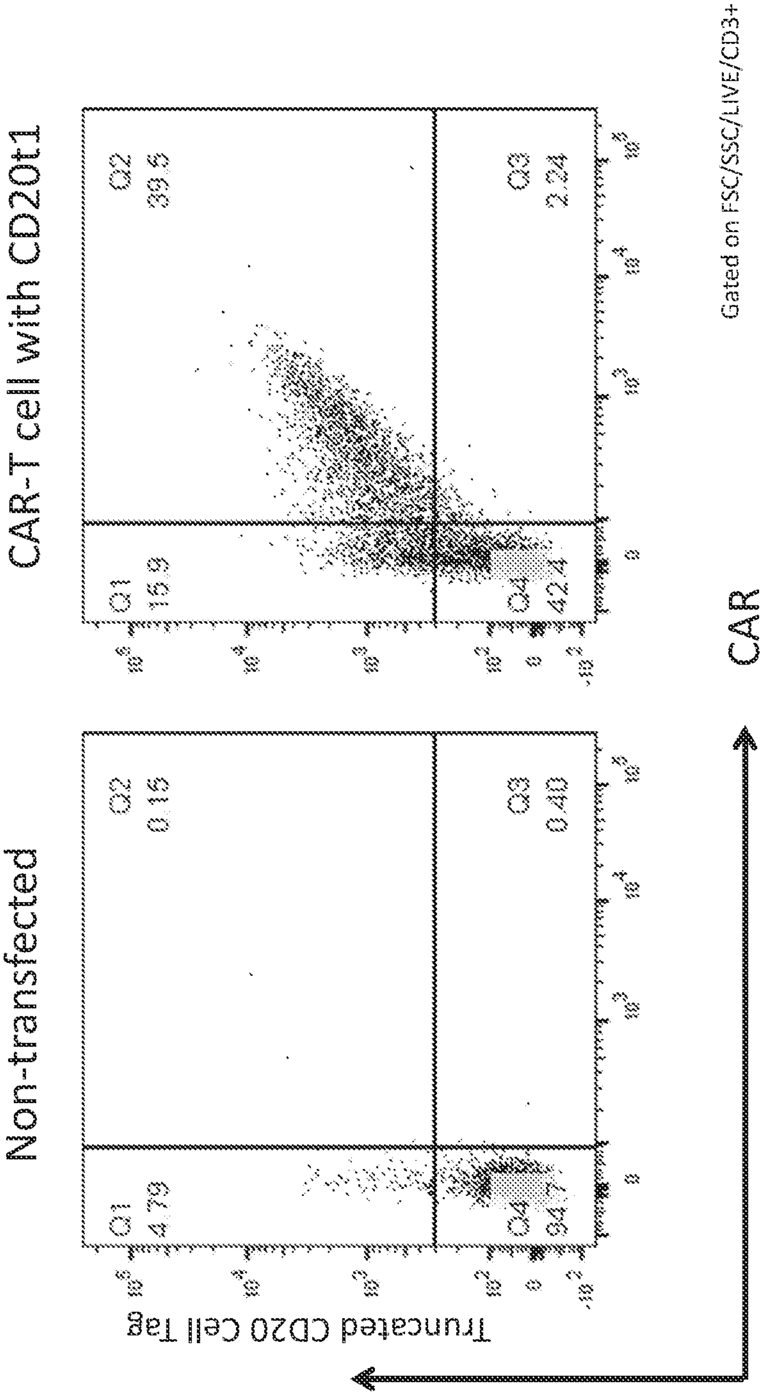
FIG. 2 shows co-expression of CD20t1 cell tag (corresponding to SEQ ID NO:109; y-axis) and a chimeric antigen receptor (CAR; x-axis) in human peripheral mononuclear cells (PBMCs) co-transfected with Sleeping Beauty transposon vectors encoding both genes (right panel) compared to non-transfected cells (left panel).

Human PBMCs were nucleofected using a Sleeping Beauty transposon coding for a CAR and CD20t1 cell tag as well as Sleeping Beauty transposase plasmid. Co-expression of CAR and CD20t was measured using flow cytometry. FIG. 2 shows that CD20t1 (SEQ ID NO:$10^9$; y-axis) and CAR (x-axis) are co-expressed from a CAR-CD20t1 construct compared to non-transfected cells.

Specific Anti-CD20 Antibody Induced ADCC of Truncated CD20 Cell Tags

Figure 3:
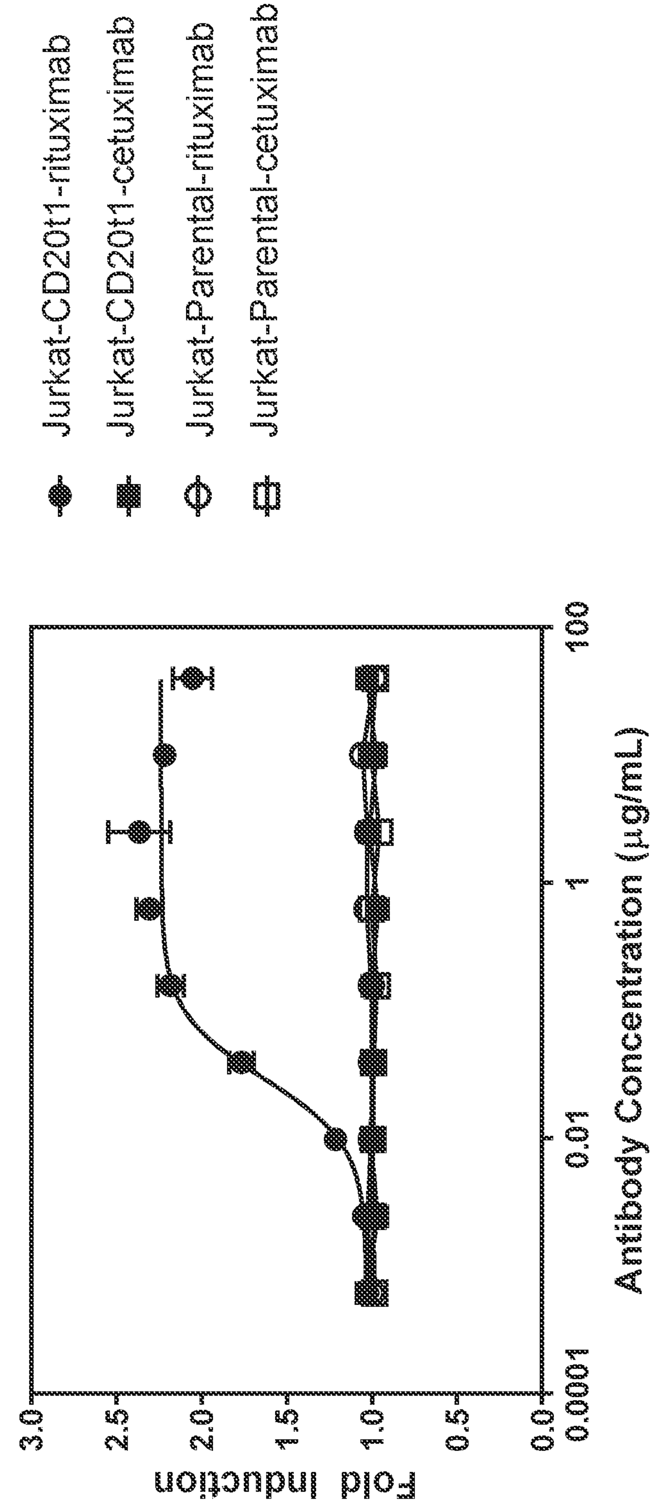
FIG. 3 shows specific dose dependent antibody-dependent cell-mediated cytotoxicity (represented by fold-induction; y-axis) induced by rituximab in Jurkat cell line transfected with CD20t-1. Non-transfected parental Jurkat cells and non-specific antibody cetuximab showed no activity.

Jurkat reporter cell line was modified to stably express CD20t1 cell tag. Expression of CD20t1 was confirmed by rituximab staining using flow cytometry. Ability of rituximab to specifically eliminate CD20t1 expressing Jurkat target cells was measured in an in vitro cytotoxicity assay. FIG. 3 shows rituximab induced ADCC activity of CD20t1 expressing cell line. In comparison, treatment with anti-EGFR cetuximab had no effect on ADCC activity.

Example 2. Expression of Truncated HER1 (HER1t) Polypeptide Construct as a Cell Tag Expression of Chimeric Cell Tags Novel chimeric cell tags were generated by using domain III of HER1 gene and domain IV of HER2, 3 or 4 genes. HER1-ErBB4 chimeric cell tags were expressed in human primary cells. Domain III of HER1 gene was genetically fused to a Domain IV of ErbB4 gene variant JM-a or a JM-b and TM domain of ErbB4 gene to generate chimeric cell tags. GMCSF alpha signal peptide was utilized as a signal peptide to direct chimeric cell tags to cell surface. HER1-ErbB4 cell tags (truncated EGFR-ErbB4 (JM-a) corresponding to SEQ ID NO:101 and truncated EGFR-ErbB4 (JM-b) corresponding to SEQ ID NO:10[5]) were cloned in pCDNA3.1 vector backbone along with control HER1t cell tag and transfected by electroporation into primary human PBMC. Expression of HER1-ErbB4 cell tags was confirmed in CD3+ T cells by flow cytometry using anti-HER1 specific antibody, cetuximab. As shown in FIG. 4D, transduced T cells expressed high levels of chimeric cell tags post transfection. Isotype antibody staining as well as non-transfected mock cells showed specificity of cetuximab staining to cell tags.

Expression of Truncated HER1t Cell Tags

Various truncated cell tags were constructed as depicted in the schematic shown in FIG. 4A. Truncated HER1t variants (HER1t1 corresponding to SEQ ID NO:57, HER1t2 corresponding to SEQ ID NO:59, HER1t3 corresponding to SEQ ID NO:61, HER1t4 corresponding to SEQ ID NO:63, HER1t5 corresponding to SEQ ID NO:65, HER1t6 corresponding to SEQ ID NO:67, and HER1t7 corresponding to SEQ ID NO:69) along with HER1t control cell tag were cloned in pCDNA3.1 vector backbone to test for expression. These expression vectors were transfected by electroporation in primary human PBMCs. Expression of truncated cell tags was confirmed in CD3+ T cells by flow cytometry using anti-HER1 specific antibody cetuximab. As shown in FIG. 4E, T cells expressed high levels of cell tags post transfection. Isotype antibody staining as well as non-transfected mock cells showed specificity of cetuximab staining to cell tags.

Figure 5A:
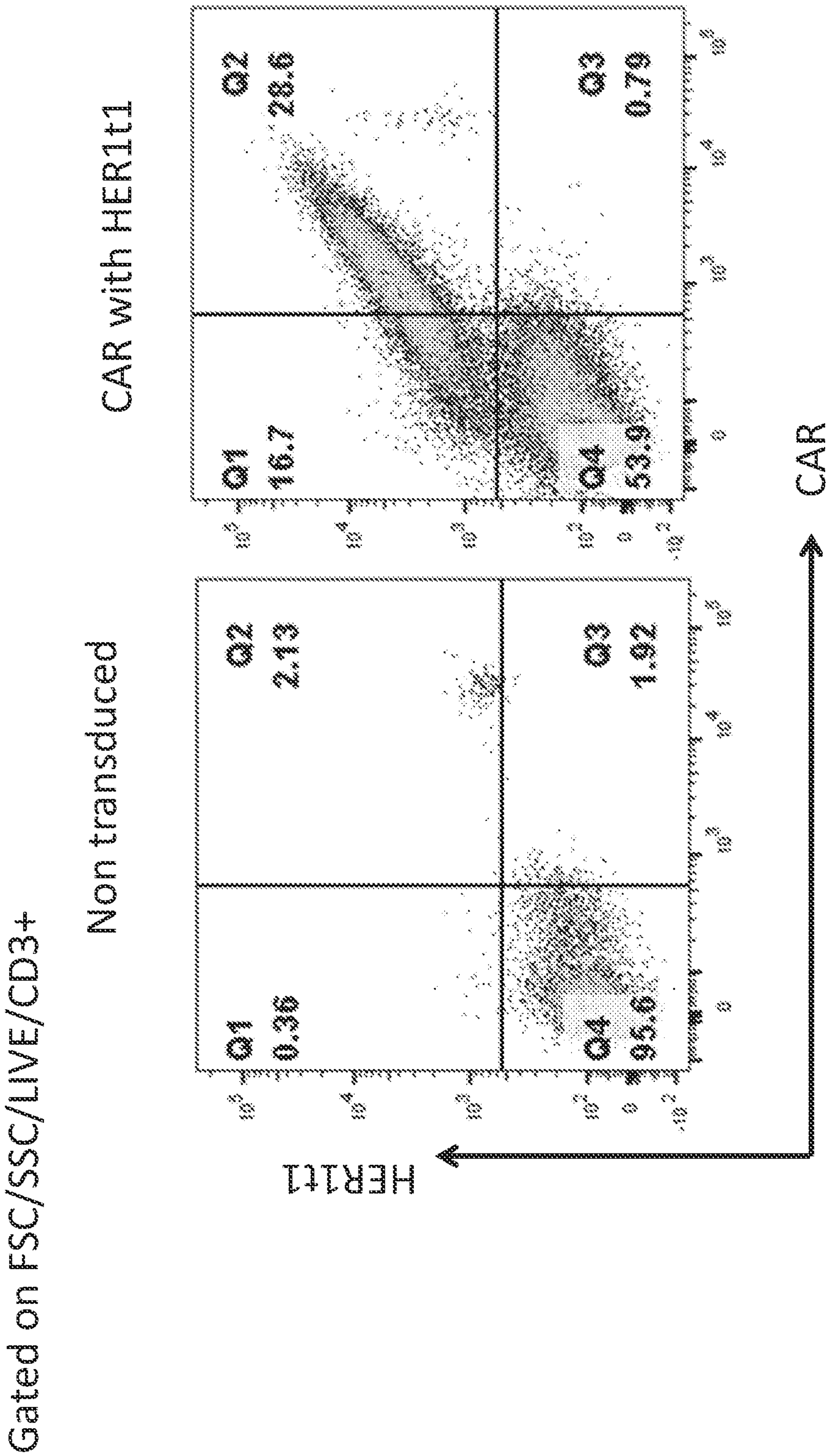
FIG. 5A shows antibody-based detection of HER1t1 expression (corresponding to SEQ ID NO:57; y-axis) and expression of CAR (x-axis) as measured by flow cytometry in cells co-transfected with lentiviral vector encoding both proteins (right panel) compared to control cells not transfected with HER1t or CAR (left panel).
Figure 5B:
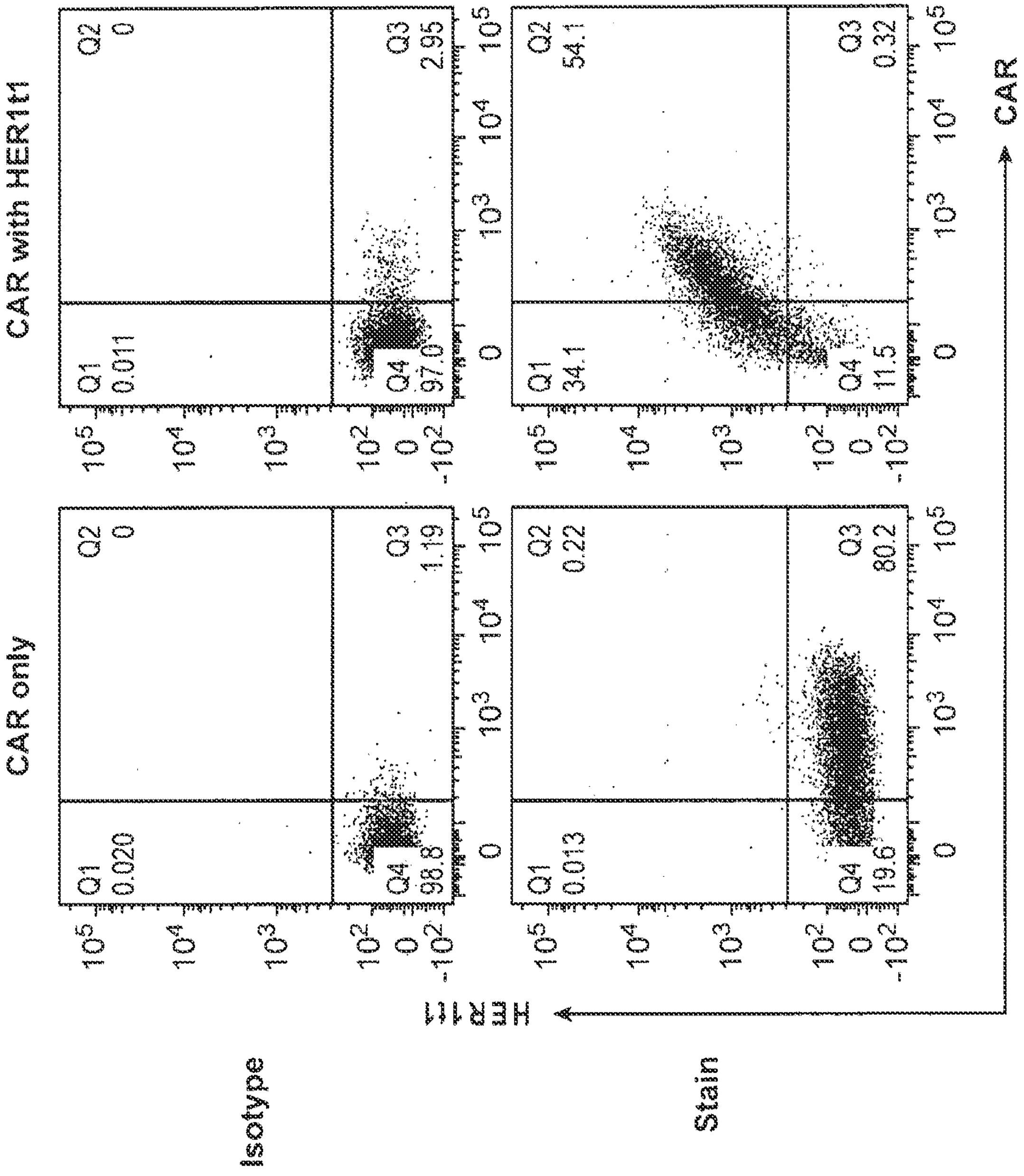
FIG. 5B shows levels of HER1t1 (corresponding to SEQ ID NO:57; y-axis) and a CAR (x-axis) in cells transfected with Sleeping Beauty transposon vectors encoding CAR alone (left panel) and CAR together with HER1t1(right panel) and stained with anti-HER1 antibody and CAR specific proteins (bottom panel) compared to an isotype control (top panel).
Figure 8:
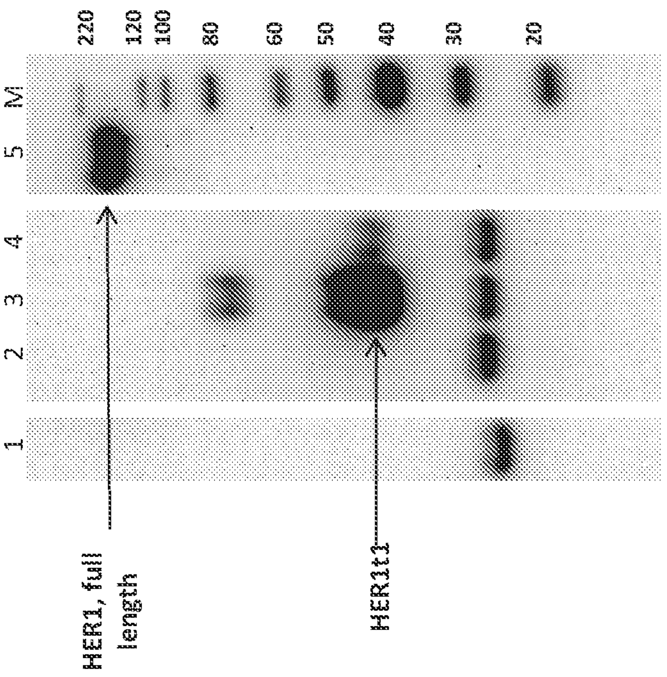

Self-inactivating lentiviral vectors encoding for either CAR alone or CAR as well as truncated HER1t1 cell tag were generated to evaluate co-expression of both genes. Activated human pan T cells were transduced with lentiviral vectors and expression of both CAR and HER1t1 was measured post transduction by flow cytometry using CAR-specific antigen-Fc fusion protein and anti-HER1 antibody cetuximab respectively. As shown in right panel of FIG. 5A and FIG. 5B, transduced T cells co-expressed both CAR (x-axis) and HER1t (y-axis). Left panel of FIG. 5A showed minimum background staining observed in non-transduced T cells. Left panel of FIG. 5B demonstrated expression of CAR but not HER1t when T cells were transduced with a lentiviral vector encoding for CAR only. Western blot analysis of truncated HER1t cell tag expressing cell lines SUP-T1 cell line was genetically modified to express HER1t1 (SUP-T1/HER1t1). SUP-T1/HER1t1 cell line was sorted by FACS for either high (High) or low (Low) levels of HER1t1 expression as measured by flow cytometry. Expression of truncated HER1t cell tag was confirmed in SUP-T1/HER1t1 (High) and SUP-T1/HER1t1 (Low) cell lines by Western blot analysis. Anti-HER1 antibody cetuximab was incubated with SUP-T1/CAR/HER1t1 or control (Jurkat and A431) cell line extracts to enable antibody to bind to HER1 derived cell tag proteins. The antibody/antigen complex was then precipitated using protein A/G-coupled agarose beads. This sample was then separated by SDS-PAGE for western blot analysis using an anti-HER1 antibody. Western blot shown in FIG. 8 confirms expression of HER1t1 in SUPT1/HER1t1 cell lines. Intensity of HER1t1 is lower in SUP-T1/HER1t1 (Low) cell line compared to SUP-T1/HER1t1 (High) cell line. Full length HER1 was detected in A431 positive control cell line. No expression of HER1 was detected in non-modified Jurkat cell line. FIG. 8: Lane 1: IP antibody only; Lane 2: Jurkat cells only; Lane 3: SUPT1/HER1t1 (high levels of HER1t1); Lane 4: SUPT1/HER1t1 (lower levels of HERt1); Lane 5: A431 cells expressing full-length HER1; Lane 6: Marker. Bold arrow points to protein precipitated by cetuximab in lanes except lane 5 where it refers to full length HER1.

Figure 6:
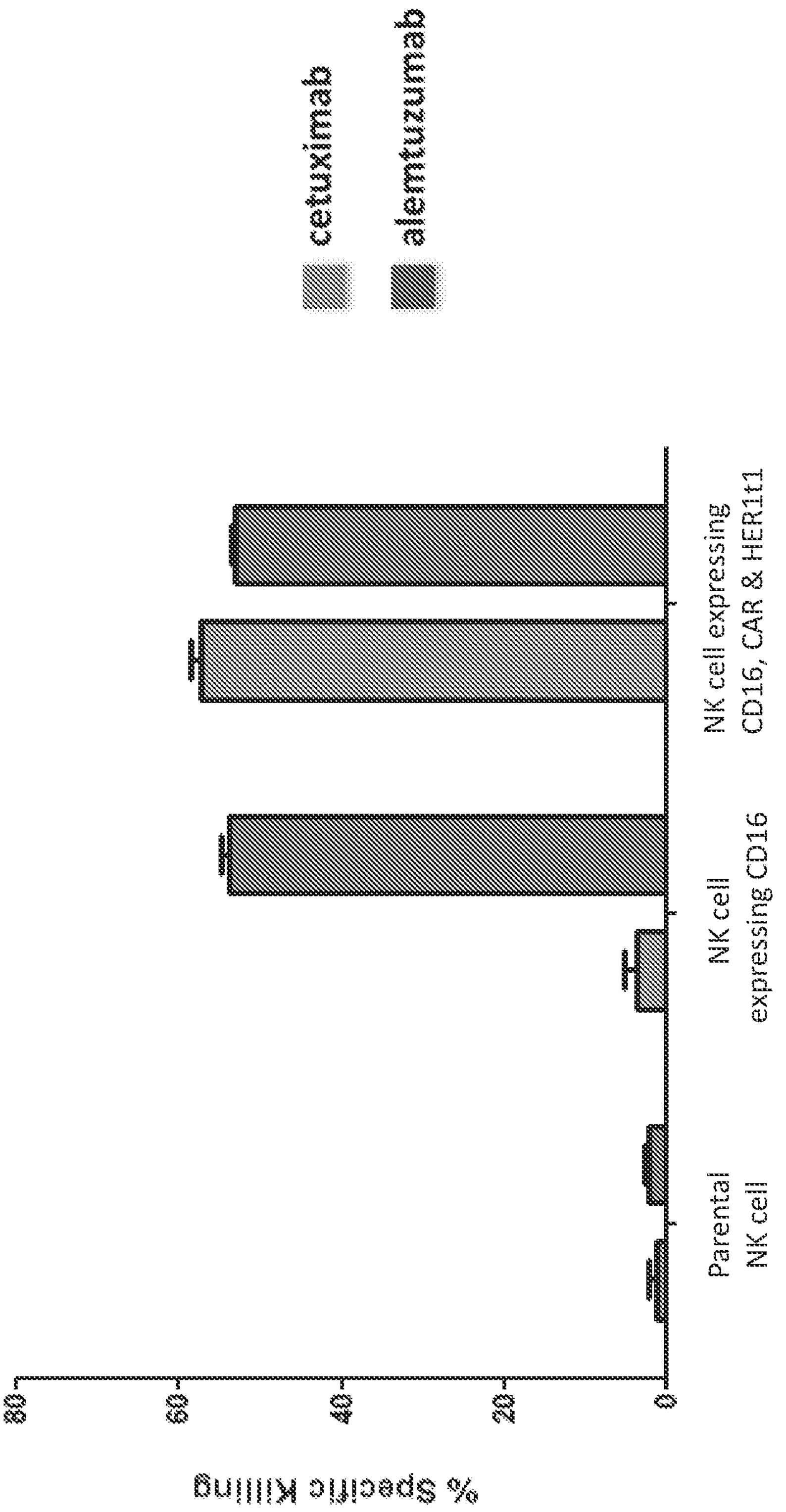

Example 3. ADCC and CDC of Truncated HER1t Cell Tag Expressing Cells by and-HER) Antibody Functionality of HER1t1 cell tag in an ADCC assay was assessed using an NK cell line. A parental NK cell line was modified to express CD16 receptor variant to induce ADCC. $CD16^+$ NK cell line was further modified to co-express a CAR and HER1t1 cell tag. Parental NK, $CD16^+$ NK and $CD16^+/CAR^+/HER1t1^+$ NK cell lines were analyzed for ADCC in presence of either anti-HER1 cetuximab or positive control alemtuzumab, capable of binding CD52 on NK cells. As shown in FIG. 6, ADCC was only observed when NK cells expressed CD16 as expected as binding of antibodies to CD16 induced effector function. Furthermore, alemtuzumab was able to induce ADCC of NK cells whether those cells expressed HER1t cell tag or not as long as CD16 was expressed. In contrast, cetuximab induced ADCC only when both HER1t1 and CD16 were expressed thus confirming specificity.

Figure 7A:
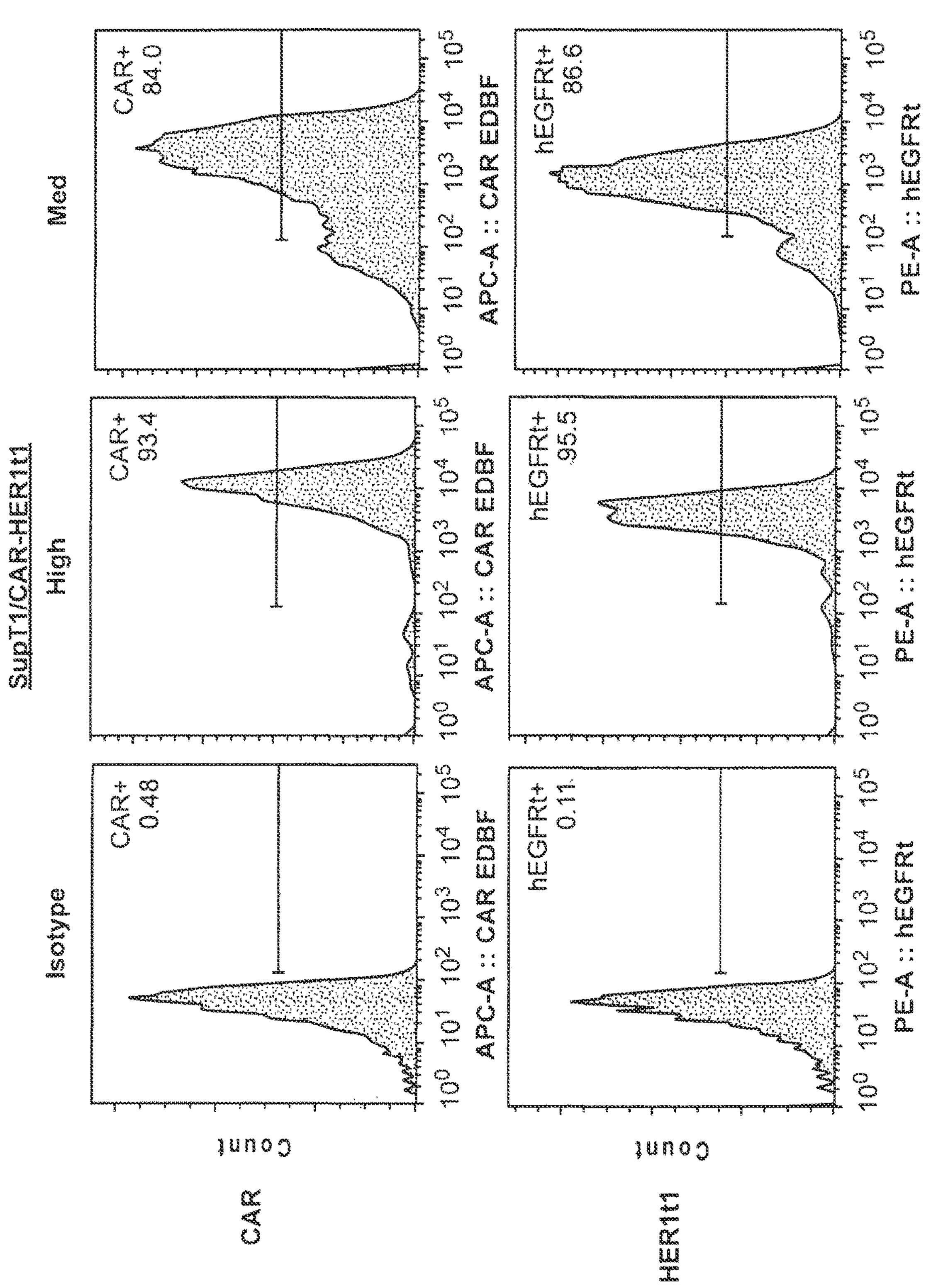
FIG. 7A shows expression of a CAR and HER1t1 cell tag (corresponding to SEQ ID NO:57) as measured by flow cytometry in genetically modified SUP-T1 reporter cell line (SUP-T1/CAR-HER1t1). SUP-T1/CAR-HER1t1 cell line was sorted by FACS to enrich for high (middle panel) or medium (right panel) level of HER1t1 expression as detected by flow cytometry. Left panel shows staining of SUP-T1/CAR-HER1t1 using isotype antibody control for flow cytometry.
Figure 7B:
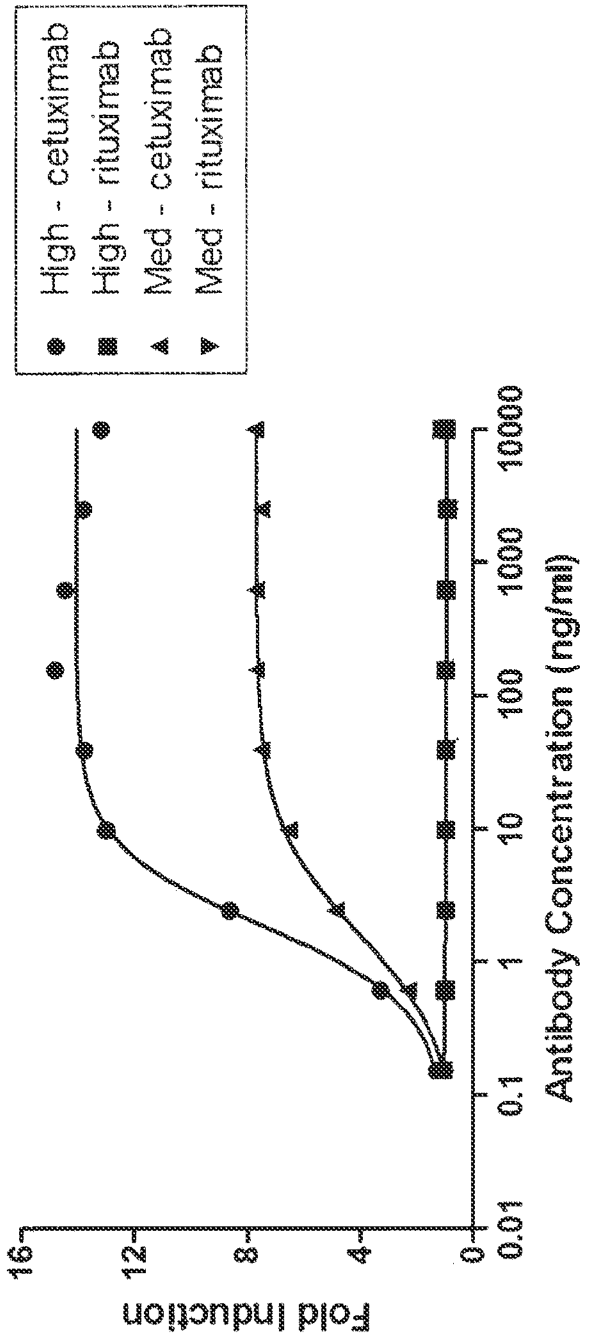
FIG. 7B shows specific ADCC (represented by fold-induction; y-axis) of SUP-T1/CAR-HER1t1 cell line induced by cetuximab which is dependent on HER1t1 expression as well as cetuximab dose levels. Non-specific antibody rituximab showed no ADCC of SUP-T1/CAR-HER1t1.

SUP-T1 (a human T lymphocyte cell line), reporter cell line was genetically modified to co-express a CAR and HER1t1 (SUP-T/CAR/HER1t1). SUP-T/CAR/HER1t1 cell line was sorted by FACS for either high (High) or medium (Med) levels of HER1t1 expression as measured by flow cytometry to evaluate effect of cell tag density on cell surface for ADCC using anti-HER1 antibody. FIG. 7A, shows expression levels of CAR and HER1t1 in sorted SUP-T1/CAR/HER1t1 populations. Left panel of FIG. 7A shows isotype antibody only staining, middle panel shows high HER1t expression and right panel shows medium HER1t expression by flow cytometry. Since CAR and HER1t1 genes are expressed from the same transcript, sorting cells based on HER1t1 affected expression of CAR in similar manner as well. SUP-T1/CAR/HER1t1 High and Med cell lines were tested in an ADCC assay using cetuximab or non-specific rituximab as control. 5:1 effector (E) to HER1t1+ target (T) cell ratio was utilized for the assay. ADCC was quantified as fold induction of reporter gene expression. As shown in FIG. 7B, cetuximab specifically induced ADCC of HER1t1 expressing cell line in dose dependent manner. Furthermore, induction of ADCC was dependent on level of HER1t1 expression on cell surface.

Figure 9B:
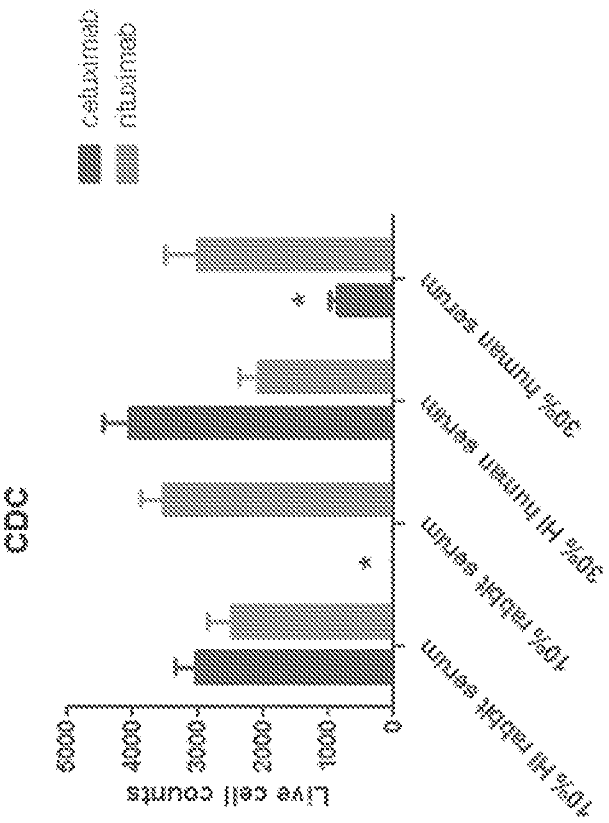
FIG. 9B shows the efficacy of elimination of CD 19 CAR-T cells co-expressing HER1t1 cell tag by CDC in the presence of cetuximab or non-specific antibody rituximab.
Figure 9A:
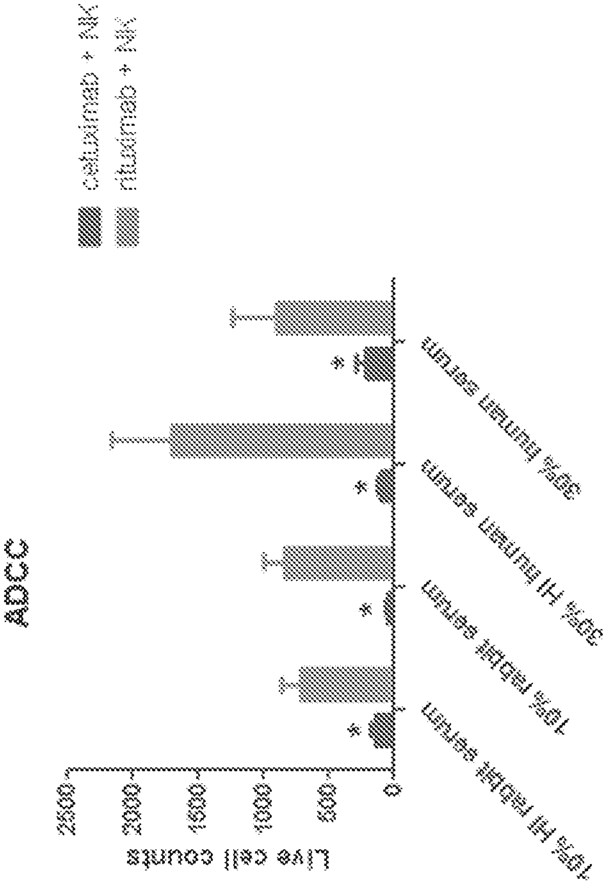
FIG. 9A shows the efficacy of elimination of CD 19 CAR-T cells co-expressing HER1t1 cell tag by ADCC.

Human donor PBMCs were transfected by electroporation with two Sleeping Beauty transposon vectors to express CD19 CAR and HER1t1 cell tag along with SB II transposase to redirect T cell specificity. The day after transfection (day 1) cells were counted, and CAR expression was measured by flow cytometry. CAR T Cells were stimulated with either γ-irradiated (100 Gy) or mitomycin C treated AaPCs at a 1:1 ratio for 4 stimulation cycles. The AaPC cells used were K562-AaPC expressing CD19 antigen. Cultures were supplemented with IL-21 (30 ng/ml) only for the first round of stimulation and subsequently with recombinant human IL-2 (50 IU/ml) and IL-21 (30 ng/ml) (Pepro Tech) for remaining stimulations. T cell cultures were phenotyped at the end of each stimulation cycle, which typically lasted 7 days. The cultures were phenotyped for CAR expression by multi-parameter flow cytometry utilizing either Protein L or anti-idiotype antibody that recognizes CD19 CAR. Ability of cetuximab to specifically eliminate CD19 CAR+/HER1t1+ T cells in vitro was tested in ADCC and complement dependent cytotoxicity (CDC) assays. CSFE-labeled CD19 CAR+/HER1t1+T target cells (T) (5e4 cells/well) were incubated with $CD16^+$ NK effector cell line (E) (2.5e5 cells/well) at E:T ratio of 5:1 with 5 μg/ml cetuximab or rituximab for 2-24 hours in triplicates. For CDC assay, 10% Rabbit serum with and without heat-inactivation (HI) as well as 30% human serum with and without heat-inactivation (HI) was utilized. Cells are stained with DAPI and data acquired with iQUE Screener plus instrument. Live cell counts were reported for each condition. As shown in FIG. 9 (left panel), cetuximab induced specific cytotoxicity of CD19 $CAR^+$/$HER1t1^+$ T cells as evident by low live cell counts in ADCC assay. As shown in FIG. 9 (right panel), cetuximab induced specific cytotoxicity of CD19 $CAR^+$/$HER1t1^+$ T cells as evident by low live cell counts in CDC assay when human or rabbit serum was not heat inactivated.

Figure 10:
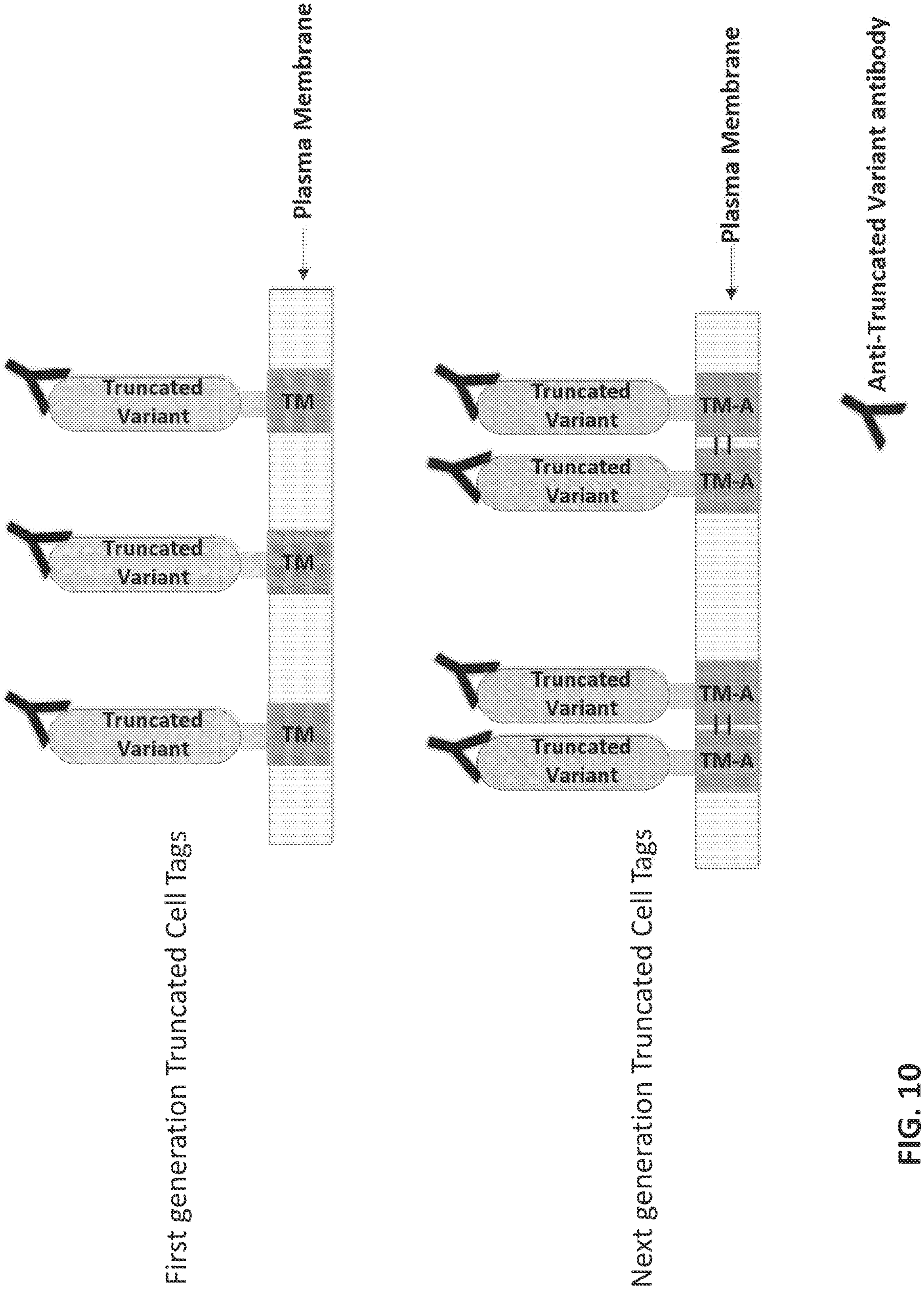
FIG. 10 is a schematic diagram showing different embodiments of polypeptide constructs described herein. First-generation truncated cell tags (top) comprise a truncated variant and a non-dimerizing transmembrane domain (TM) connected by an optional peptide linker. Next-generation truncated cell tags (bottom panel) include a transmembrane dimerization n domain (TM-A) that facilitates dimerization of truncated variants on the cell surface. In both cases, anti-truncated variant antibody binds to an epitope on the truncated variant.

Example 4. Next-Generation Kill Switch/Cell Tag Constructs Enhance ADCC and CDC FIG. 10 is a schematic diagram comparing the design of first generation and next generation polypeptide constructs comprising truncated cell tags. First-generation truncated cell tags (top) comprise a truncated variant and a non-dimerizing transmembrane domain (TM) connected by an optional peptide linker. Next-generation truncated cell tags (bottom panel) include a multimerization domain to generate cell tags that are capable of multimerizing on cell surface. The example depicted in the bottom panel of FIG. 10, utilizes a transmembrane domain (TM-A) capable of homodimerizing to induce cell tag dimers on the cell surface. Although homo-dimerization of cell surface polypeptides is shown, formation of heterodimers at the cell surface is also possible if cells are engineered to co-express polypeptide constructs having different cell surface polypeptides. In both first generation and next-generation polypeptide constructs, anti-truncated variant antibody or another binding domain recognizes and binds to the truncated variant. For such next-generation constructs, dimerization of the cell surface polypeptides can increase the avidity and amplify a signaling effect induced by antibody binding beyond that of the first generation constructs, as well as improve purification and sorting of cells using the multimer cell tag.

Figure 11:
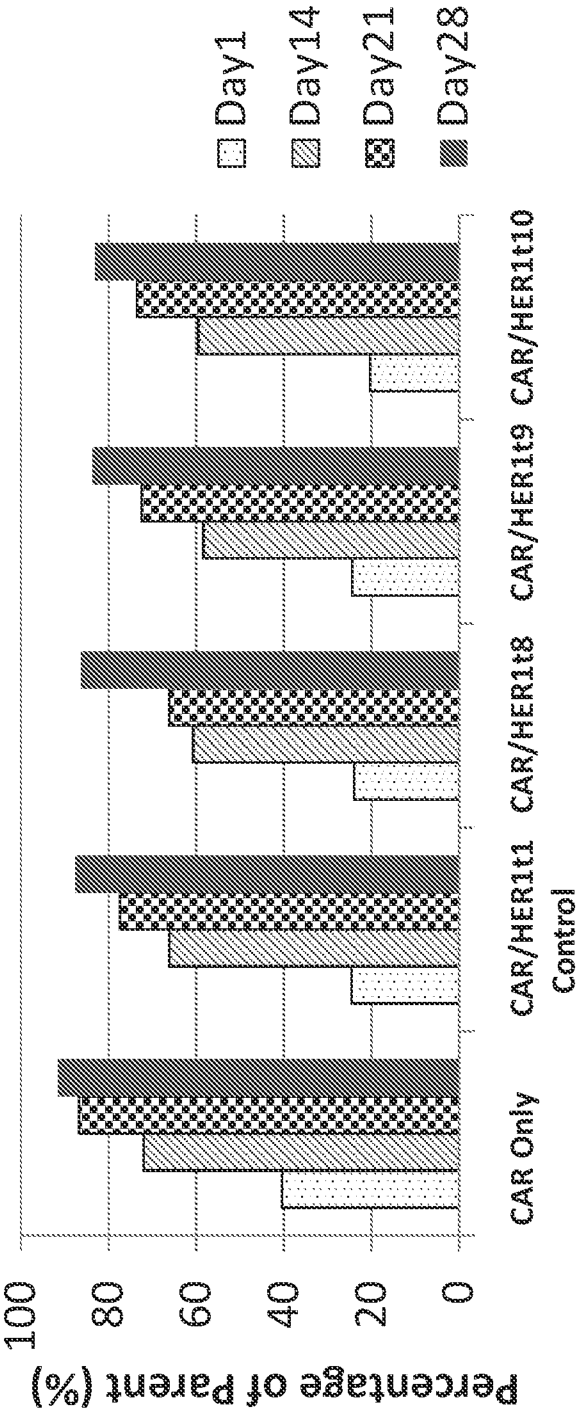
FIG. 11 demonstrates expression levels of CD19 CAR in primary T cells modified to co-express CD19 CAR and HER1t cell tag. HERt1 cell tags utilized include truncated HER1 polypeptide with a transmembrane dimerization domain (variants HER1t8 corresponding to SEQ ID NO:71, HER1t9 corresponding to SEQ ID NO:75, and HER1t10 corresponding to SEQ ID NO:79) and a polypeptide construct comprising a truncated HER1 polypeptide without a transmembrane dimerization domain (HER1t1 corresponding to SEQ ID NO:57) compared to T cells expressing CD19 CAR alone (% of Parent).

Human donor PBMC were transfected (day 0) by electroporation with Sleeping Beauty transposon vectors designed to co-express CD19 CAR and first or next-generation HER1t cell tags along with SB11 transposase to redirect T cell specificity. The day after transfection (day 1) cells were counted, and CAR expression was measured by flow cytometry. CAR-T cells were stimulated with either 7-irradiated (100 Gy) or mitomycin C treated AaPCs at a 1:1 ratio for 4 stimulation cycles. The AaPC cells used were K562-AaPC expressing CD19 antigen. Cultures were supplemented with IL-21 (30 ng/ml) only for the first round of stimulation and subsequently with recombinant human IL-2 (50 IU/ml) and IL-21 (30 ng/ml) (Pepro Tech) for remaining stimulations. T cell cultures were phenotyped at the end of each stimulation cycle, which typically lasted 7 days. The cultures were phenotyped for CAR expression by multi-parameter flow cytometry utilizing either Protein L or anti-idiotype antibody that recognized CD19 CAR and anti-HER1 antibody cetuximab that recognized various truncated HER1t cells tags. FIG. 11 demonstrates that CD19 CAR expression does not vary over time in next-generation polypeptide constructs comprising HER1t variants (for example, HER1t8 corresponding to SEQ ID NO:71, HER 1t9 corresponding to SEQ ID NO:75, and Her1t10 corresponding to SEQ ID NO:79) compared to a first generation polypeptide construct (HER1t1 corresponding to SEQ ID NO:57) and a control cell line which does not express HER1t. Percentage of $CD3^+$ T cells expressing CD19 CAR in various cultures is shown in Table 4.

TABLE 4

Quantification of CD19 CAR expression in FIG. 11.

| | Day 1 | Day 14 | Day 21 | Day 28 |
|---|---|---|---|---|
| CAR only | 40.45 | 72.07 | 86.87 | 91.56 |
| CAR/HER1t1 | 24.54 | 66.22 | 77.51 | 87.66 |
| CAR/Her1t8 | 24.02 | 60.75 | 66.26 | 86.27 |
| CAR/HER1t9 | 24.41 | 58.43 | 72.51 | 83.7 |
| CAR/HER1t10 | 20.34 | 59.57 | 73.56 | 83.03 |

Figure 12:
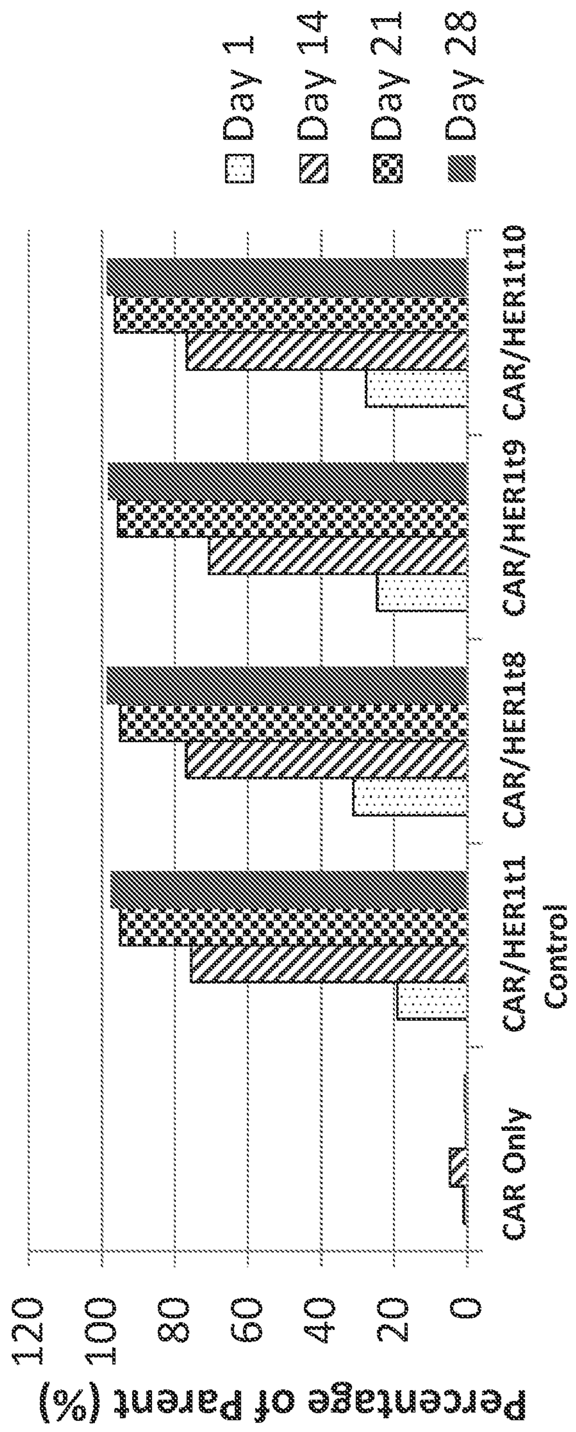
FIG. 12 demonstrates expression levels of HER1t cells tag in primary T cells modified to co-express CD19 CAR and HER1t cell tag. HER1t cell tags utilized include a truncated HER1 polypeptide with a transmembrane dimerization domain (variants HER1t8 corresponding to SEQ ID NO:71, HER1t9 corresponding to SEQ ID NO:75, and Her1t10 corresponding to SEQ ID NO:79) and a polypeptide construct comprising a truncated HER1 polypeptide without a dimerization domain (HER1t1 corresponding to SEQ ID NO:57) compared to T cells expressing CD19 CAR alone (% of Parent).

FIG. 12 shows that cell lines expressing next generation polypeptide constructs comprising HER1t variants with a transmembrane dimerization domain (variants HER1t8 corresponding to SEQ ID NO:71, HER1t9 corresponding to SEQ ID NO:75, and Her1t10 corresponding to SEQ ID NO:79) have similar HER1t expression levels over time as a line expressing a first generation HER1t polypeptide construct (HER1t1 corresponding to SEQ ID NO:57). No HER1t expression was detected in culture transfected with CAR only transposon. Table 5 shows percentage of $CD3^+$ T cells expressing HER1t variants in various cultures, whereas Table 6 shows the mean fluorescence intensity (MFI) of HER1t from FIG. 12 at days 14, 21 and 28.

TABLE 5

Quantification of HERIt expression in FIG. 12.

| | Day 1 | Day 14 | Day 21 | Day 28 |
|---|---|---|---|---|
| CAR only | 0.98 | 4.79 | 0.38 | 0.99 |
| CAR/HER1t1 | 19.1 | 75.63 | 95 | 97.69 |
| CAR/Her1t8 | 31.27 | 76.91 | 95.04 | 98.67 |
| CAR/HER1t9 | 24.68 | 70.75 | 95.56 | 98.31 |
| CAR/HER1t10 | 27.72 | 76.8 | 96.53 | 98.58 |

TABLE 6

Mean fluorescence intensity of HER1t variants at days 14, 21 and 28 from FIG. 12.

| | Day 14 | Day 21 | Day 28 |
|---|---|---|---|
| CAR only | 19,368 | 9,132 | 16,033 |
| CAR/HER1t1 | 66,766 | 123,459 | 105,492 |
| CAR/Her1t8 | 133,345 | 217,748 | 187,545 |
| CAR/HER1t9 | 92,190 | 150,762 | 126,327 |
| CAR/HER1t10 | 101,528 | 181,300 | 116,499 |

Figure 13A:
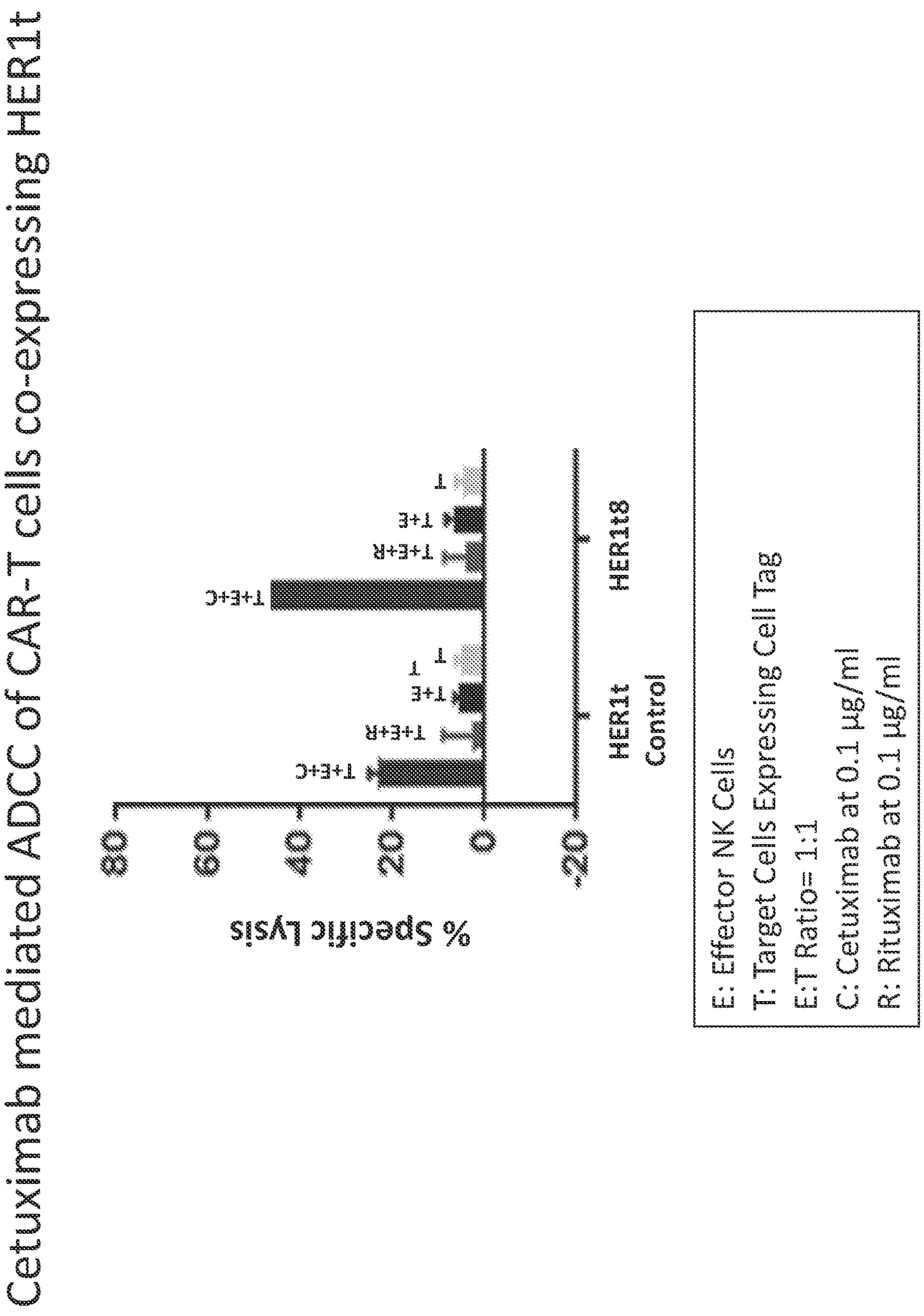
FIG. 13A and FIG. 13B shows the superior effects of cetuximab-mediated ADCC (represented by % specific lysis; y-axis) of CD19 CAR-T target cells co-expressing a polypeptide construct comprising a truncated HER1 polypeptide with a dimerization domain (variants HER1t8 corresponding to SEQ ID NO:71, HER1t9 corresponding to SEQ ID NO:75, and HER1t10 corresponding to SEQ ID NO:79) over a polypeptide construct comprising a truncated HER1 polypeptide without a dimerization domain (HER1t control corresponding to SEQ ID NO:57). NK cells were utilized as effector cells. Rituximab was utilized as non-specific antibody control for ADCC assay.
Figure 13B:
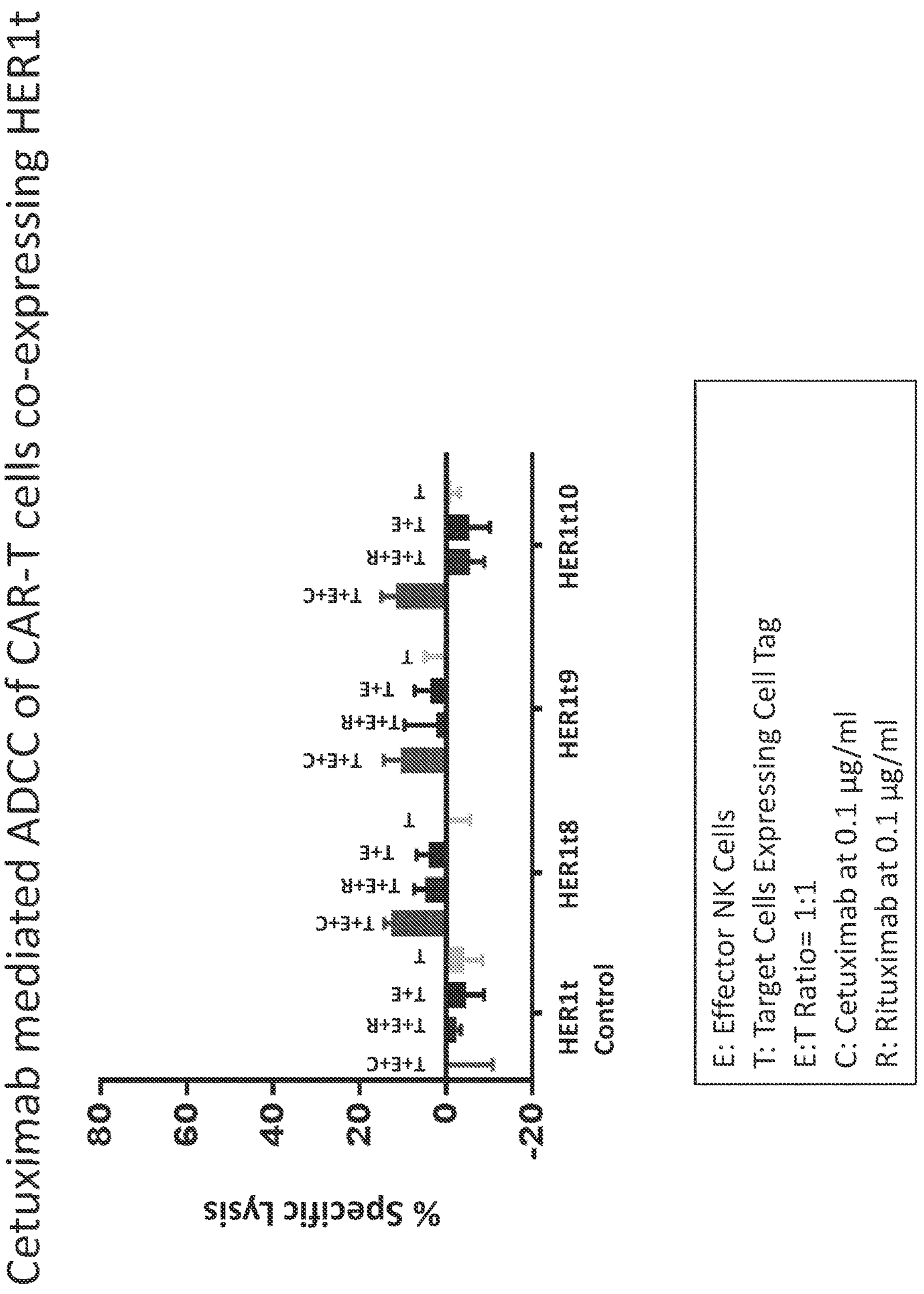

CD19 CAR-T cells expressing next generation HER1t variants were tested for cetuximab induced ADCC in an in vitro assay and compared with first generation HER1t design for efficacy. CD19 CAR-T target cells (T) were labeled with CFSE at 0.0005 μM for CAR-T cells expressing HER1t variants and 0.01 μM for CAR-T cells without HER1t. Target cells were suspended at $0.8\times10^6$ cells/ml, mixed at a 1:1 ratio and seeded at $4\times10^4$ cells/50 μl/well (each at $2\times10^4$ cells/50 μl/well). Next, $CD16^+$ NK effector cells (E) were collected, washed and resuspended at $0.2\times10^6$ cells/ml. Cells were then seeded at $2\times10^4$ cells/100 μl/well (E:T=0.5:1). Rituximab or cetuximab antibodies were prepared at 0.4 μg/ml along with a control solution lacking antibody, and solutions were added to wells as follows: (i) rituximab (anti-CD20) control: 50 μl/well at a final concentration of 0.1 μg/ml in each well; (ii) cetuximab (anti-HER1): 50 μl/well at a final concentration of 0.1 μg/ml in each well; (iii) control solution (no antibody): 50 μl/well at a final concentration of 0 μg/ml in each well. The final volume in each well was adjusted to 200 μl. Solutions were mixed well and cultured for 4, 8, 16 and 24 hours. Following incubation cells were washed and stained with CD3-BV786 in the presence of Human Fc Block. Cells were then washed two times with FACS buffer, resuspended in 50 μl of FAC buffer containing 7AAD for 10 minutes and then analyzed. FIG. 13A-B demonstrate that next-generation HER1t polypeptide constructs comprising potential dimerized HER1t variants on cell surface polypeptides (HER1t8, HER1t9 and HER1t10) mediate improved ADCC relative to polypeptide constructs comprising non-dimerizing transmembrane domain (HER1t control) in the presence of cetuximab.

Figure 14:
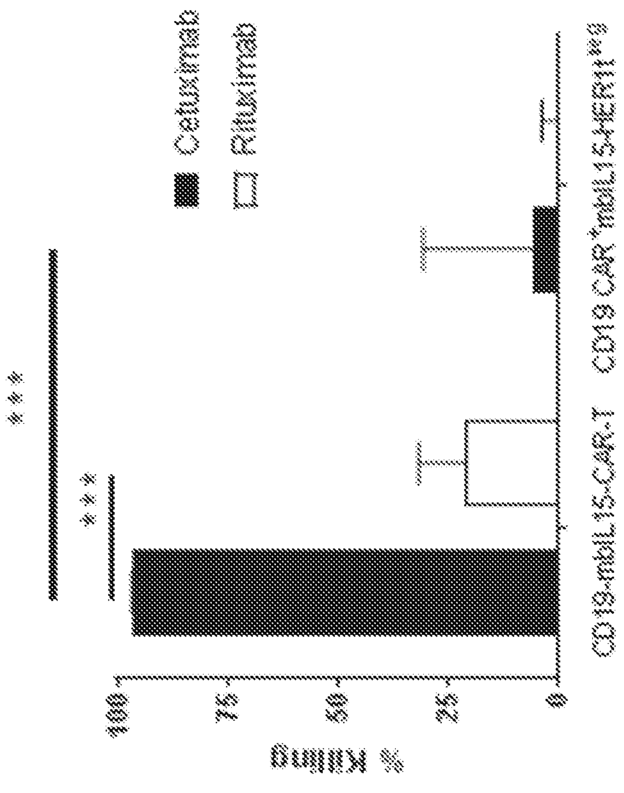
FIG. 14 shows selective elimination of genetically modified-T cells (CD19 CAR-mbIL-15-T cells) expressing HER1t1 by cetuximab-mediated ADCC.

In vitro studies were conducted to confirm the ability of cetuximab to induce ADCC against CD19 CAR-mbIL15-T cells. CD19 CAR-mbIL15-T cells were generated by electro-transfer of CD19 CAR and mbIL15-HER1t transposons and SB11 transposase. The genetically modified T cells were numerically expanded ex vivo on irradiated $CD19^+$ feeder cells for ADCC assay. Due to the bicistronic design of mbIL15-HER1t transposon, CD19 CAR-mbIL15-T cells co-expressed HER1t1 when mbIL15 is expressed. Negative control CD19 $CAR^+$mbIL15-HER 1tneg T cells lacking expression of mbIL15-HER1t generated by transfection of CD19 CAR transposon and SB11 transposase were numerically expanded ex vivo using same $CD19^+$ feeder cells. Expanded allogeneic NK cells which express endogenous FcR were used as effector cells and co-cultured overnight with labelled $CAR^+$ T cells at 10:1 E: T ratio in the presence of 10 μg/mL cetuximab, or anti-CD20 antibody (rituximab) which serves as negative control. mbIL15-HER1t+ T cells remaining in culture post antibody treatment were determined by flow cytometry to calculate percent killing. Addition of cetuximab resulted in elimination of >90% mbIL15-HER1t+ population of CD19–mbIL15-CAR T cells (FIG. 14). Rituximab showed a lower level of non-specific elimination of CD19–mbIL15-CAR-T cells. Cetuximab failed to exhibit significant level of lysis of CAR+mbIL15-HER 1tneg T cells confirming HER1t-specific mechanism of action. 10 μg/mL concentration of cetuximab utilized in this experiment is within the range previously reported in patients dosed with cetuximab. These data support the use of cetuximab to deplete CD19 CAR-mbIL15-T cells if needed due to the development of untoward clinical effects.

An in vivo study was conducted in NSG mice. On Day 0, 5E6 CAR-HER1t1 T cells and 5E6 KHYG-1-CD16high cells were injected intraperitoneally (IP) into each mice. On the same day, mice were randomized and treated with saline or cetuximab (0.5 mg: IP). Peritoneal lavage was harvested on day 1 and flow cytometry assessment was performed to assess frequency of CAR-HER1t1 T cells from mice in both groups. Absolute cell counts of CAR-HER1t1 T cells from were also performed. Data (not shown) demonstrates ability of cetuximab to specifically eliminate CAR T cells expressing HER1t1 tag in contrast to saline treated mice.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein may be employed in practicing the present disclosure. It is intended that the following claims define the scope of the present disclosure and that methods and structures within the scope of these claims and their equivalents be covered thereby.

What is claimed is:

1. A method of treating cancer in a subject in need thereof the method comprising administering to the subject: (a) an engineered effector cell expressing a chimeric antigen receptor (CAR) that specifically binds to an antigen selected from CD19, CD20, CD33, BCMA, CD123, EGFRvIII, ROR1, HER2, GD2, mesothelin, CD22, and MUC-16; and (b) a binding partner selected from cetuximab, panitumumab, and functional fragments thereof; wherein:
   - the engineered effector cell comprises a recombinant polypeptide comprising:
     - (a) a truncated non-immunogenic HER1 polypeptide consisting of: (i) an amino acid sequence having at least 90% identity with SEQ ID NO: 200; and (ii) an amino acid sequence having at least 90% identity with any one of SEQ ID NOs: 203-209; and
     - (b) a transmembrane domain comprising an amino acid sequence having at least 90% identity with any one of SEQ ID NOs: 26, 28, 30, 32, 34, 36, 38, and 40; and
   - the cancer is associated with the overexpression of the antigen.

2. The method of claim 1, wherein the engineered effector cell further comprises a Sleeping Beauty transposase.

3. The method of claim 1, where the binding partner is cetuximab or a functional fragment thereof.

4. The method of claim 1, wherein the transmembrane domain comprises an amino acid sequence having at least 90% identity with SEQ ID NO: 36 and is coupled to the truncated non-immunogenic HER1 polypeptide with a peptide linker.

5. The method of claim 1, wherein the truncated non-immunogenic HER1 polypeptide comprises an amino acid sequence having at least 95% identity with SEQ ID NO: 200.

6. The method of claim 1, wherein the truncated non-immunogenic HER1 polypeptide comprises an amino acid sequence having at least 95% identity with any one of SEQ ID NOs: 203-209.

7. The method of claim 1, wherein the truncated non-immunogenic HER1 polypeptide comprises an amino acid sequence having at least 95% identity with SEQ ID NO: 203.

8. The method of claim 1, wherein the truncated non-immunogenic HER1 polypeptide consists of an amino acid sequence having at least 95% identity with any one of SEQ ID NOs: 211-217.

9. The method of claim 1, wherein the truncated non-immunogenic HER1 polypeptide consists of an amino acid sequence having at least 95% identity with SEQ ID NO: 211.

10. The method of claim 1, wherein the transmembrane domain comprises an amino acid sequence having at least 95% identity with any one of SEQ ID NOs: 26, 28, 30, 32, 34, 36, 38, and 40.

11. The method of claim 1, wherein the recombinant polypeptide comprises an amino acid sequence having at least 95% identity with any one of SEQ ID NOs: 55, 57, 59, 61, 63, 65, 67, 69, 73, 77, 81, and 85.

12. The method of claim 1, wherein the recombinant polypeptide comprises an amino acid sequence having at least 95% identity with SEQ ID NO: 57.

13. The method of claim 1, wherein the recombinant polypeptide comprises the amino acid sequence of SEQ ID NO: 57.

14. The method of claim 1, wherein the engineered effector cell further expresses a polypeptide comprising: (a) an IL-15, or functional fragment or variant thereof; and (b) an IL-15Rα, or functional fragment or variant thereof.

15. The method of claim 1, wherein the engineered effector cell further expresses a polypeptide having at least 95% identity with the sequence of SEQ ID NO: 178.

16. The method of claim 1, wherein the engineered cell is a T-cell or natural killer cell and the antigen is CD19, CD33, BCMA, ROR1, mesothelin, CD22, or MUC-16.

17. The method of claim 16, wherein the antigen is CD19.

18. The method of claim 1, wherein the engineered effector cell is a T-cell or a natural killer cell.

19. The method of claim 1, wherein the truncated non-immunogenic HER1 polypeptide consists of: (a) an amino acid sequence having at least 99% identity with the sequence of SEQ ID NO: 200; and (b) an amino acid sequence having at least 99% identity with the sequence of any one of SEQ ID NOs: 203-209.

20. The method of claim 1, wherein the truncated non-immunogenic HER1 polypeptide consists of an amino acid sequence having at least 99% identity with the sequence of SEQ ID NO: 211.

21. The method of claim 1, wherein the transmembrane domain comprises an amino acid sequence having at least 99% identity with the sequence of any one of SEQ ID NOs: 26, 28, 30, 32, 34, 36, 38, and 40.

22. The method of claim 1, wherein the recombinant polypeptide comprises an amino acid sequence having at least 99% identity with the sequence of any one of SEQ ID NOs: 55, 57, 59, 61, 63, 65, 67, 69, 73, 77, 81, and 85.

23. The method of claim 1, wherein the recombinant polypeptide comprises an amino acid sequence having at least 99% identity with the sequence of SEQ ID NO: 57.

24. The method of claim 1, wherein the truncated non-immunogenic HER1 polypeptide consists of: (a) an amino acid sequence having the sequence of SEQ ID NO: 200; and (b) an amino acid sequence having the sequence of any one of SEQ ID NOs: 203-209.

25. The method of claim 1, wherein the truncated non-immunogenic HER1 polypeptide consists of the sequence of SEQ ID NO: 211.

26. The method of claim 1, wherein the transmembrane domain comprises an amino acid sequence having the sequence of any one of SEQ ID NOs: 26, 28, 30, 32, 34, 36, 38, and 40.

27. The method of claim 1, wherein the recombinant polypeptide comprises an amino acid sequence having the sequence of any one of SEQ ID NOs: 55, 57, 59, 61, 63, 65, 67, 69, 73, 77, 81, and 85.

28. The method of claim 1, wherein the cancer is B cell lymphoma, acute lymphoblastic leukemia (ALL), mantle cell lymphoma (MCL), breast cancer, cervical cancer, chronic lymphocytic leukemia (CLL), acute myeloid leukemia (AML), fallopian tube cancer, pancreatic cancer, liver cancer, lung cancer, ovarian cancer, prostate cancer, diffuse large B-cell lymphoma (DLBCL), Burkitt's lymphoma, follicular lymphoma (FL), or diffuse large B-cell lymphoma.

29. The method of claim 1, wherein the cancer is a hematologic malignancy.

30. The method of claim 1, wherein the cancer is a relapsed and refractory B-cell lymphoma.

31. The method of claim 1, wherein the cancer is anal cancer, appendix cancer, bile duct cancer, bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, vulvar cancer, a lymphoma, a leukemia, a myeloma, or a B-cell malignancy.

32. The method of claim 1, wherein the cancer is chronic lymphocytic leukemia (CLL), small lymphocytic lymphoma (SLL), high risk CLL, non-CLL/SLL lymphoma, prolymphocytic leukemia (P1L), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, r lymphomatoid granulomatosis, acute myeloid leukemia (AML), or chronic myeloid leukemia (CML).

* * * * *